United States Patent
Romines et al.

(10) Patent No.: US 6,169,181 B1
(45) Date of Patent: *Jan. 2, 2001

(54) COMPOUNDS USEFUL TO TREAT RETROVIRAL INFECTIONS

(75) Inventors: Karen Rene Romines, Paw Paw; Gordon L. Bundy, Portage; Theresa M. Schwartz, Kalamazoo, all of MI (US); Ruben A. Tommasi, Whitehouse Station, NJ (US); Joseph W. Strohbach, Mendon, MI (US); Steven Ronald Turner, Kalamazoo, MI (US); Suvit Thaisrivongs, Kalamazoo, MI (US); Paul Adrian Aristoff, Kalamazoo, MI (US); Paul D. Johnson, Portage, MI (US); Harvey Irving Skulnick, Kalamazoo, MI (US); Louis L. Skaletzky, Kalamazoo, MI (US); David John Anderson, Kalamazoo, MI (US); Joel Morris, Kalamazoo, MI (US); Ronald B. Gammill, Portage, MI (US); George P. Luke, Lexington, MA (US)

(73) Assignee: Pharmacia & Upjohn Company, Kalamazoo, MI (US)

(*) Notice: Under 35 U.S.C. 154(b), the term of this patent shall be extended for 0 days.

This patent is subject to a terminal disclaimer.

(21) Appl. No.: 09/188,998

(22) Filed: Nov. 9, 1998

Related U.S. Application Data

(60) Division of application No. 08/809,224, filed on Nov. 4, 1996, now Pat. No. 5,852,195, which is a continuation-in-part of application No. PCT/US95/05219, filed on May 4, 1995, now abandoned, which is a continuation-in-part of application No. 08/349,361, filed on Dec. 2, 1994, now abandoned, which is a continuation-in-part of application No. 08/238,817, filed on May 6, 1994, now abandoned.

(51) Int. Cl.$^7$ ..................... C07D 307/77; C07D 277/04; C07D 455/02; C07D 401/00
(52) U.S. Cl. ..................... 544/298; 544/333; 544/405; 546/138; 546/153; 546/282.1; 548/146; 548/182; 548/304.7; 548/311.4; 548/365.7; 549/242
(58) Field of Search ..................... 549/242; 546/282.1, 546/153, 138; 548/311.4, 304.7, 365.7, 182, 146; 544/333, 298, 405

(56) References Cited

U.S. PATENT DOCUMENTS

| | | | |
|---|---|---|---|
| 2,723,276 | 11/1955 | Grussner | 260/343.2 |
| 2,723,277 | 11/1955 | Grussner et al. | 260/343.2 |
| 2,872,457 | 2/1959 | Schroeder et al. | 260/343.2 |
| 3,325,515 | 6/1967 | Schmitt et al. | 260/343.2 |
| 3,489,774 | 1/1970 | Kuln et al. | 260/343.2 |
| 3,493,586 | 2/1970 | Kuln et al. | 260/343.5 |
| 3,764,693 | 10/1973 | Boechetti | 424/281 |
| 3,835,161 | 9/1974 | DeMuylder | 260/343.2 |
| 5,852,195 | * 12/1998 | Romines | 546/282.1 |

FOREIGN PATENT DOCUMENTS

| | | | |
|---|---|---|---|
| 674997 | 7/1966 | (BE) . | |
| 443449 | 8/1991 | (DE) | C07D 305/12 |
| 1276654 | 10/1961 | (FR) . | |
| 734142 | 7/1955 | (GB) . | |
| 3227-923 | 10/1991 | (JO) | A61K 31/37 |
| 48023942 | 8/1971 | (JP) . | |
| 8804652 | 12/1987 | (JP) | C07D 207/36 |
| 89/07939 | 9/1989 | (WO) | A61K 31/37 |

(List continued on next page.)

OTHER PUBLICATIONS

Biochemical and Biophysical Research Communications, vol. 188, No. 2, 1992, pp. 631–637.

(List continued on next page.)

*Primary Examiner*—D. Margaret Seaman
(74) *Attorney, Agent, or Firm*—Lucy X. Yang

(57) ABSTRACT

The present invention relates to compounds of formula I and II which are pyran-2-ones, 5,6-dihydro-pyran-2-ones, 4-hydroxy-benzopyran-2-ones, 4-hydroxy-cycloalkyl[b]pyran-2-ones, and derivatives thereof, useful for inhibiting a retrovirus in a mammalian cell infected with said retrovirus.

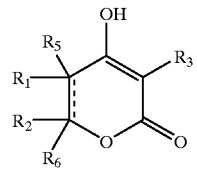

I

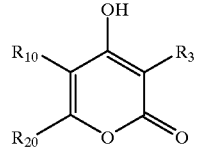

II wherein $R_{10}$ and $R_{20}$ taken together are:

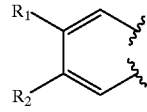

III

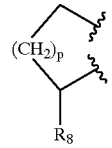

IV

12 Claims, No Drawings

FOREIGN PATENT DOCUMENTS

| | | | |
|---|---|---|---|
| 91-04663 | 4/1991 | (WO) | A01N 37/02 |
| 91/06561 | 5/1991 | (WO) | C07K 5/02 |
| 91/12804 | 9/1991 | (WO) | |
| 92/04326 | 3/1992 | (WO) | C07D 215/22 |
| 92/04327 | 3/1992 | (WO) | C07D 215/22 |
| 92/04328 | 3/1992 | (WO) | C07D 215/56 |
| 92 06687 | 4/1992 | (WO) | A61K 31/365 |
| 92/17490 | 10/1992 | (WO) | C07K 5/02 |
| 93/07128 | 4/1993 | (WO) | C07D 243/04 |
| 93/07868 | 4/1993 | (WO) | A61K 31/37 |

OTHER PUBLICATIONS

Antimicrobial Patent Fast–Alert, Week Ending Sep. 4, 1992.
C.A. Selects: Antitumor Agents, Issue 19, 1992, p. 25, No. 117: 90147q.
Phytochemistry, 31(3):953–956 (1992).
Tetrahedron, 48(9):1695–1706 (1992).
Tetrahedron Lett. 30(23):3109–12 (1989).
Termen Yuki Kagobutsu Toronkai Koen Yoshishu, 30:17–24 (1988).
Chem. Absts. 53:15072f.
Chem. Absts. 53:15072c.
Arch. Pharm. (Weinheim, Ger.), 316(12):988–94 (1983).
Chem. Ber., 110(3):1047–57 (1977) (CA 87(1):2349r).
J. Heterocycl. Chem. 23(2):413–16 (1986).
Pestic Sci., 27(1):45–63 (1989).
Acta. Chem. Scand., 43(2):193–95 (1989).
J. Org. Chem., 54(14):3389–9 (1989).
J. Org. Chem., 53(6):1218–21 (1988).
Tetrahedron Lett., 34(2):277–80 (1993).
J. Chem. Soc. Perkins Trans., 1(16):1157–9 (1985).
J. Chem. Ecol., 9(6):703–14 (1983).
J. Org. Chem., 48(7):1123–5 (1983).
Tetrahedron Lett., 21(6):551–4 (1980).
Helv. Chem. Acta, 59(7):2393–2401 (1976).
Acta. Chem. Scand., 30(7):613–18 (1976).
Tetrahedron Lett., 22:1903–4 (1976).
Synth. Commun., 20(18):2827–2836, 1990.
J. Indian Chem. Soc., 69:397–398 (Jul. 1992).
The Journal of Antibiotics, 46(7):1126 (Jul. 1993).
Derwent Abstracts, 93–168920/21 of Ep 543201.
J. Org. Chem., 48(22):3945–7 (1983).
Chem. Pharm. Bull., 29(10):2762–8 (1981).
J. Labelled Compd. Radiopharm. 28(10):1143–8 (1990).
J. Am. Chem. Soc., 113(25):9585–95 (1991).
CA 54:14239d.
CA 53:4272c.
Derwent Abstract, 92–166863/20, of EP 553248.
Synthesis of Heterocyles XV. 4–Hydroxy–2–pyronocyclenes. E. Ziegler, H. Junek, and E. Nolken ,Monatsh., 89:678–82 (1958) (CA 53:12283–4) (and English translation).
R. Effenberberger, T. Ziegler, K.–H. Schonwalder, T. Kesmarszky, B. Bauer, Chem. Ber 119: 3394–3404 (1986) (CA106:18310t).
Monatsh. Chem., 119(6–7): 727–37 (1988) (CA 110(13):114430k).
CA 54:14239b.
Monatsh. Chem. 113(4): 475–84 (1982).
Monatsh. Chem. 90: 594–9 (1959) (CA 54:14238g,h).
Bull. Soc. Chim. Fr. 5: 1719–23 (1969) (Fr) (CA 71(21): 101655p) ( & English Translation).
Monatsh. 92: 246–53 (1961) (Gr) (CA 55:27296d).
CA 94(9): 65472r.
J. Org. Chem. 28(11): 3112–14 (1963) (CA 59:15185e).
Antimicrobial Patent Fast–Alert, Week Ending Apr. 30, 1993.
CA 54:577e,g,h (1960).
CA 51:14826f,h (1957).
CA 51:14827a,b (1957).
CA 51:16453a (1957).
CA 54:5699d (1960).
CA 54:16450f (1960).
CA 53:22454a (1959).
CA 53:20046a. 1959.
Indian J. Chem., Sect. B, 25B: 1167–70 (1986) (CA 107(17):154201f).
CA 93(23):220546t.
CA 96(19):157432x.
CA 90(1):1707f.
CA 84(9):55338f.
CA 79(13):74969a.
CA 71(15):69677j.
CA 54:579e.
CA 63:14743c.
CA 63:5589c.
CA 64:12969b.
Chim. Ther. 7(4): 300–6 (1972) (Fr) (CA78(7):38016h).
CA 52:5399b.
CA 54:5699e.
CA 72(15):78882v.
Merck Index, Eleventh Edition, (1989), Entry 9950.
J. Med. Chem., 1978, vol. 21, No. 2: 231–234.
J. Am. Chem. Soc. 83: 2676–9 (1961) (CA 55:22306e (1961).
Journal of Labelled Compounds and Radiopharmaceuticals vol. XXIII, No. 2: 137–148 (1986).
Tr. Voronezh. Teckhnol. Inst. 19(2): 27–30 (1971), Abstract No. 1zh274 (Russian language) (and English translation).
Helv. Chim. Acta 74(7): 1451–8 (1991).
J. Org. Chem. 33(1): 437–8 (1968).
Eur. J. Med. Chem.—Chim Ther. 12(2): 125–30 (1977).
J. Med. Chem. 18(5): 513–19 (1975) (CA 83(5):37913q).
J. Chromatogr. 338(2): 325–34 (1985).
J. Chromatogr. 562 (1–2): 31–8 (1991).
J. Chromatogr. 529(2): 479–85 (1990).
AIDS 1993, vol. 7, No. 1, pp. 129–130.
CA Selects:AIDS & Related Immunodeficiencies, Issue 24, 1993, Abstract 119:195147j.
"Competitive Inhibition of HIV–1 Protease by 4–Hydroxy–Benzopyran–2–ones and by 4–Hydroxy–6–Phenyl–Pyran–2–Ones," Parke–Davis Pharm. Res., First National Conference on Human Retroviruses and Related Infections, Dec. 12–16, 1993, Washington, D.C.
Acta. Virol. 37:241–250 (1993).
"The Application of Computer–Assisted Drug Design in the Discovery of Nonpeptide HIV–1 Protease Inhibitors", Parke–Davis Pharm. Res., Keystone Symposia, Mar. 5–11, 1994, Santa Fe, N.M.
Structural Biology, 1(1):199–200 (Apr. 1994).
CA: 85:78002b (1976).

* cited by examiner

US 6,169,181 B1

COMPOUNDS USEFUL TO TREAT RETROVIRAL INFECTIONS

This application is a divisional application of Ser. No. 08/809,224 now U.S. Pat. No. 5,852,195, filed Nov. 4, 1996; which is a CIP application of PCT/US95/05219, filed May 4, 1995, now abandoned; which is a CIP of U.S. Ser. No. 08/349,361, filed Dec. 2, 1994, now abandoned; which is a CIP of U.S. Ser. No. 08/238,817, filed May 6, 1994, now abandoned.

FIELD OF THE INVENTION

The present invention relates to compounds useful for inhibiting a retrovirus in a human cell infected with said retrovirus. More particularly, the present invention provides pyran-2-ones, 5,6-dihydropyran-2-ones, 4-hydroxy-benzopyran-2-ones, 4-hydroxy-cycloalkyl[b]pyran-2-ones, and derivatives thereof as HIV-proteinase inhibitors.

BACKGROUND OF THE INVENTION

During the past decade, acquired immunodeficiency syndrome (AIDS) has progressed from having the status of a medical curiosity afflicting only a small number of individuals to a problem of major proportions, both medically and economically. John Saunders and Richard Storer, "New Developments in RT Inhibitors," DN&P 5(3), April 1992, pages 153–169. WHO figures reveal that more than 360,000 cases of AIDS have been reported worldwide, including nearly 175,000 cases in the U.S.A. Of these, approximately 100,000 worldwide (50,000 in the U.S.A.) were reported in the preceding 12-month period. In the U.S.A., the number of seropositive individuals is thought to be approximately two million, and estimates suggest that 5–10 million people worldwide may be seropositive. Saunders and Storer, page 153.

Since the first description of the malady in the early part of this decade, acquired immunodeficiency disease syndrome (AIDS) and its devastating consequences have been subjects of continuous and intense coverage in both the lay and scientific press. Indeed, an edition of Scientific American was entirely devoted to AIDS (Scientific American 289, #4 (1988)), and the literature on the disease and the virus is already so vast as to defy thorough citation.

On Mar. 20, 1987, the FDA approved the use of the compound, zidovudine (AZT), to treat AIDS patients with a recent initial episode of pneumocystis carinii pneumonia, AIDS patients with conditions other than pneumocystis carinii pneumonia or patients infected with the virus with an absolute CD4 lymphocyte count of less than 200/mm$^3$ in the peripheral blood. AZT is a known inhibitor of viral reverse transcriptase, an enzyme necessary for human immunodeficiency virus replication. U.S. Pat. No. 4,724,232 claims a method of treating humans having acquired immunodeficiency syndrome utilizing 3'-azido-3'-deoxy-thymidine (azidothymidine, AZT).

Following the discovery of the anti-HIV activity of AZT, much effort has been focused on a wide variety of other dideoxynucleoside analogues in the search for superior agents. In the case of the 2'.3'-dideoxy series, ddC and ddI have shown potent activity against HIV in vitro and have been evaluated in clinical trials. Saunders and Storer, page 160. The compound ddC is currently being developed by Hoffman-La Roche Co. as a potential anti-AIDS drug. Its limiting toxicity in humans is peripheral neuropathy which is reversible at low doses. Raymond R. Schinazi, Jan R. Mead and Paul M. Feorino, "Insights Into HIV Chemotherapy," AIDS Research and Human Retroviruses, Vol. 8, Number 6, 1992, pages 963–990. It has been approved by the FDA for AIDS therapy in combination with AZT. The compound ddI has also been evaluated in clinical trials. Its limiting toxicities are peripheral neuropathy and pancreatitis. It has also been shown to stimulate hepatic glycolysis leading to irreversible liver damage. Schinazi, Mead and Feorino, page 966. It has recently been approved by the FDA for the treatment of HIV-1 infections in adults and pediatric patients who are intolerant to or whose health has significantly deteriorated while on AZT treatment. Schinazi, Mead and Feorino, page 966.

Among these approved drugs, AZT is currently the only drug that has been shown to decrease the mortality and frequency of opportunistic infections associated with AIDS. Schinazi, Mead and Feorino, page 963.

Human immunodeficiency virus (HIV) has long been recognized as the causative agent in AIDS, although a minority opinion to the contrary has been expressed (e.g., P. Duesberg, Proc. Natl. Acad. Sci., USA, 86:755–764 (1989)). Sequence analysis of the complete genomes from several infective and non-infective HIV-isolates has shed considerable light on the make-up of the virus and the types of molecules that are essential for its replication and maturation to an infective species. The HIV protease is essential for the processing of the viral gag and gag-pol polypeptides into mature virion proteins. L. Ratner, et al., Nature, 313:277–284 (1985); L. H. Pearl and W. R. Taylor, Nature, 329:351 (1987). HIV exhibits the same gag/pol/env organization seen in other retroviruses. L. Ratner, et al., above; S. Wain-Hobson, et al., Cell, 40:9–17 (1985); R. Sanchez-Pescador, et al., Science, 227:484–492 (1985); and M. A. Muesing, et al., Nature, 313:450–458 (1985).

Reverse transcriptase (RT) is an enzyme unique to retroviruses that catalyzes the conversion of viral RNA into double stranded DNA. Blockage at any point during the transcription process, by AZT or any other aberrant deoxynucleoside triphosphate incapable of elongation, should have dramatic consequences relative to viral replication. Much work on the RT target is in progress based, in large measure, upon the fact that nucleosides like AZT are easily delivered to cells. However, the inefficiency of phosphorylation steps to the triphosphate, and the lack of specificity and consequent toxicity, constitute major drawbacks to use of AZT and similar nucleosides having a blocked, or missing, 3'hydroxyl group.

The T4 cell receptor for HIV, the so-called CD4 molecule, has also been targeted as an intervention point in AIDS therapy. R. A. Fisher, et al., Nature, 331:76–78 (1988); R. E. Hussey, et al., Nature, 331:78–81 (1988); and K. C. Deen, et al., Nature, 331:82–84 (1988). The exterior portion of this transmembrane protein, a molecule of 371 amino acids (sCD4) has been expressed in Chinese hamster ovary (CHO) cells and Genentech (D. H. Smith, et al., Science, 238:1704–1707 (1987)) has had a product in clinical trials since the fall of 1987. CD4 has been shown to have a narrow spectrum of activity against wild-type virus and so far has failed to control HIV infection in humans. Schinazi, Mead and Feorino, page 963. The idea behind CD4 based therapy is that the molecules can neutralize HIV by interfering with viral attachment to T4, and other cells which express CD4 on their surfaces. A variant on this theme is to attach cell toxins to CD4 for specific binding and delivery to infected cells which display glycoprotein gp-120 on their surfaces. M. A. Till, et al., Science, 242:1166–1168 (1988); and V. K. Chaudhary, et al., Nature, 335:369–372 (1988).

Another therapeutic target in AIDS involves inhibition of the viral protease (or proteinase) that is essential for processing HIV-fusion polypeptide precursors. In HIV and several other retroviruses, the proteolytic maturation of the gag and gag/pol fusion polypeptides (a process indispensable for generation of infective viral particles) has been shown to be mediated by a protease that is, itself, encoded by the pol region of the viral genome. Y. Yoshinaka, et al., Proc. Natl. Acad. Sci. USA, 82:1618–1622 (1985); Y. Yoshinaka, et al., J. Virol., 55:870–873 (1985); Y. Yoshinaka, et al., J. Virol., 57:826–832 (1986); and K. von der Helm, Proc. Natl. Acad. Sci., USA, 74:911–915 (1977). Inhibition of the protease has been shown to inhibit the processing of the HIV p55 in mammalian cell and HIV replication in T lymphocytes. T. J. McQuade, et al., Science, 247:454 (1990).

The protease (or proteinase), consisting of only 99 amino acids, is among the smallest enzymes known, and its demonstrated homology to aspartyl proteases such as pepsin and renin (L. H. Pearl and W. R. Taylor, Nature, 329:351–354 (1987); and I. Katoh, et al., Nature, 329:654–656 (1987)), led to inferences regarding the three-dimensional structure and mechanism of the enzyme (L. H. Pearl and W. R. Taylor, above) that have since been borne out experimentally. Active HIV protease has been expressed in bacteria (see, e.g., P. L. Darke, et al., J. Biol. Chem., 264:2307– 2312 (1989)) and chemically synthesized (J. Schneider and S. B. Kent, Cell, 54:363–368 (1988); and R. F. Nutt, et al., Proc. Natl. Acad. Sci., USA, 85:7129–7133 (1988)). Site directed mutagenesis (P. L. Darke, et al., above); and N. E. Kohl, et al., Proc. Natl. Acad. Sci., USA, 85:4686–4690 (1988)) and pepstatin inhibition (P. L. Darke, et al., J. Biol. Chem., 264:2307–2312 (1989); S. Seelmeier, et al., Proc. Natl. Acad. Sci., USA, 85:6612–6616 (1988); C. -Z. Giam and I. Borsos, J. Biol. Chem., 263:14617–14720 (1988); and J. Hansen, et al., EMBO J., 7:1785–1791 (1988)) have provided evidence for HIV protease's mechanistic function as an aspartyl protease. A study has demonstrated that the protease cleaves at the sites expected in peptides modeled after the regions actually cleaved by the enzyme in the gag and pol precursor proteins during viral maturation. P. L. Darke, et al., Biochem. Biophys. Res. Communs., 156:297–303 (1988). X-ray crystallographic analysis of the HIV-protease (M. A. Navia, et al., Nature, 337:615–620 (1989)) and a related retroviral enzyme from Rous sarcoma virus (M. Miller, et al., Nature, 337:576–579 (1989)) reveal an active site in the protease dimer that is identical to that seen in other aspartyl proteases, thus supporting the supposition (L. H. Pearl and W. R. Taylor, above) that the HIV enzyme is active as a dimer. See also Joseph A. Martin, "Recent Advances in the Design of HIV Proteinase Inhibitors," Antiviral Research, 17 (1992) 265–278.

To date, the scientific search for a fully effective and safe means of inhibiting retroviruses in a human hosting such a virus, and thereby effectively treating diseases caused by such a virus, such as acquired immunodeficiency syndrome (AIDS), continues.

INFORMATION DISCLOSURE

JO 3227–923-A (Sawai Seiyaku KK) discloses the use of 4-hydroxy-coumarins as therapeutic agents for HIV-infected patients; however, unsubstituted 4-hydroxy-coumarin is the only compound specifically disclosed for this use.

WO 91/04663 (Univ. of Calif. at Oakland) discloses 6-amino-1,2-benzopyrones which are useful for treating viral diseases.

WO 91/12804 (Kabi Pharmaceutical), published Sep. 5, 1991, discloses the use of N-phenyl-N-methyl-1,2-dihydro-4-hydroxy-1-methyl-2-oxo-quinoline-3-carboxamide also known as Linomide®, for the treatment of retrovirus infections.

International Publication No. WO 89/07939, published Sep. 8, 1989, discloses specific coumarin compounds which are reverse transcriptase inhibitors.

U.S. Pat. Nos. 3,489,774 and 3,493,586 disclose 3-(beta-aryl-beta-(arylthio) (or aryl seleno) propionyl-coumarin and pyrone products useful as parasiticides.

Biochemical and Biophysical Research Communications, Vol. 188, No. 2, 1992, pages 631–637, discloses chromones bearing hydroxyl substituents and a phenolic group at the 2-position (flavones) as having anti-HIV-1 proteinase activity.

Antimicrobial Patent Fast-Alert, Week Ending Sep. 4, 1992, disclose gamma-pyrones, gamma-pyridones and gamma-thio-pyrones as antiviral agents.

International Publication Nos. WO 92/04326, 92/04327 and 92/04328, all published Mar. 19, 1992, disclose antiviral heterocyclic derivatives, such as quinolinones and benzopyranones, as replication inhibitors for treating herpes simples 1 and 2, cytomegalovius and Epstein-Barr virus.

C. A. Selects: Antitumor Agents, Issue 19, 1992, page 25, No. 117: 90147q (PCT International Application WO 92 06,687) discloses the preparation of 5-iodo-5-amino-1,2-benzopyrones and analogs as cytostatic and antiviral agents.

Nowhere do these references teach or suggest the use of 4-hydroxy-α-pyrones as HIV protease inhibitors or as having antiviral activity.

Phytochemistry, 31(3):953–956 (1992), discloses compounds, such as 4-hydroxy-α-(4-methoxyphenyl)-6-[2-(4-methoxyphenyl)ethenyl]-2-oxo-, methyl ester, (E)-(−)-2H-pyran-3-acetic acid.

Tetrahedron, 48(9):1695–1706 (1992), (see also Tetrahedron Lett., 30(23):3109–12 (1989)), discloses compounds, such as 3-[1-(4-chlorophenyl)-3-(4-nitrophenyl)-2-propenyl]-4-hydroxy-6-methyl-2H-pyran-2-one; 3-[3-(4-chlorophenyl)-1-(4-nitrophenyl)-2-propenyl]-4-hydroxy-6-methyl-2H-pyran-2-one; 4-hydroxy-3-[3-(4-methoxyphenyl)-1-(4-nitrophenyl)-2-propenyl]-6-methyl-2H-pyran-2-one; and 4-hydroxy-3-[1-(4-methoxyphenyl)-3-(4-nitrophenyl)-2-propenyl]-6-methyl-2H-pyran-2-one.

Tennen Yuki Kagobutsu Toronkai Koen Yoshishu, 30:17–24 (1988), discloses compounds, such as 4-hydroxy-β-(4-methoxyphenyl)-6-[2-(4-methoxyphenyl)ethenyl]-2-oxo-, methyl ester, (E)-(−)-2H-pyran-3-propanoic acid.

Chem. Absts. 53:15072f discloses compounds, such as α-1,3-dihydroxy-2-butenylidene-β-ethyl-, δ-lactone, hydrocinnamic acid.

Chem. Absts. 53:15072c discloses compounds, such as α-1,3-dihydroxy-2-butenylidene-β-isopropyl-, δ-lactone, hydrocinnamic acid.

Arch. Pharm. (Weinheim, Ger.), 316(12):988–94 (1983), discloses compounds, such as 3-[1-(4-chlorophenyl)-3-oxobutyl]-4-hydroxy-6-methyl-2H-pyran-2-one; and 3-[1-(4-chlorophenyl)propyl]-4-hydroxy-6-methyl-2H-pyran-2-one.

Chem. Ber., 110(3):1047–57 (1977), discloses compounds, such as 6-(3,4-dimethoxyphenyl)-3-[2-(3,4-dimethoxy-phenyl)-1-(4-methoxy-2-oxo-2H-pyran-6 -yl) ethyl]-4-hydroxy-2H-pyran-2-one; and 3-[2-(3,4-dimethoxyphenyl)-1-(4-methoxy-2-oxo-2H-pyran-6-yl) ethyl]-4-hydroxy-6-[2-(4-methoxyphenyl)ethyl]-2H-pyran-2-one.

J. Heterocycl. Chem., 23(2):413–16 (1986), discloses compounds, such as 3-[(4-chlorophenyl)-1-piperidinylmethyl]-4-hydroxy-6-methyl-2H-pyran-2-one.

The following published PCT applications disclose peptides useful as retroviral protease inhibitors: International Publication No. WO 91/06561, published May 16, 1991; and International Publication No. WO 92/17490, published Oct. 15, 1992.

The following references disclose pyrone compounds which are believed to be representative of those known in the art:

EP-443449 (German language) discloses 3-hexyl-5,6-dihydro-6-pentyl-2H-pyran-2-one and 3-ethyl-6-hexadecyl-5,6-dihydro-4-hydroxy-2H-pyran-2-one. Pestic. Sci., 27(1):45–63 (1989), discloses 5,6-dihydro-4-hydroxy-6-methyl-6-(1-methyl-1-propenyl)-3-(1-oxobutyl)-2H-pyran-2-one; and 6-cyclopropyl-5,6-dihydro-4-hydroxy-6-methyl-3-(1-oxobutyl)-2H-pyran-2-one. Acta. Chem. Scand., 43(2):193–95 (1989), discloses 4-(acetyloxy)-5,6-dihydro-3,6-dimethyl-2H-pyran-2-one. J. Org. Chem., 54(14):3383–9 (1989), discloses 5,6-dihydro-4-hydroxy-3,6,6-trimethyl-2H-pyran-2-one. J. Org. Chem., 53(6):1218–21 (1988); and Tetrahedron Lett., 34(2):277–80 (1993), discloses 3-hexyldihydro-6-undecyl-2H-pyran-2,4 (3H)-dione, (6R)-. J. Chem. Soc. Perkins Trans., 1(6):1157–9 (1985), discloses dihydro-3-methyl-6-nonyl-6-[[(tetrahydro-2H-pyran-2-yl)oxy]methyl]-2H-pyran-2,4 (3H)-dione. J. Chem. Ecol., 9(6):703–14 (1983), discloses 5,6-dihydro-4-hydroxy-3,6-dimethyl-2H-pyran-2-one. J. Org. Chem., 48(7):1123–5 (1983), discloses 6-(2-chloro-1-methylethenyl-5,6-dihydro-4-hydroxy-3-methyl-2H-pyran-2-one, (Z)-(.+-.)-. Acta. Chem. Scand., 43(2):193–95 (1989); and Tetrahedron Lett., 21(6):551–4 (1980), discloses 5,6-dihydro-4-hydroxy-3,6-dimethyl-2H-pyran-2-one. Helv. Chem. Acta, 59(7):2393–2401 (1976), discloses 4-[(3,6-dihydro-4-hydroxy-5-methyl-6-oxo-2H-pyran-2-yl)methyl]-2,6-piperidinedione. Acta. Chem. Scand., 30(7):613–18 (1976); and Tetrahedron Lett., 22:1903–4 (1976), discloses 5,6-dihydro-4-hydroxy-3-methyl-6-(1-methyl-1-propenyl)-2H-pyran-2-one, (E)-. 3,3'-[(4-nitrophenyl)methylene]bis[5,6-dihydro-4-hydroxy-6-methyl-2H-pyran-2-one; and 3,3'-(phenylmethylene)bis[5,6-dihydro-4-hydroxy-6-methyl-2H-pyran-2-one are disclosed in Synth. Commun., 20(18):2827–2836, 1990.

WO 93/07868, published Apr. 29, 1993, discloses new nitroso-benzopyrone, -benzamide and -isoquinolinone derivatives as adenosine di-phospho:ribose transferase inhibitors for treating viral infections and cancer.

WO 93/07128, published Apr. 15, 1993, relates to substituted cyclic carbonyls and derivatives thereof useful as retroviral protease inhibitors.

J. Indian Chem. Soc., 69:397–398 (July 1992), discloses that coumarin-4-acetic acids were screen for their anticancer and anti-AIDS activities and were found to be inactive.

The Journal of Antibiotics, 46(7):1126 (July 1993), discloses germicidin, which is 6-(2-butyl)-3-ethyl-4-hydroxy-2-pyrone, to be an autoregulative germination inhibitor of *Streptomyces viridochromogenes* NRRL B-1551.

Derwent Abstracts, 93-168920/21 of EP 543201 discloses the use of coumarin derivatives, such as 1-(N-morpholyl)-6-(4-hydroxybenzoic acid ethyl ester) hexane, for the treatment of viral infections, such as influenza or acute rhinitis.

J. Org. Chem., 48(22):3945–7 (1983); and Chem. Pharm. Bull., 29(10):2762–8 (1981); disclose compounds such as 4-hydroxy-6-(3-pyridinyl)-2H-pyran-2-one.

J. Labelled Compd. Radiopharm., 28(10):1143–8 (1990), discloses compounds such as 4-hydroxy-6-methyl-2H-pyran-2-one.

J. Am. Chem. Soc., 113(25):9585–95 (1991), discloses compounds such as 3-(3-phenyl-2-propen-1-yl)-6-methyl-4-hydroxy-2H-pyran-2-one.

CA 54:14239d and CA 53:4272c disclose compounds such as α-(α,γ-dihydroxycinnamylidene)—, δ-lactone hydrocinnamic acid.

CA 53:15072f discloses compounds such as α-1,3-dihydroxy-2-butenylidene-β-ethyl-, δ-lactone hydrocinnamic acid.

Synth. Commun., 20(18):2827–36 (1990), discloses compounds such as 3,3'-[(4-nitrophenyl)methylenelbis[5,6-dihydro-4-hydroxy-6-methyl-2H-pyran-2-one, and 3,3'-(phenylmethylene)bis[5,6-dihydro-4-hydroxy-6-methyl-2H-pyran-2-one.

J. Org. Chem., 54(14):3383–9 (1989), discloses compounds such as 5,6-dihydro-4-hydroxy-3,6,6-trimethyl-2H-pyran-2-one.

Derwent Abstract, 92-166863/20, of EP 553248 discloses new optionally substituted 5-iodo-6-amino-1,2-benzopyrone derivatives, which are adenosine di:phosphoribose inhibitors, for treatment and prevention of viruses and tumors associated with AIDS.

Synthesis of Heterocyles. XV. 4-Hydroxy-2-pyronocyclenes. E. Ziegler, H. Junek, and E. Nolken, Monatsh., 89: 678–82 (1958) (CA 53:12283–4) discloses compounds such as the following: 4-hydroxy-3-benzyl-5,6-octamethylene-2-pyrone; 4-hydroxy-3-benzyl-5,6-pentamethylene-2-pyrone; 4-hydroxy-3-benzyl-5,6-heptamethylene-2-pyrone; 4-hydroxy-3-benzyl-5,6-hexamethylene-2-pyrone; and 4-hydroxy-3-benzyl-5,6-tridecamethylene-2-pyrone.

R. Effenberberger, T. Ziegler, K. -H. Schonwalder, T. Kesmarszky, B. Bauer, Chem. Ber 119: 3394–3404 (1986), discloses pyrone intermediates, such as those of formula J-1 (wherein n is 4; refer to Chart J below).

Monatsh. Chem., 119(6–7): 727–37 (1988) (CA 110(13) :114430k) discloses the compounds 8H-acenaphtho[1,2-b]pyran-8-one, 10-hydroxy-9-(phenylmethyl)-; and indeno[2,1-b]pyran-3(5H)-one, 1-hydroxy-2-(phenylmethyl)-.

CA 54:14239b discloses the compound 3-benzyl-4-hydroxy-2-oxoindeno-[1,2-b]pyran.

Monatsh. Chem., 113(4): 475–84 (1982) discloses compounds such as 6,7-dihydro-4-hydroxy-6-(3-methylphenyl)-7-phenyl-3-(phenylmethyl)-pyrano[2,3-c]pyrrole-2,5-dione; and 6,7-dihydro-4-hydroxy-6,7-diphenyl-3-(phenylmethyl)-pyrano[2,3-c]pyrrole-2,5-dione.

Monatsh. Chem. 90: 594–9 (1959) (CA 54:14238g,h) discloses compounds such as 5H-benzocycloheptene-8-acrylic acid, α-benzyl-6,7-dihydro-β,-9-dihydroxy-,δ-lactone; and 3-benzyl-5,6,7,8-tetrahydro-4-hydroxy-8-isopropyl-5-methyl-coumarin.

Bull. Soc. Chim. Fr. 5: 1719–23 (1069) (Fr) (CA 71(21): 101655p) discloses the compound 3-benzyl-5,6,7,8-tetrahydro-4-hydroxy-coumarin.

WO 8804652 (equivalent AU 8810440 (Jap.)) discloses the compound 3-(4-chloro-2-nitrobenzoyl)-5,6,7,8-tetrahydro-4-hydroxy-2H-1-benzopyran-2-one.

Monatsh. 92: 246–53 (1961) (Gr) (CA 55:27296d) discloses the compound 3-(3,5-dimethylsalicyl)-5,6,7,8-tetrahydro-4-hydroxy-coumarin.

CA 94(9): 65472r discloses 5,6,7,8-hexahydro-3-phenyl-2-H-cycloocta[b]pyran-2-one; and 6,7,8,9-tetrahydro-4-hydroxy-3-phenyl-cyclohepta[b]pyran-2(5H)-one.

J. Org. Chem. 28(11): 3112–14 (1963) (CA 59:15185e) discloses the compound hexanedioic acid, 2-[hydroxy(2-hydroxy-1-cyclopenten-1-yl)methylene]-, δ-lactone.

Antimicrobial Patent Fast-Alert, Week Ending Apr. 30, 1993, discloses cyclic ureas and analogues useful as retroviral protease inhibitors.

Many 4-hydroxy-coumarin type compounds are known. For example, these references—CA 54:577e,g,h (1960); U.S. Pat. No. 2,872,457 (CA 53:12305e (1959)); CA 51:14826f,h (1957); U.S. Pat. No. 2,723,276 (CA 52:5480g,h (1958)); CA 51:14827a,b (1957); CA 51:16453a (1957); CA 54:5699d (1960); CA 54:16450f (1960); CA 53:22454a (1959); and CA 53:20046a—disclose compounds such as the following: 4-hydroxy-3-(1-phenylbutyl)-coumarin; 4-hydroxy-3-(1-phenylpentyl)-coumarin; 3-(cyclohexylphenylmethyl)-4-hydroxycoumarin; 4-hydroxy-3-(2-methyl-1-phenylpropyl)-coumarin; 4-hydroxy-3-(2-phenylpropyl) coumarin; 4-hydroxy-3-(1,3-diphenylpropyl)-coumarin; 4-hydroxy-3-(1-(4-methylphenyl)-butyl)-coumarin; 4-hydroxy-3-(1-(1-naphthyl)-propyl)-coumarin; 4-hydroxy-7-methyl-3-(1-phenylpropyl)-coumarin; 7-chloro-4-hydroxy-3-(1-phenylpropyl)-coumarin; 4-hydroxy-3-[1-(4-methoxyphenyl)propyl]-coumarin; 3-(.alpha.-ethyl-p-fluorobenzyl)-4-hydroxy-coumarin; 3-(α-ethyl-p-methoxybenzyl)-4-hydroxy-coumarin; and 3-(1-phenyl-propenyl)-4-hydroxy-coumarin.

To the best of our knowledge, from our review, these references do not disclose the use of these compounds as HIV protease inhibitors. They are disclosed as being useful as: rodenticides, lowering the prothrombin level of the blood, blood anticoagulants, and pesticides.

Additional 4-hydroxy-coumarin compounds with similar uses have been disclosed in the following references:

Indian J. Chem., Sect. B, 25B: 1167–70 (1986) (CA 107(17):154201f) and CA 93(23):220546t discloses the compound 4-Hydroxy-3-(1-phenyl-2-propenyl)-coumarin.

CA 96(19):157432x; CA 90(1):1707f; CA 84(9):55338f; CA 79(13):74969a; and CA 71(15):69677j disclose the compound 4-hydroxy-3-[1-(1,2,3,4-tetrahydro)naphthyl]-coumarin; CA 54:579e discloses the compound 4-hydroxy-3-[1-indanyl]-coumarin; CA 63:14743c discloses the compound 4-hydroxy-3-(1-naphthylmethyl)-coumarin; CA 63:5589c discloses the compound 3-(1'-(2-methoxy,3-methyl,5-chloro-phenyl)propyl)-4-hydroxy-coumarin; CA 64:12969b discloses the compound 3-(α-acetonyl-α-acetylbenzyl)-4-hydroxy-coumarin.

CA 79(13):74969a; Chim. Ther. 7(4): 300–6 (1972) (Fr) (CA 78(7):38016h); CA 52:5399b; CA 54:5699e; CA 54:579e; and CA 72(15):78882v disclose 4-hydroxycoumarin compounds substituted at the 6- or 7-position by, e.g., methyl, methoxy and chloro.

J. M. Mulder, U.S. Pat. No. 3,835,161, Sep. 10, 1974, discloses the compound 3-[1-[4-(2-bromoethyl)phenyl]ethyl]-4-hydroxy-2H-1-benzopyran-2-one.

Merck Index, Eleventh Edition, (1989), Entry 9950, discusses Warfarin, its chemical name—3-α-phenyl-β-acetylethyl-4-hydroxycoumarin—and its uses as a rodenticide and an anticoagulant. J. Med. Chem., 1978, Vol. 21, No. 2: 231–234, discloses the antivitamin K activity of warfarin and discusses the anticoagulant activity of several 3-substituted 4-hydroxycoumarins such as 4-Hydroxy-3-(1-phenylbutyl)-coumarin; and 4-hydroxy-3-(α-methylbenzyl)-coumarin. J. Am. Chem. Soc. 83: 2676–9 (1961) (CA 55:22306e (1961)) discusses the resolution and absolute configuration of warfarin and discloses the preparation of compounds such as 4-hydroxy-3-(1-phenylbutyl)-coumarin.

Journal of Labelled Compounds and Radiopharmaceuticals Vol. XXIII, No. 2: 137–148 (1986), discloses several deuterium labelled metabolites of warfarin and phenprocoumon, such as the deuterium labelled analog of the compound 4-hydroxy-7-methoxy-3-(1-phenylpropyl)-coumarin.

J48023942 discloses compounds, such as 4-hydroxy-3-(α-methylbenzyl)-coumarin; 4-hydroxy-3-(3-methyl-1-phenylbutyl)-coumarin; and 2H-1-benzopyran-2-one, 4-hydroxy-7-methoxy-3-(1-phenylpropyl)-(also cited in preceding reference) and their use as rodenticides.

Tr. Voronezh. Teckhnol. Inst. 19(2): 27–30 (1971), Abstract No. 1zh274 (Russian language), discloses the compound 4-hydroxy-3-phenethylcoumarin. This reference and Helv. Chim. Acta 74(7): 1451–8 (1991) disclose the compound of 4-hydroxy-3-(3-phenylpropyl)coumarin.

J. Org. Chem. 33(1): 437–8 (1968); and Eur. J. Med. Chem.—Chim Ther. 12(2): 125–30 (1977) disclose compounds such as 4-hydroxy-3-diphenylmethylcoumarin.

U.S. Pat. No. 3,764,693 discloses the compound 4-hydroxy-3-(3-hydroxy-1-phenylbutyl)-coumarin and its anticoagulating and rodenticidal activity.

J. Med. Chem. 18(5): 513–19 (1975) (CA 83(5):37913q); J. Chromatogr. 338(2): 325–34 (1985); J. Chromatogr. 562 (1–2): 31–8 (1991); J. Labelled Compds. Radiopharm. 23(2): 137–48 (1986) (cited previously); and J. Chromatogr. 529(2): 479–85 (1990) disclose compounds such as 4-hydroxy-3-[1-[3-(phenylmethoxy)phenyl]propyl]-2H-1-benzopyran-2-one; 4-hydroxy-8-(phenylmethoxy)-3-(1-phenylpropyl)-2H-1-benzopyran-2-one; 4-hydroxy-3-[1-(4-hydroxyphenyl)propyl]-coumarin; 4-hydroxy-6-methoxy-3-(1-phenylpropyl)-coumarin; 4,7-dihydroxy-3-(1-phenylpropyl)-coumarin; 4,6-dihydroxy-3-(1-phenylpropyl)-coumarin; 4-hydroxy-3-[1-(3-hydroxyphenyl)propyl]-coumarin; and p-chlorophenprocoumon.

AIDS 1993, Vol. 7, No. 1, pages 129–130, discusses the effect of warfarin on HIV-1 replication and spread.

CA Selects:AIDS & Related Immunodeficiencies, Issue 24, 1993, Abstract 119:195147j discloses the inhibitory effect of a single dose of coumarin derivatives, warfarin, 4-hydroxy-coumarin, umbelliferone, on HIV-1 replication and cell-mediated or cell-free viral transmission.

At the First National Conference on Human Retroviruses and Related Infections, Dec. 12–16, 1993, Washington, D.C., it was disclosed that coumarins, such as warfarin, and pyrones, such as 3-(thiophenyl)-6-phenyl-4-hydroxy-pyrone, displayed HIV protease inhibition in an assay.

Biochemical and Biophysical Research Communications, Vol. 201, No. 1, pages 290–294 (May 30, 1994) discloses that warfarin and structurally related coumarin analogs are HIV-1 protease inhibitors.

J. Med. Chem. 37:2664–2677 (1994) discloses 4-hydroxy-3-(3-phenoxypropyl)-2H-1-benzopyran-2-one and structural analogs, especially 4,7-dihydroxy-3-[4-(2-methoxyphenyl)butyl]-2H-1-benzopyran-2-one, as HIV-1 protease inhibitors.

Biochemical and Biophysical Research Communications, Vol. 200, No. 3, pages 1658–1664 (May 16, 1994) discloses that 4-hydroxy-3-(3-phenoxypropyl)-1-benzopyran-2-one and 4-hydroxy-6-phenyl-3-(phenylthio)-pyran-2-one, and structural analogs of these compounds, are inhibitors of HIV-1 protease.

J. Am. Chem. Soc. 116:6989–6990 (1994) discloses 4-hydroxy-6-phenyl-3-(phenylthio)pyran-2-one, and structural analogs thereof, are HIV-1 protease inhibitors.

Acta. Virol. 37:241–250 (1993) discloses the anti-HIV activity of coumarin derivatives, warfarin, 4-hydroxy-coumarin and umbelliferone.

Antiviral Research 24:275–288 (1994) discloses bicyclic imidazo derivatives (imidazothiazoles and imidazopyridines) which inhibit HIV-1 through interaction with reverse transcriptase (RT).

U.S. Pat. No. 3,325,515 (J. Schmitt, et al.) discloses coumarin derivatives, such as 3-(4-hydroxy-3-coumarinyl)-3-phenyl-1-propionic acid methyl ester, as exhibiting anti-coagulant activity.

U.S. Pat. No. 2,723,277 (A. Grussner, et al.) discloses malonic acid derivatives, such as 3-[1'-(p-chloro-phenyl)-propyl]-4-hydroxy-coumarin, as anti-coagulant agents.

FR, A, 1276654 discloses 4-hydroxy-coumarins, such as (2'-hydroxy)-3-benzyl-4-hydroxycoumarin, which have anti-coagulant, anti-bacterial or anti-fungal properties.

BE, A, 674997 discloses 4-hydroxycoumarin derivatives, such as 3-(5-methoxytetralyl-(1))-4-hydroxycoumarin as agents for fighting rodents.

GB, A, 734142 discloses the preparation of 3-substituted-4-hydroxycoumarins, such as 3-(1-phenyl-2-acetyl)-ethyl-4-hydroxycoumarin and 3-(1-furan-2-acetyl)-ethyl-4-hydroxycoumarin, which are effective as anti-coagulants and rodenticides.

"The Application of Computer-Assisted Drug Design in the discovery of Nonpeptide HIV-1 Protease Inhibitors", Parke-Davis Pharm. Res., Keystone Symposia, Mar. 5–11, 1994, Santa Fe, N.M., discloses 4-hydroxy-3-(3-phenoxypropyl)-1-benzopyran-2-one as an HIV protease inhibitor.

Structural Biology, 1(1):199–200 (April 1994) discloses that the rat poison warfarin was a useful lead in the search for HIV proteinase inhibitors.

CA 85:78002b (1976) discloses 3-(2,4,6-trihydroxybenzyl)-4-hydroxy-2H-pyran-2-one derivatives as having anti-bacterial activity.

FR, A, 1092278 (Hoffman) (1955) discloses the preparation of coumarin derivatives, such as 3-[1'-phenyl-propene-(1')-yl]-4-hydroxycoumarin.

International Publication No. WO 94/11361, published May 26, 1994, discloses pyran-2-ones and 5,6-dihydroxypyran-2-ones as retroviral protease inhibitors.

International Publication No. WO 94/18188, published Aug. 18, 1994, discloses 4-hydroxy-benzopyran-2-ones and 4-hydroxy-cycloalkyl[b]pyran-2-ones as retroviral protease inhibitors.

The following references were cited against the immediate parent application as disclosing the state of the art:

U.S. Pat. No. 3,651,091 (Boschetti, et al.); U.S. Pat. No. 4,262,013 (Mistui, et al.); U.S. Pat. No. 4,900,754 (Regan, et al.); U.S. Pat. No. 5,294,724 (Jendralla, et al.); Australian Patent Specification 219,371 (Enders, et al.); Canadian Patent No. 1,171,424 (Willard, et al.); British Patent Specification 836,740 (Bayer); European Patent Application 0 024 348 (Willard, et al.); European Patent Application 0 588 137 (Fischer, et al.); French Patent No. 1,276,654 (Molho) (cited above); and International Publication No. WO 94/1136 (Thaisrivongs, et al.) (cited above).

"Collaborative Structure-Based Design of Small Organic Molecules as Inhibitors of HIV Proteases," Keystone Symposia, Santa Fe, N.M. (Mar. 5–11, 1994), discloses the crystallographic complexes of HIV-1 and HIV-2 protease with compounds, such as 3-(α-ethylbenzyl)-6-(α-ethylphenethyl)-4-hydroxy-2H-pyran-2-one.

"Discovery and Properties of Small Organic Molecules Inhibiting HIV-1 Protease," Keystone Symposia, Santa Fe, N.M. (Mar. 5–11, 1994), discloses an assay for determining inhibitory activity of compounds, such as 3-(α-ethylbenzyl)-6-(α-ethylphenethyl)-4-hydroxy-2H-pyran-2-one.

"Structure-based Design of Non-peptide HIV Protease Inhibitors," 35th Annual Buffalo Medicinal Chemistry Symposium, Buffalo, N.Y. (May 22–25, 1994), discloses compounds, such as 3-(α-ethylbenzyl)-6-(α-ethylphenethyl)-4-hydroxy-2H-pyran-2-one, as potential anti-HIV therapeutic agents.

In Hruby et. al. (J. Org. Chem., 58 (26):7567 (1993), a description of the copper catalyzed addition of an aryl Grignard to an unsaturated chiral amide, 3-(2-butenoyl)-4-phenyl-2-oxazolidinone, is given. In Evans et. al. (J. Am. Chem. Soc., 112:8215 (1990), the reaction between a chiral amide and 2-methoxy-2-methyl-1,3-dioxoline is described. The preparation of 2-methoxy-2-methyl-1,3-dioxoline is found in Santry et. al. (J. Am. Chem. Soc., 110 (9):2910 (1988). For references on the reaction between an ester enolate and a ketone, refer to Dongala et. al., Tetrahedron Letters, 4983 (1973), and Mitsui et. al., Tetrahedron, 23:4271 (1967). For references on the reaction between an amide enolate and a ketone, refer to Viteva et. al., Tetrahedron 50:7193 (1994); Oare et. al., J. Org. Chem. 55:132 (1990); Hullot et. al., Can. J. Chem. 55:266 (1977); Woodbury et. al., J. Org. Chem. 42:1688 (1977); Stefanovsky et. al., Tetrahedron 42:5355 (1986); and Mathew et. al., U.S. Pat. No. 5,284,975.

G. Carganico, P. Cozzi, G. Orsini, J. Med. Chem., 26:1767–1769 (1983), discloses synthesized compounds with a methyl and a hydroxyl group at the 4-position of the dihydropyrone ring and no substitution at the 3-position. The compounds of the present invention have a ketone at the 4-position (which may be in enol form) and substitution at the 3-position.

D. T. Witiak et al., J. Med. Chem., 31:1437–1445 (1988), discloses benzopyran-2-ones with a hydroxy group at the 3-position. The compounds of the present invention have alkyl substitution at that position.

B. Tait, Winter Conference on Bioorganic Medicinal Chemistry, Jan. 29–Feb. 2, 1995, Steamboat Springs, Colo., disclosed a dihydropyrone having a phenyl group and a pentyl group at the 6-position and a —S—$CH_2$—$CH_2$—phenyl group at the 3-position in the HIV protease area.

J. V. N. Vara Prasad, et al., J. Med. Chem., 38:898–905 (1995), discloses 4-hydroxy-6-phenyl-2-oxo-2H-pyran-3-yl)thiomethanes, such as (+)-3-[cyclopentyl(cyclo-pentylthio)methyl]-4-hydroxy-6-phenyl-2H-pyran-2-one, as HIV-1 protease inhibitors.

SUMMARY OF THE INVENTION

The present invention provides:
A compound of the formula I
wherein $R_1$ is H—;
wherein $R_2$ is
a) $C_3$–$C_5$ alkyl
b) phenyl-$(CH_2)_2$—,
c) het-$SO_2$NH—$(CH_2)_2$—,
d) cyclopropyl-$(CH_2)_2$—,
e) F-phenyl-$(CH_2)_2$—,
f) het-$SO_2$NH-phenyl-, or
g) $F_3$C—$(CH_2)_2$—;
or wherein $R_1$ and $R_2$ taken together are a double bond;
wherein $R_3$ is the moiety of formula X
wherein $R_4$ is
a) phenyl,
b) het,
c) cyclopropyl, d) H₃C—[O(CH₂)₂]₂—,
e) het-SO₂NH—,
f) Br—,
g) N₃—, or
h) HO₃S(CH₂)₂—N(CH₃)—C(O)—(CH₂)₆—C(O)—NH—;
wherein $R_5$ is —H;
wherein $R_6$ is
a) R₄—(CH₂)₃—CH(R₈)—,
b) H₃C—[O(CH₂)₂]₂—CH₂—,
c) C₃–C₅ alkyl,
d) phenyl-(CH₂)₂—,
e) het-SO₂NH—(CH₂)₂—,
f) (HOCH₂)₃C—NH—C(O)—NH—(CH₂)₃—,
g) (HO₂C)(H₂N)CH—(CH₂)₂—C(O)—NH—(CH₂)₃—,
h) piperazin-1-yl—C(O)—NH—(CH₂)₃,
i) HO₃S(CH₂)₂—N(CH₃)—C(O)—(CH₂)₆—C(O)—NH—(CH₂)₃—,
j) cyclopropyl-(CH₂)₂—,
k) F-phenyl-(CH₂)₂—,
l) het-SO₂NH-phenyl, or
m) F₃C—(CH₂)₂—;
wherein n is zero (0), one (1) or two (2);
wherein $R_7$ is
a) cyclopropyl,
b) CH₃—CH₂—, or
c) t-butyl;
wherein $R_8$ is
a) —CH₂—CH₃, or
b) —CH₂-cyclopropyl;
wherein $R_9$ is
a) —NR₁₂SO₂-het,
b) —NR₁₂SO₂-phenyl substituted by zero (0) or one (1) $R_{11}$,
c) —CH₂—SO₂-phenyl substituted by zero (0) or one (1) $R_{11}$, or
d) —CH₂—SO₂-het;
wherein het is a 5-, 6- or 7-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring or another heterocycle; substituted by zero (0) or one (1) $R_{10}$;
wherein $R_{10}$ is
a) —CH₃,
b) —CN,
c) —OH,
d) —C(O)OC₂H₅,
e) —CF₃,
f) —NH₂, or
g) —C(O)—NH₂;
wherein $R_{11}$ is
a) —CN,
b) —F,
c) —OH, or
d) —NO₂;
wherein $R_{12}$ is
a) —H, or
b) —CH₃;

or a pharmaceutically acceptable salt thereof.
The present invention more particularly provides:
A compound of the formula I
wherein $R_1$ is H—;
wherein $R_2$ is
a) C₃–C₅ alkyl,
b) phenyl-(CH₂)₂—, or
c) het-SO₂NH—(CH₂)₂;
or wherein $R_1$ and $R_2$ taken together are a double bond;
wherein $R_3$ is the moiety of formula X
wherein $R_4$ is
a) phenyl,
b) het,
c) cyclopropyl,
d) H₃C—[O(CH₂)₂]₂—,
e) het-SO₂NH—,
f) Br—,
g) N₃—, or
h) HO₃S(CH₂)₂—N(CH₃)—C(O)—(CH₂)₆—C(O)—NH—;
wherein $R_5$ is —H;
wherein $R_6$ is
a) R₄—(CH₂)$_n$—CH(R₈)—,
b) H₃C—[O(CH₂)₂]₂—CH₂—,
c) C₃–C₅ alkyl,
d) phenyl-(CH₂)₂—,
e) het-SO₂NH—(CH₂)₂—,
f) (HOCH₂)₃C—NH—C(O)—NH—(CH₂)₃—,
g) (HO₂C)(H₂N)CH—(CH₂)₂—C(O)—NH—(CH₂)₃—,
h) piperazin-1-yl-C(O)—NH—(CH₂)₃, or
i) HO₃S(CH₂)₂—N(CH₃)—C(O)—(CH₂)₆—C(O)—NH—(CH₂)₃—;
wherein n is zero (0), one (1) or two (2);
wherein $R_7$ is
a) cyclopropyl,
b) CH₃—CH₂—, or
c) t-butyl;
wherein $R_8$ is
a) —CH₂—CH₃, or
b) —CH₂-cyclopropyl;
wherein $R_9$ is
a) —NR₁₂SO₂-het,
b) —NR₁₂SO₂-phenyl substituted by zero (0) or one (1) $R_{11}$,
c) —CH₂—SO₂-phenyl substituted by zero (0) or one (1) $R_{11}$, or
d) —CH₂—SO₂-het;
wherein het is a 5-, 6- or 7-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring or another heterocycle; substituted by zero (0) or one (1) $R_{10}$;
wherein $R_{10}$ is
a) —CH₃,
b) —CN,
c) —OH, or
d) —C(O)OC₂H₅;
wherein $R_{11}$ is
a) —CN, b) —F,
c) —OH, or
d) —NO$_2$;
wherein R$_{12}$ is
a) —H, or
b) —CH$_3$;
or a pharmaceutically acceptable salt thereof.

The present invention provides for such compounds wherein het is the following, substituted by zero (0) or one (1) R$_{10}$,
a) 2-pyridinyl,
b) imidazol-2-yl,
c) imidazol-4-yl,
d) benzimidazol-2-yl,
e) quinolin-8-yl,
f) quinolin-2-yl,
g) pyrimidin-2-yl,
h) quinazolin-2-yl,
i) purin-6-yl,
j) thiazol-2-yl,
k) thiazol-4-yl,
l) 2-pyrazolyl,
m) 2-pyrazinyl,
n) tetrahydropyran-4-yl, or
o) tetrahydropyran-3-yl.

Also more particularly, the present invention provides for the compound of the formula I
wherein R$_1$ is H—;
wherein R$_2$ is
a) H$_3$C—(CH$_2$)$_2$—,
b) phenyl-(CH$_2$)$_2$—,
c) (CH$_3$)$_2$CH—CH$_2$, or
d) pentyl;
or wherein R$_1$ and R$_2$ taken together are a double bond;
wherein R$_3$ is the moiety of formula X
wherein R$_4$ is
a) phenyl,
b) het,
c) cyclopropyl,
d) H$_3$C—[O(CH$_2$)$_2$]$_2$—,
e) het-SO$_2$NH—,
f) Br—,
g) N$_3$—, or
h) HO$_3$S(CH$_2$)$_2$—N(CH$_3$)—C(O)—(CH$_2$)$_6$—C(O)—NH—;
wherein R$_5$ is —H;
wherein R$_6$ is
a) R$_4$—(CH$_2$)$_n$—CH(R$_8$)—,
b) H$_3$C—[O(CH$_2$)$_2$]$_2$—CH$_2$—,
c) H$_3$C—(CH$_2$)$_2$—,
d) phenyl-(CH$_2$)$_2$—,
e) (CH$_3$)$_2$CH—CH$_2$—, or
f) pentyl;
wherein n is zero (0), one (1) or two (2);
wherein R$_7$ is
a) cyclopropyl, or
b) CH$_3$—CH$_2$—;
wherein R$_8$ is
a) —CH$_2$—CH$_3$, or
b) —CH$_2$-cyclopropyl;
wherein R$_9$ is
a) —NHSO$_2$-het, or
b) —NHSO$_2$-phenyl substituted by zero (0) or one (1) R$_{11}$;
wherein het is the following, substituted by zero (0) or one (1) R$_{10}$,
a) 2-pyridinyl,
b) imidazol-2-yl,
c) imidazol-4-yl,
d) quinolin-8-yl,
e) tetrahydropyran-4-yl,
f) tetrahydropyran-3-yl, or
g) benzimidazol-2-yl;
wherein R$_{10}$ is
a) —CH$_3$;
wherein R$_{11}$ is
a) —CN,
b) —F or
c) —NO$_2$;
or a pharmaceutically acceptable salt thereof.

Most particularly, the present invention provides for the compound of the formula VI
wherein R$_2$ is
a) H$_3$C—(CH$_2$)$_2$—,
b) phenyl-(CH$_2$)$_2$—,
c) (CH$_3$)$_2$CH—CH$_2$—, or
d) pentyl;
wherein R$_3$ is the moiety of formula X
wherein R$_6$ is
a) H$_3$C—(CH$_2$)$_2$—,
b) phenyl-(CH$_2$)$_2$—,
c) (CH$_3$)$_2$CH—CH$_2$—, or
d) pentyl;
wherein R$_7$ is
a) CH$_3$—CH$_2$—, or
b) cyclopropyl;
wherein R$_9$ is
a) —NHSO$_2$-phenyl substituted by one (1) R$_{11}$, or
b) —NHSO$_2$-het;
wherein het is the following, substituted by zero (0) or one (1) R$_{10}$,
a) imidazol-4-yl, or
b) quinolin-8-yl;
wherein R$_{10}$ is —CH$_3$;
wherein R$_{11}$ is
a) —CN, or
b) —F.

Also, most particularly, the present invention provides for the compound of the formula VII
wherein R$_3$ is the moiety of formula X
wherein R$_4$ is
a) phenyl,
b) het,
c) cyclopropyl,
d) H$_3$C—[O(CH$_2$)$_2$]$_2$—,
e) het-SO$_2$NH—,
f) Br—,
g) N$_3$—, or
h) HO$_3$S(CH$_2$)$_2$—N(CH$_3$)—C(O)—(CH$_2$)$_6$—C(O)—NH—;

wherein $R_6$ is
a) $R_4$—$(CH_2)_n$—$CH(R_8)$—, or
b) $H_3C$—$[O(CH_2)_2]_2$—$CH_2$—;
wherein $R_7$ is cyclopropyl;
wherein $R_8$ is
a) —$CH_2$—$CH_3$, or
b) —$CH_2$-cyclopropyl;
wherein $R_9$ is
a) —$NHSO_2$-het, or
b) —$NHSO_2$-phenyl substituted by one (1) $R_{11}$;
wherein n is zero (0), one (1) or two (2);
wherein het is the following, substituted by zero (0) or one (1) $R_{10}$,
a) imidazol-4-yl,
b) imidazol-2-yl,
c) quinolin-8-yl,
d) tetrahydropyran-3-yl,
e) tetrahydropyran-4-yl,
f) 2-pyridinyl, or
g) benzimidazol-2-yl;
wherein $R_{10}$ is —$CH_3$;
wherein $R_{11}$ is
a) —$NO_2$,
b) —F, or
c) —CN;
or a pharmaceutically acceptable salt thereof.
The present invention also provides:
A compound of the formula II
wherein $R_{10}$ and $R_{20}$ taken together are
a) the moiety of formula III, or
b) the moiety of formula IV;
wherein p is four (4);
wherein $R_1$ is —H;
wherein $R_2$ is
a) H—,
b) $CH_8O$—, or
c) $CH_3O$—$[(CH_2)_2O]_3$—;
wherein $R_3$ is the moiety of formula V
wherein $R_4$ is
a) cyclopropyl, or
b) —$CH_2$—$CH(CH_3)_2$;
wherein $R_5$ is
a) —$NR_9SO_2$-phenyl substituted by zero (0) or one (1) $R_6$,
b) —$NR_9SO_2$-het,
c) —$CH_2$—$SO_2$-phenyl substituted by zero (0) or one (1) $R_6$, or
d) —$CH_2$—$SO_2$-het;
wherein $R_6$ is
a) —CN,
b) —F,
c) —$CH_3$,
d) —COOH, or
e) —OH;
wherein het is a 5-, 6- or 7-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring or another heterocycle; substituted by zero (0), one (1) or two (2) $R_7$;

wherein $R_7$ is
a) —$CH_3$,
b) —CN,
c) —$C(O)OC_2H_5$, or
d) —OH;
wherein $R_8$ is
a) —H,
b) —$(CH_2)_2$—$CH_3$,
c) —$CH_2$-cyclopropyl, or
d) —$CH_2$-phenyl;
wherein $R_9$ is
a) —H, or
b) —$CH_3$;
or a pharmaceutically acceptable salt thereof.
The present invention provides for such compounds wherein het is the following, substituted by zero (0) or one (1) $R_7$,
a) 2-pyridinyl,
b) imidazol-2-yl,
c) imidazol-4-yl,
d) benzimidazol-2-yl,
e) quinolin-8-yl,
f) quinolin-2-yl,
g) pyrimidin-2-yl,
h) quinazolin-2-yl,
i) purin-6-yl,
j) thiazol-2-yl,
k) thiazol-4-yl,
l) 2-pyrazolyl,
m) 2-pyrazinyl,
n) tetrahydropyran-4-yl, or
o) tetrahydropyran-3-yl.
More particularly, the present invention provides for the compound of the formula II
wherein $R_{10}$ and $R_{20}$ taken together are
a) the moiety of formula III, or
b) the moiety of formula IV;
wherein p is four (4);
wherein $R_1$ is —H;
wherein $R_2$ is
a) $CH_3O$—, or
b) $CH_3O[(CH_2)_2O]_3$—;
wherein $R_3$ is the moiety of formula V
wherein $R_4$ is
a) cyclopropyl, or
b) —$CH_2$—$CH(CH_3)_2$;
wherein $R_5$ is
a) —$NR_9SO_2$-phenyl substituted by zero (0) or one (1) $R_6$,
b) —$NR_9SO_2$-het,
c) —$CH_2$—$SO_2$-phenyl substituted by zero (0) or one (1) $R_6$, or
d) —$CH_2$—$SO_2$-het;
wherein $R_6$ is
a) —CN,
b) —F,
c) —$CH_3$, or
d) —COOH;
wherein het is the following, substituted by zero (0) or one (1) $R_7$, a) imidazol-4-yl,
b) quinolin-8-yl,
c) 2-pyridinyl, or
d) 4-pyridinyl;
wherein $R_7$ is —$CH_3$;
wherein $R_8$ is
a) —H, or
b) —$(CH_2)_2$—$CH_3$;
wherein $R_9$ is
a) —H, or
b) —$CH_3$;
or a pharmaceutically acceptable salt thereof.

Most particularly, the present invention provides for the compound of the formula VIII
wherein $R_3$ is the moiety of formula V
wherein $R_4$ is
a) cyclopropyl,
b) —$CH_2$—$CH(CH_3)_2$;
wherein $R_5$ is
a) —$NR_9SO_2$-phenyl substituted by zero (0) or one (1) $R_6$,
b) —$NR_9SO_2$-het, or
c) —$CH_2$—$SO_2$-phenyl;
wherein $R_6$ is
a) —CN, or
b) —F;
wherein het is the following, substituted by zero (0) or one (1) $R_7$,
a) 2-pyridinyl,
b) 4-pyridinyl, or
c) imidazol-4-yl;
wherein $R_7$ is —$CH_3$;
wherein $R_8$ is
a) —H, or
b) —$(CH_2)_2$—$CH_3$;;
wherein $R_1$ is
a) —H, or
b) —$CH_3$;
or a pharmaceutically acceptable salt thereof.

Also, most particularly, the present invention provides for the compound of the formula IX
wherein $R_1$ is H—:
wherein $R_2$ is
a) $CH_3O$—, or
b) $CH_3O$—$[(CH_2)_2O]_3$—;
wherein $R_3$ is the moiety of formula V
wherein $R_4$ is cyclopropyl;
wherein $R_5$ is —$NHSO_2$-het;
wherein het is the following, substituted by zero (0) or one (1) $R_7$,
a) imidazol-4-yl,
b) 2-pyridinyl, or
c) quinolin-8-yl;
wherein $R_7$ is —$CH_3$.

The present invention also provides for the compound of the formula VI wherein $R_2$ is
a) $H_3C$—$CH_2$—,
b) $H_3C$—$(CH_2)_2$—,
c) cyclopropyl-$(CH_2)_2$—,
d) F-phenyl-$(CH_2)_2$—,
e) het-$SO_2NH$-phenyl-,
f) $(H_3C)_2HC$—$CH_2$,
g) phenyl-$(CH_2)_2$—, or
h) $F_3C$—$(CH_2)_2$—;
wherein $R_3$ is the moiety of formula X
wherein $R_6$ is
a) $H_3C$—$CH_2$—,
b) $H_3C$—$(CH_2)_2$—,
c) cyclopropyl-$(CH_2)_2$—,
d) F-phenyl-$(CH_2)_2$—,
e) het-$SO_2NH$-phenyl,
f) $(H_3C)_2HC$—$CH_2$,
g) phenyl-$(CH_2)_2$—, or
h) $F_3C$—$(CH_2)_2$—;
wherein $R_7$ is
a) $H_3C$—$CH_2$—,
b) t-butyl, or
c) cyclopropyl
wherein $R_9$ is
a) —$NHSO_2$-het, or
b) —$NHSO_2$-phenyl substituted by one (1) $R_{11}$;
wherein het is the following, substituted by zero (0) or one (1) $R_{10}$,
a) imidazol-4-yl,
b) 2-pyridinyl, or
c) quinolin-8-yl;
wherein $R_{10}$ is,
a) —$CH_3$,
b) —CN,
c) —$CF_3$,
d) —$NH_2$, or
e) —$C(O)$—$NH_2$;
wherein $R_{11}$ is CN.

The present invention also provides:
A compound of the formula XI
wherein $R_1$ is —$(CH_2)_p$—$CH(R_2)$—$(CH_2)_o$—$Ar_1$;
wherein $R_2$ is
a) —$C_1$–$C_5$ alkyl, or
b) —$(CH_2)_q$-cycloalkyl;
wherein $Ar_2$ is
a) phenyl substituted by zero (0) or one (1) $R_3$, or
b) phenyl substituted by -meta-$NHSO_2Ar_2$;
wherein $Ar_2$ is
a) phenyl substituted by zero (0) or one (1) $R_3$, or
b) het;
wherein het is a 5-, 6- or 7-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring or another heterocycle; substituted by zero (0) or one (1) $R_4$;
wherein $R_3$ is
a) —CN,
b) —F,
c) —OH, or
d) —$NO_2$;
wherein $R_4$ is
a) —$CH_3$,
b) —CN,
c) —OH,
d) —$C(O)OC_2H_5$, e) —CF$_3$, or f) —NH$_2$;

wherein n is zero (0) to eight (8), inclusive;
wherein o is zero (0) to three (3), inclusive;
wherein p is zero (0) to three (3), inclusive;
wherein q is zero (0) to three (3), inclusive; or
a pharmaceutically acceptable salt thereof More particularly, the present invention provides:
The compound wherein R$_1$ is —CH(R$_2$)—Ar$_2$;
wherein R$_2$ is a) —CH$_2$—CH$_3$, or b) -t-butyl;

wherein Ar$_1$ is phenyl substituted by -meta-NHSO$_2$Ar$_2$;
wherein Ar$_2$ is 2-pyridinyl substituted by one (1) R$_4$;
wherein R$_4$ is a) —CN, or b) —CF$_3$;

wherein n is two (2) to four (4) inclusive.

The present invention also provides:
A process for producing a compound of the formula W-10
wherein R$_1$ is a) n-propyl, or b) phenethyl;

which comprises the steps of:

a) treating a compound of the formula W-9
wherein X$_A$ is as defined above, with TiCl$_4$;

b) treating the product of step a) with an amine base; and c) reacting the product of step b) with 4-heptanone or propylphenethylketone to yield the compound of formula W-10;

The process which further comprises the steps of:

d) treating the compound of formula W-10 with sodium hydride or potassium t-butoxide to obtain a compound of formula W-11 wherein R$_1$ is a) n-propyl, or b) phenethyl;

e) hydrogenating the compound of formula W-11 to obtain the compound of formula W-12 wherein R$_1$ is as defined above;

f) treating the compound of formula W-12 with a sulfonyl chloride of formula D-7 wherein R$_4$ is 5-trifluoromethyl-2-pyridinyl, in an organic solvent in the presence of an organic base to obtain a compound of the formula W-13 wherein R$_1$ is as defined above.

The present invention also provides:
A process for producing a compound of the formula X-10
wherein R$_1$ is a) n-propyl, or b) phenethyl;

which comprises the steps of:

a) treating a compound of the formula X-9
wherein X$_A$ is as defined above, with TiCl$_4$;

b) treating the product of step a) with an amine base; and c) reacting the product of step b) with 4-heptanone or propylphenethylketone to yield the compound of formula X-10;

The process which further comprises the steps of:

d) treating the compound of formula X-10 with sodium hydride or potassium t-butoxide to obtain a compound of formula X-11 wherein R$_1$ is a) n-propyl, or b) phenethyl;

e) hydrogenating the compound of formula X-11 to obtain a compound of formula X-12 wherein R$_1$ is as defined above;

f) treating the compound of formula X-12 with a sulfonyl chloride of formula D-7 wherein R$_4$ is 5-trifluoromethyl-2-pyridinyl, in an organic solvent in the presence of an organic base to obtain a compound of the formula X-13 wherein R$_1$ is as defined above.

The present invention also provides:
A process for producing a compound of the formula GGG-10
wherein R$_1$ is a) n-propyl, or b) phenethyl;

which comprises the steps of:

a) treating a compound of the formula GGG-9
wherein X$_A$ is as defined above, with TiCl$_4$;

b) treating the product of step a) with an amine base; and c) reacting the product of step b) with 4-heptanone or 1-phenyl-3-hexanone to yield the compound of formula GGG-10.

The process which further comprises the steps of:

d) treating the compound of formula GGG-10 with sodium hydride or potassium t-butoxide to obtain a compound of formula GGG-11 wherein R$_1$ is a) n-propyl, or b) phenethyl;

e) hydrogenating the compound of formula GGG-11 to obtain a compound of formula GGG-12 wherein R$_1$ is as defined above;

f) treating the compound of formula GGG-12 with a sulfonyl chloride of formula D-7 wherein R$_4$ is a) 5-trifluoromethyl-2-pyridinyl, or b) 5-cyano-2-pyridinyl, in an organic solvent in the presence of an organic base to obtain a compound of the formula GGG-13A wherein R$_1$ is as defined above.

A process for producing a compound of the formula HHH-10
wherein R$_1$ is a) n-propyl, or b) phenethyl;

which comprises the steps of:

a) treating a compound of the formula HHH-9
wherein X$_A$ is as defined above, with TiCl$_4$;

b) treating the product of step a) with an amine base; and c) reacting the product of step b) with 4-heptanone or 1-phenyl-3-hexanone to yield the compound of formula HHH-10.

The process which further comprises the steps of:

d) treating the compound of formula HHH-10 with sodium hydride or potassium t-butoxide to obtain a compound of formula HHH-11 wherein R$_1$ is a) n-propyl, or b) phenethyl;

e) hydrogenating the compound of formula HHH-11 to obtain a compound of formula HHH-12 wherein $R_1$ is as defined above;

f) treating the compound of formula HHH-12 with a sulfonyl chloride of formula D-7 wherein $R_4$ is a) 5-trifluoromethyl-2-pyridinyl, or b) 5-cyano-2-pyridinyl, in an organic solvent in the presence of an organic base to obtain a compound of the formula HHH-13A wherein $R_1$ is as defined above.

A process for producing a compound of the formula III-10 wherein $R_1$ is a) n-propyl, or b) phenethyl;

which comprises the steps of:

a) treating a compound of the formula III-9 wherein $X_A$ is as defined above, with $TiCl_4$;

b) treating the product of step a) with an amine base; and c) reacting the product of step b) with 4-heptanone or 1-phenyl-3-hexanone to yield the compound of formula III-10.

The process which further comprises the steps of:

d) treating the compound of formula III-10 with sodium hydride or potassium t-butoxide to obtain a compound of formula III-11 wherein $R_1$ is a) n-propyl, or b) phenethyl;

e) hydrogenating the compound of formula III-11 to obtain a compound of formula III-12 wherein $R_1$ is as defined above;

f) treating the compound of formula III-12 with a sulfonyl chloride of formula D-7 wherein $R_4$ is a) 5-trifluoromethyl-2-pyridinyl, or b) 5-cyano-2-pyridinyl, in an organic solvent in the presence of an organic base to obtain a compound of the formula III-13A wherein $R_1$ is as defined above.

A process for producing a compound of the formula JJJ-10 wherein $R_1$ is a) n-propyl, or b) phenethyl;

which comprises the steps of:

a) treating a compound of the formula JJJ-9 wherein $X_A$ is as defined above, with $TiCl_4$;

b) treating the product of step a) with an amine base; and c) reacting the product of step b) with 4-heptanone or 1-phenyl-3-hexanone to yield the compound of formula JJJ-10.

The process which further comprises the steps of:

d) treating the compound of formula JJJ-10 with sodium hydride or potassium t-butoxide to obtain a compound of formula JJJ-11 wherein $R_1$ is a) n-propyl, or b) phenethyl;

e) hydrogenating the compound of formula JJJ-11 to obtain a compound of formula JJJ-12 wherein $R_1$ is as defined above;

f) treating the compound of formula JJJ-12 with a sulfonyl chloride of formula D-7 wherein $R_4$ is a) 5-trifluoromethyl-2-pyridinyl, or b) 5-cyano-2-pyridinyl, in an organic solvent in the presence of an organic base to obtain a compound of the formula JJJ-13A wherein $R_1$ is as defined above.

The present invention most preferrably provides:

The compound of formula VI wherein $R_2$ is a) $H_3C-(CH_2)_2-$, or b) phenyl-$(CH_3)_2-$;

wherein $R_3$ is the moiety of formula X;

wherein $R_6$ is a) $H_3C-(CH_2)_2-$, or b) phenyl-$(CH_2)_2-$;

wherein $R_7$ is a) $H_3C-CH_2-$, or b) t-butyl;

wherein $R_9$ is $-NHSO_2$-het;

wherein het is the following, substituted by one (1) $R_{10}$, a) imidazol-4-yl, or b) 2-pyridinyl;

wherein $R_{10}$ is, a) $-CH_3$, b) $-CN$, or c) $-CF_3$.

The compounds of the present invention are named according to the IUPAC or CAS nomenclature system.

The carbon atoms content of various hydrocarbon-containing moieties is indicated by a prefix designating the minimum and maximum number of carbon atoms in the moiety, i.e., the prefix $C_1$–$C_3$ indicates a moiety of the integer "i" to the integer "j" carbon atoms, inclusive. Thus, for example, $C_1$–$C_3$ alkyl refers to alkyl of one to three carbon atoms, inclusive, or methyl, ethyl, propyl, and isopropyl, straight and branched forms thereof.

Also, the carbon atom content of various hydrocarbon-containing moieties of the present invention is indicated by a subscripted integer representing the number of carbon and hydrogen atoms in the moiety, e.g., "$C_nH_{2n}$" indicates a moiety of the integer "n" carbon atoms, inclusive, and the integer "2n" hydrogen atoms, inclusive. Thus, for example, "$C_nH_{2n}$" wherein n is one to three carbon atoms, inclusive, and two to six hydrogen atoms, inclusive, or methyl, ethyl, propyl and isopropyl, and all isomeric, straight and branched forms thereof.

Examples of alkyl of one to nine carbon atoms, inclusive, are methyl, ethyl, propyl, butyl, pentyl, hexyl, heptyl, octyl, and nonyl, and all isomeric forms thereof and straight and branched forms thereof.

Examples of alkenyl of one to five carbon atoms, inclusive, are ethenyl, propenyl, butenyl, pentenyl, all isomeric forms thereof, and straight and branched forms thereof.

By "halo" is meant the typical halogen atoms, such as fluorine, chlorine, bromine, and iodine.

The compounds of formula I and II of the present invention inhibit retroviral proteinases and thus inhibit the replication of the virus. They are useful for treating patients infected with human immunodeficiency virus (HIV) which results in acquired immunodeficiency syndrome (AIDS) and related diseases.

More particularly, the compounds of the present invention are useful as novel human retroviral protease inhibitors. Therefore, the compounds inhibit retroviral proteases and thus inhibit the replication of the virus. They are useful for treating human patients infected with a human retrovirus, such as human immunodeficiency virus (strains of HIV-1 or HIV-2) or human T-cell leukemia viruses (HTLV-I or HTLV-II) which results in acquired immunodeficiency syndrome (AIDS) and/or related diseases.

The capsid and replicative enzymes (i.e. protease, reverse transcriptase, integrase) of retroviruses are translated from the viral gag and pol genes as polyproteins that are further processed by the viral protease (PR) to the mature proteins found in the viral capsid and necessary for viral functions and replication. If the PR is absent or nonfunctional, the virus cannot replicate. The retroviral PR, such as HIV-1 PR, has been found to be an aspartic protease with active site characteristics similar to those exhibited by the more complex aspartic protease, renin.

The term human retrovirus (HRV) includes human immunodeficiency virus type I, human immunodeficiency virus type II, or strains thereof, as well as human T cell leukemia virus 1 and 2 (HTLV-1 and HTLV-2) or strains apparent to one skilled in the art, which belong to the same or related viral families and which create similar physiological effects in humans as various human retroviruses.

Patients to be treated would be those individuals: 1) infected with one or more strains of a human retrovirus as determined by the presence of either measurable viral antibody or antigen in the serum and 2) in the case of HIV, having either an asymptomatic HIV infection or a symptomatic AIDS defining infection such as i) disseminated histoplasmosis, ii) isopsoriasis, iii) bronchial and pulmonary candidiasis including pneumocystic pneumonia iv) non-Hodgkin's lymphoma or v) Kaposi's sarcoma and being less than sixty years old; or having an absolute CD4+ lymphocyte count of less than 500/mm$^3$ in the peripheral blood. Treatment would consist of maintaining an inhibitory level of the compound used according to this invention in the patient at all times and would continue until the occurrence of a second symptomatic AIDS defining infection indicates alternate therapy is needed.

More specifically, an example of one such human retrovirus is the human immunodeficiency virus (HIV, also known as HTLV-III or LAV) which has been recognized as the causative agent in human acquired immunodeficiency syndrome (AIDS), P. Duesberg, Proc. Natl. Acad. Sci. USA, 86:755 (1989). HIV contains a retro viral encoded protease, HIV-I protease, that cleaves the fusion polypeptides into the functional proteins of the mature viral particle, E. P. Lillehoj, et al., J. Virology, 62:3053 (1988); C. Debuck, et al., Proc. Natl. Acad. Sci., 84:8903 (1987). This enzyme, HIV-I protease, has been classified as an aspartyl protease and has a demonstrated homology to other aspartyl proteases such as renin, L. H. Pearl, et al., Nature 329:351 (1987); I. Katoh, et al., Nature 329:654 (1987). Inhibition of HIV-I protease blocks the replication of HIV and thus is useful in the treatment of human AIDS, E. D. Clerq, J. Med. Chem. 29:1561 (1986). Inhibitors of HIV-I protease are useful in the treatment of HIV-infected individuals who are asymptomatic or symptomatic of AIDS.

Pepstatin A, a general inhibitor of aspartyl proteases, has been disclosed as an inhibitor of HIV-I protease, S. Seelmeier, et al., Proc. Natl. Acad. Sci. USA, 85:6612 (1986). Other substrate derived inhibitors containing reduced bond isosteres or statine at the scissle position have also been disclosed, M. L. Moore, et al., Biochem. Biophys, Res. Commun. 159:420 (1989); S. Billich, et al., J. Biol. Chem. 263:17905 (1988); Sandoz, D. E. 3812–576-A.

Thus, the compounds of the present invention are useful for treating diseases caused by retroviruses, such as human acquired immunodeficiency disease syndrome (AIDS).

The compounds are also useful for treating non-human animals infected with a retrovirus, such as cats infected with feline leukemia virus. Other viruses that infect cats include, for example, feline infectious peritonitis virus, calicivirus, rabies virus, feline immunodeficiency virus, feline parvovirus (panleukopenia virus), and feline chlamydia. Exact dosages, forms and modes of administration of the compounds of the present invention to non-human animals would be apparent to one of ordinary skill in the art, such as a veterinarian.

The compounds of formula I and II of the present invention are prepared as described in the Charts, Preparations and Examples below, or are prepared by methods analogous thereto, which are readily known and available to one of ordinary skill in the art of organic synthesis.

CHART A

Nitration of the cyclopropylphenyl ketone of formula A-1, which is commercially available, with fuming nitric acid at $-40°$ C. produces a ca. 2:1 mixture of isomers. The desired m-nitro compound of formula A-2 is easily separated from the crude mixture by recrystallization from methanol. Catalytic hydrogenation of the cyclopropyl-(3-nitrophenyl) methanone of formula A-2 with 10% platinum on carbon in methanol gives the aniline of formula A-3. The aniline is then coupled with benzenesulfonyl chloride using pyridine in methylene chloride to give the sulfonamide derivative of formula A-4. Reduction of the ketone with sodium borohydride in tetrahydrofuran and ethanol then produces the carbinol of formula A-5.

The dianion of the cyclooctylpyranone of formula A-6, prepared as described in Chart B, is formed using lithium diisopropyl amide in tetrahydrofuran at $0°$ C., and then alkylated with iodopropane to give the 10-propyl-cyclooctylpyranone of formula A-7. The cyclooctylpyranone of formula A-7 and the carbinol of the formula A-5 are then coupled using p-toluenesulfonic acid in methylene chloride to give the sulfonamide derivative of formula A-8.

CHART B

The commercially available amine of the formula B-1 is protected using benzyl chloroformate and sodium bicarbonate in THF/water solution to give the compound of formula B-2. The aldehyde of formula B-2 is then reacted with a Grignard reagent to give the secondary alcohol of formula B-3, wherein, e.g., $R_1$ is isobutyl. The known cyclooctylpyranone of formula B-4 is prepared by acylation of the trimethylsilyl enol ether of cyclooctanone with malonyl dichloride as described in R. Effenberger, T. Ziegler, K. -H. Schonwalder, T. Kesmarszky, B. Bauer Chem. Ber. 119:3394–3404 (1986). The alcohol of formula B-3 is then used to alkylate the cyclooctylpyranone of formula B-4 in refluxing toluene and p-toluenesulfonic acid to obtain the compound of the formula B-5, wherein, e.g., R. is isobutyl. At this point, the enantiomers of formula B-5 are separated using a chiral HPLC column. The benzyloxy protecting group is then cleaved using 10% Pd/C in cyclohexene to give the amine of formula B-6, wherein, e.g., $R_1$ is isobutyl, which is reacted with aryl sulfonyl chlorides to give the compounds of the formula B-7, wherein, e.g., $R_1$ is isobutyl and $R_2$ is 1-methylimidazole.

CHART C

3-Bromobenzyl alcohol of formula C-1, which is commercially available, in tetrahydrofuran is treated with methyllithium, n-butyllithium and cyclpropanecarboxaldehyde in sequence at −78° C. The resulting solution is gradually warmed to room temperature and then heated at reflux affording the alcohol of formula C-2. The resulting alcohol, in dichloromethane, in the presence of molecular sieves, is treated with 4-hydroxy-5,6,7,8,9,10-hexahydrocycloocta[b]pyran-2-one of formula C-8, prepared as described in Chart B, and p-toluenesulfonic acid. The solution is heated at reflux to afford the alcohol of formula C-3. The benzyl alcohol is treated with carbon tetrabromide and triphenylphosphine in dichloromethane at 0° C. to afford compounds of formula C-4 and C-5 as an inseparable mixture after an aqueous brine workup. The mixture is then treated with any thiol (e.g., thiophenol) and an organic base and heated at reflux to afford sulfides of the formula C-6. Finally treatment of the compounds of the formula C-6 with oxone in a mixture of tetrahydrofuran, methanol and water gives sulfones of formula C-7.

CHART D

This chart describes a generic procedure for the preparation of C-3α branched 5,6-dihydropyrones via aluminum chloride ($AlCl_3$) mediated condensation with 3-nitrobenzaldehyde. Thus, the $AlCl_3$ catalyzed reaction of the compound of formula D-1, prepared as described below in the Preparations, (e.g., wherein $R_1$ is phenethyl or propyl; $R_2$ is phenethyl or propyl) with 3-nitrobenzaldehyde (formula D-2), which is commercially available, provides compounds of formula D-3 (e.g., wherein $R_1$ is phenethyl or propyl; $R_2$ is phenethyl or propyl). Subsequent reaction with trialkyl aluminums or Grignard reagents in the presence of cuprous bromide-dimethylsulfide complex ($CuBr$—$Me_2S$) provides compounds of formula D-4 (e.g., wherein $R_1$ is phenethyl or propyl; $R_2$ is phenethyl or propyl; $R_1$ is ethyl or cyclopropyl). Transfer hydrogenation with Pd/C and ammonium formate provides compounds of formula D-5 (e.g., wherein $R_1$ is phenethyl or propyl; $R_2$ is phenethyl or propyl; $R_3$ is ethyl or cyclopropyl). Treatment of the compound of formula D-5 with sulfonyl chlorides of formula D-7, wherein $R_4$ is defined below, and pyridine in methylene chloride ($CH_2Cl_2$) provides compounds of formula D-6 (e.g., wherein $R_1$ is phenethyl or propyl; $R_2$ is phenethyl or propyl; $R_3$ is ethyl or cyclopropyl; $R_4$ is 4-cyanophenyl, 4-fluorophenyl, 1-methylimidazol-4-yl, quinolin-8-yl, 2-pyridyl, 4-cyano-2-pyridyl, quinolin-2-yl, 2-hydroxyphenyl, 2-pyrimidyl, 2-quinazoline, 7H-purin-6-yl, 1H-imidazol-2-yl, 1H-benzimidazol-2-yl or thiazol-2-yl).

CHART E

Treatment of commercially available 4-hydroxy-6-methyl-2-pyrone of formula E-1 with three equivalents of lithium diisopropylamide in tetrahydrofuran and hexamethylphosphoramide is followed by bromomethylcyclopropane to afford the compound of formula E-2. Reaction between the compound of formula E-2 and the compound of formula F-5, prepared as described in Chart F, in benzene with p-toluenesulfonic acid catalyst in the presence of molecular sieves affords the compound of formula E-3. Hydrogenolysis of the compound of formula E-3 in methanol with hydrogen and palladium on charcoal gives the free amine of formula E-4. Treatment of the compound of formula E-4 with two equivalents of pyridine in dichloromethane followed by one equivalent of 4-fluorobenzenesulfonyl chloride gives the compound of formula E-5 (wherein, e.g., R is 4-fluorophenyl) which is the compound: N-(3-{cyclopropyl-[6-(2-cyclopropyl-1-cyclopropylmethyl-ethyl)-4-hydroxy-2-oxo-2H-pyran-3-yl]-methyl]-phenyl)-4-fluoro-benzenesulfonamide.

Under similar conditions, compounds of general formula E-5 are obtained by reacting amine E-4 with alkyl, aryl and heteroaryl sulfonyl chlorides in the presence of pyridine to give compounds of formula E-5 wherein R is alkyl, aryl or heteroaryl. Also, for example, the enantiomers of the compound of formula E-9 are separated chromatographically by chiral HPLC to give compounds of formula E-10 and E-11. Additional final compounds of the present invention of formula E-6, E-7, E-8, and E-12–E-16 are prepared using similar conditions.

CHART F

Nitration of commercially available cyclopropyl phenyl ketone of formula F-1 with fuming nitric acid affords the compound of formula F-2. Reduction of the compound of formula F-2 in methanol with hydrogen catalyzed by platinum on carbon gives the amine of formula F-3. The compound of formula F-3 is treated with benzylchloroformate and diisopropylethylamine in dichloromethane to give the compound of formula F-4. Reduction of the compound of formula F-4 with sodium borohydride in tetrahydrofuran and ethanol gives the compound of formula F-5.

CHART G

The dianion of commercially available 4-hydroxy-6-methyl-2-pyrone of formula G-0 is generated by deprotonation with two equivalents of lithium diisopropylamide in tetrahydrofuran and hexamethylphosphoramide. Alkylation with 2-(2-methoxy-ethoxy)-ethyl iodide, which is prepared from the commercially available alcohol by standard procedures, gives the compound of formula G-1. Reaction between the compound of formula G-1 and meta-benzyloxycarbonylamino-phenyl cyclopropyl carbinol, the compound of formula F-5, prepared as described in Chart F, in dichloromethane with p-toluenesulfonic acid catalyst in the presence of molecular sieves gives the compound of formula G-2. Hydrogenolysis of the compound of formula G-2 in ethanol with hydrogen and palladium on charcoal gives the free amine of formula G-3. Treatment of the free amine of formula G-3 with two equivalents of pyridine in dichloromethane followed by one equivalent of 1-methylimidazole-4-sulfonyl chloride gives the compound of formula G-4, which is the compound: N-(3-{cyclopropyl-[4-hydroxy-6-(3-{2-methoxy-ethoxy}-propyl)-2-oxo-2H-pyran-3-yl]-methyl}-phenyl)-1-methyl-1H-imidazole-4-sulfonamide.

CHART H

Reaction between commercially available 4-hydroxy-6-methyl-2-pyrone of formula H-0 and meta-benzyloxycarbonylaminophenyl cyclopropyl carbinol, the title compound of formula F-5, prepared as described in Chart F, in dichloromethane with p-toluenesulfonic acid catalyst in the presence of molecular sieves gives the compound of formula H-1. Alkylation of trianion of the compound of formula H-1 generated from three equivalents of lithium diisopropylamide in tetrahydrofuran with ethyl bromide affords the compound of formula H-2. Treatment of the compound of formula H-2 with lithium diisopropylamide in tetrahydrofuran and 2-(2-methoxy-ethoxy)-ethyl iodide gives the compound of formula H-3. Hydrogenolysis of the compound of formula H-3 in ethanol with hydrogen and palladium on charcoal gives the free amine of formula H-4. Treatment of the free amine of formula H-4 with two equivalents of pyridine in dichloromethane followed by one equivalent of 1-methylimidazole-4-sulfonyl chloride gives the compound of formula H-5, which is the compound: N-(3-{cyclopropyl-[6-(1-ethyl-3-{2-methoxy-ethoxy}-propyl)-4-hydroxy-2-oxo-2H-pyran-3-yl]-methyl}-phenyl)-1-methyl-1H-imidazole-4-sulfonamide. Under similar conditions, compounds of the present invention are obtained by reacting the amine of formula H-4 with alkyl, aryl and heteroaryl sulfonyl chlorides in the presence of pyridine to give additional sulfonamides of formula H-5.

CHART I

Treatment of the compound of formula H-2, prepared as described in Chart H, with three equivalents of lithium diisopropylamide in tetrahydrofuran and ethylene oxide gives the compound of formula I-1. Reaction of the compound of formula I-1 with triphenylphosphine and carbon tetrabromide in tetrahydrofuran gives the compound of formula I-2. Treatment of the compound of formula I-2 with sodium azide in aqueous ethanol gives the compound of formula I-3. Reaction of the compound of formula I-3 with hydrogen and palladium on charcoal in ethanol gives the compound of formula I-4. Treatment of the compound of formula I-4 with diisopropylethylamine in dichloromethane followed by 1-methylimidazole-4-sulfonyl chloride gives the compound of formula I-5. Reaction of the compound of formula I-5 with ammonia in methanol gives the compound of formula I-6, which is the compound: N-(3-{cyclopropyl-[6-(1-ethyl-3-{1-methyl-1H-imidazole-4-sulfonylamino}-propyl)-4-hydroxy-2-oxo-2H-pyran-3-yl]-methyl}-phenyl)-1-methyl-1H-imidazole-4-sulfonamide.

CHART J

Hydrogenolysis of the compound of formula I-1, prepared as described in Chart I, in ethanol with hydrogen and palladium on charcoal gives the compound of formula J-1. Treatment of the compound of formula J-1 with triphenylphosphine and carbon tetrabromide in tetrahydrofuran gives the compound of formula J-2. Reaction of the compound of formula J-2 with pyridine in dichloromethane followed by 1-methylimidazole-4-sulfonyl chloride gives the compound of formula J-3, which is the compound: N-(3-{[6-(3-bromo-1-ethyl-propyl)-4-hydroxy-2-oxo-2H-pyran-3-yl]-cyclopropyl-methyl}-phenyl)-1-methyl-1H-imidazole-4-sulfonamide. Treatment of the compound of formula J-3 with sodium azide in aqueous ethanol gives the compound of formula J-4, which is the compound: N-(3-{[6-(3-azido-1-ethyl-propyl)-4-hydroxy-2 -oxo-2H-pyran-3-yl]-cyclopropyl-methyl}-phenyl)-1-methyl-1H-imidazole-4-sulfonamide. Reaction of the compound of formula J-4 with hydrogen and palladium on charcoal in ethanol gives the compound of formula J-5. Treatment of the compound of formula J-5 with the triethylamine salt of suleptanic acid (Anderson, B. D.; Conradi, R. A; Knuth, K. E.; J. Pharm. Sci. 74:365 (1985)) and 1,3-diisopropylcarbodiimide gives the compound of formula J-6, which is the compound: N-(3-{cyclopropyl-[6-(1-ethyl-3-{N-[8-(methyl-{2-sulfoethyl}-amino)-1,8-dioxooctyl]-amino-propyl})-4-hydroxy-2-oxo-2H-pyran-3-yl]-methyl}-phenyl)-1-methyl-1H-imidazole-4-sulfonamide, sodium salt.

CHART K

The preparation of the compound of formula K-8, which is the compound: N-(3-{Cyclopropyl-[6-(1-(tetrahydropyran-4-ylmethyl)-propyl)-4-hydroxy-2-oxo-2H-pyran-3-yl]-methyl}-phenyl)-1-methyl-1H-imidazole-4-sulfonamide is shown in Chart K. Reduction of commercially available tetrahydropyran-4-carboxylic acid of formula K-1 with borane in tetrahydrofuran provides the compound of formula K-2. The compound of formula K-2 is treated with p-toluenesulfonyl chloride to afford the corresponding tosylate of formula K-3, which is converted to the iodide of formula K-4 by treatment with potassium iodide in refluxing acetone. Alkylation of the dianion of commercially available 4-hydroxy-6-methyl-2-pyrone of formula K-10 with ethyl bromide in tetrahydrofuran and hexamethylphosphoric triamide gives the propyl derivative of formula K-9. The compound of formula K-4 is used to alkylate the compound of formula K-9 at the 6a position, giving the compound of formula K-5. The compound of formula K-5 is further alkylated at the 3 position, using carbinol of formula F-5, prepared as described in Chart F, giving the compound of formula K-6. Removal of the benzyloxycarbonyl protecting group is accomplished using catalytic transfer hydrogenation, giving the amine of formula K-7. Treatment of the amine of formula K-7 with 1-methylimidazole-4-sulfonyl chloride in the presence of pyridine provides the compound of formula K-8.

CHART L

As shown in Chart L, the dianion of commercially available 4-hydroxy-6-methyl-2-pyrone of formula L-1 is generated by deprotonation with two equivalents of lithium diisopropylamide in tetrahydrofuran and hexamethylphosphoramide. Alkylation with benzyl bromide gives the compound of formula L-2, which is then treated with two equivalents of lithium diisopropylamide in tetrahydrofuran and hexamethylphosphoramide, followed by ethyl iodide to give the compound of formula L-3. Reaction between the compound of formula L-2 and the compound of formula F-5, prepared as described in Chart F, in benzene with p-toluenesulfonic acid catalyst in the presence of molecular sieves affords the compound of formula L-4, which is 3-[(3-benzyloxycarbonylaminophenyl)-cyclopropyl-methyl]-6-(1-ethylphenethyl)-4-hydroxy-2H-pyran-2-one. Hydrogenolysis of the compound of formula L-4 in methanol using catalytic palladium on charcoal and ammonium formate or hydrogen gas gives the free amine of formula L-5, which is 3-[(3-aminophenyl)-cyclopropyl-methyl]-6-(1-ethylphenethyl)-4-hydroxy-2H-pyran-2-one. Reacting the compound of formula L-5 and the appropriate sulfonyl chloride gives the final compounds of the present invention.

CHART M

As shown in Chart M, commercially available triethylene glycol monomethyl ether is treated with p-toluenesulfonyl chloride and pyridine to provide the tosylate of formula M-2, which is then used to alkylate commercially available 2,4-dihydroxyacetophenone to give the compound of formula M-3. Condensation with diethyl carbonate yields the compound of formula M-4. Ring closure of the compound of formula M-4 to the compound of formula M-5 is accomplished by refluxing in acetic acid. The compound of formula M-5 is alkylated at the 3-position using the carbinol of formula F-5, prepared as described in Chart F, and catalytic p-toluenesulfonic acid to give the compound of formula M-6. Removal of the benzyloxycarbonyl protecting group is accomplished using catalytic transfer hydrogenation, giving the amine of formula M-7. Treatment of the amine with 1-methylimidazole-4-sulfonyl chloride in the presence of pyridine provides the final compound of formula M-8, which is N-(3-{Cyclopropyl-[7-(2-(2-(2-methoxyethoxy)-ethoxy)ethoxy)-4-hydroxycoumarin-3-yl]-methyl}-phenyl)-1-methyl-1H-imidazole-4-sulfonamide.

CHART N

Nitration of cyclopropylphenyl ketone of formula N-1, which is commercially available, with fuming nitric acid at −40° C. produces a ca. 2:1 mixture of isomers. The desired meta-nitro compound of formula N-2 is easily separated from the crude mixture by recrystallization from methanol. Catalytic hydrogenation of cyclopropyl-(3-nitrophenyl) methanone of formula N-2 with 10% platinum on carbon in methanol at 0° C. provides the aniline of formula N-3. The product is isolated by filtration and concentration. The amino group is then protected using benzyl chloroformate and diisopropylethylamine in methylene chloride to give the ketone of formula N-4. The ketone is then reduced with sodium borohydride in 5:1 THF and ethanol to give the alcohol of formula N-5.

The compound of formula N-5 is then used to alkylate 4-hydroxy-5,6,7,8,9,10-hexahydrocycloocta[b]pyran-2-one, which is prepared as described in R. Effenberger, T. Ziegler, K. -H. Schönzoalder, T. Kesmarsky, B. Bauer, Chem. Ber. 119:3394–3404 (1986), to give the compound of formula N-6. The preferred conditions for this alkylation reaction are p-toluene-sulfonic acid in refluxing methylene chloride with a Soxhlet extractor containing molecular sieves. Finally, the compound of formula N-7 is obtained by cleaving the benzyl protective group in a transfer hydrogenation. Best results for this reactions are achieved with 10% Pd/C in neat cyclohexene.

CHART O

Treatment of the amine of formula O-1, prepared as described in Chart N, with sulfonyl chlorides and a base such as pyridine in dichloromethane gives the sulfonamides of formula O-2 wherein $R_{60}$ is, for example, 4-nitrophenyl. These sulfonamides are further modified by standard literature procedures as is apparent to those of ordinary skill in the art to give sulfonamides of formula O-3 wherein $R_{61}$ is, for example, 4-aminophenyl and other functional groups that are not readily available from readily available sulfonyl chlorides. For example, the nitro group of N-[3-[cyclopropyl (5,6,7,8,9,10-hexahydro-4-hydroxy-2-oxo-2H-cycloocta[b] pyran-3-yl)methyl]phenyl]-4-nitro-benzenesulfonamide is reduced by catalytic hydrogenation in ethyl acetate with palladium on carbon to give the amine in 4-amino-N-[3-[cyclopropyl(5,6,7,8,9,10-hexahydro-4-hydroxy-2-oxo-2H-cycloocta[b]pyran-3-yl)methyl]phenyl]-benzenesulfonamide. Also, the carboxylic acid of 3-[[[3-[cyclopropyl(5,6,7,8,9,10-hexahydro-4-hydroxy-2-oxo-2H-cycloocta[b]pyran-3-yl)methyl]phenyl]amino]sulfonyl]-benzoic acid is esterified with methanol and catalytic sulfuric acid to give the methyl ester in 3-[[[3-[cyclopropyl (5,6,7,8,9,10-hexahydro-4-hydroxy-2-oxo-2H-cycloocta[b] pyran-3-yl)methyl]phenyl]aminolsulfonyl]-benzoic acid, methyl ester. Sulfonamides of formula O-3 are also obtained from compounds of formula O-2 by further elaboration of reactive functional groups. For example, the amine of 3-amino-N-[3-[cyclopropyl(5,6,7,8,9,10-hexahydro-4-hydroxy-2-oxo-2H-cycloocta[b]pyran-3-yl)methyl]phenyl]-benzenesulfonamide is reacted with benzoyl chloride and a base such as pyridine to give the benzamide in N-[3-[[[3-[cyclopropyl(5,6,7,8,9,10-hexahydro-4-hydroxy-2-oxo-2H-cycloocta[b]pyran-3-yl)methyl]phenyl]amino]sulfonyl] henyl]-benzamide. Using commonly available sulfonyl chlorides, additional compounds of the present invention of formula II, wherein $R_{10}$ and $R_{20}$ is the moiety of formula IV, are prepared.

The sulfonyl chlorides used to make the compounds of the present invention are readily prepared by methods described in the literature by those skilled in the art, as the following examples illustrate: Reaction of a suitable thiol with $KHF_2$ in water/methanol with chlorine gas gives the sulfonyl fluoride (D. J. Brown, J. A. Hoskins, Aust. J. Chem. 25:2641 (1972)) which is then converted into the desired sulfonyl chloride (T. Norris, J. Chem. Soc., Perkin Trans. 1(11):1378 (Eng.) (1978)). Oxidation of a suitable thiol with chlorine in water with ferric chloride ($FeCl_3$) added gives the desired sulfonyl chloride (G. Pala, Ed. Sci. 13:461 (1958); W. J. Close, J. Amer. Chem. Soc. 82:1132 (1960)). Reaction of the heteroaromatic compound with fuming sulfuric acid gives a heteroaromatic sulfonic acid followed by treatment with phosphorous-oxychloride ($POCl_3$) and phosphorous chloride ($PCl_5$) gives the desired sulfonyl chloride (V. Georgian, R. J. Harrison, L. L. Skaletzky, J. Org. Chem. 27:4571 (1962)). Reaction of a heteroaromatic compound with manganese dioxide ($MnO_2$) and sodium sulfite ($Na_2SO_3$) in water gives the desired sulfonic acid followed by treatment with $POCl_3$ and $PCl_5$ gives the desired sulfonyl chloride (N. A. Androva, Izvest. 455 (1972); J. O. Morley, J. Chem. Comm. 88 (1976)). Treatment of the appropriate heteroaromatic chloride with sodium sulfate and HCl in water gives the desired sulfonic acid followed by treatment with $POCl_3$ and $PCl_5$ gives the desired sulfonyl chloride (T. R. Norton, J. Amer. Chem. Soc. 68:1330 (1946)). Treatment of the appropriate hydroxy compound with N,N-dimethylthiocarbonyl chloride (M. S. Newman, F. W. Hetzel, Org. Synth. Coll. Vol. IV:824 (1988); M. S. Newman, H. A. Karnes, J. Org. Chem. 31:3980 (1966)) followed by treatment of the resulting thiol, as described above, gives the desired sulfonyl chloride. Treatment of the appropriately protected thio-heteroaromatic compound with chlorine in acetic acid gives the desired sulfonyl chloride (Can. J. Chem. 55:421 (1977)). Using the literature procedures described above, the heteroaromatic sulfonyl chlorides of the present invention are prepared.

CHART P

The preferred procedure for the preparation of the heteroaryl sulfonamides of formula P-2 is described in Chart P. Sulfonation of the amine of formula P-1, prepared in Chart N, P-1 with various heteroarylsulfonyl chlorides of formula P-3 wherein R is, e.g., 2-pyridyl, 4-pyridyl, 5-cyanopyridin-2-yl, 2-pyrazinyl, 2-pyrimidinyl, 4,6-dimethylpyrimidin-2-yl, 4-methylpyrimidin-2-yl gives the sulfonamides of formula P-2 wherein R is the corresponding substituent.

CHART Q

Generated by sequential deprotonation with sodium hydride and n-butyl lithium in tetrahydrofuran at 0° C., the dianion of commercially available methyl acetoacetate is reacted with ketone of formula Q-1, prepared as described in Chart S (formula S-4). The resulting intermediate hydroxyester is cyclized with dilute aqueous hydroxide followed by aqueous hydrochloric acid to give the compound of formula Q-2. The compound of formula Q-2 is condensed with commercially available 3-nitrobenzaldehyde in tetrahydrofuran using aluminum trichloride as a catalyst followed by reaction of the intermediate benzylidene adduct with triethyl aluminum in the presence of copper bromide-dimethyl sulfide to provide the compound of formula Q-3. Catalytic transfer hydrogenation with Pd/C and ammonium formate in methanol affords the compound of formula Q-4. Treatment of the compound of formula Q-4 with the appropriate sulfonyl chloride and pyridine in dichloromethane provides the desired compound of formula Q-5 (wherein, e.g., $R_1$ is 5-cyano-2-pyridyl or 1-methylimidazol-4-yl).

CHART R

Catalytic hydrogenation of commercially available 3-nitropropiophenone of formula R-1 affords the amine of formula R-2. The amine of formula R-2 is treated with diisopropylethylamine and benzyl bromide to give the compound of formula R-3. The dianion of methyl acetoacetate, generated by treatment of commercially available methyl acetoacetate with sodium hydride and n-butyl lithium in tetrahydrofuran at 0° C., is reacted with the ketone of formula R-3. The intermediate hydroxy-ester is cyclized with dilute aqueous hydroxide followed by aqueous hydrochloric acid to give the compound of formula R-4. The compound of formula R-4 is condensed with 3-nitrobenzaldehyde in tetrahydrofuran using aluminum trichloride as a catalyst followed by reaction of the intermediate benzylidene adduct with triethyl aluminum in the presence of copper bromide-dimethyl sulfide to provide the compound of formula R-5. Catalytic hydrogenation with Pd/C affords the diamine of formula R-6. Treatment of the compound of formula R-6 with the appropriate sulfonyl chloride and pyridine in dichloromethane provides the desired compound of formula R-7 (wherein, e.g., $R_1$ is 5-cyano-2-pyridyl or 1-methylimidazol-4-yl).

CHART S

Commercially available 4-pentenoic acid of formula S-1 is coupled with N,O-dimethylhydroxylamine using bis(2-oxo-3-oxazolidinyl)phosphinic chloride to afford the amide of formula S-2. The amide of formula S-2 is reacted with 3-butenyl magnesium bromide in tetrahydrofuran to give the ketone of formula S-3. The ketone of formula S-3 is treated with zinc metal, cuprous chloride and diiodomethane to provide the ketone of formula S-4 (also formula Q-1, see Chart Q above).

CHART T

The compound of formula T-2 (also formula D-1) (whose preparation is specifically described in Chart D and Preparation 17 above from commercially available methyl acetoacetate and 1-phenyl-3-hexanone (formula T-1)) is condensed with 3-nitrobenzaldehyde in tetrahydrofuran using aluminum trichloride as a catalyst followed by reaction of the intermediate benzylidene adduct with t-butylCu (CN)ZnI, (the organometallic reagent derived from zinc metal, 2-iodo-2-methyl-propane, copper cyanide and lithium chloride) to provide the compound of formula T-3. (The preparation of the organometallic reagent is further described in the text corresponding to Preparation J above). Catalytic transfer hydrogenation with Pd/C and ammonium formate in methanol affords the compound of formula T-4. Treatment of the compound of formula T-4 with the appropriate sulfonyl chloride and pyridine in dichloromethane provides the desired compound of formula T-5 (wherein, e.g., $R_1$ is 5-cyano-2-pyridyl or 1-methylimidazol-4-yl).

CHART U

Commercially available 4-fluorohydrocinnamic acid of formula U-1 is coupled with N,O-dimethylhydroxylamine using diethyl cyanophosphonate to provide the amide of formula U-2. Treatment of the amide with n-propylmagnesium chloride yields the ketone of formula U-3. Condensation of the ketone with the dianion of methyl acetoacetate, followed by hydrolysis of the intermediate ester and ring closure, provides the dihydropyrone of formula U-4. Reaction of the dihydropyrone with the aldehyde of formula B-2, prepared as described in Chart B above, in the presence of $AlCl_3$ provides the benzylidene compound of formula U-5; subsequent reaction with Grignard reagents or trialkyl aluminums in the presence of cuprous bromide-dimethyl sulfide complex affords compounds of formula U-6 (wherein, e.g., $R_1$ is ethyl, tert-butyl, or cyclopropyl). Removal of the benzyloxy-carbonyl (CBZ) protecting group is accomplished using ammonium formate and palladium on charcoal to give the amines of formula U-7 (wherein, e.g., $R_1$ is ethyl, tert-butyl, or cyclopropyl). Treatment of the amines with sulfonyl chlorides and pyridine in methylene chloride provides the sulfonamides of formula U-8 (wherein, e.g., $R_1$ is ethyl, tert-butyl, or cyclopropyl and $R_2$ is alkyl, aryl, or heteroaryl).

CHART V

Commercially available 4-fluorobenzaldehyde of formula V-1 is condensed with acetone, under basic conditions, to provide 1,5-Bis-(4-fluorophenyl)-penta-1,4-dien-3-one of formula V-2. The dienone is reduced with magnesium in methanol to provide the ketone of formula V-3. The ketone of formula V-3 is converted to dihydropyrone products of formula V-8 using chemistry analogous to that described in Chart U for the sequence of reactions from U-3 to U-8.

CHART W

Commerically available trans 2-pentenoic acid of formual W-1 is converted to the corresponding acid chloride using oxalyl chloride in methylene chloride to afford the product of formula W-2. The lithium amide of formula W-3, readily available from the treatment of commerically available (S)-(+)-4-phenyl-2-oxazolidinone with n-butyl lithium in tetrahydrofuran at −78° C., is treated with the acid chloride of formula W-2, to give the unsaturated amide of formula W-4. Addition of the amide of formula W-4 to a tetrahydrofuran solution containing commerically available CuBr/ $(CH_3)_2S$ and 3-[bis(trimethylsilyl)amino]phenylmagnesium chloride at −20° C. affords the compound of formula W-5 upon acid workup (Hruby et al., J. Org. Chem., 58(26):7567 (1993)). Treatment of the aniline of formula W-5 with benzyl bromide and sodium carbonate in a water/methylene chloride mixture at reflux; or, potassium carbonate in refluxing acetonitrile, affords the compound of formula W-6. Treatment of the amide of formula W-6 with $TiCl_4$ followed by an amine base in a solvent such as methylene chloride at below −20° C., preferably at −78° C., then addition of the 2-methoxy-2-methyl-1,3-dioxoline of formula W-7 (prepared as described in Santry et al., J. Am. Chem. Soc., 110(9):2910 (1988)) affords the compound of formula W-8. Brief treatment of the compound of formula W-8 with a protic acid affords the β-ketoamide of formula W-9. Further treatment of the compound of formula W-9 with $TiCl_4$ followed by an amine base, then 4-heptanone or propylphenethylketone, affords the compound of formula W-10 wherein $R_1$ is n-propyl or phenethyl, respectively. Treatment of the compound of formula W-10 with sodium hydride or preferably potassium t-butoxide, in an ether solvent then affords the pyrone of formula W-11. Hydrogenation of the compound of formula W-11 using, e.g., a Pd on carbon as the catalyst, affords the compound of formula W-12. Finally, treatment of the compound of formula W-12 with a sulfonyl chloride of formula D-7, wherein $R_4$ is 5-trifluoromethyl-2-pyridinyl, in an organic solvent, such as methylene chloride, in the presence of an organic base, such as pyridine, provides the final compound of formula W-13, wherein $R_1$ is n-propyl or phenethyl (when $R_1$ is phenethyl, it is a pair of diastereomers).

CHART X

The final (R) enantiomer of formula X-13, wherein $R_1$ is n-propyl or phenethyl, is prepared according to the procedures of Chart W.

CHART Y

Acetyl chloride of formula Y-1 is added to the lithium amide of formula Y-2 (also X-3), readily available from the treatment of commerically available (R)-(−)-4-phenyl-2-oxazolidinone with n-butyl lithium in tetrahydrofuran at −78° C., to afford the product of formula Y-3. The compound of formula Y-3 is treated first with $TiCl_4$ in methylene chloride below room temperature, followed by the addition of a tertiary amine base with subsequent addition of the aldehyde of formula Y-4 (aldehyde of the formula Y-4 is readily available from the reaction of commerically available 3-aminobenzaldehyde with benzyl bromide and potassium or sodium carbonate in either acetonitrile or a water/methylene chloride mixture) to yield the compound of formula Y-5. Addition of the amide of formula Y-5 to a tetrahydrofuran solution containing commerically available $CuBr/(CH_3)_2S$ and ethylmagnesium chloride at −20° C. affords the compound of formula Y-6. Alternatively, the commerically available compound of formula Y-7 is treated with oxalyl chloride to afford the compound of formula Y-8. The compound of formula Y-8 is then added to a THF solution of the compound of formula Y-2 (also X-3), readily available from the treatment of commerically available (R)-(−)-4-phenyl-2-oxazolidinone with n-butyl lithium in tetrahydrofuran at −78° C., to yield the compound of formula Y-9. Reduction of the compound of formula Y-9 with iron metal in an alcohol/water mixture then affords the compound of formula Y-10. Treatment of the compound of formula Y-10 with benzyl bromide and potassium or sodium carbonate in either acetonitrile or methylene chloride/water then affords the compound of formula Y-5 which, as described above, is converted to the compound of formula Y-6. The compound of formula Y-6 is converted to final product as described for the conversion of the compound of the formula W-6 to the compound of the formula W-13 (wherein $R_1$ is propyl or phenethyl) in Chart W.

CHART Z

Preparation of the (3S) amide of formula Z-6 is accomplished in the same manner as outlined in Chart Y above, except using the compound of formula Z-2 (also W-3). The compound of the formula Z-6 is converted to final product as described for the conversion of the compound of formula X-6 to the compound of the formula X-13 (wherein $R_1$ is propyl or phenethyl) in Chart Z.

CHART AA

Preparation of the 3(S), 6(S) Diastereomers AA-12 and AA-14: Addition of the unsaturated amide of formula AA-1 (also Y-5) to a tetrahydrofuran solution containing commerically available $CuBr/(CH_3)_2S$ and ethylmagnesium chloride at −20° C. affords the compound of formula AA-2 (same as Y-6). Reduction of the compound of formula AA-2 with a metal hydride (sodium borohydride, lithium aluminum hydride) affords the compound of formula AA-3. Oxidation of the compound of formula AA-3 (Swern oxidation) affords the aldehyde of formula AA-4 which is treated with trimethylsilylcyanide to yield the trimethylsilyl protected cyanohydrin of formula AA-5. Alternatively, the compound of formula AA-2 is treated with trimethyl aluminum followed by N-methyl-O-methyl hydroxyl amine to yield the amide of formula AA-6 which is treated with lithium aluminum hydride to yield the aldehyde of formula AA-4. The trimethylsilyl cyanohydrin of formula AA-5 is reacted with a strong base (e.g. n-butyl lithium) followed by the addition of chiral epoxide of formula AA-7 (also BB-12; the synthesis of which is described in Chart BB) to yield the compound of formula AA-8. The compound of formula AA-8 is dissolved in methylene chloride and cooled to −78° C. and $TiCl_4$ is added followed by a tertiary amine base. To that solution is added trimethylorthoformate followed by additional $TiCl_4$ which yields the compound of formula AA-9. Treatment of the compound of formula AA-9 with base followed by trimethylsilyl chloride, then treatment with an oxidizing agent (ozone), followed by treatment with tetrabutyl ammonium fluoride and then either postassium tert. butoxide or sodium hydride in an ether solvent, then affords the compound of formula AA-10. Hydrogenation of the compound of formula AA-10 then affords the compound of formula AA-11. Finally, treatment of the compound of formula AA-11 with a sulfonyl chloride of formula D-7 in Chart D, wherein $R_4$ is, e.g., 5-trifluoromethyl-2-pyridinyl, in an organic solvent, such as methylene chloride, in the presence of an organic base, such as pyridine, provides the final compound of formula AA-12.

Furthermore, addition of the compound of formula AA-1 to a tetrahydrofuran solution containing commerically available $CuBr/(CH_3)_2S$ and tertiary butylmagnesium chloride at −20° C. affords the compound of formula AA-13. The compound of formula AA-13 is converted to the final product, the compound of formula AA-14, using the chemistry described for the synthesis of AA-12.

CHART BB

Chart BB describes the asymmetric synthesis of epoxides of formula BB-7 and BB-12. Alkylation of 2-methyl-2-propen-1-ol (BB-1) with commerically available benzyl bromide provides the allylic alcohol of formula BB-2 (see Lipshutz, B. H. et al.; Synthesis 1992, 191). Catalytic Sharpless epoxidation using commerically available (+) diethyl L-tartrate provides the epoxy alcohol of formula BB-8 (see: (a) Pfenniger, A.; Synthesis 1986, 89. (b) Johnson, R. A.; Sharpless, K. B. In Catalytic Asymmetric Synthesis; Ojima, I., Ed.; VCH: New York, 1993; Chapter 4.1, 103.). Alkylation of the compound of formula BB-8 with benzyl bromide (see: Lipshutz, B. H. et al.; Synthesis 1992, 191) gives the compound of formula BB-9. Reaction of the compound of formula BB-9 with commerically available ethylmagnesium bromide affords the tertiary alcohol of formula BB-10 (see: Hanson, R. M. Chem. Rev. 1991, 91, 437). Catalytic hydrogenolysis of the compound of formula BB-10 provides the diol of formula BB-11. The compound of formula BB-11 is converted to the chiral epoxide of formula BB-12 by standard methodology (for a discussion of the conversion of vicinal diols to epoxides see: Mitsunobu, O. In Comprehensive Organic Synthesis; Trost, B. M. Ed.; Pergamon Press: Oxford, 1991; Vol. 6; Chapter 1.1, 1).

In an analogous manner, the epoxide of formula BB-7 is ultimately derived from the epoxy alcohol of formula BB-3, which in turn is prepared by Sharpless epoxidation of allylic alcohol BB-2 using commerically available (−) diethyl D-tartrate.

Alternatively, reaction of the epoxy alcohol of formula BB-8 with commerically available 4-toluenesulfonyl chloride under standard conditions affords the tosylate of formula BB-13. Reaction of the compound of the formula BB-13 with ethylmagnesium bromide under conditions similar to those described for the nucleophilic opening of arenesulfonate derivatives of glycidol (see: Klunder, J. M; Onami, T.; Sharpless, K. B. J. Org. Chem. 1989, 54, 1295) affords a mixture of the desired epoxide of formula BB-12 and hydroxytosylate of formula BB-14. The hydroxytosylate of formula BB-14 is readily converted to epoxide BB-12 by the action of $K_2CO_3$ in methanol.

CHART CC

Preparation of the 3(S), 6(R) Diastereomers CC-12 and CC-14: These diastereomers are prepared in a manner identical to that described in Chart AA with the exception that the epoxide of formula CC-7 (same as BB-7) is used.

CHART DD

Preparation of the 3(R), 6(S) Diastereomers DD-12 and DD14: These disatereomers are prepared in a manner identical to that described in Chart AA with the exception that the amide of formula DD-1 (same as Z-5) is used.

CHART EE

Preparation of the 3(R), 6(R) Diastereomers EE-12 and EE-14: These disatereomers are prepared in a manner identical to that described in Chart DD with the exception that the epoxide of formula EE-7 (same as BB-7) is used.

CHART FF

The lithium amide of formula FF-2, readily available from the treatment of commerically available (S)-(+)-4-phenyl-2-oxazolidinone with n-butyl lithium in tetrahydrofuran at −78° C., is treated with acetyl chloride of formula FF-1 to give the amide of formula FF-3. Treatment of the compound of formula FF-3 with $TiCl_4$ followed by treatment with a trialkyamine followed by the addition of commerically available trimethylacetaldehyde affords the compound of formula FF-4. Addition of the amide of formula FF-4 to a tetrahydrofuran solution containing commerically available $CuBr/(CH_3)_2S$ and 3-[bis(trimethylsilyl)amino] phenylmagnesium chloride at −20° C. affords the compound of formula FF-5 upon acid workup. Treatment of the aniline of formula FF-5 with benzyl bromide and sodium carbonate in a water/methylene chloride mixture at reflux; or, potassium carbonate in refluxing acetonitrile, affords the compound of formula FF-6.

The lithium amide of formula FF-7, readily available from the treatment of commerically available (S)-(−)-4-benzyl-2-oxazolidinone with n-butyl lithium in tetrahydrofuran at −78 C, is treated with acetyl chloride of formula FF-1 to give the amide of formula FF-8. Treatment of the compound of formula FF-8 with $TiCl_4$ followed by treatment with a trialkyamine followed by the addition of commerically available trimethylacetaldehyde affords the compound of formula FF-9. Addition of the amide of formula FF-9 to a tetrahydrofuran solution containing commerically available $CuBr/(CH_3)_2S$ and 3-[bis(trimethylsilyl)amino] phenylmagnesium chloride at −20° C. affords a mixture of compounds of formulae FF-10a and FF-10b. Treatment of the aniline of formula FF-10b with benzyl bromide and sodium carbonate in a water/methylene chloride mixture at reflux; or, potassium carbonate in refluxing acetonitrile, affords the compound of formula FF-11 Treatment of the compound of formula FF-11 with $TiCl_4$ in methylene chloride followed by the addition of a tertiary amine base then addition of 2-methyl-2-methoxy-1,3-dioxolane affords an intermediate dioxolane (see W-8 in Chart W) which is treated with mild acid to give the compound of formula FF-12. Treatment of the compound of formula FF-12 with $TiCl_4$, then a tertiary amine base, followed by addition of either 4-heptanone or 1-phenyl-3-hexanone, affords the aldol product of formula FF-13. Treatment of the compound of formula FF-13 with either sodium hydride or potassium tert. butoxide in an ether solvent then affords the compound of formula FF-14. The compound of formula FF-14 is then hydrogenated under an atmosphere of hydrogen in the presence of a Pd on carbon catalyst to give the compound of formula FF-15. Finally, treatment of the compound of formula FF-15 with a sulfonyl chloride of formula D-7 in Chart D, wherein $R_4$ is, e.g., 5-trifluoromethyl-2-pyridinyl, in an organic solvent, such as methylene chloride, in the presence of an organic base, such as pyridine, provides the final compound of formula FF-16, wherein $R_1$ is, e.g., propyl or phenethyl.

CHART GG

Intermediate of formula GG-6 and final products of formula GG-16 are prepared as described in Chart FF with the exception that the (R)-(−)-4-phenyl-2-oxazolidinone and the (R)-(+)-4-benzyl-2-oxazolidinone chiral auxiliaries are used.

CHART HH

The compound of formula HH-1 (W-6), prepared as described in Chart W, is converted to the ester of formula HH-2 wherein R is t-Bu by addition of potassium t-butoxide to a solution of the compound of formula HH-1 in tetrahydrofuran at 0° C. The compound of formula HH-2 wherein R is t-Bu may also be prepared from HH-1 in two steps. First, the oxazolidinone group is cleaved by treatment of the compound of formula HH-1 with lithium hydroxide and hydrogen peroxide at 0° C. in tetrahydrofuran and water. Next, the acid intermediate is treated with N,N-dimethylformamide t-butylacetal in refluxing benzene to produce the ester of formula HH-2 (R is t-Bu). The ester of formula HH-2 wherein R is Me is prepared by heating a mixture of titanium tetrachloride and HH-1 in methanol. The compound of formula HH-3 is prepared by treatment of the ester of formula HH-2 with lithium diisopropylamide or sodium hexamethyldisilylazide to form an enolate, which is then trapped by ethyl formate to give the compound of formula HH-3. Treatment of this intermediate with tosyl chloride in 1,2-dimethoxyethane gives the compound of formula HH-4, which is then converted to the sulfur derivative of formula HH-5 by treatment with a mixture of potassium hydride and thiophenol in tetrahydrofuran. The compound of formula HH-5 is then deprotonated using t-butyllithium in tetrahydrofuran at low temperature. Addition of the epoxide of formula HH-6 (BB-7), prepared as described in Chart BB, and an equivalent of boron trifluoride diethyl etherate affords the compound of formula HH-7. This intermediate is cyclized to the compound of formula HH-8 in situ, or it is isolated and treated with sodium hydride in tetrahydrofuran to produce the cyclic compound of the formula HH-8. The sulfur group is then hydrolyzed using either sodium hydroxide in acetonitrile or aqueous copper chloride to give the dihydropyrone derivative of formula HH-9. The benzyl protecting groups are then removed by catalytic hydrogenation using 10% palladium on carbon in ethyl acetate. The resulting amine of formula HH-10 is converted to the desired sulfonamide derivative of formula HH-11 by treatment with 5-cyanopyridine-2-sulfonyl chloride, prepared using the methods described in Chart O, and pyridine in dichloromethane.

CHARTS II–OO

The diastereomer of formula II-7 is prepared according to Chart II by procedures analogous to those described for the preparation of the diastereomeric product in Chart HH. Likewise, stereoisomers of formulae JJ-11, KK-7, LL-11, MM-7, NN-11, and OO-7 are prepared according to Charts JJ, KK, LL, MM, NN, and OO, respectively, by procedures analogous to those described in Chart HH.

CHART PP

The compound of formula PP-4 (HH-8) is also generated as described in Chart PP. The acid of formula PP-2 is prepared by treatment of the t-butyl ester of formula PP-1 (HH-5), prepared as described in Chart HH, with aqueous acid. The compound of formula PP-2 is then treated with t-butyllithium in tetrahydrofuran at low temperature to produce a dianionic intermediate, which is treated with the epoxide of formula PP-3 (BB-7), prepared as described in Chart BB, and an equivalent of boron trifluoride diethyl etherate to afford the compound of formula PP-4 (HH-8).

CHARTS QQ–WW

The diastereomer of formula QQ-3 (II-4) is prepared according to Chart QQ by procedures analogous to those described for the preparation of the diastereomeric product in Chart PP. Likewise, stereoisomers of formulae RR-4 (JJ-8), SS-3 (KK-4), TT-4 (LL-8), UU-3 (MM-4), VV-4 (NN-8), and WW-3 (OO-4) are prepared according to Charts RR, SS, TT, UU, VV, and WW, respectively, by procedures analogous to those described in Chart PP.

CHART XX

The compound of formula XX-6 (HH-9) is also generated as described in Chart XX. The compound of formula XX-1 (HH-2), prepared as described in Chart HH, is heated neat in commercially-available tris(dimethylamino)methane, bis-(dimethylamino)-methoxymethane or t-butoxy-bis (dimethylamino)methane to generate the intermediate of formula XX-2. One equivalent of t-butyllithium is added to a solution of this ester in tetrahydrofuran at low temperature to produce an anionic intermediate, which is treated with the epoxide of formula XX-3 (BB-7), prepared as described in Chart BB, and an equivalent of boron trifluoride diethyl etherate to afford the compound of formula XX-4. The intermediate of formula XX-4 is cyclized to the dihydropyrone intermediate XX-5 in situ, or XX-4 is isolated and cyclized by treatment with potassium t-butoxide or sodium hydride in tetrahydrofuran. Likewise, intermediate XX-5 is hydrolyzed in situ to form the compound of formula XX-6 (HH-9), or it is isolated and converted to the dihydropyrone of formula XX-6 (HH-9) by treatment with aqueous acid or aqueous base.

CHARTS YY–EEE

The diastereomer of formula YY-5 (II-5) is prepared according to Chart YY by procedures analogous to those described for the preparation of the diastereomeric product in Chart XX. Likewise, stereoisomers of formulae ZZ-6 (JJ-9), AAA-5 (KK-5), BBB-6 (LL-9), CCC-5 (MM-5), DDD-6 (NN-9), and EEE-5 (OO-5) are prepared according to Charts ZZ, AAA, BBB, CCC, DDD, and EEE, respectively, by procedures analogous to those described in Chart XX.

CHART FFF

The diastereomers of formulae FFF-5 and FFF-7 are also prepared by separation of a diastereomeric intermediate. The diastereomeric mixture of formula FFF-1 (W-11), prepared as described in Chart W, is separated into the single diastereomers of formulae FFF-2 (less polar diastereomer) and FFF-3 (more polar diastereomer) using a preparative chiral HPLC column. The benzyl protecting groups of compounds FFF-2 and FFF-3 are then removed by catalytic hydrogenation using 10% palladium on carbon in ethyl acetate to form the amines of formulae FFF-4 and FFF-6, respectively. The amine intermediates are then converted to the desired sulfonamide derivatives of formulae FFF-5 (HH-11) and FFF-7 (II-7), respectively, by treatment with 5-cyanopyridine-2-sulfonyl chloride, prepared using the methods described in Chart O, and pyridine in dichloromethane.

CHART GGG

The m-nitrocinnamic acid chloride (available from the treatment of the commerically available acid with oxylal chloride) of formula GGG-1 is added to an ether solution of the lithiooxazolidinone of formula GGG-2 (readily available from the treatment of commerically available (R)-(+)-4-benzyl-2-oxazolidinone with n-butyl lithium) to afford the compound of formula GGG-3. The compound of formula GGG-3 is treated with either $SnCl_2.2H_2O$ in ethanol or iron powder in a mixture of ethanol/water and containing ammonium chloride, to effect the reduction of the nitro group to the corresponding amine found in the compound of formula GGG-4. The compound of formula GGG-4 is treated with excess benzyl bromide in the presence of potassium or sodium carbonate in an organic solvent (with methylene chloride/water also being added) to yield the compound of formula GGG-5. Addition of a THF solution of the compound of formula GGG-5 to a THF/dimethylsulfide mixture containing the cuprate reagent prepared from ethyl magnesium bromide and copper bromide/dimethyl sulfide complex affords the compound of formula GGG-6. The compound of GGG-6 is then treated with $TiCl_4$, then a tertiary amine, followed by the addition of 2-methyl-2-methyoxy-1,3-dioxolane of formula GGG-7 to yield the compound of formula GGG-8. Treatment of the compound of formula GGG-8 with perchloric acid then yields the compound of forumula GGG-9. Alternately, the compound of formula GGG-6 is treated with a strong base such lithium diisopropylamide in an ether solvent below room temperature and added to a solution of acetyl chloride (also in an ether solvent and cooled to below room temperature) to yield the compound of formula GGG-9. The compound of formula GGG-9 is treated with $TiCl_4$ in methylene chloride followed by the addition of a tertiary amine, then addition of either 4-heptanone or 1-phenyl-3-hexanone to yield the compound of formula GGG-10. The compound of formula GGG-10 is then treated with either sodium hydride or potassium tert-butoxide in an ether solvent to yield the compound of formula GGG-11. The compound of formula GGG-11 is then hydrogenated to yield the compound of formula GGG- 12. The compound of formula GGG-12 is then converted to the final title compound by treatment with a sulfonyl chloride of formula D-7 in Chart D, wherein $R_4$ is, e.g., 5-trifluoromethyl-2-pyridinyl, in an organic solvent, such as methylene chloride, in the presence of an organic base, such as pyridine, provide the final compound of formula GGG-13, wherein $R_1$ is, e.g., n-propyl or phenethyl.

Alternatively, addition of the compound of formula GGG-5 to a THF/dimethylsulfide solution containing a mixture of tert-butyl magnesium chloride and copper bromide/dimethylsulife complex at below 0° C. yields a mixture of compounds of formulae GGG-14a and GGG-14b. Both the compounds of formula GGG-14a and GGG-14b are converted to the final products GGG-19 and GGG-20 using the methodology described in Chart GGG for the synthesis of the C-3 ethyl compound of formula GGG-13.

CHART HHH

The final compounds of formula HHH-13, HHH-19 and HHH-20 are prepared in the same manner as described for the final compounds in Chart GGG.

CHART III

The commerically available acid of formula III-1 is converted to the compound of formula III-2 by treatment with oxalyl chloride. The acid chloride of formula III-3 is then coupled to the lithio oxazolidinone of formula III-3 (readily available from the treatment of commerically available (S)-(–)-4-benzyl-2-oxazolidinone with n-butyl lithium in an ether solvent) to yield the compound of formula III-4. Addition of the amide of formula III-4 to a tetrahydrofuran solution containing commerically available copper bromide/dimethyl sulfide complex and 3-[bis(trimethylsilyl)-amino]phenylmagnesium chloride at –20° C. affords the compounds of formula III-5a and III-5b upon acid workup. These compounds are separable by silica gel chromatography. The compound of formula III-5a is treated with benzyl bromide in either acetonitrile or a methylene chloride/water mixture in the presence of either potassium or sodium carbonate to yield the compound of formula III-6. The compound of formula III-6 is treated with $TiCl_4$ in methylene chloride followed by the addition of a tertiary amine and then 2-methyl-2-methoxy-1,3-dioxolane of formula III-7 is added to yield the compound of formula III-8. Treatment of the compound of the formula III-8 with an acid such as perchloric acid then yields the compound of formula III-9. Treatment of the compound of formula III-9 with $TiCl_4$ in methylene chloride then addition of a tertiary amine, followed by the addition of either 4-heptanone or 1-phenyl-3-hexanone then affords the compound of formula III-10. Treatment of the compound of formula III-10 with either sodium hydride or potassium tert.butoxide then affords the compound of formula III-11. The compound of formula III-11 is hydrogenated to afford the compound of formula III-12. Finally, treatment of the compound of formula III-12 with a sulfonyl chloride of formula D-7 in Chart D, wherein $R_4$ is, e.g., 5-trifluoromethyl-2-pyridinyl, in an organic solvent, such as methylene chloride, in the presence of an organic base, such as pyridine, provides the final compound of formula III-13, where in R, is, e.g., propyl or phenethyl.

In an analogous fashion, starting with the compound of formula III-5b, the final compound of foumula III-14 is also prepared.

CHART JJJ

The final compounds of formula JJJ-13 and JJJ-14 are prepared using the methodology described in Chart III.

CHART KKK

The compound of formula KKK-1 (same as JJJ-9) is treated with $TiCl_4$ in methylene chloride followed by the addition of a tertiary amine. To that solution is added commerically available hydrocinnamaldehyde to afford the compound of formula KKK-2. The compound of formula KKK-2 is oxidized (e.g. $Me_2SO$—$SO_3$/pyridine) to yield the compound of formula KKK-3. The compound of formula KKK-3 is treated with propylmagnesium chloride (where $R_1$ is, e.g., phenyl) to yield the compounds of formula KKK-4a and KKK-4b. Depending on the specific reaction conditions, the ratio of KKK-4a/KKK-4b varies. Alternatively, addition of allylzinc bromide or allylsilane in the presence of $TiCl_4$ or n-$Bu_4NF$ (see Taniguchi et. al. Chemistry Letters 2135, 1992) to the compound of formula KKK-3, followed by hydrogenation, also yields the compounds of formula KKK-4a and KKK-4b. Depending on the specific reaction conditions the ratio of KKK-4a and KKK-4b vary. The compound of KKK-4a is treated with either sodium hydride or potassium tert.butoxide to yield the compound of formula KKK-5. It is also possible that upon treatment of KKK-3 with allyl zinc bromide, allyl silane or propylmagnesium chloride the intermediate metal alkoxide (metals being magnesium, zinc and titanium) will undergo spontaneous cyclization to yield an unsaturated intermediate which upon hydrogenation leads directly to KKK-5 without the isolation of KKK-4a. The compound of formula KKK-5 is hydrogenated to yield the compound of formula KKK-6. Finally, treatment of the compound of formula KKK-6 with a sulfonyl chloride of formula D-7 in Chart D, wherein $R_4$ is, e.g., 5-trifluoromethyl-2-pyridinyl, in an organic solvent, such as methylene chloride, in the presence of an organic base, such as pyridine, provides the final compound of formula KKK-7a, wherein, e.g., $R_1$ and $R_2$ are phenyl or propyl, respectively.

In an analogous manner to that described for the conversion of the compound of formula KKK-4a to the compound of formula KKK-7a, the compound of formula KKK-4b is converted to the final product of formula KKK-7b.

In an analogous manner to that described for the conversion of the compound of formula KKK-1 to final products of the formula KKK-7a and KKK-7b, the compounds of formula KKK-14a and KKK-14b, wherein $R_1$ and $R_1$ are, e.g., methyl or phenethyl, respectively, are prepared by starting with the compound of formula KKK-8 (same as III-6).

In an analogous manner to that described for the conversion of the compound of formula KKK-1 and the compound of formula KKK-8 (each containing the 4-benzyl-2-oxazolidinone auxillary) to the final products of the formulae KKK-7a and KKK-7b, and the final formulae KKK-14a and KKK-14b respectively, , the compounds of the formula KKK-15 and the compound of the formula KKK-19 (each containing the 4-phenyl-2-oxazolidinone auxiliary) are converted to the final products of the formula KKK-7a and KKK-7b, and the final products of formula KKK-14a and KKK-14b, respectively, wherein $R_1$ and $R_2$ are, e.g., methyl or phenethyl, respectively.

CHART LLL

The compound of formula LLL-1 (same as: wherein R is phenyl, AA-1; wherein R is benzyl, GGG-5) is added to a THF solution of commerically available copper bromide/dimethylsulfide complex and tert. butylmagnesium chloride below 0° C. to afford the compound of formula LLL-2 as the major diasteromeric product. Where R is defined as benzyl in the compound of formula LLL-2, that compound is treated with TiCl$_4$ in methylene chloride below 0° C. followed by the addition of a tertiary amine, then the addition of 2-methyl-2-methoxy-1,3-dioxolane to yield the compound of formula LLL-3. The compound of formula LLL-3 is treated with a protic acid to afford the compound of formula LLL-4. The compound of formula LLL-4 is treated with TiCl$_4$ in methylene chloride below 0° C. followed by the addition of an amine base, then addition of either 4-heptanone or 1-phenyl-3-hexanone affords the compound of formula LLL-5 wherein R$_1$ is, e.g., n-propyl or phenethyl, respectively. Treatment of the compound of forumla LLL-5 with either sodium hydride or potassium tert. butoxide in an ether solvent affords the pyrone of formula LLL-6. Hydrogenation of the compound of formula LLL-6 using, e.g. a Pd on carbon as the catalyst, affords the compound of formula LLL-7. Finally, treatment of the compound of formula LLL-7 with a sulfonyl chloride of formula D-7 in Chart D, wherein R$_4$ is, e.g., 5-trifluoromethyl-2-pyridinyl, in an organic solvent, such as methylene chloride, in the presence of an organic base, such as pyridine, provides the final compound of formula LLL-8, wherein R$_1$ is, e.g., propyl or phenethyl.

The compound of formula LLL-2, where R is phenyl, is treated with TiCl$_4$ in methanol to yield the compound of formula LLL-9. The compound of formula LLL-9 is treated with a base to effect hydrolysis to give the compound of formula LLL-10. The acid of formula LLL-10 is treated with methyl lithium in an ether solvent to yield the compound of formula LLL-11. The ketone of formula LLL-11 is treated with TiCl$_4$ in methylene chloride below 0° C. followed by the addition of an amine base, then addition of either 4-heptanone or 1-phenyl-3-hexanone, to give the compound of formula LLL-12 wherein R$_1$ is, e.g., n-propyl or phenethyl, respectively. The compound of formula LLL-12 is treated with TiCl$_4$ in methylene chloride below 0° C. followed by the addition of an amine base, then the addition of trimethyl orthoformate to yield the compound of formula LLL-13. The compound of formula LLL-13, in an organic solvent such as THFor methylene chloride, is treated with a base followed by the addition of trimethylsilyl chloride. The solvent is removed from the aforementioned reaction and the resulting protected tertiary alcohol is oxidized (e.g. Ru cat./t-BuOH (see Murahashi et. al. Chemistry Letters 2237, 1992); tritylperchlorate/methylene chloride (see Mukaiyama et. al. Chemistry Letters 1255, 1985), ozone/methylene chloride (see Can. J. Chem. 49, 2465, 1971)) to afford the lactone LLL-6 directly or in a two step sequence where the intermediate ester is lactonized with the aid of either sodium hydride, potassium tert. butoxide or n-Bu$_4$NF in an ether solvent. The conversion of the compound of formula LLL-6 to the final product is described above.

Following the same strategy the compound of formula LLL-16 is converted to the final products of formula LLL-23 wherein R$_1$ is propyl or phenethyl.

CHART MMM

The diastereomers of formulae MMM-5 and MMM-7 are also prepared by separation of a diastereomeric mixture of these two compounds. Alternatively, the diastereomeric mixture of formula MMM-1 (X-11 where R$_1$ is, e.g., phenethyl) prepared as described in Chart X, is separated into the single diastereomers of formulae MMM-2 and MMM-3 using a preparative chiral HPLC column. The benzyl protecting group groups of compounds MMM-2 (less polar diastereomer) and MMM-3 (more polar diastereomer) are then removed by catalytic hydrogenation using 10% palladium on carbon in ethyl acetate to form the amines of fromulae MMM-4 and MMM-6, respectively. The amine intermediates are then converted to the desired sulfonamide derivatives of formulae MMM-5 and MMM-7, respectively, by treatment with 5-trifluoromethyl-2-pyridinylsulfonyl chloride, prepared using the methods described in Chart O, and pryidine in methylene chloride.

CHART NNN

The commercially available (1R, 2S)-(–)ephedrine of formula NNN-2 is treated with triethylamine and the acid chloride of formula NNN-1 (W-2), prepared as described in Chart W, to afford the amide of formula NNN-3. A t-butyl methyl ether solution of this amide at 0° C. is treated sequentially with 1.1 equivalents of propyl magnesium chloride and 2.0 equivalents of 3-[bis(trimethylsilyl)amino] phenyl magnesium chloride, stirred for 3 hours at 0° C., washed with ammonium chloride solution and concentrated in vacuo. The residue is then stirred with silica gel in chloroform to afford the compound of formula NNN-4. Alternatively, the above reaction mixture may be washed with 1 N hydrochloric acid solution during the workup instead of ammonium chloride solution to generate the compound of formula NNN-4. The amine is then converted to the derivative of formula NNN-5 by heating a mixture of the compound of formula NNN-4, 2.2 equivalents of benzyl bromide and 2.2 equivalents of sodium carbonate in acetonitrile. The intermediate of formula NNN-5 is then treated with 2 equivalents of lithium diisopropylamide in tetrahydrofuran to form the lithium enolate, which is trapped with acetyl chloride to afford the β-ketoamide of formula NNN-6. A solution of this amide in methylene chloride at low temperature may be treated with 1 equivalent of titanium tetrachloride and 1 equivalent of diisopropylethylamine, followed by 4-heptanone to generate the compound of formula NNN-7. Conversion of the amide of formula NNN-7 to the dihydropyrone of formula NNN-8 may be accomplished with either sodium hydride in tetrahydrofuran or with aqueous acid. The benzyl protecting groups may then be removed by catalytic hydrogenation using 10% palladium on carbon in ethyl acetate. The resulting amine of formula NNN-9 is converted to the desired sulfonamide derivative of formula NNN-10 (W-12) by treatment with 5-trifluoromethylpyridine-2-sulfonyl chloride, prepared using the methods described in Chart O, and pyridine in dichloromethane.

CHART OOO

The compound of formula OOO-7 (NNN-8) may also be generated as described in Chart OOO. The amide of formula OOO-1 (NNN-5) is treated with aqueous acid to afford the compound of formula OOO-2. The methyl ester of formula OOO-3 is formed from the compound of formula OOO-2 using catalytic acid in methanol. Treatment of the methyl ester of formula OOO-3 with lithium diisopropylamide, followed by trimethylsilyl chloride gives the compound of formula OOO-4. Treatment of this intermediate with either 2-methoxy-2-methyl-1,3-dioxolane followed by hydrolysis or treatment with acetyl chloride affords the β-keto ester of formula OOO-5. This β-keto ester is converted to the compound of formula OOO-6 by treatment of either the titanium enolate (formed using 1 equivalent of titanium tetrachloride and 1 equivalent of diisopropylethylamine in methylene chloride at low temperature) or the lithium dianion (formed using 2 equivalents of lithium diisopropylamide in tetrahydrofuran at low temperature) with 4-heptanone. The dihydropyrone of formula OOO-7 (NNN-8) is formed by treatment of the compound of formula OOO-6 with either sodium hydride in tetrahydrofuran or aqueous base.

CHART PPP

Reduction of the commercially available ethyl 4,4,4-trifluorobutyrate of formula PPP-1, with DiBAL-H followed by in situ alkylation with 2-phenethyl magnesium bromide or chloride produces the alcohol of formula PPP-2. Swern oxidation of the alcohol gives the ketone of formula PPP-3. The ketone is converted to the dihydropyrone of formula PPP-4 by alkylation with the dianion of methyl acetoacetate followed by saponification to the acid and lactonization with base.

CHART QQQ

The aluminum trichloride catalyzed reaction of the dihydropyrone of formula QQQ-1 (PPP-4), prepared as described in Chart PPP, with the CBZ-protected 3-aminobenzaldehyde (which is available from the reaction of benzyl chloroformate with commercially available 3-aminobenzaldehyde) of formula QQQ-2 and subsequent reaction with trialkyl aluminums or Grignard reagents in the presence of cuprous bromide-dimethylsulfide complexes provides compounds of formula QQQ-3. The individual stereoisomers are separated by HPLC using a chiral stationary phase to give the four possible stereoisomers of formula QQQ-4, QQQ-5, QQQ-6, and QQQ-7. Transfer hydrogenation of each stereoisomer with Pd/C and ammonium formate gives the amines of formula QQQ-8, QQQ-9, QQQ-10, and QQQ-11. Treatment of the amines with sulfonyl chlorides of general formula QQQ-12 and pyridine in methylene chloride provides compounds of general formula QQQ-13, QQQ-14, QQQ-15, and QQQ-16, wherein $R_2$ is, e.g., 5-cyano-2-pyridinyl, 1-methyl-4-imidazolyl, or 5-amino-2-pyridinyl.

CHART RRR

The procedure for the preparation of compounds of formula RRR-11 to RRR-15 is described in Chart RRR. The pyrone RRR-A is coupled to the Cbz protected benzaldehyde RRR-B in THF with $AlCl_3$ followed by treatment of the resulting intermediate with $R_1MgX$ where X=Br or Cl in THF with added $CuBr.Me_2S$ to give RRR-1. De-protection of the resulting intermediate with 10% Pd/C in methanol with added ammonium formate gives RRR-2. Separation of the racemic compound RRR-1 into its 4 enantiomers gives RRR-3 to RRR-6. De-protection of the resulting intermediates with 10% Pd/C in methanol with added ammonium formate gives the free amines RRR-7 to RRR-10. Treatment of the amines RRR-7 to RRR-10 and RRR-2 with an appropriate sulfonyl chloride gives the sulfonamides RRR-11 to RRR-14 and RRR-15, respectively.

CHART SSS

The procedure for the preparation of compounds of formula SSS-7 to SSS-9 is described in Chart SSS. The pyrone SSS-A is coupled to the Cbz protected benzaldehyde SSS-B in THF with $AlCl_3$ followed by treatment of the resulting intermediate with $R_1MgX$ where X=Br or Cl in THF with added $CuBr.Me_2S$ to give SSS-1. De-protection of the resulting intermediate with 10% Pd/C in methanol with added ammonium formate gives SSS-2. Separation of the racemic compound SSS-1 into its 2 enantiomers gives SSS-3 to SSS-4. De-protection of the resulting intermediates with 10% Pd/C in methanol with added ammonium formate gives the free amines SSS-5 to SSS-6. Treatment of the amine with an appropriate sulfonyl chloride gives the sulfonamides SSS-7 to SSS-9.

CHART TTT

The procedure for the preparation of compounds of formula TTT-6 and TTT-7 is described in Chart TTT. The pyrone TTT-A is coupled to the Cbz protected benzaldehyde TTT-B in THF with $AlCl_3$ followed by treatment of the resulting intermediate with $R_1MgX$ where X=Br or Cl in THF with added $CuBr.Me_2S$ to give TTT-1. Separation of the racemic compound TTT-1 into its 2 enantiomers gives TTT-2 and TTT-3. De-protection of the resulting intermediates with 10% Pd/C in methanol with added ammonium formate gives the free amines TTT-4 and TTT-5. Treatment of the amine with an appropriate sulfonyl chloride gives the sulfonamides TTT-6 and TTT-7.

CHART UUU

Reaction between commercially available thiourea in hot ethanol with commercially available 2-chloro-5-nitropyridine of formula UUU-1 affords the isothiourea compound of formula UUU-2. Treatment of the compound of formula UUU-2 with aqueous sodium carbonate and sodium hydroxide provides the thiol compound of formula UUU-3. Oxidation of the compound of formula UUU-3 with chlorine gas provides the sulfonyl chloride compound of formula UUU-4. Treatment of the compound of formula D-5 (e.g., the compound of formula T-4 wherein $R_1$ is 2-phenylethyl, $R_2$ is propyl, $R_1$ is tert-butyl) in dichloromethane with two equivalents of pyridine followed by one equivalent of the compound of formula UUU-4 gives the sulfonamide compound of formula UUU-5 (wherein $R_1$ is 2-phenylethyl, $R_2$ is propyl, $R_3$ is tert-butyl). Reduction of the compound of formula UUU-5 with palladium on carbon and ammonium formate affords the compound of formula UUU-6, which is the compound: 5-amino-N-[3-(1-[5,6-dihydro-4-hydroxy-2-oxo-6-(2-phenylethyl)-6-propyl-2H-pyran-3-yl]-2,2-dimethylpropyl)phenyl]-2-pyridinesulfonamide (Formula UUU-6: $R_1$ is 2-phenylethyl, $R_2$ is propyl, $R_3$ is tert-butyl).

CHART VVV

The compound of Formula VVV-1, which is 2-mercapto-5-carbamoylpyridine, is prepared via published procedure (J. Chem. Soc. 1948, 1939–1945). Treatment of a suspension of this compound in dilute hydrochloric acid with chlorine gas at 0° provides the sulfonyl chloride of Formula VVV-2.

CHART WWW

Amines of the generic formula WWW-1 are reacted with benzyl chloroformate to provide CBZ derivatives WWW-2. The individual stereoisomers of formula WWW-2 are generally separated by chiral HPLC methods, and then converted back to the free amines WWW-3 via hydrogenolysis. Sulfonation of the amines in the usual manner known to one of ordinary skill in the art provides the final compounds of formula WWW-4, in stereochemically pure form.

CHART XXX

Dihydropyrone XXX-1, which is prepared by procedures analogous to those in described in Preparations 17 and 84, is condensed with meta-nitrobenzaldehyde in the presence of aluminum trichloride to provide the benzylidene intermediate XXX-2. Conjugate reduction of the double bond using sodium cyanoborohydride, followed by reduction of the nitro group via catalytic hydrogenation, affords amine of formula XXX-4, which is converted to the sulfonamides XXX-5 by treatment with the appropriate sulfonyl chloride in dichloromethane and pyridine.

CHART YYY

Dihydropyrones of Formula YYY-1, wherein $R_1$ and $R_2$ are propyl or phenethyl, and which are synthesized as described in Preparation 84, are condensed with the aldehyde of Formula B-2 using aluminum trichloride to provide the benzylidene intermediates of formula YYY-2. Conjugate addition of tert-butylmagnesium chloride in the presence of copper (I) bromide-dimethyl sulfide provides compounds of Formula YYY-3. Hydrogenolytic deprotection affords amines of formula YYY-4, which are converted to the sulfonamides of formula YYY-5 using the appropriate sulfonyl chloride in dichloromethane with added pyridine. The procedures used are analogous to those described for Chart D.

CHART ZZZ

Polymeric meta-aminobenzaldehyde is protected by treating with benzyl bromide and potassium carbonate in acetonitrile at reflux to yield the compound of formula ZZZ-2. A vinyl anion is generated from 2-bromovinyltrimethylsilane of formula ZZZ-3 by treatment with t-butyl lithium at $-78°$ C. to $-20°$ C. The vinyl anion so generated is cooled to $-78°$ C. and the diprotected meta-aminobenzaldehyde of formula ZZZ-2 is added to afford the desired allylic alcohol of formula ZZZ-3. The alcohol is easily converted to the acetate or carbonate of formula ZZZ-5 by standard means (e.g., $CH_3COCl$, pyridine, $CH_2Cl_2$, $0°$ C.). These substrates participate in palladium catalyzed allylic substitutions as delineated in Charts AAAA–CCCC (C. G. Frost; J. Howarth; J. M. J. Williams, Tetrahedron: Asymmetry (1992) 3:1089–1122).

CHART AAAA

The sodium salt of methyl acetoacetate of formula AAAA-1 generated by treating methyl acetoacetate with sodium hydride at $0°$ C. in either DMF or THF acts as the nucleophile in a palladium catalyzed allylic substitution. If this reaction is run in the presence of palladium allyl chloride dimer of formula AAAA-3 as the palladium source and a chiral phosphine ligand (P. von Matt; A. Pfaltz, Angew. Chem. Int. Ed. Engl. (1993) 32:566–568), a kinetic resolution of the starting allylic acetate or carbonate results in the synthesis of optically enriched allylated product of formula AAAA-4. If the reaction with nucleophile is slow, the acetate generated from formation of the pi-allyl palladium intermediate isomerizes the two possible diastereomeric pi-allyl complexes so that a stereoselective synthesis of the allylated product occurs (B. M. Trost; P. E. J. Strege, Am. Chem. Soc. (1977) 99:1649). Treatment of the resulting vinyl silane of formula AAAA-4 with para-toluenesulfonic acid in acetonitrile at reflux affords the desilylated olefin of formula AAAA-5. The dihydropyrone product of formula AAAA-7 is formed by generating the dianion of the ketoester under standard conditions (J. R. Peterson; T. J. Winger; C. P. Miller, Syn. Comm. (1988) 18(9):949–963), (NaH, n-butyllithium, THF) and quenching with an appropriate symmetrical ketone of formula AAAA-6 (such as 4-heptanone). Hydrolysis of the ester (0.1 N NaOH/THF) and acidic work-up provide the dihydropyrone product of formula AAAA-7. Standard hydrogenation conditions reduce the olefin and deprotect the amine. Subsequent treatment of the amino compound with the appropriate sulfonyl chloride of formula AAAA-8 (pyridine, $CH_2Cl_2$) provides the desired sulfonamide protease inhibitor of formula AAAA-9.

CHART BBBB

Alternatively, the palladium catalyzed allylic substitution may be performed with the sodium anion of the requisite dihydropyrone J. R. (Peterson; T. J. Winger; C. P. Miller, Syn. Comm. (1988) 18(9):949–963) of formula BBBB-1 (dihydropyrone, NaH, THF or DMF, $0°$ C.) as the nucleophilic partner. Once again, if palladium allyl chloride dimer of formula BBBB-3 and a chiral phosphine ligand (P. von Matt; A. Pfaltz, Angew. Chem. Int. Ed. Engl. (1993) 32:566–568) are employed as catalyst, a kinetic resolution results in the synthesis of optically pure allylated dihydropyrone of formula BBBB-4; and a stereoselective synthesis of the allylated product will occur if the reaction with nucleophile is slow relative to isomerization of the two possible diastereomeric pi-allyl complexes by acetate generated from formation of the pi-allyl palladium intermediate. Subsequent, desilylation (p-TsOH, $CH_3CN$), olefin reduction and amine deprotection ($H_2$/Pd/C), and sulfonylation of the amine ($ArSO_2Cl$, pyridine, $CH_2Cl_2$) with a compound of the formula BBBB-5 provides the desired dihydropyrone protease inhibitor of formula BBBB-6.

CHART CCCC

Treatment of m-bis(benzyl)aminobenzoic acid of formula CCCC-1 with oxalyl chloride to form the acid chloride and reaction with bis(trimethylsilyl)acetylene and $AlCl_3$ in methylene chloride affords the propargylic ketone of formula CCCC-2. Asymmetric reduction of the ketone with a chiral borane (H. C. Brown; Beeraraghavan Ramachandran, P. Acc. Chem. Res. (1992) 25:16–24) such as DIP chloride [(+) or (−)-β-chlorodiisopinocampheylborane] and acetylene reduction with REDAL provides the allylic alcohol of formula CCCC-3, primarily as a single enantiomer. Formation of the carbonate of formula CCCC-4 (methyl chloroformate, pyridine, $CH_2Cl_2$, $0°$ C.) and subjection to palladium catalyzed allylic substitution with the desired dihydropyrone of formula CCCC-5 as nucleophile affords primarily one enantiomer of the allylated dihydropyrone of formula CCCC-6 (retention of configuration) (T. Hayashi; T. Hagihara; M. Konishi; M. J. Kumada, Am. Chem. Soc. (1983) 105:7768–7770). This product is transformed into the desired protease inhibitor of formula CCCC-7 as previously described in Chart BBBB.

CHART DDDD

The known cycloalkylpyranones of formula DDDD-1 are prepared by acylation of the trimethylsilyl enol ether of the corresponding cycloalkyl ketone with malonyl dichloride as described in R. Effenberger, T. Ziegler, K. -H. Schonwalder, T. Kesmarszky, B. Bauer Chem. Ber. 119: 3394–3404 (1986). Catalytic hydrogenation of the cycloalkylpyranones of formula DDDD-1 with platinum oxide ($PtO_2$) in acetic acid produces the cycloalkyldihydropyrones of Formula DDDD-2. The intermediate of formula DDDD-3 is then formed by aluminum chloride ($AlCl_3$) catalyzed condensation of the compound of formula DDDD-2 with 3-nitrobenzaldehyde, which is commercially available. Subsequent reaction of the intermediate of formula DDDD-3 with trialkyl aluminums in the presence of copper bromide-dimethyl sulfide complex ($CuBr—Me_2S$) or zinc reagents generated from zinc metal, alkyl halide, cuprous cyanide (CuCN) and lithium chloride (LiCl) provides compounds of formula DDDD-4 which contain a C-3a branched substituent. Catalytic hydrogenation of compounds of the formula DDDD-4 with Pd/C in ethanol (EtOH) provides the amine derivatives of the formula DDDD-5. Treatment of the compounds of formula DDDD-5 with sulfonyl chlorides of formula DDDD-6 and pyridine in methylene chloride ($CH_2Cl_2$) provides compounds of the formula DDDD-7 (e.g., wherein n is 1, 2, or 3; $R_1$ is ethyl or t-butyl; $R_2$ is 4-cyanophenyl or 5-cyano-2-pyridyl).

Procedures by which the compounds of the present invention are prepared are also described in International application, PCT/US93/10645, filed Nov. 9, 1993 (WO 94/11361, published May 26, 1994), and International application, PCT/US94/00938, filed Feb. 3, 1994 (WO 94/18188, published Aug. 18, 1994), both of which are incorporated by reference herein.

As is apparent to those of ordinary skill in the art, the compounds of the present invention can occur in several diastereomeric forms, depending on the configuration around the asymmetric carbon atoms. All such diastereomeric forms are included within the scope of the present invention.

Also, the dihydropyrones of the present invention can be separated into individual stereoisomers or prepared as individual diastereomers. A diastereomeric pair can be prepared wherein C-3α is a homogeneous center and C-6 is a mixture. All such enantiomeric and diastereomeric forms, and mixtures thereof, are included within the scope of the present invention.

The compounds of the present invention of formula I can exist in several tautomeric forms, including the particular enol forms as depicted by formula I and IA and the keto form of formula IB. (For formulas I, IA and IB, the dashed line indicates that a double bond may be present or absent.) All such tautomeric forms are included within the scope of the present invention. For compounds of the present invention which are 4-hydroxy-pyran-2-ones of formula VII, the enol form predominates. For compounds of the present invention which are 5,6-dihydro-4-hydroxy-pyran-2-ones of formula VI, a mixture of the enol and keto forms is commonly expected.

Also, the compounds of the present invention of formula II can exist in several tautomeric forms of the 4-hydroxy-pyrone ring, including the particular enol forms depicted by formulas II and IIA, and the particular keto form depicted by formula IIB, and mixtures thereof. All such tautomeric forms are included within the scope of the present invention.

The compounds of the present invention may be in either free form or in protected form at one or more of the remaining (not previously protected) carboxyl, amino, hydroxy, or other reactive groups. The protecting groups may be any of those known in the art. Examples of nitrogen and oxygen protecting groups are set forth in T. W. Greene, Protecting Groups in Organic Synthesis, Wiley, New York, (1981); J. F. W. McOmie, ed. Protective Groups in Organic Chemistry, Plenum Press (1973); and J. Fuhrhop and G. Benzlin, Organic Synthesis, Verlag Chemie (1983). Included among the nitrogen protective groups are t-butoxycarbonyl (BOC), benzyloxycarbonyl, acetyl, allyl, phthalyl, benzyl, benzoyl, trityl and the like.

The present invention provides for compounds of formula I and II or pharmacologically acceptable salts and/or hydrates thereof. Pharmacologically acceptable salts refers to those salts which would be readily apparent to a manufacturing pharmaceutical chemist to be equivalent to the parent compound in properties such as formulation, stability, patient acceptance and bioavailability. Examples of salts of the compounds of formula I include acidic salts, such as sodium, potassium, lysine, arginine and calcium salts, and basic salts, such as the hydrochloride salt, wherein the R substituents in formula I contain a basic moiety. Examples of salts of the compounds of formula II include the hydrohalide salts, such as the hydrochloride and hydroiodide salts; and the sodium, potassium, calcium, lysine and arginine salts.

Also included as salts of the compounds of formulae I and II of the present invention are the bis-salts, such as the bis-arginine, bis-lysine, bis-sodium, bis-potassium and bis-calcium salts, provided that the compound contains, for example, $-NHSO_2-$, $-SO_3H$, $-CONH-$, $-OH$ or COOH. The bis-sodium salt is most preferred.

The compounds of the present invention are useful for treating patients infected with human immunodeficiency virus (HIV) which results in acquired immunodeficiency syndrome (AIDS) and related diseases. For this indication, these compounds may be administered by oral, intranasal, transdermal, subcutaneous and parenteral (including intramuscular and intravenous) routes in doses of 0.1 mg to 100 mg/kg of body weight per day.

Those skilled in the art would know how to formulate the compounds of this invention into appropriate pharmaceutical dosage forms. Examples of the dosage forms include oral formulations, such as tablets or capsules, or parenteral formulations, such as sterile solutions.

When the compounds in this invention are administered orally, an effective amount is from about 0.1 mg to 100 mg per kg of body weight per day. Either solid or fluid dosage forms can be prepared for oral administration. Solid compositions, such as compressed tablets, are prepared by mixing the compounds of this invention with conventional ingredients such as talc, magnesium stearate, dicalcium phosphate, magnesium aluminum silicate, calcium sulfate, starch, lactose, acacia, methyl cellulose, or functionally similar pharmaceutical diluents and carriers. Capsules are prepared by mixing the compounds of this invention with an inert pharmaceutical diluent and placing the mixture into an appropriately sized hard gelatin capsule. Soft gelatin capsules are prepared by machine encapsulation of a slurry or solution of the compounds of this invention with an acceptable inert oil such as vegetable oil or light liquid petrolatum.

Pharmaceutically acceptable formulations of the disodium salts of the compounds of the present invention include: soft elastic capsules (SEC) containing a suspension of the salt; salt tablets; salt spray coated sucrose beads; or salt spray dried matrix with an enteric or non-enteric polymer.

Formulations of the compounds of the present invention, which present the compounds in free acid form, preferably contain the free acid in non-crystalline form. Examples of such formulations include: soft elastic capsules containing free acid solution; non-crystalline spray dried matrix of the free acid with an enteric or non-enteric polymer; or a solid non-crystalline matrix of free acid in polyethyleneglycol (PEG) or Gelucire 44/14 (Gattefosse, Saint Priest, France).

Syrups are prepared by dissolving the compounds of this invention in an aqueous vehicle and adding sugar, aromatic flavoring agents and preservatives. Elixirs are prepared using a hydroalcoholic vehicle such as ethanol, suitable sweeteners such as sugar or saccharin and an aromatic flavoring agent. Suspensions are prepared with an aqueous vehicle and a suspending agent such as acacia, tragacanth, or methyl cellulose.

When the compounds of this invention are administered parenterally, they can be given by injection or by intravenous infusion. An effective amount is from about 0.1 mg to 100 mg per kg of body weight per day. Parenteral solutions are prepared by dissolving the compounds of this invention in liquid vehicle and filter sterilizing the solution before placing in a suitable sealable vial or ampule. Parenteral suspensions are prepared in substantially the same way except a sterile suspension vehicle is used and the compounds of this invention are sterilized with ethylene oxide or suitable gas before it is suspended in the vehicle.

The exact route of administration, dose, or frequency of administration would be readily determined by those skilled in the art and is dependant on the age, weight, general physical condition, or other clinical symptoms specific to the patient to be treated.

Patients to be treated would be those individuals: 1) infected with one or more than one strain of a human immunodeficiency virus as determined by the presence of either measurable viral antibody or antigen in the serum and 2) having either an asymptomatic HIV infection or a symptomatic AIDS defining infection such as i) disseminated histoplasmosis, ii) isoporiasis, iii) bronchial and pulmonary candidiasis including pneumocystis pneumonia, iv) non-Hodgkin's lymphoma, or v) Kaposi's sarcoma and being less than sixty years old; or having an absolute CD4+ lymphocyte count of less than 500/mm$^3$ in the peripheral blood. Treatment would consist of maintaining an inhibitory level of the compounds of this invention in the patient at all times and would continue until the occurrence of a second symptomatic AIDS defining infection indicates alternate therapy is needed.

The utility of representative compounds of the present invention has been demonstrated in the biological tests described below:

The HIV protease screening assay is based on fluorescently labeled substrate which can be resolved from nonlabeled cleavage product using special beads coated with streptavidin. The substrate is biotinylated at the amino terminal arginine and fluorescently labeled with fluorescein isothiocynate (FITC) at the carboxyl terminal lysine. This assay has been employed to detect novel, nonpeptidic inhibitors of HIV-1 protease. Substrate (20 μM of 0.2 μM), sample (10 μl of desired concentraion), and enzyme (10 μl of 0.1 μM) are added to a 96 well pandex plate. The assay is run in 0.1 M sodium acetate buffer at pH 5.5 in the presence of 1.0 M sodium chloride and 0.05% NP-40 with incubated in the dark for one hour at room temperature. Strepavidin coated polystyrene beads {40 μl of 0.1% (w/v)} are added and the plate is incubated in the dark for an additional half hour. The labeled cleavage product is separated from the unreacted substrate via filtration and is read on the Idexx screen machine. The data are analyzed by appropriate computer algorithms to ascertain percent inhibition values.

Determination of $K_i$ values utilizes the same materials and equipment employed for percent inhibition studies. Two-fold serial dilutions are made for a given inhibitor from 2, 3 or 4 starting concentrations with a total of 24, 36 or 48 individual inhibitor concentrations. These dilutions are performed utilizing the BioMek robotics system. The assay consists of 10 μL of 40 nM HIV-1 protease, 10 μL of the various inhibitor concentrations, and 20 μL of 200 μM substrate (40 μL total). The reaction is allowed to proceed for 90 min at room temperature, terminated with 40 μL of avidin beads and processed (supra vide). An inhibitor with a known $K_i$ is run in parallel to verify the validity of the assay. The data is processed utilizing a computer program employing a nonlinear least square analysis of the data to generate the $K_i$ values.

The % inhibition values and/or $K_i$ values of representative compounds of the present invention tested in the HIV protease screening assay are listed in Table I below.

In the enzyme inhibition assay described above, the sensitivity of $K_i$ value determination is in part limited by the ability to continue to lower the enzyme concentration for compounds with high binding affinity. To prevent de-dimerization at low enzyme concentration, a tandemly linked enzyme is prepared in which the two monomers are covalently linked by an appropriate stretch of amino acid residues. Using the latter enzyme, the sensitivity of the inhibition assay is improved since much lower enzyme concentration can be utilized, as compared to the condition using the wild-type enzyme.

Protocol for K. value determination with tandem HIV protease: Due to the greater stability (no dedimerization) of the single chain tethered (tandem) HIV protease enzyme, in which the two monomeric units are engineered to be linked by a polypeptide stretch, the method for the determination of $K_i$ values for inhibitors uses very low concentrations of enzyme (0.2 nM) and increased incubation times (96 hours) at room temperature to improve the sensitivity in the measurement of $K_i$ values for very potent inhibitors. The starting inhibitor concentrations are determined based on preliminary enzyme inhibition screening results which estimate the expected potency of the inhibitor. Inhibitor concentrations are then prepared using the Biomek 1000 (Beckman) and the Quadra 96 (Tomtec). Substrate (biotinylated at the amino terminal arginine and fluorescently labeled with fluorescein at the carboxyl terminal lysine), inhibitor and the tandem enzyme are allowed to react in solution at pH 5.5 (buffers identical to those used with the native dimeric enzyme) in the dark for 96 hours. Streptavidin coated polystyrene beads are added to stop the reaction. The labeled cleavage product is separated from unreacted substrate via filtration. Residual fluorescence is quantitated with the Idexx SM2000 (Idexx) and the resulting data are analyzed using the NLLSF program.

The % inhibition values and/or $K_i$ values of representative compounds of the present invention tested in the HIV protease screening assay and/or tandem HIV protease assay are listed in Table II below.

Several compounds of the present invention, such as N-[3-(1-[5,6-Dihydro-4-hydroxy-2-oxo-6-(2-phenethyl)-6-propyl-2H-pyran-3-yl]-2,2-dimethylpropyl)phenyl]-1-methyl-1H-imidazole-4-sulfonamide were tested in known human cell lines, such as human T-cell lines, e.g., MT4 and H9, which were infected with HIV-1$_{IIIB}$, and certain of these compounds were further tested in peripheral blood mononuclear cells (PBMC), which were infected with HIV-1$_{JRCSF}$ (a clinical isolate). The compounds were found to inhibit retroviral replication.

The following compounds of the present invention are preferred:

5-Cyano-N-[3-(1-[5,6-dihydro-4-hydoxy-2-oxo-6-(2-phenethyl)-6-propyl-2H-pyran-3-yl]-2,2-dimethylpropyl)phenyl]-2-pyridinesulfonamide N-[3-{1-(4-Hydroxy-5,6-dihydro-2-oxo-6-phenethyl-6-propyl-2H-pyran-3-yl)propyl}phenyl]-5-cyanopyridine-2-sulfonamide N-[3-(1-[5,6-Dihydro-4-hydroxy-2-oxo-6-(2-phenethyl)-6-propyl-2H-pyran-3-yl]-2,2-dimethylpropyl)phenyl]-1-methyl-1H-imidazole-4-sulfonamide N-[3-[1-(4-hydroxy-2-oxo-6-phenethyl-6-propyl-5,6-dihydro-2H-pyran-3-yl)-propyl]-phenyl]-1-methyl-1H-imidazole-4-sulfonamide N-[3-{1-(4-Hydroxy-5,6-dihydro-2-oxo-6-(2-(4-fluorophenyl)ethyl)-6-propyl-2H-pyran-3-yl)-2,2-dimethylpropyl}phenyl]-5-cyanopyridine-2-sulfonamide N-[3-{1-(4-Hydroxy-5,6-dihydro-2-oxo-6-(2-(4-fluorophenyl)ethyl)-6-propyl-2H-pyran-3-yl)propyl}phenyl]-5-cyanopyridine-2-sulfonamide N-[3-{1-(4-Hydroxy-5,6-dihydro-2-oxo-6-(2-(4-fluorophenyl)ethyl)-6-propyl-2H-pyran-3-yl)-2,2-dimethylpropyl}phenyl]-1-methyl-1H-imidazole-4-sulfonamide N-[3-{1-(4-Hydroxy-5,6-dihydro-2-oxo-6,6-dipropyl-2H-pyran-3-yl)-2,2-dimethylpropyl}phenyl]-5-cyanopyridine-2-sulfonamide N-[3-{1-(4-Hydroxy-5,6-dihydro-2-oxo-6,6-dipropyl-2H-pyran-3-yl)propyl}phenyl]-5-cyanopyridine-2-sulfonamide N-[3-{1-(4-Hydroxy-5,6-dihydro-2-oxo-6,6-dipropyl-2H-pyran-3-yl)-2,2-dimethylpropyl}phenyl]-1-methyl-1H-imidazole-4-sulfonamide N-[3-{1-(4-Hydroxy-5,6-dihydro-2-oxo-6,6-bis(2-(4-fluorophenyl)ethyl)-2H-pyran-3-yl)-2,2-dimethylpropyl}phenyl]-5-cyanopyridine-2-sulfonamide N-[3-{1-(4-Hydroxy-5,6-dihydro-2-oxo-6,6-bis(2-(4-fluorophenyl)ethyl)-2H-pyran-3-yl)propyl}phenyl]-5-cyanopyridine-2-sulfonamide N-[3-{1-(4-Hydroxy-5,6-dihydro-2-oxo-6,6-bis(2-(4-fluorophenyl)ethyl)-2H-pyran-3-yl)-2,2-dimethylpropyl}phenyl]-1-methyl-1H-imidazole-4-sulfonamide N-[3-(1-[6,6-Bis-(2-cyclopropyl-ethyl)-5,6-dihydro-4-hydroxy-2-oxo-2H-pyran-3-yl]-2,2-dimethyl-propyl)phenyl]-5-cyano-2-pyridinesulfonamide N-[3-(1-[6,6-Bis-(2-cyclopropyl-ethyl)-5,6-dihydro-4-hydroxy-2-oxo-2H-pyran-3-yl]propyl)phenyl]-5-cyano-2-pyridinesulfonamide N-[3-(1-[6,6-Bis-(2-cyclopropyl-ethyl)-5,6-dihydro-4-hydroxy-2-oxo-2H-pyran-3-yl]-2,2-dimethyl-propyl)phenyl]-1-methyl-1H-imidazole-4-sulfonamide 5-cyano-N-[3-(R or S)-[1-[5,6-dihydro-4-hydroxy-2-oxo-6-(2-phenethyl)-6-(R or S)-(3,3,3-trifluoropropyl)-2H-pyran-3-yl]-2,2-dimethylpropyl]phenyl]-2-pyridinesulfonamide N-[3-(R or S)-[1-[5,6-dihydro-4-hydroxy-2-oxo-6-(R or S)-(2-phenethyl)-6-(3,3,3-trifluoropropyl)-2H-pyran-3-yl]-2,2-dimethylpropyl]phenyl]-1-methyl-1H-imidazole-4-sulfonamide, 5-amino-N-[3-(R or S)-[1-[5,6-dihydro-4-hydroxy-2-oxo-6-(2-phenethyl)-6-(R or S)-(3,3,3-trifluoropropyl)-2H-pyran-3-yl]-2,2-dimethylpropyl]phenyl]-2-pyridine-sulfonamide, N-[3-(R or S)-[1-[5,6-dihydro-4-hydroxy-2-oxo-6-(2-phenethyl)-[6-(R or S)-propyl]-2H-pyran-3-yl]-2,2-dimethylpropyl]phenyl]-2-pyridinesulfonamide, 5-Trifluoromethyl-N-[3-[1-[4-hydroxy-2-oxo-6,6-di-n-propyl-5,6-dihydro-2H-pyran-3-yl]-propyl]-phenyl]-2-pyridinesulfonamide, 5-Trifluoromethyl-N-[3-(R or S)-[1-[4-hydroxy-2-oxo-6,6-di-n-propyl-5,6-dihydro-2H-pyran-3-yl]-propyl]-phenyl]-2-pyridinesulfonamide, or (3R or S)-N-[3-[1-(5,6-Dihydro-4-hydroxy-2-oxo-6,6-dipropyl-2H-pyran-3-yl)propyl]phenyl]-6-(trifluoromethyl)-2-pyridinesulfonamide 5-Trifluoromethyl-N-[3-(R or S)-[1-[4-hydroxy-2-oxo-6,6-di-phenethyl-5,6-dihydro-2H-pyran-3-yl]-propyl]-phenyl]-2-pyridinesulfonamide, 5-Trifluoromethyl-N-[3-[1-[5,6-dihydro-4-hydroxy-2-oxo-6-(2-phenethyl)-6-n-propyl-2H-pyran-3-yl]-2,2-dimethylpropyl]-phenyl]-2-pyridinesulfonamide, 5-Trifluoromethyl-N-[3(R or S)-[1-[5,6-dihydro-4-hydroxy-2-oxo-6(R or S)-(2-phenethyl)-6(R or S)-n-propyl-2H-pyran-3-yl]-2,2-dimethylpropyl]-phenyl]-2-pyridine-sulfonamide, 5-Trifluoromethyl-N-[3(R or S)-[1-[5,6-dihydro-4-hydroxy-2-oxo-6(R or S)-(2-phenethyl)-6(R or S)-n-propyl-2H-pyran-3-yl]-propyl]-phenyl]-2-pyridinesulfonamide, or (3R or S, 6R or S)-N-[3-[1-(5,6-Dihydro-4-hydroxy-2-oxo-6-propyl-6-phenethyl-2H-pyran-3-yl)propyl]phenyl]-5-(trifluoromethyl)-2-pyridinesulfonamide 5-Amino-N-[3-(1-[5,6-dihydro-4-hydroxy-2-oxo-6-(2-phenylethyl)-6-propyl-2H-pyran-3-yl]-2,2-dimethylpropyl)phenyl]-2-pyridinesulfonamide, 5-Cyano-N-[3(R or S)-(1-[5,6-dihydro-4-hydroxy-2-oxo-6(R or S)-(2-phenylethyl)-6-propyl-2H-pyran-3-yl]-2,2-dimethylpropyl)phenyl]-2-pyridine-sulfonamide, 5-Cyano-N-[3-(1-[5,6-dihydro-6,6-diisobutyl-4-hydroxy-2-oxo-2H-pyran-3-yl]-2,2-dimethylpropyl)phenyl]-2-pyridinesulfonamide, N-[3(R or S)-[1-(5,6-Dihydro-4-hydroxy-2-oxo-6(R or S)-[2-phenylethyl]-6-propyl-2H-pyran-3-yl)-2,2-dimethylpropyl]phenyl]-1-methyl-1H-imidazole-4-sulfonamide, 5-Cyano-N-[3-(1-[5,6-dihydro-4-hydroxy-2-oxo-6-(2-phenylethyl)-6-propyl-2H-pyran-3-yl]cyclopropylmethyl)phenyl]-2-pyridinesulfonamide, 5-Amino-N-[3(R or S)-(1-[5,6-dihydro-4-hydroxy-2-oxo-6(R or S)-(2-phenylethyl)-6-propyl-2H-pyran-3-yl]-2,2-dimethylpropyl)phenyl]-2-pyridine-sulfonamide, 5-Amino-N-[3(R or S)-(1-[5,6-dihydro-4-hydroxy-2-oxo-6(R or S)-(2-phenylethyl)-6-propyl-2H-pyran-3-yl]propyl)phenyl]-2-pyridinesulfonamide, 5-Amino-N-[3(R or S)-(1-[6(R or S)-(2-[4-fluorophenyl]ethyl)-5,6-dihydro-4-hydroxy-2-oxo-6-propyl-2H-pyran-3-yl]-2,2-dimethylpropyl)phenyl]-2-pyridine-sulfonamide, N-[3(R or S)-(1-[5,6-Dihydro-6,6-dipropyl-4-hydroxy-2-oxo-2H-pyran-3-yl]-2,2-dimethylpropyl)phenyl]-1-methyl-1H-imidazole-4-sulfonamide, 5-Amino-N-[3(R or S)-(1-[5,6-dihydro-6,6-dipropyl-4-hydroxy-2-oxo-2H-pyran-3-yl]-2,2-dimethylpropyl)phenyl]-2-pyridinesulfonamide, 5-Cyano-N-[3(R or S)-(1-[5,6-dihydro-6,6-dipropyl-4-hydroxy-2-oxo-2H-pyran-3-yl]-2,2-dimethylpropyl)phenyl]-2-pyridinesulfonamide, N-[3(R or S)-(1-[6,6-Bis(2-phenylethyl)-5,6-dihydro-4-hydroxy-2-oxo-2H-pyran-3-yl]propyl)phenyl]-1-methyl-1H-imidazole-4-sulfonamide, N-[3(R or S)-(1-[6,6-Bis(2-phenylethyl)-5,6-dihydro-4-hydroxy-2-oxo-2H-pyran-3-yl]propyl)phenyl]-5-cyano-2-pyridinesulfonamide, N-[3-{1-(4-Hydroxy-5,6-dihydro-2-oxo-6,6-bis(2-phenylethyl)-2H-pyran-3-yl)propyl}phenyl]-5-cyanopyridine-2-sulfonamide, N-[3-{1(R or S)-(4-Hydroxy-5,6-dihydro-2-oxo-6(R or S)-phenethyl-6-propyl-2H-pyran-3-yl)propyl}phenyl]-5-cyanopyridine-2-sulfonamide, N-[3-{1(R or S)-(4-Hydroxy-5,6-dihydro-2-oxo-6(S or R)-phenethyl-6-propyl-2H-pyran-3-yl)propyl}phenyl]-1-methyl-1H-imidazole-4-sulfonamide, N-[3-{1-(4-Hydroxy-5,6-dihydro-2-oxo-6,6-bis(2-phenylethyl)-2H-pyran-3-yl)-2,2-dimethylpropyl}phenyl]-1-methyl-1H-imidazole-4-sulfonamide, N-[3-{1(R or S)-(4-Hydroxy-5,6-dihydro-2-oxo-6(R or S)-(2-(4-fluorophenyl)ethyl)-6-propyl-2H-pyran-3-yl)-2,2-dimethylpropyl}phenyl]-5-cyanopyridine-2-sulfonamide, N-[3-{1(R or S)-(4-Hydroxy-5,6-dihydro-2-oxo-6(R or S)-(2-(4-fluorophenyl)ethyl)-6-propyl-2H-pyran-3-yl)-2,2-dimethylpropyl}phenyl]-1-methyl-1H-imidazole-4-sulfonamide, N-[3-{1(S or R)-(4-Hydroxy-5,6-dihydro-2-oxo-6,6-bis(2-phenylethyl)-2H-pyran-3-yl)-2,2-dimethylpropyl}phenyl]-5-aminopyridine-2-sulfonamide N-[3-{1(S or R)-(4-Hydroxy-5,6-dihydro-2-oxo-6,6-bis(2-phenylethyl)-2H-pyran-3-yl)-2,2-dimethylpropyl}phenyl]-1-methyl-1H-imidazole-4-sulfonamide N-[3-{1(S or R)-(4-Hydroxy-5,6-dihydro-2-oxo-6,6-bis(2-phenylethyl)-2H-pyran-3-yl)-2,2-dimethylpropyl}phenyl]-5-cyanopyridine-2-sulfonamide N-[3-{1(R or S)-(4-Hydroxy-5,6-dihydro-2-oxo-6,6-dipropyl-2H-pyran-3-yl)-propyl}phenyl]-5-cyanopyridine-2-sulfonamide The following compounds of the present invention are more preferred:

5-Cyano-N-[3-(1-[5,6-dihydro-4-hydoxy-2-oxo-6-(2-phenethyl)-6-propyl-2H-pyran- 3-yl]-2,2-dimethylpropyl)phenyl]-2-pyridinesulfonamide 5-cyano-N-[3-(R or S)-[1-[5,6-dihydro-4-hydroxy-2-oxo-6-(2-phenethyl)-6-(R or S)-(3,3,3-trifluoropropyl)-2H-pyran-3-yl]-2,2-dimethylpropyl]phenyl]-2-pyridinesulfonamide, 5-Trifluoromethyl-N-[3-(R or S)-[1-[4-hydroxy-2-oxo-6,6-di-n-propyl-5,6-dihydro-2H-pyran-3-yl]-propyl]-phenyl]-2-pyridinesulfonamide, or (3R or S)-N-[3-[1-(5,6-Dihydro-4-hydroxy-2-oxo-6,6-dipropyl-2H-pyran-3-yl)propyl]phenyl]-5-(trifluoromethyl)-2-pyridinesulfonamide 5-Trifluoromethyl-N-[3(R or S)-[1-[5,6-dihydro-4-hydroxy-2-oxo-6(R or S)-(2-phenethyl)-6(R or S)-n-propyl-2H-pyran-3-yl]-propyl]-phenyl]-2-pyridinesulfonamide, or (3R or S, 6R or S)-N-[3-[1-(5,6-Dihydro-4-hydroxy-2-oxo-6-propyl-6-phenethyl-2H-pyran-3-yl)propyl]phenyl]-5-(trifluoromethyl)-2-pyridinesulfonamide 5-Cyano-N-[3(R or S)-(1-[5,6-dihydro-4-hydroxy-2-oxo-6(R or S)-(2-phenylethyl)-6-propyl-2H-pyran-3-yl]-2,2-dimethylpropyl)phenyl]-2-pyridine-sulfonamide, N-[3(R or S)-[1-(5,6-Dihydro-4-hydroxy-2-oxo-6(R or S)-[2-phenylethyl]-6-propyl-2H-pyran-3-yl)-2,2-dimethylpropyl]phenyl]-1-methyl-1H-imidazole-4-sulfonamide, N-[3-{1(R or S)-(4-Hydroxy-5,6-dihydro-2-oxo-6(S or R)-phenethyl-6-propyl-2H-pyran-3-yl)propyl}phenyl]-5-cyanopyridine-2-sulfonamide, N-[3-{1(R or S)-(4-Hydroxy-5,6-dihydro-2-oxo-6(R or S)-(2-(4-fluorophenyl)-ethyl)-6-propyl-2H-pyran-3-yl)-2,2-dimethylpropyl}phenyl]-5-cyanopyridine-2-sulfonamide, N-[3-{1(R or S)-(4-Hydroxy-5,6-dihydro-2-oxo-6(R or S)-(2-(4-fluorophenyl)-ethyl)-6-propyl-2H-pyran-3-yl)-2,2-dimethylpropyl}phenyl]-1-methyl-1H-imidazole-4-sulfonamide, and N-[3-{1(R or S)-(4-Hydroxy-5,6-dihydro-2-oxo-6,6-dipropyl-2H-pyran-3-yl)-propyl}phenyl]-5-cyanopyridine-2-sulfonamide.

The following compounds of the present invention are most preferred (see Chart EEE):

N-[3-{1(R or S)-(4-Hydroxy-5,6-dihydro-2-oxo-6(S or R)-phenethyl-6-propyl-2H-pyran-3-yl)propyl}phenyl]-5-cyanopyridine-2-sulfonamide of formula EEE-1, N-[3-{1(R or S)-(4-Hydroxy-5,6-dihydro-2-oxo-6,6-dipropyl-2H-pyran-3-yl)-propyl}phenyl]-5-cyanopyridine-2-sulfonamide of formula EEE-2, N-[3(R or S)-[1-(5,6-Dihydro-4-hydroxy-2-oxo-6(R or S)-[2-phenylethyl]-6-propyl-2H-pyran-3-yl)-2,2-dimethylpropyl]phenyl]-1-methyl-1H-imidazole-4-sulfonamide of formula EEE-3, 5-Trifluoromethyl-N-[3(R or S)-[1-[5,6-dihydro-4-hydroxy-2-oxo-6(R or S)-(2-phenethyl)-6(R or S)-n-propyl-2H-pyran-3-yl]-propyl]-phenyl]-2-pyridinesulfonamide of formula EEE-4, or (3R or S, 6R or S)-N-[3-[1-(5,6-Dihydro-4-hydroxy-2-oxo-6-propyl-6-phenethyl-2H-pyran-3-yl)propyl]phenyl]-5-(trifluoromethyl)-2-pyridinesulfonamide 5-Trifluoromethyl-N-[3-(R or S)-[1-[4-hydroxy-2-oxo-6,6-di-n-propyl-5,6-dihydro-2H-pyran-3-yl]-propyl]-phenyl]-2-pyridinesulfonamide of formula EEE-5, or (3R or S)-N-[3-[1-(5,6-Dihydro-4-hydroxy-2-oxo-6,6-dipropyl-2H-pyran-3-yl)propyl]phenyl]-5-(trifluoromethyl)-2-pyridinesulfonamide.

Also the following compounds of the present invention, which are readily prepared by the synthetic procedures set out herein, are most preferred:

(3R)-N-[3-[-(5,6-Dihydro-4-hydroxy-2-oxo-6,6-dipropyl-2H-pyran-3-yl)propyl]phenyl]-5-(trifluoromethyl)-2-pyridinesulfonamide (3R)-N-[3-[1-(5,6-Dihydro-4-hydroxy-2-oxo-6-propyl-6-phenethyl-2H-pyran-3-yl)propyl]phenyl]-5-(trifluoromethyl)-2-pyridinesulfonamide.

DESCRIPTION OF THE PREFERRED EMBODIMENTS

In the Preparations and Examples below and throughout this document:

| | |
|---|---|
| ° C. | is degrees Centigrade. |
| $^1$H-NMR | is proton nuclear magnetic resonance spectrum. |
| $^{13}$C-NMR | is carbon nuclear magnetic resonance spectrum. |
| δ | is chemical shift (parts per million) relative to TMS. |
| AlCl$_3$ | is aluminum chloride. |
| Anal. | is analytical data. |
| Br | is benzyl. |
| CBZ | is benzyloxycarbonyl. |
| CDCl$_3$ | is deuterio-chloroform. |
| CD$_3$OD | is deuterio-methanol. |
| CH$_2$Cl$_2$ | is methylene chloride. |
| cm$^{-1}$ | is reciprocal centimeters. |
| CuBr$_2$ | is cupric bromide. |
| DMSO | is dimethylsulfoxide. |
| DMSO$_{D6}$ | is deuterio dimethylsulfoxide. |
| EI MS | is electron impact mass spectroscopy. |
| EtOAc | is ethyl acetate. |
| Et$_3$Al | is triethyl aluminum. |
| FAB MS | is fast-atom-bombardment mass spectroscopy. |
| HCl | is hydrochloric acid. |
| H$_2$O | is water. |
| HOBT | is 1-hydroxybenzotriazole hydrate. |
| HRMS | is high-resolution mass spectroscopy. |
| KOH | is potassium hydroxide. |
| M | is molar (concentration). |
| MeOH | is methanol. |
| Me$_2$S | is dimethyl sulfide. |
| mg | is milligram. |
| MgSO$_4$ | is magnesium sulfate. |
| mL | is milliliter. |
| mmHg | is millimeter of mercury. |

-continued

| | |
|---|---|
| MP | is melting point. |
| N | is normal (concentration). |
| NaCl | is sodium chloride. |
| NaOH | is sodium hydroxide. |
| NaH | is sodium hydride. |
| NaHCO$_3$ | is sodium bicarbonate. |
| Na$_2$CO$_3$ | is sodium carbonate. |
| Na$_2$SO$_4$ | is sodium sulfate. |
| NH$_4$Cl | is ammonium chloride. |
| Pd/C | is palladium on charcoal. |
| R$_f$ | is chromatographic movement relative to solvent front. |
| TFA | is trifluoroacetic acid. |
| THF | is tetrahydrofuran. |
| TMS | is tetramethyl silane. |

The following Preparations and Examples illustrate the present invention:

Preparation 1 Cyclopropyl-(3-nitrophenyl)methanone (Formula A-2) Refer to Chart A.

A 500-mL, three-necked, round-bottomed flask with a gas outlet and a 250-mL pressure-equalizing addition funnel is charged with cyclopropyl phenyl ketone of formula A-1 (30 mL) and cooled to −40° C. The addition funnel is charged with nitric acid (180 mL), which is added to the reaction mixture dropwise over 2 h. The reaction mixture is stirred another 3.5 h at −40–0° C., and then quenched by pouring onto 500 mL of ice. The mixture is extracted with three 150-mL portions of ethyl acetate. The organic layers are combined, washed with two 250-mL portions of saturated sodium bicarbonate, dried over magnesium sulfate, filtered, and concentrated to give 41.117 g of yellow solid in an orange oil. Recrystallization from 65 mL of methanol yields 20.664 g of the title product as light yellow crystals.

Physical characteristics are as follows:

$^1$H NMR (CDCl$_3$) δ 8.85, 8.43, 8.33, 7.70, 2.72, 1.36–1.31, 1.20–1.14 ppm.

Preparation 2 Cyclopropyl-(3-aminophenyl)methanone (Formula A-3) Refer to Chart A.

A 500-mL Parr hydrogenation flask is charged with 2.1 g of 10% platinum on carbon and a solution of the title product of Preparation 1 (20.6 g) in 250 mL of methanol. The reaction mixture is shaken for 50 min under 44 psi of hydrogen, then filtered through Celite twice. The light green solution is then concentrated to give 15.744 g of the title product as a green oil.

Physical characteristics are as follows:

$^1$H NMR (CDCl$_3$) δ 7.42, 7.30–7.23, 6.88, 3.83, 2.63, 1.24–1.19, 1.05–0.99 ppm.

Preparation 3 N-[3-cyclopropylmethanone] benzenesulfonamide (Formula A-4) Refer to Chart A.

A 500-mL, three-necked, round-bottomed flask with a nitrogen inlet is charged with the title product of Preparation 2 (15.7 g) and 200 mL of methylene chloride. Benzenesulfonyl chloride (12 mL) and pyridine (7.8 mL) are added, and the reaction mixture is stirred at room temperature for 45 min. 10% HCl (200 mL) is added to quench the reaction. The organic layer is separated, dried over magnesium sulfate, filtered, and concentrated to give 28.638 g of orange solid. Recrystallization from 75 mL of hot methylene chloride yields the title product (22.264 g) as a pink solid.

Physical characteristics are as follows:

MP 98–101° C.

$^1$H NMR (CDCl$_3$) δ 7.81–7.73, 7.62, 7.55–7.35, 2.60, 1.30–1.25, 1.10–1.03 ppm.

$^{13}$C NMR (CDCl$_3$) δ 200.4, 138.8, 137.2, 133.0, 129.5, 129.0, 127.0, 125.1, 124.7, 120.5, 17.3, 12.1 ppm.

IR (mineral oil) 3239, 3222, 1653, 1449, 1339, 1259, 1176, 1165, 1093, 939, 687 cm$^{-1}$.

Elemental analysis, found: C, 63.70; H, 5.01; N, 4.78.

MS (EI) m/e 301, 260, 160, 141, 77.

For high resolution, found: 301.0772.

Preparation 4 N-[3-cyclopropylmethanol] benzenesulfonamide (Formula A-6) Refer to Chart A.

A 500-mL, three-necked, round-bottomed flask with a nitrogen inlet is charged with the title compound of Preparation 3 (21.133 g), 200 mL of tetrahydrofuran, and 100 mL of ethanol. The flask is cooled to 0° C. in an ice bath, and sodium borohydride (10.6 g) is added in small portions over 20 minutes. The reaction mixture is stirred at room temperature for ca. 18 h, and then cooled again in an ice bath to 0° C. 10% HCl (100 mL) is added dropwise over 45 min, and the mixture is stirred another 1 h at 0° C. The reaction mixture is then extracted with three 100-mL portions of methylene chloride. The organic layers are combined, dried over magnesium sulfate, filtered and concentrated to give 25.015 g of pale yellow oil. Column chromatography on 150 g of silica gel (elution with 50–65% ether in hexane followed by 2–5% methanol in methylene chloride) yields 18.692 g of the title product as a white solid.

Physical characteristics are as follows:

MP 112–114° C.

$^1$H NMR (CDCl$_3$) δ 7.69, 7.42, 7.32, 7.25, 7.12, 7.05–6.96, 3.82, 3.19, 1.03–0.94, 0.51–0.46, 0.39–0.29, 0.19–0.16 ppm.

$^{13}$C NMR (DMSO) δ 147.0, 139.7, 137.4, 132.9, 129.3, 128.6, 126.8, 121.8, 118.5, 117.8, 75.0, 19.2, 3.1, 2.3 ppm.

IR (mineral oil) 3523, 3249, 1449, 732 cm$^{-1}$.

Elemental analysis, found: C, 63.41; H, 5.79; N, 4.86.

MS (EI) m/e 303, 275, 262, 77.

For high resolution, found: 303.0935.

Preparation 5 4-Hydroxy-10-propyl-2H-cycloocta[b]pyran-2-one (Formula A-7) Refer to Chart A.

A 250-mL, three-necked, round-bottomed flask with a nitrogen inlet and a 125-mL pressure-equalizing addition funnel is charged with diisopropyl amine (3.6 mL) and 15 mL of tetrahydrofuran. The addition funnel is charged with 4-hydroxy-2H-cycloocta[b]pyran-2-one of formula A-6 (2.292 g) and 35 mL of tetrahydrofuran. The flask is cooled to 0° C. in an ice bath, n-butyllithium (16.3 mL of 1.6 M solution in hexanes) is added dropwise over 3 min, and the reaction mixture is stirred another 15 min at 0° C. The solution of 4-hydroxy-2H-cycloocta[b]pyran-2-one in THF is added dropwise over 35 min, and the reaction mixture is stirred for another 25 min at 0° C. Hexamethylphosphoramide (4 mL) is added in one portion, and iodopropane (1.3 mL) is added dropwise over 2 min. The reaction mixture is allowed to warm to room temperature and stirred for ca. 18 h. 30 mL of 10% HCl is added and the aqueous layer is separated. The pH of the aqueous layer is lowered from 10 to 2 with concentrated HCl, and the aqueous layer is extracted with two 50-mL portions of methylene chloride. The organic layers are combined, dried over magnesium sulfate, filtered, and concentrated to give an orange oil, which is partitioned between 100 mL of 1 N sodium hydroxide and 50 mL of ether. The aqueous layer pH is adjusted from 14 to 1 with concentrated hydrochloric acid, and is then extracted with two 50-mL portions of methylene chloride. The organic layers are then combined, dried over magnesium sulfate, and concentrated to give an orange oil, which is diluted with 100 mL of ether and washed with three 25-mL portions of 10% HCl. The organic layer is then dried over magnesium sulfate, filtered, and concentrated to give 1.829 g of orange solid. Column chromatography on 100 g of silica gel (elution with 0–10% methanol in methylene chloride) gives 1.358 g of a pale orange solid. An additional column chromatography on 150 g of silica gel (elution with 10% ether and 1% acetic acid in methylene chloride) gives 0.705 g of the title product as a yellow solid.

Physical characteristics are as follows:
$^1$H NMR (CDCl$_3$) δ 11.38, 5.68, 3.02–2.93, 2.20, 1.98–1.82, 1.73–1.58, 1.46–1.25, 1.24–1.08, 0.89 ppm.
$^{13}$C NMR (CDCl$_3$) δ 172.3, 168.3, 165.3, 114.8, 89.7, 38.6, 36.0, 33.3, 30.1, 27.2, 25.5, 22.9, 21.0, 13.9 ppm.
IR (mineral oil) 1679, 1641, 1617, 1492 cm$^{-1}$.
Elemental analysis, found: C, 70.90; H, 8.36.
MS (EI) m/e 236, 208, 166.
For high resolution, found: 236.1414.

EXAMPLE 1
N-[3-[cyclopropyl(5,6,7,8,9,10-hexahydro-4-hydroxy-2-oxo-10-propyl-2H-cycloocta[b]pyran-3-yl)methyl]phenyl] benzenesulfonamide (Formula A-8) Refer to Chart A.

A 100-mL, three-necked, round-bottomed flask with a 35-mL pressure-equalizing addition funnel filled with 3 A molecular sieves and fitted with a reflux condenser and a nitrogen inlet is charged with the title compound of Preparation 5 (0.196 g), p-toluenesulfonic acid (0.040 g), and 30 mL of methylene chloride. The title product of Preparation 4 (0.252 g) is added, and the reaction mixture is heated to reflux for 2 h, then stirred at room temperature for an additional hour. The reaction mixture is then diluted with 20 mL of methylene chloride and washed with 60 mL of 1:1 saturated sodium bicarbonate and brine, 30 mL of water, and 30 mL of brine. The aqueous layers are combined and extracted with 30 mL of methylene chloride. The organic layers are then combined, dried over magnesium sulfate, filtered, and concentrated to give 0.576 g of crude material. Column chromatography on 35 g of silica gel (elution with 20–80% ether in hexane) yields 0.096 g of the title compound as a white solid.

Physical characteristics are as follows:
MP 87–90° C. (decomposition).
MS (EI) m/e 521, 493, 380, 275, 262, 249, 144, 77.
For high resolution, found: 521.2236.

EXAMPLES 2–7

Following procedures analogous to those described above, the following additional compounds of the present invention are prepared:

2) 4-Cyano-N-[3-(R or S)-[cyclopropyl(5,6,7,8,9,10-hexahydro-4-hydroxy-2-oxo-(R or S)-10-propyl-2H-cycloocta[b]pyran-3-yl)methyl]phenyl]benzenesulfonamide 3) 4-Cyano-N-[3-(R or S)-[cyclopropyl(5,6,7,8,9,10-hexahydro-(R or S)-10-cyclopropylmethyl-4-hydroxy-2-oxo-2H-cycloocta[b]pyran-3-yl)methyl]phenyl]benzenesulfonamide 4) 4-Cyano-N-[3-(R or S)-[cyclopropyl(5,6,7,8,9,10-hexahydro-(R or S)-10-benzyl-4-hydroxy-2-oxo-2H-cycloocta[b]pyran-3-yl)methyl]phenyl]benzenesulfonamide 5) N-[3-(R or S)-[cyclopropyl(5,6,7,8,9,10-hexahydro-4-hydroxy-2-oxo-(R or S)-10-propyl-2H-cycloocta[b]pyran-3-yl)methyl]phenyl]-1-methyl-1H-imidazole-4-sulfonamide 6) N-[3-(R or S)-[cyclopropyl(5,6,7,8,9,10-hexahydro-(R or S)-10-cyclopropylmethyl-4-hydroxy-2-oxo-2H-cycloocta[b]pyran-3-yl)methyl]phenyl]-1-methyl-1H-imidazole-4-sulfonamide 7) N-[3-(R or S)-[cyclopropyl(5,6,7,8,9,10-hexahydro-(R or S)-10-benzyl-4-hydroxy-2-oxo-2H-cycloocta[b]pyran-3-yl)methyl]phenyl]-1-methyl-1H-imidazole-4-sulfonamide Preparation 6 (3-Benzaldehyde)-carbamic acid, phenylmethyl ester (Formula B-2) Refer to Chart B.

A flask with a nitrogen inlet is charged with sodium bicarbonate (10.4 g) in 200 mL of THF and 200 mL of water, and m-aminobenzaldehyde of formula B-1 (10.0 g) and benzyl chloroformate (13.6 mL) are added sequentially. The mixture is stirred at room temperature for 40 min. Ether is then added, and the organic layer is separated, washed with saturated sodium bicarbonate, dried over sodium sulfate, filtered and concentrated to give a brown oil. Column chromatography on 300 g of silica gel yields 16.3 g of the title compound as a pale yellow oil. An analytical sample is crystallized from ethyl acetate-hexane.

Physical characteristics are as follows:
MP 100–104° C.
$^1$H NMR (CDCl$_3$) δ 9.98, 7.91, 7.69, 7.59, 7.43–7.35, 6.83, 5.23 ppm.
$^{13}$C NMR (CDCl$_3$) δ 191.8, 153.0, 138.6, 137.1, 135.6, 129.7, 128.6, 128.4, 128.3, 124.6, 124.2, 119.1, 67.2 ppm.
IR (mineral oil) 3269, 2954, 2925, 2868, 2855, 1729, 1682, 1597, 1560, 1465, 1455, 1326, 1294, 1237, 1229, 1170, 1155, 1048, 695 cm$^{-1}$.
Elemental analysis, found: C, 70.74; H, 5.14; N, 5.33.
MS (EI) m/e 255, 211, 91.
For high resolution, found 255.0900.

Preparation 7 [3-(1-Hydroxy-3-methylbutyl)phenyl]-carbamic acid, phenylmethyl ester (Formula B-3 wherein R$_1$ is isobutyl) Refer to Chart B.

A flask with a nitrogen inlet is charged with the title compound of Preparation 6 (4.0 g) and 60 mL of dry tetrahydrofuran. The mixture is cooled to 0° C., and isobutyl magnesium chloride (17.2 mL) is added. The reaction mixture is then allowed to warm to room temperature and stir for 2 hours. Saturated ammonium chloride is added to quench the reaction, and the mixture is partitioned between ether and water. The organic layer is washed with water and concentrated to give 5.78 g of pale yellow oil. The crude material is crystallized from ethyl acetate-hexane to yield 4.13 g of the title compound as white crystals.

Physical characteristics are as follows:
MP 73–77° C.
$^1$H NMR (CDCl$_3$) δ 7.41–7.33, 7.25, 7.05, 6.74, 5.19, 4.73–4.65, 1.91, 1.73–1.65, 1.47, 0.93 ppm.
IR (Nujol) 3400, 3249, 3085, 2953, 2925, 2869, 2855, 1697, 1615, 1602, 1563, 1450, 1283, 1245, 1177, 1067, 1017, 798, 773, 740, 696 cm$^{-1}$.
Elemental analysis, found: C, 72.58; H, 7.25; N, 4.55.
MS (EI) m/z 313, 257, 213, 91.

Preparation 8 [3-[1-(5,6,7,8,9,10-Hexahydro-4-hydroxy-2-oxo-2H-cycloocta[b]pyran-3-yl)-3-methylbutyl]phenyl-carbamic acid, phenylmethyl ester (Formula B-5 wherein R$_1$ is isobutyl) Refer to Chart B.

A 200-mL, three-necked flask with a Dien-Stark trap and a nitrogen inlet is charged with p-toluenesulfonic acid (0.66 g) and toluene (100 mL) and warmed to reflux to collect 20 mL in the Dien-Stark trap. The reaction mixture is cooled to room temperature, and the trap is emptied. 4-Hydroxy-2H-cycloocta[b]pyran-2-one of formula B-4 (2.48 g) and the title compound of Preparation 7 (4.0 g) are added to the reaction mixture and then heated to reflux for 6.5 h. The reaction mixture is allowed to stand at room temperature overnight, then poured into 350 mL of ethyl acetate, washed with two 25-mL portions of water, 25 mL of saturated sodium bicarbonate, and 25 mL of water. The organic layer is concentrated to give 7.9 g of yellow oil. Column chromatography on 150 g of silica gel (elution with 10–50% ethyl acetate in hexane) gives 0.217 g of the title product as an off-white foam.

Physical characteristics are as follows:
MP 73–78° C. (decomposition).
$^1$H NMR (CDCl$_3$) δ 7.38–7.25, 7.13, 6.72, 6.01, 5.19, 4.48, 2.58, 2.41, 1.93, 1.74, 1.62–1.33, 0.96 ppm.

Preparation 9 (R or S)-[3-[1-(5,6,7,8,9,10-Hexahydro-4-hydroxy-2-oxo-2H-cycloocta[b]pyran-3-yl)-3-methylbutyl]phenyl]-carbamic acid, phenylmethyl ester (Formula B-5 wherein R$_1$ is isobutyl) Refer to Chart B.

A stock solution of the title compound of Preparation 8 (32 mg/mL) in 30% isopropyl alcohol and 0.1% acetic acid in hexane is chromatographed on a 2.0×25 cm (R, R) Whelk-O 1 column at 2 mL per injection using an automated chromatographic system. The eluant is monitored at 310 nm, the flow rate was 10 mL/min and appropriate fractions from multiple injections combined and concentrated in vacuo to give snowy white solids.

Physical characteristics are as follows:
The retention time of the title compound is 18.8 min.

Preparation 10 (R or S)-[3-[1-(5,6,7,8,9,10-Hexahydro-4-hydroxy-2-oxo-2H-cycloocta[b]pyran-3-yl)-3-methylbutyl]phenyl]-carbamic acid, phenylmethyl ester (Formula B-5 wherein R$_1$ is isobutyl) Refer to Chart B.

The title compound of Preparation 8 is separated as described in Preparation 9 above.

Physical characteristics are as follows:
The retention time of the title compound is 22.1 min.

Preparation 11 (R or S)-3-[1-(3-Aminophenyl)-3-methylbutyl]-5,6,7,8,9,10-hexahydro-4-hydroxy-2H-cycloocta[b]pyranone (Formula B-6 wherein R$_1$ is isobutyl) Refer to Chart B.

A flask with a nitrogen inlet is charged with a solution of the title compound of Preparation 9 (0.637 g) in 6 mL of ethanol. Cyclohexene (6 mL) and 10% palladium on carbon (0.16 g) are added, and the reaction mixture is heated at reflux for 2 h. The mixture is then filtered through Celite and concentrated to give 0.205 g of the title compound as an off-white foam.

Physical characteristics are as follows:
MP 158–162° C.
MS (EI) m/z 355, 312, 299, 161, 106
For high resolution, found: 355.2144.

EXAMPLE 8
(R or S)-N-[3-1-(5,6,7,8,9,10-Hexahydro-4-hydroxy-2-oxo-2H-cycloocta[b]pyran-3-yl)-3-methylbutyl]phenyl]-1-methyl-1H-imidazole-4-sulfonamide (Formula B-7 wherein R$_1$ is isobutyl and R$_2$ is 1-methylimidazole) Refer to Chart B.

A flask with a nitrogen inlet is charged with the title compound of Preparation 11 (0.095 g), 1-methylimidazole-4-sulfonyl chloride (0.048 g), and 5 mL of methylene chloride (CH$_2$Cl$_2$). Pyridine (0.53 mL) is added, and the reaction mixture is stirred at room temperature for ca. 18 h. A precipitate forms, which is filtered to give 0.097 g of a white solid. Recrystallization from methanol-chloroform yields 0.065 g of the title compound as a white powder.

Physical characteristics are as follows:
MP 207–210° C.
$^1$H NMR (CDCl$_3$) δ 10.4, 10.0, 7.70, 7.11, 7.05, 6.92, 4.21, 3.64, 2.54, 2.16, 1.62, 1.53, 1.43, 1.34, 0.85 ppm.
MS (EI) m/z 499, 456, 443, 306, 251, 160, 145
For high resolution, found: 499.2151

Preparation 12 (R or S)-3-[1-(3-Aminophenyl)-3-methylbutyl]-5,6,7,8,9,10-hexahydro-4-hydroxy-2H-cycloocta[b]pyranone (Formula B-6 wherein R$_1$ is isobutyl) Refer to Chart B.

Following the general procedure of Preparation 11, and making non-critical variations, but substituting the title product of Preparation 10 for the title product of Preparation 9, 0.189 g of the title compound is obtained as a grey solid.

Physical characteristics are as follows:
MS (EI) m/z 355, 312, 299, 161
For high resolution, found: 355.2135

EXAMPLE 9
(R or S)-N-[3-1-(5,6,7,8,9,10-Hexahydro-4-hydroxy-2-oxo-2H-cycloocta[b]pyran-3-yl)-3-methylbutyl]phenyl]-1-methyl-1H-imidazole-4-sulfonamide (Formula B-7 wherein R$_1$ is isobutyl and R$_2$ is 1-methylimidazole) Refer to Chart B.

Following the general procedure of Example 8, and making non-critical variations, but substituting the title product of Preparation 12 for the title product of Preparation 11, 0.047 g of the title compound is obtained as a white solid.

Physical characteristics are as follows:
$^1$H NMR (CDCl$_3$) δ 10.45, 10.06, 7.70, 7.11, 7.05, 6.94, 4.21, 3.64, 2.55, 2.16, 1.62, 1.53, 1.42, 1.35, 0.86 ppm.
MS (EI) m/z 499, 456, 443, 354, 306, 160, 145
For high resolution, found: 499.2146

Preparation 13 [3-(Cyclopropyl-hydroxymethyl)-phenyl]-methanol (Formula C-2) Refer to Chart C.

To a solution of 6.5 mL of 3-bromobenzylalcohol of formula C-1 in 900 mL of tetrahydrofuran under nitrogen at −78° C. is added 46 mL of a 1.4 M solution of methyllithium in diethyl ether. The solution is stirred for 20 min and then 66 mL of a 1.6 M solution of n-butyllithium in hexane is added. The solution is stirred 25 min and then 6 mL of cyclopropanecarboxaldehyde is added. The solution is stirred 1.5 h, warmed to 0° C. and stirred for 40 min. Next the solution is warmed to room temperature and stirred for 30 min. Finally the solution is heated at reflux for 1 h. The solution is poured onto 800 mL of water and acidified with concentrated HCl followed by 5% aqueous HCl to adjust the pH to approximately 6. The layers are separated and the aqueous extracted with two portions of ethyl acetate. The combined organics are dried (Na$_2$SO$_4$) and concentrated to afford a yellow oil which is chromatographed over 900 g 230–400 mesh silica gel (2:1 ethyl acetate: hexane) to afford a 6.61 g (68%) of the desired alcohol as a yellow oil.

Physical characteristics are as follows:
$^1$H NMR (CDCl$_3$) δ 7.41–7.26, 4.67, 3.99–3.96, 2.18, 1.28–1.14, 0.68

Preparation 14 3-[cyclopropyl[3-[hydroxymethyl]phenyl]methyl]-5,6,7,8,9,10-hexahydro-4-hydroxy-2H-cycloocta[b]pyran-2-one (Formula C-3) Refer to Chart C.

To a solution of 501 mg of the title product of Preparation 13 in 50 mL of dichloromethane in the presence of molecular sieves 3A under nitrogen is added 492 mg of 4-hydroxy-5,6,7,8,9,10-hexahydrocycloocta[b]pyran-2-one followed by 49 mg of p-toluenesulfonic acid monohydrate. The solution is heated at reflux for 2 h and then an additional 105 mg p-toluenesulfonic acid monohydrate is added and heating continued for a further hour. The solution is concentrated in vacuo to afford a white foam which is treated with water and then 1 N KOH and extracted with one portion of ethyl acetate. The organic layer is washed with one portion of 1 N KOH. The combined aqueous layers are acidified with 5% aqueous HCl and extracted with three portions of ethyl acetate. The combined organics are dried (Na$_2$SO$_4$) and concentrated in vacuo to afford a yellow oil which is chromatographed over 180 g of 230–400 mesh silica gel (2:1 ethyl acetate: hexane) to afford 436 mg of the desired benzyl alcohol as a white foam.

Physical characteristics are as follows:
MP 65–70° C.
$^1$H NMR (CDCl$_3$) δ 7.25–7.03, 4.36, 3.70–3.67, 2.41–2.37, 2.24–2.23, 1.53–1.50, 1.35–1.05, 0.54–0.43, 0.42–0.21, 0.07–0.02.

Preparation 15 3-[Cyclopropyl [3-[bromomethyl]phenyl] methyl]-5,6,7,8,9,10-hexahydro-4-hydroxy-2H-cyclooctа[b]pyran-2-one; and 3-[cyclopropyl [3-[chloromethyl] phenyl]methyl]-5,6,7,8,9,10-hexahydro-4-hydroxy-2H-cyclooctа[b]pyran-2-one (Formulas C-4,5) Refer to Chart C.

To a solution of 1.01 g of the title product of Preparation 14 in 70 mL of dichloromethane under nitrogen at 0° C. is added 2.00 g of triphenylphosphine and 2.58 g of carbon tetrabromide in sequence. The solution is stirred 1 h and then poured onto brine. The layers are separated and the aqueous extracted with three portions of ethyl acetate. The combined organics are dried ($Na_2SO_4$) and concentrated to afford a yellow oil which is triturated with ether. The solid is filtered off and the filtrate concentrated and chromatographed over 180 g of 230–400 mesh silica gel (1:1 hexane: ethyl acetate) to afford 374 mg of the desired title product as a mixture of bromide and chloride. The solids isolated from the filtration are chromatographed as above to afford an additional 699 mg of the title product as a mixture of bromide and chloride.

Physical characteristics are as follows:

Mass Spectrum m/e 418, 416 ($M^+$ for Br), 388, 374, 372 ($M^+$ for Cl), 337, 246, 233, 220, 207, 195, 179, 153, 143, 129.

Preparation 16 3-[Cyclopropyl[3-[(phenylthio)methyl] phenyl]methyl]-5,6,7,8,9,10-hexahydro-4-hydroxy-2H-Cyclooctа[b]pyran-2-one (Formula C-6) Refer to Chart C.

To a solution of 138 mg of the title products of Preparation 15 in 5 mL of dichloromethane is added 0.04 mL of thiolphenol and 0.17 mL of diisopropylethylamine in sequence. The solution is heated at reflux for 1 h and then allowed to stand at room temperature overnight. The solution is poured onto brine and treated with 5% aqueous hydrochloric acid. The layers are separated and the aqueous extracted with three portions of ethyl acetate. The combined organics are dried ($Na_2SO_4$) and concentrated to afford a yellow oil which is chromatographed over 80 g of 230–400 mesh silica gel (2:1 hexane: ethyl acetate) to afford 111 mg of the desired sulfide as a white foam.

Physical characteristics are as follows:

MP 137–139° C.

Mass Spectrum m/e 446 ($M^+$), 418, 337, 295, 233, 220, 207, 185, 145, 128, 109, 91, 79, 55, 40, EXAMPLE 10
3-[Cyclopropyl[3-[(phenylsulfonyl)methyl]phenyl]methyl]-5,6,7,8,9,10-hexahydro-4-hydroxy-2H-Cyclooctа[b]pyran-2-one (Formula C-7) Refer to Chart C.

To a solution of 119 mg of the title product of Preparation 16 in 5 mL of tetrahydrofuran and 5 mL of methanol at 0° C. is added a solution of 279 mg of oxone in 5 mL of water. The solution is stirred 2.5 h and then warmed to room temperature and stirred 2 h. The solution is filtered and the solids washed with chloroform. The filtrate is diluted with water and the layers are separated. The aqueous is extracted with three portions of ethyl acetate. The combined organics are dried ($Na_2SO_4$) and concentrated to afford a clear oil which is chromatographed over 80 g of 230–400 mesh silica gel (1:1 hexane: ethyl acetate) to afford 78 mg of the title product as a white foam.

Physical characteristics are as follows:

MP 80–85° C.

Mass Spectrum m/e 479 ($M^++1$), 463, 450, 391, 337, 309, 207, 161, 149, 127, 115, 71, 57, 41.

Exact mass found: 479.1885.

EXAMPLES 11–39

The following compounds of the present invention are prepared by an analogous synthetic route to that described above:

11) 3-[cyclopropyl[3-[(4-cyanophenylsulfonyl)methyl] phenyl]methyl]-5,6,7,8,9,10-hexahydro-4-hydroxy-2H-cyclooctа[b]pyran-2-one The starting material, 4-cyanobenzenethiol, is prepared from 4-cyanobenzenesulfonyl chloride according to a general literature procedure: Wagner, A. W. Ber Deutsch Chem Ges, 99:375 (1966).

Physical characteristics are as follows:

MP 100–105° C.

Mass Spectrum m/e 504 ($M^++1$), 337, 247, 207, 143.

Exact mass found 504.1843.

12) 3-[cyclopropyl[3-[(4-fluorophenylsulfonyl)methyl] phenyl]methyl]-5,6,7,8,9,10-hexahydro-4-hydroxy-2H-cyclooctа[b]pyran-2-one Physical characteristics are as follows:

MP 95–100° C.

$^1$H NMR (CDCl$_3$) δ 7.61–7.57, 7.40–7.37, 7.27–7.20, 7.13–7.07, 7.02–6.99, 6.42, 4.30, 3.88–3.85, 2.64–2.61, 2.51–2.47, 1.83–1.40, 1.40–1.27, 0.69–0.58, 0.48–0.43, 0.19–0.14.

13) 3-[cyclopropyl[3-[(4-methylphenylsulfonyl)methyl] phenyl]methyl]-5,6,7,8,9,10-hexahydro-4-hydroxy-2H-cyclooctа[b]pyran-2-one Physical characteristics are as follows:

MP 100–105° C.

$^1$H NMR (CDCl$_3$) δ 7.37–7.34, 7.25–7.22, 7.17–7.05, 6.86–6.84, 4.15, 3.60–3.58, 2.52–2.42, 2.42–2.30, 2.28, 1.70–1.14, 0.57–0.32, 0.32–0.20, 0.06-(–)0.16.

14) 3-[cyclopropyl[3-[(4-carboxyphenylsulfonyl)methyl] phenyl]methyl]-5,6,7,8,9,10-hexahydro-4-hydroxy-2H-cyclooctа[b]pyran-2-one Physical characteristics are as follows:

MP 90–95° C.

Mass Spectrum m/e 523 ($M^++1$), 337, 247, 207, 143.

Exact mass found 523.1785.

15) 3-[cyclopropyl[3-[(2-(1-methylimidazoyl)sulfonyl) methyl]phenyl]methyl]-5,6,7,8,9,10-hexahydro-4-hydroxy-2H-cyclooctа[b]pyran-2-one Physical characteristics are as follows:

MP 95–103° C.

$^1$H NMR (CDCl$_3$) δ 7.36–7.34, 7.29–7.27, 7.14, 7.06–7.03, 6.98 (s, 1H), 6.86, 4.30, 3.73–3.70, 3.20, 2.67–2.54, 1.90–1.36, 0.71–0.50, 0.46–0.33, 0.18–0.03.

16) 3-[cyclopropyl[3-[(2-pyrimidinylsulfonyl)methyl] phenyl]methyl]-5,6,7,8,9,10-hexahydro-4-hydroxy-2H-cyclooctа[b]pyran-2-one 17) 3-[cyclopropyl[3-[(2-pyridinylsulfonyl)methyl] phenyl]methyl]-5,6,7,8,9,10-hexahydro-4-hydroxy-2H-cyclooctа[b]pyran-2-one 18) 3-[cyclopropyl[3-[(1-methyl-4-imidazolylsulfonyl) methyl]phenyl]methyl]-5,6,7,8,9,10-hexahydro-4-hydroxy-2H-cyclooctа[b]pyran-2-one 19) 3-[cyclopropyl[3-[(5-cyano-2-pyridinylsulfonyl) methyl]phenyl]methyl]-5,6,7,8,9,10-hexahydro-4-hydroxy-2H-cyclooctа[b]pyran-2-one 20) 3-[cyclopropyl[3-[(2-benzimidazolylsulfonyl) methyl]phenyl]methyl]-5,6,7,8,9,10-hexahydro-4-hydroxy-2H-cyclooctа[b]pyran-2-one 21) 3-[cyclopropyl[3-[(2-quinolinylsulfonyl)methyl] phenyl]methyl]-5,6,7,8,9,10-hexahydro-4-hydroxy-2H-cyclooctа[b]pyran-2-one 22) 3-[cyclopropyl[3-[(4-cyanophenylsulfonyl)methyl] phenyl]methyl]-4-hydroxy-coumarin 23) 3-[cyclopropyl[3-[(2-pyridinylsulfonyl)methyl]phenyl]methyl]-4-hydroxy-coumarin 24) 3-[cyclopropyl[3-[(1-methyl-4-imidazolylsulfonyl)methyl]phenyl]methyl]-4-hydroxy-coumarin 25) 3-[cyclopropyl[3-[(5-cyano-2-pyridinylsulfonyl)methyl]phenyl]methyl]-4-hydroxy-coumarin 26) 3-[cyclopropyl[3-[(2-benzimidazolylsulfonyl)methyl]phenyl]methyl]-4-hydroxy-coumarin 27) 3-[cyclopropyl[3-[(2-quinolinylsulfonyl)methyl]phenyl]methyl]-4-hydroxy-coumarin 28) 3-[cyclopropyl[3-[(4-cyanophenylsulfonyl)methyl]phenyl]methyl]-4-hydroxy-6-[1-(phenylmethyl)propyl]-2H-pyran-2-one 29) 3-[cyclopropyl[3-[(2-pyridinylsulfonyl)methyl]phenyl]methyl]-4-hydroxy-6-[1-(phenylmethyl)propyl]-2H-pyran-2-one 30) 3-[cyclopropyl[3-[(1-methyl-4-imidazolylsulfonyl)methyl]phenyl]methyl]-4-hydroxy-6-[1-(phenylmethyl)propyl]-2H-pyran-2-one 31) 3-[cyclopropyl[3-[(5-cyano-2-pyridinylsulfonyl)methyl]phenyl]methyl]-4-hydroxy-6-[1-(phenylmethyl)propyl]-2H-pyran-2-one 32) 3-[cyclopropyl[3-[(2-benzimidazolylsulfonyl)methyl]phenyl]methyl]-4-hydroxy-6-[1-(phenylmethyl)propyl]-2H-pyran-2-one 33) 3-[cyclopropyl[3-[(2-quinolinylsulfonyl)methyl]phenyl]methyl]-4-hydroxy-6-[1-(phenylmethyl)propyl]-2H-pyran-2-one 34) 3-[cyclopropyl[3-[(4-cyanophenylsulfonyl)methyl]phenyl]methyl]-4-hydroxy-6-(2-phenylethyl)-6-(1-propyl)-5,6-dihydro-2H-pyran-2-one 35) 3-[cyclopropyl[3-[(2-pyridinylsulfonyl)methyl]phenyl]methyl]-4-hydroxy-6-(2-phenylethyl)-6-(1-propyl)-5,6-dihydro-2H-pyran-2-one 36) 3-[cyclopropyl[3-[(1-methyl-4-imidazolylsulfonyl)methyl]phenyl]methyl]-4-hydroxy-6-(2-phenylethyl)-6-(1-propyl)-5,6-dihydro-2H-pyran-2-one 37) 3-[cyclopropyl[3-[(5-cyano-2-pyridinylsulfonyl)methyl]phenyl]methyl]-4-hydroxy-6-(2-phenylethyl)-6-(1-propyl)-5,6-dihydro-2H-pyran-2-one 38) 3-[cyclopropyl[3-[(2-benzimidazolylsulfonyl)methyl]phenyl]methyl]-4-hydroxy-6-(2-phenylethyl)-6-(1-propyl)-5,6-dihydro-2H-pyran-2-one 39) 3-[cyclopropyl[3-[(2-quinolinylsulfonyl)methyl]phenyl]methyl]-4-hydroxy-6-(2-phenylethyl)-6-(1-propyl)-5,6-dihydro-2H-pyran-2-one Preparation 17 5,6-Dihydro-4-Hydroxy-6-phenethyl-6-propyl-2H-pyran-2-one (Formula D-1: $R_1$ is phenethyl, $R_2$ is propyl) Refer to Chart D.

Methyl acetoacetate (1.47 mL) is added to a suspension of sodium hydride (567 mg, 60% dispersion in mineral oil) in THF (30 mL) at 0° C. After 15 minutes, n-butyl lithium (8.5 mL, 1.6 M solution in hexane) is added dropwise and the reaction is stirred 15 minutes. 1-Phenyl-3-hexanone (2.0g) is then added via syringe all at once to the reaction mixture. The reaction is stirred an additional hour, then poured into a saturated ammonium chloride solution. It is extracted with EtOAc, dried over anhydrous sodium sulfate and evaporated in vacuo. The material obtained is dissolved in THF (25 mL) and a 0.1 N sodium hydroxide (113 mL) solution is added. After stirring three hours, the mixture is extracted with ethyl acetate (1×). The aqueous layer is adjusted to pH 3 with hydrochloric acid, then extracted with $CH_2Cl_2$ (3×25 mL), dried over anhydrous magnesium sulfate and evaporated to afford the title product as a white solid.

Physical characteristics are as follows:
$^1$H NMR (300 MHz, $CDCl_3$): δ 0.96, 1.21, 1.48, 1.72, 1.98, 2.73, 3.43, 7.15–7.32.
Anal. Found: C, 73.77; H, 7.96.

Preparation 18 4-Hydroxy -3-[1-(3-nitrophenyl)-propyl]-5,6-dihydro-6-phenethyl-6-propyl-2H-pyran-2-one (Formula D-4: $R_1$ is phenethyl, $R_2$ is propyl, $R_3$ is ethyl) Refer to Chart D.

To a solution of the title product of Preparation 17 (Formula D-1: $R_1$ is phenethyl, $R_2$ is propyl) (1 g) and 3-nitrobenzaldehyde (Formula D-2) (581 mg) in dry THF at 0° C. is added $AlCl_3$ (1.0 g) as one solid portion. The cooling bath is removed and the yellow solution is allowed to stir at room temperature for 2 hrs. The reaction mixture is quenched by the addition of solid $Na_2CO_3$-$10H_2O$ (2.2 g) and vigorously stirred for 5 min. The mixture is filtered through celite with ether and the filtrate is evaporated to dryness in vacuo. The benzylidene intermediate of formula D-3 and CuBr—$Me_2S$ (237 mg) are dissolved in dry THF and a solution of $Et_3Al$ (4.23 mL; 1 M in hexane) is added at room temperature, dropwise over 5 min. When the reaction is complete (as determined by tlc), it is quenched by the addition of water and the reaction mixture is transferred to a separatory funnel with ether. The aqueous layer is extracted with ether (3×15 mL) and the combined organic layers are washed with brine, dried ($MgSO_4$), filtered and evaporated in vacuo to provide an oil. Flash chromatography on silica gel with Hexanes/EtOAc (3:1) provides 1.1 g of the title product as a light yellow foam.

Physical characteristics are as follows:
$^1$H NMR complicated by presence of diastereomers.
$^1$H NMR (300 MHz, $CD_3OD$) δ 0.93, 1.37, 1.74, 1.82–2.14, 2.29, 2.52–2.71, 4.19, 6.98–7.24, 7.44, 7.72, 8.02, 8.26.

Preparation 19 3-[Cyclopropyl-(3-nitrophenyl)-methyl]-4-hydroxy-5,6-dihydro-6-phenethyl-6-propyl-2H-pyran-2-one (Formula D-4: $R_1$ is phenethyl, $R_2$ is propyl, $R_3$ is cyclopropyl) Refer to Chart D.

To a solution of the title product of Preparation 17 (Formula D-1: $R_1$ is phenethyl, $R_2$ is propyl) (1 g) and 3-nitrobenzaldehyde (Formula D-2) (581 mg) in dry THF at 0° C. is added $AlCl_3$ (1.0 g) as one solid portion. The cooling bath is removed and the yellow solution is allowed to stir at room temperature for 2 hrs. The reaction mixture is quenched by the addition of solid $Na_2CO_3$-$10H_2O$ (2.2 g) and vigorously stirred for 5 min. The mixture is filtered through celite with ether and the filtrate is evaporated to dryness in vacuo. The benzylidene intermediate of formula D-3 and CuBr—$Me_2S$ (237 mg) are dissolved in dry THF and cooled to −78° C. A solution of cyclopropylmagnesium bromide (15.6 mL; 0.25 M in THF) is added dropwise over 10 min and the reaction mixture is stirred for 30 min. The reaction is quenched by the addition of water and neutralized by the addition of 1N HCl. The reaction mixture is transferred to a separatory funnel with ether and the aqueous layer is extracted with ether (3×15 mL). The combined organic layers are washed with brine, dried ($MgSO_4$), filtered and evaporated in vacuo to provide an oil. Flash chromatography on silica gel with Hexanes/EtOAc (3:1) provides 0.9 g of the title product as a light yellow foam.

Physical characteristics are as follows:
$^1$H NMR complicated by presence of diastereomers.
$^1$H NMR (300 MHz, $CD_3OD$) δ 0.25, 0.53, 0.74, 0.94, 1.41, 1.68–2.13, 2.57–2.72, 3.38, 7.04–7.23, 7.46, 7.82, 8.03, 8.30.

Preparation 203-[1-(3-Aminophenyl)-propyl]-4-hydroxy-5,6-dihydro-6-phenethyl-6-propyl-2H-pyran-2-one (Formula D-5: $R_1$ is phenethyl, $R_2$ is propyl, $R_3$ is ethyl) Refer to Chart D.

To a solution of the title product of Preparation 18 (Formula D-4: $R_1$ is phenethyl, $R_2$ is propyl, $R_3$ is ethyl) (350 mg) in MeOH at room temperature is added 10% Pd/C (35 mg) and ammonium formate (521 mg). The resulting mixture is stirred for 2 hrs. and then filtered through celite with $CH_2Cl_2$. The filtrate is evaporated in vacuo and the residue is triturated with $CH_2Cl_2$ (3×10 mL). The combined organic solution is filtered and evaporated in vacuo to provide the 325 mg of the title compound as a light yellow foam.

Physical characteristics are as follows:
$^1$H NMR complicated by presence of diastereomers.
$^1$H NMR (300 MHz, $CDCl_3$) δ 0.89, 1.40, 1.64–2.07, 2.20, 2.62, 3.94, 6.54, 6.72–7.25.

The compounds of formula D-5, wherein $R_1$ is propyl, $R_2$ is propyl and $R_3$ is ethyl or t-butyl are prepared by analogous procedures.

Physical characteristics of the compound of the formula D-5, wherein $R_1$ is and $R_2$ are propyl and $R_3$ is ethyl, are as follows:
$^1$H NMR: 0.9, 1.3, 1.5–1.8, 2.0, 2.2, 2.5, 3.9, 4.5, 6.5, 6.8, 7.0 ppm
TLC $R_f$: 0.32 (10% ethyl acetate in dichloromethane).

EXAMPLE 40

4-Cyano-N-[3-[1-(4-hydroxy-2-oxo-6-phenethyl-6-propyl-5,6-dihydro-2H-pyran-3-yl)-propyl]-phenyl]-benzenesulfonamide (Formula D-6: $R_1$ is phenethyl, $R_2$ is propyl, $R_3$ is ethyl, $R_4$ is 4-cyanophenyl) Refer to Chart D.

To a solution of the title product of Preparation 20 (Formula D-5: $R_1$ is phenethyl, $R_2$ is propyl, $R_3$ is ethyl) (30 mg) and 4-cyanobenzenesulfonyl chloride of formula D-7, wherein $R_4$ is cyanophenyl, (16.1 mg) in $CH_2Cl_2$ (1 mL) at room temperature is added pyridine (13 μL) via syringe. The resulting solution is stirred for 3 hrs, after which the starting amine is consumed. The mixture is flash chromatographed on silica gel with the 5% EtOAc in $CH_2Cl_2$ to provide 21 mg of the title product as a white foam.

Physical characteristics are as follows:
$^1$H NMR complicated by presence of diastereomers.
$^1$H NMR (300 MHz, $CDCl_3$) δ 0.6–1.1, 1.2–2.2, 2.4–2.7, 3.86–4.01, 6.89–7.45, 7.66–7.92.
HRMS found: 559.2267.

EXAMPLE 41

N-[3-[1-(4-hydroxy-2-oxo-6-phenethyl-6-propyl-5,6-dihydro-2H-pyran-3-yl)-propyl]-phenyl]-1-methyl-1H-imidazole-4-sulfonamide (Formula D-6: $R_1$ is phenethyl, $R_2$ is propyl, $R_3$ is ethyl, $R_4$ is 1-methylimidazol-4-yl) Refer to Chart D.

The title compound is prepared from the amine of Preparation 20 (Formula D-5; $R_1$ is phenethyl, $R_2$ is propyl, $R_3$ is ethyl) and 1-methyl-imidazole-4-sulfonyl chloride of formula D-7 wherein $R_4$ is 1-methylimidazol-4-yl, using the general procedure for sulfonylation of Example 40 to yield the title compound as an off-white amorphous solid after flash chromatography with 4% MeOH/EtOAc.

Physical characteristics are as follows:
$^1$H NMR complicated by presence of diastereomers and tautomerism.
$^1$H NMR (300 MHz, $CDCl_3$) δ 0.75–0.96, 1.17–1.43, 1.45–2.11, 2.43–2.68, 3.24, 3.64, 3.94, 6.72–7.51.
HRMS found: 538.2383.

EXAMPLE 42

N-[3-[1-(4-hydroxy-2-oxo-6-phenethyl-6-propyl-5,6-dihydro-2H-pyran-3-yl)-propyl]-phenyl]-8-quinolinesulfonamide (Formula D-6: $R_1$ is phenethyl, $R_2$ is propyl, $R_3$ is ethyl, $R_4$ is quinolin-8-yl) Refer to Chart D.

The title compound is prepared from the amine of Preparation 20 (Formula D-5: $R_1$ is phenethyl, $R_2$ is propyl, $R_3$ is ethyl) and 8-quinolinesulfonyl chloride of formula D-7 wherein 44 is quinolin-8-yl, using the general procedure for sulfonylation of Example 40 to yield the title compound as a white amorphous solid after flash chromatography with 5% EtOAc/$CH_2Cl_2$.

Physical characteristics are as follows:
$^1$H NMR complicated by presence of diastereomers and tautomerism.
$^1$H NMR (300 MHz, $CDCl_3$) δ 0.66, 0.90, 1.17–1.44, 1.58–2.03, 2.38–2.64, 3.77, 6.68–7.27, 7.35–7.69, 8.02, 8.26, 9.14.
HRMS found: 585.2402.

EXAMPLE 43

N-[3-[1-(4-hydroxy-2-oxo-6,6-dipropyl-5,6-dihydro-2H-pyran-3-yl)-propyl]-phenyl]-8-quinolinesulfonamide (Formula D-6: $R_1$ is $R_2$ is propyl, $R_3$ is ethyl, $R_4$ is quinolin-8-yl) Refer to Chart D.

The title compound is prepared from the amine of Preparation 20 (Formula D-5: R. is propyl, $R_2$ is propyl, $R_3$ is ethyl) and 8-quinolinesulfonyl chloride of formula D-7 wherein $R_4$ is quinolin-8-yl, using the general procedure for sulfonylation of Example 40 to yield the title compound as a white amorphous solid after flash chromatography with 5% EtOAc/$CH_2Cl_2$.

Physical characteristics are as follows:
$^1$H NMR complicated by presence of diastereomers and tautomerism.
$^1$H NMR (300 MHz, $CD_3OD$) δ 0.67, 0.85, 1.27, 1.54, 2.01, 3.73, 6.78, 6.90, 7.04, 7.57, 8.12, 8.29, 8.38, 9.13.
HRMS found: 523.2276.
Anal. found: C, 66.09; H, 6.60; N, 5.13.

EXAMPLE 44

N-[3-[1-(4-hydroxy-2-oxo-6,6-dipropyl-5,6-dihydro-2H-pyran-3-yl)-propyl]-phenyi]-1-methyl-1H-imidazolesulfonamide (Formula D-6: $R_1$ is propyl, $R_2$ is propyl, $R_3$ is ethyl, $R_4$ is 1-methylimidazol-4-yl) Refer to Chart D.

The title compound is prepared from the amine of Preparation 20 (Formula D-5: $R_1$ is propyl, $R_2$ is propyl, $R_3$ is ethyl) and 1-methyl-imidazole-4-sulfonyl chloride of formula D-7 wherein $R_4$ is 1-methylimidazol-4-yl, using the general procedure for sulfonylation of Example 40 to yield the title compound as an off-white amorphous solid after flash chromatography with 4% MeOH/EtOAc.

Physical characteristics are as follows:
$^1$H NMR (300 MHz, $CD_3OD$) δ 0.88, 1.32, 1.64, 1.93, 2.16, 2.56, 3.68, 3.91, 6.87, 7.03, 7.14, 7.53, 7.64.
HRMS found: 476.2223.

EXAMPLE 45

4-Fluoro-N-[3-[1-(4-hydroxy-2-oxo-6,6-dipropyl-5,6-dihydro-2H-pyran-3-yl)-propyl]-phenyl]-benzenesulfonamide (Formula D-6: $R_1$ is propyl, $R_2$ is propyl, $R_3$ is ethyl, $R_4$ is 4-fluorophenyl) Refer to Chart D.

The title compound is prepared from the amine of Preparation 20 (Formula D-5: $R_1$ is propyl, $R_2$ is propyl, $R_3$ is ethyl) and 4-fluoro-benzenesulfonyl chloride of formula D-7 wherein $R_4$ is 4-fluorophenyl, using the general procedure for sulfonylation of Example 40 to yield the title compound as a white amorphous solid after flash chromatography with 5% EtOAc/$CH_2Cl_2$.

Physical characteristics are as follows:

$^1$H NMR complicated by presence of diastereomers and tautomerism.

$^1$H NMR (300 MHz, CDCL$_3$) δ 0.51–1.03, 1.15–1.73, 1.81–2.48, 2.73, 3.91, 6.69, 6.88, 7.09, 7.78.

HRMS found: 490.2085.

EXAMPLE 46

4-Cyano-N-[3-[1-(4-hydroxy-2-oxo-6,6-dipropyl-5,6-dihydro-2H-pyran-3-yl)-propyl]-phenyl]-benzenesulfonamide (Formula D-6: R$_1$ is propyl, R$_2$ is propyl, R$_3$ is ethyl, R$_4$ is 4-cyanophenyl) Refer to Chart D.

The title compound is prepared from the amine of Preparation 20 (Formula D-5: R$_1$ is propyl, R$_2$ is propyl, R$_3$ is ethyl) and 4-cyano-benzenesulfonyl chloride of formula D-7 wherein R$_4$ is 4-cyanophenyl, using the general procedure for sulfonylation of Example 40 to yield the title compound as a white amorphous solid after flash chromatography with 5% EtOAc/CH$_2$Cl$_2$.

Physical characteristics are as follows:

$^1$H NMR complicated by presence of diastereomers and tautomerism.

$^1$H NMR (300 MHz, CDCl$_3$) δ 0.68–0.96, 1.15–1.42, 1.44–1.76, 1.83–2.12, 3.18, 3.88, 6.69–7.18, 7.71, 7.85.

HRMS found: 497.2126.

EXAMPLE 47

N-[3-[1-(4-hydroxy-6,6-diisobutyl-2-oxo-5,6-dihydro-2H-pyran-3-yl)-propyl]-phenyl]-1-methyl-1H-imidazole-4-sulfonamide (Formula D-6: R$_1$ is isobutyl, R$_2$ is isobutyl, R$_3$ is ethyl, R$_4$ is 1-methylimidazol-4-yl) Refer to Chart D.

The title compound is prepared from the amine of Preparation 20 (Formula D-5: R$_1$ is propyl, R$_2$ is isobutyl, R$_3$ is ethyl) and 1-methyl-imidazole-4-sulfonyl chloride of formula D-7 wherein R$_4$ is 1-methylimidazol-4-yl, using the general procedure for sulfonylation of Example 40 to yield the title compound as an off-white amorphous solid after flash chromatography with 4% MeOH/EtOAc.

Physical characteristics are as follows:

$^1$H NMR (300 MHz, CD$_3$OD) δ 0.82–0.94, 1.52–1.83, 1.86–2.03, 2.06–2.22, 2.60, 3.68, 3.92, 6.87, 7.03, 7.16, 7.56, 7.65.

HRMS found: 504.2531.

Anal. found: C, 62.03; H, 7.43; N, 8.20.

EXAMPLE 48

N-[3-[1-(4-hydroxy-2-oxo-6,6-dipropyl-5,6-dihydro-2H-pyran-3-yl)-cyclopropylmethyl]-phenyl]-1-methyl-1H-imidazolesulfonamide (Formula D-6: R$_1$ is propyl, R$_2$ is propyl, R$_3$ is cyclopropyl, R$_4$ is 1-methylimidazol-4-yl) Refer to Chart D.

The title compound is prepared from the amine of Preparation 20 (Formula D-5: R$_1$ is propyl, R$_2$ is propyl, R$_3$ is cyclopropyl) and 1-methyl-imidazole-4-sulfonyl chloride of formula D-7 wherein R$_4$ is 1-methylimidazol-4-yl, using the general procedure for sulfonylation of Example 40 to yield the title compound as an off-white amorphous solid after flash chromatography with 4% MeOH/EtOAc.

Physical characteristics are as follows:

$^1$H NMR (300 MHz, CD$_3$OD) δ 0.12, 0.43, 0.68, 0.90–0.97, 1.36, 1.71, 2.60, 3.12, 3.67, 6.88, 7.06, 7.24, 7.51, 7.65.

HRMS found: 488.2225.

Anal. found: C, 61.25; H, 6.94; N, 8.42.

EXAMPLE 49

N-[3-[1-(4-Hydroxy-2-oxo-6,6-dipropyl-5,6-dihydro-2H-pyran-3-yl)-cyclopropylmethyl]-phenyl]-8-quinolinesulfonamide (Formula D-6: R$_1$ is propyl, R$_2$ is propyl, R$_3$ is cyclopropyl, R$_4$ is quinolin-8-yl) Refer to Chart D.

The title compound is prepared from the amine of Preparation 20 (Formula D-5: R$_1$ is propyl, R$_2$ is propyl, R$_3$ is cyclopropyl) and 8-quinolinesulfonyl chloride of formula D-7 wherein R$_4$ is quinolin-8-yl, using the general procedure for sulfonylation of Example 40 to yield the title compound as a white amorphous solid after flash chromatography with 5% EtOAc/CH$_2$Cl$_2$.

Physical characteristics are as follows:

$^1$H NMR (300 MHz, CD$_3$OD) δ −0.14, 0.01, 0.35, 0.89, 1.35, 1.63, 2.52, 2.94, 6.79, 6.94, 7.09, 7.64, 8.12, 8.28, 8.41, 9.13.

HRMS found: 535.2256

Anal. found: C, 67.58; H, 6.53; N, 5.11.

EXAMPLE 50

4-Cyano-N-[3-[1-(4-hydroxy-2-oxo-6,6-dipropyl-5,6-dihydro-2H-pyran-3-yl)-cyclopropylmethyl]-phenyl]-benzenesulfonamide (Formula D-6: R$_1$ is propyl, R$_2$ is propyl, R$_3$ is cyclopropyl, R$_4$ is 4-cyanophenyl) Refer to Chart D.

The title compound is prepared from the amine of Preparation 20 (Formula D-5: R$_1$ is propyl, R$_2$ is propyl, R$_3$ is cyclopropyl) and 4-cyano-benzenesulfonyl chloride of formula D-7 wherein R$_4$ is 4-cyanophenyl, using the general procedure for sulfonylation of Example 40 to yield the title compound as a white amorphous solid after flash chromatography with 5% EtOAc/CH$_2$Cl$_2$.

Physical characteristics are as follows:

$^1$H NMR (300 MHz, CD$_3$OD) δ 0.13, 0.44, 0.62, 0.91, 1.19, 1.67, 2.57, 3.14, 6.80, 7.12, 7.25, 7.83.

HRMS found: 509.2096

Anal. found: C, 65.86; H, 6.39; N, 5.48.

EXAMPLE 51

4-Fluoro-N-[3-[1-(4-hydroxy-2-oxo-6,6-dipropyl-5,6-dihydro-2H-pyran-3-yl)-cyclopropylmethyl]-phenyl]-benzenesulfonamide (Formula D-6: R$_1$ is propyl, R$_2$ is propyl, R$_3$ is cyclopropyl, R$_4$ is 4-fluorophenyl) Refer to Chart D.

The title compound is prepared from the amine of Preparation 20 (Formula D-5: R$_1$ is propyl, R$_2$ is propyl, R$_3$ is cyclopropyl) and 4-fluoro-benzenesulfonyl chloride of formula D-7 wherein R$_4$ is 4-fluorophenyl, using the general procedure for sulfonylation of Example 40 to yield the title compound as a white amorphous solid after flash chromatography with 5% EtOAc/CH$_2$Cl$_2$.

Physical characteristics are as follows:

$^1$H NMR (300 MHz, CD$_3$OD) δ 0.11, 0.43, 0.62, 0.92, 1.34, 1.65, 2.57, 3.13, 6.79, 7.03–7.24, 7.75.

HRMS found: 502.2063.

Anal. found: C, 63.96; H, 6.29; N, 2.71.

Preparation 21 Chiral HPLC resolution of 4-Hydroxy-3-[1-(3-nitrophenyl)-propyl]-5,6-dihydro-6,6-dipropyl-2H-pyran-2-one (Formula D-4: R$_1$ is propyl, R$_2$ is propyl, R$_3$ is ethyl) Refer to Chart D.

A solution of the title product of Preparation 18 (Formula D-4: R$_1$ is propyl, R$_2$ is propyl, R$_3$ is ethyl) (30 mg/mL) in 15% isopropyl alcohol in hexane is chromatographed on a 2.0×25 cm (R,R) Whelk-O 1 (Regis technologies, Inc., Morton Grove, Ill. 60053) column at 1 mL per injection using an automated chromatographic system. The eluant is monitored at 270 nM and appropriate fractions from multiple injections combined and concentrated in vacuo to give tan oils. Fractions from multiple injections are analyzed on a 0.46×25 cm (S,S) Whelk-O 1 column with the same solvent at 1.0 mL/min. The first peak from the 1.0 cm column is >99% ee (Rt is min) and the latter peak is 92% ee (Rt is min). Prior to further use, the resolved materials are subjected to flash chromatography on silica gel with 3:1 hexanes/EtOAc. The resolved materials are converted to the amines of Formula D-5 using the conditions described in Preparation 20.

Physical characteristics are as follows:

The resolved materials were found to exhibit identical $^1$H NMR and tlc behavior as the racemic material.

EXAMPLE 52

(R or S)-N-[3-[1-(4-Hydroxy-2-oxo-6,6-dipropyl-5,6-dihydro-2H-pyran-3-yl)-propyl]-phenyl]-8-quinolinesulfonamide (Formula D-6: $R_1$ is propyl, $R_2$ is propyl, $R_3$ is ethyl, $R_4$ is quinolin-8-yl) Refer to Chart D.

The title compound is prepared from the amine of Preparation 21 (Formula D-5: $R_1$ is propyl, $R_2$ is propyl, $R_3$ is ethyl) and 8-quinolinesulfonyl chloride of formula D-7 wherein $R_4$ is quinolin-8-yl, using the general procedure for sulfonylation of Example 40 to yield the title compound as a white amorphous solid after flash chromatography with 5% EtOAc/CH$_2$Cl$_2$.

Physical characteristics are as follows:

$^1$H NMR and tlc behavior is identical to that of racemic mixture.

$^1$H NMR (300 MHz, CD$_3$OD) δ 0.67, 0.85, 1.27, 1.54, 2.01, 3.73, 6.78, 6.90, 7.04, 7.57, 8.12, 8.29, 8.38, 9.13.

MS m/e (rel%): 523 (100), 524 (34), 129 (11), 525 (11), 522 (10), 130 (7), 139 (5), 134 (4).

EXAMPLE 53

(R or S)-N-[3-[1-(4-hydroxy-2-oxo-6,6-dipropyl-5,6-dihydro-2H-pyran-3-yl)-propyl]-phenyl]-1-methyl-1H-imidazole-4-sulfonamide (Formula D-6: $R_1$ is propyl, $R_2$ is propyl, $R_3$ is ethyl, $R_4$ is 1-methylimidazol-4-yl) Refer to Chart D.

The title compound is prepared from the amine of Preparation 21 (Formula D-5: $R_1$ is propyl, $R_2$ is propyl, $R_3$ is ethyl) and 1-methyl-imidazole-4-sulfonyl chloride of formula D-7 wherein $R_4$ is 1-methylimidazol-4-yl, using the general procedure for sulfonylation of Example 40 to yield the title compound as an off-white amorphous solid after flash chromatography with 4% MeOH/EtOAc.

Physical characteristics are as follows:

$^1$H NMR and tlc behavior is identical to racemic mixture.

$^1$H NMR (300 MHz, CD$_3$OD) δ 0.88, 1.32, 1.64, 1.93, 2.16, 2.56, 3.68, 3.91, 6.87, 7.03, 7.14, 7.53, 7.64.

MS m/e (rel%): 476 (100), 477 (28), 139 (14), 492 (12), 134 (11), 278 (10), 478 (10), 83 (9), 552 (8), 145 (7).

EXAMPLE 54

(S or R)-N-[3-[1-(4-Hydroxy-2-oxo-6,6-dipropyl-5,6-dihydro-2H-pyran-3-yl)-propyl]-phenyl]-8-quinolinesulfonamide (Formula D-6: $R_1$ is propyl, $R_2$ is propyl, $R_3$ is ethyl, $R_4$ is quinolin-8-yl) Refer to Chart D.

The title compound is prepared from the amine of Preparation 21 (Formula D-5: $R_1$ is propyl, $R_2$ is propyl, $R_3$ is ethyl) and 8-quinolinesulfonyl chloride of formula D-7 wherein $R_4$ is quinolin-8-yl, using the general procedure for sulfonylation of Example 40 to yield the title compound as a white amorphous solid after flash chromatography with 5% EtOAc/CH$_2$Cl$_2$.

Physical characteristics are as follows:

$^1$H NMR and tlc behavior is identical to that of racemic mixture.

$^1$H NMR (300 MHz, CD$_3$OD) δ 0.67, 0.85, 1.27, 1.54, 2.01, 3.73, 6.78, 6.90, 7.04, 7.57, 8.12, 8.29, 8.38, 9.13.

MS m/e (rel%): 523 (100), 524 (34), 522 (24), 539 (13), 525 (10), 129 (10), 130 (5), 134 (5), 128 (5), 540 (5).

EXAMPLE 55

(S or R)-N-[3-[1-(4-hydroxy-2-oxo-6,6-dipropyl-5,6-dihydro-2H-pyran-3-yl)-propyl]-phenyl]-1-methyl-1H-imidazole-4-sulfonamide (Formula D-6: $R_1$ is propyl, $R_2$ is propyl, $R_3$ is ethyl, $R_4$ is 1-methylimidazol-4-yl) Refer to Chart D.

The title compound is prepared from the amine of Preparation 21 (Formula D-5: $R_1$ is propyl, $R_2$ is propyl, $R_3$ is ethyl) and 1-methyl-imidazole-4-sulfonyl chloride of formula D-7 wherein $R_4$ is 1-methylimidazol-4-yl, using the general procedure for sulfonylation of Example 40 to yield the title compound as an off-white amorphous solid after flash chromatography with 4% MeOH/EtOAc.

Physical characteristics are as follows:

$^1$H NMR and tlc behavior is identical to racemic mixture.

$^1$H NMR (300 MHz, CD$_3$OD) δ 0.88, 1.32, 1.64, 1.93, 2.16, 2.56, 3.68, 3.91, 6.87, 7.03, 7.14, 7.53, 7.64.

MS m/e (rel%): 476 (100), 477 (28), 139 (19), 490 (15), 498 (14), 83 (12), 478 (9), 55 (9), 145 (9), 134 (7).

EXAMPLE 56

(R or S)-N-[3-[1-(4-Hydroxy-2-oxo-6,6-dipropyl-5,6-dihydro-2H-pyran-3-yl)-cyclopropylmethyl]-phenyl]-1-methyl-1H-imidazole-4-sulfonamide (Formula D-6: $R_1$ is propyl, $R_2$ is propyl, $R_3$ is cyclopropyl, $R_4$ is 1-methylimidazol-4-yl) Refer to Chart D.

The title compound is prepared from the amine of Preparation 21 (Formula D-5: $R_1$ is propyl, $R_2$ is propyl, $R_3$ is cyclopropyl) and 1-methyl-imidazole-4-sulfonyl chloride of formula D-7 wherein $R_4$ is 1-methylimidazol-4-yl, using the general procedure for sulfonylation of Example 40 to yield the title compound as an off-white amorphous solid after flash chromatography with 4% MeOH/EtOAc.

Physical characteristics are as follows:

$^1$H NMR and tlc behavior is identical to racemic mixture.

$^1$H NMR (300 MHz, CD$_3$OD) δ 0.12, 0.43, 0.68, 0.90–0.97, 1.36, 1.71, 2.60, 3.12, 3.67, 6.88, 7.06, 7.24, 7.51, 7.65.

MS m/e (rel%): 488 (100), 489 (30), 139 (18), 145 (14), 490 (10), 55 (10), 83 (9), 564 (7), 146 (7), 510 (7).

EXAMPLE 57

(S or R)-N-[3-[1-(4-Hydroxy-2-oxo-6,6-dipropyl-5,6-dihydro-2H-pyran-3-yl)-cyclopropylmethyl]-phenyl]-1-methyl-1H-imidazole-4-sulfonamide (Formula D-6: $R_1$ is propyl, $R_2$ is propyl, $R_3$ is cyclopropyl, $R_4$ is 1-methylimidazol-4-yl) Refer to Chart D.

The title compound is prepared from the amine Preparation 21 (Formula D-5: $R_1$ is propyl, $R_2$ is propyl, $R_3$ is cyclopropyl) and 1-methyl-imidazole-4-sulfonyl chloride of formula D-7 wherein $R_4$ is 1-methylimidazol-4-yl, using the general procedure for sulfonylation of Example 40 to yield the title compound as an off-white amorphous solid after flash chromatography with 4% MeOH/EtOAc.

Physical characteristics are as follows:

$^1$H NMR and tlc behavior is identical to racemic mixture.

$^1$H NMR (300 MHz, CD$_3$OD) δ 0.12, 0.43, 0.68, 0.90–0.97, 1.36, 1.71, 2.60, 3.12, 3.67, 6.88, 7.06, 7.24, 7.51, 7.65.

MS m/e (rel%): 488 (100), 489 (29), 139 (18), 145 (16), 83 (10), 55 (10), 490 (10), 510 (8), 146 (8), 144 (7).

EXAMPLE 58

4-Cyano-N-[3-[1-(4-Hydroxy-2-oxo-6-phenethyl-6-propyl-5,6-dihydro-2H-pyran-3-yl)-cyclopropylmethyl]-phenyl]- benzene-sulfonamide (Formula D-6: $R_1$ is phenethyl, $R_2$ is propyl, $R_3$ is cyclopropyl, $R_4$ is 4-cyanophenyl) Refer to Chart D.

The title compound is prepared from the amine of Preparation 20 (Formula D-5: $R_1$ is phenethyl, $R_2$ is propyl, $R_3$ is cyclopropyl) and 4-fluoro-benzenesulfonyl chloride of formula D-7 wherein $R_4$ is 4-cyanophenyl, using the general procedure for sulfonylation of Example 40 to yield the title compound as a white amorphous solid after flash chromatography with 5% EtOAc/$CH_2Cl_2$.

Physical characteristics are as follows:
$^1$H NMR (300 MHz, $CD_3OD$) δ 0.11, 0.42, 0.61, 0.95, 1.24, 1.74–2.00, 2.61–2.73, 3.30, 6.83–7.23, 7.71–7.84.
HRMS found: 571.2267

EXAMPLE 59
4-Fluoro-N-[3-[1-(4-Hydroxy-2-oxo-6-phenethyl-6-propyl-5,6-dihydro-2H-pyran-3-yl)-cyclopropylmethyl]-phenyl]-benzenesulfonamide (Formula D-6: $R_1$ is phenethyl, $R_2$ is propyl, $R_3$ is cyclopropyl, $R_4$ is 4-fluorophenyl) Refer to Chart D.

The title compound is prepared from the amine of Preparation 20 (Formula D-5: $R_1$ is phenethyl, $R_2$ is propyl, $R_3$ is cyclopropyl) and 4-fluoro-benzenesulfonyl chloride of formula D-7 wherein $R_4$ is 4-fluorophenyl, using the general procedure for sulfonylation of Example 40 to yield the title compound as a white amorphous solid after flash chromatography with 5% EtOAc/$CH_2Cl_2$.

Physical characteristics are as follows:
$^1$H NMR complicated by presence of diastereomers.
$^1$H NMR (300 MHz, $CD_3OD$) δ 0.11, 0.43, 0.67, 0.96, 1.41, 1.67–2.13, 2.62, 3.16, 6.84, 7.02–7.31, 7.72.
HRMS found: 564.2211.

EXAMPLE 60
N-[3-[1-(4-Hydroxy-2-oxo-6-phenethyl-6-propyl-5,6-dihydro-2H-pyran-3-yl)-cyclopropylmethyl]-phenyl]-8-quinolinesulfonamide (Formula D-6: $R_1$ is phenethyl, $R_2$ is propyl, $R_3$ is cyclopropyl, $R_4$ is quinolin-8-yl) Refer to Chart D.

The title compound is prepared from the amine of Preparation 20 (Formula D-5: $R_1$ is phenethyl, $R_2$ is propyl, $R_3$ is cyclopropyl) and 8-quinolinesulfonyl chloride of formula D-7 wherein $R_4$ is quinolin-8-yl, using the general procedure for sulfonylation of Example 40 to yield the title compound as a white amorphous solid after flash chromatography with 5% EtOAc/$CH_2Cl_2$.

Physical characteristics are as follows:
$^1$H NMR complicated by presence of diastereomers.
$^1$H NMR (300 MHz, $CD_3OD$) δ −0.13, 0.01, 0.35, 0.93, 1.46, 1.54, 1.58–2.06, 2.56, 2.96, 6.81–7.23, 7.50–7.68, 8.08, 8.24, 8.37, 9.12.
HRMS found: 597.2398

EXAMPLE 61
N-[3-[1-(4-Hydroxy-2-oxo-6-phenethyl-6-propyl-5,6-dihydro-2H-pyran-3-yl)-cyclopropylmethyl]-phenyl]-1-methyl-1H-imidazole-4-sulfonamide (Formula D-6: $R_1$ is phenethyl, $R_2$ is propyl, $R_3$ is cyclopropyl, $R_4$ is 1-methyl-imidazol-4-yl) Refer to Chart D.

The title compound is prepared from the amine of Preparation 20 (Formula D-5: $R_1$ is phenethyl, $R_2$ is propyl, $R_3$ is cyclopropyl) and 1-methyl-imidazole-4-sulfonyl chloride of formula D-7 wherein $R_4$ is 1-methylimidazol-4-yl using the general procedure for sulfonylation of Example 40 to yield the title compound as a white amorphous solid after flash chromatography with 5% EtOAc/$CH_2Cl_2$.

Physical characteristics are as follows:
$^1$H NMR complicated by presence of diastereomers.
$^1$H NMR (300 MHz, $CD_3OD$) δ 0.13, 0.42, 0.67, 0.95, 1.44, 1.68–2.13, 2.56, 3.17, 6.91, 7.01–7.33, 7.52, 7.63.
HRMS found: 550.2370.

EXAMPLE 62
N-[3-[1-(4-Hydroxy-2-oxo-6,6-diphenethyl-5,6-dihydro-2H-pyran-3-yl)-cyclopropylmethyl]-phenyl]-1-methyl-1H-imidazole-4-sulfonamide (Formula D-6: $R_1$ is phenethyl, $R_2$ is phenethyl, $R_3$ is cyclopropyl, $R_4$ is 1-methyl-imidazol-4-yl) Refer to Chart D.

The title compound is prepared from the amine of Preparation 20 (Formula D-5: $R_1$ is phenethyl, $R_2$ is phenethyl, $R_3$ is cyclopropyl) and 1-methyl-imidazole-4-sulfonyl chloride of formula D-7 wherein $R_4$ is 1-methylimidazol-4-yl, using the general procedure for sulfonylation of Example 40 to yield the title compound as a white amorphous solid after flash chromatography with 5% EtOAc/$CH_2Cl_2$.

Physical characteristics are as follows:
$^1$H NMR (300 MHz, $CD_3OD$) δ 0.13, 0.42, 0.68, 1.73, 1.88–2.17, 2.68, 3.19, 3.64, 6.93, 7.02–7.31, 7.52, 7.64.
HRMS found: 612.2530.

EXAMPLE 63
N-[3-[1-(4-Hydroxy-2-oxo-6,6-dipentyl-5,6-dihydro-2H-pyran-3-yl)-propyl]-phenyl]-1-methyl-1H-imidazole-4-sulfonamide (Formula D-6: $R_1$ is pentyl, $R_2$ is pentyl, $R_3$ is ethyl, $R_4$ is 1-methyl-imidazol-4-yl) Refer to Chart D.

The title compound is prepared from the amine of Preparation 20 (Formula D-5: $R_1$ is pentyl, $R_2$ is pentyl, $R_3$ is ethyl) and 1-methyl-imidazole-4-sulfonyl chloride of formula D-7 wherein $R_4$ is 1-methylimidazole-4-yl, using the general procedure for sulfonylation of Example 40 to yield the title compound as a white amorphous solid after flash chromatography with 5% EtOAc/$CH_2Cl_2$.

Physical characteristics are as follows:
$^1$H NMR (300 MHz, $CD_3OD$) δ 0.87, 1.25, 1.55–1.68, 1.92, 2.13, 2.57, 3.66, 3.93, 6.86, 7.03, 7.16, 7.55, 7.63.

EXAMPLE 64
4-Cyano-N-[3-[1-(4-Hydroxy-2-oxo-6,6-dipentyl-5,6-dihydro-2H-pyran-3-yl)-propyl]-phenyl]-benzenesulfonamide (Formula D-6:
$R_1$ is pentyl, $R_2$ is pentyl, $R_3$ is ethyl, $R_4$ is 4-cyanophenyl) Refer to Chart D.

The title compound is prepared from the amine of Preparation 20 (Formula D-5: $R_1$ is pentyl, $R_2$ is pentyl, $R_3$ is ethyl) and 1-methyl-imidazole-4-sulfonyl chloride of formula D-7 wherein $R_4$ is 4-cyanophenyl, using the general procedure for sulfonylation of Example 40 to yield the title compound as a white amorphous solid after flash chromatography with 5% EtOAc/$CH_2Cl_2$.

Physical characteristics are as follows:
$^1$H NMR (300 MHz, $CD_3OD$) δ 0.86, 1.23, 1.52–1.67, 1.93, 2.14, 2.56, 3.93, 6.80, 7.05, 7.18, 7.80, 7.86.

EXAMPLES 65–93
Using the general procedure of Example 40, but substituting the appropriate reactants, the following compounds of the present invention are prepared:

EXAMPLE 65
N-[3-[1(R or S)-(6(R or S)-4-Hydroxy-2-oxo-6-phenethyl-6-propyl-5,6-dihydro-2H-pyran-3-yl)-propyl]-phenyl]-1-methyl-1H-imidazole-4-sulfonamide (Formula D-6: $R_1$ is phenethyl, $R_2$ is propyl, $R_3$ is ethyl, $R_4$ is 1-methylimidazol-4-yl) Refer to Chart D.

EXAMPLE 66
N-[3-[1(R or S)-(6(S or R)-4-Hydroxy-2-oxo-6-phenethyl-6-propyl-5,6-dihydro-2H-pyran-3-yl)-propyl]-phenyl]-1-methyl-1H-imidazole-4-sulfonamide (Formula D-6: $R_1$ is phenethyl, $R_2$ is propyl, $R_3$ is ethyl, $R_4$ is 1-methylimidazol-4-yl) Refer to Chart D.

EXAMPLE 67
N-[3-[1(S or R)-(6(R or S)-4-Hydroxy-2-oxo-6-phenethyl-6-propyl-5,6-dihydro-2H-pyran-3-yl)-propyl]-phenyl]-1-methyl-1H-imidazole-4-sulfonamide (Formula D-6: $R_1$ is phenethyl, 14 is propyl, $R_3$ is ethyl, $R_4$ is 1-methylimidazol-4-yl) Refer to Chart D.

EXAMPLE 68
N-[3-[1(S or R)-(6(S or R)-4-Hydroxy-2-oxo-6-phenethyl-6-propyl-5,6-dihydro-2H-pyran-3-yl)-propyl]-phenyl]-1-methyl-1H-imidazole-4-sulfonamide (Formula D-6: $R_1$ is phenethyl, $R_2$ is propyl, $R_3$ is ethyl, $R_4$ is 1-methylimidazol-4-yl) Refer to Chart D.

EXAMPLE 69
N-[3-[t-Butyl-(4-hydroxy-2-oxo-6-phenethyl-6-propyl-5,6-dihydro-2H-pyran-3-yl)-methyl]-phenyl]-1-methyl-1H-imidazole-4-sulfonamide (Formula D-6: $R_1$ is phenethyl, $R_2$ is propyl, $R_3$ is t-butyl, $R_4$ is 1-methylimidazol-4-yl) Refer to Chart D.

EXAMPLE 70
4-Cyano-N-[3-[t-butyl-(4-hydroxy-2-oxo-6-phenethyl-6-propyl-5,6-dihydro-2H-pyran-3-yl)-methyl]-phenyl]-benzenesulfonamide (Formula D-6: $R_1$ is phenethyl, $R_2$ is propyl, $R_3$ is t-butyl, $R_4$ is 4-cyanophenyl) Refer to Chart D.

EXAMPLE 71
4-Fluoro-N-[3-[t-butyl-(4-hydroxy-2-oxo-6-phenethyl-6-propyl-5,6-dihydro-2H-pyran-3-yl)-methyl]-phenyl]-benzenesulfonamide (Formula D-6: $R_1$ is phenethyl, $R_2$ is propyl, $R_3$ is t-butyl, $R_4$ is 4-fluorophenyl) Refer to Chart D.

EXAMPLE 72
N-[3-[t-Butyl-(4-hydroxy-2-oxo-6-phenethyl-6-propyl-5,6-dihydro-2H-pyran-3-yl)-methyl]-phenyl]-8-quinolinesulfonamide (Formula D-6: $R_1$ is phenethyl, $R_2$ is propyl, $R_3$ is t-butyl, $R_4$ is quinolin-8-yl) Refer to Chart D.

EXAMPLE 73
N-[3-[1-(6-(2-(1-Methyl-1H-imidazole-4-sulfonylamino)-ethyl)-4-hydroxy-2-oxo-6-propyl-5,6-dihydro-2H-pyran-3-yl)-propyl]-phenyl]-1-methyl-1H-imidazole-4-sulfonamide (Formula D-6: $R_1$ is 2-(1-methylimidazole-4-sulfonylamino)-ethyl, $R_2$ is propyl, $R_3$ is ethyl, $R_4$ is 1-methylimidazol-4-yl) Refer to Chart D.

EXAMPLE 74
N-[3-[1-(4-Hydroxy-2-oxo-6,6-diphenethyl-5,6-dihydro-2H-pyran-3-yl)-propyl]-phenyl]-2-pyridinesulfonamide (Formula D-6: $R_1$ is phenethyl, $R_2$ is phenethyl, $R_3$ is ethyl, $R_4$ is 2-pyridyl) Refer to Chart D.

EXAMPLE 75
4-Cyano-N-[3-[1-(4-hydroxy-2-oxo-6,6-diphenethyl-5,6-dihydro-2H-pyran-3-yl)-propyl]-phenyl]-2-pyridinesulfonamide (Formula D-6: $R_1$ is phenethyl, $R_2$ is phenethyl, $R_3$ is ethyl, $R_4$ is 4-cyano-2-pyridyl) Refer to Chart D.

EXAMPLE 76
N-[3-[1-(4-Hydroxy-2-oxo-6,6-diphenethyl-5,6-dihydro-2H-pyran-3-yl)-propyl]-phenyl]-2-quinolinesulfonamide (Formula D-6: $R_1$ is phenethyl, $R_2$ is phenethyl, $R_3$ is ethyl, $R_4$ is quinolin-2-yl) Refer to Chart D.

EXAMPLE 77
2-Hydroxy-N-[3-[1-(4-hydroxy-2-oxo-6,6-diphenethyl-5,6-dihydro-2H-pyran-3-yl)-propyl]-phenyl]-benzenesulfonamide (Formula D-6: $R_1$ is phenethyl, $R_2$ is phenethyl, $R_3$ is ethyl, $R_4$ is 2-hydroxyphenyl) Refer to Chart D.

EXAMPLE 78
N-[3-[1-(4-Hydroxy-2-oxo-6,6-diphenethyl-5,6-dihydro-2H-pyran-3-yl)-propyl]-phenyl]-2-pyrimidinesulfonamide (Formula D-6: $R_1$ is phenethyl, $R_2$ is phenethyl, $R_3$ is ethyl, $R_4$ is 2-pyrimidyl) Refer to Chart D.

EXAMPLE 79
N-[3-[1-(4-Hydroxy-2-oxo-6,6-diphenethyl-5,6-dihydro-2H-pyran-3-yl)-propyl]-phenyl]-2-quinazolinesulfonamide (Formula D-6: $R_1$ is phenethyl, $R_2$ is phenethyl, $R_3$ is ethyl, $R_4$ is quinazolin-2-yl) Refer to Chart D.

EXAMPLE 80
N-[3-[1-(4-Hydroxy-2-oxo-6,6-diphenethyl-5,6-dihydro-2H-pyran-3-yl)-propyl]-phenyl]-7H-purine-6-sulfonamide (Formula D-6: $R_1$ is phenethyl, $R_2$ is phenethyl, $R_3$ is ethyl, $R_4$ is 7H-purin-6-yl) Refer to Chart D.

EXAMPLE 81
N-[3-[1-(4-Hydroxy-2-oxo-6,6-diphenethyl-5,6-dihydro-2H-pyran-3-yl)-propyl]-phenyl]-1H-imidazole-2-sulfonamide (Formula D-6: $R_1$ is phenethyl, $R_2$ is phenethyl, $R_3$ is ethyl, $R_4$ is 1H-imidazol-2-yl) Refer to Chart D.

EXAMPLE 82
N-[3-[1-(4-Hydroxy-2-oxo-6,6-diphenethyl-5,6-dihydro-2H-pyran-3-yl)-propyl]-phenyl]-1H-benzimidazole-2-sulfonamide (Formula D-6: $R_1$ is phenethyl, $R_2$ is phenethyl, $R_3$ is ethyl, $R_4$ is 1H-benzimidazol-2-yl) Refer to Chart D.

EXAMPLE 83
N-[3-[1-(4-Hydroxy-2-oxo-6,6-diphenethyl-5,6-dihydro-2H-pyran-3-yl)-propyl]-phenyl]-thiazole-4-sulfonamide (Formula D-6: $R_1$ is phenethyl, $R_2$ is phenethyl, $R_3$ is ethyl, $R_4$ is thiazol-2-yl) Refer to Chart D.

EXAMPLE 84
N-[3-[1-(4-Hydroxy-2-oxo-6-phenethyl-6-propyl-5,6-dihydro-2H-pyran-3-yl)-propyl]-phenyl]-2-pyridinesulfonamide (Formula D-6: $R_1$ is propyl, $R_2$ is phenethyl, $R_3$ is ethyl, $R_4$ is 2-pyridyl) Refer to Chart D.

EXAMPLE 85
4-Cyano-N-[3-[1-(4-hydroxy-2-oxo-6-phenethyl-6-propyl-5,6-dihydro-2H-pyran-3-yl)-propyl]-phenyl]-2-pyridinesulfonamide (Formula D-6: $R_1$ is propyl, $R_2$ is phenethyl, $R_3$ is ethyl, $R_4$ is 4-cyano-2-pyridyl) Refer to Chart D.

EXAMPLE 86
N-[3-[1-(4-Hydroxy-2-oxo-6-phenethyl-6-propyl-5,6-dihydro-2H-pyran-3-yl)-propyl]-phenyl]-2-quinolinesulfonamide (Formula D-6: $R_1$ is propyl, $R_2$ is phenethyl, $R_3$ is ethyl, $R_4$ is quinolin-2-yl) Refer to Chart D.

EXAMPLE 87
2-Hydroxy-N-[3-[1-(4-hydroxy-2-oxo-6-phenethyl-6-propyl-5,6-dihydro-2H-pyran-3-yl)-propyl]-phenyl]-benzenesulfonamide (Formula D-6: $R_1$ is propyl, $R_2$ is phenethyl, $R_3$ is ethyl, $R_4$ is 2-hydroxyphenyl) Refer to Chart D.

EXAMPLE 88

N-[3-[1-(4-Hydroxy-2-oxo-6-phenethyl-6-propyl-5,6-dihydro-2H-pyran-3-yl)-propyl]-phenyl]-2-pyrimidinesulfonamide (Formula D-6: $R_1$ is propyl, $R_2$ is phenethyl, $R_3$ is ethyl, $R_4$ is 2-pyrimidyl) Refer to Chart D.

EXAMPLE 89

N-[3-[1-(4-Hydroxy-2-oxo-6-phenethyl-6-propyl-5,6-dihydro-2H-pyran- 3-yl)-propyl]-phenyl]-2-quinazolinesulfonamide (Formula D-6: $R_1$ is propyl, $R_2$ is phenethyl, $R_3$ is ethyl, $R_4$ is quinazolin-2-yl) Refer to Chart D.

EXAMPLE 90

N-[3-[1-(4-Hydroxy-2-oxo-6-phenethyl-6-propyl-5,6-dihydro-2H-pyran-3-yl)-propyl]-phenyl]-7H-purine-6-sulfonamide (Formula D-6: $R_1$ is propyl, $R_2$ is phenethyl, $R_8$ is ethyl, $R_4$ is 7H-purin-6-yl) Refer to Chart D.

EXAMPLE 91

N-[3-[1-(4-Hydroxy-2-oxo-6-phenethyl-6-propyl-5,6-dihydro-2H-pyran-3-yl)-propyl]-phenyl]-1H-imidazole-2-sulfonamide (Formula D-6: $R_1$ is propyl, $R_2$ is phenethyl, $R_3$ is ethyl, $R_4$ is 1H-imidazol-2-yl) Refer to Chart D.

EXAMPLE 92

N-[3-[1-(4-Hydroxy-2-oxo-6-phenethyl-6-propyl-5,6-dihydro-2H-pyran-3-yl)-propyl]-phenyl]1H-benzimidazole-2-sulfonamide (Formula D-6: $R_1$ is propyl, $R_2$ is phenethyl, $R_3$ is ethyl, $R_4$ is 1H-benzimidazol-2-yl) Refer to Chart D.

EXAMPLE 93

N-[3-[1-(4-Hydroxy-2-oxo-6-phenethyl-6-propyl-5,6-dihydro-2H-pyran-3-yl)-propyl]-phenyl]-thiazole-4-sulfonamide (Formula D-6: $R_1$ is propyl, $R_2$ is phenethyl, $R_3$ is ethyl, $R_4$ is thiazol-2-yl) Refer to Chart D.

EXAMPLE 93A

4-Fluoro-N-[3-[1-(4-hydroxy-2-oxo-6-phenethyl-6-propyl-5,6-dihydro-2H-pyran-3-yl)-propyl]-phenyl]-benzenesulfonamide (Formula D-6: $R_1$ is phenethyl, $R_2$ is propyl, $R_3$ is ethyl, $R_4$ is 4-fluorophenyl) Refer to Chart D.

The title compound is prepared from the amine of Preparation 20 (Formula D-5: $R_1$ is phenethyl, $R_2$ is propyl, $R_3$ is ethyl) and 4-fluoro benzenesulfonyl chloride using the general procedure for sulfonylation of Example 40 to yield the title compound as an off-white amorphous solid after flash chromatography with 5% EtOAc/$CH_2Cl_2$.

Physical characteristics are as follows:
$^1$H NMR complicated by presence of diastereomers.
$^1$H NMR (300 MHz, $CD_3OD$) δ 0.75–0.96, 1.31–1.48, 1.57–2.01, 2.09–2.22, 2.48–2.71, 3.92, 3.94, 6.86–7.24, 7.72.

Preparation 22 6-(2-Cyclopropyl-1-cyclopropylmethyl-ethyl)-4-hydroxy-2H-pyran-2-one (Formula E-2) Refer to Chart E.

To a cold (−78° C.) stirred solution of 1.5 ml of diisopropylamine in 9 ml of dry tetrahydrofuran, under argon, is added 6.2 ml of a 1.6 M solution of n-butyllithium in hexane. The solution is warmed to 0° C. and then treated with a solution of 378 mg of commercially available 4-hydroxy-6-methyl-2-pyrone of formula E-1 in 8 ml of hexamethylphosphoramide. After 30 minutes at 0° C., 0.32 ml of bromomethylcyclopropane is added; after another ten minutes, a second portion of the same amount is added. The reaction is stirred, allowed to warm to room temperature overnight, and is then partitioned between ethyl acetate and excess dilute hydrochloric acid. The organic phase is washed with brine, dried over magnesium sulfate, and concentrated under reduced pressure. The residue is flash chromatographed on silica gel 60 (230–400 mesh) using 25% ethyl acetate in dichloromethane containing 1% acetic acid to provide 371 mg of the title compound, along with 206 mg of monoalkylated material.

Physical characteristics are as follows:
$^1$H NMR δ 0.0, 0.4, 0.6, 1.5, 1.6, 2.2, 5.6, 6.1, 7.2–7.3, 11.5;
EI MS m/z=234;
TLC $R_f$ 0.29 (25% ethyl acetate in dichloromethane containing 1% acetic acid).

Preparation 23 3-(α-Cyclopropyl-meta-(benzyloxycarbonylamino)benzyl)-6-(2-cyclopropyl-1-cyclopropylmethyl-ethyl)-4-hydroxy-2H-pyran-2-one (Formula E-3) Refer to Chart E.

A mixture of 367 mg of the title compound of Preparation 22, 470 mg of the title compound of Preparation F-5, 60 mg of p-toluenesulfonic acid monohydrate, and 1 g of 3 Å molecular sieves in 5 ml of benzene is heated with stirring overnight under argon. The mixture is diluted with dichloromethane and ether and filtered through a pad of sodium sulfate. The solvent is removed under reduced pressure and the residue is flash chromatographed on silica gel 60 (230–400 mesh) using 5–20% ethyl acetate in dichloromethane to afford 399 mg of the title compound.

Physical characteristics are as follows:
$^1$H NMR δ −0.06, 0.3, 0.5, 1.4, 1.5, 2.5, 3.5, 5.1, 7.2–7.4;
EI HRMS m/z=513.2513;
TLC $R_f$ 0.28 (5% ethyl acetate in dichloromethane).

Preparation 24 3-(α-Cyclopropyl-meta-aminobenzyl)-6-(2-cyclopropyl-1-cyclopropylmethyl-ethyl)-4-hydroxy-2H-pyran-2-one (Formula E-4) Refer to Chart E.

A mixture of 391 mg of the title compound of Preparation 23 and 100 mg of 5% palladium on carbon in 10 ml of methanol is shaken overnight under 40 psi of hydrogen. The mixture is then filtered through Celite, and the filtrate is concentrated under reduced pressure to provide 280 mg of the title compound.

Physical characteristics are as follows:
$^1$H NMR δ 0.0, 0.2–0.7, 1.4, 1.6, 1.8, 2.6, 6.8, 7.2–7.4;
TLC $R_f$ 0.38 (30% ethyl acetate in dichloromethane.)

EXAMPLE 94

N-(3-{Cyclopropyl-[6-(2-cyclopropyl-1-cyclopropylmethyl-ethyl)-4-hydroxy-2-oxo-2H-pyran-3-yl]-methyl}-phenyl)-4-fluoro-benzenesulfonamide (Formula E-6) Refer to Chart E.

To a mixture of 57 mg of the title compound of Preparation 24 and 24 μL of pyridine in 0.5 mL of dichloromethane is added 29 mg of 4-fluorobenzenesulfonyl chloride. After stirring overnight, the solution is diluted with ethyl acetate and washed with dilute aqueous hydrochloric acid, brine, dried over sodium sulfate, and concentrated under reduced pressure. The residue is purified by flash column chromatography on silica gel 60 (230–400 mesh) using 10% ethyl acetate in dichloromethane to give 56 mg of the title compound.

Physical characteristics are as follows:
$^1$H-NMR ($CDCl_3$) δ −0.07, 0.13, 0.33, 0.54, 1.39, 1.51, 1.72, 2.55, 3.39, 6.12, 6.87, 7.00, 7.08, 7.19, 7.27, 7.72, 9.72;
EI-MS: [M+]=537.1977 found.

EXAMPLES 95–97

Following the procedure described above and using starting materials and reagents known and available to one of ordinary skill in organic synthesis, the following additional compounds are prepared:

EXAMPLE 95

4-Cyano-N-(3-{cyclopropyl-[6-(2-cyclopropyl-1-cyclopropylmethyl-ethyl)-4-hydroxy-2-oxo-2H-pyran-3-yl]-methyl}-phenyl)-benzenesulfonamide (Formula E-7) Refer to Chart E.

Physical characteristics are as follows:
$^1$H-NMR (CDCl$_3$) δ −0.03, 0.13, 0.23, 0.36, 0.44, 0.57, 1.41, 1.58, 1.75, 2.57, 3.32, 5.98, 6.89, 7.11, 7.21, 7.68, 7.82;
EI-MS: [M+]=544.2035 found.

EXAMPLE 96

N-(3-{Cyclopropyl-[6-(2-cyclopropyl-1-cyclopropylmethyl-ethyl)-4-hydroxy-2-oxo-2H-pyran-3-yl]-methyl}-phenyl)-8-quinolinesulfonamide (Formula E-8) Refer to Chart E.

Physical characteristics are as follows:
$^1$H-NMR (CDCl$_3$) δ −0.07, 0.18, 0.37, 0.54, 1.37, 1.51, 2.53, 3.31, 5.96, 6.87, 7.00, 7.13, 7.48, 7.54, 7.92, 8.23, 9.07;
EI-MS: [M+]=570.2188 found.

EXAMPLE 97

N-(3-{Cyclopropyl-[6-(2-cyclopropyl-1-cyclopropylmethyl-ethyl)-4-hydroxy-2-oxo-2H-pyran-3-yl]-methyl}-phenyl)-1-methyl-1H-imidazole-4-sulfonamide (Formula E-9) Refer to Chart E.

Physical characteristics are as follows:
$^1$H-NMR (CDCl$_3$-CD$_3$OD) δ −0.08, 0.13, 0.33, 0.56, 1.37, 1.51, 1.73, 2.54, 3.21, 3.60, 5.95, 6.82, 7.0, 7.19, 7.37, 7.5;
EI-MS: [M+]=523.2142 found.

EXAMPLE 98

Chiral HPLC Separation of N-(3-{Cyclopropyl-[6-(2-cyclopropyl-1-cyclopropylmethyl-ethyl)-4-hydroxy-2-oxo-2H-pyran-3-yl]-methyl}-phenyl)-1-methyl-1H-imidazole-4-sulfonamide (Formula E-9) to give (R or S)-N-(3-{Cyclopropyl-[6-(2-cyclopropyl-1-cyclopropylmethyl-ethyl)-4-hydroxy-2-oxo-2H-pyran-3-yl]-methyl}-phenyl)-1-methyl-1H-imidazole-4-sulfonamide (Formula E-10) and (R or S)-N-(3-{Cyclopropyl-[6-(2-cyclopropyl-1-cyclopropylmethyl-ethyl)-4-hydroxy-2-oxo-2H-pyran-3-yl]-methyl}-phenyl)-1-methyl-1H-imidazole-4-sulfonamide (Formula E-11) Refer to Chart E.

A stock sample of the title compound of Example 97 (3 mg/ml) in 5.0 mL each of mobile phase (30% isopropanol, 0.1% acetic acid, and 0.2% water in hexane) and isopropanol is prepared. The stock sample is filtered through a 0.45 micron syringe filter and washed with ethanol to give 14.0 mL of clear filtrate. This solution is chromatographed on a 2.0×2.5 cm (R,R) Whelk-O 1 (Regis Technologies, Inc., Morton Grove, Ill. 60053) column at 3.50 mL per injection using an automated chromatographic system. The eluant is monitored and the pools corresponding to the desired peaks from multiple injections are combined, concentrated under reduced pressure and azeotroped with toluene. The residues are dissolved in methanol, filtered through a syringe filter and the filtrates concentrated under reduced pressure to give the title compounds (>95% pure):

(R or S)-N-(3-{Cyclopropyl-[6-(2-cyclopropyl-1-cyclopropylmethyl-ethyl)-4-hydroxy-2-oxo-2H-pyran-3-yl]-methyl}-phenyl)-1-methyl-1H-imidazole-4-sulfonamide (Formula E-10) Physical characteristics are as follows:
$^1$H-NMR (CDCl$_3$-CD$_3$OD) δ −0.07, 0.14, 0.34, 0.57, 1.32, 1.55, 1.75, 2.51, 3.24, 3.60, 5.87, 6.85, 7.03, 7.15, 7.27, 7.37;
EI-MS: [M+]=523.2149 found.

(R or S)-N-(3-{Cyclopropyl-[6-(2-cyclopropyl-1-cyclopropylmethyl-ethyl)-4-hydroxy-2-oxo-2H-pyran-3-yl]-methyl}-phenyl)-1-methyl-1H-imidazole-4-sulfonamide (Formula E-11)

Physical characteristics are as follows:
$^1$H-NMR (CDCl$_3$-CD$_3$OD) δ −0.07, 0.14, 0.33, 0.55, 1.33, 1.56, 1.75, 2.51, 3.23, 3.60, 5.88, 6.86, 7.03, 7.14, 7.27, 7.38;
EI-MS: [M+]=523.2137 found.

EXAMPLES 99–103

Following the procedure described above and using starting materials and reagents known and available to one of ordinary skill in organic synthesis, the following additional compounds are prepared:

EXAMPLE 99

N-(3-{Cyclopropyl-[6-(2-cyclopropyl-1-cyclopropylmethyl-ethyl)-4-hydroxy-2-oxo-2H-pyran-3-yl]-methyl}-phenyl)-2-pyridine-sulfonamide (Formula E-12)

Physical characteristics are as follows:
$^1$H-NMR (CDCl$_3$-CD$_3$OD) δ −0.05, 0.07, 0.17, 0.34, 0.55, 1.35, 1.55, 1.7, 2.5, 3.24, 5.86, 6.90, 7.03, 7.15, 7.39, 7.78, 8.60;
EI-MS: [M+]=520;
TLC R$_f$ 0.35 (25% ethyl acetate in dichloromethane).

EXAMPLE 100

N-(3-{Cyclopropyl-[6-(2-cyclopropyl-1-cyclopropylmethyl-ethyl)-4-hydroxy-2-oxo-2H-pyran-3-yl]-methyl}-phenyl)-1-methyl-1H-imidazole-2-sulfonamide (Formula E-13)

Physical characteristics are as follows:
$^1$H-NMR (CDCl$_3$-CD$_3$OD) δ −0.05, 0.15, 0.35, 0.56, 1.35, 1.55, 1.75, 2.53, 3.23, 3.39, 5.89, 6.81, 6.90, 6.97, 7.09, 7.25;
EI-MS: [M+]=523;
TLC R$_f$ 0.31 (5% methanol in dichloromethane).

EXAMPLE 101

N-(3-{Cyclopropyl-[6-(2-cyclopropyl-1-cyclopropylmethyl-ethyl)-4-hydroxy-2-oxo-2H-pyran-3-yl]-methyl}-phenyl)-1H-benzo-imidazole-2-sulfonamide (Formula E-14)

Physical characteristics are as follows:
$^1$H-NMR (CDCl$_3$-CD$_3$OD) δ −0.07, 0.1, 0.15, 0.35, 0.56, 1.38, 1.58, 1.65, 2.55, 3.28, 5.95, 6.73, 6.96, 7.10, 7.28, 7.58;
FAB-MS: [M+H]=560.2220 found.

EXAMPLE 102

N-(3-{Cyclopropyl-[6-(2-cyclopropyl-1-cyclopropylmethyl-ethyl)-4-hydroxy-2-oxo-2H-pyran-3-yl]-methyl}-phenyl)-1H-imidazole-2-sulfonamide (Formula E-15)

Physical characteristics are as follows:
$^1$H-NMR (CDCl$_3$-CD$_3$OD) δ 0.0, 0.25, 0.4, 0.6, 1.4, 1.6, 1.65, 2.6, 3.35, 6.0, 6.8, 7.0, 7.2, 7.4;
EI-MS: [M+]=509;
TLC R$_f$ 0.25 (5% methanol in dichloromethane).

EXAMPLE 103

N-(3-{Cyclopropyl-[6-(2-cyclopropyl-1-cyclopropylmethyl-ethyl)-4-hydroxy-2-oxo-2H-pyran-3-yl]-methyl}-phenyl)-2-quinolinesulfonamide (Formula E-16)

Physical characteristics are as follows:

¹H-NMR (CDCl₃) δ 0.0, 0.2, 0.4, 0.6, 1.4, 1.6, 1.7, 2.6, 3.3, 6.0, 7.0–7.2, 7.3, 7.7, 7.8–8.0, 8.2, 8.3;

EI-MS: [M+]=570;

TLC $R_f$ 0.53 (5% methanol in dichloromethane).

Preparation 25 Cyclopropyl meta-nitrophenyl ketone (Formula F-2) Refer to Chart F.

A 250 ml three necked flask fitted with thermometer and addition funnel is charged with 130 ml of fuming 90% nitric acid and cooled to −10° C. Into the stirred liquid is added dropwise 21 ml of commercially available cyclopropyl phenyl ketone of formula F-1. The rate of addition is regulated to maintain the reaction temperature at about −10° C. Upon completion of addition, the resulting clear yellow solution is stirred for another 10 minutes at −10° C., then poured into 1 L of crushed ice. The precipitated solid is extracted with 700 ml of toluene, and the extract is washed twice with 5% sodium hydroxide solution, once with brine, and dried over magnesium sulfate. The solvent is removed under reduced pressure and the residue is recrystallized from methanol at −25° C. to give 14.6 g of the title compound as dense, pale yellow prisms. The mother liquor contained substantial amounts of the ortho isomer.

Physical characteristics are as follows:

¹H NMR δ 1.2, 1.3, 2.7, 7.70, 8.3, 8.4, 8.85;

IR 1664, 1529, 1352,1225, 1082, 1017, 852, 689 cm⁻¹;

Anal. Found: C, 62.89; H, 4.73; N, 7.32;

EI MS m/z 191;

TLC $R_f$ 0.32 (25% ethyl acetate in hexane).

Preparation 26 meta-Aminophenyl cyclopropyl ketone (Formula F-3) Refer to Chart F.

A solution of 5.76 g of the title compound of Preparation 25 is prepared with the aid of heat in 100 ml of methanol. To this is added 450 mg of 5% platinum on carbon catalyst, and the mixture is stirred vigorously under 1 atmosphere of hydrogen. After 5 hours, the mixture is filtered through a pad of Celite and the filtrate concentrated under reduced pressure to afford 4.89 g of the title compound as a greenish oil.

Physical characteristics are as follows:

¹H NMR δ 1.0, 1.2, 2.6, 3.9, 6.8, 7.2, 7.4;

TLC $R_f$ 0.50 (80% ethyl acetate in hexane).

Preparation 27 meta-Benzyloxycarbonylaminophenyl cyclopropyl ketone (Formula F-4) Refer to Chart F.

To a cold (0° C.), stirred solution of 4.89 g of the title compound of Preparation 26 and 6.3 ml of diisopropylethylamine in 90 ml of dichloromethane is added dropwise 4.7 ml of benzyl chloroformate. The completed solution is allowed to warm to room temperature. After 4 hours, the mixture is washed with dilute hydrochloric acid, and the aqueous phase extracted with two additional portions of dichloromethane. The combined organic phase is dried over magnesium sulfate and concentrated under reduced pressure to a yellow solid. This is triturated with two 30 ml portions of hexane, these being discarded, and the remaining solid is dried under vacuum to afford 8.74 g of the title compound.

Physical characteristics are as follows:

TLC $R_f$ 0.45 (5% ethyl acetate in dichloromethane).

Preparation 28 meta-Benzyloxycarbonylaminophenyl cyclopropyl carbinol (Formula F-5) Refer to Chart F.

To a stirred solution of 8.74 g of compound F-4 of Preparation 27 in 100 ml of tetrahydrofuran and 100 ml of ethanol is added, in portions, 4.5 g of sodium borohydride. After 3 hours at room temperature, the mixture is cooled in ice for the addition of 100 ml of 1N hydrochloric acid. The mixture is thrice extracted with dichloromethane, and the combined extract dried over magnesium sulfate. Solvent is removed under reduced pressure and the residue flash chromatographed on silica gel 60 (230–400 mesh) using 40% ethyl acetate in hexane to provide 8.48 g of the title compound as a white crystalline solid. This is optionally recrystallized from ethyl acetate-hexane.

Physical characteristics are as follows:

¹H NMR δ 0.3–0.6, 1.1, 2.35, 3.92, 5.17, 7.1, 7.2–7.4;

IR 1693, 1599, 1559, 1449, 1235, 1054, 697 cm⁻¹;

Anal. Found: C, 72.57; H, 6.51; N, 4.61;

Preparation 29 4-Hydroxy-6-[3-(2-methoxy-ethoxy)-propyl]-pyran-2-one (Formula G-1) Refer to Chart G.

To a flame-dried flask under an argon atmosphere is added 2.80 mL of diisopropylamine and 20.0 mL of dry tetrahydrofuran. The solution is cooled to −78° C. and treated with 12.5 mL (1.6 M in hexane) of n-butyllithium. The solution is warmed to 0° C. for 30 minutes, then treated wtih 5.0 mL of dry hexamethylphosphoramide. The lithium diisopropylamide solution is then treated with 1.20 g of commercially available 4-hydroxy-6-methyl-2-pyrone of formula G-0 as a solution in 16 mL of dry tetrahydrofuran and 14 mL of dry hexamethylphosphoramide. After 30 minutes the mixture is treated with 2.30 g of 2-(2-methoxy-ethoxy)-ethyl iodide as a solution in 12 mL of dry tetrahydrofuran. The mixture is stirred 1 hour at 0° C. and then warmed to room temperature. After 1 hour the reaction is quenched with excess 1 N aqueous hydrochloric acid. The mixture is concentrated under reduced pressure and partioned between dichlormethane and water. The aqueous phase is extracted with sufficient volumes of dichlormethane to remove the title compound. The combined organic extracts are washed with brine, dried over magnesium sulfate and concentrated under reduced pressure. The residue is purified by flash column chromatography on silica gel 60 (230–400 mesh) eluting with 30% ethyl acetate in dichloromethane containing 3% acetic acid to 80% ethyl acetate in dichloromethane containing 5% acetic acid to give 1.34 g of the title compound.

Physical characteristics are as follows:

¹H-NMR (CDCl₃) δ 1.93, 2.54, 3.39, 3.55, 5.55, 5.90;

TLC $R_f$ 0.26 (50% ethyl acetate in dichloromethane containing 5% acetic acid).

Preparation 30 3-(α-Cyclopropyl-meta-(benzyloxycarbonylamino)benzyl)-4-hydroxy-6-[3-(2-methoxy-ethoxy)-propyl]-pyran-2-one (Formula G-2) Refer to Chart G.

A mixture of 146 mg of the title compound of Preparation 29, 340 mg of the title compound of Preparation 28, prepared as described in Chart F, 25 mg of p-toluenesulfonic acid monohydrate, and 0.5 g of 3 A molecular sieves in 5 mL of dichloromethane is heated overnight with stirring. The mixture is cooled and the solvent removed under reduced pressure. The residue is purified by flash column chromatography on silica gel 60 (230–400 mesh) eluting with 5% to 10% methanol in ethyl acetate to give 129 mg of the title compound.

Physical characteristics are as follows:

¹H-NMR (CDCl₃) δ 0.25, 0.45, 0.67, 1.77, 2.39, 3.38, 3.51, 5.13, 5.84, 7.17, 7.32, 7.42; EI-MS: [M+]=507.2257 found;

TLC $R_f$ 0.28 (50% ethyl acetate in dichloromethane).

Preparation 31 3-(α-Cyclopropyl-meta-aminobenzyl)-4-hydroxy-6-[3-(2-methoxy-ethoxy)-propyl]-pyran-2-one (Formula G-3) Refer to Chart G.

A mixture of 124 mg of the title compound of Preparation 30 and 35 mg of 5% palladium on charcoal in 5 mL of ethanol is shaken overnight under 50 psi of hydrogen. The mixture is filtered through Celite with ethanol washes of the filter cake. The filtrates are combined and the solvent removed under reduced pressure to give 92 mg of the title compound. Physical characteristics are as follows:

TLC R$_f$ 0.12 (ethyl acetate).

EXAMPLE 104
N-(3-{Cyclopropyl-[4-hydroxy-6-(3-{2-methoxy-ethoxy}-propyl)-2-oxo-2H-pyran-3-yl]-methyl}-phenyl)-1-methyl-1H-imidazole-4-sulfonamide (Formula G-4) Refer to Chart G.

To a mixture of 37 mg of the title compound of Preparation 31 and 18 μL of pyridine in 0.5 mL of dichloromethane is added 20 mg of 1-methylimidazole-4-sulfonyl chloride. After stirring overnight, the solvent is removed under reduced pressure. The residue is azeotroped with toluene and is then purified by flash column chromatography on silica gel 60 (230–400 mesh) using 2% to 8% methanol in dichloromethane to give 32 mg of the title compound.

Physical characteristics are as follows:
$^1$H-NMR (CDCl$_3$) δ 0.1, 0.24, 0.45, 0.65, 1.75, 1.85, 2.46, 3.30, 3.34, 3.50, 5.98, 6.98, 7.08, 7.19, 7.29, 7.42;
EI-MS: [M+]=517.1874 found;
TLC R$_f$ 0.22 (5% methanol in dichloromethane).

Preparation 32 3-(α-Cyclopropyl-meta-(benzyloxycarbonylamino)benzyl)-4-hydroxy-6-methyl-pyran-2-one (Formula H-1) Refer to Chart H.

A mixture of 493 mg of commercially available 4-hydroxy-6-methyl-2-pyrone of formula H-0, 592 mg of the title compound of Preparation 28, prepared as described in Chart F and 56 mg of p-toluenesulfonic acid monohydrate in 20 mL of dichloromethane is heated to reflux through an addition funnel containing 3 Å molecular sieves for 6 hours. The mixture is cooled and the solvent removed under reduced pressure. The residue is purified by flash column chromatography on silica gel 60 (230–400 mesh) eluting with 60% to 100% ethyl acetate in dichloromethane to give 470 mg of the title compound.

Physical characteristics are as follows:
$^1$H-NMR (CDCl$_3$) δ 0.23, 0.43, 0.66, 1.78, 3.41, 5.09, 5.89, 7.00, 7.14, 7.29, 7.37, 10.1;
EI-MS: [M+]=405;
TLC R$_f$ 0.52 (ethyl acetate).

Preparation 33 3-(α-Cyclopropyl-meta-(benzyloxycarbonylamino)benzyl)-4-hydroxy-6-propyl-pyran-2-one (Formula H-2) Refer to Chart H.

To a flame-dried flask under an argon atmosphere is added 0.45 mL of diisopropylamine and 3.0 mL of dry tetrahydrofuran. The solution is cooled to −78° C. and treated with 2.0 mL (1.6 M in hexane) of n-butyllithium. The solution is warmed to 0° C. for 15 minutes, then cooled to −78° C. The lithium diisopropylamide solution is treated with 405 mg of the title compound of Preparation 32 as a solution in 4 mL of dry tetrahydrofuran. After 1 hour at −78° C. the mixture is treated with 85 μL of ethyl bromide. The mixture is then stirred at −78° C. for 3 hours. The reaction is quenched with excess 1 N aqueous hydrochloric acid. The mixture is warmed and partioned between ethyl acetate and phosphate buffer. The aqueous phase is extracted twice with ethyl acetate. The combined organic extracts are dried over magnesium sulfate and concentrated under reduced pressure. The residue is purified by flash column chromatography on silica gel 60 (230–400 mesh) eluting with 10% to 20% ethyl acetate in dichloromethane to give 277 mg of the title compound.

Physical characteristics are as follows:
$^1$H-NMR (CDCl$_3$) δ 0.24, 0.45, 0.65, 0.88, 1.55, 1.79, 2.28, 3.42, 5.10, 5.95, 6.89, 7.15, 7.3, 10.0;
EI-MS: [M+]=433;
TLC R$_f$ 0.33 (10% ethyl acetate in dichloromethane).

Preparation 34 3-(α-Cyclopropyl-meta-(benzyloxycarbonylamino)benzyl)-6-[1-ethyl-3-(2-methoxy-ethoxy)-propyl]-4-hydroxy-pyran-2-one (Formula H-3) Refer to Chart H.

To a flame-dried flask under an argon atmosphere is added 0.30 mL of diisopropylamine and 2.0 mL of dry tetrahydrofuran. The solution is cooled to −78° C. and treated with 1.3 mL (1.6 M in hexane) of n-butyllithium. The solution is warmed to 0° C. for 15 minutes, then cooled to −78° C. The lithium diisopropylamide solution is treated with 277 mg of the title compound of Preparation 33 as a solution in 3 mL of dry tetrahydrofuran. After 1 hour at −78° C., the mixture is treated with 180 mg of 2-(2-methoxy-ethoxy)-ethyl iodide in 3 mL of tetrahydrofuran. The mixture is then stirred at −78° C. for 3 hours. The reaction is quenched with excess 1 N aqueous hydrochloric acid. The mixture is warmed and partioned between ethyl acetate and phosphate buffer. The aqueous phase is extracted thrice with ethyl acetate. The combined organic extracts are washed with brine, dried over magnesium sulfate and concentrated under reduced pressure. The residue is purified by flash column chromatography on silica gel 60 (230–400 mesh) eluting with 25% to 40% ethyl acetate in dichloromethane to give 198 mg of the title compound.

Physical characteristics are as follows:
$^1$H-NMR (CDCl$_3$) δ 0.25, 0.46, 0.66, 0.75, 1.5, 1.76, 2.36, 3.4, 5.15, 5.96, 7.2, 7.3, 7.42, 10.0;
EI-MS: [M+]=535;
TLC R$_f$ 0.29 (25% ethyl acetate in dichloromethane).

Preparation 35 3-(α-Cyclopropyl-meta-aminobenzyl)-6-[1-ethyl-3-(2-methoxy-ethoxy)-propyl]-4-hydroxy-pyran-2-one (Formula H-4) Refer to Chart H.

A mixture of 180 mg of the title compound of Preparation 34 and 50 mg of 5% palladium on charcoal in 2 mL of ethanol is shaken overnight under 50 psi of hydrogen. The mixture is filtered through Celite with ethanol washes of the filter cake. The filtrates are combined and the solvent removed under reduced pressure to give 127 mg of the title compound.

Physical characteristics are as follows:
TLC R$_f$ 0.19 (ethyl acetate).

EXAMPLE 105
N-(3-{Cyclopropyl-[6-(1-ethyl-3-{2-methoxy-ethoxy}-propyl)-4-hydroxy-2-oxo-2H-pyran-3-yl]-methyl}-phenyl)-1-methyl-1H-imidazole-4-sulfonamide (Formula H-5) Refer to Chart H.

To a mixture of 32 mg of the title compound of Preparation 35 and 13 μL of pyridine in 0.8 mL of dichloromethane is added 14.5 mg of 1-methylimidazole-4-sulfonyl chloride. After stirring overnight, the solvent is removed under reduced pressure. The residue is azeotroped with toluene and is then purified by flash column chromatography on silica gel 60 (230–400 mesh) using 1% to 4% methanol in dichloromethane to give 38 mg of the title compound.

Physical characteristics are as follows:
$^1$H-NMR (CDCl$_3$) δ 0.05, 0.25, 0.45, 0.65, 0.83, 1.5–2.0, 2.45, 3.3–3.5, 3.62, 6.00, 6.99, 7.1–7.3, 7.48;
EI-MS: [M+]=545.2186 found;
TLC R$_f$ 0.24 (5% methanol in dichloromethane).

EXAMPLE 106
4-Cyano-N-(3-{cyclopropyl-[6-(1-ethyl-3-{2-methoxy-ethoxy}-propyl)-4-hydroxy-2-oxo-2H-pyran-3-yl]-methyl}-phenyl)-benzenesulfonamide Following the procedure described above and using starting materials and reagents known and available to one of ordinary skill in organic synthesis, the title compound is prepared.

Physical characteristics are as follows:
$^1$H-NMR (CDCl$_3$) δ 0.15, 0.25, 0.45, 0.65, 0.78, 1.2–1.8, 2.4, 3.3–3.6, 3.54, 5.89, 6.95, 7.1–7.3, 7.6–7.9;
FAB-MS: [M+H]=567.2176 found;
TLC R$_f$ 0.40 (50% ethyl acetate in dichloromethane).
Preparation 36 3-(α-Cyclopropyl-meta-(benzyloxycarbonylamino)benzyl)-6-(1-ethyl-3-hydroxy-propyl)-4-hydroxy-pyran-2-one (Formula I-1) Refer to Chart I.

To a flame-dried flask under an argon atmosphere is added 0.46 mL of diisopropylamine and 3.5 mL of dry tetrahydrofuran. The solution is cooled to −78° C. and treated with 2.0 mL (1.6 M in hexane) of n-butyllithium. The solution is warmed to 0° C. for 20 minutes, then cooled to −78° C. The lithium diisopropylamide solution is treated with 433 mg of the title compound of Preparation 33 as a solution in 4 mL of dry tetrahydrofuran. After 1 hour at −78° C. the mixture is treated with gaseous ethylene oxide for 5 minutes. The mixture is then stirred at −78° C. for 15 minutes. The reaction is quenched with excess 1 N aqueous hydrochloric acid. The mixture is warmed and partioned between dichloromethane and phosphate buffer. The aqueous phase is extracted twice with dichloromethane. The combined organic extracts are washed with brine, dried over magnesium sulfate and concentrated under reduced pressure. The residue is purified by flash column chromatography on silica gel 60 (230–400 mesh) eluting with 2% to 8% methanol in dichloromethane to give 144 mg of the title compound.

Physical characteristics are as follows:
$^1$H-NMR (CDCl$_3$) δ 0.22, 0.45, 0.65, 0.7, 1.3–1.7, 1.8, 2.25, 3.4, 5.1, 5.91, 7.1–7.4;
FAB-MS: [M+H]=478;
TLC R$_f$ 0.29 (5% methanol in dichloromethane).
Preparation 37 6-(3-Bromo-1-ethyl-propyl)-3-(α-cyclopropyl-meta-(benzyloxycarbonylamino)benzyl)-4-hydroxy-pyran-2-one (Formula I-2) Refer to Chart I.

To a stirring solution of 114 mg of the title compound of Preparation 36 in 3 mL of tetrahydrofuran is added 160 mg of triphenylphosphine and 200 mg of carbon tetrabromide. After 2 hours, the solvent is removed under reduced pressure and the residue is purified by flash column chromatography on silica gel 60 (230–400 mesh) eluting with 70% to 100% diethyl ether in hexane to give 113 mg of the title compound.

Physical characteristics are as follows:
$^1$H-NMR (CDCl$_3$) δ 0.25, 0.35, 0.55, 0.65, 0.84, 1.5–2.2, 3.2, 3.35, 3.52, 5.16, 5.95, 6.79, 7.1–7.4;
FAB-MS: [M+H]=504.1404 found;
TLC R$_f$ 0.29 (75% diethyl ether in hexane).
Preparation 38 6-(3-Azido-1-ethyl-propyl)-3-(α-cyclopropyl-meta-(benzyloxycarbonylamino)benzyl)-4-hydroxy-pyran-2-one (Formula I-3) Refer to Chart I.

To a stirring solution of 113 mg of the title compound of Preparation 37 in 2.0 mL of ethanol is added 55 mg of sodium azide and 0.5 mL of water. The reaction mixture is heated overnight and then cooled. The solvent is removed under reduced pressure and the residue is purified by flash column chromatography on silica gel 60 (230–400 mesh) eluting with diethyl ether to give 89 mg of the title compound.

Physical characteristics are as follows:
$^1$H-NMR (CDCl$_3$) δ 0.23, 0.33, 0.51, 0.68, 0.82, 1.4–2.0, 2.33, 3.1–3.3, 3.5, 5.15, 5.94, 6.84, 7.1–7.4;
EI-MS: [M+]=502;
TLC R$_f$ 0.52 (10% ethyl acetate in dichloromethane).
Preparation 39 6-(3-Amino-1-ethyl-propyl)-3-(α-cyclopropyl-meta-aminobenzyl)- 4-hydroxy-pyran-2-one (Formula I-4) Refer to Chart I.

A mixture of 87 mg of the title compound of Preparation 38 and 35 mg of 5% palladium on charcoal in 4 mL of ethanol is shaken for 4 hours under 40 psi of hydrogen. The mixture is filtered through Celite with ethanol washes of the filter cake. The filtrates are combined and the solvent removed under reduced pressure to give 70 mg of the title compound as a mixture with 6-(3-amino-1-ethyl-propyl)-3-(α-cyclopropyl-meta-(benzyloxycarbonylamino)benzyl)-4-hydroxy-pyran-2-one.

Physical characteristics are as follows:
TLC R$_f$ 0.05 (5% methanol in dichloromethane).
Preparation 40 3-(Cyclopropyl-{3-[1-methyl-1H-imidazole-4-sulfonylamino]-phenyl}-methyl)-6-({1-ethyl-3-[1-methyl-1H-imidazole-4-sulfonylamino]}-propyl)-2-oxo-2H-pyran-4-yl 1-methyl-1H-imidazole-4-sulfonate (Formula I-5) Refer to Chart I.

To a mixture of 70 mg of the title compound of Preparation 39 and 6-(3-amino-1-ethyl-propyl)-3-(α-cyclopropyl-meta-(benzyloxycarbonylamino)benzyl)-4-hydroxy-pyran-2-one, also from Preparation 39, in 1.5 mL of dichloromethane is added 120 μL of diisopropylethylamine and 92 mg of 1-methylimidazole-4-sulfonyl chloride. After stirring overnight, the solvent is removed under reduced pressure. The residue is azeotroped with toluene and is then purified by flash column chromatography on silica gel 60 (230–400 mesh) using 2% to 6% methanol in dichloromethane to give 49 mg of the title compound.

Physical characteristics are as follows:
$^1$H-NMR (CDCl$_3$) δ 0.2–0.5, 0.75, 0.90, 1.4–2.0, 2.55, 3.0–3.4, 3.6–3.7, 6.63, 7.0–7.7;
FAB-MS: [M+H]=775;
TLC R$_f$ 0.14 (5% methanol in dichloromethane).

EXAMPLE 107

N-(3-{Cyclopropyl-[6-(1-ethyl-3-{1-methyl-1H-imidazole-4-sulfonylamino}-propyl)-4-hydroxy-2-oxo-2H-pyran-3-yl]-methyl}-phenyl)-1-methyl-1H-imidazole-4-sulfonamide (Formula I-6) Refer to Chart I.

A solution of 49 mg of the title compound of Preparation 40 in 4 mL methanol containing ammonia is cooled to 0° C. and treated with gaseous ammonia. After 5 minutes ammonia introduction is ceased, the flask is tightly capped and warmed to room temperature. After standing overnight the solvent is removed under reduced pressure and the residue is purified by flash column chromatography on silica gel 60 (230–400 mesh) eluting with 3% to 9% methanol in dichloromethane to give 32 mg of the title compound.

Physical characteristics are as follows:
$^1$H-NMR (CDCl$_3$) δ 0.2–0.5, 0.75, 0.90, 1.4–2.0, 2.55, 3.0–3.4, 3.6–3.7, 6.63, 7.0–7.7;
EI-MS: [M+]=523;
TLC R$_f$ 0.33 (5% methanol in dichloromethane).
Preparation 41 3-(α-Cyclopropyl-meta-aminobenzyl)-6-(1-ethyl-3-hydroxy-propyl)-4-hydroxy-pyran-2-one (Formula J-1) Refer to Chart J.

A mixture of 477 mg of the title compound of Preparation 36 and 150 mg of 5% palladium on charcoal in 10 mL of ethanol is shaken overnight under 45 psi of hydrogen. The mixture is filtered through Celite with ethanol washes of the filter cake. The filtrates are combined and the solvent is removed under reduced pressure to give 340 mg of the title compound.

Physical characteristics are as follows:
TLC R$_f$ 0.10 (5% methanol in dichloromethane).
Preparation 42 6-(3-Bromo-1-ethyl-propyl)-3-(α-cyclopropyl-meta-aminobenzyl)-4-hydroxy-pyran-2-one (Formula J-2) Refer to Chart J.

To a stirring solution of 340 mg of the title compound of Preparation 41 in 7 mL of tetrahydrofuran is added 525 mg of triphenylphosphine and 663 mg of carbon tetrabromide. After 30 minutes, the solvent is removed under reduced pressure and the residue is purified by flash column chromatography on silica gel 60 (230–400 mesh) eluting with 30% to 50% ethyl acetate in dichloromethane to give 228 mg of the title compound.

Physical characteristics are as follows:
$^1$H-NMR (CDCl$_3$) δ 0.19, 0.42, 0.58, 0.75, 1.4–2.4, 3.14, 3.3, 5.26, 6.15, 6.47, 6.91, 7.00;
TLC R$_f$ 0.45 (5% methanol in dichloromethane).

EXAMPLE 108

N-(3-{[6-(3-Bromo-1-ethyl-propyl)-4-hydroxy-2-oxo-2H-pyran-3-yl]-cyclopropyl-methyl}-phenyl)-1-methyl-1H-imidazole-4-sulfonamide (Formula J-3) Refer to Chart J.

To a mixture of 102 mg of the title compound of Preparation 42 and 40 μL of pyridine in 1.0 mL of dichloromethane is added 45 mg of 1-methylimidazole-4-sulfonyl chloride. After stirring overnight, the solvent is removed under reduced pressure. The residue is azeotroped with toluene and is then purified by flash column chromatography on silica gel 60 (230–400 mesh) using 2% to 5% methanol in dichloromethane to give 86 mg of the title compound.

Physical characteristics are as follows:
$^1$H-NMR (CDCl$_3$-CD$_3$OD) δ 0.2, 0.44, 0.60, 0.82, 1.4–2.2, 2.5, 3.1–3.4, 3.62, 5.93, 6.92, 7.07, 7.19, 7.30, 7.40;
FAB-MS: [M+H]=550.1037 found;
TLC R$_f$ 0.36 (5% methanol in dichloromethane).

EXAMPLE 109

N-(3-{[6-(3-Azido-1-ethyl-propyl)-4-hydroxy-2-oxo-2H-pyran-3-yl]-cyclopropyl-methyl}-phenyl)-1-methyl-1H-imidazole-4-sulfonamide (Formula J-4) Refer to Chart J.

To a stirring solution of 113 mg of the title compound of Example 108 in 1.2 mL of ethanol is added 50 mg of sodium azide and 0.4 mL of water. The reaction mixture is heated overnight and then cooled. The solvent is removed under reduced pressure and the residue is purified by flash column chromatography on silica gel 60 (230–400 mesh) eluting with 3% to 6% methanol in dichloromethane to give 57 mg of the title compound.

Physical characteristics are as follows:
$^1$H-NMR (CDCl$_3$-CD$_3$OD) δ 0.25, 0.48, 0.66, 0.90, 1.3–1.8, 2.42, 2.9–3.2, 3.68, 5.94, 6.93, 7.12, 7.19, 7.23, 7.35, 7.46;
FAB-MS: [M+H]=550.1037 found;
TLC R$_f$ 0.36 (5% methanol in dichloromethane).

Preparation 43 N-(3-{[6-(3-Amino-1-ethyl-propyl)-4-hydroxy-2-oxo-2H-pyran-3-yl]-cyclopropyl-methyl}-phenyl)-1-methyl-1H-imidazole-4-sulfonamide (Formula J-5) Refer to Chart J.

A mixture of 104 mg of the title compound of Example 109 and 30 mg of 5% palladium on charcoal in 2 mL of each of methanol and ethanol is shaken overnight under 45 psi of hydrogen. The mixture is filtered through Celite with methanol washes of the filter cake. The filtrates are combined and the solvent is removed under reduced pressure to give 69 mg of the title compound.

Physical characteristics are as follows:
TLC R$_f$ 0.05 (5% methanol in dichloromethane).

EXAMPLE 110

2-[[8-[[3-[3-[Cyclopropyl[3-[[(1-methyl-1H-imidazol-4-yl)sulfonyl]amino]phenyl]methyl]-4-hydroxy-2-oxo-2H-pyran-6-yl]pentyl]amino]-1,8-dioxooctyl]methylamino]-ethane sulfonic acid, monosodium salt (Formula J-6) Refer to Chart J.

A suspension of 69 mg of the title compound of Preparation 43 in 1.0 mL of dichloromethane is treated with 0.22 mL (0.65 M in acetonitrile) of the triethylamine salt of suleptanic acid and 25 μL of diisopropylcarbodiimide. After 1 hour the mixture is treated with 0.5 mL of dimethylformamide. After stirring overnight the solvent is removed under reduced pressure and the residue is purified by flash column chromatography on silica gel 60 (230–400 mesh) eluting with 10% to 30% methanol in dichloromethane. The crude product is dissolved in water saturated n-butanol and partioned with saturated aqueous sodium sulfate. The aqueous phase is extracted twice with additional portions of water saturated n-butanol. The combined n-butanol layers are filtered through a pad of sodium sulfate and concentrated under reduced pressure to give 94 mg of the title compound.

Physical characteristics are as follows:
$^1$H-NMR (CDCl$_3$-CD$_3$OD) δ 0.05–0.6, 0.83, 1.1–2.5, 2.9–3.7, 3.68, 5.84, 6.8–7.6;
FAB-MS: [M+H]=786.2838 found;
TLC R$_f$ 0.21 (20% methanol in dichloromethane).

EXAMPLES 111–134

Utilizing procedures described above and using starting materials and reagents known and available to one of ordinary skill in organic synthesis, the following additional compounds are prepared:

111) N-(3-{Cyclopropyl-[4-hydroxy-6-(3-{[(2-hydroxy-1,1-bis{hydroxymethyl}-ethyl)-aminol-carbonyl]-amino-propyl)-2-oxo-2H-pyran-3-yl]-methyl}-phenyl)-benzenesulfonamide 112) N-(3-{Cyclopropyl-[4-hydroxy-6-(3-{[(2-hydroxy-1,1-bis{hydroxymethyl}-ethyl)-amino]-carbonyl}-amino-propyl)-2-oxo-2H-pyran-3-yl]-methyl}-phenyl)-2-pyridinesulfonamide 113) N-(3-{Cyclopropyl-[4-hydroxy-6-(3-{[(2-hydroxy-1,1-bis{hydroxymethyl}-ethyl)-amino]-carbonyl}-amino-propyl)-2-oxo-2H-pyran-3-yl]-methyl}-phenyl)-1H-imidazole-2-sulfonamide 114) N-(3-{Cyclopropyl-[4-hydroxy-6-(3-{[(2-hydroxy-1,1-bis{hydroxymethyl}-ethyl)-amino]-carbonyl}-amino-propyl)-2-oxo-2H-pyran-3-yl]-methyl}-phenyl)-1H-benzoimidazole-2-sulfonamide 115) N-(3-{Cyclopropyl-[4-hydroxy-6-(3-{[(2-hydroxy-1,1-bis{hydroxymethyl}-ethyl)-amino]-carbonyl}-amino-propyl)-2-oxo-2H-pyran-3-yl]-methyl}-phenyl)-1-methyl-1H-imidazole-4-sulfonamide 116) N-(3-{Cyclopropyl-[4-hydroxy-6-(3-{[(2-hydroxy-1,1-bis{hydroxymethyl}-ethyl)-amino]-carbonyl}-amino-propyl)-2-oxo-2H-pyran-3-yl]-methyl]-phenyl)-1-methyl-1H-imidazole-2-sulfonamide 117) N-(3-{Cyclopropyl-[4-hydroxy-6-(3-{γ-L-glutamyl}-amino-propyl)-2-oxo-2H-pyran-3-yl]-methyl}-phenyl)-benzenesulfonamide 118) N-(3-{Cyclopropyl-[4-hydroxy-6-(3-{y-L-glutamyl}-amino-propyl)-2-oxo-2H-pyran-3-yl]-methyl}-phenyl)-2-pyridinesulfonamide 119) N-(3-tCyclopropyl-[4-hydroxy-6-(3-γ-L-glutamyl]-amino-propyl)-2-oxo-2H-pyran-3-yl]-methyl}-phenyl)-1H-imidazole-sulfonamide 120) N-(3-{Cyclopropyl-[4-hydroxy-6-(3-{γ-L-glutamyl}-amino-propyl)-2-oxo-2H-pyran-3-yl]-methyl}-phenyl)-1H-benzoimidazole-sulfonamide 121) N-(3-{Cyclopropyl-[4-hydroxy-6-(3-{γ-L-glutamyl}-amino-propyl)-2-oxo-2H-pyran-3-yl]-methyl}-phenyl)-1-methyl-1H-imidazole-4-sulfonamide 122) N-(3-{Cyclopropyl-[4-hydroxy-6-(3-{L-glutamyl}-amino-propyl)-2-oxo-2H-pyran-3-yl]-methyl}-phenyl)-1-methyl-1H-imidazole-2-sulfonamide 123) N-(3-{Cyclopropyl-[4-hydroxy-6-(3-{[piperazin-1-yl]-carbonyl}-amino-propyl)-2-oxo-2H-pyran-3-yl]-methyl}-phenyl)-benzenesulfonamide 124) N-(3-{Cyclopropyl-[4-hydroxy-6-(3-{[piperazin-1-yl]-carbonyl}-amino-propyl)-2-oxo-2H-pyran-3-yl]-methyl}-phenyl)-2-pyridinesulfonamide 125) N-(3-{Cyclopropyl-[4-hydroxy-6-(3-{[piperazin-1-yl]-carbonyl}-amino-propyl)-2-oxo-2H-pyran-3-yl]-methyl}-phenyl)-1H-imidazole-2-sulfonamide 126) N-(3-{Cyclopropyl-[4-hydroxy-6-(3-{[piperazin-1-yl]-carbonyl}-amino-propyl)-2-oxo-2H-pyran-3-yl]-methyl}-phenyl)-1H-benzoimidazole-2-sulfonamide 127) N-(3-{Cyclopropyl-[4-hydroxy-6-(3-{[piperazin-1-yl]-carbonyl}-amino-propyl)-2-oxo-2H-pyran-3-yl]-methyl}-phenyl)-1-methyl-1H-imidazole-4-sulfonamide 128) N-(3-{Cyclopropyl-[4-hydroxy-6-(3-{[piperazin-1-yl]-carbonyl}-amino-propyl)-2-oxo-2H-pyran-3-yl]-methyl}-phenyl)-1-methyl-1H-imidazole-2-sulfonamide 129) $^2$-[[$^8$-[[$^3$-[$^3$-[Cyclopropyl[3-[[phenylsulfonyl]amino]phenyl]methyl]-4-hydroxy-2-oxo-2H-pyran-6-yl]propyl]amino]-1,8-dioxooctyl]methylamino]-ethanesulfonic acid, monosodium salt 130) 2-[[8-[[3-[3-[Cyclopropyl[3-[[(2-pyridyl)sulfonyl]aminolphenyl]methyl]-4-hydroxy-2-oxo-2H-pyran-6-yl]propyl]amino]-1,8-dioxooctyl]methylamino]-ethane sulfonic acid, monosodium salt 131) $^2$-[[8-[[3-[3-[Cyclopropyl[3-[[(1H-benzimidazol-2-yl)sulfonyl]amino]phenyl]methyl-4-hydroxy-2-oxo-2H-pyran-6-yl]propyl]amino]-1,8-dioxooctyl]methyl amino]-ethanesulfonic acid, monosodium salt 132) 2-[[8-[[3-[3-[Cyclopropyl[3-[[(1H-imidazol-2-yl)sulfonyl]amino]phenyl]methyl]-4-hydroxy-2-oxo-2H-pyran-6-yl]propyl]amino]-1,8-dioxooctyl]methylamino]-ethane sulfonic acid, monosodium salt 133) 2-[[8-[[3-[3-[Cyclopropyl[3-[[(1-methyl-1H-imidazol-4-yl)sulfonyl]amino]phenyl]methyl]-4-hydroxy-2-oxo-2H-pyran-6-yl]propyl]amino]-1,8-dioxooctyl]methylamino]-ethanesulfonic acid, monosodium salt 134) 2-[[8-[[3-[3-[Cyclopropyl[3-[[(1-methyl-1H-imidazol-2-yl)sulfonyl]amino]phenyl]methyl]-4-hydroxy-2-oxo-2H-pyran-6-yl]propyl]amino]-1,8-dioxooctyl]methylamino]-ethane sulfonic acid, monosodium salt Preparation 44 (Tetrahydropyran-4-yl)-methanol (Formula K-2) Refer to Chart K.

To a cold (0°), stirred solution of 651 mg of tetrahydropyran-4-carboxylic acid in 2.5 ml of dry tetrahydrofuran, under argon, is added dropwise 10 ml of a 1.0 M solution of borane in tetrahydrofuran. After 18 hours at room temperature, the solution is recooled to 0° and quenched with 1 ml of 1M KOH. The mixture is acidified with 1M aqueous hydrochloric acid and extracted four times with dichloromethane. The extract is dried over magnesium sulfate and concentrated carefully under reduced pressure to afford 0.72 g of the alcohol as a colorless liquid.

Physical characteristics are as follows:
$^1$H NMR δ 1.2–1.4, 1.6, 1.8, 3.3–3.4, 3.6, 4.0 ppm.

Preparation 45 (Tetrahydropyran-4-yl)-methyl p-toluenesulfonate (Formula K-3) Refer to Chart K.

To a cold (0°), stirred solution of 5 mmol of the title compound of Preparation 44 and 0.81 ml of pyridine in 5 ml of dichloromethane is added 1.05 g of p-toluenesulfonyl chloride, and the solution is allowed to warm to room temperature. After 18 hours the mixture is partitioned between ethyl acetate and dilute aqueous hydrochloric acid, and the organic phase is washed with brine and dried over magnesium sulfate. Following removal of solvent under reduced pressure, the residue is flash chromatographed on silica using 50% ethyl acetate in hexane to afford 1.23 g of the title compound as a colorless liquid.

Physical characteristics are as follows:
$^1$H NMR δ 1.2–1.4, 1.6, 1.9–2.0, 2.46, 3.34, 3.85, 3.95, 7.3, 7.8 ppm.
MS: 270

Preparation 46 (Tetrahydropyran-4-yl)-methyl iodide (Formula K-4) Refer to Chart K.

A solution of 800 mg of tosylate of Preparation 45 and 887 mg of sodium iodide in 6 ml of acetone is refluxed under nitrogen for six hours, then partitioned between ether and dilute aqueous sodium thiosulfate. The organic phase is washed with brine, dried over magnesium sulfate, and concentrated carefully under atmospheric pressure to give 648 mg of the iodide as a colorless liquid.

Physical characteristics are as follows:
$^1$H NMR δ 1.2–1.4, 1.6–1.9, 3.1, 3.37, 3.97 ppm.

Preparation 47 6-(1-(Tetrahydropyran-4-ylmethyl)-propyl)-4-hydroxypyran-2-one (Formula K-6) Refer to Chart K.

To a cold (–78°) stirred solution of 0.90 ml of diisopropylamine in 5 ml of tetrahydrofuran, under argon, is added via syringe 3.7 ml of a 1.6 M solution of n-butyllithium in hexane. The solution is warmed to 0°, and after ten minutes, a solution of 431 mg of the title compound of Preparation 50 in 3 ml of hexamethylphosphoramide is added via cannula. After 20 minutes, the deep red solution is cooled to –50°, and 605 mg of iodide of Preparation 46 in 1 ml of tetrahydrofuran is added via cannula. The reaction is allowed to warm slowly to 0° and then quenched by addition of pH 7 phosphate buffer. Following removal of tetrahydrofuran under reduced pressure, the residual liquid is acidified with dilute aqueous hydrochloric acid and the resulting precipitate extracted with two portions of ethyl acetate. The organic is washed with dilute aqueous hydrochloric acid and brine, dried over magnesium sulfate, and concentrated under reduced pressure. Flash chromatography of the residue on silica using 5% acetic acid and 30–40% ethyl acetate in dichloromethane provides 553 mg of the title compound as a thick yellow gum.

Physical characteristics are as follows:
TLC $R_f$ 0.36 (5% acetic acid, 65% ethyl acetate in dichloromethane)
$^1$H NMR δ 0.85, 1.2–1.8, 2.45, 3.34, 3.9, 5.56, 5.94 ppm.
MS: 252

Preparation 48 3-[(3-Benzyloxycarbonylaminophenyl)-cyclopropylmethyl]-6-(1-(tetrahydropyran-4-ylmethyl)-propyl-4-hydroxy-pyran-2-one (Formula K-6) Refer to Chart K.

A solution of 549 mg of alkylation product of Preparation 47, 970 mg of 3-benzyloxycarbonylaminophenyl cyclopropyl carbinol, and 60 mg of p-toluenesulfonic acid monohydrate in 5 ml of dichloromethane is refluxed through 10 ml of 3A sieves for 18 hours. Following removal of solvent under reduced pressure, the residue is flash chromatographed on silica using 25–100% ethyl acetate in dichloromethane to 5% methanol in ethyl acetate, providing 511 mg of the title compound as a tan solid.

Physical characteristics are as follows:
TLC $R_f$ 0.32 (30% ethyl acetate in dichloromethane)
$^1$H NMR δ 0.2, 0.5, 0.7, 0.8, 1.3–1.7, 3.27, 3.42, 3.86, 5.13, 5.96, 7.1–7.4 ppm.
MS: 531

Preparation 49 3-[(3-Aminophenyl)-cyclopropylmethyl]-6-(1-(tetrahydropyran-4-ylmethyl)-propyl)-4-hydroxy-pyran-2-one (Formula K-7) Refer to Chart K.

A mixture of 510 mg of the title compound of Preparation 48, 605 mg of ammonium formate, and 100 mg of 5% palladium on carbon in 8 ml of methanol is stirred under argon for three hours, then filtered through diatomaceous earth. The filtrate is concentrated under reduced pressure, and the residue flash chromatographed on silica using 2–4% methanol in dichloromethane to afford 280 mg of the title amine as a white solid.

Physical characteristics are as follows:
TLC $R_f$ 0.33 (5% methanol in dichloromethane)
$^1$H NMR δ 0.24, 0.42, 0.53, 0.68, 0.84, 1.1–1.7, 2.35, 3.33, 3.6, 3.9, 5.82, 6.5, 6.83, 6.9, 7.11 ppm.

EXAMPLE 135

N-(3-{Cyclopropyl-[6-(1-(tetrahydropyran-4-ylmethyl)-propyl)-4-hydroxy-2-oxo-2H-pyran-3-yl]-methyl}-phenyl)-1-methyl-1H-imidazole-4-sulfonamide (Formula K-8) Refer to Chart K.

To a stirred solution of 60 mg of the amine of Preparation 49 and 24 μL of pyridine in 0.5 ml of dichloromethane is added 27 mg of 1-methylimidazole-4-sulfonyl chloride. After 18 hours the reaction is flashed on silica using 3–6% methanol in dichloromethane to afford 70 mg of the title compound as a white solid.

Physical characteristics are as follows:
TLC $R_f$ 0.24 (5% methanol in dichloromethane)
$^1$H NMR δ 0.12, 0.26, 0.45, 0.60, 0.82, 1.1–1.9, 2.3, 3.3, 3.58, 3.9, 6.00, 6.9–7.5 ppm.
HRMS: 541.2238

Preparation 50 4-Hydroxy-6-propylpyran-2-one (Formula K-9) Refer to Chart K.

To a cold (−78°), stirred solution of 6.3 ml of diisopropylamine in 40 ml of dry tetrahydrofuran, under argon, is added 27.5 ml of a 1.6 M solution of butyllithium in hexane. The solution is brought to 0°, and into this is cannulated a solution of 2.52 g of 4-hydroxy-6-methyl-2-pyrone of formula K-10 in 20 ml of hexamethylphosphoric triamide. The deep red solution is stirred 30 minutes at 0°, then cooled to −45° for the addition of 1.5 ml of ethyl bromide. The solution is warmed to 0° and quenched with 60 ml of 1N aqueous hydrochloric acid. Tetrahydrofuran is removed under reduced pressure and the residue extracted five times with ethyl acetate. The organic phase is washed with brine, dried over magnesium sulfate, and concentrated under reduced pressure. Flash chromatography of the residue on silica gel using 4% acetic acid and 16% ethyl acetate in dichloromethane provides 2.34 g of the title compound as a waxy yellow solid.

Physical characteristics are as follows:
TLC $R_f$ 0.29 (5% acetic acid and 15% ethyl acetate in dichloromethane)
$^1$H NMR δ 0.98, 1.6, 2.4, 5.63, 6.05

Preparation 51 4-Hydroxy-6-phenethyl-2H-pyran-2-one (Formula L-2) Refer to Chart L.

To a flame-dried flask containing a stirred solution of 0.90 mL of diisopropylamine in 6 mL of anhydrous tetrahydrofuran at −78° C. under an argon atmosphere is added 4.0 mL of a 1.6 M solution of n-butyllithium in hexane. The resulting solution is allowed to warm to 0° C. for 20 min, and is then treated via cannula with a solution of 378 mg of commercially available 4-hydroxy-6-methyl-2-pyrone of formula L-1 in 15 mL of tetrahydrofuran. The resulting red, thick slurry is slowly treated with 6.0 mL of distilled hexamethylphosphoramide and allowed to stir for 30 min. The red, cloudy solution is then treated with 0.36 mL of benzyl bromide. The reaction quickly becomes a deep orange solution and is allowed to stir at 0° C. for an additional 60 min. The mixture is quenched with excess 1 N aqueous hydrochloric acid and the resulting yellow, biphasic mixture is concentrated to remove the tetrahydrofuran. The resulting mixture is partitioned between dichloromethane and water and the acidic aqueous phase is further extracted with additional portions of dichloromethane. The combined organic phase is dried over magnesium sulfate and then concentrated under reduced pressure. The resulting material is diluted with a large volume of diethyl ether and washed with dilute aqueous hydrochloric acid. The ethereal phase is washed with two additional portions of aqueous hydrochloric acid, once with brine, dried over magnesium sulfate, and finally concentrated under reduced pressure. The residue is flash column chromatographed on silica gel 60 (230–400 mesh) eluting with 1% acetic acid and 20% to 40% ethyl acetate in dichloromethane to give 440 mg of the title compouund as a tan solid.

Physical characteristics are as follows:
$^1$H NMR δ 2.7, 3.0, 5.46, 5.84, 7.1–7.3.
TLC $R_f$ 0.38 (1% acetic acid and 25% ethyl acetate in dichloromethane.)
MP 137–138° C.

Preparation 52 6-(α-Ethyl-phenethyl)-4-hydroxy-2H-pyran-2-one (Formula L-3) Refer to Chart L.

To a cold (−78° C.) stirred solution of 0.29 ml of diisopropylamine in 4 ml of dry tetrahydrofuran, under argon, is added 1.2 ml of a 1.6 M solution of n-butyllithium in hexane. The solution is warmed to 0° C., kept at that temperature for ten minutes, then cooled to −30° C. Into this solution is cannulated a solution of 189 mg of the title compound of Preparation 51 in 4 ml of tetrahydrofuran. The resulting heterogeneous mixture is warmed to 0°, and sufficient hexamethylphosphoramide (ca 1 ml) is added to render the mixture mostly homogeneous. After the mixture is stirred for 30 minutes at 0° C., 77 μL of ethyl iodide is added dropwise. After another 90 minutes, the reaction is quenched with excess 1N aqueous hydrochloric acid, and tetrahydrofuran is removed under reduced pressure. The residue is extracted with three portions of ethyl acetate, and the combined organic extract washed with dilute aqueous hydrochloric acid, dried over magnesium sulfate, and concentrated under reduced pressure. The residue is flash chromatographed on silica gel 60 (230–400 mesh) using 1% acetic acid and 25% ethyl acetate in dichloromethane to provide 182 mg of the title compound.

Physical characteristics are as follows:
$^1$H NMR δ 0.85, 1.6, 2.6, 2.9, 5.59, 5.86, 7.0–7.3.
FAB MS [m+H]=245.1185.
TLC $R_f$ 0.33 (1% acetic acid and 25% ethyl acetate in dichloromethane.)

Preparation 53 3-(α-Cyclopropyl-meta-(benzyloxycarbonylamino)benzyl)-6-(α-ethyl-phenethyl)-4-hydroxy-2H-pyran-2-one (Formula L-4) Refer to Chart L.

A mixture of 181 mg of the title compound of Preparation 52, 220 mg of the compound of formula F-5, 28 mg of p-toluenesulfonic acid monohydrate, and 600 mg of 3 Å molecular sieves in 2 ml of benzene is refluxed under argon for 21 hours, then cooled and filtered through Celite. The filtrate is concentrated under reduced pressure, and the residue flash chromatographed on silica gel 60 (230–400 mesh) using 50–100% ethyl acetate in hexane to provide 250 mg of a mixture of materials. This is re-subjected to silica gel chromatography, using 5–20% ethyl acetate in dichloromethane, to afford 154 mg (40%) of the title compound.

Physical characteristics are as follows:
$^1$H NMR δ 0.26, 0.48, 0.67, 0.81, 1.6, 1.8, 2.5, 2.7, 2.9, 3.48, 5.14, 5.86, 6.81, 7.0–7.5, 9.46.

EI HRMS m/z=523.2350.

TLC $R_f$ 0.27 (5% ethyl acetate in dichloromethane.)

Preparation 54 3-(α-Cyclopropyl-meta-aminobenzyl)-6-(α-ethyl-phenethyl)-4-hydroxy-2H-pyran-2-one (Formula L-5) Refer to Chart L.

A mixture of 146 mg of the title compound of Preparation 53 and 50 mg of 5% palladium on carbon in 2 ml of methanol is shaken under 40 psi of hydrogen for two hours, then filtered through Celite. The filtrate is concentrated under reduced pressure to give 105 mg (96%) of the title compound.

Physical characteristics are as follows:

$^1$H NMR δ 0.25, 0.5, 0.65, 0.81, 1.6, 2.5, 2.7, 2.9, 3.4, 5.79, 6.5, 6.8–7.3.

TLC $R_f$ 0.38 (30% ethyl acetate in dichloromethane).

EXAMPLES 136–150

Utilizing procedures analogous to those described above, and reacting the compound of formula L-5 with the appropriate sulfonyl chloride, the following additional compounds of the present invention are prepared. Individual stereoisomers are prepared by chiral HPLC resolution of intermediates such as the compounds of formulas L-3, L-4, L-5 and L-6. (Refer to Chart L). 136) N-(3-{Cyclopropyl-[6-(1-ethylphenethyl)-4-hydroxy-2-oxo-2H-pyran-3-yl]-methyl}-phenyl)-1-methyl-1H-imidazole-4-sulfonamide Physical characteristics are as follows:

TLC $R_f$ 0.29 (5% methanol in dichloromethane)

$^1$H NMR δ 0.2, 0.5, 0.65, 0.86, 1.63, 1.80, 2.51, 2.8, 3.3, 3.62, 5.7, 6.8–7.4 ppm.

HRMS: 533.1998

137) N-(3-(R or S)-{Cyclopropyl-[6-(1-(R)-ethylphenethyl)-4-hydroxy-2-oxo-2H-pyran-3-yl]-methyl}-phenyl)-1-methyl-1H-imidazole-4-sulfonamide Physical characteristics are as follows:

TLC $R_f$ 0.32 (5% methanol in dichloromethane)

$^1$H NMR δ 0.18, 0.43, 0.63, 0.83, 1.6, 1.75, 2.5, 2.7–2.9, 3.3, 3.55, 5.76, 6.9–7.4 ppm.

HRMS: 533.1983

138) N-(3-(R or S)-[Cyclopropyl-[6-(1-(R)-ethylphenethyl)-4-hydroxy-2-oxo- 2H-pyran-3-yl]-methyl}-phenyl)-1-methyl-1H-imidazole-4-sulfonamide Physical characteristics are as follows:

TLC $R_f$ 0.30 (5% methanol in dichloromethane)

$^1$H NMR δ 0.2, 0.5, 0.65, 0.86, 1.63, 1.80, 2.51, 2.8, 3.3, 3.62, 5.7, 6.8–7.4 ppm.

HRMS: 533.1993

139) N-(3-(R or S)-{Cyclopropyl-[6-(1-(S)-ethylphenethyl)-4-hydroxy-2-oxo-2H-pyran-3-yl]-methyl}-phenyl)-1-methyl-1H-imidazole-4-sulfonamide Physical characteristics are as follows:

TLC $R_f$ 0.30 (5% methanol in dichloromethane)

$^1$H NMR δ 0.2, 0.5, 0.65, 0.86, 1.63, 1.80, 2.51, 2.8, 3.3, 3.62, 5.7, 6.8–7.4 ppm.

HRMS: 533.1993

140) N-(3-(R or S)-{Cyclopropyl-[6-(1-(S)-ethylphenethyl)-4-hydroxy-2-oxo-2H-pyran-3-yl]-methyl}-phenyl)-1-methyl-1H-imidazole-4-sulfonamide Physical characteristics are as follows:

TLC $R_f$ 0.30 (5% methanol in dichloromethane)

$^1$H NMR δ 0.17, 0.44, 0.62, 0.83, 1.6, 1.75, 2.50, 2.7–3.0, 3.3, 3.53, 5.80, 6.9–7.4 ppm.

HRMS: 533.1990

141) N-(3-(R or S)-{Cyclopropyl-[6-(1-(R)-ethylphenethyl)-4-hydroxy-2-oxo-2H-pyran-3-yl]-methyl}-phenyl)-2-pyridinesulfonamide Physical characteristics are as follows:

TLC $R_f$ 0.34 (30% ethyl acetate in dichloromethane)

$^1$H NMR δ 0.2, 0.45, 0.6, 0.86, 1.5–1.9, 2.5, 2.8–3.0, 3.2, 5.7, 6.9–7.4, 7.8, 8.6 ppm.

MS: 530

142) N-(3-(R or S)-{Cyclopropyl-[6-(1-(R)-ethylphenethyl)-4-hydroxy-2-oxo-2H-pyran-3-yl]-methyl}-phenyl)-2-pyridinesulfonamide Physical characteristics are as follows:

TLC $R_f$ 0.35 (30% ethyl acetate in dichloromethane)

$^1$H NMR δ 0.11, 0.20, 0.43, 0.58, 0.85, 1.5–1.8, 2.5, 2.7–3.0, 3.3, 5.69, 6.9–7.4, 7.8, 8.6 ppm.

MS: 530

143) N-(3-(R or S)-{Cyclopropyl-[6-(1-(R)-ethylphenethyl)-4-hydroxy-2-oxo-2H-pyran-3-yl]-methyl}-phenyl)-1-methyl-1H-imidazole-2-sulfonamide Physical characteristics are as follows:

TLC $R_f$ 0.34 (5% methanol in dichloromethane)

$^1$H NMR δ 0.19, 0.5, 0.65, 0.89, 1.6–1.9, 2.5, 2.8–3.0, 3.3, 3.40, 5.70, 6.8–7.4 ppm.

MS: 533

144) N-(3-(R or S)-{Cyclopropyl-[6-(1-(R)-ethylphenethyl)-4-hydroxy-2-oxo-2H-pyran-3-yl]-methyl}-phenyl)-1-methyl-1H-imidazole-2-sulfonamide Physical characteristics are as follows:

TLC $R_f$ 0.34 (5% methanol in dichloromethane)

$^1$H NMR δ 0.20, 0.44, 0.65, 0.88, 1.6–1.8, 2.5, 2.8–3.0, 3.3, 3.42, 5.73, 6.8–7.4 ppm.

MS: 533

145) N-(3-{Cyclopropyl-[6-(1-(tetrahydropyran-4-ylmethyl)-propyl)-4-hydroxy-2-oxo-2H-pyran-3-yl]-methyl}-phenyl)-1-methyl-1H-imidazole-2-sulfonamide Physical characteristics are as follows:

TLC $R_f$ 0.22 (5% methanol in dichloromethane)

$^1$H NMR δ 0.16, 0.24, 0.47, 0.64, 0.86, 1.2–1.9, 3.2–3.4, 3.47, 3.7–4.0, 5.89, 6.9–7.4 ppm.

MS: 541

145A) N-(3-[Cyclopropyl[4-hydroxy-2-oxo-6-[1-[(tetrahydro-2H-pyran-3-yl)methyl]propyl]-2H-pyran-3-yl]methyl]phenyl]-8-quinolinesulfonamide Physical characteristics are as follows:

MW Found: m/z 588.

145B) N-(3-[Cyclopropyl[4-hydroxy-2-oxo-6-[1-[(tetrahydro-2H-pyran-3-yl)methyl]propyl]-2H-pyran-3-yl]methyl]phenyl]-1-methyl-1H-imidazole-4-sulfonamide Physical characteristics are as follows:

MW Found: m/z 541.

146) N-(3-{Cyclopropyl-[6-(1-(R)-ethylphenethyl)-4-hydroxy-2-oxo-2H-pyran-3-yl]-methyl}-phenyl)-benzimidazole-2-sulfonamide Physical characteristics are as follows:

TLC $R_f$ 0.40 (50% ethyl acetate in dichloromethane)

$^1$H NMR δ 0.1–0.6, 0.85, 1.5–1.7, 2.5, 2.7–3.0, 3.3, 5.74, 6.7–7.3, 7.5–7.7 ppm.

HRMS: 570.2054

147) N-(3-{Cyclopropyl-[6-(1-(R)-ethylphenethyl)-4-hydroxy-2-oxo-2H-pyran-3-yl]-methyl}-phenyl)-1H-imidazole-2-sulfonamide Physical characteristics are as follows:

TLC $R_f$ 0.31 (5% methanol in dichloromethane)

$^1$H NMR δ 0.2, 0.4, 0.6, 0.87, 1.5–1.8, 2.5, 2.8–3.0, 3.3, 5.54, 6.8, 6.9–7.4 ppm.

148) N-(3-(R or S)-{Cyclopropyl-[6-(1-(R)-ethylphenethyl)-4-hydroxy-2-oxo-2H-pyran-3-yl]-methyl}-phenyl)-4-cyanobenzenesulfonamide Physical characteristics are as follows:

TLC $R_f$ 0.47 (20% ethyl acetate in dichloromethane)

$^1$H NMR δ 0.1, 0.2, 0.4, 0.6, 0.84, 1.5–1.8, 2.5, 2.7–3.0, 3.3, 5.70, 6.9, 7.0–7.3, 7.6, 7.8 ppm.

HRMS: 554.1886

149) N-(3-(R or S)-{Cyclopropyl-[6-(1-(R)-ethylphenethyl)-4-hydroxy-2-oxo-2H-pyran-3-yl]-methyl}-phenyl)-4-cyanobenzenesulfonamide Physical characteristics are as follows:

TLC $R_f$ 0.35 (15% ethyl acetate in dichloromethane)

$^1$H NMR δ 0.1, 0.2, 0.4, 0.6, 0.85, 1.5–1.9, 2.5, 2.7–3.0, 3.3, 5.7, 6.9–7.3, 7.6, 7.8 ppm.

HRMS: 554.1876

150) N-(3-{Cyclopropyl-[6-(1-ethylphenethyl)-4-hydroxy-2-oxo-2H-pyran-3-yl]-methyl}-phenyl)-4-nitrobenzenesulfonamide Physical characteristics are as follows:

TLC $R_f$ 0.28 (10% ethyl acetate in dichloromethane)

$^1$H NMR δ 0.1, 0.2, 0.4, 0.6, 0.83, 1.5–1.9, 2.5, 2.7–3.0, 3.3, 5.70, 6.9–7.3, 7.9, 8.2 ppm.

HRMS: 574.1773

Preparation 55 (2-(2-(2-Methoxyethoxy)-ethoxy)-ethoxy)-p-toluenesulfonate (Formula M-2) Refer to Chart M.

To a stirred suspension of 19.1 g of p-toluenesulfonyl chloride in 100 ml of dichloromethane is added a mixture of 16 ml of triethylene glycol monomethyl ether and 10 ml of pyridine, followed by 200 mg of dimethylaminopyridine. After three days the mixture is concentrated under reduced pressure, and the residue partitioned between ethyl acetate and dilute aqueous hydrochloric acid. The organic phase is washed with water, aqueous sodium bicarbonate, and brine, and dried over magnesium sulfate. After removal of solvent under reduced pressure, the residue is flash chromatographed on silica using 25% ethyl acetate in dichloromethane to afford 18.25 g of the title compound as a colorless liquid.

Physical characteristics are as follows:

TLC $R_f$ 0.27 (20% ethyl acetate in dichloromethane)

$^1$H NMR δ 2.45, 3.38, 3.5–3.8, 4.15, 7.35, 7.8 ppm.

IR 2879, 1357, 1190, 1177, 1108, 1099, 924, 665 cm$^{-1}$

MS: 318

Preparation 56 2-Hydroxy-4-(2-(2-(2-methoxyethoxy)-ethoxy)-ethoxy)-acetophenone (Formula M-3) Refer to Chart M.

A mixture of 1.52 g of 2,4-dihydroxyacetophenone, 3.82 g of the tosylate of Preparation 55, 3.26 g of cesium carbonate, and 0.2 g of potassium iodide in 20 ml of dioxane is heated overnight at 100°, then cooled and partitioned between dichloromethane and dilute aqueous hydrochloric acid. The aqueous phase is extracted with two additional portions of dichloromethane, and the combined organic phase dried over magnesium sulfate and then concentrated under reduced pressure. Flash chromatography of the residue on silica gel using 80–100% ethyl acetate in hexane provides 2.91 g of the title compound as a nearly colorless liquid.

Physical characteristics are as follows:

TLC $R_f$ 0.35 (80% ethyl acetate in hexane)

$^1$H NMR δ 2.56, 3.38, 3.5–3.9, 4.2, 6.4–6.5, 7.6 ppm.

IR 1635, 1372, 1257, 1133 cm$^{-1}$

MS: 298

Preparation 57 3-(2-Hydroxy-4-(2-(2-(2-methoxyethoxy)-ethoxy)-ethoxy)-phenyl-3-oxopropionic acid ethyl ester (Formula M-4) Refer to Chart M.

To a stirred solution of 1.49 g of the title compound of Preparation 56 in 10 ml of diethyl carbonate is added, in portions, 600 mg of 60% sodium hydride dispersion in mineral oil. The resulting mixture is heated at 80° for two hours, then cooled and partitioned between dichloromethane and dilute aqueous hydrochloric acid. The organic phase is dried over magnesium sulfate and concentrated under reduced pressure, and the residue purified by flash chromatography on silica gel using 20–30% ethyl acetate in dichloromethane to afford 0.91 g of the title compound as a yellow oil.

Physical characteristics are as follows:

TLC $R_f$ 0.44 (3% acetic acid and 30% ethyl acetate in dichloromethane)

$^1$H NMR δ 1.3, 3.38, 3.5–4.0, 4.2, 6.4–6.5, 7.6 ppm.

MS: 370

Preparation 58 4-Hydroxy-(2-(2-(2-methoxyethoxy)-ethoxy)-ethoxy)-coumarin (Formula M-5) Refer to Chart M.

A solution of 789 mg of the title compound of Preparation 57 in 10 ml of acetic acid is refluxed for two hours, then concentrated under reduced pressure. Flash chromatography of the residue on silica using 5–10% acetic acid in ethyl acetate provides 634 mg of the title compound as a buff colored solid.

Physical characteristics are as follows:

TLC $R_f$ 0.31 (10% acetic acid in ethyl acetate)

$^1$H NMR δ 3.37, 3.5–3.9, 4.1, 5.67, 6.6, 6.7, 7.6 ppm.

MS: 324

Preparation 59 3-[(3-Benzyloxycarbonylaminophenyl)-cyclopropylmethyl]-4-hydroxy-7-{2-[2-(2-methoxyethoxy)-ethoxyl-ethoxy}-coumarin (Formula M-6) Refer to Chart M.

A mixture of 704 mg of the title compound of Preparation 58, 775 mg of meta-benzyloxycarbonylaminophenyl cyclopropyl carbinol of formula F-5, and 62 mg of p-toluenesulfonic acid monohydrate in 8 ml of dichloromethane is refluxed for 18 hours through ca. 10 ml of 3A sieves. The solution is then concentrated under reduced pressure and the residue flash chromatographed on silica gel using 10–20% of (10% acetic acid in ethyl acetate) in dichloromethane to afford 760 mg of the title compound.

Physical characteristics are as follows:

TLC $R_f$ 0.33 (2% acetic acid and 20% ethyl acetate in dichloromethane)

$^1$H NMR δ 0.27, 0.46, 0.71, 1.61, 3.33, 3.5–3.9, 4.1, 5.13, 6.6, 6.7, 7.1–7.6 ppm.

Preparation 60 3-[(3-Aminophenyl)-cyclopropylmethyl]-4-hydroxy-7-{2-[2-(2-methoxyethoxy)-ethoxy]-ethoxy}-coumarin (Formula M-7) Refer to Chart M.

A solution of 760 mg of the title compound of Preparation 59, 800 mg of ammonium formate, and 200 mg of 5% palladium on charcoal catalyst in 8 ml of methanol is stirred under argon for one hour, then filtered through a pad of diatomaceous earth. The filtrate is concentrated under reduced pressure and the residue triturated with dichloromethane. Removal of solvent under reduced pressure provides 591 mg of the title amine.

Physical characteristics are as follows:

TLC $R_f$ 0.29 (5% methanol in dichloromethane)

EXAMPLE 151

N-(3-{Cyclopropyl-[7-(2-(2-(2-methoxyethoxy)-ethoxy) ethoxy)-4-hydroxycoumarin-3-yl]-methyl}-phenyl)-1-methyl-1H-imidazole- 4-sulfonamide (Formula M-8) Refer to Chart M.

To a stirred solution of 70 mg of the title compound of Preparation 60 and 24 μL of pyridine in 0.5 ml of dichloromethane is added 27 mg of 1-methylimidazole-4-sulfonyl chloride. After 18 hours, the solution is flash chromatographed on silica gel using 5–15% methanol in dichloromethane, affording 76 mg of the title sulfonamide as a pink amorphous foam.

Physical characteristics are as follows:

TLC $R_f$ 0.21 (5% methanol in dichloromethane)

$^1$H NMR δ 0.16, 0.29, 0.45, 0.61, 1.71, 3.34, 3.4–3.9, 4.1, 6.6–6.8, 7.0–7.4, 7.7 ppm.

HRMS: 614.2179

EXAMPLES 152–154

Utilizing procedures analogous to those described above, the following additional compounds of the present invention are prepared:

152) N-(3-{Cyclopropyl-[7-methoxy-4-hydroxycoumarin-3-yl]-methyl}-phenyl)-1-methyl-1H-imidazole-4-sulfonamide Physical characteristics are as follows:

TLC $R_f$ 0.29 (5% methanol in dichloromethane)

$^1$H NMR δ 0.18, 0.35, 0.50, 0.63, 1.61, 3.51, 3.7, 3.84, 6.7–6.8, 7.1–7.4, 7.7 ppm.

HRMS: 481.1301

153) N-(3-{Cyclopropyl-[7-(2-(2-(2-methoxyethoxy)ethoxy)ethoxy)-4-hydroxycoumarin-3-yl]-methyl}-phenyl)-8-quinolinesulfonamide Physical characteristics are as follows:

TLC $R_1$ 0.41 (5% methanol in dichloromethane)

$^1$H NMR δ −0.03, 0.31, 0.47, 1.30, 3.36, 3.5–3.8, 3.9, 4.2, 6.6–7.6, 7.8, 8.0, 8.2 ppm.

HRMS: 661.2219

154) N-(3-{Cyclopropyl-[7-(2-(2-(2-methoxyethoxy)ethoxy)ethoxy)-4-hydroxycoumarin-3-yl]-methyl}-phenyl)-2-pyridinesulfonamide Physical characteristics are as follows:

TLC $R_f$ 0.31 (5% methanol in dichloromethane)

$^1$H NMR δ 0.13, 0.34, 0.49, 0.63, 1.6, 3.36, 3.5–3.9, 4.1, 6.68, 6.8, 7.1–7.4, 7.6–7.8, 8.5 ppm.

HRMS: 611.2051

EXAMPLES 155–190

The following additional compounds of the present invention are prepared by procedures analogous to those described above:

155) N-(3-{Cyclopropyl-[6-(1-(tetrahydropyran-4-ylmethyl)-propyl)-4-hydroxy-2-oxo-2H-pyran-3-yl]-methyl}-phenyl)-2-pyridinesulfonamide 156) N-(3-{Cyclopropyl-[6-(1-(tetrahydropyran-4-ylmethyl)-propyl)-4-hydroxy-2-oxo-2H-pyran-3-yl]-methyl}-phenyl)-4-cyano-2-pyridinesulfonamide 157) N-(3-{Cyclopropyl-[6-(1-(tetrahydropyran-4-ylmethyl)-propyl)-4-hydroxy-2-oxo-2H-pyran-3-yl]-methyl}-phenyl)-2-quinolinesulfonamide 158) N-(3-{Cyclopropyl-[6-(1-(tetrahydropyran-4-ylmethyl)-propyl)-4-hydroxy-2-oxo-2H-pyran-3-yl]-methyl}-phenyl)-2-hydroxybenzenesulfonamide 159) N-(3-{Cyclopropyl-[6-(1-(tetrahydropyran-4-ylmethyl)-propyl)-4-hydroxy-2-oxo-2H-pyran-3-yl]-methyl}-phenyl)-2-pyrazolesulfonamide 160) N-(3-{Cyclopropyl-[6-(1-(tetrahydropyran-4-ylmethyl)-propyl)-4-hydroxy-2-oxo-2H-pyran-3-yl]-methyl}-phenyl)-2-quinazolinesulfonamide 161) N-(3-{Cyclopropyl-[6-(1-(tetrahydropyran-4-ylmethyl)-propyl)-4-hydroxy-2-oxo-2H-pyran-3-yl]-methyl}-phenyl)-7H-purine-6-sulfonamide 162) N-(3-{Cyclopropyl-[6-(1-(tetrahydropyran-4-ylmethyl)-propyl)-4-hydroxy-2-oxo-2H-pyran-3-yl]-methyl}-phenyl)-1H-imidazole-2-sulfonamide 163) N-(3-{Cyclopropyl-[6-(1-(tetrahydropyran-4-ylmethyl)-propyl)-4-hydroxy-2-oxo-2H-pyran-3-yl]-methyl}-phenyl)-benzimidazole-2-sulfonamide 164) N-(3-{Cyclopropyl-[6-(1-(tetrahydropyran-4-ylmethyl)-propyl)-4-hydroxy-2-oxo-2H-pyran-3-yl]-methyl}-phenyl)-thiazole-4-sulfonamide 165) N-(3-{Cyclopropyl-[6-(1-(tetrahydropyran-4-ylmethyl)-propyl)-4-hydroxy-2-oxo-2H-pyran-3-yl]-methyl}-phenyl)-4-ethoxycarbonyl-1H-imidazole-2-sulfaonamide 166) N-(3-{Cyclopropyl-[6-(1-(tetrahydropyran-4-ylmethyl)-propyl)-4-hydroxy-2-oxo-2H-pyran-3-yl]-methyl}-phenyl)-3-hydroxy-2-pyridinesulfonamide 167) N-(3-{Cyclopropyl-[6-(1-ethylphenethyl)-4-hydroxy-2-oxo-2H-pyran-3-yl]-methyl}-phenyl)-2-pyridinesulfonamide 168) N-(3-{Cyclopropyl-[6-(1-ethylphenethyl)-4-hydroxy-2-oxo-2H-pyran-3-yl]-methyl}-phenyl)-4-cyano-2-pyridinesulfonamide 169) N-(3-{Cyclopropyl-[6-(1-ethylphenethyl)-4-hydroxy-2-oxo-2H-pyran-3-yl]-methyl}-phenyl)-2-quinolinesulfonamide 170) N-(3-{Cyclopropyl-[6-(1-ethylphenethyl)-4-hydroxy-2-oxo-2H-pyran-3 -yl]-methyl}-phenyl)-2-hydroxybenzenesulfonamide 171) N-(3-{Cyclopropyl-[6-(1-ethylphenethyl)-4-hydroxy-2-oxo-2H-pyran-3-yl]-methyl}-phenyl)-2-pyrazolesulfonamide 172) N-(3-{Cyclopropyl-[6-(1-ethylphenethyl)-4-hydroxy-2-oxo-2H-pyran-3-yl]-methyl}-phenyl)-2-quinazolinesulfonamide 173) N-(3-{Cyclopropyl-[6-(1-ethylphenethyl)-4-hydroxy-2-oxo-2H-pyran-3-yl]-methyl}-phenyl)-7H-purine-6-sulfonamide 174) N-(3-{Cyclopropyl-[6-(1-ethylphenethyl)-4-hydroxy-2-oxo-2H-pyran-3-yl]-methyl}-phenyl)-1H-imidazole-2-sulfonamide 175) N-(3-{Cyclopropyl-[6-(1-ethylphenethyl)-4-hydroxy-2-oxo-2H-pyran-3-yl]-methyl}-phenyl)-benzimidazole-2-sulfonamide 176) N-(3-{Cyclopropyl-[6-(1-ethylphenethyl)-4-hydroxy-2-oxo-2H-pyran-3-yl]-methyl}-phenyl)-thiazole-4-sulfonamide 177) N-(3-{Cyclopropyl-[6-(1-ethylphenethyl)-4-hydroxy-2-oxo-2H-pyran-3-yl]-methyl}-phenyl)-4-ethoxycarbonyl-1H-imidazole-2-sulfaonamide 178) N-(3-{Cyclopropyl-[6-(1-ethylphenethyl)-4-hydroxy-2-oxo-2H-pyran-3-yl]-methyl}-phenyl)-3-hydroxy-2-pyridinesulfonamide 179) N-(3-{Cyclopropyl-[4-hydroxycoumarin-3-yl]-methyl}-phenyl)-2-pyridinesulfonamide 180) N-(3-{Cyclopropyl-[4-hydroxycoumarin-3-yl]-methyl}-phenyl)-4-cyano-2-pyridinesulfonamide 181) N-(3-{Cyclopropyl-[4-hydroxycoumarin-3-yl]-methyl}-phenyl)-2-quinolinesulfonamide 182) N-(3-{Cyclopropyl-[4-hydroxycoumarin-3-yl]-methyl}-phenyl)-2-hydroxybenzenesulfonamide 183) N-(3-{Cyclopropyl-[4-hydroxycoumarin-3-yl]-methyl}-phenyl)-2-pyrazolesulfonamide 184) N-(3-{Cyclopropyl-[4-hydroxycoumarin-3-yl]-methyl}-phenyl)-2-quinazolinesulfonamide 185) N-(3-{Cyclopropyl-[4-hydroxycoumarin-3-yl]-methyl}-phenyl)-7H-purine-6-sulfonamide 186) N-(3-{Cyclopropyl-[4-hydroxycoumarin-3-yl]-methyl}-phenyl)-1H-imidazole-2-sulfonamide 187) N-(3-{Cyclopropyl-[4-hydroxycoumarin-3-yl]-methyl}-phenyl)-benzimidazole-2-sulfonamide 188) N-(3-{Cyclopropyl-[4-hydroxycoumarin-3-yl]-methyl}-phenyl)-thiazole-4-sulfonamide 189) N-(3-{Cyclopropyl-[4-hydroxycoumarin-3-yl]-methyl}-phenyl)-4-ethoxycarbonyl-1H-imidazole-2-sulfaonamide 190) N-(3-{Cyclopropyl-[4-hydroxycoumarin-3-yl]-methyl}-phenyl)-3-hydroxy-2-pyridinesulfonamide Preparation 61 Cyclopropyl-(3-nitrophenyl)methanone (Formula N-2) Refer to Chart N.

Charge a jacketed 1 L three neck round bottom flask equipped with stirrer and addition funnel under nitrogen with 580 mL fuming nitric acid and cool to −40° C. Slowly, over 1.5 hours, add cyclopropyl phenyl ketone of formula N-1 (100 g) keeping the temperature below −35° C. Stir 3 hours, monitoring reaction by TLC. Pour reaction mixture into 3 kg ice/water. Extract with 3×500 mL ethyl acetate. Wash combined organic phase with 2×1.5 L saturated aqueous sodium bicarbonate, dry over magnesium sulfate, filter and concentrate to 138 g. Dissolve residue in 270 mL methanol, cool to −20° C. for 18 hours, filter and wash cake with cold methanol. Dry product under reduced pressure for 72 hours, obtaining 63.86 g. GC analysis (15 m. DB-1, $T_0$=100° C., 10° C./min., RT −6.0 min.) indicates material to be >98% pure.

Physical characteristics are as follows:

$^1$H NMR (CDCl$_3$) δ 8.86, 8.43, 8.34, 7.70, 2.72, 1.33, 1.17 ppm.

IR (Nujol) 2954, 2925, 1664, 1614, 1529, 1442, 1386, 1352, 1225, 1082, 1047, 852, 720, 689 cm$^{-1}$.

Elemental analysis, Found: C, 62.89; H, 4.73; N, 7.32.

MS (EI) 191, 150, 104, 69 m/z.

Preparation 62 Cyclopropyl-(3-aminophenyl)methanone (Formula N-3) Refer to Chart N.

Charge platinum on carbon (8.7 g) to Paar bottle. Charge a flask with cyclopropyl(3-nitrophenyl)methanone of Preparation 61 (86.7 g) and methanol (1.56 L) and warm to dissolve, then cool with ice bath to 9° C. Hydrogenate for 50 minutes, keeping temperature below 35° C. and monitoring reaction by TLC. Filter reaction mixture through solka floc and concentrate under reduced pressure to 70 g.

Physical characteristics are as follows:

$^1$H NMR (CDCl$_3$) δ 7.99, 7.47–7.19, 6.84, 3.84, 2.60, 1.23–1.15, 1.03–0.96 ppm.

$^{13}$C. NMR (CDCl$_3$) δ 200.9, 146.8, 139.1, 129.4, 119.3, 118.4, 113.9, 17.2, 11.6 ppm.

Preparation 63 Cyclopropyl-(3-aminocarbobenzoxyphenyl)methanone (Formula N-4) Refer to Chart N.

Charge a 3 L round bottom flask equipped with mechanical stirrer and addition funnel under nitrogen with cyclopropyl-(3-aminophenyl)methanone of Preparation 62 (70.0 g), diisopropylethylamine (DIPEA, 90.2 mL) and methylene chloride (CH$_2$Cl$_2$) (1.3 L). Cool reaction mixture to 0° C. Dilute the benzylchloroformate (67.5 mL) with methylene chloride (186 mL) and add to the substrate solution over one hour keeping temperature at 0–5° C. A heavy precipitate will form. Allow to warm with stirring for 1.5 hours monitoring reaction by TLC. Pour reaction mixture into 600 mL 1N HCl/600 g ice/4.2 L methylene chloride and stir to dissolve. Separate phases and dry organic phase over magnesium sulfate, filter and concentrate to a dryness. Slurry solids in 3 mL/g hexane, filter, and vacuum dry for 125 g.

Physical characteristics are as follows:

$^1$H NMR (CDCl$_3$) δ 8.01, 7.76–7.69, 7.43–7.33, 7.18, 5.21, 2.64, 1.25–1.20, 1.03–0.97 ppm.

$^{13}$C NMR (CDCl$_3$) δ 200.6, 153.4, 138.7, 138.5, 135.9, 129.3, 128.6, 128.4, 123.1, 122.8, 118.1, 67.2, 17.3, 12.0 ppm.

Preparation 64 Cyclopropyl-(3-aminocarbobenzoxyphenyl)methanol (Formula N-5) Refer to Chart N.

Charge a 2 L three neck round bottom flask equipped with overhead stirrer under nitrogen with cyclopropyl-(3-aminocarbobenzoxyphenyl)methanone of Preparation 63 (25 g), tetrahydrofuran (THF) (450 mL) and ethanol (90 mL). Cool reaction mixture to 0–5° C. and add the sodium borohydride pellets (12.4 g) in three equal portions over 30 minutes. Allow to warm to 23° C. and stir for 20 hours, monitoring reaction by TLC. Recool reaction mixture to 0–5° C. and slowly quench by adding 90 mL 1N hydrochloric acid, keeping the temperature below 10° C. Pour with stirring into methylene chloride (600 mL) and 1N hydrochloric acid (400 mL). Separate the phases and wash the organic phase with saturated sodium chloride solution (1 L). Dry over magnesium sulfate, filter, and concentrate to 23.7 g.

Physical characteristics are as follows:

$^1$H NMR (CDCl$_3$) δ 7.41–7.35, 7.33, 7.17, 7.10, 5.17, 3.93, 2.36, 1.16–1.12, 0.60–0.32 ppm.

$^{13}$C NMR (CDCl$_3$) δ 153.5, 145.0, 137.9, 136.1, 129.0, 128.6, 128.3, 121.2, 117.9, 116.5, 67.9, 67.0, 19.1, 3.6, 2.8 ppm.

Preparation 65 Carbamic acid, [3-[cyclopropyl(5,6,7,8,9,10-hexahydro-4-hydroxy-2-oxo-2H-cycloocta[b]pyran-3-yl)methyl]phenyl]-, phenylmethyl ester (Formula N-6) Refer to Chart N.

A 12-L, three-necked, round-bottomed flask with a Soxhlet extractor containing 3 A molecular sieves (180 g) and nitrogen inlet is charged with cyclooctene-1-acrylic acid, i, 2-dihydroxy-6-lactone (59.6 g), p-toluenesulfonic acid (14.9 g), and methylene chloride (7.2 L). The title compound of Preparation 64 (90.0 g) is added, and the reaction mixture is warmed to reflux for 1 h. The reaction mixture is then cooled to 20° C. and washed with 1:1 saturated sodium chloride/saturated sodium bicarbonate (3 L), water (3 L), and saturated sodium chloride (3 L), backwashing each aqueous phase with methylene chloride (2×1.5 L). The organic layers are then combined, dried over magnesium sulfate, filtered and concentrated to ca. 1.5 L. The reaction mixture is cooled to −20° C. for 72 h, filtered, and dried under reduced pressure to give 103.5 g. The crude product is then slurried with 12.5 mL/g of hexane, filtered, and dried to give 102.4 g of the title compound. An additional 10.9 g of the title compound is obtained by concentrating the mother liquors from the crystallization and recrystallizing the residue from ethyl acetate.

Physical characteristics are as follows:

MP 113–115° C. (decomposition).

$^1$H NMR (CDCl$_3$) δ 7.48, 7.38–7.26, 7.17, 6.70, 6.29, 5.20, 3.95, 2.64–2.60, 2.47–2.43, 1.76–1.72, 1.61–1.42, 0.88, 0.73–0.72, 0.63–0.55, 0.29–0.26 ppm.

$^{13}$C NMR (CDCl$_3$) δ 165.6, 164.0, 161.3, 142.2, 138.5, 129.9, 128.5, 128.3, 128.2, 122.9, 118.0, 117.9, 117.6, 110.7, 106.0, 67.0, 43.7, 30.7, 29.1, 28.8, 26.2, 25.8, 22.1, 13.0, 4.9, 3.8 ppm.

IR (Nujol) 3304, 2995, 2953, 2923, 2855, 1734, 1698, 1665, 1666, 1633, 1610, 1595, 1553, 1491, 1463, 1455, 1445, 1406, 1377, 1313, 1222, 1175, 1085, 1068, 740, 696 cm$^{-1}$.

MS (EI) m/z 473, 445, 382, 338, 91.

For high resolution, Found: 473.2202.

Preparation 66 3-[(3-Aminophenyl)cyclopropylmethyl]-5,6,7,8,9,10-hexahydro-4-hydroxy-2H-cycloocta[b]pyran-2-one (Formula N-7) Refer to Chart N.

In a 100-mL, three-necked, round-bottomed flask with a reflux condensor and nitrogen inlet, 10% palladium on carbon (1.0 g) is added to a mixture of the title product of formula N-6, prepared in Preparation 65 (1.95 g) in cyclohexene (50 mL) and the mixture is refluxed for 4h. The mixture is then filtered through Celite, washed with methylene chloride ($CH_2Cl_2$), and concentrated to give 1.25 g of the title compound as a white solid.

Physical characteristics are as follows:

MP 75–79° C.

IR (Nujol) 2995, 2951, 2921, 2868, 1660, 1619, 1605, 1590, 1551, 1491, 1460, 1447, 1428, 1404, 1247, 1226, 1202, 1191, 1172, 1126 cm$^{-1}$.

MS (EI) m/z 339, 310, 213, 187, 159.

$^1$H NMR (CDCl$_3$) δ 7.16, 6.96, 6.84, 6.63, 5.67, 3.87, 2.61, 2.48–2.37, 1.98, 1.75, 1.63–1.26, 0.74–0.65, 0.61–0.53, 0.28–0.22 ppm.

$^{13}$C NMR (CDCl$_3$) δ 164.2, 161.1, 142.8, 130.2, 117.7, 117.6, 114.7, 114.6, 114.5, 110.9, 106.2, 43.5, 30.6, 29.1, 28.8, 26.2, 25.8, 22.0, 12.8, 4.7, 3.7 ppm.

For high resolution, Found: 339.1845.

Preparation 67 4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide (Formula 0–3 wherein $R_{61}$ is 4-cyanophenyl) Refer to Chart 0.

A solution of the title product of Preparation 66 (660 mg), pyridine (320 μL), and 4-cyanobenzenesulfonyl chloride (440 mg) in dichloromethane (40 mL) is stirred at room temperature for 18 hr. The crude reaction mixture is evaporated to a volume of 5 ml and chromatographed on silica gel using 50% ethyl acetate in hexane as eluent to give the title compound (641 mg) as a white amorphous solid. This amorphous solid is alternatively crystallized from acetone-:hexane to give 499 mg.

Physical characteristics are as follows:

White solid mp: 183–183.5° C.

Elemental analysis: found, C, 66.76; H, 5.68; N, 5.38; s, 6.30.

MS(EI):504, 476, 463, 338, 309, 233, 220, 207, 195, 186, 153, 144, 130, 117, 102.

HRMS: 504.1710.

TLC(silica gel GF): R,—0.4 in 50% ethyl acetate in hexane.

EXAMPLE 191

Disodium-4-cyano-N-[3-[cyclopropyl(5,6,7,8,9,10-hexahydro-4-hydroxy-2-oxo-2H-cycloocta[b]pyran-3-yl)methyl]phenyl]-benzenesulfonamide To 12.6 g of the title product of Preparation 67 is added 500 ml of methanol and, with rapid stirring, 50 ml of a 1N aqueous NaOH solution. The reaction solution is allowed to stir at room temperature for 1 hour. The yellow solution is evaporated to dryness at 35° C. and the resulting amorphous residue is dissolved in absolute ethanol and re-evaporated to dryness. The yellow residue is kept under high vacuum at room temperature for 18 hours to yield 14 g of a yellow amorphous solid.

Physical characteristics are as follows:

TLC(silica gel GF): R$_f$=0.8 streak from the origin (20% ethylacetate in methylene chloride)

K.F. Water: 6.16%

Melt Solvate: 4.2% ethanol

Weight Loss at Room Temperature: 4.99%

Ash: found: 7.83%; Calc'd: 7.50% (corrected for 6.16% water and 4.2% ethanol)

Preparation 68 N-methyl-3[(3-aminophenyl)cyclopropylmethyl]-5,6,7,8,9,10-hexahydro-4-hydroxy-2H-cycloocta[b]pyran-2-one To 678 mg of the title product of Preparation 66 is added 100 ml of absolute ethanol and 330 mg of 10% Pd/C. 183 microliters of a 35% $CH_2O/H_2O$ solution is added and the mixture allowed to shake on a Paar apparatus, under 50 lbs of hydrogen, for 2 hours at room temperature. The reaction is filtered over celite and the filter cake is washed well with ethanol. The resulting amber solution is evaporated to dryness. The resulting residue is chromatographed using 10% ethyl acetate in methylene chloride to give 110 mg of the title proudct. This material is used without further purification in the synthesis of the following sulfonamides.

Physical characteristics are as follows:

TLC(silica gel GF): R$_f$=0.5 in 10% ethyl acetate in methylene chloride.

$^1$H NMR (CDCl$_3$) δ 7.19, 6.90, 6.71, 6.54–6.52, 3.90, 2.80, 2.63–2.59, 2.43–2.39, 1.75–1.26, 0.70–0.53, 0.28–0.22 ppm.

EXAMPLE 192

4-Cyano-N-methyl-N-[3-[cyclopropyl(5,6,7,8,9,10-hexahydro-4-hydroxy-2-oxo-2H-cycloocta[b]pyran-3-yl)methyl]phenyl]-benzenesulfonamide A solution of the title compound of Preparation 68 (35 mg), pyridine (16 μL), and 4-cyanobenzenesulfonyl chloride (20.1 mg) in dichloromethane (2 mL) is stirred at room temperature for 18 hr. The crude reaction mixture is chromatographed on silica gel using 10% ethyl acetate in methylene chloride as eluent to give 27 mg of the title compound as a white amorphous solid.

Physical characteristics are as follows:

MS(EI): 518, 490, 352, 233, 207, 172, 158, 143, 129, 115, 102, 81, 54, 43.

TLC(silica gel GF): R$_f$=0.7 in 10% ethyl acetate in methylene chloride.

$^1$H NMR (CDCl$_3$) δ 7.75–7.72, 7.63–7.60, 7.38–7.19, 6.97–6.94, 6.62, 3.86, 3.19, 2.66–2.62, 2.54–2.50, 1.76–1.20, 0.70–0.59, 0.47–42, 0.24–0.19 ppm.

EXAMPLE 193

4-Fluoro-N-methyl-N-[3-[cyclopropyl(5,6,7,8,9,10-hexahydro-4-hydroxy-2-oxo-2H-cycloocta[b]pyran-3-yl)methyl]phenyl]-benzenesulfonamide A solution of the title compound of Preparation 68 (20 mg), pyridine (11 μL), and 4-fluorobenzenesulfonyl chloride (10.7 mg) in dichloromethane (2 mL) is stirred at room temperature for 18 hr. The crude reaction mixture is chromatographed on silica gel using 10% ethyl acetate in methylene chloride as eluent to give 19 mg of the title compound as a white amorphous solid.

Physical characteristics are as follows:

MS(EI):512, 483, 470, 366, 352, 324, 247, 227, 207, 172, 158, 147, 118, 55.

HRMS: Found: 512.1915

TLC(silica gel GF): R$_f$=0.7 in 10% ethyl acetate in methylene chloride.

$^1$H NMR (CDCl$_3$) δ 7.53–7.48, 7.33–7.23, 7.13–7.07, 6.99–6.97, 6.38, 3.93, 3.16, 2.63–2.61, 2.49–2.46, 1.76–1.25, 0.78–0.61, 0.51–0.45, 0.30–0.17 ppm.

EXAMPLE 194

N-methyl-N-[3-[cyclopropyl(5,6,7,8,9,10-hexahydro-4-hydroxy-2-oxo-2H-cycloocta[b]pyran-3-yl)methyl]phenyl]-benzenesulfonamide A solution of the title compound of Preparation 68 (33.4 mg), pyridine (16 μL), and benzenesulfonyl chloride (16.6 mg) in dichloromethane (2 mL) is stirred at room temperature for 18 hr. The crude reaction mixture was chromatographed on silica gel using 10% ethyl acetate in methylene chloride as eluent to give 20 mg of the title compound as a white amorphous solid.

Physical characteristics are as follows:
TLC(silica gel GF): $R_f$=0.7 in 10% ethyl acetate in methylene chloride.
$^1$H NMR (CDCl$_3$) δ 7.59–7.41, 7.33–7.23, 6.98–6.96, 6.44, 3.90, 3.16, 2.64–2.60, 2.50–2.48, 1.75–1.20, 0.67–0.40, 0.23–0.20 ppm.

EXAMPLE 195

N-methyl-N-[3-[cyclopropyl(5,6,7,8,9,10-hexahydro-4-hydroxy-2-oxo-2H-cycloocta[b]pyran-3-yl)methyl]phenyl]-1H-Imidazole-1-methyl-sulfonamide A solution of the title compound of Preparation 68 (33.4 mg), pyridine (16 μL), and N-methyl-imidazole-3-sulfonyl chloride (16 mg) in dichloromethane (2 mL) is stirred at room temperature for 18 hr. The crude reaction mixture is chromatographed on silica gel using 50% ethyl acetate in methylene chloride as eluent to give 28 mg of the title compound as a white amorphous solid.

Physical characteristics are as follows:
TLC(silica gel GF): R=0.5 in 50% ethyl acetate in methylene chloride.
$^1$H NMR (CDCl$_3$) δ 7.43, 7.33, 7.27–7.15, 3.84–3.81, 3.69, 3.35, 2.63–2.59, 2.50–2.46, 1.75–1.26, 0.68, 0.55, 0.47–0.42, 0.24–0.20 ppm.

Utilizing procedures analogous to those described above, the following compounds of the present invention are prepared:

196) 5-cyano-N-[3-[cyclopropyl(5,6,7,8,9,10-hexahydro-4-hydroxy-2-oxo-2H-cyclooeta[b]pyran-3-yl)methyl]phenyl]-2-pyridinesulfonamide 197) N-[3-[cyclopropyl(5,6,7,8,9,10-hexahydro-4-hydroxy-2-oxo-2H-cycloocta[b]pyran-3-yl)methyl]phenyl]-2-quinolinesulfonamide 198) N-[3-[cyclopropyl(5,6,7,8,9,10-hexahydro-4-hydroxy-2-oxo-2H-cycloocta[b]pyran -3-yl )methyl]phenyl]-2-imidazole sulfonamide 199) N-[3-[cyclopropyl(5,6,7,8,9,10-hexahydro-4-hydroxy-2-oxo-2H-cycloocta[b]pyran-3-yl)methyl]phenyl]-2-pyrimidinesulfonamide 200) N-[3-[cyclopropyl(5,6,7,8,9,10-hexahydro-4-hydroxy-2-oxo-2H-cycloocta[b]pyran-3-yl)methyl]phenyl]-2-benzimidazolesulfonamide 201) N-[3-[cyclopropyl(5,6,7,8,9,10-hexahydro-4-hydroxy-2-oxo-2H-cycloocta[b]pyran-3-yl)methyl]phenyl]-2-quinazolinesulfonamide 202) N-[3-[cyclopropyl(5,6,7,8,9,10-hexahydro-4-hydroxy-2-oxo-2H-cycloocta[b]pyran-3-yl)methyl]phenyl]-6-purinesulfonamide 203) 5-cyano-N-[3-[cyclopropyl(5,6,7,8,9,10-hexahydro-4-hydroxy-2-oxo-2H-cycloocta[b]pyran-3-yl)methyl]phenyl]-N-methyl-2-pyridinesulfonamide 204) N-[3-[cyclopropyl(5,6,7,8,9,10-hexahydro-4-hydroxy-2-oxo-2H-cycloocta[b]pyran-3-yl)methyl]phenyl]-N-methyl-2-quinolinesulfonamide 205) N-[3-[cyclopropyl(5,6,7,8,9,10-hexahydro-4-hydroxy-2-oxo-2H-cycloocta[b]pyran-3-yl)methyl]phenyl]-N-methyl-2-imidazolesulfonamide 206) N-[3-[cyclopropyl(5,6,7,8,9,10-hexahydro-4-hydroxy-2-oxo-2H-cycloocta[b]pyran-3-yl)methyl]phenyl]-N-methyl-2-pyrimidinesulfonamide 207) N-[3-[cyclopropyl(5,6,7,8,9,10-hexahydro-4-hydroxy-2-oxo-2H-cycloocta[b]pyran-3-yl)methyl]phenyl]-2-benzimidazolesulfonamide 208) N-[3-[cyclopropyl(5,6,7,8,9,10-hexahydro-4-hydroxy-2-oxo-2H-cycloocta[b]pyran-3-yl)methyl]phenyl]-2-quinazolinesulfonamide 209) N-[3-[cyclopropyl(5,6,7,8,9,10-hexahydro-4-hydroxy-2-oxo-2H-cycloocta[b]pyran-3-yl)methyl]phenyl]-N-methyl-6-purinesulfonamide 210) N-[3-[cyclopropyl(5,6,7,8,9,10-hexahydro-4-hydroxy-2-oxo-2H-cycloocta[b]pyran-3-yl)methyl]phenyl]-N-methyl-4-thiazolesulfonamide 211) N-[3-[cyclopropyl(5,6,7,8,9,10-hexahydro-4-hydroxy-2-oxo-2H-cycloocta[b]pyran-3-yl)methyl]phenyl]-N-methyl-2-pyridinesulfonamide 212) 5-cyano-N-[6-(1'-benzylpropyl)-4-hydroxy-3-(1'-cyclopropylmethylphenyl)-2-pyrone]-N-methyl-2-pyridinesulfonamide 213) N-[6-(1'-benzylpropyl)-4-hydroxy-3-(1'-cyclopropylmethylphenyl)-2-pyrone]-N-methyl-2-quinolinesulfonamide 214) N-[6-(1'-benzylpropyl)-4-hydroxy-3-(1'-cyclopropylmethylphenyl)-2-pyrone]-N-methyl-2-imidazolesulfonamide 215) N-[6-(1'-benzylpropyl)-4-hydroxy-3-(1'-cyclopropylmethylphenyl)-2-pyrone]-N-methyl-2-pyrimidinesulfonamide 216) N-[6-(1'-benzylpropyl)-4-hydroxy-3-(1'-cyclopropylmethylphenyl)-2-pyrone]-N-methyl-2-benzimidazolesulfonamide 217) N-[6-(1'-benzylpropyl)-4-hydroxy-3-(1'-cyclopropylmethylphenyl)-2-pyrone]-N-methyl-2-quinazolinesulfonamide 218) N-[6-(1'-benzylpropyl)-4-hydroxy-3-(1'-cyclopropylmethylphenyl)-2-pyrone]-N-methyl-6-purinesulfonamide 219) N-[6-(1'-benzylpropyl)-4-hydroxy-3-(1'-cyclopropylmethylphenyl)-2-pyrone]-N-methyl-4-thiazolesulfonamide 220) N-[6-(1'-benzylpropyl)-4-hydroxy-3-(1'-cyclopropylmethylphenyl)-2-pyrone]-N-methyl-2-pyridinesulfonamide 221) 5-cyano-N-[3-(1'-cyclopropylmethylphenyl)-4-hydroxycoumarin]-N-methyl-2-pyridinesulfonamide 222) N-[3-(1'-cyclopropylmethylphenyl)-4-hydroxycoumarin]-N-methyl-2-quinolinesulfonamide 223) N-[3-(1'-cyclopropylmethylphenyl)-4-hydroxycoumarin]-N-methyl-2-imidazolesulfonamide 224) N-[3-(1'-cyclopropylmethylphenyl)-4-hydroxycoumarin]-N-methyl-2-pyrimidinesulfonamide 225) N-[3-(1'-cyclopropylmethylphenyl)-4-hydroxycoumarin]-N-methyl-2-benzimidazolesulfonamide 226) N-[3-(1'-cyclopropylmethylphenyl)-4-hydroxycoumarin]-N-methyl-2-quinazolinesulfonamide 227) N-[3-(1'-cyclopropylmethylphenyl)-4-hydroxycoumarin]-N-methyl-6-purinesulfonamide 228) N-[3-(1'-cyclopropylmethylphenyl)-4-hydroxycoumarin]-N-methyl-4-thiazolesulfonamide 229) N-[3-(1'-cyclopropylmethylphenyl)-4-hydroxycoumarin]-N-methyl-2-pyridinesulfonamide 230) 5-cyano-N-[3-[1-(4-hydroxy-2-oxo-6,6-diphenethyl-5,6-dihydro-2H-pyran-3-yl)-propyl]-phenyl]-N-methyl-2-pyridinesulfonamide 231) N-[3-[1-(4-hydroxy-2-oxo-6,6-diphenethyl-5,6-dihydro-2H-pyran-3-yl)-propyl]-phenyl]-N-methyl-2-quinolinesulfonamide 232) N-[3-[1-(4-hydroxy-2-oxo-6,6-diphenethyl-5,6-dihydro-2H-pyran-3-yl)-propyl]-phenyl]-N-methyl-2-imidazolesulfonamide 233) N-[3-[1-(4-hydroxy-2-oxo-6,6-diphenethyl-5,6-dihydro-2H-pyran-3-yl)-propyl]-phenyl]-N-methyl-2-pyrimidinesulfonamide 234) N-[3-[1-(4-hydroxy-2-oxo-6,6-diphenethyl-5,6-dihydro-2H-pyran-3-yl)-propyl]-phenyl]-N-methyl-2-benzimidazolesulfonamide 235) N-[3-[1-(4-hydroxy-2-oxo-6,6-diphenethyl-5,6-dihydro-2H-pyran-3-yl)-propyl]-phenyl]-N-methyl-2-quinazolinesulfonamide 236) N-[3-[1-(4-hydroxy-2-oxo-6,6-diphenethyl-5,6-dihydro-2H-pyran-3-yl)-propyl]-phenyl]-N-methyl-6-purinesulfonamide 237) N-[3-[1-(4-hydroxy-2-oxo-6,6-diphenethyl-5,6-dihydro-2H-pyran-3-yl)-propyl]-phenyl]-N-methyl-4-thiazolesulfonamide 238) N-[3-[1-(4-hydroxy-2-oxo-6,6-diphenethyl-5,6-dihydro-2H-pyran-3-yl)-propyl]-phenyl]-N-methyl-2-pyridinesulfonamide

EXAMPLE 239

2-Pyridylsulfonamide, N-[4-[cyclopropyl(5,6,7,8,9,10-hexahydro-4-hydroxy-2-oxo-2H-cycloocta[b]pyran-3-yl)methyl]phenyl]-(Formula P-2, R is 2-pyridyl) Refer to Chart P.

3-[(3-Aminophenyl)cyclopropylmethyl]-5,6,7,8,9,10-hexahydro-4-hydroxy-2H-cycloocta[b]pyran-2-one of Preparation 66 (100 mg) is dissolved in methylene chloride (3 mL) and pyridine (70 μL) added. 2-Pyridylsulfonyl chloride (52 mg) is added and the solution stirred for 2 hr at 25° C. Chloroform (25 mL) is added and the combined extracts washed with 1N.HCl (20 mL) and dried over sodium sulfate. Removal of the solvent gives a pink gum which is chromatographed over silica gel using the flash column technique eluting with 60% ethyl acetate-hexane. The title compound is obtained as a white solid (80 mg).

Physical characteristics are as follows:
MS m/z 480, 339, 338, 186, 145, 144, 132, 130, 78, 55.

EXAMPLE 240

4-Pyridylsulfonamide, N-[4-[cyclopropyl(5,6,7,8,9,10-hexahydro-4-hydroxy-2-oxo-2H-cycloocta[b]pyran-3-yl)methyl]phenyl]-(Formula P-2, R is 4-pyridyl) Refer to Chart P.

Using procedures described in Example 239, the title compound is obtained as a white solid.

Physical characteristics are as follows:
MS m/z 480, 338, 207, 186, 145, 144, 117, 79, 78, 55

EXAMPLE 241

5-Cyanopyridin-2-yl-sulfonamide, N-[4-[cyclopropyl(5,6,7,8,9,10-hexahydro-4-hydroxy-2-oxo-2H-cycloocta[b]pyran-3-yl)methyl]phenyl]-(Formula P-2, R is 5-cyanopyridin-2-yl) Refer to Chart P.

The title compound is prepared using procedures described in Example 239.

EXAMPLE 242

2-Pyrazinylsulfonamide, N-[4-[cyclopropyl(5,6,7,8,9,10-hexahydro-4-hydroxy-2-oxo-2H-cycloocta[b]pyran-3-yl)methyl]phenyl]-(Formula P-2, R is 2-pyrazinyl) Refer to Chart P.

The title compound is prepared using procedures described in Example 239.

EXAMPLE 243

2-Pyrimidinylsulfonamide, N-[4-[cyclopropyl(5,6,7,8,9,10-hexahydro-4-hydroxy-2-oxo-2H-cycloocta[b]pyran-3-yl)methyl]phenyl]-(Formula P-2, R is 2-pyrimidinyl) Refer to Chart P.

The title compound is prepared using procedures described in Example 239.

EXAMPLE 244

4-6-Dimethylpyrimidin-2-yl-sulfonamide, N-[4-[cyclopropyl(5,6,7,8,9,10-hexahydro-4-hydroxy-2-oxo-2H-cycloocta[b]pyran-3-yl)methyl]phenyl]-(Formula P-2, R is 4,6-dimethylpyrimidin-2-yl) Refer to Chart P.

The title compound is prepared using procedures described in Example 239.

EXAMPLE 245

4-Methylpyrimidin-2-yl-sulfonamide, N-[4-[cyclopropyl(5,6,7,8,9,10-hexahydro-4-hydroxy-2-oxo-2H-cycloocta[b]pyran-3-yl)methyl]phenyl]-(Formula P-2, R is 4-methylpyrimidin-2-yl) Refer to Chart P.

The title compound is prepared using procedures described in Example 239.

Preparation 69 6,6-Bis-(2-cyclopropyl-ethyl)-dihydro-pyran-2,4-dione (Formula Q-2) Refer to Chart Q.

To a suspension of 150 mg of sodium hydride (60% dispersion in mineral oil) in 4 ml of dry THF under argon atmosphere at 0° C. is added dropwise 0.38 ml of methyl acetoacetate. After 10 minutes 2.3 ml of butyllithium (1.6 M in hexanes) is added. After 10 minutes a solution of 0.48 g of the compound of formula Q-1 (prepared as described in Preparation 79 (Formula S-4, refer to Chart S)) in 3 ml of tetrahydrofuran is added. The reaction mixture is stirred for 1 hour, then partitioned between ethyl acetate and dilute aqueous hydrogen chloride. The aqueous phase is extracted with two additional portions of ethyl acetate. The organic phases are combined, washed with brine, dried over magnesium sulfate and concentrated under reduced pressure. The residue is diluted with 5 mL of methanol and the resulting solution treated with 12 mL of water followed by 3.0 ml of 1 M aqueous sodium hydroxide. After 2 hours of vigorous stirring the methanol is removed under reduced pressure. The aqueous phase is washed once with diethyl ether; the ether phase is discarded. The aqueous phase is cooled to 0° C., then acidified with dilute aqueous hydrogen chloride. The resulting precipitate is extracted with four portions of dichloromethane. The combined dichloromethane extracts are dried over magnesium sulfate and concentrated under reduced pressure. The residue is dissolved in diethyl ether-hexane and the solution is chilled to provide to provide 0.42 g of the title compound as a pale yellow solid.

Physical characteristics are as follows:
$^1$H NMR δ 0.0, 0.4, 0.6, 1.2, 1.7, 2.6, 3.4.

Preparation 70 6,6-Bis-(2-cyclopropyl-ethyl)-5,6-dihydro-4-hydroxy-3-[1-(3-nitro-phenyl)-propyl]-pyran-2-one (Formula Q-3) Refer to Chart Q.

To a stirred solution of 0.41 g of the title compound of Preparation 69 (Formula Q-2) and 0.25 g of the 3-nitrobenzaldehyde in 5 ml of dry tetrahydrofuran is added a solution of 0.44 g of aluminum trichloride in 4.5 ml of tetrahydrofuran. After 2 hours, the reaction mixture is treated with 1.0 g of sodium carbonate decahydrate, stirred 10 minutes, diluted with diethyl ether and finally charged with magnesium sulfate. The resulting mixture is filtered through a pad of Celite with diethyl ether rinses. The filtrates are combined and concentrated under reduced pressure. The resulting residue is charged with 103 mg of copper (I) bromide-dimethyl sulfide complex and 5 ml of dry tetrahydrofuran under an argon atmosphere. The reaction mixture is treated dropwise with 2.5 mL of triethyl aluminum (1.0 M in hexane) over 1.5 hours. The reaction is then slowly treated with ice and partitioned between diethyl ether and dilute aqueous hydrogen chloride. The aqueous phase is extracted with three additional portions of diethyl ether. The combined ether extracts are washed with brine, dried over magnesium sulfate, and concentrated under reduced pressure. Flash column chromatography of the residue on silica gel using 20% to 40% ethyl acetate in hexane affords 0.44 g of the title compound as a tan foam.

Physical characteristics are as follows:
$^1$H NMR δ 0.0, 0.4, 0.6, 1.0, 1.2, 1.7–1.9, 2.0–2.4, 2.6, 4.2, 7.5, 7.8, 8.1, 8.3

Preparation 71 3-[1-(3-Amino-phenyl)-propyl]-6,6-bis-(2-cyclopropyl-ethyl)-5,6-dihydro-4-hydroxy-pyran-2-one (Formula Q-4) Refer to Chart Q.

To a solution of 0.44 g of the title compound of Preparation 70 (Formula Q-3) in 6 ml of methanol is added 0.65 g of ammonium formate and 50 mg of 10% palladium on carbon. The black slurry is stirred under argon for 3 hours, then filtered through pad of Celite with methanol washes. The filtrates are combined and the solvent is removed under reduced pressure. The residue is triturated with four portions of dichloromethane. The combined dichloromethane washes are concentrated under reduced pressure to provide 0.37 g of the title compound as a white foam.

Physical characteristics are as follows:
$R_f$ 0.08 (50% diethyl ether in hexane)

EXAMPLE 246

N-[3-(1-[6,6-Bis-(2-cyclopropyl-ethyl)-5,6-dihydro-4-hydroxy-2-oxo-2H-pyran-3-yl]propyl)phenyl]-1-methyl-1H-imidazole-4-sulfonamide (Formula Q-5: $R_1$ is 1-methylimidazol-4-yl) Refer to Chart Q.

To a flask containing 57 mg of the title compound of Preparation 71 (Formula Q-4) and 24 μl of pyridine in 1.0 ml of dichloromethane is added 27 mg of 1-methylimidazole-4-sulfonyl chloride. After 6 hours the reaction mixture is concentrated under reduced pressure. The pyridine is azeotroped thrice with toluene. The resulting residue is flash column chromatographed on silica gel using 2% to 6% methanol in dichloromethane to provide 51 mg of the title compound as a white foam.

Physical characteristics are as follows:
$^1$H NMR δ 0.0, 0.4, 0.6, 0.9, 1.1–1.4, 1.7–2.2, 2.5, 3.7, 3.95, 6.9, 7.1, 7.4, 7.5
HRMS: 528.2537 (FAB)

EXAMPLE 247

N-[3-(1-[6,6-Bis-(2-cyclopropyl-ethyl)-5,6-dihydro-4-hydroxy-2-oxo-2H-pyran-3-yl]propyl)phenyl]-5-cyano-2-pyridinesulfonamide (Formula Q-5: $R_1$ is 5-cyano-2-pyridyl) Refer to Chart Q.

Using the general sulfonylation procedure described in Example 246, 57 mg of the amine of Preparation 71 (Formula Q-4) is reacted with 30 mg of 5-cyanopyridine-2-sulfonyl chloride. Flash column chromatography on silica gel using 1% to 3% methanol in dichloromethane provides 62 mg of the title compound as a tan foam.

Physical characteristics are as follows:
$^1$H NMR δ 0.0, 0.4, 0.6, 0.9, 1.1–1.4, 1.6–2.2, 2.5, 3.95, 6.9–7.2, 8.0, 8.2, 9.0
HRMS: 550.2370 (FAB)

Preparation 72 3-Aminopropiophenone (Formula R-2) Refer to Chart R.

To a solution of 3-nitropropiophenone (Formula R-1) (1.79 g) in diethyl ether is added 5% Pt/C catalyst (0.20 g). The resulting suspension is placed under a hydrogen gas atmosphere and stirred for 6 hours. The reaction mixture is filtered through a pad of Celite and the pad washed with additional portions of diethyl ether. The combined filtrates are concentrated under reduced pressure to provide 1.49 g of the title compound as pale yellow, low melting solid.

Physical characteristics are as follows:
$^1$H NMR δ 1.2, 3.0, 6.9, 7.2–7.4
$R_f$ 0.45 (33% ethyl acetate in hexane)

Preparation 73 1-[3-(Dibenzyl-amino)-phenyl]-propan-1-one (Formula R-3) Refer to Chart R.

To a solution of the title compound of Preparation 72 of Formula R-2 (1.5 g) in dichloromethane (50 mL) is added diisopropylethylamine (6.0 mL) followed by benzyl bromide (3.6 mL). After stirring for 6 hours the reaction mixture is heated to reflux overnight. The reaction mixture is cooled to room temperature, diluted with diethyl ether (50 mL) and washed sequentially with dilute aqueous potassium hydrogen sulfate, water, saturated aqueous sodium bicarbonate, and brine. The organic layer is dried over sodium sulfate and concentrated under reduced pressure. The residue is purified by flash column chromatography on silica gel eluting with 5% to 20% ethyl acetate in hexane to provide 2.38 g of the title compound as pale yellow solid.

Physical characteristics are as follows:
$^1$H NMR δ 1.1, 2.9, 4.7, 6.9, 7.2–7.4
Anal. Found: C, 83.88; H, 7.03; N, 4.20.
MS: 329 (EI)

Preparation 74 6-[3-(Dibenzyl-amino)-phenyl]-dihydro-pyran-2,4-dione (Formula R-4) Refer to Chart R.

Using the general procedure described in Preparation 69 for the formation of the dihyropyranone ring, the compound of Formula R-3 of Preparation 73 (1.96 g) is reacted with the dianion of methyl acetoacetate and cyclized to provide 0.76 g of the title compound.

Physical characteristics are as follows:
$^1$H NMR δ 0.8, 1.9, 2.6–2.9, 3.1–3.2, 4.7, 6.5–6.7, 7.1–7.4
MS: 413 (EI)

Preparation 75 6-[3-(Dibenzyl-amino)-phenyl]-5,6-dihydro-6-ethyl-4-hydroxy-3-[1-(3-nitro-phenyl)-propyl]-pyran-2-one (Formula R-5) Refer to Chart R.

Using the general procedure described in Preparation 70, aluminum trichloride catalyzed condensation of 3-nitrobenzaldehyde with the compound of Formula R-4 of Preparation 74 (727 mg), followed by copper catalyzed conjugate addition with triethyl aluminum provides 800 mg of the title compound.

Physical characteristics are as follows:
$^1$H NMR δ 0.6, 1.6–2.1, 2.8, 3.4, 3.8, 4.4, 6.4–6.6, 6.8–7.4, 7.7–8.0
MS: 576 (EI)

Preparation 76 6-(3-Amino-phenyl)-3-[1-(3-amino-phenyl)-propyl]-6-ethyl-5,6-dihydro-4-hydroxy-pyran-2-one (Formula R-6) Refer to Chart R.

Using the general procedure described in Preparation 71, catalytic hydrogenation of the compound of Formula R-5 of Preparation 75 (114 mg) with ammonium formate and Pd/C affords 61 mg of the title compound. Alternatively, the compound of Formula R-5 of Preparation 75 (114 mg) is reduced with Pd/C and hydrogen gas to give 72 mg of the title compound.

Physical characteristics are as follows:
$^1$H NMR δ 0.6–0.9, 1.8–2.1, 3.0, 3.8, 6.4–6.6, 6.95, 7.1
$R_f$ 0.40 (10% methanol in dichloromethane)

EXAMPLE 248

N-(3-[1-(6-Ethyl-5,6-dihydro-4-hydroxy-6-[3-([(1-methyl-1H-imidazol-4-yl)sulfonyl]amino)phenyl]-2-2H-pyran-3-yl)propyl]phenyl)-1-methyl-1H-imidazole-4-sulfonamide (Formula R-7: $R_1$ is 1-methylimidazol-4-yl) Refer to Chart R.

Using the general sulfonylation procedure described in Example 246, the compound of Formula R-6 of Preparation 76 (61 mg) is reacted with 1-methylimidazole-4-sulfonyl chloride to provide 59 mg of the title compound.

Physical characteristics are as follows:
$^1$H NMR δ 0.3–0.7, 1.6–2.0, 3.0, 3.4–3.7, 6.7–7.5
HRMS: 655.1995 (FAB)

EXAMPLE 249

5-Cyano-N-(3-[1-(6-[3-([(5-cyano-2-pyridinyl)sulfonyl] amino) phenyl]-6-ethyl-5,6-dihydro-4-hydroxy-2-oxo-2H-pyran-3-yl)propyl]phenyl)-2-pyridinesulfonamide (Formula R-7: R is 5-cyano-2-pyridyl) Refer to Chart R.

Using the general sulfonylation procedure described in Example 246, the compound of Formula R-6 of Preparation 76 (66 mg) is reacted with 5-cyano-2-pyridine sulfonyl chloride to provide 40 mg of the title compound.

Physical characteristics are as follows:
$^1$H NMR δ 0.3–0.9, 1.3, 1.6–1.9, 3.0, 3.7, 6.6–7.2, 7.9–8.2, 8.8–9.0
HRMS: 699.1679 (FAB)

Preparation 77 N-Methoxy-N-methyl-4-pentenoic amide (Formula S-2) Refer to Chart S.

To a suspension of 4-pentenoic acid (Formula S-1) (2.00 g) and N,O-dimethylhydroxylamine hydrochloride (2.15 g) in dichloromethane (50 mL) at 0° C. is added diisopropylethylamine (11.5 mL) followed by bis(2-oxo-3-oxazolidinyl)phosphinic chloride (5.60 g). After stirring overnight, the reaction mixture is concentrated under reduced pressure. The residue is partioned between dilute aqueous potassium hydrogen sulfate and diethyl ether. The aqueous phase is extracted with two additional portions of diethyl ether. The organic extracts are combined, washed with brine, dried over sodium sulfate and concentrated under reduced pressure. The residue is purified by flash column chromatography on silica gel eluting with 50% to 80% diethyl ether in hexane to provide 2.58 g of the title compound as a tan oil.

Physical characteristics are as follows:
$^1$H NMR δ 2.3–2.6, 3.20, 3.70, 4.9–5.1, 5.75–5.95
$R_f$ 0.17 (25% diethyl ether in hexane)

Preparation 78 Nona-1,8-dien-5-one (Formula S-3) Refer to Chart S

To a flame-dried flask under an argon atmosphere containing a solution of the title compound of Preparation 77 (Formula S-2) (1.45 g) in dry tetrahydrofuran (10 mL) at 0° C. is added 3-butenyl-1-magnesium bromide (20 mL, 1 M solution in tetrahydrofuran. (Preparation of this Grignard reagent from magnesium metal and 4-bromo-1-butene is described in J.Org.Chem. 43:4247 (1978)). After 1 hour at 0° C., the reaction mixture is warmed to room temperature; after 1 hour at room temperature, the reaction mixture is poured into dilute aqueous potassium hydrogen sulfate and partioned against diethyl ether. The aqueous phase is extracted with three additional portions of diethyl ether. The organic extracts are combined, washed with brine, dried over sodium sulfate and carefully concentrated under reduced pressure. The resulting liquid is purified by distillation to provide 1.32 g of the title compound as a tan oil.

Physical characteristics are as follows:
$^1$H NMR δ 2.3, 2.5, 5.0, 5.7–5.9
$R_f$ 0.66 (25% diethyl ether in hexane)

Preparation 79 1,5-Dicyclopropyl-pentan-3-one (Formula S-4) Refer to Chart S.

To a flame-dried flask under an argon atmosphere equipped with a reflux condenser containing zinc metal (8.0 g) and cuprous chloride (1.25 g) is added a solution of the title compound of Preparation 78 (Formula S-3) (1.32 g) in dry diethyl ether (10 mL). The resulting suspension is charged with diiodomethane (5.0 mL) and the reaction flask placed in 40° C. ultrasound bath (Branson8 2200) and sonicated. After 2 hours heating is ceased and sonication is continued overnight. The reaction mixture is then diluted with diethyl ether (50 mL), cooled to 0° C., and treated with excess saturated aqueous ammonium chloride. After 0.25 hours of vigorous stirring, the mixture is filtered and the layers separated. The aqueous phase is extracted with two additional portions of diethyl ether. The organic extracts are combined and washed sequentially with dilute aqueous sodium thiosulfate, saturated aqueous sodium bicarbonate, brine; dried over magnesium sulfate and then carefully concentrated under reduced pressure. The resulting residue is purified by flash column chromatography on silica gel eluting with 5% to 20% diethyl ether in hexane to provide 0.48 g of the title compound as an oil.

Physical characteristics are as follows:
$^1$H NMR δ 0.0, 0.4, 0.65, 1.45, 2.50
$R_f$ 0.44 (10% diethyl ether in hexane)

Preparation 80 3-[2,2-Dimethyl-1-(3-nitro-phenyl)-propyl]-5,6-dihydro-4-hydroxy-6-phenethyl-6-propyl-pyran-2-one (Formula T-3) Refer to Chart T.

To a flame-dried flask containing a slurry of 977 mg of activated zinc metal in 1.0 mL of dry tetrahydrofuran under an argon atmosphere is added 40 μL of 1,2-dibromoethane. The mixture is placed in 45° C. ultrasound bath (Branson 2200) and sonicated with stirring. After 10 minutes the mixture is treated with 0.25 mL of chlorotrimethylsilane (1.0 M in tetrahydrofuran). After 10 minutes, the mixture is diluted with 4 mL of tetrahydrofuran and treated dropwise with 1.50 mL of 2-iodo-2-methylpropane. The mixture is stirred and sonicated at 45 0° C. for an additional 3 hours, then cooled to room temperature without stirring. In a separate flask 954 mg of anhydrous lithium chloride is heated in an 110° C. oil bath in vacuo for 1 hour. The LiCl flask is cooled to room temperature, placed under an argon atmosphere and charged with 1.01 g of copper (I) cyanide followed by 10 mL of tetrahydrofuran. After 15 minutes of stirring at room temperature, the LiCl—CuCN mixture is cooled to −30° C. and treated via cannula with the organozinc mixture prepared as described above in the first flask. The reaction flask is warmed from −30° C. to 0° C., stirred 10 minutes then cooled to −78° C. The preparation of this organometallic reagent is analogous to literature procedures (Org. Syn. 70:195–203 (1991)) described for related reagents.

In a separate flask a stirred solution of 1.56 g of 6-phenethyl-6-propyl-dihydro-pyran-2,4-dione of Formula T-2 (prepared from the compound of Formula T-1 as described in Preparation 17 above) and 915 mg of the 3-nitrobenzaldehyde in 22 mL of dry tetrahydrofuran is treated with a solution of 1.60 g of aluminum trichloride in 14 mL of tetrahydrofuran. After 2 hours, the reaction mixture is treated with 3.6 g of sodium carbonate decahydrate, stirred 5 minutes, diluted with diethyl ether and finally charged with magnesium sulfate. The resulting mixture is filtered through a pad of Celite with diethyl ether washes. The filtrates are combined and concentrated under reduced pressure. The resulting residue is charged with 9 mL of dry tetrahydrofuran under an argon atmosphere and is added via cannula to the cooled (−78° C.) organometallic reagent solution prepared as described above. After 0.5 hours the reaction mixture is warmed to 0° C. After 0.5 hours at 0° C. the reaction is poured into cold dilute ammonium chloride and the aqueous phase is made acidic with dilute aqueous hydrogen chloride. The mixture is treated with ethyl acetate and filtered through a pad of Celite with ethyl acetate washes. The layers are separated and the aqueous phase is extracted with three additional portions of ethyl acetate. The combined ethyl acetate extracts are washed with aqueous sodium thiosulfate, brine; dried over magnesium sulfate, and concentrated under reduced pressure. Flash column chromatography of the residue on silica gel eluting with 30% to 50% ethyl acetate in hexane affords 1.73 g of the title compound as a tan foam.

Physical characteristics are as follows:
$^1$H NMR δ 0.9, 1.1, 1.3, 1.6–2.0, 2.5–2.8, 4.3, 6.9–7.3, 7.8, 8.0, 8.5
HRMS: 452.2449 (FAB)

Preparation 81 3-[1-(3-Amino-phenyl)-2,2-dimethyl-propyl]-5,6-dihydro-4-hydroxy-6-phenethyl-6-propyl-pyran-2-one (Formula T-4) Refer to Chart T.

To a solution of 1.72 g of the title compound of Preparation 80 (Formula T-3) in 25 mL of methanol is added 3.0 g of ammonium formate and 400 mg of 10% palladium on carbon. The black slurry is stirred under nitrogen for 3 hours, then filtered through pad of Celite with methanol washes. The filtrates are combined and the solvent is removed under reduced pressure. The residue is repeatedly triturated with portions of dichloromethane and the combined dichloromethane washes concentrated under reduced pressure. The residue is flash column chromatographed on silica gel eluting with 10% ethyl acetate in dichloromethane to provide 1.48 g of the title compound as a white foam.

Physical characteristics are as follows:
$^1$H NMR δ 0.7–0.9, 1.1, 1.3–2.6, 4.2, 6.55, 6.9–7.3
HRMS: 422.2686 (FAB)

EXAMPLE 250

N-[3-(1-[5,6-Dihydro-4-hydroxy-2-oxo-6-(2-phenethyl)-6-propyl-2H-pyran-3-yl]-2,2-dimethylpropyl)phenyl]-1-methyl-1H-imidazole-4-sulfonamide (Formula T-5: $R_1$ is 1-methylimidazol-4-yl) Refer to Chart T.

To a solution of 1.48 g of the title compound of Preparation 81 (Formula T-4) in 25 ml of dichloromethane at 0° C. is added 0.57 mL of pyridine followed by 632 mg of 1-methylimidazole-4-sulfonyl chloride. After 3 hours the reaction mixture is warmed to room temperature and concentrated under reduced pressure. Pyridine is azeotroped thrice with toluene. The resulting residue is flash column chromatographed on silica gel using 2% to 6% methanol in dichloromethane to provide 1.7 g of the title compound as a white solid.

Physical characteristics are as follows:
$^1$H NMR δ 0.8–1.0, 0.97, 1.35, 1.6–2.0, 2.5–2.7, 3.6, 4.1, 6.9–7.5
HRMS: 566.2684

The individual stereoisomers of this compound are the following:

N-[3-(1(S)-[5,6-dihydro-4-hydroxy-2-oxo-6(R)-(2-phenethyl)-6-propyl-2H-pyran-3-yl]-2,2-dimethylpropyl) phenyl]-1-methyl-1H-imidazole-4-sulfonamide (Formula KK-8 wherein $R_4$ is 1-methyl-1H-imidazol-4-yl) Refer to Chart KK;

N-[3-(1(R)-[5,6-dihydro-4-hydroxy-2-oxo-6(R)-(2-phenethyl)-6-propyl-2H-pyran-3-yl]-2,2-dimethylpropyl) phenyl]-1-methyl-1H-imidazole-4-sulfonamide (Formula LL-8 wherein $R_4$ is 1-methyl-1H-imidazol-4-yl) Refer to Chart LL;

N-[3-(1(S)-[5,6-dihydro-4-hydroxy-2-oxo-6(S)-(2-phenethyl)-6-propyl-2H-pyran-3-yl]-2,2-dimethylpropyl) phenyl]-1-methyl-1H-imidazole-4-sulfonamide (Formula MM-8 wherein $R_4$ is 1-methyl-1H-imidazol-4-yl) Refer to Chart MM; and N-[3-(1(R)-[5,6-dihydro-4-hydroxy-2-oxo-6(S)-(2-phenethyl)-6-propyl-2H-pyran-3-yl]-2,2-dimethylpropyl) phenyl]-1-methyl-1H-imidazole-4-sulfonamide (Formula NN-8 wherein $R_4$ is 1-methyl-1H-imidazol-4-yl) Refer to Chart NN.

EXAMPLE 251

5-Cyano-N-[3-(1-[5,6-dihydro-4-hydoxy-2-oxo-6-(2-phenethyl)-6-propyl-2H-pyran-3-yl]-2,2-dimethylpropyl) phenyl]-2-pyridinesulfonamide (Formula T-5: $R_1$ is 5-cyano-2-pyridyl) Refer to Chart T.

Using the general sulfonylation procedure described in Example 250, 42 mg of the amine of Preparation 81 (Formula T-4) is reacted with 20 mg of 5-cyanopyridine-2-sulfonyl chloride. Flash column chromatography on silica gel using 1% to 3% methanol in dichloromethane provides 56 mg of the title compound as a white foam.

Physical characteristics are as follows:
$^1$H NMR δ 0.8–1.0, 0.92, 1.35, 1.6–2.0, 2.5–2.7, 4.0, 6.9–7.4, 8.0, 8.9
HRMS: 588.2532

Preparation 82 N-Methoxy, N-methyl 3-(4-fluorophenyl) propionamide (Formula U-2) Refer to Chart U.

To a cold (0°), stirred solution of 5.0 g of 3-(4-fluorophenyl)propionic acid of Formula U-1, 3.2 g of (N,O)-dimethylhydroxylamine hydrochloride, and 11.4 ml of diisopropylethylamine in 40 ml of dichloromethane is slowly added a solution of 5.0 ml of diethyl cyanophosphonate in 10 ml of dichloromethane. After 18 hours, the solution is concentrated under reduced pressure. The residue is dissolved in ethyl acetate, and the solution washed with dilute HCl, water, aqueous sodium bicarbonate, and brine, and dried over magnesium sulfate. Removal of the solvent under reduced pressure provides 6.94 g of the title compound.

Physical characteristics are as follows:
$^1$H NMR δ 2.7, 2.9, 3.17, 3.61, 7.0, 7.2 ppm
IR 1665, 1511, 1222, 1033, 990 cm$^{-1}$
TLC $R_f$ 0.34 (5% ethyl acetate in dichloromethane)

Preparation 83 1-(4-Fluorophenyl)-3-hexanone (Formula U-3) Refer to Chart U.

A stirred solution of 4.68 g of the title compound of Preparation 82 (Formula U-2) in 25 ml of dry THF under argon is cooled to −15°, and to the solution is added 17 ml of a 1M solution of propylmagnesium chloride in ether. The resulting solid mass is warmed to 0°, kept at that temperature for 90 minutes, then partitioned between ether and cold dilute HCl. The aqueous phase is extracted with one additional portion of ether, and the combined organic phase washed with brine and dried over magnesium sulfate. Following removal of solvent by distillation at atmospheric pressure, the residue is purified by evaporative distillation (ca 160°@13 mmHg) to provide 3.51 g of the title compound as a colorless liquid.

Physical characteristics are as follows:
$^1$H NMR δ 0.89, 1.6, 2.36, 2.7, 2.9, 6.9, 7.1 ppm IR 2965, 1714, 1511, 1222 cm$^{-1}$ Preparation 84 5,6-Dihydro-4-hydroxy-6-(2-(4-fluorophenyl)ethyl)-6-propyl-2H-pyran-2-one (Formula U-4) Refer to Chart U.

To a cold (00), stirred slurry of 950 mg of sodium hydride (60% dispersion in mineral oil) in 30 ml of dry THF, under argon, is added dropwise 2.3 ml of methyl acetoacetate. After 5 minutes, 13.5 ml of butyllithium (1.6M in hexanes) is added, and the mixture stirred another 5 minutes before addition of a solution of 3.51 g of the title compound of Preparation 83 (Formula U-3) in 4 ml of THF. The solution is stirred for 1 hour, then partitioned between ethyl acetate and cold dilute HCl. The aqueous phase is extracted with two additional portions of ethyl acetate, and the combined organic phase washed with brine and dried over magnesium sulfate. Removal of the solvent under reduced pressure provides the intermediate ester with the following physical characteristics: TLC $R_f$ 0.45 (50% ethyl acetate in hexane).

The ester is stirred in 20 ml of 1M sodium hydroxide, 80 ml of water, and 40 ml of methanol for 90 minutes, then the methanol is removed under reduced pressure. The aqueous phase is washed once with ether, the ether phase being discarded, and then acidified with dilute HCl. The resulting precipitate is extracted with four portions of dichloromethane, and the extract dried over magnesium sulfate and concentrated under reduced pressure. The residue is dissolved in 1:1 ether-hexane and the solution chilled to provide crystals, which are filtered, washed with ether-hexane, and dried under vacuum to afford 3.24 g of the title compound.

Physical characteristics are as follows:
$^1$H NMR δ 0.96, 1.4, 1.8, 2.0, 2.5, 2.7, 7.0, 7.1 ppm IR 2962, 1655, 1604, 1510, 1221 cm$^{-1}$
M.P. 113–114.50
Anal. Found: C, 68.85; H, 6.99.
MS: M+ 278
$R_f$ 0.44 (5% methanol in dichloromethane)

Preparation 85 3-(1-(3-Benzyloxycarbonylaminophenyl)-2,2-dimethylpropyl)-5,6-dihydro-4-hydroxy-6-(2-(4-fluorophenyl)ethyl)-6-propyl-2H-pyran-2-one (Formula U-6: $R_1$ is tert-butyl) Refer to Chart U.

To a stirred solution of 3.06 g of the title compound of Preparation 84 (Formula U-4) and 2.81 of the title compound of Preparation 6 above (Formula B-2) in 30 ml of dry THF is added a solution of 2.93 g of AlCl$_3$ in 20 ml of THF. After two hours, 6.4 g of sodium carbonate decahydrate is added, and after five minutes the mixture is filtered through Celite with ether rinses. Removal of the solvent under reduced pressure provides the intermediate benzylidene compound of Formula U-5.

To this is added, under argon, 1.13 g of copper (I) bromide-dimethyl sulfide complex and 30 ml of THF, and the mixture is cooled to 0° for dropwise addition of 18.1 ml of tert-butylmagnesium chloride (1.0M in THF). After 10 minutes, the reaction is partitioned between ether and cold dilute HCl. The organic phase is washed with brine, dried over magnesium sulfate, and concentrated under reduced pressure. Flash chromatography of the residue on silica gel using 30–35% ethyl acetate in hexane affords 1.83 g of the title compound as a foam.

Physical characteristics are as follows:
$^1$H NMR δ 0.87, 1.1, 1.3, 1.6–2.2, 2.5, 5.12, 6.8–7.6 ppm
HRMS: 574.2955
$R_f$ 0.29 (35% ethyl acetate in hexane)

Preparation 86 3-(1-(3-Aminophenyl)-2,2-dimethylpropyl)-5,6-dihydro-4 -hydroxy-6-(2-(4-fluorophenyl)ethyl)-6-propyl-2H-pyran-2-one (Formula U-7: $R_1$ is tert-butyl) Refer to Chart U.

A mixture of 1.83 g of the title compound of Preparation 85 (Formula U-6), 2.0 g of ammonium formate, and 400 mg of 10% palladium on carbon in 25 ml of methanol is stirred under argon for 90 minutes, then filtered through Celite. The solvent is removed under reduced pressure and the residue flash chromatographed on silica gel using 10% ethyl acetate in dichloromethane to provide 1.24 g of the title compound as a white foam.

Physical characteristics are as follows:
$R_f$ 0.28 (10% ethyl acetate in dichloromethane) The compound of Formula U-7 wherein $R_1$ is ethyl is prepared from U-4 by analogous procedures as in the preparation of U-7 wherein $R_1$ is tert-butyl (Preparations 85 and 86).

EXAMPLE 252
N-[3-{1-(4-Hydroxy-5,6-dihydro-2-oxo-6-(2-(4-fluorophenyl)ethyl)-6-propyl-2H-pyran-3-yl)-2,2-dimethylpropyl}phenyl]-1-methyl-1H-imidazole-4-sulfonamide (Formula U-8: $R_1$ is tert-butyl, $R_2$ is 1-methylimidazole-4-yl) Refer to Chart U.

To a cold (0°), stirred solution of 88 mg of the title compound of Preparation 86 (Formula U-7) and 32 μl of pyridine in 0.5 ml of dichloromethane is added 36 mg of 1-methylimidazole-4-sulfonyl chloride. After 90 minutes the reaction mixture is flash chromatographed on silica using 3–4% methanol in dichloromethane to provide 112 mg of the title compound as a white foam.

Physical characteristics are as follows:
$^1$H NMR δ 0.8–1.0, 0.96, 1.3, 1.7, 2.35, 2.5, 3.6, 3.7, 6.8–7.5 ppm
HRMS: 583.2525
$R_f$ 0.31 (5% methanol in dichloromethane)

EXAMPLE 253
N-[3-{1-(4-Hydroxy-5,6-dihydro-2-oxo-6-(2-(4-fluorophenyl)ethyl)-6-propyl-2H-pyran-3-yl)-2,2-dimethylpropyl}phenyl]-5-cyanopyridine-2-sulfonamide (Formula U-8: $R_1$ is tert-butyl, $R_2$ is 5-cyanopyridine-2-yl) Refer to Chart U.

Using the general sulfonylation procedure of Example 252, 88 mg of the amine of Preparation 86 (Formula U-7, $R_1$ is tert-butyl) is reacted with 5-cyanopyridine-2-sulfonyl chloride. Flash chromatography on silica using 10–15% ethyl acetate in dichloromethane provides 107 mg of the title compound as an amorphous white solid.

Physical characteristics are as follows:
$^1$H NMR δ 0.92, 1.3, 1.7, 2.5, 6.8–7.5, 8.0, 8.9 ppm
HRMS: 606.2423

EXAMPLE 254
N-[3-{1-(4-Hydroxy-5,6-dihydro-2-oxo-6-(2-(4-fluorophenyl)ethyl)-6-propyl-2H-pyran-3-yl)propyl}phenyl]-1-methyl-1H-imidazole-4-sulfonamide (Formula U-8: $R_1$ is ethyl, $R_2$ is 1-methylimidazole-4-yl) Refer to Chart U.

Using the general sulfonylation procedure of Example 252, 82 mg of the amine of Formula U-7, wherein $R_1$ is ethyl, is reacted with 1-methylimidazole-4-sulfonyl chloride. Flash chromatography on silica using 3% methanol in dichloromethane provides 101 mg of the title compound as an amorphous white solid.

Physical characteristics are as follows:
$^1$H NMR δ 0.8, 1.3, 1.6–2.2, 2.5, 3.5, 3.6, 3.9, 6.8–7.4 ppm
HRMS: 555.2192
$R_f$ 0.29 (5% methanol in dichloromethane)

EXAMPLE 255
N-[3-{1-(4-Hydroxy-5,6-dihydro-2-oxo-6-(2-(4-fluorophenyl)ethyl)-6-propyl-2H-pyran-3-yl)propyl}phenyl]-5-cyanopyridine-2-sulfonamide (Formula U-8: $R_1$ is ethyl, $R_2$ is 5-cyanopyridine-2-yl) Refer to Chart U.

Using the general sulfonylation procedure of Example 252, 82 mg of the amine of Formula U-7, wherein $R_1$ is ethyl, is reacted with 5-cyanopyridine-2-sulfonyl chloride. Flash chromatography on silica using 10–15% ethyl acetate in dichloromethane provides 101 mg of the title compound as an amorphous white solid.

Physical characteristics are as follows:
$^1$H NMR δ 0.9, 1.3, 1.6–2.2, 2.5, 3.9, 6.9–7.3, 8.0, 8.1, 8.9 ppm
HRMS: 557.2059
$R_f$ 0.44 (20% ethyl acetate in dichloromethane)

Preparation 87 1,5-Bis-(4-fluorophenyl)-penta-1,4-dien-3-one (Formula V-2) Refer to Chart V.

To a rapidly stirred, ambient temperature solution of 10 g of sodium hydroxide in 100 ml of water and 80 ml of ethanol is added a mixture of 12.4 g of 4-fluorobenzaldehyde of Formula V-1 and 2.9 g of acetone. After 45 minutes, the resulting precipitate is filtered off, washed well with water, and dried under vacuum. Recrystallization from ethyl acetate-hexane yields 10.7 g of the title compound as light yellow platelets.

Physical characteristics are as follows:
$^1$H NMR δ 6.9–7.2, 7.6–7.7 ppm
IR 1653, 1587, 1508, 984, 835 cm$^{-1}$
MS: M+ 270
Anal. Found: C, 75.40; H, 4.41.
$R_f$ 0.35 (dichloromethane)
M.P. 152–1540

Preparation 88 1,5-Bis-(4-fluorophenyl)-pentane-3-one (Formula V-3) Refer to Chart V.

To a solution of 5.41 g of dienone of Preparation 87 (Formula V-2) in 10 ml of THF and 50 ml of methanol is added 2.0 g of magnesium chips. A water bath is used to maintain the temperature of the reaction near ambient. After the magnesium has been consumed, the reaction mixture is partitioned between dichloromethane and dilute HCl, with two additional dichloromethane extractions of the aqueous phase. The combined organic phase is dried over magnesium sulfate and concentrated under reduced pressure. Flash chromatography of the residue on silica using 50% dichloromethane in hexane affords 3.66 g of the title compound as a yellow oil.

Physical characteristics are as follows:
$^1$H NMR δ 2.67, 2.85, 6.9, 7.1 ppm
IR 2932, 1716, 1603, 1511, 1223, 1159, 828 cm$^{-1}$
MS: M+ 274
$R_f$ 0.28 (50% dichloromethane in hexane)

Preparation 89 4-Hydroxy-5,6-dihydro-6,6-bis(2-(4-fluorophenyl)ethyl)-2H-pyran-2-one (Formula V-4) Refer to Chart V.

Using the general acetoacetate condensation and ring closure procedure of Preparation 84 (Formula U-4), 3.9 g of the ketone of Preparation 88 (Formula V-3) is converted to 2.86 g of the title compound, which may be recrystallized from dichloromethane-hexane.

Physical characteristics are as follows:
$^1$H NMR δ 2.1, 2.57, 2.7, 7.0, 7.1 ppm
IR 2924, 1659, 1578, 1508, 1241, 1216 cm$^{-1}$
MS: M+ 358
Anal. Found: C, 70.17; H, 5.50.
M.P. 140–1410

Preparation 90 3-[1-(3-Benzyloxycarbonylaminophenyl)-2,2-dimethylpropyl]-6,6-bis[2-(4-fluorophenyl)ethyl]-4-hydroxy-5,6-dihydro-2H-pyran-2-one (Formula V-6: $R_1$ is tert-butyl) Refer to Chart V.

Using the general benzylidene condensation and cuprate addition procedure of Preparation 85 (Formula U-6), 1.075 g of the dihydropyrone of Preparation 89 (Formula V-4) is converted to 707 mg of the title compound (via the intermediate compound of Formula V-5), which is purified by flash chromatography on silica gel using 40% ethyl acetate in hexane.

Physical characteristics are as follows:
$^1$H NMR δ 1.07, 2.0, 2.6, 3.9, 5.16, 6.8–7.5 ppm
HRMS: 654.3023
$R_f$ 0.25 (40% ethyl acetate in hexane)

Preparation 91 3-[1-(3-Aminophenyl)-2,2-dimethylpropyl]-6,6-bis[2-(4-fluorophenyl)ethyl]-4-hydroxy-5,6-dihydro-2H-pyran-2-one (Formula V-7: $R_1$ is tert-butyl) Refer to Chart V.

Using the general transfer hydrogenolysis procedure of Preparation 86 (Formula U-7), 684 mg of the carbamate of Preparation 90 (Formula V-6, $R_1$ is tert-butyl) is converted to 497 mg of the title compound, which is purified by flash chromatography on silica gel using 5–10% ethyl acetate in dichloromethane.

Physical characteristics are as follows:
$^1$H NMR δ 1.09, 2.0, 2.6, 6.8–7.1 ppm
$R_f$ 0.34 (10% ethyl acetate in dichloromethane)

The compound of Formula V-7 wherein $R_1$ is ethyl is prepared from V-4 by analogous procedures as in the preparation of V-7 wherein $R_1$ is tert-butyl (Preparations 90 and 91).

EXAMPLE 256

N-[3-{1-(4-Hydroxy-5,6-dihydro-2-oxo-6,6-bis(2-(4-fluorophenyl)ethyl)-2H-pyran-3-yl)-2,2-dimethylpropyl}phenyl]-1-methyl-1H-imidazole-4-sulfonamide (Formula V-8: $R_1$ is tert-butyl, $R_2$ is 1-methylimidazole-4-yl) Refer to Chart V.

Using the general sulfonylation procedure of Example 252, 78 mg of the amine of Preparation 91 (Formula V-7, $R_1$ is tert-butyl) is reacted with 1-methylimidazole-4-sulfonyl chloride. Flash chromatography on silica using 3–4% methanol in dichloromethane provides 92 mg of the title compound as an amorphous white solid.

Physical characteristics are as follows:
$^1$H NMR δ 0.94, 1.7–2.1, 2.5, 3.50, 6.8–7.4 ppm
HRMS: 664.2647
$R_f$ 0.34 (5% methanol in dichloromethane)

EXAMPLE 257

N-[3-{1-(4-Hydroxy-5,6-dihydro-2-oxo-6,6-bis(2-(4-fluorophenyl)ethyl)-2H-pyran-3-yl)-2,2-dimethylpropyl}phenyl]-5-cyanopyridine-2-sulfonamide (Formula V-8: $R_1$ is tert-butyl, $R_2$ is 5-cyanopyridine-2-yl) Refer to Chart V.

Using the general sulfonylation procedure of Example 252, 78 mg of the amine of Preparation 91 (Formula V-7, $R_1$ is tert-butyl) is reacted with 5-cyanopyridine-2-sulfonyl chloride. Flash chromatography on silica using 10–15% ethyl acetate in dichloromethane provides 91.5 mg of the title compound as an amorphous white solid.

Physical characteristics are as follows:
$^1$H NMR δ 0.92, 1.9, 2.6, 3.2, 6.8–7.5, 8.0, 8.9 ppm
HRMS: 686.2488
$R_f$ 0.28 (10% ethyl acetate in dichloromethane)

EXAMPLE 258

N-[3-{1-(4-Hydroxy-5,6-dihydro-2-oxo-6,6-bis(2-(4-fluorophenyl)ethyl)-2H-pyran-3-yl)propyl}phenyl]-1-methyl-1H-imidazole-4-sulfonamide (Formula V-8: $R_1$ is ethyl, $R_2$ is 1-methylimidazole-4-yl) Refer to Chart V.

Using the general sulfonylation procedure of Example 252, 74 mg of the amine of Formula V-7, wherein $R_1$ is ethyl, is reacted with 1-methylimidazole-4-sulfonyl chloride. Flash chromatography on silica using 3–4% methanol in dichloromethane provides 77 mg of the title compound as an amorphous white solid.

Physical characteristics are as follows:
$^1$H NMR δ 0.87, 2.0, 2.6, 3.62, 4.0, 4.05, 6.9–7.5 ppm
HRMS: 636.2350
$R_f$ 0.31 (5% methanol in dichloromethane)

EXAMPLE 259

N-[3-{1-(4-Hydroxy-5,6-dihydro-2-oxo-6,6-bis(2-(4-fluorophenyl)ethyl)-2H-pyran-3-yl)propyl}phenyl]-5-cyanopyridine-2-sulfonamide (Formula V-8: $R_1$ is ethyl, $R_2$ is 5-cyanopyridine-2-yl) Refer to Chart V.

Using the general sulfonylation procedure of Example 252, 74 mg of the amine of Formula V-7, wherein $R_1$ is ethyl, is reacted with 5-cyanopyridine-2-sulfonyl chloride. Flash chromatography on silica using 10% ethyl acetate in dichloromethane provides 83 mg of the title compound as an amorphous white solid.

Physical characteristics are as follows:
$^1$H NMR δ 0.83, 2.0, 2.6, 3.96, 6.8–7.2, 8.0, 8.8 ppm
HRMS: 658.2200
$R_f$ 0.49 (10% ethyl acetate in dichloromethane)

EXAMPLE 260

N-[3-{1-(4-Hydroxy-5,6-dihydro-2-oxo-6,6-dipropyl-2H-pyran-3-yl)-2,2-dimethylpropyl}phenyl]-5-cyanopyridine-2-sulfonamide (Formula D-6: $R_1$ is propyl, $R_2$ is propyl, $R_3$ is tert-butyl, $R_4$ is 5-cyanopyridine-2-yl) Refer to Chart D.

Using the general sulfonylation procedure of Example 252, 54 mg of the amine of Formula D-5 ($R_1$ and $R_2$ are propyl, $R_3$ is tert-butyl), prepared by procedures analogous to those described for the preparation of D-5 (where $R_1$ is phenethyl, $R_2$ is propyl, $R_3$ is ethyl) in Preparation 20, is coupled with 5-cyanopyridine-2-sulfonyl chloride of Formula D-7 ($R_4$ is 5-cyanopyridine-2-yl) to yield, after flash chromatography on silica gel using 10–15% ethyl acetate in dichloromethane, 62 mg of the title compound as an amorphous solid.

Physical characteristics are as follows:
$^1$H NMR δ 0.90, 1.2–1.8, 2.5, 7.0–7.4, 8.1, 8.2, 8.9 ppm
HRMS: 525.2305
$R_f$ 0.44 (20% ethyl acetate in dichloromethane)

EXAMPLE 261

N-[3-{1-(4-Hydroxy-5,6-dihydro-2-oxo-6,6-dipropyl-2H-pyran-3-yl)-2,2-dimethylpropyl}phenyl]-1-methyl-1H-imidazole-4-sulfonamide (Formula D-6: $R_1$ is propyl, $R_2$ is propyl, $R_3$ is tert-butyl, $R_4$ is 1-methylimidazole-4-yl) Refer to Chart D.

Using the general sulfonylation procedure of Example 252, 54 mg of the amine of Formula D-5 ($R_1$ and $R_2$ are propyl, $R_3$ is tert-butyl), is coupled with 1-methylimidazole-4-sulfonyl chloride of Formula D-7 ($R_4$ is 1-methylimidazole-4-yl) to yield, after flash chromatography on silica gel using 3–5% methanol in dichloromethane, 53 mg of the title compound as an amorphous solid.

Physical characteristics are as follows:
$^1$H NMR δ 0.9, 0.96, 1.2–1.8, 2.5, 3.6, 3.7, 6.9–7.5 ppm
MS: 503.2422
$R_f$ 0.26 (5% methanol in dichloromethane)

EXAMPLE 262

N-[3-1-(4-Hydroxy-5,6-dihydro-2-oxo-6,6-dipropyl-2H-pyran-3-yl)propyl}phenyl]-5-cyanopyridine-2-sulfonamide (Formula D-6:
$R_1$ is propyl, $R_2$ is propyl, $R_3$ is ethyl, $R_4$ is 5-cyanopyridine-2-yl) Refer to Chart D.

Using the general sulfonylation procedure of Example 252, 67 mg of the amine of Formula D-5 ($R_1$ and $R_2$ are propyl, $R_3$ is ethyl) of Preparation 20 is coupled with 5-cyanopyridine-2-sulfonyl chloride of Formula D-7 ($R_4$ is 5-cyanopyridine-2-yl) to yield, after flash chromatography on silica gel using 10% ethyl acetate in dichloromethane, 78 mg of the title compound as an amorphous solid.

Physical characteristics are as follows:
$^1$H NMR δ 0.6–1.0, 1.2–1.8, 3.4, 3.5, 6.9–7.4, 8.0–8.2, 8.9 ppm
HRMS: 498.2072
$R_f$ 0.38 (15% ethyl acetate in dichloromethane)

EXAMPLE 263

N-[3-{1-(4-Hydroxy-5,6-dihydro-2-oxo-6-phenethyl-6-propyl-2H-pyran-3-yl)propyl}phenyl]-5-cyanopyridine-2-sulfonamide (Formula D-6: $R_1$ is phenethyl, $R_2$ is propyl, $R_3$ is ethyl, $R_4$ is 5-cyanopyridine-2-yl) Refer to Chart D.

Using the general sulfonylation procedure of Example 252, 79 mg of the amine of Formula D-5 ($R_1$ is phenethyl, $R_2$ is propyl, $R_3$ is ethyl) of Preparation 20 is coupled with 5-cyanopyridine-2-sulfonyl chloride of Formula D-7 ($R_4$ is 5-cyanopyridine-2-yl) to yield, after flash chromatography on silica gel using 10% ethyl acetate in dichloromethane, 102 mg of the title compound as an amorphous solid.

Physical characteristics are as follows:
$^1$H NMR δ 0.7–1.0, 1.2–2.6, 3.4, 3.5, 6.9–7.3, 7.9–8.2, 8.9 ppm
HRMS: 560.2231
$R_f$ 0.37 (15% ethyl acetate in dichloromethane)

EXAMPLES 264–265

The following compounds are prepared using the general sulfonylation procedure of Example 246. The requisite amine is prepared analogously from the compound of Formula Q-1 (Preparation 69) following Preparations 80 and 81.

264) N-[3-(1-[6,6-Bis-(2-cyclopropyl-ethyl)-5,6-dihydro-4-hydroxy-2-oxo-2H-pyran-3-yl]-2,2-dimethyl-propyl)phenyl]-1-methyl-1H-imidazole-4-sulfonamide Physical characteristics are as follows:
$^1$H NMR δ 0.0, 0.4, 0.6, 1.0, 1.2, 1.7, 2.5, 3.7, 4.1, 6.9–7.6
HRMS: 556.2833 (FAB)

265) N-[3-(1-[6,6-Bis-(2-cyclopropyl-ethyl)-5,6-dihydro-4-hydroxy-2-oxo-2H-pyran-3-yl]-2,2-dimethyl-propyl)phenyl]-5-cyano-2-pyridinesulfonamide Physical characteristics are as follows:
$^1$H NMR δ 0.0, 0.4, 0.6, 1.0, 1.2, 1.7, 2.5, 4.1, 7.0–7.5, 8.0, 8.1, 9.0
HRMS: 578.2689 (FAB)

Preparation 92 (3(2E),4S)-3-(2-pentenyl)-4-phenyl-2-oxazolidinone (Formula W-4) Refer to Chart W.

A 1 L round-bottomed flask with nitrogen inlet and addition funnel is charged with 6.92 g of (S)-(+)-4-phenyl-2-oxazolidinone and 250 mL of tetrahydrofuran and then cooled to −78° C. To the aforementioned solution is added 25.6 mL of n-butyl lithium during which time a white solid separated from the reaction solution, W-3. To that suspension is added 4.88 g of trans-2-pentenoyl chloride of formula W-2 (prepared from the treatment of commerically available trans-2-pentenoyl acid of formula W-1 with oxalyl chloride) in a small volume of THF. The resulting pale yellow homogeneous solution is allowed to warm to room temperature and stirred for another 20 min. The reaction mixture is quenched by the addition of saturated ammonium chloride solution and is extracted with ethyl acetate. The organic layer is separated, washed with brine and water, dried over magnesium sulfate, filtered and concentrated to give a white solid. Recrystallization from hot hexane gives 9.13 g of the title compound.

Physical characteristics are as follows:
MP 86–88° C.
$^1$H NMR (CDCl$_3$) δ 7.42–7.23, 7.18–7.09, 5.49, 4.70, 4.28, 2.28, 1.08 ppm.
$[\alpha]_D$ (CHCl$_3$)=+109
Anal. found: C, 68.59; H, 6.25; N, 5.70.

Preparation 93 (3(3R),4S)-3-[3-(3-Aminophenyl)-1-oxopentyl]-4-phenyl-2-oxazolidinone (Formula W-5) Refer to Chart W.

A 1 L three-necked, round-bottomed flask with nitrogen inlet and addition funnel is charged with 8.90 g of copper (I)

bromide-dimethyl sulfide complex and 125 mL of THF and then cooled to −40° C. To that suspension is added 43 mL of a 1 M solution (in THF) of 3-[bis(trimethylsilyl)amino]phenylmagnesium chloride dropwise over 15 miniutes. The reaction mixture is warmed 0° C. for 30 minutes and then a 25 mL THF solution containing 8.85 g of (3(2E),4S)-3-(2-pentenoyl)-4-phenyl-2-oxazolidinone of Preparation 92 (formula W-4) is added. The reaction mixture is stirred for 30 minutes at 0° C. and quenched by the addition of 1N HCl and then the pH readjusted with 1N NaOH to pH 8. The reaction is washed with water, brine and the organic is dried ($Na_2SO_4$). The organic solvent is evaporated in vacuo and the resulting oil chromatographed over 600 g of silica gel, eluting with ethyl acetate/hexane to afford 7.91 g of the title product.

Physical characteristics are as follows:
MP 94–95° C.
$^1$H NMR ($CDCl_3$) δ 7.28–7.25, 7.07–6.99, 6.60–6.51, 5.38, 4.63, 4.16, 3.52–3.44, 3.10–2.92, 1.65–1.53, 0.76 ppm.
IR (mineral oil) 3437, 3355, 1773, 1696, 1605, 1337, 1322, 1299, 1263, 1212, 1096, 1070, 791, 762, 704 $cm^{-1}$.
Anal. found: C, 71.00; H, 6.67; N, 8.17.
EI-MS: [M+]=338.
$[α]_D$ (19.87 mg/2 mL $CHCl_3$) =+60°

Preparation 94 3-[3-(3-[Bis(phenylmethyl)amino]phenyl)-1-oxopentyl]-4-phenyl-2-oxazolidinone, (3R)(4S) (Formula W-6) Refer to Chart W.

To a mixture of 25 mL of $Na_2CO_3$ and 80 mL of methylene chloride was added 7.90 g of (3(3R),4S)-3-[3-(3-aminophenyl)-1-oxopentyl]-4-phenyl-2-oxazolidinone of Preparation 93 (formula W-5) followed by 15.94 g of benzyl bromide. That mixture is heated at 65° C. for 18 hours, the methylene chloride layer separated, dried ($Na_2SO_4$) and solvent evaporated to yield the crude product as a dark viscous oil. That oil is chromatographed over 700 g of silica gel eluding with 25% ethyl acetate/hexane to yield 8.55 g of the title compound.

Physical characteristics are as follows:
MP 92–3° C.
$^1$H NMR ($CDCl_3$) δ 7.24, 7.02, 6.53, 5.34, 4.59, 4.14, 3.44, 3.07, 2.89, 1.50, 0.64 ppm
Anal. found: C, 78.47; H, 6.68; N, 5.26.
$[α]_D$ (19.602 mg/2 mL $CHCl_3$)=+32°

Preparation 95 (3R)(4S) 3-[3-(3-[bis(phenylmethyl)amino]phenyl)-2-(2-methyl-1,3-dioxolan-2-yl)-1-oxopentyl]-4-phenyl-2-oxazolidinone (Formula W-8) Refer to Chart W.

To 25 mL of methylene chloride is added 2.1 g of the amide of formula W-6 of Preparation 94 and the resulting solution cooled to −78° C. under an atmosphere of nitrogen. To that solution is added 872 μL of neat $TiCl_4$ followed by the addition of 732 μL of diisopropylethylamine. The resulting mixture is warmed to 0° C. for 30 minutes and then cooled back to −78° C. and 1.3 g of 2-methoxy-2-methyl-1,3-dioxolane of formula W-7 and the resulting reaction is warmed to 0° C. and stirred for 1 hour, then quenched with saturated ammonium chloride and extracted with methylene chloride. The organic extract is dried ($Na_2SO_4$) and solvent removed in vacuo to afford the crude material. Silica gel chromatography using 100 g of support and eluding with 10% hexane/methylene chloride afforded 1.76 g of the title product.

Physical characteristics are as follows:
$^1$H NMR ($CDCl_3$) δ 7.36, 7.08, 5.99, 5.42, 4.80, 4.68, 4.60, 4.25, 3.68, 3.57, 3.48, 3.07, 2.90, 1.5, 0.86, 0.54 ppm
Anal. found: C, 75.34; H, 6.99; N, 4.87.
$[α]_D$ (18.086 mg/2 mL $CHCl_3$)=+25°

Preparation 96 (3R)(4S)-3-[2-acetyl-3-[3-(bis(phenylmethyl)amino)phenyl]-1-oxopentyl]-4-phenyl-2-oxazolidinone (Formula W-9) Refer to Chart W.

To 25 mL of tetrahydrofuran and 10 mL of 30% $HClO_4$ is added 5.0 g of the title compound of Preparation 95 (formula W-8) and the resulting solution stirred at 40° C. for 3 hours. The reaction is neutralized with saturated $NaHCO_3$ to pH 8 and then extracted with 400 mL of ether. The ether layer is washed with water, brine and then dried ($Na_2SO_4$) and solvent evaporated in vacuo to afford an oil. Chromatography over 300 g of silica gel eluting with 15% acetone/hexane afforded 4.12 g of the title compound.

Physical characteristics are as follows:
$^1$H NMR ($CDCl_3$) δ 7.31, 7.08, 6.59, 6.55, 5.42, 4.67, 4.61, 4.22, 3.09, 1.63, 1.56, 0.61 ppm
Anal. found: C, 77.11; H, 6.76; N, 4.98.
$[α]_D$ (20.172 mg/2 mL $CHCl_3$)=−10°

Preparation 97 (3R)(4S) 3-[2-[1-(3-[bis(phenylmethyl)amino]phenyl)propyl]-5-hydroxy-1,3-dioxo-5-propyloctyl]-4-phenyl-2-oxazolidinone (Formula W-10) Refer to Chart W.

To 25 mL of methylene chloride is added 1.32 g of the compound of Preparation 96 (formula W-9) and the resulting solution cooled to −78° C. under an atmosphere of nitrogen. To that solution is added 279 μL of $TiCl_4$ and 450 μL of diisopropylethylamine and stirring continued for 1 hour. To this solution is added 689 μL of heptanone and the reaction temperature raised to 0° C. for 1.5 hours. The reaction is then quenched by the addition of a saturated ammonium chloride solution and the mixture extracted with methylene chloride. The organic extract is washed with saturated $NaHCO_3$, dried ($Na_2SO_4$) and evaporated in vacuo to yield the crude product. Chromatography over 100 g of silica gel eluting with 5% hexane/methylene chloride affords 1.16 g of the title compound as an off white foam.

Physical characteristics are as follows:
$^1$H NMR ($CDCl_3$) 7.36, 7.07, 6.58, 6.54, 5.44, 5.24, 4.69, 4.61, 4.27, 3.21, 3.01, 2.48, 1.90, 1.54, 1.15, 0.81, 0.76, 0.58 ppm
Anal. found: C, 76.62; H, 7.63; N, 4.17.
$[α]_D$ (15.380 mg/2 mL $CHCl_8$)=+16°

Preparation 98 (3S)-3-[1-(3-(Bis(phenylmethyl)amino)phenyl)propyl]-6,6-dipropyl-5,6-dihydro-4-hydroxy-2H-pyran-2-one (Formula W-11) Refer to Chart W.

To 10 mL of dry tetrahydrofuran is added 770 mg of the title compound of Preparation 97 (formula W-10) and the resulting solution cooled to 0° C. under an atmosphere of nitrogen. To that solution is added 150 mg of a 60% oil dispersion of sodium hydride and the reaction is warmed to 20° C. and stirring continued for 16 hours. The reaction is quenched with saturated ammonium chloride and extracted with ethyl acetate. The extract is dried and evaporated in vacuo to yield the crude product. Chromatography over 100 g of silica gel eluting with 15% EtOAc/hexane affords 560 mg of the title product.

Physical characteristics are as follows:
$^1$H NMR ($CDCl_3$) 7.34, 6.69, 5.87, 4.69, 4.60, 4.09, 2.28, 2.17, 1.89, 1.73, 1.55, 1.32, 0.88 ppm
[Anal. found: C, 79.71; H, 8.07; N, 2.61].
$[[α]_D$ (15.998 mg/2 mL $CHCl_3$)=−56°]

Preparation 99 (3S)-3-[1-(3-aminophenyl)propyl]-6,6-dipropyl-5,6-dihydro-4-hydroxy-2H-pyran-2-one (Formula W-12) Refer to Chart W.

The title compound of Preparation 98 (formula W-11) ((3R)-3-[1-(3-bis-benzylaminophenyl)propyl]-6,6-bispropyl-5,6-dihydro-4-hydroxypyran-2-one) 110 mg is added to 20 mL of ethyl acetate. To that solution is added 50 mg of 10% Pd/C and the resulting mixture is hydrogenated at 50 psi for 6 hours. The reaction is filtered through celite to yield 83 mg of the title product.

Physical characteristics are as follows:

IR 2957, 2922, 2855, 2871, 2854, 1378, 1605, 1459, 1617, 1262, 1319, 1251, 1282, 1107 cm$^{-1}$.

[α]$_D$ (6.526 mg/2 mL CH$_3$OH)=−34°

Preparation 100 (4R)3-(1-oxo-2-pentenyl)-4-phenyl-2-oxazolidinone (Formula X-4) Refer to Chart X.

A 2-L, three-necked, round-bottomed flask with nitrogen inlet and addition funnel is charged with (R)-(−)-4-phenyl-2-oxazolidinone (31.2 g) and tetrahydrofuran (1.2 L) and cooled to −78° C. The addition funnel is charged with n-butyllithium (1.6 M in hexanes, 117 mL), which is added dropwise to the reaction mixture over 20 min. A white precipitate is formed which is X-3. The reaction mixture is stirred for an additional 30 min at −78° C. The addition funnel is then charged with trans-2-pentenoyl chloride of formula X-2, prepared from the acid of formula X-1, (24.4 g) and tetrahydrofuran (50 mL), and this solution is added to the reaction mixture dropwise over 10 min. The resulting pale yellow homogeneous solution is allowed to warm to room temperature and is stirred for another 30 min. The reaction mixture is quenched by the addition of saturated ammonium chloride solution and is extracted with ethyl acetate (2500 mL). The organic layer is separated, washed with brine and water, dried over magnesium sulfate, filtered and concentrated to give 48 g of a white solid. The solid is recrystallized from ethyl acetate (100 mL) and hexane (200 mL) to give 38.0 g the title product as a white solid.

Physical characteristics are as follows:

MP 86–88° C.

$^1$H NMR (CDCl$_3$) δ 7.42–7.23, 7.18–7.09, 5.49, 4.70, 4.28, 2.28, 1.08 ppm.

IR (mineral oil) 1785, 1764, 1686, 1638, 1349, 1336, 1329, 1257, 1234, 1214, 1087, 1076, 756, 716, 699 cm$^{-1}$

EI-MS: [M+]=245.

Preparation 101 (3(3S),4R)-3-[3-(3-aminophenyl)-1-oxopentyl]-4-phenyl-2-oxazolidinone (Formula X-5) Refer to Chart X.

A 2-L, three-necked, round-bottomed flask with nitrogen inlet and addition funnel is charged with copper (I) bromide-dimethyl sulfide complex (25.1 g) and tetrahydrofuran (250 mL) and cooled to −40° C. The addition funnel is charged with 3-[bis(trimethylsilyl)amino]phenylmagnesium chloride (1.0 M in THF, 122 mL), which is added dropwise to the reaction mixture over 20 min. The reaction mixture is then allowed to warm from −40° C. to −20° C. over 20 min. The addition funnel is charged with 25 g of the title compound of Preparation 100 (formula X-4) and tetrahydrofuran (100 mL), and this solution is added to the reaction mixture dropwise over 30 min at 0° C. The reaction mixture is then stirred for 15 min at 0 ° C. and quenched by the addition of saturated ammonium chloride solution (adjusted to pH 8 by addition of ammonium hydroxide). The reaction mixture is poured into ether (2 L) and washed with the ammonium chloride solution until the aqueous layer is no longer blue in color. The organic layer is separated, washed with water, dried over magnesium sulfate, filtered and concentrated to give 58 g of a yellow oil. The crude reaction mixture is then stirred at room temperature in a slurry of silica gel (75 g) and methylene chloride (100 mL) for 1 h. The mixture is filtered, washed with methanol, and concentrated to give 49 g of an oil. Column chromatography on 300 g silica (eluting with 10–75% ethyl acetate-hexane, 100% ethyl acetate) yields 30.9 g of a yellow oil. The oil is crystallized from ethyl acetate (75 mL) and hexane (150 mL) to give 21.4 g of the title compound as a white solid.

Physical characteristics are as follows:

MP 94–97° C.

$^1$H NMR (CDCl$_3$) δ 7.28–7.25, 7.07–6.99, 6.60–6.51, 5.38, 4.63, 4.16, 3.52–3.44, 3.10–2.92, 1.65–1.53, 0.76 ppm.

IR (mineral oil) 3437, 3355, 1773, 1696, 1605, 1337, 1322, 1299, 1263, 1212,1096, 1070, 791, 762, 704 cm$^{-1}$.

EI-MS: [M+]=338.

Preparation 102 (3(3S),4R)-3-[3-(3-(phenylmethyl)amino)phenyl)-1-oxopentyl]-4-phenyl-2-oxazolidinone (Formula X-6) Refer to Chart X.

To a mixture of 80 mL of Na$_2$CO$_3$ and 280 mL of methylene chloride is added 21.0 g of (3(3S),4R)-3-[3-(3-aminophenyl)-1-oxopentyl]-4-phenyl-2-oxazolidinone (formula X-5) of Preparation 101 followed by 23.4 g of benzyl bromide. That mixture is heated at 650° C. for 18 hours, the methylene chloride layer separated, dried (Na$_2$SO$_4$) and solvent evaportated to yield the crude product as a dark viscous oil. The oil is chromatographed over 700 g of silica gel eluding with 25% ethyl acetate/hexane to yield 31.42 g of the title compound.

Physical characteristics are as follows:

MP 91.8–93.5

$^1$H NMR (CDCl$_3$) δ 7.32, 7.08, 6.60, 5.34, 4.67, 4.15, 3.43, 3.02, 2.91, 1.56, 0.65 ppm Preparation 103 (3S)(4S)-3-[3-[3-(Bis(phenylmethyl)amino]phenyl]-2-(2-methyl-1,3-dioxolan-2-yl]-1-oxopentyl]-4-phenyl-2-oxazolidinone (Formula X-8) Refer to Chart X.

To 12 mL of methylene chloride, under nitrogen, is added 1.55 grams of (3(3S),4R)-3-[3-(3-bisbenzylaminophenyl)pentanoyl]-4-phenyl-2-oxazolidinone (formula X-6) of Preparation 102 and the resulting solution cooled to −78° C. To the aforementioned solution is added 646 μl of TiCl$_4$ followed by the addition of 525 μl of diisopropylethylamine. After stirring at 0° C. for 30 minutes the reaction is cooled back to −78° C. and 886 μl of 2-methoxy-2-methyl-1,3-dioxolane (formula X-7) (also W-7) is added. The reaction is stirred for 1 hour and then quenched by the addition of saturated NH$_4$Cl, then saturated NaHCO$_3$ (pH 8) and finally extraction of the aqueous with both methylene chloride and ethyl ether. Evaporation of solvent affords a viscous oil which is chromatographed over 150 g of silica gel eluting with 7% hexane/methylene chloride to afford 1.14 g of the title compound.

Physical characteristics are as follows:

IR (mineral oil) 2920, 2954, 2854, 2870, 1776, 1376, 1453, 1196, 699 cm$^{-1}$.

Anal. found: C, 75.27; H, 6.68; N, 4.55.

Preparation 104 (3S)(4R) 3-[2-Acetyl-3-[3-[bis(phenylmethyl)amino]-phenyl]-1-oxopentyl]-4-phenyl-2-oxazolidinone (Formula X-9) Refer to Chart X.

To 15 mL of THF is added 960 mg of (3(3S),4R)-3-[2-(2-methyl-1,3-dioxan-2-yl)-3-(3-bisbenzylaminophenyl)pentanoyl]-4-phenyl-2-oxazolidinone (formula X-8) of Preparation 103. To that solution is then added 4 mL of 30% perchloric acid and the resulting mixture stirred at 40° C. for 2 hours. The reaction is cooled to room temperature and quenced with the addition of excess saturated NaHCO$_3$. The reaction is extracted with 200 mL of ethyl ether, dried (Na$_2$SO$_4$) and solvent removed in vacuo to yield 981 mg of the crude product. Chromatography over 100 g of silica gel eluding with 10% pentane/methylene chloride affords 854 mg of the title compound.

Physical characteristics are as follows:

$^1$H NMR (CDCl$_3$) δ 7.40, 7.08, 6.61, 6.56, 5.41, 4.96, 4.66, 4.61, 4.21, 3.09, 1.63, 1.65, 0.61

IR (mineral oil) 1778, 1718, 1600, 1695, 1452, 1335, 1385, 1200 cm$^{-1}$.

EI-MS: [M+]=560.

Anal. found: C, 76.81; H, 6.59; N, 4.84.

Preparation 105 (3S)(4R) 3-[2-[1-[3-[bis(phenylmethyl) amino]phenyl]-propyl]-5-hydroxy-1,3-dioxo-5-propyloctyl]-4-phenyl-2-oxazolidinone (Formula X-10) Refer to Chart X.

To 8 mL of methylene chloride under nitrogen is added 440 mg of (3(3S),4R)-3-[2-(acetyl)-3-(3-bisbenzylaminophenyl)pentanoyl]-4-phenyl-2-oxazolidinone (formula X-9) of Preparation 104 and that solution is cooled to −78° C. To that solution is added 90 µl of $TiCl_4$ followed by the addtion of 143 µl of diisopropylethylamine. That solution is warmed to 0° C. for 40 minutes and then cooled back to −78° C. at which time 126 µl of 4-heptanone is added and the reaction temperature is elevated to 0° C. and stirring continued for 1.5 hours. The reaction is quenced with the addition of saturated $NH_4Cl$ followed by the addtion of saturated $NaHCO_3$. The reaction is extracted with methlene chloride (3×60 mL), dried ($Na_2SO_4$) and evaporated in vaco to yeild the crude product as an oil. That material is chromatographed over silica gel (100 g) eluting with 10% pentane/methylene chloride to afford 293 mg of the title compound.

Physical characteristics are as follows:
$^1H$ NMR ($CDCl_3$) δ 7.28, 7.07, 6.56, 5.44, 5.24, 4.68, 4.61, 4.26, 3.21, 3.10, 2.48, 1.90, 1.55, 1.21, 0.81, 0.74, 0.58

IR (mineral oil) 2959, 2931, 1779, 1720, 1690, 1600, 1494, 1452, 1385, 1359, 1334, 1238, 698 cm$^{-1}$.

Preparation 106 (3R) 3-[1-[3-[bis(phenylmethyl)amino] phenyl]propyl]-5,6-dihydro-4-hydroxy-6,6-dipropyl-2H-pyran-2-one (Formula X-11) Refer to Chart X.

To 3 mL of THF was added 28 mg of NaH under nitrogen. To that suspension is added 418 mg of (3(3S),4R)-3-[2-((3-hydroxy-3-propyl)hexanoyl)-3-(3-bisbenzyl-aminophenyl) pentanoyl]-4-phenyl-2-oxazolidinone (Formula X-10) of Preparation 105 also in 3 mL of THF at 20° C. The reaction is stirred for 16 hours, cooled to 0° C. and quenched by addition of 1N HCl. The reaction is then made basic with the addition of saturated $NaHCO_3$. The aqueous is extracted several times with ethyl acetate, the organic extracts dried ($Na_2SO_4$) and solvent is removed in vacuo to yield 518 mg of crude product. Chromatography over silica gel eluting with 15% EtOAc/hexane affords 128 mg of the title compound.

Physical characteristics are as follows:
IR (mineral oil) 2959, 2931, 2873, 1636, 1599, 1451, 1465, 1386, 1363, 1328, 1249, 1260, 696 cm$^1$.

EI-MS: [M+]=511.

Preparation 107 (3R) 3-[1-[3-[amino]phenyl]propyl]-5,6-dihydro-4-hydroxy-6,6-dipropyl-2H-pyran-2-one (Formula X-12) Refer to Chart X.

The dihydropyrone of formula X-11 ((3R)-3-[1-(3-bisbenzylaminophenyl)-propyl]-6,6-bispropyl-5,6-dihydro-4-hydroxypyran-2-one ) of Preparation 106, 110 mg, is added to 20 mL of ethyl acetate. To that solution is added 50 mg of 10% Pd/C and the resulting mixture is hydrogenated at 50 psi for 6 hours. The reaction is filtered through celite to yield 83 mg of the title product.

Physical characteristics are as follows:
IR (mineral oil) 2961, 2932, 2873, 1682, 1623, 1604, 1458, 1384, 1369, 1319, 1282, 1259, 1150, 1108 cm$^{-1}$.

EI-MS: [M+]=331

Preparation 108 2-Phenethyl-2-propen-1-ol (Formula BB-2) Refer to Chart BB.

To a cooled (−10° C.) solution of N,N,N,N,-tetramethyl-1,2-ethylenediamine (24.1 mL) in hexane (50 mL) is slowly added butyl lithium (100 mL of a 1.6 M solution in hexane). After stirring for 45 minutes at −10° C. the mixture is cooled (−78° C.) and 2-methyl-2-propen-1-ol (BB-1, 6.41 mL) is added dropwise. The reaction is allowed to warm to room temperature and stirred an additional 72 h. The mixture is cooled to −78° C. and a solution of benzyl bromide (8.6 mL) in anhydrous THF (10 mL) is added slowly. The mixture is stirred at −78° C. for 1 hour then gradually allowed to warm to room temperature. After stirring an additional 2 hours, the reaction is quenched by the addition of saturated aqueous $NH_4Cl$. The organic layer is diluted with diethyl ether and washed with brine, dried ($MgSO_4$), filtered and concentrated in vacuo. Purification by flash chromatography using methylene chloride/ethyl acetate/hexane (1:1:6) as eluent affords the title compound (3.5 g) as an oil.

Physical characteristics are as follows:
$^1H$ NMR ($CDCl_3$) δ 7.31–7.16, 5.07, 4.93, 4.09, 2.82–2.76, 2.41–2.36 ppm.

$^{13}C$ NMR ($CDCl_3$) δ 148.30, 141.69, 128.24, 125.80, 109.76, 65.90, 34.52, 34.16 ppm.

Preparation 109 (2S)-2-Phenethyloxiranemethanol (Formula BB-8) Refer to Chart BB.

To a cooled (−20° C.) slurry of molecular sieves (4 Å, crushed and freshly activated, 150 mg) in methylene chloride (1.5 mL) is added diethyl L-tartrate (22 mg) and titanium (I) isopropoxide (25 mg). The mixture is stirred for 30 min at −20° C. and tert-butyl hydroperoxide (0.84 mL of a 5–6 M solution in nonane) is added. After an additional 25 min at −20° C., a solution of allylic alcohol of formula BB-2 (300 mg) of Preparation 108 in methylene chloride (0.5 mL) is slowly added. The mixture is stirred overnight at −20° C. then warmed to −10° C. After an additional 4 hours the reaction is warmed to 0–5° C. and quenched with the addition of water (1 mL). After warming to room temperature, stirring is continued for 1 hour and tartrates hydrolysed by the addition of a 30% aqueous NaOH solution saturated with NaCl (0.1 mL). After 30 minutes, the mixture is filtered through Celite and the aqueous phase extracted with several portions of methylene chloride. The combined organic layers are dried ($MgSO_4$), filtered and concentrated in vacuo to provide a residue which is purified by flash chromatography using hexane and a gradient of ethyl acetate (10–20%) as eluent to afford the title product of formula BB-3 (223 mg) as an oil. The enantiomeric excess of the reaction is determined to be 86% by analysis of the $^1H$ NMR ($C_6D_6$) of the Mosher ester formed by the reaction of BB-3 with (S)-(+)-α-methoxy-α-(trifluoromethyl)phenylacetyl chloride (J. A. Dale, D. L. Dull, H. S. Mosher, J. Org. Chem. (1969) 34: 2543).

Physical characteristics are as follows:
$^1H$ NMR ($CDCl_3$) δ 7.34–7.16, 3.83–3.61, 2.89–2.87, 2.72–2.64, 2.17–2.04, 1.89–1.79 ppm $^{13}C$ NMR ($CDCl_3$) δ 141.17, 137.58, 128.49, 128.21, 126.11, 63.00 59.57, 49.92, 33.58, 30.82 ppm.

Preparation 110 (2S)-2-Phenethyl-2-phenylmethoxymethyloxirane (Formula BB-9) Refer to Chart BB.

To a cooled (0–5° C.) slurry of sodium hydride (124 mg of a 60% suspension in mineral oil) in THF (10 mL) is added alcohol of formula BB-3 (460 mg) of Preparation 109. The mixture is stirred at 0–5° C. for 5 minutes, allowed to warm to room temperature and stirred an additional 30 minutes. Benzyl bromide (441 mg) is added and the mixture stirred at room temperature overnight. The reaction is quenched with brine (10 mL) and diluted with ethyl ether. The organic layer is washed with brine, dried ($MgSO_4$), filtered and concentrated in vacuo to provide a residue which is purified by flash chromatography using hexane and a gradient of ethyl acetate (2–5%) as eluent to afford the title product (510 mg) as an oil.

Physical characteristics are as follows:
$^1$H NMR (CDCl$_3$) δ 7.34–7.13, 4.59–4.49, 3.64–3.45, 2.75–2.59, 2.19–2.09, 1.94–1.84
$^{13}$C NMR (CDCl$_3$) δ 141.42, 137.93, 128.58, 128.38, 127.88, 125.94, 73.23, 71.98, 58.21, 50.37, 33.65, 30.83 ppm.

Preparation 110a (3S)-1-Phenyl-3-(phenylmethoxymethyl) hexan-3-ol (Formula BB-10) Refer to Chart BB.

To a cooled (−45° C.) solution of Li$_2$CuCl$_4$ (0.28 mL of a 0.1 M solution in THF) in THF (2 mL) is added ethylmagnesium bromide (0.203 mL of a 3 M solution in ethyl ether). The brown solution is stirred at −45 0° C. for 45 minutes and the epoxide of formula BB-4 (150 mg) of Preparation 110 is added dropwise over ca. 10 minutes. After one hour the reaction is quenched by the addition of saturated aqueous NH$_4$Cl and the aqueous layer extracted with ethyl acetate. The combined organic layers are washed with brine, dried (MgSO$_4$), filtered and concentrated in vacuo to provide a residue which is purified by flash chromatography using hexane/ethyl acetate (5%) as eluent to afford the title product (150 mg) as an oil.

Physical characteristics are as follows:
$^1$H NMR (CDCl$_3$) δ 7.38–7.14, 4.54, 3.37, 2.66–2.58, 2.20, 1.88–1.76, 1.58–1.52, 1.39–1.25, 0.92
$^{13}$C NMR (CDCl$_3$) δ 142.61, 138.10, 128.41, 128.33, 127.71, 127.63, 125.68, 75.45, 73.79, 73.44, 38.95, 38.52, 29.86, 16.79, 14.37 ppm.

Preparation 110b (2R)-2-Phenethyl-2-(p-toluenesulfonyloxymethyl) oxirane (Formula BB-13) Refer to Chart BB.

To a cooled (ca. −10° C.) solution of the compound of formula BB-8 (245 mg) of -Preparation 109 in methylene chloride (4 mL) is added 4-toluenesulfonyl chloride (302 mg), triethylamine (160 mg) and 4-dimethylaminopyridine (8 mg). The mixture is stirred at ca. −10° C. overnight then warmed to 0–5° C. for 1 hour. The mixture is diluted with methylene chloride, washed with saturated aqueous NaHCO$_3$ and brine, dried (MgSO$_4$), filtered and concentrated in vacuo to provide a residue which is purified by flash chromatography using hexane/ethyl acetate (5%) as eluent to afford the title compound (448 mg).

Physical characteristics are as follows:
$^1$H NMR (CDCl$_3$) δ 7.79, 7.33, 7.28–7.08, 4.13–3.98, 2.64–2.58, 2.44, 2.11–2.00, 1.92–1.82
$^{13}$C NMR (CDCl$_3$) δ 145.17, 140.67, 132.53, 129.96, 128.48, 128.19, 127.95, 126.15, 71.98, 56.49, 50.63, 32.89, 30.37, 21.64 ppm.

Preparation 110c (2S)-2-Phenethyl-2-propyl oxirane (Formula BB-12) Refer to Chart BB.

To a cooled (−45° C.) solution of Li$_2$CuCl$_4$ (0.3 mL of a 0.1 M solution in THF) in THF (2 mL) is added ethylmagnesium bromide (0.22 mL of a 3 M solution in ethyl ether). The brown solution is stirred at −45° C. for 45 minutes, cooled to −65° C. then tosylate of formula BB-13 (200 mg) of Preparation 110b is added dropwise over ca. 10 minutes. The mixture is stirred for 2.5 hours, warmed to −50° C. for 2 hours and then quenched by the addition of saturated aqueous NH$_4$Cl. The aqueous layer is extracted with ethyl acetate and the combined organic layers washed with brine, dried (MgSO$_4$), filtered and concentrated in vacuo to provide a residue which is purified by flash chromatography using hexane/ ethyl acetate (5%) as eluent to afford the title product (60 mg) and hydroxytosylate of formula BB-14 (47 mg).

Hydroxytosylate of formula BB-14 is converted to the epoxide of formula BB-12 as follows: To a cooled (0–5° C.) solution of the compound of formula BB-14 (43 mg) in methanol (2 mL) is added anhydrous K$_2$CO$_3$ (20 mg). After 1 hour at 0–5° C. the mixture is warmed to room temperature, stirred an additional 90 minutes then quenched by the addition of saturated aqueous NH$_4$Cl. The aqueous layer is extracted with ethyl acetate and the combined organic layers washed with brine, dried (MgSO$_4$), filtered and concentrated in vacuo to provide a residue which is purified by flash chromatography using hexane/ethyl acetate (5%) to afford the epoxide of formula BB-12 (20 mg).

Physical characteristics for BB-12 are as follows:
$^1$H NMR (CDCl$_3$) δ 7.31–7.16, 2.68, 2.59, 1.98–1.82, 1.73–1.37, 0.94
$^{13}$C NMR (CDCl$_3$) δ 141.71, 128.41, 128.24, 125.92, 59.11, 52.57, 36.42, 36.02, 31.03, 18.19, 14.22 ppm.

Physical characteristics for BB-14 are as follows:
$^1$H NMR (CDCl$_3$) δ 7.79, 7.34, 7.29–7.11, 3.90, 2.58–2.53, 2.44, 1.87, 1.77–1.72, 1.54–1.48, 1.31–1.21, 0.89
$^{13}$C NMR (CDCl$_3$) δ 145.10, 141.66, 132.50, 129.97, 128.45, 128.25, 127.97, 125.96, 74.33, 73.07, 38.37, 37.87, 29.37, 21.66, 16.47, 14.48 ppm.

Preparation 111 (4S)-3-acetyl-4-phenyl-2-oxazolidinone (Formula FF-3) Refer to Chart FF To a solution of (S)-(+)-4-phenyl-2-oxazolidinone of formula FF-2 (20 g) in anhydrous tetrahydrofuran (600 mL), cooled to −78° C. is added a solution of 1.6 M n-butyllithium in hexanes (77.8 mL) and the resulting suspension stirred at −78° C. for 30 minutes. The suspension is treated with acetyl chloride of formula FF-1 (10.23 mL) and then gradually allowed to warm to room temperature. The reaction mixture is quenched with 1 L of saturated ammonium chloride and then partitioned between water and ethyl acetate. The organic layer is separated and the aqueous layer reextracted twice with ethyl acetate. The combined organic layers are washed with brine, dried over anhydrous sodium sulfate, and concentrated in vacuo. The crude solid is recrystallized from ethyl acetate/hexane affording (21.27 g,) as a white solid.

Physical Characteristics are as follows:
Mp 86–87° C.
$^1$H NMR (CDCl$_3$) δ 7.42–7.26, 5.44–5.40, 4.68, 4.30–4.26, 2.52 ppm
$^{13}$C NMR (CDCl$_3$) δ 169.50, 153.71, 138.81, 128.97, 128.53, 125.73, 69.73, 57.20, 23.59 ppm Preparation 112 (3(2E),4S)-3-[4,4-dimethyl (2-pentenoyl)]-4-phenyl-2-oxazolidinone (Formula FF-4) Refer to Chart FF To a solution of the compound of formula FF-3 of Preparation 111 (21.27 g) in anhydrous methylene chloride (500 mL), cooled to −78° C., is added titanium tetrachloride (12.0 mL) in a dropwise manner. The suspension is treated with diisopropylethylamine (19.9 mL) and is allowed to stir at −78° C. for 30 minutes. The suspension is then treated with trimethylacetaldehyde (11.4 mL) followed by diisopropylethylamine (19.9 mL) and allowed to gradually warm to room temperature. After 1 hour the reaction mixture is quenched with water (200 mL) and stirred vigorously for 15 minutes. The organic layer is separated and the aqueous layer is reextracted with methylene chloride. The combined organic layers are washed with brine, dried over anhydrous sodium sulfate, and concentrated in vacuo. The crude solid is recrystallized from ethyl acetate/hexane affording 21.6 grams of the title compound as a off-white solid:

Physical characteristics are as follows:
Mp 148–149° C.
$^1$H NMR (CDCl$_3$) δ 7.42–7.05 , 5.51–5.46, 4.69, 4.30–4.25, 1.09ppm
$^{13}$C NMR (CDCl$_3$) δ 165.17, 161.61, 153.70, 139.16, 129.12, 128.61, 125.97, 115.71, 69.88, 57.74, 34.31, 28.56 ppm;

Preparation 113 (3(3S),4S)-3-[3-(3-Aminophenyl)-4,4-dimethylpentanoyl]-4-phenyl-2-oxazolidinone (Formula FF-5) Rerfer to Chart FF.

To a slurry of copper (I) bromide dimethylsulfide complex (18.76 g) in anhydrous tetrahydrofuran (60 mL), cooled to −78° C., is added a 1.0 M solution of 3-[bis(trimethylsilyl) amino]phenylmagnesium chloride in tetrahydrofuran (182.2 mL) and the resulting slurry stirred at −78° C. for 5 minutes. The slurry is allowed to warm to −15° C. for 15 minutes and then cooled to −78° C. The slurry is then treated with the compound of formula FF-4 of Preparation 112 (16.6 g) added via a solid addition funnel and allowed to stir at −78° C. for 3 hours. The reaction mixture is poured into saturated ammonium chloride (200 mL) and then partitioned between water and ethyl acetate. The organic layer is separated and the aqueous layer (pH 8) is basified to pH 9.5 with concentrated ammonium hydroxide. The aqueous layer is reextracted three times with ethyl acetate, the combined organic layers are washed with brine, dried over anhydrous sodium sulfate, and concentrated in vacuo. The crude residue is slurried in chloroform (400 mL) and 200 g of silica gel (230–400 mesh) at room temperature for 2 hours. The slurry is filtered and the solids washed several times with chloroform followed by methanol. The filtrate is concentrated in vacuo. Purification by flash chromatography eluting with hexane/ethyl acetate (15–40%) afford 17.52 grams of the title comound as a light yellow solid.

Physical characteristics are as follows:

$^1$H NMR (CDCl$_3$) δ 7.26–7.12 , 7.01, 6.74–6.70, 6.61–6.50, 5.32–5.28, 4.56, 4.11–3.95 , 3.48, 2.97–2.91 , 0.91 ppm $^{13}$C NMR (CDCl$_3$) δ 172.34, 153.51, 145.37, 142.24, 138.12, 128.67, 128.23, 127.68, 124.71, 119.80, 116.49, 113.02, 69.39, 57.39, 52.30, 34.75, 33.49, 27.83 ppm Preparation 114 (3(3S),4S)-3-[3-(3-Bisbenzylaminophenyl)-4,4-dimethylpentanoyl]-4-phenyl-2-oxazolidinone (Formula FF-6) Refer to Chart FF-6

To a solution of the compound of formula FF-5 of Preparation 113 (15.0 g) in methylene chloride (190 mL) at room temperature is added saturated sodium carbonate (48.7 mL) followed by benzyl bromide (14.3 mL) and the resulting mixture is refluxed for 24 hours. The reaction mixture is allowed to cool to room temperature and partitioned between water (300 mL) and methylene chloride. The organic layer is separated, washed with brine, dried over anhydrous sodium sulfate, and concentrated in vacuo. Purification by flash chromatography eluting with hexane/ethyl acetate (10–25%) affords 15.1 grams of the title compound as a white solid.

Physical characteristics are as follows:

$^1$H NMR (CDCl$_3$) δ 7.29–6.99, 6.69–6.49, 5.32–5.26, 4.71–4.50, 4.06–3.94, 2.90–2.81, 0.73ppm $^{13}$C NMR (CDCl$_3$) δ 172.79, 153.78, 148.32, 142.08, 139.04, 138.48, 129.07, 128.59, 128.37, 127.89, 126.83, 124.92, 118.44, 114.64, 110.87, 69.70, 57.68, 54.77, 52.97, 34.84, 33.79,27.97 ppm Preparation 115 [S,[R*,S*(E)]]-N-(2-hydroxy-1-methyl-2-phenylethyl)-methyl-N-pentenamide (Formula NNN-3) See Chart NNN.

A 250-mL, three-necked, round-bottomed flask with nitrogen inlet and addition funnel is charged with the compound of formula NNN-1 (6.6 g) (prepared from the treatment of commercially available trans-2-pentenoic acid with oxalyl chloride) and tetrahydrofuran (80 mL). The addition funnel is charged with a solution of (1R, 2S)-ephedrine of formula NNN-2 (7.2 g) and triethylamine (6.0 mL) in tetrahydrofuran (15 mL), which is added dropwise to the reaction mixture. After stirring an additional hour, the reaction mixture is poured into 200 mL of ethyl acetate, washed with three 25-mL portions of water, and concentrated in vacuo to yield 13.5 g of an oil. Column chromatography on 100 g silica (elution with 10–100% ethyl acetate-hexane) yields 10.75 g of the title compound as a colorless oil.

Physical characteristics are as follows:

HRMS found: 248.1652.

Preparation 116 [1R-[1R*(R*)2S*11-3-Amino-o-ethyl-N-(2-hydroxy-1-methyl-2-phenylethyl)-N-methyl-benzenepropanamide (Formula NNN-4) See Chart NNN.

A 50-mL, three-necked round-bottomed flask with a nitrogen inlet is charged with the title compound of Preparation 115 (0.247 g) and 5 mL of t-butyl methyl ether and cooled to 0° C. Propyl magnesium chloride (0.55 mL of 2.0 M solution in ether) is added dropwise, and the reaction mixture is stirred for an additional 15 min. 3-[Bis(trimethylsilyl) amino]phenylmagnesium chloride (2.0 mL of 1.0 M solution in tetrahydrofuran, 2.0 mmol) is added dropwise, and the resulting mixture is stirred for an additional 2 h at 0° C. and 1 h at room temperature. The reaction mixture is then quenched with saturated aqueous ammonium chloride solution (pH adjusted to 8 with ammonium hydroxide) and partitioned between 100 mL of ethyl acetate and 5 mL of water. The organic layer is separated, washed with additional ammonium chloride solution and water, and concentrated in vacuo to give 0.72 g of a yellow oil. The crude oil is then dissolved in chloroform, and silica gel is added to the solution. The resulting mixture is stirred at room temperature for 1.5 h, then filtered through Celite, rinsing with methanol, and concentrated in vacuo to give 0.38 g of a yellow oil. Column chromatography on 50 g of silica gel (elution with 20– 100% ethyl acetate-hexane) yields 0.174 g of the title compound as an oil.

Physical characteristics are as follows:

HRMS found: 340.2162.

Preparation 117 [1R-[1R*(R*)2S*11-3-bis(phenylmethyl) amino]-p-ethyl-N-(2-hydroxy-1-methyl-2-phenylethyl)-N-methyl-benzenepropanamide (Formula NNN-5) See Chart NNN.

A 50-mL, three-necked, round-bottomed flask with a condenser fitted with a nitrogen inlet is charged with the title product of Preparation 116 (0.548 g) in 8 mL of acetonitrile. Sodium carbonate (0.375 g) and benzyl bromide (0.42 mL) are added, and the reaction mixture is heated to reflux for 4 h. The reaction mixture is then concentrated in vacuo and partitioned between 100 mL of ethyl acetate and 10 mL of water. The organic layer is separated, washed with another 10 mL of water, and concentrated in vacuo to give 1.0 g of a yellow oil. Column chromatography on 65 g of silica gel (elution with 20–100% ethyl acetate-hexane and 5% methanol-methylene chloride) yields 0.447 g of the title compound as a pale yellow oil.

Physical characteristics are as follows:

HRMS found: 520.3102.

Preparation 118 1-phenyl-6,6,6-trifluoro-3-hexanol (Formula PPP-2) Refer to Chart PPP.

To a stirred solution of 4.0 g of ethyl 4,4,4-trifluorobutyrate of formula PPP-1 in 25 mL of tetrahydrofuran at −70° C. 24 mL of DiBAL-H (1M in toluene) is added dropwise and the solution stirred for 90 min. In a separate flask containing 680 mg of magnesium turnings and 5 mL of tetrahydrofuran is added 1-phenyl-2-bromoethane in 20 mL of tetrahydrofuran at a rate to maintain reflux. Heating of the mixture is continued for an additional 1 h, then cooled to room temperature and added via cannula to the DiBAL-H reaction above. The resulting white suspension is stirred 30 min at −70° C. and then allowed to warm to room temperature. The reaction is quenched with saturated aqueous ammonium chloride, diluted with 1 N hydrochloric acid to dissolve the precipitated salts and extracted with ethyl acetate. The organic layers are combined, washed with water and brine, dried over anhydrous sodium sulfate, filtered and concentrated in vacuo. The crude product is flash chromatographed on silica gel eluting with 20% ethyl acetate in hexane to give 2.0 g of the title compound as a colorless oil.

Physical characteristics are as follows:
HRMS: 232.1088
IR (neat liquid): 3385, 2950, 1455, 1255, 1140, 700 cm$^{-1}$.

Preparation 119 1-phenyl-6,6,6-trifluoro-3-hexanone (Formula PPP-3) Refer to Chart PPP.

To a solution of 0.48 mL of oxalyl chloride in 10 mL of dichloromethane at −60° C. is added dropwise 0.81 mL of dimethylsulfoxide. The solution is stirred for 5 min then treated with 860 mg of 1-phenyl-6,6,6-trifluoro-3-hexanol of formula PPP-2 of Preparation 118 in 5 mL of dichloromethane and stirred for 15 min. Triethylamine (1.5 mL) is added, the mixture is allowed to warm to room temperature, diluted with water and the layers separated. The aqueous layer is extracted with dichloromethane, the organic layers combined, dried over anhydrous sodium sulfate, filtered, and concentrated. The resulting oil is flash chromatographed on silica gel to give 600 mg of the title compound as an oil.

Physical characteristics are as follows:
$^1$H NMR (CDCl$_3$): δ 7.2–7.3, 2.9, 2.7, 2.6, 2.4.
$^{13}$C NMR (CDCl$_3$): δ 206, 140, 129, 128, 126, 125, 44, 35, 30, 28.

Preparation 120 5,6-dihydro-4-hydroxy-6-phenethyl-6-(3',3',3'-trifluoropropyl)-2H-pyran-2-one (Formula PPP-4) Refer to Chart PPP.

A suspension of 350 mg of 50% sodium hydride in 10 mL of tetrahydrofuran at 0° C. is treated dropwise with 0.78 mL of methyl acetoacetate. After stirring 30 min, 4.5 mL of 1.6 M n-butyllithium in hexane is added and stirring continued for 15 min. A solution of 840 mg of 1-phenyl-6,6,6-trifluoro-3-hexanone in 5 mL of tetrahydrofuran of formula PPP-3 of Preparation 119, is added, stirred at 0° C. for 15 min, then allowed to warm to room temperature and stirred for 1 h. The reaction mixture is quenched with saturated aqueous ammonium chloride and extracted with ethyl acetate. The organic layers are washed with water and brine, concentrated in vacuo, then disolved in 20 mL of tetrahydrofuran. The solution is diluted with 60 mL of water and treated with 20 mL of 1 N sodium hydroxide, stirred for 3 h at room temperature, concentrated in vacuo to remove the tetrahydrofuran, cooled to 5° C., and acidified with concentrated hydrochloric acid. The mixture is extracted with dichloromethane, dried over anhydrous sodium sulfate, filtered and concentrated. The crude material is flash chromatographed on silica gel eluting with 30% ethyl acetate in hexane to give 870 mg of the title compound.

Physical characteristics are as follows:
ANAL: C, 61.14, H, 5.45.

Preparation 121 [3-[1-[5,6-dihydro-4-hydroxy-2-oxo-6-(2-phenethyl)-6-(3,3,3-trifluoropropyl)-2H-pyran-3-yl]-2,2-dimethylpropyl]phenyl-carbamic acid, phenylmethylester (Formula QQQ-3 where R$_1$=t-Bu) Refer to Chart QQQ.

The title compound of Preparation 120 (850 mg) in 25 mL of tetrahydrofuran at 0° C. is treated with 750 mg of aluminum trichloride, stirred 15 min, and then 700 mg of 3-benzyloxycarbonylaminobenzaldehyde is added. The mixture is allowed to stir at room temperature for 2 h then treated with 2 g of sodium carbonate monohydrate and 0.1 mL of water, stirred for 30 min, and filtered through celite washing the filter cake with tetrahydrofuran. The filtrate is concentrated in vacuo. The resulting material is dissolved in 25 mL of tetrahydrofuran and 285 mg of cuprous bromide-dimethylsulfide complex is added and the mixture stirred for 15 min before adding 11 mL of 1 M t-butylmagnesium bromide in tetrahydrofuran dropwise over 15–20 min. The resulting brown mixture is stirred an additional 15 min then quenched at 0° C. with 50 mL of water. The layers are separated and the aqueous layer acidified with concentrated hydrochloric acid to dissolve inorganic salts and then extracted with ethyl acetate. The combined organic layers are washed with water and brine, dried over anhydrous sodium sulfate, filtered, and concentrated in vacuo. Flash chromatography on silica gel eluting with ethyl acetate in hexane gives 1.19 g of the title compound as a white to buff colored foam.

Physical characteristics are as follows:
$^1$H NMR (CDCl$_3$): δ 7.1–7.7, 6.7, 6.5, 4.4, 1.8–2.8, 1.16.
HRMS: 609.2711.

Preparation 122 Preparative resolution of [3-[1-[5,6-dihydro-4-hydroxy-2-25 oxo-6-(2-phenethyl)-6-(3,3,3-trifluoropropyl)-2H-pyran-3-yl]-2,2-dimethylpropyl] phenyl-carbamic acid, phenyl-methylester (Formula QQQ-3 where R$_1$=t-Bu) into 4 isomers, 3(R or S)-[1-[5,6-dihydro-4-hydroxy-2-oxo-6-(R or S)-(2-phenethyl)-6-(R or S)-(3,3,3-trifluoropropyl)-2H-30 pyran-3-yl]-2,2-dimethyl-propyl] phenyl-carbamic acid, phenylmethylester (Formulas QQQ-4–7 where R$_1$ is t-Bu) Refer to Chart QQQ.

The first phase of the resolution is accomplished with a 5.1×25 cm (R,R)Whelk-O 1 column eluted with 15% (V/V) isopropanol in hexane at 99 mL/min. 35 ((R,R)Whelk-O 1 is a registered trademark of Regis Technologies, Inc., Morton Grove, Ill. 60053.) The peaks eluting at approximately 54 and 87 min are, respectively, pure Isomer 3 and Isomer 2 as judged from System A, below. The mixture of unresolved Isomer 1 and Isomer 4 eluted at approximately 64 minutes and is further treated as described below.

In the second phase of the resolution, the mixture from above that elutes near 64 minutes is injected onto a 2.1×25 cm Chiralcel OD column (Chiral Technologies, Inc.) and eluted with 35% isopropanol in hexane (V/V) at 8 mL/min. The peaks that elute near 8.7 and 23.9 minutes are, respectively, Isomer 1 and Isomer 4.

In both phase of the resolution of enantiomers, fractions are pooled after assay with System A and pools are concentrated to dryness on a rotary evaporator at 30mm and a bath set at 50° maximum.

The four constituent enantiomers are (in order of elution from system A) designated (Peak #1), (Peak #2), (Peak #3) and (Peak #4). System A consists of a 0.46×25 cm Chiralcel OD-H column eluted at 1.0 mL/min with 20% isopropanol in hexane (V/V). (Chiralcel OD-H is a registered trademark of Chiral Technologies, Inc., Exton Pa. 19341.)

Preparation 123 3(R or S)-[1-(3-aminophenyl)-2,2-dimethylpropyl]-4-hydroxy-5,6-dihydro-6-(R or S)-phenethyl-6-(3,3,3-trifluoropropyl)-2H-pyran-2-one (Formula QQQ-8, R$_1$=t-Bu) Refer to Chart QQQ.

A solution of 210 mg of the compound identified as peak 1 from Preparation 122 in 10 mL of methanol is treated with 400 mg of ammonium formate and 40 mg of 10% palladium on charcoal, stirred 2 h, filtered through celite washing the filter cake with methanol. The filtrate is diluted with ethyl acetate and washed with water and brine, dried over anhydrous sodium sulfate and concentrated in vacuo to give 160 mg of the title compound as a white foam.

Physical characteristics are as follows:

$^1$H NMR (CD$_3$OD): δ 6.9–7.3, 6.6, 4.1, 2.6–2.7, 1.9–2.4, 1.0.

TLC (silica gel GF): R$_f$=0.24 (40% ethyl acetate in hexane).

EXAMPLE 266
5-cyano-N-[3-(R or S)-[1-[5,6-dihydro-4-hydroxy-2-oxo-6-(2-phenethyl)-6-(R or S)-(3,3,3-trifluoropropyl)-2H-pyran-3-yl]-2,2-dimethylpropyl]phenyl]-2-pyridinesulfonamide (Formula QQQ-13, R$_1$ is t-Bu [R$_2$ is [5-cyano-2-pyridinyl]) Refer to Chart QQQ.

A solution of the title product of Preparation 123 (50 mg), pyridine (30 μL), and 5-cyano-pyridine-2-sulfonyl chloride (30 mg) in dichloromethane at 0° C. is stirred for 2 h. The crude reaction mixture is chromatographed on silica gel to give the title compound as a white amorphous solid.

Physical characteristics are as follows:
FAB HRMS: 642.2267.

EXAMPLE 267
N-[3-(R or S)-[1-[5,6-dihydro-4-hydroxy-2-oxo-6-(R or S)-(2-phenethyl)-6-(3,3,3-trifluoropropyl)-2H-pyran-3-yl]-2,2-dimethylpropyl]phenyl]-1-methyl-1H-imidazole-4-sulfonamide (Formula QQQ-13, R$_1$ is t-Bu, [R$_1$ is 1-methyl-4-imidazolyl]) Refer to Chart QQQ.

Following the procedure described in EXAMPLE 266 and substituting 5-cyano-2-pyridine sulfonyl chloride with 1-methylimidazole-4-sulfonyl chloride the title compound is prepared.

Physical characteristics are as follows:
HRMS: 619.2298

EXAMPLE 268
5-amino-N-[3-(R or S)-[1-[5,6-dihydro-4-hydroxy-2-oxo-6-(2-phenethyl)-6-(R or S)-(3,3,3-trifluoropropyl)-2H-pyran-3-yl]-2,2-dimethylpropyl]phenyl]-2-pyridinesulfonamide (Formula QQQ-13, R$_1$=t-Bu, [R$_2$ is 5-amino-2-pyridinyl]) Refer to Chart QQQ.

A solution of the title product of Preparation 123 (50 mg), pyridine (30 μL), and 5-nitro-pyridine-2-sulfonyl chloride (30 mg) in dichloromethane at 0° C. is stirred for 2 h. The crude reaction mixture is chromatographed on silica gel to give the sulfonamide as a white amorphous solid. The white solid is dissolved in 4 mL of methanol and treated with 25 mg of ammonium formate and 5 mg of 10% palladium on carbon, stirred for 1 h at room temperature, diluted with water and extracted with dichloromethane, dried over anhydrous sodium sulfate, filtered, and concentrated in vacuo to give the title compound as an off-white amorphous solid.

Physical characteristics are as follows:
FAB HRMS: 632.2393.

Preparation 124 3(R or S)-[1-(3-aminophenyl)-2,2-dimethyl-propyl]-4-hydroxy-5,6-dihydro-6(S or R)-phenethyl-6-(3',3',3'-trifluoropropyl)-2H-pyran-2-one (Formula QQQ-9, [R$_1$ is t-Bu]) Refer to Chart QQQ.

Following the procedure described in Preparation 123 beginning with the compound isolated from peak 2 from Preparation 122 and using starting materials and reagents known and available to one of ordinary skill in organic synthesis the title compound is prepared.

Physical characteristics are as follows:
$^1$H NMR (CD$_3$OD): δ 6.9–7.3, 6.6, 4.1, 2.6–2.7, 1.9–2.4, 1.0.

TLC (silica gel GF): R=0.$^{24}$ (40% ethyl acetate in hexane).

EXAMPLE 269
5-cyano-N-[3-(R or S)-[1-[5,6-dihydro-4-hydroxy-2-oxo-6-(2-phenethyl)-6-(R or S)-(3,3,3-trifluoropropyl)-2H-pyran-3-yl]-2,2-dimethylpropyl]phenyl]-2-pyridinesulfonamide (Formula QQQ-14, R$_1$ is t-Bu [R$_2$ is 5-cyano-2-pyridinyl]) Refer to Chart QQQ.

A solution of the title product of Preparation 124 (50 mg), pyridine (30 μL), and 5-cyanopyridine-2-sulfonyl chloride (30 mg) in dichloromethane at 0° C. is stirred for 2 h. The crude reaction mixture is chromatographed on silica gel to give the title compound as a white amorphous solid.

Physical characteristics are as follows:
FAB HRMS: 642.2260.

EXAMPLE 270
N-[3-(R or S)-[1-[5,6-dihydro-4-hydroxy-2-oxo-6-(R or S)-(2-phenethyl)-6-(3,3,3-trifluoropropyl)-2H-pyran-3-yl]-2,2-dimethylpropyl]phenyl]-1-methyl-1H-imidazole-4-sulfonamide (Formula QQQ-14, R$_1$ is t-Bu [R$_2$ is 1-methyl-4-imidazolyl]) Refer to Chart QQQ.

Following the procedure described in Example 266 substituting 5-cyano-2-pyridine sulfonyl chloride with 1-methylimidazole-4-sulfonyl chloride the title compound is prepared.

Physical characteristics are as follows:
HRMS: 619.2362

EXAMPLE 271
5-amino-N-[3-(R or S)-[1-[5,6-dihydro-4-hydroxy-2-oxo-6-(2-phenethyl)-6-(R or S)-(3,3,3-trifluoropropyl)-2H-pyran-3-yl]-2,2-dimethylpropyl]phenyl]-2-pyridinesulfonamide (Formula QQQ-14, R$_1$ is t-Bu [R$_2$ is 5-amino-2-pyridinyl]) Refer to Chart QQQ.

Following the procedure described in Example 268 the title compound is prepared.

Physical characteristics are as follows:
FAB HRMS: 632.2387

Preparation 125 3-(S or R)-[1-(3-aminophenyl)-2,2-dimethyl-propyl]-4-hydroxy-5,6-dihydro-6-(R or S)-phenethyl-6-(R or S)-(3',3',3'-trifluoropropyl)-2H-pyran-2-one (Formula QQQ-10 [R$_1$ is t-Bu]) Refer to Chart QQQ.

Following the procedure described in Preparation 123 beginning with the compound isolated from peak 3 from Preparation 122 and using starting materials and reagents known and available to one of ordinary skill in organic synthesis the title compound is prepared.

Physical characteristics are as follows:
$^1$H NMR (CD$_3$OD): δ 6.9–7.3, 6.6, 4.1, 2.6–2.7, 1.9–2.4, 1.0.

TLC (silica gel GF): R$_f$=0.24 (40% ethyl acetate in hexane).

EXAMPLE 272
5-cyano-N-[3-(R or S)-[1-[5,6-dihydro-4-hydroxy-2-oxo-6-(2-phenethyl)-6-(R or S)-(3,3,3-trifluoropropyl)-2H-pyran-3-yl]-2,2-dimethylpropyl]phenyl]-2-pyridinesulfonamide (Formula QQQ-15, R$_1$ is t-Bu, [R$_2$ is 5-cyano-2-pyridinyl]) Refer to Chart QQQ.

A solution of the title product of Preparation 125 (50 mg), pyridine (30 mL), and 5-cyanopyridine-2-sulfonyl chloride (30 mg) in dichloromethane at 0° C. is stirred for 2 h. The crude reaction mixture is chromatographed on silica gel to give the title compound as a white amorphous solid.

Physical characteristics are as follows:
FAB HRMS: 642.2254

EXAMPLE 273
N-[3-(R or S)-[1-[5,6-dihydro-4-hydroxy-2-oxo-6-(R or S)-(2-phenethyl)-6-(3,3,3-trifluoropropyl)-2H-pyran-3-yl]-2,2-dimethylpropyl]phenyl]-1-methyl-1H-imidazole-4-sulfonamide (Formula QQQ-15, R$_1$ is t-Bu, [R$_2$ is 1-methyl-4-imidazolyl]) Refer to Chart QQQ.

Following the procedure described in Example 266 substituting 5-cyano-2-pyridine sulfonyl chloride with 1-methylimidazole-4-sulfonyl chloride the title compound is prepared.
Physical characteristics are as follows:
FAB HRMS: 642.2397

EXAMPLE 274
5-amino-N-[3-(R or S)-[1-[5,6-dihydro-4-hydroxy-2-oxo-6-(2-phenethyl)-6-(R or S)-(3,3,3-trifluoropropyl)-2H-pyran-3-yl]-2,2-dimethylpropyl]phenyl]-2-pyridinesulfonamide (Formula QQQ-15, $R_1$ is t-Bu [$R_2$ is 5-amino-2-pyridinyl]) Refer to Chart QQQ.

Following the procedure described in Example 268 the title compound is prepared.
Physical characteristics are as follows:
FAB HRMS: 632.2393
Preparation 126 3-(S or R)-[1-(3-aminophenyl)-2,2-dimethyl-propyl]-4-hydroxy-5,6-dihydro-6 (S or R)-phenethyl-6-(3',3',3'-trifluoropropyl)-2H-pyran-2-one (Formula QQQ-11 [$R_1$ is t-Bu]) Refer to Chart QQQ.

Following the procedure described in Preparation 123 beginning with the compound isolated from peak 4 from Preparation 122 and using starting materials and reagents known and available to one of ordinary skill in organic synthesis the title compound is prepared.
Physical characteristics are as follows:
$^1$H NMR (CD$_3$OD): δ 6.9–7.3, 6.6, 4.1, 2.6–2.7, 1.9–2.4, 1.0.
TLC (silica gel GF): $R_f$=0.24 (40% ethyl acetate in hexane).

EXAMPLE 275
5-cyano-N-[3-(R or S)-[1-[5,6-dihydro-4-hydroxy-2-oxo-6-(2-phenethyl)-6-(R or S)-(3,3,3-trifluoropropyl)-2H-pyran-3-yl]-2,2-dimethylpropyl]phenyl]-2-pyridinesulfonamide (Formula QQQ-16, $R_1$ is t-Bu, [$R_2$ is 5-cyano-2-pyridinyl]) Refer to Chart QQQ.

A solution of the title product of Preparation 126 (50 mg), pyridine (30 mL), and 5-cyanopyridine-2-sulfonyl chloride (30 mg) in dichloromethane at 0° C. is stirred for 2 h. The crude reaction mixture is chromatographed on silica gel to give the title compound as a white amorphous solid.
Physical characteristics are as follows:
FAB HRMS: 642.2248.

EXAMPLE 276
N-[3-(R or S)-[1-[5,6-dihydro-4-hydroxy-2-oxo-6-(R or S)-(2-phenethyl)-6-(3,3,3-trifluoropropyl)-2H-pyran-3-yl]-2,2-dimethylpropyl]phenyl]-1-methyl-1H-imidazole-4-sulfonamide (Formula QQQ-16, $R_1$ is t-Bu, [$R_2$ is 1-methyl-4-imidazolyl]) Refer to Chart QQQ.

Following the procedure described in Example 266 substituting 5-cyano-2-pyridine sulfonyl chloride with 1-methylimidazole-4-sulfonyl chloride the title compound is prepared.
Physical characteristics are as follows:
FAB HRMS: 620.2403

EXAMPLE 277
5-amino-N-[3-(R or S)-[1-[5,6-dihydro-4-hydroxy-2-oxo-6-(2-phenethyl)-6-(R or S)-(3,3,3-trifluoropropyl)-2H-pyran-3-yl]-2,2 -dimethylpropyl]phenyl]-2-pyridinesulfonamide (Formula QQQ-16, $R_1$ is t-Bu, [$R_2$ is 5-amino-2-pyridinyl]) Refer to Chart QQQ.

Following the procedure described in Example 268 the title compound is prepared.

Physical characteristics are as follows:
FAB HRMS: 632.2406

EXAMPLE 278
N-[3-(R or S)-[1-[5,6-dihydro-4-hydroxy-2-oxo-6-(2-phenethyl)-[6-(R or S)-propyl]-2H-pyran-3-yl]-2,2-dimethylpropyl]phenyl]-2-pyridinesulfonamide Following procedures analogous to those described above and using Isomer 2 of Preparation 143 the title compound is prepared.
Physical characteristics are as follows:
FAB HRMS: 562.2527.

EXAMPLE 279
N-[3-(R or S)-[1-[5,6-dihydro-4-hydroxy-2-oxo-6-(2-phenethyl)-6-(R or S)-propyl-2H-pyran-3-yl]-2,2-dimethylpropyl]phenyl]-2-pyridinesulfonamide Following procedures analogous to those described above and using Isomer 1 of Preparation 143 the title compound is prepared.
Physical characteristics are as follows:
FAB HRMS: 562.2528.
Preparation 127 2-Mercapto-4-trifluoromethylpyridine To 1.0 g of 2-chloro-4-trifluoromethylpyridine (Lancaster Chemical Co) is added 10 ml of absolute ethanol and 417 mg of thiourea. The reaction mixture is heated at reflux for 4 hours and 1.25 ml of a solution of 7.44 g KOH in 20 ml of water is added. The solution is heated at reflux for an additional 1 hour. The reaction solution is cooled and poured into 100 ml of a 0. 1N NaOH solution. The resulting solution is extracted three times with 100 ml of methylene chloride and the resulting aqueous solution is acidified to pH 4 by addition of glacial acetic acid. The aqueous solution is extracted three times with 100 ml of methylene chloride and the organic solution is dried over anhydrous sodium sulfate. Filtration followed by evaporation to dryness gives 501 mg of a yellow crystalline solid.
Physical characteristics are as follows:
Found C: 40.22; H: 2.33; N: 8.07; S: 17.59.
HRMS: 179.0019
Preparation 128 2-Chlorosulfonyl-4-trifluoromethylpyridine
To 425 mg of 2-mercapto-4-trifluoromethylpyridine of Preparation 127 is added 10 ml of 1N aqueous HCl. The reaction mixture is cooled to 0° C. and Cl$_2$ gas is bubbled into the cold reaction mixture for 15 minutes. The reaction mixture is filtered and the resulting solid is washed well with water. The white solid is dissolved in methylene chloride and is washed twice with saturated aqueous NaHCO$_3$ followed by one wash with water. After drying the organic solution over sodium sulfate (anhydrous), the solution is filtered and evaporated to dryness to give 300 mg of 2-chlorosulfonyl-4-trifluoromethylpyridine which is used directly without further purification, and stored at −78° C. until ready for use.
Preparation 129 2-Chlorosulfonyl-5-trifluoromethylpyridine
Substituting 2-mercapto-5-trifluoromethylpyridine for 2-mercapto-4-trifluoro-methylpyridine in the reaction above in Preparation 128 gives 2-chlorosulfonyl-5-trifluoromethylpyridine as a colorless oil which slowly crystallizes. This material is used without further purification and stored at −78° C. until ready for use.
Preparation 130 3-[1-[5,6-Dihydro-4-hydroxy-2-oxo-6,6-di-n-propyl-2H-pyran-3-yl]-propyl]phenyl-carbamic acid, (Formula SSS-1; $R_1$ is ethyl; Refer to Chart SSS).

To 7.2 g of AlCl$_3$ at −70° C., under N$_2$, is added 180 ml of THF. The mixture is allowed to stir at 0° C. for 15 minutes and 5.38 g of Formula SSS-A; Refer to Chart SSS, prepared by procedures analogous to those described in Preparation 17, is added. The reaction mixture is stirred for 15 minutes and 6.88 g of 3-aminoCbZ-benzaldehyde (Formula SSS-B; Refer to Chart SSS) is added. The reaction mixture is stirred for 15 minutes at 0° C. followed by 3 hours at room temperature. The reaction is cooled to 0° C. and 35 g of sodium carbonate monohydrate is added, with vigorous stirring, followed by 1.6 ml of water. After stirring at 0° C. for an additional 15 minutes, 120 ml of THF is added and the mixture filtered through celite. The celite is washed well with THF and the THF solution is evaporated to dryness under vacuum to an amber foam. The residue is dissolved in 180 ml of THF, the solution is cooled to −5° C. and 3.2 g of CuBr.Me$_2$S added. The mixture is stirred for 15 minutes and 65 ml of a 2M ethylmagnesium chloride in THF solution is added, dropwise, with temperatures not rising above 0° C. The reaction is allowed to stir for an additional 15 minutes and 9 ml of water is slowly added followed by 45 ml of 1N HCl. These additions are done at 0° C. The reaction mixture is poured into 2 L of ethyl ether and 200 ml of water is added. The aqueous layer is separated and the organic layer is extracted three times with 10% aqueous ammonium carbonate followed by once with water. The organic solution is dried over anhydrous sodium sulfate, filtered and evaporated to dryness to give 10.2 g of a crude amorphous foam. This crude material is chromatographed over silica gel using 2% ethyl acetate in methelene chloride as eluent to give 4.74 g of 3-[1-[5,6-dihydro-4-hydroxy-2-oxo-6,6-di-n-propyl-2H-pyran-3-yl]-propyl]phenyl-carbamic acid.

Preparation 130A 3-[1-[5,6-dihydro-4-hydroxy-2-oxo-6-phenethyl-6-propyl)-2H-pyran-3-yl]-propyl]-phenyl-carbamic acid (Formula RRR-1; R$_1$ is ethyl; Refer to Chart RRR).

Following the procedure of Preparation 130 beginning with the compound from Preparation 17 the title compound is prepared.

Physical characteristics are as follows:
$^1$H NMR (CD$_3$OD): δ 6.9–7.5, 5.1, 4.0, 1.4–2.7, 0.9.
TLC (silica gel GF): Rf=0.28, 30% ethyl acetate in hexane.

Preparation 131
Preparative chiral resolution of 3-[1-[5,6-dihydro-4-hydroxy-2-oxo-6,6-di-n-propyl-2H-pyran-3-yl]-propyl] phenyl-carbamic acid (Formula SSS-1; R$_1$ is ethyl; Refer to Chart SSS) to give two isomers of 3(R or S)-[1-[5,6-dihydro-4-hydroxy-2-oxo-6,6-di-n-propyl-2H-pyran-3-yl]-propyl]phenyl-carbamic acid (Formulas SSS-3 and SSS-4; R$_1$ is ethyl; Refer to Chart SSS).

Samples of the title compound of Preparation 130 are injected onto a 2.1×25 cm Chiralcel OD column and eluted with 20% isopropanol (V/V) in hexane at 10 mL/min. The material eluting near 19.1 minutes is 3(R or S)-[1-[5,6-dihydro-4-hydroxy-2-oxo-6,6-di-n-propyl-2H-pyran-3-yl]-propyl]phenyl-carbamic acid, (a)25D +26o (methanol), (Formula SSS-3; Refer to Chart SSS) (peak 1) and that eluting near 37.7 minutes is 3(R or S)-[1-[5,6-dihydro-4-hydroxy-2-oxo-6,6-di-n-propyl-2H-pyran-3-yl]-propyl] phenyl-carbamic acid ((α)$^{25}$$_D$-27o (methanol), (Formula SSS-4; Refer to Chart SSS) (peak 2). The pools are concentrated separately on a rotary evaporator (ca. 30 mm, bath at 50° maximum) to give white amorphous solids.

Preparation 132 3(R or S)-[1-(3-aminophenyl)-propyl]-4-hydroxy-5,6-dihydro-6,6-dipropyl-2H-pyran-2-one (Formula SSS-5; R$_1$ is ethyl; Refer to Chart SSS).

To 1.04 g of 3(R or S)-[1-[5,6-dihydro-4-hydroxy-2-oxo-6,6-di-n-propyl-2H-pyran-3-yl]-propyl]phenyl-carbamic acid (Formula SSS-3; Refer to Chart SSS) of Preparation 131, the compound identified as peak 1 from the chiral resolution of the product of Preparation 131, is added 20 ml of methanol and 1.29 g of ammonium formate. When dissolution is complete, 275 mg of 10% Pd/C is added and the reaction mixture is stirred at room temperature for 60 minutes. The reaction mixture is filtered (celite) and the methanolic solution is evaporated to dryness to give a crude solid. The crude solid is partitioned between methylene chloride and water. The organic layer is washed twice with water and dried over anhydrous sodium sulfate. The methylene chloride solution is filtered and evaporated to dryness to give 625 mg of 3(R or S)-[1-(3-aminophenyl)-propyl]-4-hydroxy-5,6-dihydro-6,6-dipropyl-2H-pyran-2-one as an amorphous foam.

Physical characteristics are as follows:
MS(EI): 331
(α)$^{25}$$_D$ +38° (c=0.3715, methanol).

Preparation 133 3(R or S)-[1-(3-aminophenyl)-propyl]-4-hydroxy-5,6-dihydro-6,6-di-n-propyl-2H-pyran-2-one (Formula SSS-6; R$_1$ is ethyl; Refer to Chart SSS).

To 825 mg of 3(R or S)-[1-(3-aminophenyl)-propyl]-4-hydroxy-5,6-dihydro-6,6-dipropyl-2H-pyran-2-one (Formula SSS-4; Refer to Chart SSS), of Preparation 131, the compound identified as peak 2 from the chiral resolution of the product of Preparation 131, is added 20 ml of methanol and 1.02 g of ammonium formate. When dissolution is complete, 210 mg of 10% Pd/C is added and the reaction mixture is stirred at room temperature for 60 minutes. The reaction mixture is filtered (celite) and the methanolic solution is evaporated to dryness. The crude solid is partitioned between methylene chloride and water. The organic layer is washed twice with water and dried over anhydrous sodium sulfate. The methylene chloride solution is filtered and evaporated to dryness to give 483 mg of title compound as an amorphous foam.

Physical characteristics are as follows:
MS(EI): 331
(α)$^{25}$$_D$ −39° (c=.2680, methanol).

EXAMPLE 280
5-Trifluoromethyl-N-[3-[1-[4-hydroxy-2-oxo-6,6-di-n-propyl-5,6-dihydro-2H-pyran-3-yl]-propyl]-phenyl]-2-pyridinesulfonamide (Formula SSS-9; R$_1$ is ethyl; R$_2$ is 5-trifluoromethylpyridine;

Refer to Chart SSS).

The title compound of Preparation 130 is deprotected as in Preparation 132 to give the compound of formula SSS-2. To 132 mg of formula SSS-2 is added 15 ml of methylene chloride and 66 microliters of pyridine. The reaction solution is cooled to −5° C. and 98 mg of 2-chlorosulfonyl-5-trifluoromethylpyridine (product of Preparation 129) is added. After stirring at 0° C. for 60 minutes the solution is placed on a silica gel column and eluted with 10% ethyl acetate in methylene chloride until the 5-trifluoromethyl-N-[3-[1-[4-hydroxy-2-oxo-6,6-di-n-propyl-5,6-dihydro-2H-pyran-3-yl]-propyl]-phenyl]-2-pyridinesulfonamide is collected. Rf=0.6 in 10% ethyl acetate in methylene chloride. Evaporation of the organic solution to dryness gives 177 mg of 5-trifluoromethyl-N-[3-[1-[4-hydroxy-2-oxo-6,6-di-n-propyl-5,6-dihydro-2H-pyran-3-yl]-propyl]-phenyl]-2-pyridinesulfonamide.

Physical characteristics are as follows:
MS(EI): 540, 497, 411, 401, 383, 342, 331, 197, 174, 146, 133.
HRMS: 540.1938
Rf=0.6 in 10% ethyl acetate in methylene chloride.
$^1$H NMR(MeOD): δ 8.91, 8.21–8.19, 7.12, 6.98–6.96, 6.86–6.83, 3.85–3.79, 2.46, 2.10–1.98, 1.84–1.75, 1.58–1.47, 1.27–1.15, 0.82–0.72 ppm

EXAMPLE 281

5-Trifluoromethyl-N-[3-(R or S)-[1-[4-hydroxy-2-oxo-6,6-di-n-propyl-5,6-dihydro-2H-pyran-3-yl]-propyl]-phenyl]-2-pyridine-sulfonamide (Formula SSS-7; $R_1$ is ethyl; $R_2$ is 5-trifluoro-methylpyridine; Refer to Chart SSS).

To 66 mg of the title product from Preparation 132 (Formula SSS-5; Chart SSS) is added 8 ml of methylene chloride and 33 microliters of pyridine. The reaction solution is cooled to −5° C. and 49 mg of 2-chlorosulfonyl-5-trifluoro-methylpyridine (product of Preparation 129) is added. After stirring at 0° C. for 60 minutes the solution is placed on a silica gel column and eluted with 10% ethyl acetate in methylene chloride until the 5-trifluoromethyl-N-[3-(R or S)-[1-[4-hydroxy-2-oxo-6,6-di-n-propyl-5,6-dihydro-2H-pyran-3-yl]-propyl]-phenyl]-2-pyridinesulfonamide is collected. Rf=0.6 in 10% ethyl acetate in methylene chloride. Evaporation of the organic solution to dryness gives 69 mg of the title compound.

Physical characteristics are as follows:

MS(EI): 540, 497, 411, 401, 383, 342, 331, 197, 174, 146, 133.

Rf=0.6 in 10% ethyl acetate in methylene chloride $^1$H NMR(MeOD): 88.91, 8.21–8.19, 7.12, 6.98–6.96, 6.86–6.83, 3.85–3.79, 2.46, 2.10–1.98, 1.84–1.75, 1.58–1.47, 1.27–1.15,.82–0.72ppm

EXAMPLE 282

5-Trifluoromethyl-N-[3-(R or S)-[1-[4-hydroxy-2-oxo-6,6-di-n-propyl-5,6-dihydro-2H-pyran-3-yl]-propyl]-phenyl]-2-pyridine-sulfonamide (Formula SSS-8; $R_1$ is ethyl; $R_2$ is 5-trifluoromethylpyridine; Refer to Chart SSS).

Following the procedure of Example 281 but substituting the product of Preparation 133 (formula SSS-6) gives 5-trifluoromethyl-N-[3-(R or S)-[1-[4-hydroxy-2-oxo-6,6-di-n-propyl-5,6-dihydro-2H-pyran-3-yl]-propyl]-phenyl]-2-pyridinesulfon-amide as an amorphous foam.

Physical characteristics are as follows:

MS(EI): 540, 497, 411, 401, 383, 342, 331, 197, 174, 146, 133.

Rf=0.6 in 10% ethyl acetate in methylene chloride $^1$H NMR(MeOD): δ 8.91, 8.21–8.19, 7.12, 6.98–6.96, 6.86–6.83, 3.85–3.79, 2.46, 2.10–1.98, 1.84–1.75, 1.58–1.47, 1.27–1.15,.82–0.72ppm

EXAMPLE 283

4-Trifluoromethyl-N-[3-(R or S)-[1-[4-hydroxy-2-oxo-6,6-di-n-propyl-5,6-dihydro-2H-pyran-3-yl]-propyl]-phenyl]-2-pyridine-sulfonamide (Formula SSS-7; $R_1$ is ethyl; $R_2$ is 4-trifluoromethylpyridine; Refer to Chart SSS).

Following the procedure of Example 281 but substituting the product of Preparation 128 for the pyridylsulfonylchloride gives 4-trifluoromethyl-N-[3-(R or S)-[1-[4-hydroxy-2-oxo-6,6-di-n-propyl-5,6-dihydro-2H-pyran-3-yl]-propyl]-phenyl]-2-pyridinesulfonamide as an amorphous foam.

Physical characteristics are as follows:

MS(EI): 146, 145, 139, 133, 71, 57, 55, 43, 41

HRMS: 540.1902

EXAMPLE 284

4-Trifluoromethyl-N-[3-(R or S)-[1-[4-hydroxy-2-oxo-6,6-di-n-propyl-5,6-dihydro-2H-pyran-3-yl]-propyl]-phenyl]-2-pyridine-sulfonamide (Formula SSS-8; $R_1$ is ethyl; $R_2$ is 4-trifluoro-methylpyridine; Refer to Chart SSS).

Following the procedure of Example 282 but substituting the product of Preparation 128 for the pyridylsulfonylchloride gives 4-trifluoromethyl-N-[3-(R or S)-[1-[4-hydroxy-2-oxo-6,6-di-n-propyl-5,6-dihydro-2H-pyran-3-yl-propyl]-phenyl]-2-pyridinesulfonamide as an amorphous foam.

Physical characteristics are as follows:

MS(EI): 146, 145, 139, 133, 71, 57, 55, 43, 41

HRMS: 540.1896

EXAMPLE 285

5-Trifluoromethyl-N-[3-(R or S)-[1-[4-hydroxy-2-oxo-6,6-di-n-propyl-5,6-dihydro-2H-pyran-3-yl]-2,2-dimethylpropyl]-phenyl]-2-pyridinesulfonamide (Formula TTT-6; $R_1$ is t-butyl; $R_2$ is n-propyl; $R_3$ is 5-trifluoromethyl-2-pyridinyl; Refer to Chart TTT).

Following the procedure of Example 281 but using Isomer 1 of Preparation 144 (Formula TTT-4; Chart TTT; $R_1$ is t-butyl, $R_2$ is n-propyl) gives 5-trifluoro-methyl-N-[3-(R or S)-[1-[4-hydroxy-2-oxo-6,6-di-n-propyl-5,6-dihydro-2H-pyran-3-yl]-2,2-dimethylpropyl]-phenyl]-2-pyridinesulfonamide as an amorphous solid.

Physical characteristics are as follows:

MS(EI): 163, 162, 147, 146, 69, 57, 56, 43, 41

HRMS: 568.2213

EXAMPLE 286

5-Trifluoromethyl-N-[3-(R or S)-[1-[4-hydroxy-2-oxo-6,6-di-n-propyl-5,6-dihydro-2H-pyran-3-yl]-2,2-dimethylpropyl]-phenyl]1-2-pyridinesulfonamide (Formula TTT-7; $R_1$ is t-butyl; $R_2$ is n-propyl; $R_3$ is 5-trifluoromethylpyridine; Refer to Chart TTT).

Following the procedure of Example 281 but substituting Isomer 2 of Preparation 144 (Formula TTT-5; Chart TTT; $R_1$ is t-butyl; $R_2$ is n-propyl) gives 5-trifluoromethyl-N-[3-[1(R or S)-4-hydroxy-2-oxo-6,6-di-n-propyl-5,6-dihydro-2H-pyran-3-yl]-2,2-dimethylpropyl]-phenyl]-2-pyridinesulfonamide as an amorphous solid.

Physical characteristics are as follows:

HRMS: 568.2237

EXAMPLE 287

5-Trifluoromethyl-N-[3-(R or S)-[1-[4-hydroxy-2-oxo-6,6-di-phenethyl-5,6-dihydro-2H-pyran-3-yl]-propyl]-phenyl]-2-pyridinesulfonamide (Formula TTT-6; $R_1$ is ethyl; $R_2$ is phenyl; $R_3$ is 5-trifluoromethylpyridine; Refer to Chart TTT).

Following the procedure of Example 281 but using Isomer 1 of Preparation 145 (Formula TTT-4; Chart TTT; $R_1$ is ethyl; $R_2$ is phenyl) gives 5-trifluoromethyl-N-[3-(R or S)-[1-[4-hydroxy-2-oxo-6,6-di-n-propyl-5,6-dihydro-2H-pyran-3-yl]-propyl]-phenyl]-2-pyridinesulfonamide as an amorphous solid.

Physical characteristics are as follows:

MS(EI): 665, 647, 456, 455, 333, 134, 133, 117, 105, 91

EXAMPLE 288

5-Trifluoromethyl-N-[3-(R or S)-[1-[4-hydroxy-2-oxo-6,6-di-phenethyl-5,6-dihydro-2H-pyran-3-yl]-propyl]-phenyl]-2-pyridinesulfonamide (Formula TTT-7; $R_1$ is ethyl; $R_2$ is phenyl; $R_3$ is 5-trifluoromethylpyridine; Refer to Chart TTT).

Following the procedure of Example 281 but substituting Isomer 2 of Preparation 145 (Formula TTT-5; Chart TTT; $R_1$ is ethyl; $R_2$ is phenyl) gives 5-trifluoromethyl-N-[3-(R or S)-[1-[4-hydroxy-2-oxo-6,6-di-n-propyl-5,6-dihydro-2H-pyran- 3-yl]-propyl]-phenyl]-2-pyridinesulfonamide as an amorphous solid.

Physical characteristics are as follows:

HRMS: 665.2300

MS(EI): 665, 647, 456, 455, 333, 134, 133, 117, 105, 91

EXAMPLE 289

4-Trifluoromethyl-N-[3-(R or S)-[1-[4-hydroxy-2-oxo-6,6-di-phenethyl-5,6-dihydro-2H-pyran-3-yl]-propyl]-phenyl]-

2-pyridinesulfonamide (Formula TTT-6; $R_1$ is ethyl; $R_2$ is phenyl; $R_3$ is 4-trifluoromethylpyridine; Refer to Chart TTT).

Following the procedure of Example 281 but substituting Isomer 1 of Preparation 145 (Formula TTT-4; Chart TTT; $R_1$ is ethyl; $R_2$ is phenyl) gives 5-trifluoromethyl-N-[3-(R or S)-[1-[4-hydroxy-2-oxo-6,6-di-n-propyl-5,6-dihydro-2H-pyran-3-yl]-propyl]-phenyl]-2-pyridinesulfonamide as an amorphous solid.

Physical characteristics are as follows:
MS(EI): 666, 665, 647, 134, 133, 117, 105, 91
HRMS: 665.2306

EXAMPLE 290

4-Trifluoromethyl-N-[3-(R or S)-[1-[4-hydroxy-2-oxo-6,6-di-phenethyl-5,6-dihydro-2H-pyran-3-yl]-propyl]-phenyl]-2-pyridinesulfonamide (Formula TTT-7; $R_1$ is ethyl; $R_2$ is phenyl; $R_3$ is 4-trifluoromethylpyridine; Refer to Chart TTT).

Following the procedure of Example 281 but substituting Isomer 2 of Preparation 145 (Formula TTT-5; Chart TTT; $R_1$ is ethyl; $R_2$ is phenyl) gives 4-trifluoromethyl-N-[3-(R or S)-[1-[4-hydroxy-2-oxo-6,6-di-n-propyl-5,6-dihydro-2H-pyran-3-yl]-propyl]-phenyl]-2-pyridinesulfonamide as an amorphous solid.

Physical characteristics are as follows:
HRMS: 665.2306
MS(EI): 666, 665, 647, 134, 133, 117, 105, 91

EXAMPLE 291

4-Trifluoromethyl-N-[3-(R or S)-[1-[4-hydroxy-2-oxo-6,6-di-n-propyl-5,6-dihydro-2H-pyran-3-yl]-2,2-dimethylpropyl]-phenyl]-2-pyridinesulfonamide (Formula TTT-6; $R_1$ is t-butyl; $R_2$ is methyl; $R_3$ is 4-trifluoromethylpyridine; Refer to Chart TTT).

Following the procedure of Example 283 but substituting Isomer 1 of Preparation 144 (Formula TTT-4; Chart TTT; $R_1$ is t-butyl; $R_2$ is methyl) gives 4-trifluoromethyl-N-[3-(R or S)-[1-[4-hydroxy-2-oxo-6,6-di-n-propyl-5,6-dihydro-2H-pyran-3-yl]-2,2-dimethylpropyl]-phenyl]-2-pyridinesulfonamide as an amorphous solid.

Physical characteristics are as follows:
MS(EI): 525, 512, 428, 411, 302, 284, 258, 146, 57
HRMS: 568.2209

EXAMPLE 292

4-Trifluoromethyl-N-[3-(R or S)-[1-[4-hydroxy-2-oxo-6,6-di-n-propyl-5,6-dihydro-2H-pyran-3-yl]-2,2-dimethylpropyl]-phenyl]-2-pyridinesulfonamide (Formula TTT-7; $R_1$ is t-butyl; $R_2$ is methyl; $R_3$ is 4-trifluoromethylpyridine; Refer to Chart TTT).

Following the procedure of Example 283 but substituting Isomer 2 of Preparation 144 (Formula TTT-5; Chart TTT; $R_1$ is t-butyl; $R_2$ is methyl) gives 4-trifluoromethyl-N-[3-(R or S)-[1-[4-hydroxy-2-oxo-6,6-di-n-propyl-5,6-dihydro-2H-pyran-3-yl]-2,2-dimethylpropyl]-phenyl]-2-pyridinesulfonamide as an amorphous solid.

Physical characteristics are as follows:
MS(EI): 569, 551, 511, 493, 439, 371, 360, 303, 284, 161, 139
HRMS (MI+H$^+$): 569.2297

Preparation 134 N-[3-[1-[5,6-Dihydro-4-hydroxy-2-oxo-6-(2-phenethyl)-6-n-propyl-2H-pyran-3-yl]-2,2-dimethylpropyl]phenyl-carbamic acid, phenylmethyl ester (Formula RRR-1; $R_1$ is t-butyl; Refer to Chart RRR).

To 4.8 g of AlCl$_3$ at −70° C., under N$_2$, is added 120 ml of THF. The mixture is allowed to stir at 0° C. for 15 minutes and 4.68 g of (formula RRR-A) of Preparation 17 is added. The reaction mixture is stirred for 15 minutes and 4.59 g of 3-aminoCbZ-benzaldehyde (formula RRR-B) is added. The reaction mixture is stirred for 15 minutes at 0° C. followed by 3 hours at room temperature. The reaction is cooled to 0° C. and 26 g of sodium carbonate monohydrate (0.21M) is added, with vigorous stirring, followed by 1.08 ml of water. After stirring at 0° C. for an additional 15 minutes, the mixture is treated with 120 ml of THF and filtered through celite. The celite is washed well with THF and the THF solution is evaporated to dryness under vacuum to an amber foam. The residue is dissolved in 120 ml of THF, the solution is cooled to −5° C. and 2. 1 g of CuBr.Me$_2$S added. The mixture is stirred for 15 minutes and 65 mL of a 1M t-butylmagnesium chloride in THF solution is added, dropwise, with temperatures not rising above 0° C. The reaction is allowed to stir for an additional 15 minutes at 0° C. and 6 ml of water is slowly added followed by 30 ml of 1N HCl. The reaction mixture is poured into 1.3L of ethyl ether. The aqueous layer is separated and the organic layer is extracted three times with 10% aqueous ammonium carbonate followed by once with water. The organic solution is dried over anhydrous sodium sulfate, filtered and evaporated to dryness to give an amorphous foam. This crude material is chromatographed over silica gel using 30% ethyl acetate in hexane as eluent to give 6.15 g the title product.

Preparation 135 Preparative resolution of N-[3-[1-[5,6-Dihydro-4-hydroxy-2-oxo-6-(2-phenethyl)-6-n-propyl-2H-pyran-3-yl]-2,2-dimethylpropyl]phenyl-carbamic acid, phenylmethyl ester (Formula RRR-1; $R_1$ is t-butyl) into four isomers, 3-(R or S)-[1-[5,6-Dihydro-4-hydroxy-2-oxo-6-(R or S)-(2-phenethyl)-6-(R or S)-n-propyl-2H-pyran-3-yl]-2, 2-dimethyl-propyl]phenyl-carbamic acid, phenylmethyl ester (Formulas RRR-3 to 6; $R_1$ is t-butyl; Refer to Chart RRR).

The four constituent enantiomers are (in order of elution from system A) Isosmer 1 (Formula RRR-4; refer to Chart RRR), Isomer 2 (Formula RRR-3; refer to Chart RRR), Isomer 3 (Formula RRR-5; refer to Chart RRR), and Isomer 4 (Formula RRR-6; refer to Chart RRR). System A consists of a 0.46×25 cm Chiralcel OD-H column eluted at 0.5 mL/min with 20% isopropanol and 0.1% trifluoroacetic acid in hexane (V/V). (Chiralcel OD-H is a registered trademark of Chiral Technologies, Inc., Exton Pa. 19341.)

The first phase of the resolution is accomplished with a 2.1×25 cm (R,R) Whelk-O 1 column eluted with 20% (V/V) isopropanol in hexane at 12 mL/min. ((R,R) Whelk-O 1 is a registered trademark of Regis Technologies, Inc., Morton Grove, Ill. 60053.) The peaks eluting at approximately 35 and 41 min are, respectively, a mixture of Isomer 3 and Isomer 4 and a mixture of Isomers 1 and 2 and as judged from System A, above. The two mixtures are further treated as below.

In the second phase of the resolution, the mixture from above that elutes near 41 minutes is injected onto a 2.1×25 cm Chiralcel OD column (Chiral Technologies, Inc.) and elutes with 15% isopropanol and 0.05% trifluoracetic acid in hexane (V/V) at 9.0 mL/min. The peaks that elute near 11.0 and 22.0 minutes are designated respectively, peaks 1 and 2 and as judged from System A.

In the final phase of the resolution, the mixture that elutes from the Whelk-O column near 35 minutes is injected onto a 2.2×25 cm Chiralcel OD column and elutes with 35% isopropanol and 0.1% trifluoroacetic acid (V/V) in hexane at 9.0 mL/min. The isomer that elutes near 9.7 minutes is designated peak 3 and the one that elutes near 16.6 minutes is designated peak 4.

Preparation 136 3-[1-(3-Aminophenyl)-2,2-dimethyl-propyl]-5,6-dihydro-4-hydroxy-6-phenethyl-6-n-propyl-pyran-2-one (Formula RRR-2, Refer to Chart RRR).

To 590 mg of 3-[1-[5,6-dihydro-4-hydroxy-2-oxo-6-(2-phenethyl)-6-n-propyl-2H-pyran-3-yl]-2,2-dimethylpropyl] phenyl-carbamic acid of Preparation 134, is added 10ml of methanol and 660 mg of ammonium formate. When all the reactants are dissolved, 140 mg of 10% Pd/C is added and the reaction is allowed to stir at room temperature for 60 minutes. The reaction is filtered (celite) and the filter pad is washed well with methanol and the methanol solution is evaporated under vacuum to a crude solid. The solid is partitioned between water and methylene chloride, and the methylene chloride layer is washed twice with water, dried over anhydrous sodium sulfate and evaporated to dryness to give 372 mg of 3-[1-(3-amino-pheny)-2,2-dimethyl-propyl]-5,6-dihydro-4-hydroxy-6-phenethyl-6-n-propyl-pyran-2-one. This material is identical to material described earlier (Formula T-4; refer to Chart T).

Preparation 137 3(R or S)-[1-(3-amino-phenyl)-2,2-dimethyl-propyl]-5,6-dihydro-4-hydroxy-6(R or S)-phenethyl-6(R or S)-propyl-pyran-2-one (Formula RRR-7; $R_1$ is t-butyl; Refer to Chart RRR).

Following the procedure of Preparation 136 but substituting the compound in Preparation 135 designated peak 2 for the compound of Preparation 134 gives 3(R or S)-[1-(3-amino-pheny)-2,2-dimethyl-propyl]-5,6-dihydro-4-hydroxy-6(R or S)-phenethyl-6(R or S)-propyl-pyran-2-one as an amorphous foam.

Physical characteristics are as follows:
MS(EI): 421, 365, 164, 163, 147, 146, 118, 107, 91, 57.
HRMS: 421.2617

Preparation 138 3(R or S)-[1-(3-Amino-pheny)-2,2-dimethyl-propyl]-5,6-dihydro-4-hydroxy-6(R or S)-phenethyl-6(R or S)-propyl-pyran-2-one (Formula RRR-8; $R_1$ is t-butyl; Refer to Chart RRR).

Following the procedure of Preparation 136 but substituting the compound of Preparation 135 designated peak 1 for the compound of Preparation 134 gives 3(R or S)-[1-(3-amino-pheny)-2,2-dimethyl-propyl]-5,6-dihydro-4-hydroxy-6(R or S)-phenethyl-6 (R or S)-propyl-pyran-2-one as an amorphous foam.

Physical characteristics are as follows:
MS(EI): 421, 365, 164, 163, 147, 146, 118, 107, 91, 57.

EXAMPLE 293

5-Trifluoromethyl-N-[3-[1-[5,6-dihydro-4-hydroxy-2-oxo-6-(2-phenethyl)-6-n-propyl-2H-pyran-3-yl]-2,2-dimethylpropyl]-phenyl]-2-pyridinesulfonamide (Formula RRR-15; $R_1$ is t-butyl; $R_2$ is 5-trifluoromethyl; Refer to Chart RRR).

Following the procedure of Example 281 but substituting the product of Preparation 136 for the product of Preparation 132 gives 5-trifluoromethyl-N-[3-[1-[5,6-dihydro-4-hydroxy-2-oxo-6-(2-phenethyl)-6-n-propyl-2H-pyran-3-yl]-2,2-dimethylpropyl]-phenyl]-2-pyridinesulfonamide as an amorphous foam.

Physical characteristics are as follows:
MS(EI): 497, 411, 401, 383, 343, 331, 197, 174, 146, 133
HRMS: 540.1938

EXAMPLE 294

5-Trifluoromethyl-N-[3(R or S)-[1-[5,6-dihydro-4-hydroxy-2-oxo-6(R or S)-(2-phenethyl)-6(R or S)-n-propyl-2H-pyran-3-yl]-2,2-dimethylpropyl]-phenyl]-2-pyridinesulfonamide (Formula RRR-11; $R_1$ is t-butyl; $R_2$ is 5-trifluoromethyl; Refer to Chart RRR).

Following the procedure of Example 281 but substituting the product of Preparation 137 for the product of Preparation 132 gives 5-trifluoromethyl-N-[3 (R or S)-[1-[5,6-dihydro-4-hydroxy-2-oxo-6(R or S)-(2-phenethyl)-6(R or S)-n-propyl-2H-pyran-3-yl]-2,2-dimethylpropyl]-phenyl]-2-pyridinesulfonamide as an amorphous foam.

Physical characteristics are as follows:
MS(EI): 373, 355, 201, 146, 145, 118, 117, 91, 57.
HRMS: 630.2394

EXAMPLE 295

5-Trifluoromethyl-N-[3 (R or S)-[1-[5,6-dihydro-4-hydroxy-2-oxo-6(R or S)-(2-phenethyl)-6(R or S)-n-propyl-2H-pyran-3-yl]-2,2-dimethylpropyl]-phenyl]-2-pyridinesulfonamide (Formula RRR-12; $R_1$ is t-butyl; $R_2$ is 5-trifluoromethyl; Refer to Chart RRR).

Following the procedure of Preparation 281 but substituting the product of Preparation 138 for the product of Preparation 132 gives 5-trifluoromethyl-N-[3(R or S)-(-(1-[5,6-dihydro-4-hydroxy-2-oxo-6(R or S)-(2-phenethyl)-6(R or S)-n-propyl-2H-pyran-3-yl]-2,2-dimethylpropyl)phenyl]-2-pyridinesulfonamide as an amorphous foam.

Physical characteristics are as follows:
MS(EI): 373, 355, 201, 146, 145, 118, 117, 91, 57.
HRMS: 630.2379

EXAMPLE 296

4-Trifluoromethyl-N-[3(R or S)-[1-[5,6-dihydro-4-hydroxy-2-oxo-6(R or S)-(2-phenethyl)-6(R or S)-n-propyl-2H-pyran-3-yl]-2,2-dimethylpropyl]-phenyl]-2-pyridinesulfonamide (Formula RRR-11, $R_1$ is t-butyl; $R_2$ is 4-trifluoromethyl; Refer to Chart RRR).

Following the procedure of Example 294 but substituting the product of Preparation 128 for the product of Preparation 129 gives 4-trifluoromethyl-N-[3(R or S)-[1-[5,6-dihydro-4-hydroxy-2-oxo-6(R or S)-(2-phenethyl)-6(R or S)-n-propyl-2H-pyran-3-yl]-2,2-dimethylpropyl]-phenyl]-2-pyridinesulfonamide as an amorphous foam.

Physical characteristics are as follows:
MS(EI): 633, 632, 631, 614, 613, 346, 201, 146, 91, 57.
HRMS: 631.2444

EXAMPLE 297

4-Trifluoromethyl-N-[3(R or S)-[1-[5,6-dihydro-4-hydroxy-2-oxo-6(R or S)-(2-phenethyl)-6(R or S)-n-propyl-2H-pyran-3-yl]-2,2-dimethylpropyl]-phenyl]-2-pyridinesulfonamide (Formula RRR-12; $R_1$ is t-butyl; $R_2$ is 4-trifluoromethyl; Refer to Chart RRR).

Following the procedure of Example 295 but substituting the product of Preparation 128 for the product of Preparation 129 gives 4-trifluoromethyl-N-[3(R or S)-[1-[5,6-dihydro-4-hydroxy-2-oxo-6(R or S)-(2-phenethyl)-6(R or S)-n-propyl-2H-pyran-3-yl]-2,2-dimethylpropyl]-phenyl]-2-pyridinesulfonamide as an amorphous foam.

Physical characteristics are as follows:
MS(EI): 633, 632, 631, 614, 613, 346, 201, 146, 91, 57.
HRMS: 631.2450

EXAMPLE 298

5-Trifluoromethyl-N-[3(R or S)-[1-[5,6-dihydro-4-hydroxy-2-oxo-6(R or S)-(2-phenethyl)-6(R or S)-n-propyl-2H-pyran-3-yl]-propyl]-phenyl]-2-pyridinesulfonamide (Formula RRR-11; $R_1$ is ethyl; $R_2$ is 5-trifluoromethyl; Refer to Chart RRR).

Following the procedure of Example 294 but substituting the product of Preparation 147A gives 5-trifluoromethyl-N-[3(R or S)-(-(1-[5,6-dihydro-4-hydroxy-2-oxo-6(R or S)-(2-phenethyl)-6(R or S)-n-propyl-2H-pyran-3-yl]-propyl) phenyl]-2-pyridinesulfonamide as an amorphous foam.

Physical characteristics are as follows:
MS(EI): 605, 604, 603, 602, 586, 585, 393, 201, 133, 91
HRMS: 603.2153

EXAMPLE 298A
5-Trifluoromethyl-N-[3(R or S)-[1-[5,6-dihydro-4-hydroxy-2-oxo-6(R or S)-(2-phenethyl)-6(R or S)-n-propyl-2H-pyran-3-yl]-propyl]-phenyl]-2-pyridinesulfonamide (Formula RRR-12; $R_1$ is ethyl; $R_2$ is 5-trifluoromethyl; Refer to Chart RRR).

Following the procedure of Example 294 but substituting the amine derived from Isomer 1 of Preparation 147 (derived following the procedure of Preparation 147A) gives the title compound as an amorphous foam.

Physical characteristics are as follows:
$^1$H NMR (CD$_3$OD): δ 8.9, 8.2, 8.0, 7.0–7.3, 3.9, 2.4–2.7, 1.2–2.2, 0.8–1.0.

TLC (silica gel GF): Rf=0.19, 40% ethyl acetate in hexane.

Preparation 139 (5-Nitro-pyridin-2-yl)-isothiourea hydrochloride (Formula UUU-2) Refer to Chart UUU.

A solution of 3.81 g of thiourea in 75 mL of hot absolute ethanol is treated with 7.61 g of 2-chloro-5-nitropyridine (Formula UUU-1) and is heated at reflux for 6 hours. The mixture is then cooled to 0° C. and the precipitated solid is collected. The solid is washed sequentially with cold absolute ethanol and chloroform. The solid is dried in vacuo to afford 6.91 g of the title product as a light brown solid.

Physical characteristics are as follows:
MP 175° C. (dec.)
$^1$H NMR (CD$_3$OD) δ 7.9, 8.6, 9.4 ppm Preparation 140 5-Nitro-2-thiopyridine (Formula UUU-3) Refer to Chart UUU.

A solution of 1.65 g of sodium carbonate in 50 mL of water is treated with 2.35 g of the title compound of Preparation 139. The mixture is charged with a solution of 2.75 g of sodium hydroxide in 50 mL of water and the resulting mixture is warmed to room temperature. After stirring for 1 hour, the mixture is heated to 95° C. for 1 hour and finally cooled to room temperature. The aqueous mixture is extracted with two portions of diethyl ether and then carefully acidified with 6 N aqueous hydrochloric acid. The orange precipitated solid is collected and washed sequentially with cold dilute aqueous hydrochloric acid and water. The solid is dried in vacuo to afford 1.27 g of the title product as an orange solid.

Physical characteristics are as follows:
MP 167–170° C.
$^1$H NMR (CDCl$_3$-CD$_3$OD) δ 7.4, 7.9, 8.5 ppm Preparation 141 5-Nitro-2-pyridinesulfonyl chloride (Formula UUU-4) Refer to Chart UUU.

To a suspension of 1.27 g of the title compound of Preparation 140 in 25 mL of 1 N aqueous hydrochloric acid and 5 mL of acetic acid at 0° C. is vigorously bubbled in chlorine gas. After 15 minutes, the chlorine gas addition is ceased and replaced with nitrogen gas. The resulting solid is collected and washed sequentially with cold dilute aqueous hydrochloric acid and water. The solid is dried in vacuo to afford 1.60 g of the title product as a tan solid.

Physical characteristics are as follows:
MP 77–80° C.
$^1$H NMR (CDCl$_3$) δ 8.3, 8.8, 9.6 ppm Preparation 142 N-[3-(1-[5,6-Dihydro-4-hydroxy-2-oxo-6-(2-phenylethyl)-6-propyl-2H-pyran-3-yl]-2,2-dimethylpropyl)phenyl]-5-nitro-2-pyridinesulfonamide (Formula UUU-5: $R_1$ is 2-phenylethyl, $R_2$ is propyl, $R_3$ is tert-butyl) Refer to Chart To a solution of 210 mg of the title compound of Preparation 81 (Formula T-4) in 2 mL of dichloromethane at 0° C. is added 80 μL of pyridine followed by 111 mg of the title compound of Preparation 141 (Formula UUU-4). After warming to room temperature overnight, the reaction mixture is column chromatographed on flash silica gel eluting with 3% to 9% ethyl acetate in dichloromethane to provide 303 mg of the title compound as a yellow foam.

Physical characteristics are as follows:
$^1$H NMR (CDCl$_3$-CD$_3$OD) δ 0.8–1.0, 1.2–1.4, 1.6–1.9, 2.4–2.7, 4.0, 6.9–7.4, 8.0, 8.5, 9.4 ppm
HRMS 608.2412 (EI)

EXAMPLE 299
5-Amino-N-[3-(1-[5,6-dihydro-4-hydroxy-2-oxo-6-(2-phenylethyl)-6-propyl-2H-pyran-3-yl]-2,2-dimethylpropyl)phenyl]-2-pyridinesulfonamide (Formula UUU-6: $R_1$ is 2-phenylethyl, $R_2$ is propyl, $R_3$ is tert-butyl) Refer to Chart UUU.

To a solution of 300 mg of the title compound of Preparation 142 (Formula UUU-5) in 5 mL of methanol under argon is added 500 mg of ammonium formate followed by 100 mg of 10% palladium on carbon. After 1 hour, the reaction mixture is filtered through a pad of Celite with methanol washes. The combined filtrates are concentrated under reduced pressure and the residue is repeatedly triturated with portions of dichloromethane. The combined dichloromethane washes are concentrated under reduced pressure and the residue is column chromatographed on flash silica gel eluting with 50% ethyl acetate in dichloromethane to provide 246 mg of the title compound as a white solid.

Physical characteristics are as follows:
$^1$H NMR (CDCl$_3$-CD$_3$OD) δ 0.8–1.0, 1.2–1.4, 1.5–2.0, 2.4–2.6, 4.0, 6.7, 6.8–7.3, 7.4, 7.9 ppm
HRMS 577.2617 (EI)

EXAMPLE 300–327

Following the procedures and preparations described above and using starting materials known and available to one of ordinary skill in organic synthesis, the following additional compounds in Table 3 of the present invention are made from the compounds prepared in the following preparations:

Preparation 143 Preparative separation of N-[3-[1-[5,6-Dihydro-4-hydroxy-2-oxo-6-(2-phenethyl)-6-n-propyl-2H-pyran-3-yl]-2,2-dimethylpropyl]phenyl-carbamic acid phenylmethyl ester, to give 4 isomers.

The title compound of Preparation 134 is separated into four constituent steroisomers which are (in order of elution from system A) 4 isomers: Isomer 1, Isomer 2, Isomer 3, and Isomer 4 with the following approximate observed retention times 10.5, 14.9, 21.4 and 65.2 minutes respectively. System A consists of a 0.46×25 cm Chiralcel OD-H column eluting at 0.5 mL/min with 20% isopropanol and 0.1% trifluoroacetic acid in hexane (V/V). (Chiralcel OD-H is a registered trademark of Chiral Technologies, Inc., Exton PA 19341.) The first phase of the separation is accomplished with a 2.1×25 cm (R,R) Whelk-O 1 column eluting with 20% (V/V) isopropanol in hexane at 12 mL/min. ((R,R)Whelk-O 1 is a registered trademark of Regis Technologies, Inc., Morton Grove, Ill. 60053.) The peaks eluting at approximately 35 and 41 min are, respectively, a mixture of Isomers 3 and 4 and a mixture of Isomers 1 and 2 as judged from System A, above. The two mixtures are further treated as below.

In the second phase of the separation, the mixture from above that elutes near 41 minutes is injected onto a 2.1×25 cm Chiralcel OD column (Chiral Technologies, Inc.) and eluting with 15% isopropanol and 0.05% trifluoroacetic acid in hexane (V/V) at 9.0 mL/min. The peaks that elute near 11.0 and 22.0 minutes are, respectively, Isomer 1 and Isomer 2 as judged from System A.

In the final phase of the separation, the mixture that elutes from the (R,R) Whelk-O 1 column near 35 minutes is injected onto a 2.2×25 cm Chiralcel OD column eluting with 35% isopropanol and 0.1% trifluoroacetic acid (V/V) in hexane at 9.0 mL/min. The isomer that elutes near 9.7 minutes is Isomer 3 and the one that elutes near 16.6 minutes is Isomer 4.

In both phases of the separation of stereoisomers, fractions are pooled after assay with System A and pools are concentrated to dryness on a rotary evaporator.

Preparation 144 Resolution of N-[3-(1-[5,6-Dihydro-6,6-dipropyl-4-hydroxy-2-oxo-2H-pyran-3-yl]-2,2-dimethylpropyl)-phenyl]carbamic acid, phenylmethyl ester to give 2 isomers.

Samples of the starting compound (up to 1.0 gm each run) are injected onto a 5.1×50 cm Chiralcel OD column (Chiral Technologies, Inc.). The enantiomers elute at about 23 min (This corresponds to the benzyloxycarbonyl protected analogue of amine (Isomer 1) (EI-MS: 359 [M+]; $^1$H NMR (CDCl$_3$-CD$_3$OD): 7.1–6.9, 6.5, 4.2, 2.6–2.3, 1.8–1.2, 1.1, 0.9; TLC: R-0.42 (10% ethyl acetate in dichloromethane)), and at about 33 min (This corresponds to the benzyloxycarbonyl protected analogue of amine (Isomer 2) (EI-MS: 359 [M+]; $^1$H NMR (CDCl$_3$-CD$_3$OD): 7.1–6.9, 6.5, 4.2, 2.6–2.3, 1.8–1.2, 1.1, 0.9; TLC: R-0.42 (10% ethyl acetate in dichloromethane)). The mobile phase is 20% isopropanol and 0.1% acetic acid in hexane (V/V) pumped at 60 mL/min. The purity is checked on a 0.46×25 cm Chiralcel OD-H column (Chiral Technologies, Inc.). The mobile phase is 20% isopropanol in hexane (V/V) and 0.05% trifluoroacetic acid pumped at 0.5 mL/min. The observed retention times are 8.9 and 16.7 min (monitor set at 238 nm) for Isomer 1 and Isomer 2, respectively.

Preparation 145 Resolution of N-[3-(1-[6,6-Bis(2-phenylethyl)-5,6-dihydro-4-hydroxy-2-oxo-2H-pyran-3-yl]propyl)phenyl]carbamic acid, phenylmethyl ester to give 2 isomers.

Samples of the starting compound (up to 1.3 gm each run) are injected onto a 5.1×50 cm Chiralcel OD column (Chiral Technologies, Inc.). The enantiomers are eluted with 20% isopropanol and 0.025% acetic acid in hexane (V/V) at 60 mL/min until the first enantiomer elutes. At this point (approximately 120 min into the run) the flow rate is increased to 90 mL/min to expedite elution of the second enantiomer. The enantiomers elute near 91.2 min (This is the corresponding benzyloxycarbonyl analogue of amine Isomer 1 and near 132 min (This is the corresponding benzyloxycarbonyl analogue of amine Isomer 2. The purity is checked on a 0.46×25 cm Chiralcel OD-H column. The mobile phase is 30% isopropanol in hexane (V/V) pumped at 0.5 mL/min.

Preparation 146 5-Carbamoylpyridine-2-sulfonyl chloride (Formula VVV-2) Refer to Chart VVV.

Into a cold (0°), stirred suspension of 400 mg of 2-mercapto-5-carbamoylpyridine of formula VVV-1 in 7.5 ml of 1N HCl is passed a brisk stream of chlorine gas. After ten minutes, the suspension is filtered, and the solid washed well with water and dried in vacuo. Obtained is 517 mg of the title compound as a nearly white solid.

EXAMPLE 328

N-[3-{1-(4-Hydroxy-5,6-dihydro-2-oxo-6-(2-(4-fluorophenyl)ethyl)-6-propyl-2H-pyran-3-yl)-2,2-dimethylpropyl}phenyl]-4-cyanobenzenesulfonamide (Formula U-8: R$_1$ is tert-butyl, R$_2$ is 4-cyanophenyl) Refer to Chart U.

Using the general sulfonation procedure of Example 252, 88 mg of the amine of Preparation 86 (Formula U-7, R$_1$ is tert-butyl) is reacted with 4-cyanobenzenesulfonyl chloride. Flash chromatography on silica gel using 10% ethyl acetate in dichloromethane provides 117 mg of the title compound as an amorphous white solid.

Physical characteristics are as follows:
$^1$H NMR δ 0.90, 1.3, 1.7, 2.5, 3.6, 6.8–7.4, 7.6, 7.8 ppm
HRMS: 605.2478
R$_f$ 0.36 (10% ethyl acetate in dichloromethane)

EXAMPLE 329

N-[3-{1-(4-Hydroxy-5,6-dihydro-2-oxo-6-(2-(4-fluorophenyl)ethyl)-6-propyl-2H-pyran-3-yl)-2,2-dimethylpropyl)phenyl]-8-quinolinesulfonamide (Formula U-8: R$_1$ is tert-butyl, R$_1$ is 8-quinolyl) Refer to Chart U.

Using the general sulfonylation procedure of Example 252, 88 mg of the amine of Preparation 86 (Formula U-7, R$_1$ is tert-butyl) is reacted with 8-quinolinesulfonyl chloride. Flash chromatography on silica gel using 5–10% ethyl acetate in dichloromethane provides 101 mg of the title compound as an amorphous white solid.

Physical characteristics are as follows:
$^1$H NMR δ 0.63, 0.9, 1.1, 1.3, 1.6–1.9, 2.4–2.6, 6.7–7.6, 8.0, 8.2, 9.1 ppm
HRMS: 631.2638
R$_f$ 0.30 (5% ethyl acetate in dichloromethane)

EXAMPLE 330

N-[3-{1-(4-Hydroxy-5,6-dihydro-2-oxo-6,6-bis(2-phenylethyl)-2H-pyran-3-yl)propyl}phenyl]-1-methyl-1H-imidazole-4-sulfonamide (Formula D-6: R$_1$ is phenethyl, R$_2$ is phenethyl, R$_3$ is ethyl, R$_4$ is 1-methylimidazole-4-yl) Refer to Chart D.

Using the general sulfonylation procedure of Example 252, 77 mg of the amine of Formula D-5, wherein R$_1$ and R$_2$ are phenethyl and R$_3$ is ethyl, is reacted with 1-methylimidazole-4-sulfonyl chloride. Flash chromatography on silica gel using 3% methanol in dichloromethane provides 97.0 mg of the title compound as a crystalline white solid.

Physical characteristics are as follows:
$^1$H NMR δ 0.88, 1.9–2.2, 2.6, 3.6–3.8, 3.97, 6.9–7.5 ppm
HRMS: 600.2521
R$_f$ 0.31 (5% methanol in dichloromethane)

EXAMPLE 331

N-[3-{1-(4-Hydroxy-5,6-dihydro-2-oxo-6,6-bis(2-phenylethyl)-2H-pyran-3-yl)propyl}phenyl]-5-cyanopyridine-2-sulfonamide (Formula D-6: R$_1$ is phenethyl, R$_2$ is phenethyl, R$_8$ is ethyl, R$_4$ is 5-cyanopyridine-2-yl) Refer to Chart D.

Using the general sulfonylation procedure of Example 252, 77 mg of the amine of Formula D-5, wherein R$_1$ and R$_2$ phenethyl and R$_3$ is ethyl, is reacted with 5-cyanopyridine-2-sulfonyl chloride. Flash chromatography on silica gel using 10% ethyl acetate in dichloromethane provides 88.3 mg of the title compound as a crystalline white solid.

Physical characteristics are as follows:
$^1$H NMR δ 0.85, 1.8–2.2, 2.5–2.7, 3.97, 6.9–7.4, 7.9, 8.8 ppm.
HRMS: 622.2355
R$_f$ 0.28 (10% ethyl acetate in dichloromethane)

EXAMPLE 332

N-[3-{1-(4-Hydroxy-5,6-dihydro-2-oxo-6-(2-(4-fluorophenyl)ethyl)-6-propyl-2H-pyran-3-yl)propyl}phenyl]-5-carbamoylpyridine-2-sulfonamide (Formula U-8: $R_1$ is ethyl, $R_2$ is 5-carbamoylpyridine-2-yl) Refer to Chart U.

Using the general sulfonylation procedure of Example 252, 82 mg of the amine of Formula U-7, wherein $R_1$ is ethyl, is reacted with 5-carbamoylpyridine-2-sulfonyl chloride of Preparation 146. Flash chromatography on silica gel using 3–6% methanol in dichloromethane provides 55.4 mg of the title compound as an amorphous solid.

Physical characteristics are as follows:
$^1$H NMR δ 0.7–0.9, 1.3, 1.6–2.1, 2.5, 3.9, 6.8–7.3, 7.8, 8.2 ppm.
HRMS: 596.2216
$R_f$ 0.16 (5% methanol in dichloromethane)

EXAMPLE 333

N-[3-{1-(4-Hydroxy-5,6-dihydro-2-oxo-6,6-bis(2-(4-fluorophenyl)ethyl)-2H-pyran-3-yl)propyl}phenyl]-5-carbamoylpyridine-2-sulfonamide (Formula V-8: $R_1$ is ethyl, $R_2$ is 5-carbamoylpyridine-2-yl) Refer to Chart V.

Using the general sulfonylation procedure of Example 252, 98 mg of the amine of formula V-7, wherein $R_1$ is ethyl) is reacted with 5-carbamoylpyridine-2-sulfonyl chloride of Preparation 146. Flash chromatography on silica using 3–6% methanol in dichloromethane provides 58.3 mg of the title compound as an amorphous solid.

Physical characteristics are as follows:
$^1$H NMR δ 0.83, 1.8–2.2, 2.5–2.6, 6.8–7.2, 7.8, 8.1, 9.0 ppm.
HRMS: 676.2297
$R_f$ 0.17 (5% methanol in dichloromethane)

EXAMPLE 334

N-[3-{1-(4-Hydroxy-5,6-dihydro-2-oxo-6,6-dipropyl-2H-pyran-3-yl)propyl}phenyl]-5-carbamoylpyridine-2-sulfonamide (Formula D-6: $R_1$ is propyl, $R_2$ is propyl, $R_3$ is ethyl, $R_4$ is 5-carbamoyl-pyridine-2-yl) Refer to Chart D.

Using the general sulfonylation procedure of Example 252, 66 mg of the amine of Formula D-5 ($R_1$ and $R_2$ are propyl, $R_5$ is ethyl) is coupled with 5-carbamoylpyridine-2-sulfonyl chloride of Preparation 146 to yield, after flash chromatography on silica gel using 3–6% methanol in dichloromethane, 83.8 mg of the title compound as an amorphous white solid.

Physical characteristics are as follows:
$^1$H NMR δ 0.7–0.9, 1.2–2.1, 3.87, 7.0–7.3, 7.8, 8.2 ppm.
HRMS: 516.2156
$R_f$ 0.22 (5% methanol in dichloromethane)

Preparation 147 Resolution of N-[3-[1-(4-Hydroxy-5,6-dihydro-2-oxo-6-phenethyl-6-propyl-2H-pyran-3-yl)propyl]phenyl]-carbamic acid, phenylmethyl ester to give 4 isomers (Formula WWW-2: $R_1$ is phenethyl, $R_2$ is propyl, $R_3$ is ethyl) Refer to Chart WWW and RRR.

The four isomers of the product of Preparation 130A (Formula RRR-1; $R_1$=ethyl) are (in order of increasing retention time on System B): (ca. 16.9 min) (Isomer 1), (ca. 28.0 min) (Isomer 2), (ca. 38.2 min) (Isomer 3) and (ca. 49.8 min) (Isomer 4). System B consists of a 0.46×25 cm Chiralcel OD-H column (Chiral Technologies, Inc.) eluting with 25% isopropanol in hexane (V/V) at 0.5 mL/min.

In Phase one of the complete resolution repeatedly inject 55 mg samples of the product of Preparation 130A onto a 2.1×25 cm (R,R) Whelk-O 1 column (Regis Technologies, Inc.). Elute the isomers at 10 mL/min with 35% isopropanol and 0.5% acetic acid in hexane (V/V). The first of the three peaks to elute (near 12 min) is a mixture of Isomers 1 (Formula RRR-4 of Chart RRR) and 2 (Formula RRR-3 of Chart RRR) as shown by injecting aliquots in System B. Resolve this mixture in Phase 2, below.

The second phase consists of a 2.1×25 cm Chiralcel OD column kept at 30°. Inject 60 mg batches of the mixture obtained in the first phase and elute the enantiomers with 25% isopropanol and 0.05% trifluoroacetic acid (V/V) at 9 mL/min. Separately pooled and concentrated, the fractions eluting near 14.5 and 23.9 min to give Isomers 1 (Formula RRR-4 where $R_1$ is ethyl of Chart RRR) and 2 (formula RRR-3 where $R_1$ is ethyl of Chart RRR) respectively.

Preparation 147A 3-(R or S)-[1-(3-aminophenyl)-propyl]-4-hydroxy-5,6-dihydro-6-(R or S)-phenethyl-6-(R or S)-propyl-2H-pyran-2-one (Formula RRR-7; $R_1$ is ethyl; Refer to Chart RRR).

Following the procedure of Preparation 132 beginning with the peak identified as peak 2 (Formula RRR-3; $R_1$ is ethyl of Chart RRR) from the chiral resolution of the product of Preparation 147, the title compound is prepared.

Physical characteristics are as follows:
$^1$H NMR (CD$_3$-OD): δ 6.5–7.3, 3.9–4.0, 2.5–2.7, 1.2–2.3, 0.8–1.0.
TLC (silica gel GF): Rf=0.31, 40% ethyl acetate in hexane.

EXAMPLE 335

N-[3-{1(R or S)-(4-Hydroxy-5,6-dihydro-2-oxo-6(R or S)-phenethyl-6-propyl-2H-pyran-3-yl)propyl}phenyl]-5-cyanopyridine-2-sulfonamide (Formula WWW-4: $R_1$ is phenethyl, $R_2$ is propyl, $R_3$ is ethyl, $R_4$ is 5-cyanopyridine-2-yl) [Isomer 1] Refer to Chart WWW.

The title compound is prepared using the general sulfonylation procedure of Example 252, using the amine of Formula WWW-3, where $R_1$ is phenethyl, $R_2$ is propyl, and $R_3$ is ethyl. The amine is derived from the first stereoisomer of Formula WWW-2 to elute from a Chiralcel OD chiral HPLC column of Preparation 147. The title compound is obtained as an amorphous solid after flash chromatography on silica using 10% ethyl acetate in dichloromethane.

Physical characteristics are as follows:
$^1$H NMR δ 0.7–1.0, 1.2–2.6, 3.3–3.6, 6.9–7.3, 7.7–8.2, 8.8–9.0 ppm.
HRMS: 560.2210
$R_f$ 0.41 (15% ethyl acetate in dichloromethane)

EXAMPLE 336

N-[3-{1(R or S)-(4-Hydroxy-5,6-dihydro-2-oxo-6(S or R)-phenethyl-6-propyl-2H-pyran-3-yl)propyl}phenyl]-5-cyanopyridine-2-sulfonamide (Formula WWW-4: $R_1$ is phenethyl, 12 is propyl, $R_3$ is ethyl, $R_4$ is 5-cyanopyridine-2-yl) [Isomer 2] Refer to Chart WWW.

The title compound is prepared using the general sulfonylation procedure of Example 252, using the amine that is the title product of Preparation 147A (Formula WWW-3, where $R_1$ is phenethyl, $R_2$ is propyl, and $R_3$ is ethyl). The amine is derived from the second stereoisomer of Formula WW-2 to elute from a Chiralcel OD chiral HPLC column of Preparation 147A. The title compound is obtained as an amorphous solid after flash chromatography on silica using 10% ethyl acetate in dichloromethane.

Physical characteristics are as follows:
$^1$H NMR δ 0.6–2.6, 3.3–3.6, 6.9–7.3, 7.7–8.2, 8.8–9.0 ppm.
HRMS: 560.2215
$R_f$ 0.41 (15% ethyl acetate in dichloromethane)

EXAMPLE 337

N-[3-{1(S or R)-(4-Hydroxy-5,6-dihydro-2-oxo-6(R or S)-phenethyl-6-propyl-2H-pyran-3-yl)propyl}phenyl]-5-cyanopyridine-2-sulfonamide (Formula WWW-4: $R_1$ is phenethyl, $R_2$ is propyl, $R_5$ is ethyl, $R_4$ is 5-cyanopyridine-2-yl) [Isomer 3] Refer to Chart WWW.

The title compound is prepared using the general sulfonylation procedure of Example 252, using the amine of Formula WWW-3, where $R_1$ is phenethyl, $R_2$ is propyl, and $R_3$ is ethyl. The amine is derived from the third stereoisomer of Formula WWW-2 to elute from a Chiralcel OD chiral HPLC column of Preparation 147. The title compound is obtained as an amorphous solid after flash chromatography on silica using 10% ethyl acetate in dichloromethane.

Physical characteristics are as follows:
$^1$H NMR δ 0.6–2.6, 3.3–3.6, 6.9–7.3, 7.7–8.2, 8.8–9.0 ppm.
HRMS: 560.2210
$R_f$ 0.41 (15% ethyl acetate in dichloromethane)

EXAMPLE 338
N-[3-{1(S or R)-(4-Hydroxy-5,6-dihydro-2-oxo-6(S or R)-phenethyl-6-propyl-2H-pyran-3-yl)propyl]phenyl]-5-cyano-pyridine-2-sulfonamide (Formula WW-4: $R_1$ is phenethyl, $R_2$ is propyl, $R_3$ is ethyl, $R_4$ is 5-cyanopyridine-2-yl) [Isomer 4] Refer to Chart WWW.

The title compound is prepared using the general sulfonylation procedure of Example 252, using the amine of Formula WWW-3, where $R_1$ is phenethyl, $R_2$ is propyl, and $R_3$ is ethyl. The amine is derived from the fourth stereoisomer of Formula WWW-2 to elute from a Chiralcel OD chiral HPLC column of Preparation 147. The title compound is obtained as an amorphous solid after flash chromatography on silica using 10% ethyl acetate in dichloromethane.

Physical characteristics are as follows:
$^1$H NMR δ 0.7–1.0, 1.2–2.6, 3.3–3.6, 6.9–7.3, 7.7–8.2, 8.8–9.0 ppm.
HRMS: 560.2210
$R_f$ 0.41 (15% ethyl acetate in dichloromethane)

EXAMPLE 339
N-[3-{1(R or S)-(4-Hydroxy-5,6-dihydro-2-oxo-6(R or S)-phenethyl-6-propyl-2H-pyran-3-yl)propyl}phenyl]-1-methyl-1H-imidazole-4-sulfonamide (Formula WWW-4: $R_1$ is phenethyl, $R_2$ is propyl, $R_3$ is ethyl, $R_4$ is 1-methylimidazol-4-yl) [Isomer 1] Refer to Chart WWW.

The title compound is prepared using the general sulfonylation procedure of Example 252, using the amine of Formula WWW-3, where $R_1$ is phenethyl, $R_2$ is propyl, and $R_3$ is ethyl. The amine is derived from the first stereoisomer of Formula WWW-2 to elute from a Chiralcel OD chiral HPLC column of Preparation 147. The title compound is obtained as an amorphous solid after flash chromatography on silica using 3% methanol in dichloromethane.

Physical characteristics are as follows:
$^1$H NMR δ 0.7–2.8, 3.2–3.7, 3.9, 7.0–7.6 ppm.
HRMS: 537.2317
$R_f$ 0.36 (5% methanol in dichloromethane)

EXAMPLE 340
N-[3-{1(R or S)-(4-Hydroxy-5,6-dihydro-2-oxo-6(S or R)-phenethyl-6-propyl-2H-pyran-3-yl)propyl}phenyl]-1-methyl-1H-imidazole-4-sulfonamide (Formula WWW-4: $R_1$ is phenethyl, $R_2$ is propyl, $R_3$ is ethyl, $R_4$ is 1-methylimidazol-4-yl) [Isomer 2] Refer to Chart WWW.

The title compound is prepared using the general sulfonylation procedure of Example 252, using the amine of Formula WWW-3, where $R_1$ is phenethyl, $R_2$ is propyl, and $R_3$ is ethyl. The amine is derived from the second stereoisomer of Formula WWW-2 to elute from a Chiralcel OD chiral HPLC column of Preparation 147. The title compound is obtained as an amorphous solid after flash chromatography on silica using 3–4% methanol in dichloromethane.

Physical characteristics are as follows:
$^1$H NMR δ 0.7–2.7, 3.3–3.7, 4.0, 7.0–7.5 ppm.
HRMS: 537.2275
$R_f$ 0.36 (5% methanol in dichloromethane)

EXAMPLE 341
N-[3-{1(S or R)-(4-Hydroxy-5,6-dihydro-2-oxo-6(R or S)-phenethyl-6-propyl-2H-pyran-3-yl)propyl}phenyl]-1-methyl-1H-imidazole-4-sulfonamide (Formula WW-4: $R_1$ is phenethyl, $R_2$ is propyl, $R_3$ is ethyl, $R_4$ is 1-methylimidazol-4-yl) [Isomer 3] Refer to Chart WWW.

The title compound is prepared using the general sulfonylation procedure of Example 252, using the amine of Formula WWW-3, where $R_1$ is phenethyl, $R_2$ is propyl, and $R_3$ is ethyl. The amine is derived from the third stereoisomer of Formula WWW-2 to elute from a Chiralcel OD chiral HPLC column of Preparation 147. The title compound is obtained as an amorphous solid after flash chromatography on silica using 3% methanol in dichloromethane.

Physical characteristics are as follows:
$^1$H NMR δ 0.7–2.7, 3.3–3.7, 4.0, 7.0–7.5 ppm.
HRMS: 537.2329
$R_f$ 0.36 (5% methanol in dichloromethane)

EXAMPLE 342
N-[3-{1(S or R)-(4-Hydroxy-5,6-dihydro-2-oxo-6(S or R)-phenethyl-6-propyl-2H-pyran-3-yl)propyl}phenyl]-1-methyl-1H-imidazole-4-sulfonamide (Formula WWW-4: $R_1$ is phenethyl, $R_2$ is propyl, $R_3$ is ethyl, $R_4$ is 1-methylimidazol-4-yl) [Isomer 4] Refer to Chart WWW.

The title compound is prepared using the general sulfonylation procedure of Example 252, using the amine of Formula WWW-3, where $R_1$ is phenethyl, $R_2$ is propyl, and $R_3$ is ethyl. The amine is derived from the fourth stereoisomer of Formula WWW-2 to elute from a Chiralcel OD chiral HPLC column of Preparation 147. The title compound is obtained as an amorphous solid after flash chromatography on silica using 3% methanol in dichloromethane.

Physical characteristics are as follows:
$^1$H NMR δ 0.7–2.8, 3.2–3.7, 3.9, 7.0–7.6 ppm.
HRMS: 537.2312
$R_f$ 0.36 (5% methanol in dichloromethane)

Preparation 148 3-[(3-Nitrophenyl)methyl]-6,6-diphenethyl-4-hydroxy-5,6-dihydro-2H-pyran-2-one (Formula XXX-3) Refer to Chart XXX.

To a solution of 172 mg of 6,6-Diphenethyl-4-hydroxy-5,6-dihydro-2H-pyran-2-one of formula XXX-1 and 81 mg of meta-nitrobenzaldehyde in 2 ml of dry THF, under argon, is added a solution of 142 mg of AlCl$_3$ in 1 ml of THF. The solution is stirred at room temperature for 2 hours, then quenched with 310 mg of sodium carbonate decahydrate, diluted with ether, and filtered through Celite with ether rinses. Following removal of solvent under reduced pressure, 264 mg of crude benzylidene of Formula XXX-2 is obtained. This material is dissolved in 5 ml of methanol, and the solution cooled to 0° for the addition of 44 mg of sodium cyanoborohydride. After an hour, a further 20 mg aliquot of sodium cyanoborohydride is added. After another 30 minutes, the mixture is acidified with dilute HCl to pH 1 and extracted with three portions of dichloromethane. The extract is dried (MgSO$_4$) and then concentrated under reduced pressure. Flash chromatography of the residue on silica using 5–20% ethyl acetate in dichloromethane provides 211 mg of the title compound as an amorphous white solid.

Physical characteristics are as follows:
$^1$H NMR δ 2.0, 2.7, 3.8, 7.0–7.4, 7.6, 8.0, 8.2 ppm.
MS: M+ 457
$R_f$ 0.25 (5% ethyl acetate in dichloromethane)

Preparation 149 3-[(3-Aminophenyl)methyl]-6,6-diphenethyl-4-hydroxy-5,6-dihydro-2H-pyran-2-one (Formula XXX-4) Refer to Chart XXX.

A mixture of 211 mg of the product of Preparation 148 (Formula XXX-3) and 50 mg of 10% palladium on carbon in 5 ml of methanol is stirred at room temperature under 1 atmosphere hydrogen gas. After two hours, the mixture is filtered through Celite and concentrated under reduced pressure. Flash chromatography of the residue on silica using 25% ethyl acetate in dichloromethane affords 133.6 mg of the title compound.

Physical characteristics are as follows:
$^1$H NMR δ 2.0, 2.6, 3.6, 4.1, 6.5, 6.6, 6.7, 6.9–7.3 ppm.
MS: M+ 427
$R_f$ 0.33 (25% ethyl acetate in dichloromethane)

EXAMPLE 343

N-[3-{1-(4-Hydroxy-5,6-dihydro-2-oxo-6,6-bis(2-phenylethyl)-2H-pyran-3-yl)-2,2-dimethylpropyl}phenyl]-1-methyl-1H-imidazole-4-sulfonamide (Formula YYY-5) $R_1$ and $R_2$ are phenethyl, $R_3$ is 1-methylimidazole-4-yl) Refer to Chart YYY.

Using the general sulfonylation procedure of Example 252, 77 mg of the amine of formula YYY-4 ($R_1$ and $R_2$ are phenethyl) is reacted with 1-methylimidazole-4-sulfonyl chloride. Flash chromatography on silica using 3% methanol in dichloromethane provides 90.7 mg of the title compound as an amorphous white solid.

Physical characteristics are as follows:
$^1$H NMR δ 0.96, 1.0, 1.6–2.7, 3.45, 6.8–7.5 ppm.
HRMS: 628.2832
$^1R_f$ 0.38 (3% methanol in dichloromethane)

EXAMPLE 344

N-[3-{1-(4-Hydroxy-5,6-dihydro-2-oxo-6,6-bis(2-phenylethyl)-2H-pyran-3-yl)-2,2-dimethylpropyl}phenyl]-5-cyanopyridine-2-sulfonamide (Formula YYY-5) $R_1$ and $R_2$ are phenethyl, $R_3$ is 5-cyanopyridine-2-yl) Refer to Chart YYY Using the general sulfonylation procedure of Example 252, 77 mg of the amine of Formula YYY-4 ($R_1$ and $R_2$ are phenethyl) is reacted with 5-cyanopyridine-2-sulfonyl chloride. Flash chromatography on silica using 10% ethyl acetate in dichloromethane provides 86.1 mg of the title compound as an amorphous white solid.

Physical characteristics are as follows:
$^1$H NMR δ 0.96, 1.8–2.2, 2.5–2.8, 4.1, 4.3, 6.9–7.4, 7.9–8.0, 8.9 ppm.
HRMS: 650.2681
$R_f$ 0.27 (10% ethyl acetate in dichloromethane)

Preparation 150 Resolution of N-[3-[1-(4-Hydroxy-5,6-dihydro-2-oxo-6-(2-(4-fluorophenyl)ethyl-6-propyl-2H-pyran-3-yl)-2,2-dimethylpropyl]phenyl]carbamic acid, phenylmethyl ester to give 4 isomers (Formula WWW-2: $R_1$ is 4-fluorophenethyl, $R_2$ is propyl, $R_3$ is t-butyl) Refer to Chart WWW.

System C is used to track the enantiomers and to monitor the preparative columns. System C consists of a 0.46×25 cm Chiralcel OD-H column (Chiral Technologies, Inc.) with 15% isopropanol in hexane (V/V) at 0.5 mL/min. The peaks eluting near 13.5, 18.8, 37.1 and 79.7 min are, respectively, Isomer 1, Isomer 2, Isomer 3, and Isomer 4.

Separate Isomers 3 and 4 from the mixture on a 2.1×25 cm (R,R) Whelk-O 1 column (Regis Technologies, Inc.). These two isomers elute at about 23.9 and 26.8 min when the column is developed with 20% isopropanol in hexane (V/V) at 10 mL/min at 30°. The desired isomers elute as an unresolved mixture near 28.9 min and are separated in the second stage of the resolution.

For the second stage inject the unresolved mixture onto a 2.1×25 cm Chiralcel OD column (Chiral technologies, Inc.) kept at 30°. With 12% isopropanol in hexane (V/V) at 12 ml/min, Isomer 1 emerges near 14.5 min and Isomer 2 emerges near 20.8 min.

EXAMPLE 345

N-[3-{1(R or S)-(4-Hydroxy-5,6-dihydro-2-oxo-6(R or S)-(2-(4-fluorophenyl)ethyl)-6-propyl-2H-pyran-3-yl)-2,2-dimethyl-propyl}phenyl]-5-cyanopyridine-2-sulfonamide (Formula WWW-4: $R_1$ is 4-fluorophenethyl, $R_2$ is propyl, $R_3$ is tert-butyl, $R_4$ is 5-cyanopyridine-2-yl) [Isomer 1] Refer to Chart WWW.

The title compound is prepared using the general sulfonylation procedure of Example 252, using the amine of Formula WWW-3, where $R_1$ is 4-fluorophenethyl, $R_2$ is propyl, and $R_3$ is ethyl. The amine is derived from the first stereoisomer of Formula WWW-2 to elute from a Chiralcel OD chiral HPLC column of Preparation 150. The title compound is obtained as an amorphous solid after flash chromatography on silica using 10% ethyl acetate in dichloromethane.

Physical characteristics are as follows:
$^1$H NMR δ 0.7–2.7, 3.2, 3.5, 3.6, 3.7, 4.1, 6.8–7.4, 7.5, 7.8–8.2, 8.8 ppm.
HRMS: 606.2429
$R_f$ 0.40 (15% ethyl acetate in dichloromethane)

EXAMPLE 346

N-[3-{1(R or S)-(4-Hydroxy-5,6-dihydro-2-oxo-6(S or R)-(2-(4-fluorophenyl)ethyl)-6-propyl-2H-pyran-3-yl)-2,2-dimethylpropyl}phenyl]-5-cyanopyridine-2-sulfonamide (Formula WWW-4: $R_1$ is 4-fluorophenethyl, $R_2$ is propyl, $R_3$ is tert-butyl, $R_4$ is 5-cyanopyridine-2-yl) [Isomer 2] Refer to Chart WWW.

The title compound is prepared using the general sulfonylation procedure of Example 252, using the amine of Formula WWW-3, where $R_1$ is 4-fluorophenethyl, $R_2$ is propyl, and $R_3$ is ethyl. The amine is derived from the second stereoisomer of Formula WWW-2 to elute from a Chiralcel OD chiral HPLC column of Preparation 150. The title compound is obtained as an amorphous solid after flash chromatography on silica using 10% ethyl acetate in dichloromethane.

Physical characteristics are as follows:
$^1$H NMR δ 0.6, 0.7–2.6, 3.4, 3.5, 3.7, 4.2, 6.8–7.3, 7.5, 7.8–8.2, 8.8–9.0 ppm.
MS: 606.2434
$R_f$ 0.40 (15% ethyl acetate in dichloromethane)

EXAMPLE 347

N-[3-{1(S or R)-(4-Hydroxy-5,6-dihydro-2-oxo-6(R or S)-(2-(4-fluorophenyl)ethyl)-6-propyl-2H-pyran-3-yl)-2,2-dimethyl-propyl}phenyl]-5-cyanopyridine-2-sulfonamide (Formula WWW-4: $R_1$ is 4-fluorophenethyl, $R_2$ is propyl, $R_3$ is tert-butyl, $R_4$ is 5-cyanopyridine-2-yl) [Isomer 3] Refer to Chart WWW.

The title compound is prepared using the general sulfonylation procedure of Example 252, using the amine of Formula WWW-3, where $R_1$ is 4-fluorophenethyl, $R_2$ is propyl, and $R_3$ is ethyl. The amine is derived from the third stereoisomer of Formula WWW-2 to elute from a Chiralcel OD chiral HPLC column of Preparation 150. The title compound is obtained as an amorphous solid after flash chromatography on silica using 10% ethyl acetate in dichloromethane.

Physical characteristics are as follows:
$^1$H NMR δ 0.6, 0.7–2.6, 3.4, 3.5, 3.7, 4.2, 6.8–7.3, 7.5, 7.8–8.2, 8.8–9.0 ppm.

MS: 606.2423
R$_f$ 0.40 (15% ethyl acetate in dichloromethane)

EXAMPLE 348

N-[3-{1(S or R)-(4-Hydroxy-5,6-dihydro-2-oxo-6(S or R)-(2-(4-fluorophenyl)ethyl)-6-propyl-2H-pyran-3-yl)-2,2-dimethyl-propyl}phenyl]-5-cyanopyridine-2-sulfonamide (Formula WWW-4: R$_1$ is 4-fluorophenethyl, R$_2$ is propyl, R$_3$ is tert-butyl, R$_4$ is 5-cyanopyridine-2-yl) [Isomer 4] Refer to Chart WWW.

The title compound is prepared using the general sulfonylation procedure of Example 252, using the amine of Formula WWW-3, where R$_1$ is 4-fluorophenethyl, R$_2$ is propyl, and R$_3$ is ethyl. The amine is derived from the third stereoisomer of Formula WWW-2 to elute from a Chiralcel OD chiral HPLC column of Preparation 150. The title compound is obtained as an amorphous solid after flash chromatography on silica using 10% ethyl acetate in dichloromethane.

Physical characteristics are as follows:
$^1$H NMR δ 0.7–2.7, 3.2, 3.5, 3.6, 3.7, 4.1, 6.8–7.4, 7.5, 7.8–8.2, 8.8 ppm.
HRMS: 606.2429
R$_f$ 0.40 (15% ethyl acetate in dichloromethane)

EXAMPLE 349

N-[3-{1(R or S)-(4-Hydroxy-5,6-dihydro-2-oxo-6(R or S)-(2-(4-fluorophenyl)ethyl)-6-propyl-2H-pyran-3-yl)-2,2-dimethyl-propyl}phenyl]-1-methyl-1H-imidazole-4-sulfonamide (Formula WWW-4: R$_1$ is 4-fluorophenethyl, R$_2$ is propyl, R$_3$ is tert-butyl, R$_4$ is 1-methylimidazol-4-yl [Isomer 1] Refer to Chart WWW.

The title compound is prepared using the general sulfonylation procedure of Example 252, using the amine of Formula WWW-3, where R$_1$ is 4-fluorophenethyl, R$_2$ is propyl, and R$_3$ is ethyl. The amine is derived from the first stereoisomer of Formula WWW-2 to elute from a Chiralcel OD chiral HPLC column of Preparation 150. The title compound is obtained as an amorphous solid after flash chromatography on silica using 3% methanol in dichloromethane.

Physical characteristics are as follows:
$^1$H NMR δ 0.8–1.0, 1.4, 1.7, 2.3–2.7, 3.6, 3.9, 4.1, 6.8–7.5 ppm.
HRMS: 584.2585
R$_f$ 0.34 (5% methanol in dichloromethane)

EXAMPLE 350

N-[3-{1(R or S)-(4-Hydroxy-5,6-dihydro-2-oxo-6(S or R)-(2-(4-fluorophenyl)ethyl)-6-propyl-2H-pyran-3-yl)-2,2-dimethyl-propyl}phenyl]-1-methyl-1H-imidazole-4-sulfonamide (Formula WWW -4: R$_1$ is 4-fluorophenethyl, R$_2$ is propyl, R$_3$ is tert-butyl, R$_4$ is 1-methylimidazol-4-yl [Isomer 2] Refer to Chart WWW.

The title compound is prepared using the general sulfonylation procedure of Example 252, using the amine of Formula WWW-3, where R$_1$ is 4-fluorophenethyl, R$_2$ is propyl, and R$_3$ is ethyl. The amine is derived from the second stereoisomer of Formula WWW-2 to elute from a Chiralcel OD chiral HPLC column of Preparation 150. The title compound is obtained as an amorphous solid after flash chromatography on silica using 3% methanol in dichloromethane.

Physical characteristics are as follows:
$^1$H NMR δ 0.7–1.1, 1.3, 1.7, 2.3–2.7, 3.6, 3.9, 4.1, 6.8–7.5 ppm.
HRMS: 584.2585
R$_f$ 0.34 (5% methanol in dichloromethane)

EXAMPLE 351

N-[3-{1(S or R)-(4-Hydroxy-5,6-dihydro-2-oxo-6(R or S)-(2-(4-fluorophenyl)ethyl)-6-propyl-2H-pyran-3-yl)-2,2-dimethyl-propyl}phenyl]-1-methyl-1H-imidazole-4-sulfonamide (Formula WWW-4: R$_1$ is 4-fluorophenethyl, R$_2$ is propyl, R$_3$ is tert-butyl, R$_4$ is 1-methylimidazol-4-yl [Isomer 3] Refer to Chart WWW.

The title compound is prepared using the general sulfonylation procedure of Example 252, using the amine of Formula WWW-3, where R$_1$ is 4-fluorophenethyl, R$_2$ is propyl, and R$_3$ is ethyl. The amine is derived from the third stereoisomer of Formula WWW-2 to elute from a Chiralcel OD chiral HPLC column of Preparation 150. The title compound is obtained as an amorphous solid after flash chromatography on silica using 3% methanol in dichloromethane.

Physical characteristics are as follows:
$^1$H NMR δ 0.7–1.1, 1.3, 1.7, 2.3–2.7, 3.6, 3.9, 4.1, 6.8–7.5 ppm.
HRMS: 584.2591
R$_f$ 0.34 (5% methanol in dichloromethane)

EXAMPLE 352

N-[3-{1(S or R)-(4-Hydroxy-5,6-dihydro-2-oxo-6(S or R)-(2-(4-fluorophenyl)ethyl)-6-propyl-2H-pyran-3-yl)-2,2-dimethyl-propyl}phenyl]-1-methyl-1H-imidazole-4-sulfonamide (Formula WWW-4: R$_1$ is 4-fluorophenethyl, R$_2$ is propyl, R$_3$ is tert-butyl, R$_4$ is 1-methylimidazol-4-yl [Isomer 4] Refer to Chart WWW.

The title compound is prepared using the general sulfonylation procedure of Example 252, using the amine of Formula WWW-3, where R$_1$ is 4-fluorophenethyl, R$_2$ is propyl, and R$_3$ is ethyl. The amine is derived from the fourth stereoisomer of Formula WWW-2 to elute from a Chiralcel OD chiral HPLC column of Preparation 150. The title compound is obtained as an amorphous solid after flash chromatography on silica using 3% methanol in dichloromethane.

Physical characteristics are as follows:
$^1$H NMR δ 0.8–1.0, 1.4, 1.7, 2.3–2.7, 3.6, 3.9, 4.1, 6.8–7.5 ppm.
HRMS: 584.2580
R$_f$ 0.34 (5% methanol in dichloromethane)

EXAMPLE 353

N-[3-{1-(4-Hydroxy-5,6-dihydro-2-oxo-6,6-bis(2-phenylethyl)-2H-pyran-3-yl)methyl}phenyl]-5-cyanopyridine-2-sulfonamide (Formula XXX-5, R$_1$ is 5-cyanopyridine-2-yl) Refer to Chart Using the general sulfonylation procedure of Example 252, 64 mg of the amine of formula XXX-4 is reacted with 5-cyanopyridine-2-sulfonyl chloride. Flash chromatography on silica using 2–3% methanol in dichloromethane provides 73.2 mg of the title compound as an amorphous white solid.

Physical characteristics are as follows:
$^1$H NMR δ 1.8–2.1, 2.6, 6.9–7.3, 7.9, 8.8 ppm.
HRMS: 594.2068
R$_f$ 0.40 (3% methanol in dichloromethane)

EXAMPLE 354

N-[3-{1-(4-Hydroxy-5,6-dihydro-2-oxo-6,6-bis(2-phenylethyl)-2H-pyran-3-yl)methyl}phenyl]-5-aminopyridine-2-sulfonamide (Formula UUU-6, R$_1$ and R$_2$ are phenethyl, R$_3$ is H). Refer to Chart UUU.

Using the general sulfonylation procedure of Example 252, 69 mg of the amine of formula XXX-4 is reacted with 5-nitropyridine-2-sulfonyl chloride. Flash chromatography on silica using 2–3% methanol in dichloromethane provides 107 mg of the intermediate nitro compound of formula UUU-5 ($R_1$ and $R_2$ are phenethyl, $R_3$ is H). Reduction to the amine is accomplished using hydrogen gas and palladium on carbon catalyst. Flash chromatography on silica gel using 4–6% methanol in di-chloromethane provides 65.0 mg of the title compound as an amorphous white solid.

Physical characteristics are as follows:
$^1$H NMR δ 1.9–2.1, 2.6, 3.5–4.0, 6.7, 6.9–7.3, 7.5, 7.9 ppm.
HRMS: 584.2215
$R_f$ 0.24 (5% methanol in dichloromethane)

Preparation 151 Resolution of N-[3-[1-(4-Hydroxy-5,6-dihydro-2-oxo-6,6-bis(2-phenylethyl)-2H-pyran-3-yl)-2,2-dimethylpropyl]-phenyl]carbamic acid, phenylmethyl ester to give 2 enantiomers (Formula WWW-2: $R_1$ and $R_2$ are phenethyl, $R_3$ is t-butyl) Refer to Chart WWW.

Inject 40 mg batches of the starting compound onto a 2.1×25 cm (R,R) Whelk-O 1 column (Regis Technologies, Inc.) that is maintained at 30°. The 2 enantiomers elute at about 37 min (Enantiomer 1) and 43 min (Enantiomer 2) using 25% isopropanol and 0.05% acetic acid at 12 mL/min. Fractions are pooled on the basis of results from analysis on a 0.46×25 cm (R,R) Whelk-O 1 column eluted with 30% isopropanol and 0.1% acetic acid (V/V) at 1.0 mL/min. The isomers elute at (Isomer 1) 19.1 and (Isomer 2) 23.0 min respectively.

EXAMPLE 355

N-[3-{1(R or S)-(4-Hydroxy-5,6-dihydro-2-oxo-6,6-bis(2-phenylethyl)-2H-pyran-3-yl)-2,2-dimethylpropyl}phenyl]-5-aminopyridine-2-sulfonamide (Formula WWW-4, $R_1$ and $R_2$ are phenethyl, $R_3$ is tert-butyl, $R_4$ is 5-aminopyridine-2-yl) [Enantiomer 1] Refer to Chart WWW.

Using the general sulfonylation procedure of Example 252, 73 mg of the amine of Formula WWW-3 ($R_1$ and $R_2$ are phenethyl, $R_3$ is tert-butyl) is reacted with 5-nitropyridine-2-sulfonyl chloride. The amine used is derived from the first enantiomer of Formula WWW-2 to elute from an (R,R) Whelk-O chiral HPLC column of Preparation 151. Flash chromatography on silica using 5–10% ethyl acetate in dichloromethane provides 94.0 mg of the intermediate nitro compound of formula UUU-5 ($R_1$ and $R_2$ are phenethyl, $R_3$ is tert-butyl). Reduction to the amine is accomplished using hydrogen gas and palladium on carbon catalyst. Flash chromatography on silica gel using 4% methanol in dichloromethane provides 74.8 mg of the title compound as an amorphous white solid.

Physical characteristics are as follows:
$^1$H NMR δ 0.95, 2.0, 2.6, 6.8, 6.9–7.4, 7.5, 7.9 ppm.
HRMS: 640.2828
$R_f$ 0.27 (5% methanol in dichloromethane)

EXAMPLE 356

N-[3-{1(S or R)-(4-Hydroxy-5,6-dihydro-2-oxo-6,6-bis(2-phenyl-ethyl)-2H-pyran-3-yl)-2,2-dimethylpropyl}phenyl]-5-amino-pyridine-2-sulfonamide (Formula WWW-4, $R_1$ and $R_2$ are phenethyl, $R_3$ is tert-butyl, $R_4$ is 5-aminopyridine-2-yl) [Enantiomer 2] Refer to Chart WWW.

Using the general sulfonylation procedure of Example 252, 73 mg of the amine of Formula WWW-3 ($R_1$ and $R_2$ are phenethyl, $R_3$ is tert-butyl) is reacted with 5-nitropyridine-2-sulfonyl chloride. The amine used is derived from the second enantiomer of Formula WWW-2 to elute from an (R,R) Whelk-O chiral HPLC column of Preparation 151. Flash chromatography on silica using 5–10% ethyl acetate in dichloromethane provides 91.3 mg of the intermediate nitro compound of formula UUU-5 ($R_1$ and $R_2$ are phenethyl, $R_3$ is tert-butyl). Reduction to the amine is accomplished using hydrogen gas and palladium on carbon catalyst. Flash chromatography on silica gel using 4% methanol in dichloromethane provides 54.3 mg of the title compound as an amorphous white solid.

Physical characteristics are as follows:
$^1$H NMR δ 0.95, 2.0, 2.6, 6.8, 6.9–7.4, 7.5, 7.9 ppm.
HRMS: 640.2828
$R_f$ 0.27 (5% methanol in dichloromethane)

EXAMPLE 357

N-[3-{1(R or S)-(4-Hydroxy-5,6-dihydro-2-oxo-6,6-bis(2-phenylethyl)-2H-pyran-3-yl)-2,2-dimethylpropyl}phenyl]-1-methyl-1H-imidazole-4-sulfonamide (Formula WWW-4, $R_1$ and $R_2$ are phenethyl, $R_1$ is tert-butyl, $R_4$ is 1-methylimidazol-4-yl) [Enantiomer 1] Refer to Chart WWW.

The title compound is prepared using the general sulfonylation procedure of Example 252, using the amine of Formula WWW-3, where $R_1$ and $R_2$ are phenethyl and $R_3$ is tert-butyl. The amine is derived from the first enantiomer of Formula WWW-2 to elute from an (R,R) Whelk-O chiral HPLC column of Preparation 151. The title compound is obtained as an amorphous solid after flash chromatography on silica using 3% methanol in dichloromethane.

Physical characteristics are as follows:
$^1$H NMR δ 0.98, 2.0, 2.6, 3.6, 3.8, 6.9–7.5 ppm.
HRMS: 628.2832
$R_f$ 0.38 (5% methanol in dichloromethane)

EXAMPLE 358

N-[3-{1(S or R)-(4-Hydroxy-5,6-dihydro-2-oxo-6,6-bis(2-phenylethyl)-2H-pyran-3-yl)-2,2-dimethylpropyl}phenyl]-1-methyl-1H-imidazole-4-sulfonamide (Formula WWW-4, $R_1$ and $R_2$ are phenethyl, $R_5$ is tert-butyl, $R_4$ is 1-methylimidazol-4-yl) [Enantiomer 2] Refer to Chart WWW.

The title compound is prepared using the general sulfonylation procedure of Example 252, using the amine of Formula WWW-3, where $R_1$ and $R_2$ are phenethyl and $R_3$ is tert-butyl. The amine is derived from the second enantiomer of Formula WWW-2 to elute from an (R,R) Whelk-O chiral HPLC column of Preparation 151. The title compound is obtained as an amorphous solid after flash chromatography on silica using 3% methanol in dichloromethane.

Physical characteristics are as follows:
$^1$H NMR δ 0.98, 2.0, 2.6, 3.6, 3.8, 6.9–7.5 ppm.
HRMS: 628.2838
$R_f$ 0.38 (5% methanol in dichloromethane)

EXAMPLE 359

N-[3-{1(R or S)-(4-Hydroxy-5,6-dihydro-2-oxo-6,6-bis(2-phenylethyl)-2H-pyran-3-yl)-2,2-dimethylpropyl}phenyl]-5-cyanopyridine-2-sulfonamide (Formula WWW-4, $R_1$ and $R_2$ are phenethyl, $R_3$ is tert-butyl, $R_4$ is 5-cyanopyridine-2-yl) [Enantiomer 1] Refer to Chart WWW.

The title compound is prepared using the general sulfonylation procedure of Example 252, using the amine of Formula WWW-3, where $R_1$ and $R_2$ are phenethyl and $R_3$ is tert-butyl. The amine is derived from the first enantiomer of Formula WWW-2 to elute from an (R,R) Whelk-O chiral HPLC column of Preparation 151. The title compound is obtained as an amorphous solid after flash chromatography on silica using 10% ethyl acetate in dichloromethane.

Physical characteristics are as follows:
$^1$H NMR δ 0.87, 1.9, 2.6, 6.8–7.4, 7.9, 8.8 ppm.
HRMS: 650.2681
$R_f$ 0.46 (15% ethyl acetate in dichloromethane)

EXAMPLE 360

N-[3-{1(S or R)-(4-Hydroxy-5,6-dihydro-2-oxo-6,6-bis(2-phenylethyl)-2H-pyran-3-yl)-2,2-dimethylpropyl}phenyl]-

5-cyanopyridine-2-sulfonamide (Formula WWW-4, $R_1$ and $R_2$ are phenethyl, $R_5$ is tert-butyl, $R_4$ is 5-cyanopyridine-2-yl) [Enantiomer 2] Refer to Chart WWW.

The title compound is prepared using the general sulfonylation procedure of Example 252, using the amine of Formula WWW-3, where $R_1$ and $R_2$ are phenethyl and $R_3$ is tert-butyl. The amine is derived from the second enantiomer of Formula WWW-2 to elute from an (R,R) Whelk-O chiral HPLC column of Preparation 151. The title compound is obtained as an amorphous solid after flash chromatography on silica using 10% ethyl acetate in dichloromethane.

Physical characteristics are as follows:
$^1$H NMR δ 0.87, 1.9, 2.6, 6.8–7.4, 7.9, 8.8 ppm.
HRMS: 650.2681
$R_f$ 0.46 (15% ethyl acetate in dichloromethane)

Preparation 152 Resolution of N-[3-[1-(4-Hydroxy-5,6-dihydro-2-oxo-6,6 -dipropyl-2H-pyran-3-yl)-propyl]phenyl]carbamic acid, phenylmethyl ester to give 2 isomers (Formula WWW-2: $R_1$ and $R_2$ are propyl, $R_3$ is ethyl) Refer to Chart WWW.

Samples of the starting compound are injected onto a 2.1×25 cm Chiralcel OD column and eluted with 20% isopropanol (V/V) in hexane at 10 mL/min. The material eluting near 19.1 minutes is one isomer (Enantiomer 1) and that eluting near 37.7 minutes is another isomer (Enantiomer 2). The pools are concentrated separately on a rotary evaporator (ca. 30 mm, bath at 50° maximum) to give white solids.

EXAMPLE 361

N-[3-{1(R or S)-(4-Hydroxy-5,6-dihydro-2-oxo-6,6-dipropyl-2H-pyran-3-yl)-propyl}phenyl]-5-cyanopyridine-2-sulfonamide (Formula WWW-4, $R_1$ and $R_2$ are propyl, $R_3$ is ethyl, $R_4$ is 5-cyanopyridine-2-yl) [Enantiomer 1] Refer to Chart WWW.

Following procedures analogous to those described above, but using Enantiomer 1 of Preparation 152, the title compound is obtained.

Physical characteristics are as follows:
$^1$H NMR δ 0.8–1.0, 1.2–2.2, 3.90, 6.9–7.2, 8.0, 8.15, 8.9 ppm.
HRMS: 497.1984
$R_f$ 0.38 (15% ethyl acetate in dichloromethane)

EXAMPLE 362

N-[3-{1(S or R)-(4-Hydroxy-5,6-dihydro-2-oxo-6,6-dipropyl-2H-pyran-3-yl)-propyl}phenyl]-5-cyanopyridine-2-sulfonamide (Formula WWW-4, $R_1$ and $R_2$ are propyl, $R_3$ is ethyl, $R_4$ is 5-cyanopyridine-2-yl) [Enantiomer 2] Refer to Chart WWW.

Following procedures analogous to those described above, but using Enantiomer 2 of Preparation 152, the title compound is obtained.

Physical characteristics are as follows:
$^1$H NMR δ 0.8–1.0, 1.2–2.2, 3.90, 6.9–7.2, 8.0, 8.15, 8.9 ppm.
HRMS: 497.1980
$R_f$ 0.38 (15% ethyl acetate in dichloromethane)

EXAMPLE 363

N-[3-{1(R or S)-(4-Hydroxy-5,6-dihydro-2-oxo-6,6-dipropyl-2H-pyran-3-yl)-propyl}phenyl]-5-aminopyridine-2-sulfonamide (Formula WWW-4, $R_1$ and $R_2$ are propyl, $R_3$ is ethyl, $R_4$ is 5-aminopyridine-2-yl) [Enantiomer 1] Refer to Chart WWW.

Following procedures analogous to those described above, but using Enantiomer 1 of Preparation 152, the title compound is obtained.

Physical characteristics are as follows:
$^1$H NMR δ 0.7–0.9, 1.2–2.2, 3.8, 6.8–7.2, 7.5, 7.9 ppm.
HRMS: 487.2122
$R_f$ 0.28 (5% methanol in dichloromethane)

EXAMPLE 364

N-[3-{1(S or R)-(4-Hydroxy-5,6-dihydro-2-oxo-6,6-dipropyl-2H-pyran-3-yl)-propyl]phenyl]-5-aminopyridine-2-sulfonamide (Formula WWW-4, $R_1$ and $R_2$ are propyl, $R_3$ is ethyl, $R_4$ is 5-aminopyridine-2-yl) [Enantiomer 2] Refer to Chart WWW.

Following procedures analogous to those described above, but using Enantiomer 2 of Preparation 152, the title compound is obtained.

Physical characteristics are as follows:
$^1$H NMR δ 0.7–0.9, 1.2–2.2, 3.8, 6.8–7.2, 7.5, 7.9 ppm.
HRMS: 487.2140
$R_f$ 0.28 (5% methanol in dichloromethane)

Preparation 153 Resolution of N-[3-[1-(4-Hydroxy-5,6-dihydro-2-oxo-(2-(4-fluorophenyl)ethyl)-6-propyl-2H-pyran-3-yl)propyl]-phenyl]carbamic acid, phenylmethyl ester to give 4 isomers (Formula WWW-2: $R_1$ is 4-fluorophenethyl, $R_2$ is propyl, and $R_3$ is ethyl) Refer to Chart WWW.

The enantiomers are defined by elution order from System D. HPLC System D consists of a 0.46×25 cm Chiralcel OD-H column (Chiral Technologies, Inc.) with 20% isopropanol and 0.05% trifluoroacetic acid in hexane (V/V) pumped at 0.5 mL/min. The retention times in this system are (Isomer 1) 21.6, (Isomer 2) 34.5, (Isomer 3) 55.2 and (Isomer 4) 66.6 min.

Separate the enantiomers on a 2.1×25 cm Chiralcel OD column (Chiral Technologies, Inc.). Aliquots are injected and the enantiomers eluted with 17.5% isopropanol in hexane (V/V) at 10 ml/min. Fractions eluting near 24.6, 42.9, 66.3 and 77.4 min are pooled appropriately after assay with System D. In order of elution, the four isomers are designated Isomers 1–4, respectively.

In all cases, whenever solvent is stripped from a pool the following protocol is used: Solvent is removed from pools of fractions on a rotary evaporator with house vacuum (ca. 30 mm Hg) and a water bath set at 45±5°. If acetic acid is present in the solvent, add ca. 10 mL of toluene/L of pool before the flask goes dry. Residues are then washed into tared flasks using methylene chloride and the solvent is stripped as above. Final solvent removal is accomplished at ambient temperature, 1 mmHg pressure for 2–24 hours before weighing.

EXAMPLE 365

N-[3-{1(R or S)-(4-Hydroxy-5,6-dihydro-2-oxo-6(R or S)-(2-(4-fluorophenyl)ethyl)-6-propyl-2H-pyran-3-yl)propyl}phenyl]-5-cyanopyridine-2-sulfonamide (Formula WWW-4: $R_1$ is 4-fluoro-phenethyl, $R_2$ is propyl, $R_3$ is ethyl, $R_4$ is 5-cyanopyridine-2-yl) [Isomer 1] Refer to Chart WWW.

Following procedures analogous to those described above, but using Isomer 1 of Preparation 153, the title compound is obtained.

Physical characteristics are as follows:
$^1$H NMR δ 0.8–1.0, 1.3, 1.6–2.2, 2.5, 3.9, 6.8–7.3, 7.9–8.1, 8.9 ppm.
HRMS: 578.2120
$R_f$ 0.35 (15% ethyl acetate in dichloromethane)

EXAMPLE 366

N-[3-{1(R or S)-(4-Hydroxy-5,6-dihydro-2-oxo-6(S or R)-(2-(4-fluorophenyl)ethyl)-6-propyl-2H-pyran-3-yl)propyl]phenyl]-5-cyanopyridine-2-sulfonamide (Formula WW-4:

$R_1$ is 4-fluoro-phenethyl, $R_2$ is propyl, $R_3$ is ethyl, $R_4$ is 5-cyanopyridine-2-yl) [Isomer 2] Refer to Chart WWW Following procedures analogous to those described above, but using Isomer 2 of Preparation 153, the title compound is obtained.

Physical characteristics are as follows:
$^1$H NMR δ 0.8–1.0, 1.3, 1.6–2.2, 2.5, 3.9, 6.8–7.3, 7.9–8.1, 8.9 ppm.
HRMS: 578.2120
$R_f$ 0.35 (15% ethyl acetate in dichloromethane)

EXAMPLE 367

N-[3-{1(S or R)-(4-Hydroxy-5,6-dihydro-2-oxo-6(R or S)-(2-(4-fluorophenyl)ethyl)-6-propyl-2H-pyran-3-yl)propyl}phenyl]-5-cyanopyridine-2-sulfonamide (Formula WWW-4: $R_1$ is 4-fluoro-phenethyl, $R_2$ is propyl, $R_3$ is ethyl, $R_4$ is 5-cyanopyridine-2-yl) [Isomer 3] Refer to Chart WWW.

Following procedures analogous to those described above, but using Isomer 3 of Preparation 153, the title compound is obtained.

Physical characteristics are as follows:
$^1$H NMR δ 0.8–1.0, 1.3, 1.6–2.2, 2.5, 3.9, 6.8–7.3, 7.9–8.1, 8.9 ppm.
HRMS: 578.2126
$R_f$ 0.35 (15% ethyl acetate in dichloromethane)

EXAMPLE 367A

N-[3-{1(S or R)-(4-Hydroxy-5,6-dihydro-2-oxo-6(S or R)-(2-(4-fluorophenyl)ethyl)-6-propyl-2H-pyran-3-yl)propyl}phenyl]-5-cyanopyridine-2-sulfonamide (Formula WWW-4: $R_1$ is 4-fluorophenethyl, $R_2$ is propyl, $R_3$ is ethyl, $R_4$ is 5-cyanopyridine-2-yl) [Isomer 4] Refer to Chart WWW.

Following procedures analogous to those described above, but using Isomer 4 of Preparation 153, the title compound is obtained.

Physical characteristics are as follows:
$^1$H NMR δ 0.8–1.0, 1.3, 1.6–2.2, 2.5, 3.9, 6.8–7.3, 7.9–8.1, 8.9 ppm.
HRMS: 578.2126
$R_f$ 0.35 (15% ethyl acetate in dichloromethane)

EXAMPLE 368

N-[3-{1(R or S)-(4-Hydroxy-5,6-dihydro-2-oxo-6(R or S)-(2-(4-fluorophenyl)ethyl)-6-propyl-2H-pyran-3-yl)propyl}phenyl]-1-methyl-1H-imidazole-4-sulfonamide (Formula WWW-4: $R_1$ is 4-fluorophenethyl, $R_1$ is propyl, $R_3$ is ethyl, $R_4$ is 1-methylimidazol-4-yl) [Isomer 1] Refer to Chart WWW.

Following procedures analogous to those described above, but using Isomer 1 of Preparation 153, the title compound is obtained.

Physical characteristics are as follows:
$^1$H NMR δ 0.8–1.0, 1.3, 1.6–2.2, 2.6, 3.63, 4.0, 6.9–7.5 ppm.
HRMS: 556.2265
$R_f$ 0.29 (5% methanol in dichloromethane)

EXAMPLE 369

N-[3-{1(R or S)-(4-Hydroxy-5,6-dihydro-2-oxo-6(R or S)-(2-(4-fluorophenyl)ethyl)-6-propyl-2H-pyran-3-yl)propyl}phenyl]-5-aminopyridine-2-sulfonamide (Formula WWW-4: $R_1$ is 4-fluorophenethyl, $R_2$ is propyl, $R_3$ is ethyl, $R_4$ is 5-aminopyridine-2-yl) [Isomer 1] Refer to Chart WWW.

Following procedures analogous to those described above, but using Isomer 1 of Preparation 153, the title compound is obtained.

Physical characteristics are as follows:
$^1$H NMR δ 0.8–1.0, 1.3, 1.6–2.2, 2.5, 3.9, 6.8–7.2, 7.5, 7.9 ppm.
HRMS: 568.2271
$R_f$ 0.27 (5% methanol in dichloromethane)

Preparation 154 Hexahydro-2H-1-benzopyran-2,4(3H)-dione (Formula DDDD-2, wherein n is 1) Refer to Chart DDDD.

A solution of 0.42 g of platinum oxide and 1.66 g of the compound of formula DDDD-1 wherein n is 1 in 100 mL of acetic acid is placed on a Parr hydrogenation apparatus under an initial pressure of 50 psi of hydrogen for 1.5 h. The reaction mixture is then filtered through Celite and concentrated in vacuo to give a beige solid. The crude material is purified by flash column chromatography on silica gel 60 (230–400 mesh) eluting with 0–5% methanol in chloroform to give 0.94 g of the title product as a white solid.

Physical characteristics are as follows:
$^1$H NMR (CDCl$_3$) δ 4.84–4.80, 3.54, 3.40, 2.60–2.53, 2.08–2.02, 1.79–1.65, 1.62–1.54, 1.44–1.40 ppm.
$^{13}$C NMR (CDCl$_3$) δ 203.0, 167.4, 74.3, 47.7, 45.6, 29.1, 23.5, 23.2, 19.7 ppm.
IR (mineral oil) 3092, 2768, 2714, 2695, 2662, 1657, 1614, 1577, 1444, 1352, 1345, 1340, 1323, 1308, 1295, 1287, 1260, 1244, 1211, 1188, 1057, 1004, 938, 909, 890, 843, 832, 600 cm$^{-1}$.
EI-MS: [M+]=168.
Anal. found: C, 64.16; H, 7.16.

Preparation 155 4a,5,6,7,8,8a-Hexahydro-4-hydroxy-3-[1-(3-nitrophenyl)-propyl]-2H-1-benzopyran-2-one (Formula DDDD-4, wherein n is 1 and $R_1$ is ethyl) Refer to Chart DDDD.

A solution of 3.17 g of aluminum trichloride in 30 mL of tetrahydrofuran is added to a solution of 2.00 g of the title compound of Preparation 154 and 1.82 g of 3-nitrobenzaldehyde in 20 mL of tetrahydrofuran. The resulting mixture is then stirred at room temperature for 2.5 h, at which time, 7.28 g of sodium carbonate decahydrate is added, and the reaction mixture is stirred an additional 20 min. The mixture is then dried over magnesium sulfate, filtered through Celite, and concentrated in vacuo to yield 6.05 g of a yellow gum. This crude material is immediately dissolved in 50 mL of tetrahydrofuran containing 0.73 g of cuprous bromide-dimethyl sulfide complex, and 13.1 mL of a 1.0 M solution of triethyl aluminum in hexanes are added to the reaction mixture. After stirring at room temperature for 1 h, the reaction is quenched by the addition of water, and the resulting mixture is partitioned between ether and water. The organic layer is separated, washed with brine, and concentrated in vacuo to produce 4.0 g of a yellow oil. The crude material is purified by flash column chromatography eluting with 10–50% ethyl acetate in hexanes to yield 0.63 g of the title product as a yellow foam.

Physical characteristics are as follows.
MP 86–91° C.
IR (mineral oil) 3085, 1635, 1569, 1528, 1448, 1394, 1365, 1349, 1325, 1307, 1288, 1270, 1251, 1244 cm$^{-1}$.

EXAMPLE 370

5-Cyano-N-[3–1-(4a,5,6,7,8,8a-hexahydro-4-hydroxy-2-oxo-2H-1-benzopyran-3-yl)propyl]phenyl]-2-pyridinesulfonamide (Formula DDDD-7, wherein n is 1, $R_1$ is ethyl, and $R_2$ is 5-cyano-2-pyridyl) Refer to Chart DDDD.

A solution of 0.63 g of the title compound of Preparation 155 in 50 mL of ethanol with 0.3 g of 10% palladium on carbon is placed on a Parr hydrogenation apparatus at an initial pressure of 50 psi of hydrogen for 3 h. The reaction mixture is then filtered through Celite and concentrated in vacuo to give 0.519 g of crude intermediate. 0.25 g of this intermediate is immediately dissolved in 5 mL of methylene chloride, and 0.168 g of 5-cyano-2-pyridylsulfonyl chloride and 0.134 mL of pyridine are added to the solution. The resulting mixture is stirred at room temperature for 18 h. The reaction mixture is then purifed by flash column chromatography on silica gel 60 (230–400 mesh) eluting with 0–2.5% methanol in chloroform to give 0.164 g of the title product as a white foam.

Physical characteristics are as follows:
MP 122–125 ° C.
HRMS found: 468.1611

EXAMPLE 371
4-Cyano-N-[3-1-(4a,5,6,7,8,8a-hexahydro-4-hydroxy-2-oxo-2H-1-benzopyran-3-yl)propyl]phenyl]-benzenesulfonamide (Formula DDDD-7, wherein n is 1, $R_1$ is ethyl, and $R_2$ is 4-cyanophenyl) Refer to Chart DDDD.

Following the general procedure of Example 370, and making non-critical variations, but substituting 4-cyanophenylsulfonyl chloride for 5-cyano-2-pyridylsulfonyl chloride, 0.236 g of the title compound is obtained as white foam.

Physical characteristics are as follows:
MP 127–130° C.
HRMS found: 466.1583.

Preparation 156 4-Hexahydro-cyclohepta[b]pyran-2,4(3H,4aH)-dione (Formula DDDD-2, wherein n is 2) Refer to Chart DDDD.

Following the general procedure of Preparation 154, and making non-critical variations, but substituting the cycloheptylpyranone of Formula DDDD-1 wherein n is 2 for the cyclohexylpyranone of Formula DDDD-1 wherein n is 1, 0.337 g of the title compound is obtained as white solid.

Physical characteristics are as follows:
$^1$H NMR CDCl$_3$) δ 4.97–4.91, 3.52, 3.42, 2.64–2.58, 2.22–2.11, 2.01–1.72, 1.59–1.36 ppm.
$^{13}$C NMR (CDCl$_3$) δ 203.0, 167.2, 78.0, 52.1, 46.5, 32.1, 28.6, 27.1, 25.7, 21.3 ppm.
IR (mineral oil) 3074, 2791, 2755, 2736, 2687, 2637, 2608, 2585, 1655, 1625, 1586, 1500, 1480, 1443, 1333, 1324, 1293 (s), 1265, 1254, 1240, 1222, 1196, 1173, 1082, 1053, 1016, 909, 889, 832, 611 cm$^{-1}$.
EI-MS: [M+]=182.
Anal. found: C, 66.16; H, 7.90.

Preparation 157 5,6,7,8,9,9a-Hexahydro-4-hydroxy-3-[1-(3-nitrophenyl)-propyl]-cyclohepta[b]pyran-2(4aH)-one (Formula DDDD-4, wherein n is 2 and $R_1$ is ethyl) Refer to Chart DDDD.

Following the general procedure of Preparation 155, and making non-critical variations, but substituting the title compound of Preparation 156 for the title compound of Preparation 154, 2.5 g of the title compound is obtained as a yellow foam.

Physical characteristics are as follows:
MP 75–78° C.
IR (mineral oil) 3071, 2667, 1638, 1528, 1395, 1350, 1305, 1276, 1250, 1143, 1130, 1120, 1100, 1066, 782, 764, 741, 697, 685 cm$^{-1}$.
HRMS found: 345.1590.
Anal. found: C, 58.74; H, 5.63; N, 3.48.

EXAMPLE 372
5-Cyano-N-[3-[1-(2,4a,5,6,7,8,9,9a-octahydro-4-hydroxy-2-oxocyclohepta[b]pyran-3-yl)propyl]phenyl]-2-pyridinesulfonamide (Formula DDDD-7, wherein n is 2, $R_1$ is ethyl, and $R_2$ is 5-cyano-2-pyridyl) Refer to Chart DDDD.

Following the general procedure of Example 370, and making non-critical variations, but substituting the title compound of Preparation 157 for the title compound of Preparation 155, 0.206 g of the title compound is obtained as a white foam.

Physical characteristics are as follows:
MP 163–166 ° C.
IR (mineral oil) 3352, 3128, 3100, 3073, 3029, 1760, 1726, 1641, 1608, 1593, 1584, 1411, 1397, 1355, 1295, 1282, 1242, 1207, 1173, 1125, 1106, 1086, 1074, 1028, 974, 967, 721, 701, 645, 638 cm$^{-1}$.
HRMS found: 481.1693.

Preparation 158 Octahydro-2H-cycloocta[b]pyran-2,4(3H)-dione (Formula DDDD-2, wherein n is 3) Refer to Chart DDDD.

Following the general procedure of Preparation 154, and making non-critical variations, but substituting the cyclooctylpyranone of Formula DDDD-1 wherein n=3 for the cycloheptylpyranone of Formula DDDD-1 wherein n=2, 1.72 g of the title compound is obtained as a white solid.

Physical characteristics are as follows:
$^1$H NMR (CDCl$_3$) δ 4.84–4.78, 3.61, 3.40, 2.75–2.70, 2.14–1.97, 1.90–1.72, 1.68–1.44 ppm.
$^{13}$C NMR (CDCl$_3$) δ 204.2, 167.2, 78.2, 49.5, 46.1, 28.5, 27.3, 26.2, 24.7, 23.9, 22.1 ppm.
IR (mineral oil) 2659, 2617, 1650, 1612, 1579, 1444, 1356, 1332, 1307, 1287, 1265, 1244, 1227, 1209, 1041, 1035, 1003, 962, 946, 860, 832, 824 cm$^{-1}$.
HRMS found: 196.1100.
Anal. found: C, 67.06; H, 8.23.

Preparation 159 3-[2,2-Dimethyl-1-(3-nitrophenyl)propyl]-4a,5,6,7,8,9,10,10a-octahydro-4-hydroxy-2H-cyclo-octa[b]pyran-2-one (Formula DDDD-4, wherein n is 3 and $R_1$ is t-butyl) Refer to Chart DDDD.

A solution of 1.36 g of aluminum trichloride in 30 mL of tetrahydrofuran is added to a solution of 1.0 g of the title compound of Preparation 158 and 0.77 g of 3-nitrobenzaldehyde in 20 mL of tetrahydrofuran. The resulting mixture is then stirred at room temperature for 2.3 h, at which time, 3.06 g of sodium carbonate decahydrate is added, and the reaction mixture is stirred an additional 15 min. The mixture is then dried over magnesium sulfate, filtered through Celite, and concentrated in vacuo to yield a yellow foam. This crude intermeidate is immediately dissolved in 5 mL of tetrahydrofuran for use in the second step.

A dry flask is charged with 0.82 g of activated zinc, 3 mL of tetrahydrofuran, 0.035 mL of dibromoethane, and 0.21 mL of a 1 M solution of trimethylsilyl chloride in tetrahydrofuran. After the addition of each reagent the mixture is sonicated for 15 m at 45° C. The mixture is diluted further by the addition of 2 mL tetrahydrofuran and 1.32 mL of t-butyl iodide is added dropwise. The resulting mixture is sonicated for 3 h at 45° C. A separate mixture of 0.85 g of copper (I) cyanide and 0.80 g of lithium chloride in 4 mL of tetrahydrofuran is stirred at room temperature for 1 h until almost homogeneous and cooled to −30° C. The organozinc solution is then added via cannula to the copper cyanide solution and the resulting mixture is allowed to warm to 0° C. and to stir for 15 min. The reaction mixture is then cooled to −78° C., and the solution of crude intermediate prepared above is added. After stirring for 20 min at −78° C. and 30 min at 0° C., the reaction is quenched with a saturated solution of aqueous ammonium chloride and diluted with an additional 60 mL of tetrahydrofuran. The organic layer is separated, washed with water, and concentrated in vacuo to give 2.17 g of an orange foam. The crude material is then purified by flash column chromatography eluting with 10–30% ethyl acetate in hexanes followed by recrystallization in methylene chloride/hexanes to yield 0.60 g of the title product as a yellow solid.

Physical characteristics are as follows: 15 MP 158–161° C.

IR (mineral oil) 3077, 2646, 1632, 1599, 1529, 1477, 1450, 1396, 1357, 1349, 1334, 1317, 1283, 1273, 1252, 1232, 1217, 1205, 1181 cm$^{-1}$.

EXAMPLE 373

5-Cyano-N-[3-[2,2-dimethyl-1-(4a,5,6,7,8,9,10,10a-octahydro-4-hydroxy-2-oxo-2H-cycloocta[b]pyran-3-yl)propyl]phenyl]-2-pyridinesulfonamide (Formula DDDD-7, wherein n is 2, $R_1$ is t-butyl, and $R_2$ is 5-cyano-2-pyridyl) Refer to Chart DDDD.

Following the general procedure of Example 370, and making non-critical variations, but substituting the title compound of Preparation 159 for the title compound of Preparation 157, 0.034 g of the title compound is obtained as white crystals.

Physical characteristics are as follows:

MP 182–185° C.

IR (mineral oil) 3246, 3121, 3098, 2615, 1655, 1633, 1607, 1585, 1575, 1491, 1411, 1395, 1354, 1335, 1322, 1311, 1298, 1281, 1275, 1262, 1255, 1233, 1206, 1178, 1121, 1109, 1028, 977, 702, 657, 646, 635, 605 cm$^{-1}$.

HRMS found: 524.2216.

Anal. found: C, 63.86; H, 6.41; N, 7.82.

Preparation 160 (3(3R),4S)-3-[2-[1-[3-[bis(phenylmethyl)amino]phenyl]-propyl]-5-hydroxy-1,3-dioxo-5-(2-phenylethyl)octyl]-4-phenyl-2-oxazolidinone (Formula W-10 wherein $R_1$ is 2 -phenylethyl) Refer to Chart W.

To 100 mL of methylene chloride is added 5.0 g of the title compound of Preparation 95 (W-8) and the resulting solution cooled to –78° C. under an atmosphere of nitrogen. To that solution is added 1.0 mL of TiCl$_4$ and 1.63 mL of diisopropylethylamine, and the resulting solution is stirred for 1 hour. Then, 3.30 g of 1-phenyl-3-hexanone is added, and the reaction temperature raised to 0° C. for 2.5 hours. The reaction is then quenched by the addition of a saturated ammonium chloride solution, and the mixture is extracted with methylene chloride. The organic extract is washed with saturated sodium bicarbonate solution and evaporated in vacuo to yield 9.7 g of a yellow oil. Column chromatography on 900 g silica (elution with 10% hexane-methylene chloride, 100% methylene chloride) affords 3.30 g of the title compound as a yellow foam.

Physical characteristics are as follows:

$^1$H NMR (CDCl$_3$) δ 7.33–7.23, 7.14, 7.04, 6.61–6.50, 5.45, 5.22, 4.71, 4.60, 4.48, 4.26, 3.33, 3.15–3.03, 2.58, 2.47–2.31, 1.93, 1.40–1.28, 1.24–1.13, 1.11–0.96, 0.88–0.77, 0.62–0.57 ppm.

MP 121–126° C.

$^{13}$C NMR (CDCl$_3$) δ 167.2, 167.1, 153.7, 142.6, 141.0, 138.2, 138.1, 129.6, 129.5, 129.2, 128.9, 128.8, 128.6, 128.4, 128.3, 127.0, 125.8, 125.6, 125.6, 73.1, 70.0, 69.9, 63.9, 57.9, 54.8, 54.7, 51.5, 51.4, 48.3, 41.3, 41.0, 40.8, 40.5, 29.8, 29.6, 27.1, 26.9, 16.8, 16.6, 14.6, 11.7, 11.6 ppm.

IR (mineral oil) 3525, 3061, 3026, 1777, 1720, 1690, 1601, 1495, 1361, 1335, 1238, 1199, 1104, 735, 698 cm$^{-1}$.

EI-MS: [M+]=736.

Anal. found: C, 78.03; H, 7.11; N, 3.79.

Preparation 161 (3S)-3-[1-[3-Bis(phenylmethyl)amino]phenyl]propyl]-5,6-dihydro-4-hydroxy-6-(2-phenylethyl-6-propyl-pyran-2-one (Formula W-11 wherein $R_1$ is 2-phenylethyl) Refer to Chart W.

To 5 mL of dry tetrahydrofuran is added 2.7 g of the title compound of Preparation 160 and the resulting solution is cooled to 0° C. under an atmosphere of nitrogen. To that solution is added 0.45 mL of a 1 M solution of potassium t-butoxide in tetrahydrofuran. The reaction mixture is then warmed to 20° C. and stirred for 2 hours. The reaction is quenched with saturated ammonium chloride and extracted with ethyl acetate. The organic layer is washed with water, dried and evaporated in vacuo to yield 0.28 g of a yellow oil. Column chromatography on 80 g of silica gel (elution with 10–30% acetone/hexane) affords 0.195 g of a yellow foam. Crystallization from ethyl acetate/hexane yields 0.146 g of the title compound.

Physical characteristics are as follows:

MP 128–131° C.

$^1$H NMR (CDCl$_3$) δ 7.35–7.12, 6.73–6.64, 5.84, 4.73–4.57, 4.12, 2.69–2.61, 2.38–2.20, 1.95–1.65, 1.41–1.32, 0.98–0.87 ppm.

$^{13}$C NMR (CDCl$_3$) δ 204.1, 204.0, 171.7, 171.4, 169.6, 140.9, 140.8, 140.6, 140.5, 140.4, 139.9, 139.8, 138.3, 129.7, 129.6, 129.5, 128.9, 128.6, 128.5, 128.4, 128.2, 128.1, 127.1, 126.9, 126.8, 126.7, 126.5, 126.4, 126.3, 126.2, 126.0, 125.9, 116.8, 112.6, 112.5, 112.4, 112.3, 112.2, 112.1, 112.0, 82.0, 81.9, 81.8, 80.4, 80.3, 58.6, 58.5, 54.5, 51.4, 50.4, 50.1, 49.9, 47.8, 47.4, 47.0, 46.6, 43.0, 42.9, 42.2, 41.9, 40.2, 40.1, 40.0, 39.2, 29.8, 29.7, 29.6, 29.1, 29.0, 26.8, 26.7, 24.7, 24.6, 24.3, 16.9, 16.5, 14.0, 12.3 ppm.

IR (mineral oil) 3023, 1637, 1599, 1584, 1575, 1494, 1347, 1300, 1257, 1243, 1234, 920, 731, 704, 695 cm$^{-1}$.

EI-MS: [M+]=573.

Anal. found: C, 81.53; H, 7.82; N, 2.34.

$[\alpha]_D$ (CHCl$_3$)=–83°

Preparation 162 (3S) -3-[1-(3-Aminophenyl)propyl]-5,6-dihydro-4-hydroxy-6-(2-phenylethyl)-6-propyl-pyran-2-one (Formula W-12 wherein $R_1$ is 2-phenylethyl) Refer to Chart W.

0.63 g of the title compound of Preparation 161 is dissolved in 45 mL of ethyl acetate and 15 mL of methanol. To that solution is added 0.47 g of 10% Pd/C, and the resulting mixture is hydrogenated at 50 psi for 2.5 hours. The reaction is then filtered through celite and concentrated in vacuo to yield 0.466 g of an off-white foam. Column chromatography on 80 g of silica gel (elution with 20–50% ethyl acetate-hexane) affords 0.389 g of the title compound as an off-white solid.

Physical characteristics are as follows:

MP 155–159° C.

$^1$H NMR (CD$_3$OD) δ 7.26–7.20, 7.15–7.04, 6.95, 6.81, 6.74, 6.54–6.51, 3.98–3.91, 2.68–2.54, 2.25–2.17, 2.02–1.67, 1.43–1.28, 0.99–0.87 ppm.

$^{13}$C NMR (CD$_3$OD) δ 171.2, 171.0, 148.5, 148.2, 143.9, 130.4, 130.2, 127.8, 120.8, 117.8, 115.3, 107.4, 82.7, 44.6, 44.4, 41.8, 41.7, 41.5, 38.4, 31.8, 26.8, 26.7, 18.8, 15.6, 14.3 ppm.

IR (mineral oil) 3085, 3061, 3026, 1617, 1605, 1495, 1314, 1258, 1168, 1119, 1065, 1030, 923, 776, 699 cm$^{-1}$.

EI-MS: [M+]=393.

Anal. found: C, 76.13; H, 8.16; N, 3.37.

$[\alpha]_D$ (MeOH)=–41°

EXAMPLE 374

N-[3-[1-(S)-[5,6,-Dihydro-4-hydroxy-2-oxo-6-(2-phenylethyl)-6-propyl-2H-pyran-3-yl]propyl]phenyl]-5-(triflouromethyl)-2-pyridinesulfonamide (Formula W-13 wherein $R_1$ is 2-phenyl-ethyl) Refer to Chart W.

To a solution of 0.200 g of the title compound of Preparation 162 in 5 mL of methylene chloride is added 0.12 mL of pyridine. The resulting mixture is cooled to 0° C. and 0.132 g of 5-trifluromethylpyridine-2-sulfonyl chloride is added. The reaction mixture is then stirred at room temperature for 1.5 h, concentrated in vacuo, and partitioned between ethyl acetate and water. The organic layer is concentrated in vacuo to 0.39 g of pink oil. Column chromatography on 50 g silica gel (elution with 20–50% ethyl acetate/hexane) affords 0.252 g of title compound as a white foam.

MP 170–173° C.

$^1$H NMR (CD$_3$OD) δ 8.95–8.92, 8.23–8.16, 8.04–8.00, 7.25–6.90, 4.86, 3.98–3.90, 3.31, 3.30, 2.69–2.46, 2.18–2.09, 1.96–1.65, 1.41–1.28, 0.99–0.81 ppm.

$^{13}$C NMR (CD$_3$OD) δ 167.3, 147.7, 147.5, 142.9, 142.8, 137.7, 137.0, 129.5, 129.2, 126.9, 126.2, 126.1, 124.1, 122.6, 122.5, 120.3, 120.2, 81.8, 81.7, 43.6, 43.2, 40.9, 40.5, 37.5, 30.9, 25.8, 25.6, 17.9, 14.7, 13.3, 13.2 ppm.

IR (mineral oil) 3087, 3027, 1642, 1606, 1595, 1327, 1260, 1173, 1142, 1110, 1074, 1016, 720, 700, 613 cm$^{-1}$.

FAB-MS: [M+H]=603.

Anal. found: C, 61.79; H, 5.86; N, 4.48; S, 5.16.

[α]$_D$ (MeOH)=−31°.

Preparation 163 (3S,6R)-3-[1-[3-bis(phenylmethyl)amino]phenyl]propyl]-5,6-dihydro-4-hydroxy-6-(2-phenylethyl-6-propyl-pyran-2-one (Formula FFF-2) Refer to Chart FFF.

The title compound of Preparation 161 is chromatographed on a 5.1×30 cm Cyclobond I 2000 column in an ice bath at 90 mg per injection using an automated chromatographic system and a mobile phase of acetonitrile containing 0.1% diethyl-amine and 0.05% glacial acetic acid (v/v). The eluant is monitored at 260 nm, the flow rate is 45 mL/min, and appropriate fractions from multiple injections are combined and concentrated in vacuo to give 0.300 g of a dark oil. The oil is partitioned between ethyl acetate, saturated aqueous sodium bicarbonate solution, and water. The organic layer is separated and concentrated in vacuo. Column chromatography on 50 g of silica gel (elution with 10–20% acetone/hexane) affords 0.22 g of the title compound of the compound as a colorless oil.

Physical characteristics are as follows:

The retention time of the title compound is 57 min.

Preparation 164 (3S,6S)-3-[1-[3-bis(phenylmethyl)amino]phenyl]propyl]-5,6-dihydro-4-hydroxy-6-(2-phenylethyl-6-propyl-pyran-2-one (Formula FFF-3) Refer to Chart FFF.

The title compound of Preparation 161 is separated as described in Preparation 163 above. Further purification as described in Preparation 163 affords 0.117 g of the title compound as a colorless oil.

Physical characteristics are as follows:

The retention time of the title compound is 66 min.

Preparation 165 (3S,6R)-3-[1-(3-aminophenyl)propyl]-5,6-dihydro-4-hydroxy-6-(2-phenylethyl)-6-propyl-pyran-2-one (Formula FFF-4) Refer to Chart FFF.

Following the general procedure of Preparation 162, and making non-critical variations, but substituting the title product of Preparation 163 for the title product of Preparation 161, 0.022 g of the title compound is obtained.

Physical characteristics are as follows:

$^1$H NMR (CD$_3$OD) δ 7.25–7.18, 7.15–7.12, 7.07–7.05, 6.97, 6.82-, 6.76–6.71, 6.53, 4.00–3.92, 2.67–2.54, 2.29–2.15, 2.06–1.92, 1.90–1.62, 1.46–1.28, 0.97–0.88 ppm.

EXAMPLE 375

(3S,6R)-N-[3-[1-[5,6,-dihydro-4-hydroxy-2-oxo-6-(2-phenylethyl)-6-propyl-2H-pyran-3-yl]propyl]phenyl]-5-(triflouromethyl)-2-pyridinesulfonamide (Formula FFF-5) Refer to Chart FFF.

Following the general procedure of Example 374, and making non-critical variations, but substituting the title product of Preparation 165 for the title product of Preparation 162, 0.024 g of the title compound is obtained as a white foam.

Physical characteristics are as follows:
MP 156–159° C.

$^1$H NMR (CD$_3$OD) δ 8.90, 8.20–8.17, 8.02–7.99, 7.28–6.88, 4.00–3.90, 2.71–2.46, 2.20–2.10, 1.98–1.67, 1.41–1.28, 0.98–0.81 ppm.

EXAMPLE 376

(3S)-N-[3-[1-(5,6-Dihydro-4-hydroxy-2-oxo-6,6-dipropyl-2H-pyran-3-yl)propyl]phenyl]-5-(trifluoromethyl)-2-pyridine-sulfonamide (Formula W-13) Refer to Chart W.

The title compound of Preparation 99 (formula W-12) 182 mg is dissolved in 5 mL of methylene chloride and 133 μL of pyridine added. The reaction is cooled to 0° C. and 142 mg of 5-trifluoromethyl-2-pyridinesulfonylchloride added. The reaction is stirred for 30 minutes and the methylene chloride is evaporated and the resulting material diluted with ethyl acetate. The organic solution is washed with water, brine and then dried over sodium sulfate. Evaporation of solvent gives 580 mg of crude product. Silica gel chromatography (50 g) eluting with 50% ethyl acetate/hexane affords 211 mg of the desired product as a white foam.

Physical characteristics are as follows:
Anal. found: C, 57.80; H, 5.95; N, 5.01; S, 5.64.
[α]$_D$ (18.094 mg/2 mL CHCl$_3$)=−30°

EXAMPLE 377

(3R)-N-[3-[1-(5,6-Dihydro-4-hydroxy-2-oxo-6,6-dipropyl-2H-pyran-3-yl)propyl]phenyl]-5-(trifluoromethyl)-2-pyridinesulfonamide (Formula X-13) Refer to Chart X.

The title compound of Preparation 107 (formula X-12) 170 mg is dissolved in 5 mL of methylene chloride and 136 μL of pyridine added. The reaction is cooled to 0° C. and 132 mg of 5-trifluoromethyl-2-pyridinesulfonylchloride is added. The reaction is stirred for 30 minutes and the methylene chloride is evaporated and the resulting material diluted with ethyl acetate. The organic solution is washed with water, brine and then dried over sodium sulfate. Evaporation of solvent gives crude product which is chromatographed over 50 g of silica gel eluting with 50% ethyl acetate/hexane affords 225 mg of the desired product as a white foam.

Physical characteristics are as follows:
[α]$_D$ (mg/2 mL CHCl$_3$)=+29°

Preparation 166 (3S)(4R) 3-[2-[1-[3-[Bis(phenylmethyl)amino]phenyl]-propyl]-5-hydroxy-1,3-dioxo-5-phenethyloctyl]-4-phenyl-2-oxazolidinone (Formula X-10 where R$_1$ is phenethyl) Refer to Chart X.

To 1.12 g of the title compound of Preparation 104 is added 20 mL of methylene chloride and the resulting solution cooled to −78° C. To that solution is added 237 μL of TiCl$_4$ followed by 400 mL of diisopropylethylamine and the resulting solution is stirred at −78° C. for 1 hour. To the aforementioned solution is added 776 μL of 1-phenyl-3-hexanone and stirring continued at −40° C. for 40 minutes and then the temperature is raised to −10° C. for 1.5 hours. The reaction is quenched with the addition of a saturated ammonium chloride solution, then extraction with methylene chloride and evaporation of the organic extracts. The crude material is chromatographed over 200 g of silica gel eluting with 10% hexane/methylene chloride to afford 870 mg of the title compound.

Physical characteristics are as follows:
IR (mineral oil) 2956, 2926, 2854, 1777, 1600, 1494, 1452, 698 cm$^{-1}$.

[α]$_D$ (16.578 mg in CHCl$_3$)=+4°

Mass Spectrum: molecular ion at 736.

Anal. found. C, 78.00; H, 7.14; N, 3.61.

Preparation 167 (3R) 3-[1-[3-[Bis(phenylmethyl)amino]phenyl]propyl]-5,6-dihydro-4-hydroxy-6-phenethyl-6- propyl-2H-pyran-2-one (Formula X-11 where $R_1$ is phenethyl) Refer to Chart X.

The compound of Preparation 166 (750 mg) is added to 5 mL of dry THF and potassium tert. butoxide (1.0 M in THF; 1.2 mL) is added. The reaction is stirred at 20° C. for 30 minutes and then quenched by the addition of a saturated ammonium chloride solution. The reaction is extracted with ethyl acetate, the organic extracts washed with water and brine and finally evaporated to afford the crude product. Silica gel chromatography over 100 g of silica gel eluting with 15% ethyl acetate/hexane affords 511 mg of the title product.

Physical characteristics are as follows:
IR (mineral oil) 2956, 2855, 1628, 1599, 1577, 1494, 1385, 1364, 697 cm$^{-1}$.
Anal. found: C, 81.30; H, 7.68; N, 2.30.
Mass spectrum: molecular ion at 573.
$[\alpha]_D$ (18.116 mg/2 mL CH$_3$OH)=+38°

Preparation 168 (3R) 3-[1-[3-aminophenyl]propyl]-5,6-dihydro-4-hydroxy-6-phenethyl-6-propyl-2H-pyran-2-one (Formula X-12 where $R_1$ is phenethyl) Refer to Chart X.

The compound of Preparation 167 (370 mg) is dissolved in 35 mL of ethyl acetate and 6 ml of methanol. To that solution is added 200 mg of 10% Pd on Carbon catalyst and the reaction is hydrogenated under 50 psi of hydrogen for 2 hours. The reaction is evaporated and chromatographed over 60 g of silica gel to yield 244 mg of the title compound.

Physical characteristics are as follows:
IR (mineral oil) 3025, 2954, 2871, 2854, 1635, 1619, 1604, 1494, 1456, 1383, 1378, 1256 cm$^{-1}$.
$[\alpha]_D$ (16.764 mg/mL in CH$_3$OH)=+39°.
Mass spectrum: molecular ion at 393.
Anal. found: C, 75.79; H, 8.05; N. 3.27.

EXAMPLE 378

(3R)-N-[3-[1-(5,6-Dihydro-4-hydroxy-2-oxo-6-propyl-6-phenethyl-2H-pyran-3-yl)propyl]phenyl]-5-(trifluoromethyl)-2-pyridinesulfonamide (Formula X-13 where $R_1$ is phenethyl) Refer to Chart X.

The product of Preparation 168 (156 mg) is added to 5 mL of methylene chloride. To that solution is added 96 μL of pyridine and then the reaction is cooled to 0° C. To the aforementioned solution is added 102 mg of 5-trifluoromethyl-2-pyridinyl sulfonyl chloride. The reaction is stirred for 1 hour and then poured into ethyl acetate, washed with water, brine and dried with MgSO$_4$. The solvent is evaporated in vacuo and the resulting material chromatographed over 100 g of silica gel eluting with 50% ethyl acetate/hexane to yield 200 mg of the title compound.

Physical characteristics are as follows:
Mass spectrum: molecular ion at 602.
IR (mineral oil) 2953, 2922, 2870, 2853, 1642, 1605, 1459, 1457, 1326, 1259, 1180, 1171, 1141 cm$^{-1}$.
UV (EtOH),, (e) 216 (22300), 264 sh (10700), 270 (11500), 279 (12100) Anal. found: C, 57.53; H, 5.98; N, 4.84.

EXAMPLE 379

(3R,6S)-N-[3-[1-(5,6-Dihydro-4-hydroxy-2-oxo-6-propyl-6-phenethyl-2H-pyran-3-yl)propyl]phenyl]-5-(trifluoromethyl)-2-pyridinesulfonamide (Formula X-13 where $R_1$ is phenethyl) Refer to Chart X.

The product of Example 378 is added to isopropanol and injected onto a 0.46×25 cm Cyclobond I 2000 column (Advanced Separations Technoloyies, Inc., Whippany, N.J.). The column is in an ice-water bath. The sample is eluted at 1.0 mL/min. with acetonitrile containing 0.1% diethylamine and 0. 6% glacial acetic acid (V/V). The monitor is set at 250 nm. The earlier eluting diastereomer is identical to the compound of Example 298. The second eluting diastereomer is purified over 60 g of silica gel eluting with 40% ethyl acetate/hexane to afford 13 mg of the title compound.

Physical characteristics are as follows:
Opposite stereochemistry at C-6 to the compound of Example 298.
$^1$H-NMR (CD$_3$OD, δ) 8.91, 8.19, 8.16, 8.02, 7.99, 7.25, 7.18, 7.15, 7.13, 7.11, 7.04, 6.97, 6.89, 6.75, 3.95,2.69, 2.64, 2.53, 2.48, 2.13, 1.91, 1.71, 1.68, 1.37, 1.19, 1.17, 1.14, 0.94, 0.92, 0.89, 0.85, 0.83, 0.80, 0.93.

Preparation 169 (3S)-3-[(3-Bis(phenylmethyl)amino)phenyl]-4,4-dimethylpentanoic acid methyl ester (Formula LLL-9) Refer to Chart LLL.

To anhydrous methanol (2 mL) at room temperature is added titanium (IV) chloride (0.07 mL). The resulting light green solution is stirred for 2 h, treated with the compound of formula LLL-2 wherein R is phenyl (100 mg), prepared by procedures analogous to those described in Chart FF, and refluxed for 18 h. The reaction mixture is allowed to cool and is partitioned between 1N HCl and diethyl ether. The organic layer is separated washed with brine, dried over anhydrous sodium sulfate, and concentrated in vacuo. Purification by flash chromatography eluting with hexane/ethyl acetate (95:5) affords the title compound (58 mg) as a light amber oil.

Physical characteristics are as follows:
$^1$H NMR (CDCl$_3$) δ 7.32–7.20, 7.04, 6.61–6.48, 4.61, 3.48, 2.85–2.80, 2.72–2.55, 0.75 ppm
$^{13}$C NMR (CDCl$_3$) δ 173.69, 148.45, 142.51, 138.91, 128.53, 128.17, 126.78, 117.98, 114.49, 110.89, 54.54, 52.24, 51.40, 35.56, 33.65, 27.87 ppm
MS (EI) m/z 415.

Preparation 170 (3S)-3-[(3-Bis(phenylmethyl)amino)phenyl]-4,4-dimethyl-pentanoic acid (Formula LLL-10) Refer to Chart LLL.

The compound of formula LLL-9 (406 mg) of Preparation 169 is slurried in glacial acetic acid (2.6 mL) and 6N sulfuric acid. The reaction mixture is refluxed for 5 h, allowed to cool and is partitioned between water and diethyl ether. The aqueous layer is separated and extracted two more times with diethyl ether. The combined organic layers are washed with brine, dried over anhydrous sodium sulfate, and concentrated in vacuo. The resulting light brown residue is dissolved in diethyl ether and treated with dicyclohexylamine (0.16 mL) at 0° C. The solids are isolated, washed with diethyl ether and dried in vacuo. The light brown solid is suspended in diethyl ether and washed with 0.25N HCl. The organic layer is washed with brine, dried over anhydrous sodium sulfate, and concentrated in vacuo, affording the title product (54 mg) as a light brown amorphous solid.

Physical charactistics are as follows:
$^1$H NMR (CDCl$_3$) δ 7.31–7.19, 7.04, 6.61–6.48, 4.61, 2.81–2.56, 0.74 ppm
$^{13}$C NMR (CDCl$_3$) δ 179.15, 148.56, 142.28, 138.83, 128.55, 128.23, 126.76, 117.90, 114.49, 110.98, 54.51, 51.83, 35.45, 33.67, 27.84 ppm
MS (EI) m/z 401.

Preparation 171 N-[(S)-4-Benzyl-2-oxazolidinone]3-aminocinnamate amide (Formula HHH-4) Refer to Chart HHH.

A 1 liter round-bottomed flask with nitrogen inlet and addition funnel is charged with 10.02 g of commerically available (S)-4-benzyl-2-oxazolidinone and 260 mL of tetrahydrofuran and then cooled to −78° C. To the aforementioned solution is added 37 mL of n-butyl lithium during which time a white solid separates from the reaction solution. To that suspension is added 11.46 g of trans-3-nitrocinnamic acid chloride (prepared from the treatment of commerically available 3-nitrocinnamic acid with oxalyl chloride) in a small volume of THF. The resulting pale yellow homogeneous solution is allowed to warm to room temperature and quenched with a saturated ammonium chloride solution and is extracted with ethyl acetate. The organic layer is separated, washed with brine and water, dried over magnesium sulfate, filtered and concentrated to give a reddish brown syrup (formula HHH-3 in Chart HHH) which is used without further purification. The aforementioned crude reaction mixture is added to ethanol containing 64.18 grams of $SnCl_2.2H_2O$ and that mixture heated at reflux for 20 minutes. The reaction is cooled to room temperature and poured into ice. The mixture is brought to pH 9–10 with saturated aqueous $Na_2CO_3$. The mixture is filtered and the filter cake washed extensively with ethyl acetate. The filtrate is washed with brine and the organic phase is dried ($Na_2SO_4$), filtered, and concentrated in vacuo to give a yellow solid. Recrystallization from ethanol gives 11.56 g of the title product.

Physical characteristics are as follows:

IR (mineral oil) 3450, 3369, 2924, 1771, 1678, 1620, 1462, 1392, 1357, 1347, 1214 $cm^{-1}$ $[\alpha]_D$ (14.418 mg/mL in $CHCl_3$)=+51°

Preparation 172 N-[(S)-4-Benzyl-2-oxazolidinone]3-(bis(phenylmethyl)-amino) cinnamate amide (Formula HHH-5) Refer to Chart HHH.

The amine of formula HHH-4 from Preparation 172 (10.13 g), 10.48 g of potassium carbonate, 8.3 mL of benzyl bromide and 100 mL of acetonitrile is heated at reflux for 3 hours. The reaction is cooled to room temperature and partitioned between water and ethyl acetate. The aqueous is extracted several additional times with ethyl acetate. The combined ethyl acetate extracts are dried ($Na_2SO_4$), filtered and concentrated in vacuo. The residue is purified via silica gel chromatography eluting with 25% ethyl acetate/hexane to yield 8.87 g of the title product.

Physical characteristics are as follows:

$^{13}$C-NMR ($CDCl_3$, ppm) 165, 153, 149, 147, 138, 135, 129.6, 129.3 128.8, 128.6, 127, 126.9, 126.5, 116.54, 116.50, 114, 113, 65, 55, 54, 37

IR (mineral oil) 2954, 2870, 2854, 1776, 1677, 1616, 1595, 1493, 1454, 1353, 1209, 988 $cm^{-1}$ Preparation 173 (3S)(4S)3-[3-(3-(bis(phenylmethyl) aminophenyl) pentanoyl]-4-phenyl-2-oxazolidinone (Formula HHH-6) Refer to Chart W.

A 100-mL, three-necked flask equipped with a stir-bar, 25-mL pressure-equalizing addition funnel, and a nitrogen inlet is charged with copper (I) bromide dimethyl sulfide complex (1.69 g), 20 mL of tetrahydrofuran and 10 mL of dimethyl sulfide. The addition funnel is charged with the title compound of Preparation 172 (2.747 g) and 10 mL of tetrahydrofuran. The reaction mixture is cooled to −40° C. and ethyl magnesium bromide (5.5 mL of a 3.0 M solution in ether) is added dropwise over 5 min. The resulting black mixture is stirred another 10 min at −40° C. and then allowed to warm to −10° C. The solution of the title compound of Preparation 172 in tetrahydrofuran is added dropwise to the reaction mixture over 17 min. The addition funnel is then rinsed with another 3 mL of tetrahydrofuran, and the reaction mixture is stirred for 2.5 h at ca. −40 to −60° C. The reaction is quenched by pouring the mixture into 50 mL of saturated aqueous ammonium chloride solution, and the organic solvents are removed by concentration in vacuo. The resulting residue is partitioned between 75 mL of ethyl acetate and 50 mL of water and filtered through glass wool. The organic layer is then separated, washed with two 100-mL portions of 10% ammonium hydroxide solution and 50 mL of brine, dried over magnesium sulfate, filtered and concentration in vacuo to yield 3.59 g of a yellow oil. Column chromatography on 150 g of silica gel (elution with 5–15% ethyl acetate/hexane) affords two diastereomeric products. 1.602 g of the title compound (the less polar diastereomer) is isolated as a pale yellow oil Physical characteristics are as follows:

$^1$H NMR ($CDCl_3$) δ 7.32–7.17, 7.06, 6.60, 6.55, 4.63, 4.43–4.37, 4.00, 3.85, 3.37, 3.20, 3.08, 3.02–2.92, 2.62, 1.71–1.48, 0.73 ppm]

Also isolated from the column is 0.310 g of the more polar diastereomer as a pale yellow oil.

Physical characteristics are as follows:

$^1$H NMR ($CDCl_3$) δ 7.32–7.18, 7.12, 7.05, 6.64–6.56, 4.63, 4.60–4.52, 4.08–4.04, 3.48–3.38, 3.07–2.96, 2.48, 1.69–1.48, 0.73 ppm.

In addition, fractions containing 0.708 g of a ca. 1:4 ratio mixture of the less polar to more polar diastereomers are collected from the column.

Preparation 174 (3S,6S)-3-[1-(3-aminophenyl)propyl]-5,6-dihydro-4-hydroxy-6-(2-phenylethyl)-6-propyl-2H-pyran-2-one (Formula FFF-6) Refer to Chart FFF.

Following the general procedure of Preparation 162, and making non-critical variations, but substituting the title product of Preparation [U-141164] for the title product of Preparation 161, 0.040 g of crude title compound is obtained. This compound is used immediately in the next step without further purification.

EXAMPLE 380

(3S,6S)-N-[3-[1-[5,6-dihydro-4-hydroxy-2-oxo-6-(2-phenylethyl)-6-propyl-2H-pyran-3-yl]propyl]phenyl]-5-(triflouromethyl)-2-pyridinesulfonamide (Formula FFF-7) Refer to Chart FFF.

Following the general procedure of Example 374, and making non-critical variations, but substituting the title product of Preparation 174 for the title product of Preparation 162, 0.015 g of the title compound is obtained as a white foam.

Physical characteristics are as follows:

$^1$H NMR ($CD_3OD$) δ 8.95, 8.25–8.21, 8.07–8.02, 7.25–6.93, 3.94–3.88, 2.70–2.51, 2.20–2.18, 1.97–1.66, 1.40–1.30, 0.92–0.81 ppm.

Thus, for example, the compounds of the present invention include the following individual stereoisomers:

5-cyano-N-[3-(R)-[1-[5,6-dihydro-4-hydroxy-2-oxo-6-(2-phenethyl)-6-(R)-(3,3,3-trifluoropropyl)-2H-pyran-3-yl]-2,2-dimethylpropyl]phenyl]-2-pyridinesulfonamide, 5-cyano-N-[3-(S)-[1-[5,6-dihydro-4-hydroxy-2-oxo-6-(2-phenethyl)-6-(S)-(3,3,3-trifluoropropyl)-2H-pyran-3-yl]-2,2-dimethylpropyl]phenyl]-2-pyridinesulfonamide, 5-cyano-N-[3-(R)-[1-[5,6-dihydro-4-hydroxy-2-oxo-6-(2-phenethyl)-6-(S)-(3,3,3-trifluoropropyl)-2H-pyran-3-yl]-2,2-dimethylpropyl]phenyl]-2-pyridinesulfonamide, 5-cyano-N-[3-(S)-[1-[5,6-dihydro-4-hydroxy-2-oxo-6-(2-phenethyl)-6-(R)-(3,3,3-trifluoropropyl)-2H-pyran-3-yl]-2,2-dimethylpropyl]phenyl]-2-pyridinesulfonamide, N-[3-(R)-[1-[5,6-dihydro-4-hydroxy-2-oxo-6-(R)-(2-phenethyl)-6-(3,3,3 -trifluoropropyl)-2H-pyran-3-yl]-2,2-dimethylpropyl]phenyl]-1-methyl-1H-imidazole-4-sulfonamide, N-[3-(S)-[1-[5,6-dihydro-4-hydroxy-2-oxo-6-(S)-(2-phenethyl)-6-(3,3,3-trifluoropropyl)-2H-pyran-3-yl]-2,2-dimethylpropyl]phenyl]-1-methyl-1H-imidazole-4-sulfonamide, N-[3-(R)-[1-[5,6-dihydro-4-hydroxy-2-oxo-6-(S)-(2-phenethyl)-6-(3,3,3-trifluoropropyl)-2H-pyran-3-yl]-2,2-dimethylpropyl]phenyl]-1-methyl-1H-imidazole-4-sulfonamide, N-[3-(S)-[1-[5,6-dihydro-4-hydroxy-2-oxo-6-(R)-(2-phenethyl)-6-(3,3,3-trifluoropropyl)-2H-pyran-3-yl]-2,2-dimethylpropyl]phenyl]-1-methyl-1H-imidazole-4-sulfonamide, 5-amino-N-[3-(R)-[1-[5,6-dihydro-4-hydroxy-2-oxo-6-(2-phenethyl)-6-(R)-(3,3,3-trifluoropropyl)-2H-pyran-3-yl]-2,2-dimethylpropyl]phenyl]-2-pyridinesulfonamide, 5-amino-N-[3-(R)-[1-[5,6-dihydro-4-hydroxy-2-oxo-6-(2-phenethyl)-6-(S)-(3,3,3-trifluoropropyl)-2H-pyran-3-yl]-2,2-dimethylpropyl]phenyl]-2-pyridinesulfonamide, 5-amino-N-[3-(S)-[1-[5,6-dihydro-4-hydroxy-2-oxo-6-(2-phenethyl)-6-(R)-(3,3,3-trifluoropropyl)-2H-pyran-3-yl]-2,2-dimethylpropyl]phenyl]-2-pyridinesulfonamide, 5-amino-N-[3-(S)-[1-[5,6-dihydro-4-hydroxy-2-oxo-6-(2-phenethyl)-6-(S)-(3,3,3-trifluoropropyl)-2H-pyran-3-yl]-2,2-dimethylpropyl]phenyl]-2-pyridinesulfonamide, N-[3-(R)-[1-[5,6-dihydro-4-hydroxy-2-oxo-6-(2-phenethyl)-6-(R)-propyl-2H-pyran-3-yl]-2,2-dimethylpropyl]phenyl]-2-pyridinesulfonamide, N-[3-(R)-[1-[5,6-dihydro-4-hydroxy-2-oxo-6-(2-phenethyl)-6-(S)-propyl-2H-pyran-3-yl]-2,2-dimethylpropyl]phenyl]-2-pyridinesulfonamide, N-[3-(S)-[1-[5,6-dihydro-4-hydroxy-2-oxo-6-(2-phenethyl)-6-(R)-propyl-2H-pyran-3-yl]-2,2-dimethylpropyl]phenyl]-2-pyridinesulfonamide, N-[3-(S)-[1-[5,6-dihydro-4-hydroxy-2-oxo-6-(2-phenethyl)-6-(S)-propyl-2H-pyran-3-yl]-2,2-dimethylpropyl]phenyl]-2-pyridinesulfonamide, 5-Trifluoromethyl-N-[3-(R)-[1-[4-hydroxy-2-oxo-6,6-di-n-propyl-5,6-dihydro-2H-pyran-3-yl]-propyl]-phenyl]-2-pyridinesulfonamide, 5-Trifluoromethyl-N-[3-(S)-[1-[4-hydroxy-2-oxo-6,6-di-n-propyl-5,6-dihydro-2H-pyran-3-yl]-propyl]-phenyl]-2-pyridinesulfonamide, 4-Trifluoromethyl-N-[3-(R)-[1-[4-hydroxy-2-oxo-6,6-di-n-propyl-5,6-dihydro-2H-pyran-3-yl]-propyl]-phenyl]-2-pyridinesulfonamide, 4-Trifluoromethyl-N-[3-(S)-[1-[4-hydroxy-2-oxo-6,6-di-n-propyl-5,6-dihydro-2H-pyran-3-yl]-propyl]-phenyl]-2-pyridinesulfonamide, 5-Trifluoromethyl-N-[3-(R)-[1-[4-hydroxy-2-oxo-6,6-di-n-propyl-5,6-dihydro-2H-pyran-3-yl]-2,2-dimethylpropyl]-phenyl]1-2-pyridinesulfonamide, 5-Trifluoromethyl-N-[3-(S)-[1-[4-hydroxy-2-oxo-6,6-di-n-propyl-5,6-dihydro-2H-pyran-3-yl]-2,2-dimethylpropyl]-phenyl]1-2-pyridinesulfonamide, 5-Trifluoromethyl-N-[3-(R)-[1-[4-hydroxy-2-oxo-6,6-di-phenethyl-5,6-dihydro-2H-pyran-3-yl]-propyl]-phenyl]-2-pyridinesulfonamide, 5-Trifluoromethyl-N-[3-(S)-[1-[4-hydroxy-2-oxo-6,6-di-phenethyl-5,6-dihydro-2H-pyran-3-yl]-propyl]-phenyl]-2-pyridinesulfonamide, 4-Trifluoromethyl-N-[3-(R)-[1-[4-hydroxy-2-oxo-6,6-di-phenethyl-5,6-dihydro-2H-pyran-3-yl]-propyl]-phenyl]-2-pyridinesulfonamide, 4-Trifluoromethyl-N-[3-(S)-[1-[4-hydroxy-2-oxo-6,6-di-phenethyl-5,6-dihydro-2H-pyran-3-yl]-propyl]-phenyl]-2-pyridinesulfonamide, 4-Trifluoromethyl-N-[3-(R)-[1-[4-hydroxy-2-oxo-6,6-di-n-propyl-5,6-dihydro-2H-pyran-3-yl]-2,2-dimethylpropyl]-phenyl]-2-pyridinesulfonamide, 4-Trifluoromethyl-N-[3-(S)-[1-[4-hydroxy-2-oxo-6,6-di-n-propyl-5,6-dihydro-2H-pyran-3-yl]-2,2-dimethylpropyl]-phenyl]-2-pyridinesulfonamide, 5-Trifluoromethyl-N-[3(R)-[1-[5,6-dihydro-4-hydroxy-2-oxo-6(R)-(2-phenethyl)-6(R)-n-propyl-2H-pyran-3-yl]-2,2-dimethylpropyl]-phenyl]-2-pyridinesulfonamide, 5-Trifluoromethyl-N-[3(R)-[1-[5,6-dihydro-4-hydroxy-2-oxo-6(S)-(2-phenethyl)-6(S)-n-propyl-2H-pyran-3-yl]-2,2-dimethylpropyl]-phenyl]-2-pyridinesulfonamide, 5-Trifluoromethyl-N-[3(S)-[1-[5,6-dihydro-4-hydroxy-2-oxo-6(R)-(2-phenethyl)-6(R)-n-propyl-2H-pyran-3-yl]-2,2-dimethylpropyl]-phenyl]-2-pyridinesulfonamide, 5-Trifluoromethyl-N-[3(S)-[1-[5,6-dihydro-4-hydroxy-2-oxo-6(S)-(2-phenethyl)-6(S)-n-propyl-2H-pyran-3-yl]-2,2-dimethylpropyl]-phenyl]-2-pyridinesulfonamide, 4-Trifluoromethyl-N-[3(R)-[1-[5,6-dihydro-4-hydroxy-2-oxo-6(R)-(2-phenethyl)-6(R)-n-propyl-2H-pyran-3-yl]-2,2-dimethylpropyl]-phenyl]-2-pyridinesulfonamide, 4-Trifluoromethyl-N-[3(R)-[1-[5,6-dihydro-4-hydroxy-2-oxo-6(S)-(2-phenethyl)-6(S)-n-propyl-2H-pyran-3-yl]-2,2-dimethylpropyl]-phenyl]-2-pyridinesulfonamide, 4-Trifluoromethyl-N-[3(S)-[1-[5,6-dihydro-4-hydroxy-2-oxo-6(R)-(2-phenethyl)-6(R)-n-propyl-2H-pyran-3-yl]-2,2-dimethylpropyl]-phenyl]-2-pyridinesulfonamide, 4-Trifluoromethyl-N-[3(S)-[1-[5,6-dihydro-4-hydroxy-2-oxo-6(S)-(2-phenethyl)-6(S)-n-propyl-2H-pyran-3-yl]-2,2-dimethylpropyl]-phenyl]-2-pyridinesulfonamide, 5-Trifluoromethyl-N-[3(R)-[1-[5,6-dihydro-4-hydroxy-2-oxo-6(R)-(2-phenethyl)-6(R)-n-propyl-2H-pyran-3-yl]-propyl]-phenyl]-2-pyridinesulfonamide, 5-Trifluoromethyl-N-[3(R)-[1-[5,6-dihydro-4-hydroxy-2-oxo-6(S)-(2-phenethyl)-6 -(S)-n-propyl-2H-pyran-3-yl]-propyl]-phenyl]-2-pyridinesulfonamide, 5-Trifluoromethyl-N-[3(S)-[1-[5,6-dihydro-4-hydroxy-2-oxo-6(R)-(2-phenethyl)-6-(R)-n-propyl-2H-pyran-3-yl]-propyl]-phenyl]-2-pyridinesulfonamide, 5-Trifluoromethyl-N-[3(S)-[1-[5,6-dihydro-4-hydroxy-2-oxo-6(S)-(2-phenethyl)-6-(S)-n-propyl-2H-pyran-3-yl]-propyl]-phenyl]-2-pyridinesulfonamide, 5-Cyano-N-[3(R)-(1-[5,6-dihydro-4-hydroxy-2-oxo-6(R)-(2-phenylethyl)-6-propyl-2H-pyran-3-yl]-2,2-dimethylpropyl)phenyl]-2-pyridinesulfonamide, 5-Cyano-N-[3(R)-(1-[5,6-dihydro-4-hydroxy-2-oxo-6(S)-(2-phenylethyl)-6-propyl-2-H-pyran-3-yl]-2,2-dimethylpropyl)phenyl]-2-pyridinesulfonamide, 5-Cyano-N-[3-(S)-(1-[5,6-dihydro-4-hydroxy-2-oxo-6(R)-(2-phenylethyl)-6-propyl-2H-pyran-3-yl]-2,2-dimethylpropyl)phenyl]-2-pyridinesulfonamide, 5-Cyano-N-[3(S)-(1-[5,6-dihydro-4-hydroxy-2-oxo-6(S)-(2-phenylethyl)-6-propyl-2H-pyran-3-yl]-2,2-dimethylpropyl)phenyl]-2-pyridinesulfonamide, N-[3(R)-[1-(5,6-Dihydro-4-hydroxy-2-oxo-6(R)-[2-phenylethyl]-6-propyl-2H-pyran-3-yl)-2,2-dimethylpropyl]phenyl]-1-methyl-1H-imidazole-4-sulfonamide, N-[3(R)-[1-(5,6-Dihydro-4-hydroxy-2-oxo-6(S)-[2-phenylethyl]-6-propyl-2H-pyran-3-yl)-2,2-dimethylpropyl]phenyl]-1-methyl-1H-imidazole-4-sulfonamide, N-[3(S)-[I-(5,6-Dihydro-4-hydroxy-2-oxo-6(R)-[2-phenylethyl]-6-propyl-2H-pyran-3-yl)-2,2-dimethylpropyl]phenyl]-1-methyl-1H-imidazole-4-sulfonamide, N-[3(S)-[1-(5,6-Dihydro-4-hydroxy-2-oxo-6(S)-[2-phenylethyl]-6-propyl-2H-pyran-3-yl)-2,2-dimethylpropyl]phenyl]-1-methyl-1H-imidazole-4-sulfonamide, 5-Amino-N-[3(R)-(1-[5,6-dihydro-4-hydroxy-2-oxo-6(S)-(2-phenylethyl)-6-propyl-2H-pyran-3-yl]-2,2-dimethylpropyl)phenyl]-2-pyridinesulfonamide, 5-Amino-N-[3(S)-(1-[5,6-dihydro-4-hydroxy-2-oxo-6(R)-(2-phenylethyl)-6-propyl-2H-pyran-3-yl]-2,2-dimethylpropyl)phenyl]-2-pyridinesulfonamide , 5-Amino-N-[3(S)-(1-[5,6-dihydro-4-hydroxy-2-oxo-6(S)-(2-phenylethyl)-6-propyl-2H-pyran-3-yl]-2,2-dimethylpropyl)phenyl]-2-pyridinesulfonamide, 5-Amino-N-[3(R)-(1-[5,6-dihydro-4-hydroxy-2-oxo-6(R)-(2-phenylethyl)-6-propyl-2H-pyran-3-yl]-2,2-dimethylpropyl)phenyl]-2-pyridinesulfonamide, 5-Amino-N-[3(R)-(1-[5,6-dihydro-4-hydroxy-2-oxo-6 (R)-(2-phenylethyl)-6-propyl-2H-pyran-3-yl]propyl) phenyl-2-pyridinesulfonamide, 5-Amino-N-[3(R)-(1-[5,6-dihydro-4-hydroxy-2-oxo-6 (S)-(2-phenylethyl)-6-propyl-2H-pyran-3-yl]propyl) phenyl]-2-pyridinesulfonamide, 5-Amino-N-[3(S)-(1-[5,6-dihydro-4-hydroxy-2-oxo-6 (R)-(2-phenylethyl)-6-propyl-2H-pyran-3-yl]propyl) phenyl]-2-pyridinesulfonamide, 5-Amino-N-[3(S)-(1-[5,6-dihydro-4-hydroxy-2-oxo-6 (S)-(2-phenylethyl)-6-propyl-2H-pyran-3-yl]propyl) phenyl]-2-pyridinesulfonamide, 5-Amino-N-[3(R)-(1-[6(R)-(2-[4-fluorophenyl]ethyl)-5, 6-dihydro-4-hydroxy-2-oxo-6-propyl-2H-pyran-3-yl]-2,2-dimethylpropyl)phenyl]-2-pyridinesulfonamide, 5-Amino-N-[3(R)-(1-[6(S)-(2-[4-fluorophenyl]ethyl)-5, 6-dihydro-4-hydroxy-2-oxo-6-propyl-2H-pyran-3-yl]-2,2-dimethylpropyl)phenyl]-2-pyridinesulfonamide, 5-Amino-N-[3(S)-(1-[6(R)-(2-[4-fluorophenyl]ethyl)-5, 6-dihydro-4-hydroxy-2-oxo-6-propyl-2H-pyran-3-yl]-2,2-dimethylpropyl)phenyl]-2-pyridinesulfonamide, 5-Amino-N-[3(S)-(1-[6(S)-(2-[4-fluorophenyl]ethyl)-5, 6-dihydro-4-hydroxy-2-oxo-6-propyl-2H-pyran-3-yl]-2,2-dimethylpropyl)phenyl]-2-pyridinesulfonamide, N-[3(R)-(1-[5,6-Dihydro-6,6-dipropyl-4-hydroxy-2-oxo-2H-pyran-3-yl]-2,2-dimethylpropyl)phenyl]-1-methyl-1H-imidazole-4-sulfonamide, N-[3(S)-(1-[5,6-Dihydro-6,6-dipropyl-4-hydroxy-2-oxo-2H-pyran-3-yl]-2,2-dimethylpropyl)phenyl]-1-methyl-1H-imidazole-4-sulfonamide, 5-Amino-N-[3(R)-(1-[5,6-dihydro-6,6-dipropyl-4-hydroxy-2-oxo-2H-pyran-3-yl]-2,2-dimethylpropyl) phenyl]-2-pyridinesulfonamide, 5-Amino-N-[3(S)-(1-[5,6-dihydro-6,6-dipropyl-4-hydroxy-2-oxo-2H-pyran-3-yl]-2,2-dimethylpropyl) phenyl]-2-pyridinesulfonamide, 5-Cyano-N-[3(R)-(1-[5,6-dihydro-6,6-dipropyl-4-hydroxy-2-oxo-2H-pyran-3-yl]-2,2-dimethylpropyl) phenyl]-2-pyridinesulfonamide, 5-Cyano-N-[3(S)-(1-[5,6-dihydro-6,6-dipropyl-4-hydroxy-2-oxo-2H-pyran-3-yl]-2,2-dimethylpropyl) phenyl]-2-pyridinesulfonamide, N-[3(R)-(1-[6,6-Bis(2-phenylethyl)-5,6-dihydro-4-hydroxy-2-oxo-2H-pyran-3-yl]propyl)phenyl]-1-methyl-1H-imidazole-4-sulfonamide, N-[3(S)-(1-[6,6-Bis(2-phenylethyl)-5,6-dihydro-4-hydroxy-2-oxo-2H-pyran-3-yl]propyl)phenyl]-1-methyl-1H-imidazole-4-sulfonamide, N-[3(R)-(1-[6,6-Bis(2-phenyl-ethyl)-5,6-dihydro-4-hydroxy-2-oxo-2H-pyran-3-yl]propyl)phenyl]-5-cyano-2-pyridinesulfonamide, N-[3(S)-(1-[6,6-Bis(2-phenyl-ethyl)-5,6-dihydro-4-hydroxy-2-oxo-2H-pyran-3-yl]propyl)phenyl]-5-cyano-2-pyridinesulfonamide, N-[3-{1(R)-(4-Hydroxy-5,6-dihydro-2-oxo-6(R)-phenethyl-6-propyl-2H-pyran-3-yl)propyl}phenyl]-5-cyanopyridine-2-sulfonamide, N-[3-{1(R)-(4-Hydroxy-5,6-dihydro-2-oxo-6(S)-phenethyl-6-propyl-2H-pyran-3-yl)propyl}phenyl]-5-cyanopyridine-2-sulfonamide, N-[3-{1(S)-(4-Hydroxy-5,6-dihydro-2-oxo-6(R)-phenethyl-6-propyl-2H-pyran-3 -yl)propyl}phenyl]-5-cyanopyridine-2-sulfonamide, N-[3-{1(S)-(4-Hydroxy-5,6-dihydro-2-oxo-6(S)-phenethyl-6-propyl-2H-pyran-3-yl)propyl}phenyl]-5-cyanopyridine-2-sulfonamide, N-[3-{1(R)-(4-Hydroxy-5,6-dihydro-2-oxo-6(R)-phenethyl-6-propyl-2H-pyran-3-5 yl)propyl}phenyl]-1-methyl-1H-imidazole-4-sulfonamide, N-[3-{1(R)-(4-Hydroxy-5,6-dihydro-2-oxo-6(S)-phenethyl-6-propyl-2H-pyran-3-yl)propyl}phenyl]-1-methyl-1H-imidazole-4-sulfonamide, N-[3-{1(S)-(4-Hydroxy-5,6-dihydro-2-oxo-6(R)-phenethyl-6-propyl-2H-pyran-3-yl)propyl}phenyl]-1-methyl-1H-imidazole-4-sulfonamide, N-[3-{1(S)-(4-Hydroxy-5,6-dihydro-2-oxo-6(S)-phenethyl-6-propyl-2H-pyran-3-yl)propyl}phenyl]-1-methyl-1H-imidazole-4-sulfonamide, N-[3-{1(R)-(4-Hydroxy-5,6-dihydro-2-oxo-6(R)-(2-(4-fluorophenyl)ethyl)-6-propyl-2H-pyran-3-yl)-2,2-dimethylpropyl}phenyl]-5-cyanopyridine-2-sulfonamide, N-[3-{1(R)-(4-Hydroxy-5,6-dihydro-2-oxo-6(S)-(2-(4-fluorophenyl)ethyl)-6-propyl-2H-pyran-3-yl)-2,2-dimethylpropyl}phenyl]-5-cyanopyridine-2-sulfonamide, N-[3-{1(S)-(4-Hydroxy-5,6-dihydro-2-oxo-6(R)-(2-(4-fluorophenyl)ethyl)-6-propyl-2H-pyran-3-yl)-2,2-dimethylpropyl}phenyl]-5-cyanopyridine-2-sulfonamide, N-[3-{1(S)-(4-Hydroxy-5,6-dihydro-2-oxo-6(S)-(2-(4-fluorophenyl)ethyl)-6-propyl-2H-pyran-3-yl)-2,2-dimethylpropyl}phenyl]-5-cyanopyridine-2-sulfonamide, N-[3-{1(R)-(4-Hydroxy-5,6-dihydro-2-oxo-6(R)-(2-(4-fluorophenyl)ethyl)-6-propyl-2H-pyran-3-yl)-2,2-dimethylpropyl}phenyl]-1-methyl-1H-imidazole-4-sulfonamide, N-[3-{1(R)-(4-Hydroxy-5,6-dihydro-2-oxo-6(S)-(2-(4-fluorophenyl)ethyl)-6-propyl-2H-pyran-3-yl)-2,2-dimethylpropyl}phenyl]-1-methyl-1H-imidazole-4-25 sulfonamide, N-[3-{1(S)-(4-Hydroxy-5,6-dihydro-2-oxo-6(R)-(2-(4-fluorophenyl)ethyl)-6-propyl-2H-pyran-3-yl)-2,2-dimethylpropyl}phenyl]-1-methyl-1H-imidazole-4-sulfonamide, N-[3-1(S)-(4-Hydroxy-5,6-dihydro-2-oxo-6(S)-(2-(4-fluorophenyl)ethyl)-6-propyl-2H-pyran-3-yl)-2,2-dimethylpropyl}phenyl]-1-methyl-1H-imidazole-4-sulfonamide, N-[3-{1(R)-(4-Hydroxy-5,6-dihydro-2-oxo-6,6-bis(2-phenylethyl)-2H-pyran-3-yl)-2,2-dimethylpropyl}phenyl]-5-aminopyridine-2-sulfonamide, N-[3-1(S)-(4-Hydroxy-5,6-dihydro-2-oxo-6,6-bis(2-phenylethyl)-2H-pyran-3-yl)-2,2-dimethylpropyl}phenyl]-5-aminopyridine-2-sulfonamide, N-[3-{1(R)-(4-Hydroxy-5,6-dihydro-2-oxo-6,6-bis(2-phenylethyl)-2H-pyran-3-yl)-2,2-dimethylpropyl}phenyl]-1-methyl-1H-imidazole-4-sulfonamide, N-[3-{1(S)-(4-Hydroxy-5,6-dihydro-2-oxo-6,6-bis(2-phenylethyl)-2H-pyran-3-yl)-2,2-dimethylpropyl}phenyl]-1-methyl-1H-imidazole-4-sulfonamide, N-[3-{1(R)-(4-Hydroxy-5,6-dihydro-2-oxo-6,6-bis(2-phenylethyl)-2H-pyran-3-yl)-2,2-dimethylpropyl}phenyl]-5-cyanopyridine-2-sulfonamide, N-[3-{1(S)-(4-Hydroxy-5,6-dihydro-2-oxo-6,6-bis(2-phenylethyl)-2H-pyran-3-yl)-2,2-dimethylpropyl}phenyl]-5-cyanopyridine-2-sulfonamide, N-[3-{1(R)-(4-Hydroxy-5,6-dihydro-2-oxo-6,6-dipropyl-2H-pyran-3-yl)-propyl}phenyl]-5-cyanopyridine-2-sulfonamide, N-[3-{1(S)-(4-Hydroxy-5,6-dihydro-2-oxo-6,6-dipropyl-2H-pyran-3-yl)-propyl}phenyl]-5-cyanopyridine-2-sulfonamide, N-[3-{1(R)-(4-Hydroxy-5,6-dihydro-2-oxo-6,6-dipropyl-2H-pyran-3-yl)-propyl}phenyl]-5-aminopyridine-2-sulfonamide, N-[3-{1(S)-(4-Hydroxy-5,6-dihydro-2-oxo-6,6-dipropyl-2H-pyran-3-yl)-propyl}phenyl]-5-aminopyridine-2-sulfonamide, N-[3-{1(R)-(4-Hydroxy-5,6-dihydro-2-oxo-6(R)-(2-(4-fluorophenyl)ethyl)-6-propyl-2H-pyran-3-yl)propyl}phenyl]-5-cyanopyridine-2-sulfonamide, N-[3-{1(S)-(4-Hydroxy-5,6-dihydro-2-oxo-6(R)-(2-(4-fluorophenyl)ethyl)-6-propyl-2H-pyran-3-yl)propyl}phenyl]-5-cyanopyridine-2-sulfonamide, N-[3-1(R)-(4-Hydroxy-5,6-dihydro-2-oxo-6(S)-(2-(4-fluorophenyl)ethyl)-6-propyl-2H-pyran-3-yl)propyl}phenyl]-5-cyanopyridine-2-sulfonamide, N-[3-{1(S)-(4-Hydroxy-5,6-dihydro-2-oxo-6(8)-(2-(4-fluorophenyl)ethyl)-6-propyl-2H-pyran-3-yl)propyl}phenyl]-5-cyanopyridine-2-sulfonamide, N-[3-{1(R)-(4-Hydroxy-5,6-dihydro-2-oxo-6(R)-(2-(4-fluorophenyl)ethyl)-6-propyl-2H-pyran-3-yl)propyl}phenyl]-1-methyl-1H-imidazole-4-sulfonamide, N-[3-{1(S)-(4-Hydroxy-5,6-dihydro-2-oxo-6(S)-(2-(4-fluorophenyl)ethyl)-6-propyl-2H-pyran-3-yl)propyl}phenyl]-1-methyl-1H-imidazole-4-sulfonamide, N-[3-{1(R)-(4-Hydroxy-5,6-dihydro-2-oxo-6(S)-(2-(4-fluorophenyl)ethyl)-6-propyl-2H-pyran-3-yl)propyl}phenyl]-1-methyl-1H-imidazole-4-sulfonamide, N-[3-{1(S)-(4-Hydroxy-5,6-dihydro-2-oxo-6(R)-(2-(4-fluorophenyl)ethyl)-6-propyl-2H-pyran-3-yl)propyl}phenyl]-1-methyl-1H-imidazole-4-sulfonamide, N-[3-{1(R)-(4-Hydroxy-5,6-dihydro-2-oxo-6(R)-(2-(4-fluorophenyl)ethyl)-6-propyl-2H-pyran-3-yl)propyl}phenyl]-5-aminopyridine-2-sulfonamide, N-[3-{1(S)-(4-Hydroxy-5,6-dihydro-2-oxo-6(S)-(2-(4-fluorophenyl)ethyl)-6 -propyl-2H-pyran-3-yl)propyl}phenyl]-5-aminopyridine-2-sulfonamide, N-[3-{1(R)-(4-Hydroxy-5,6-dihydro-2-oxo-6(S)-(2-(4-fluorophenyl)ethyl)-6-propyl-2H-pyran-3-yl)propyl}phenyl]-5-aminopyridine-2-sulfonamide, N-[3-{1(S)-(4-Hydroxy-5,6-dihydro-2-oxo-6(R)-(2-(4-fluorophenyl)ethyl)-6-propyl-2H-pyran-3-yl)propyl}phenyl]-5-aminopyridine-2-sulfonamide,

FORMULA CHART

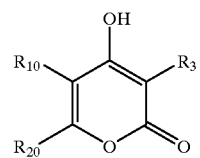

I

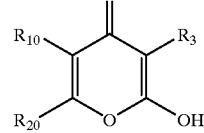

IA

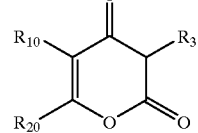

IB

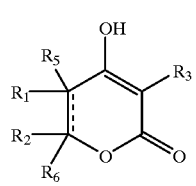

II

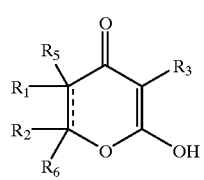

IIA

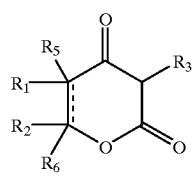

IIB

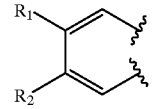

III

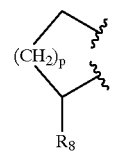

IV

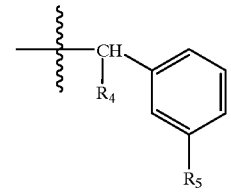

V

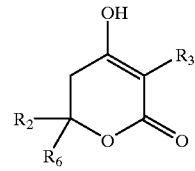

VI

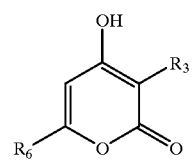

VII

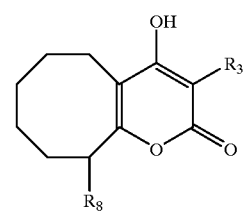

VIII

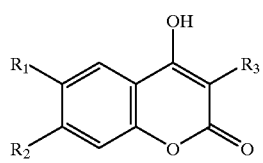
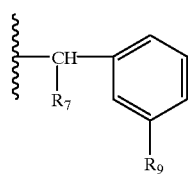
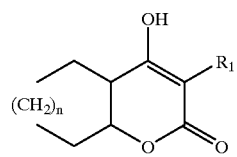
CHART A
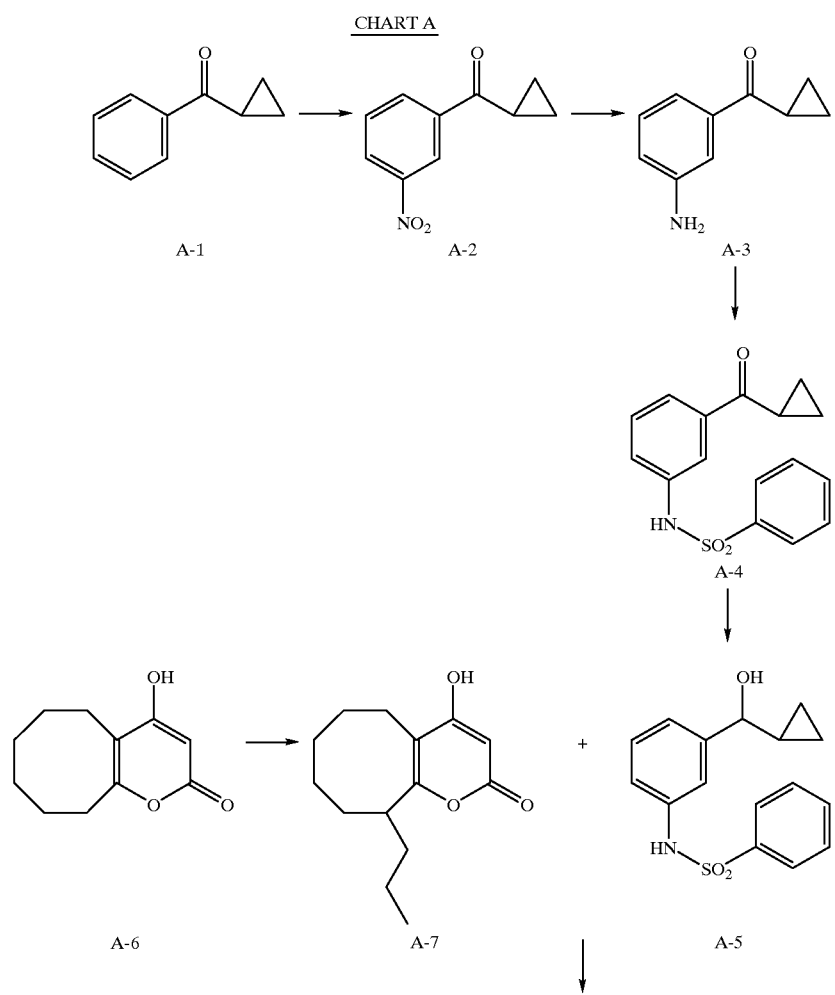

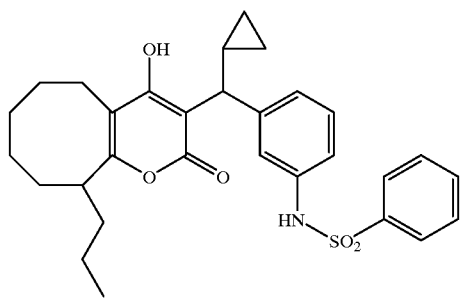
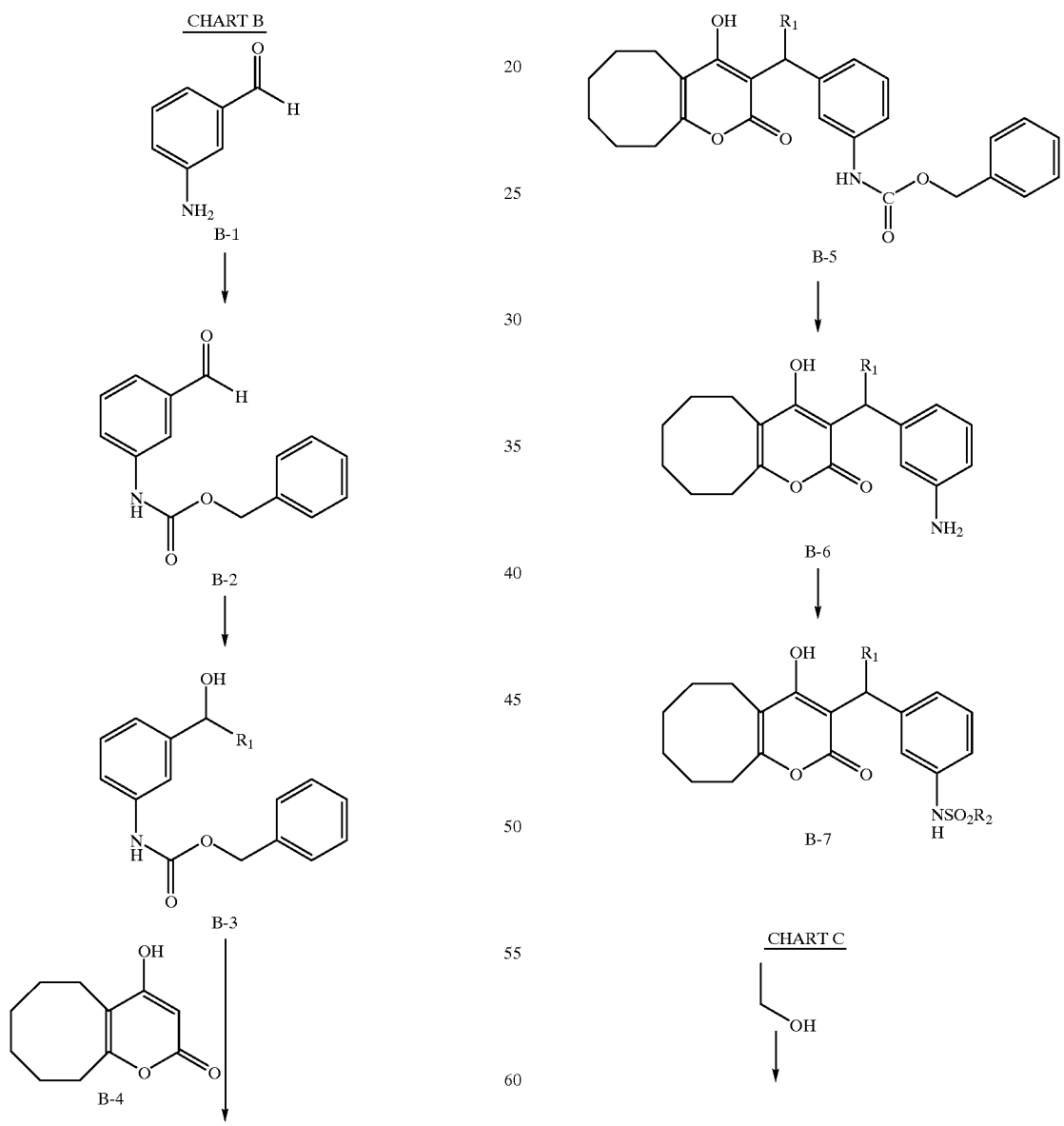
CHART B
CHART C

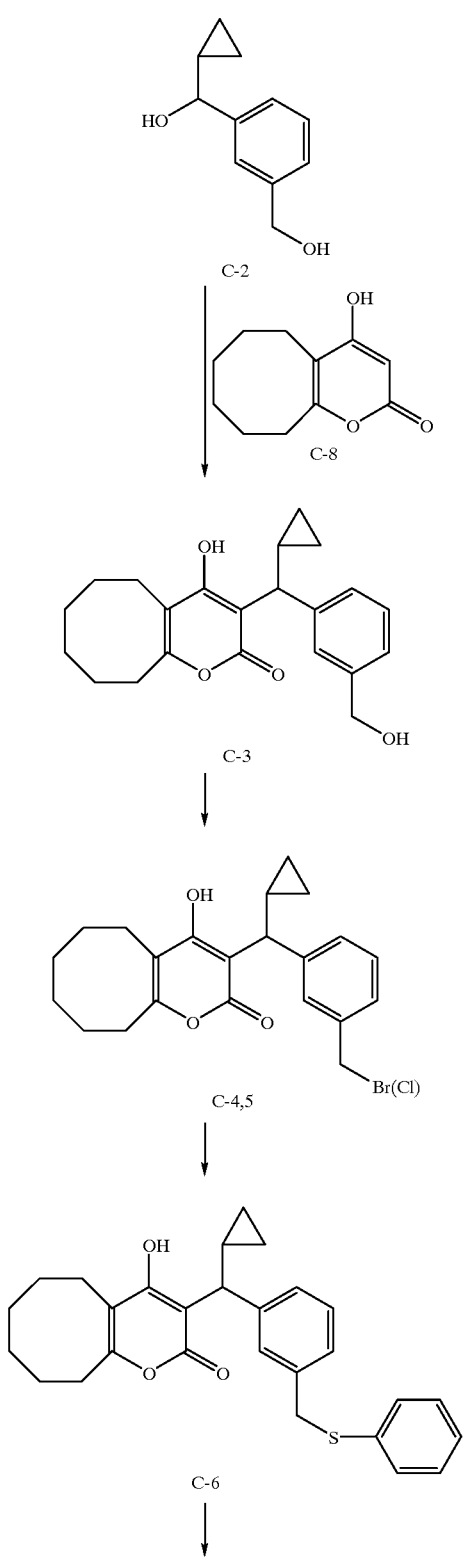
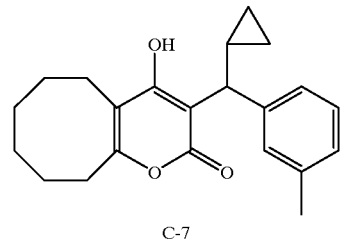
C-7
CHART D
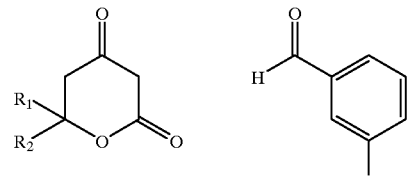
D-1  D-2
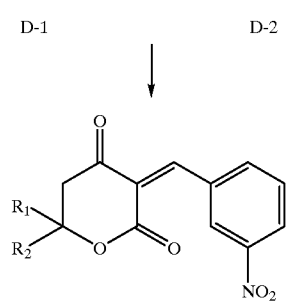
D-3
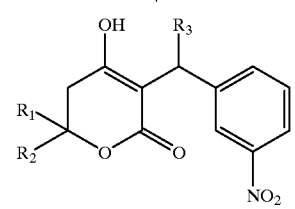
D-4
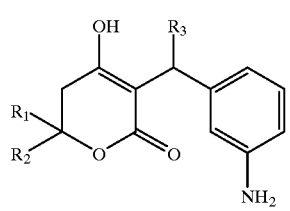
D-5
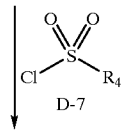
D-7

-continued
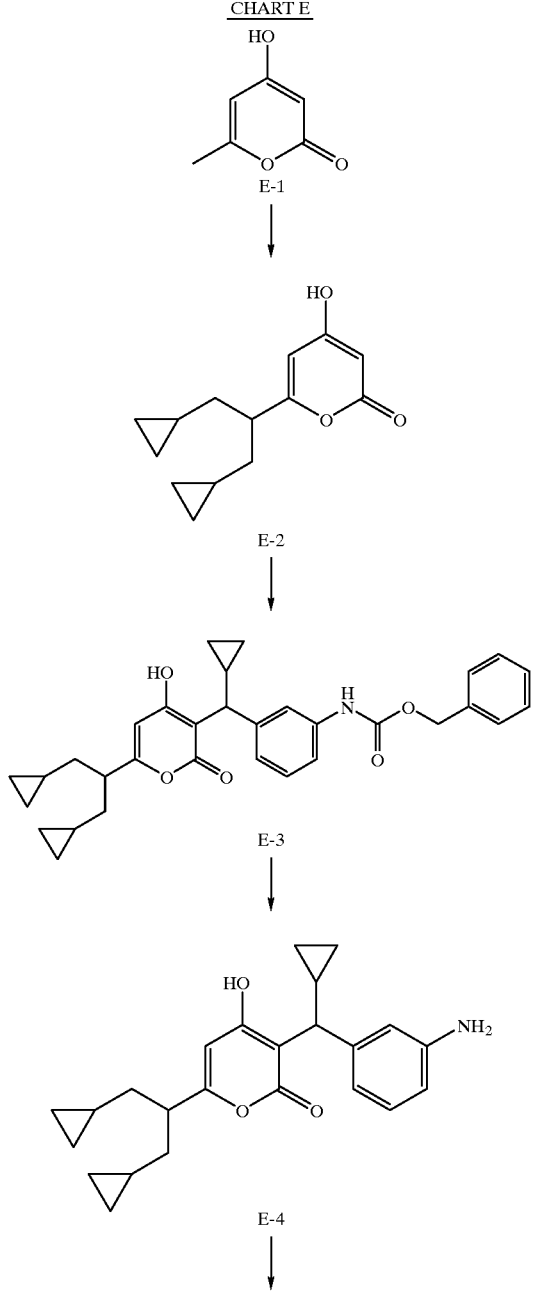
D-6
CHART E
E-1
E-2
E-3
E-4
-continued
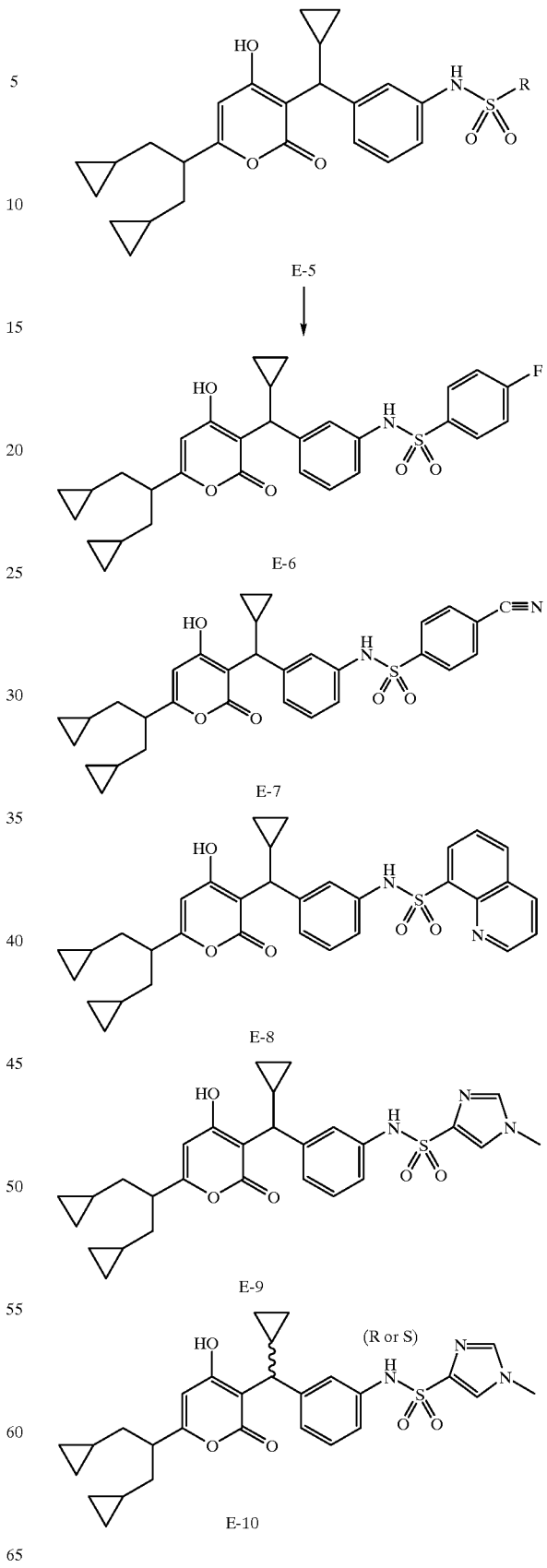
E-5
E-6
E-7
E-8
E-9
E-10 (R or S)

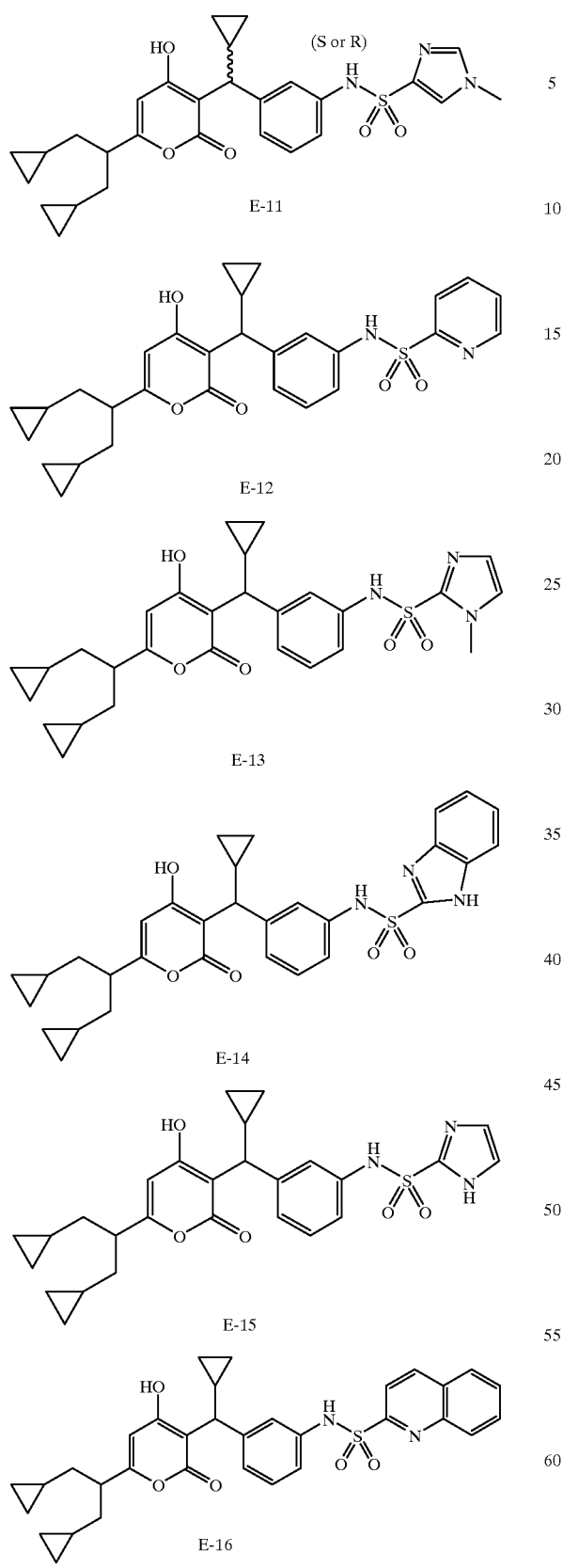
CHART F
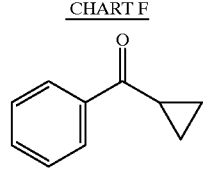
F-1
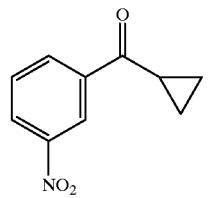
F-2
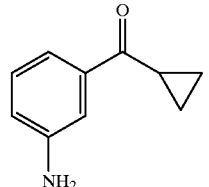
F-3
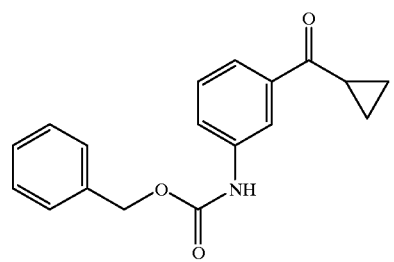
F-4
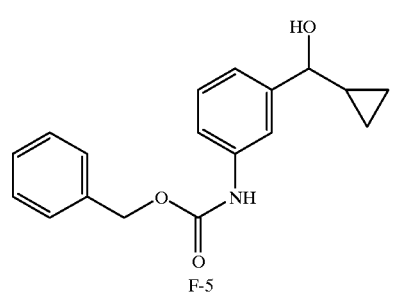
F-5

185 186
-continued
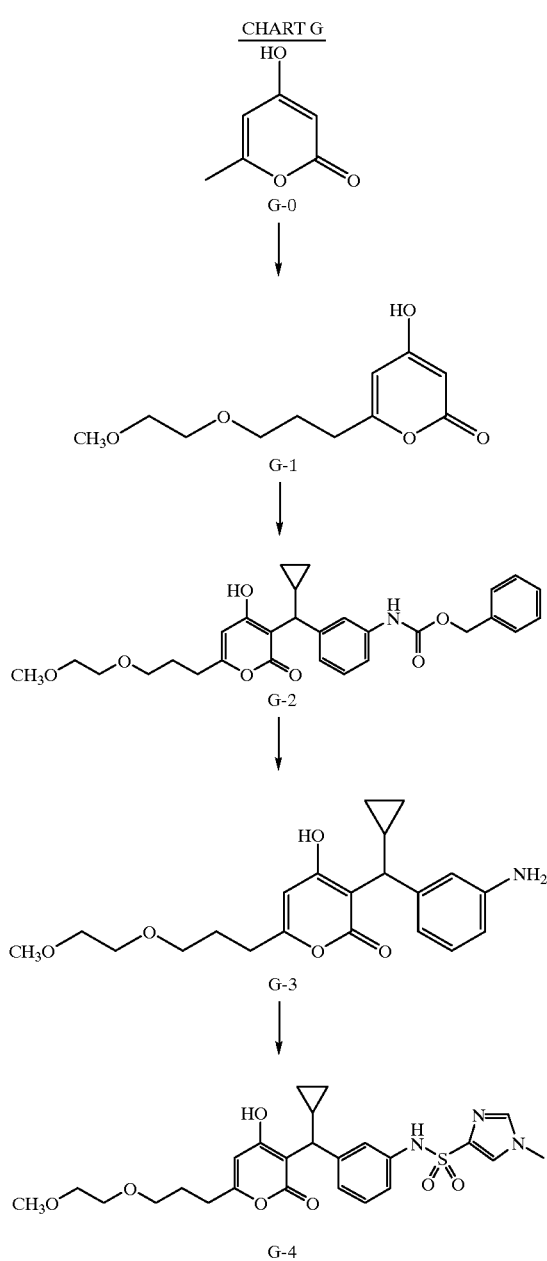
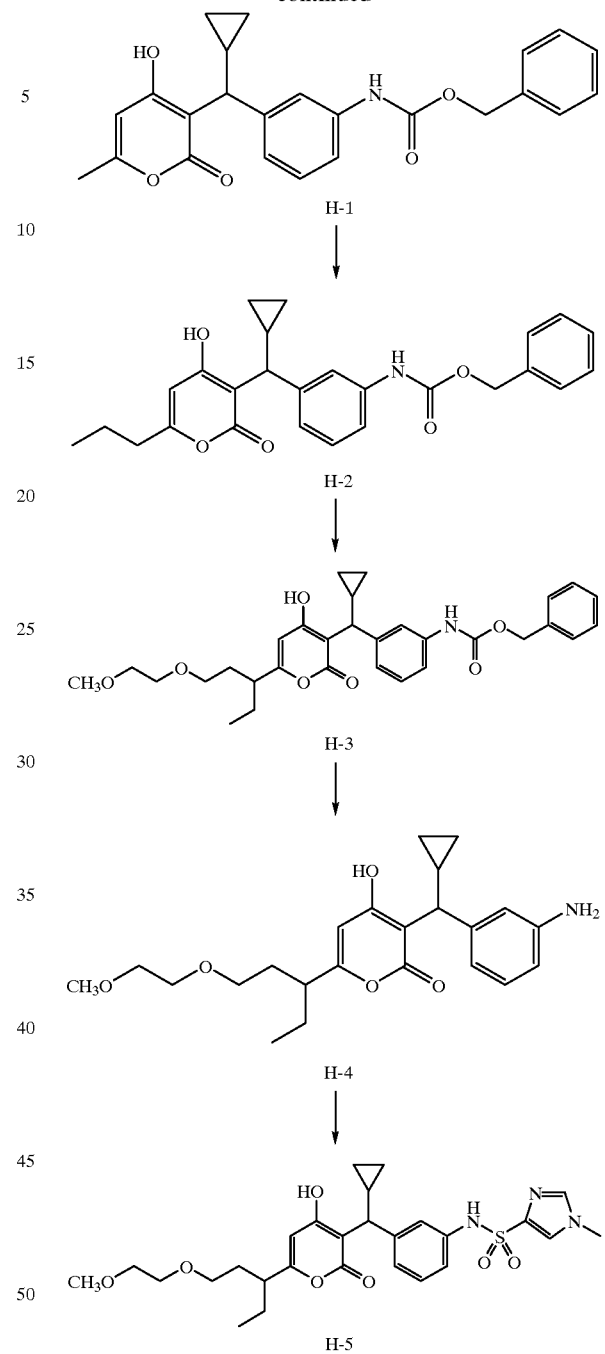
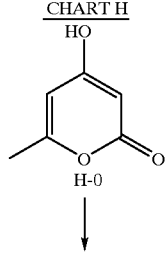
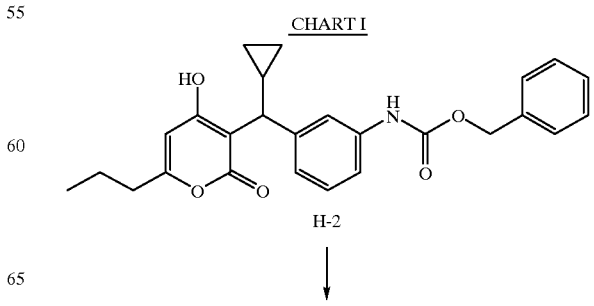

187
-continued
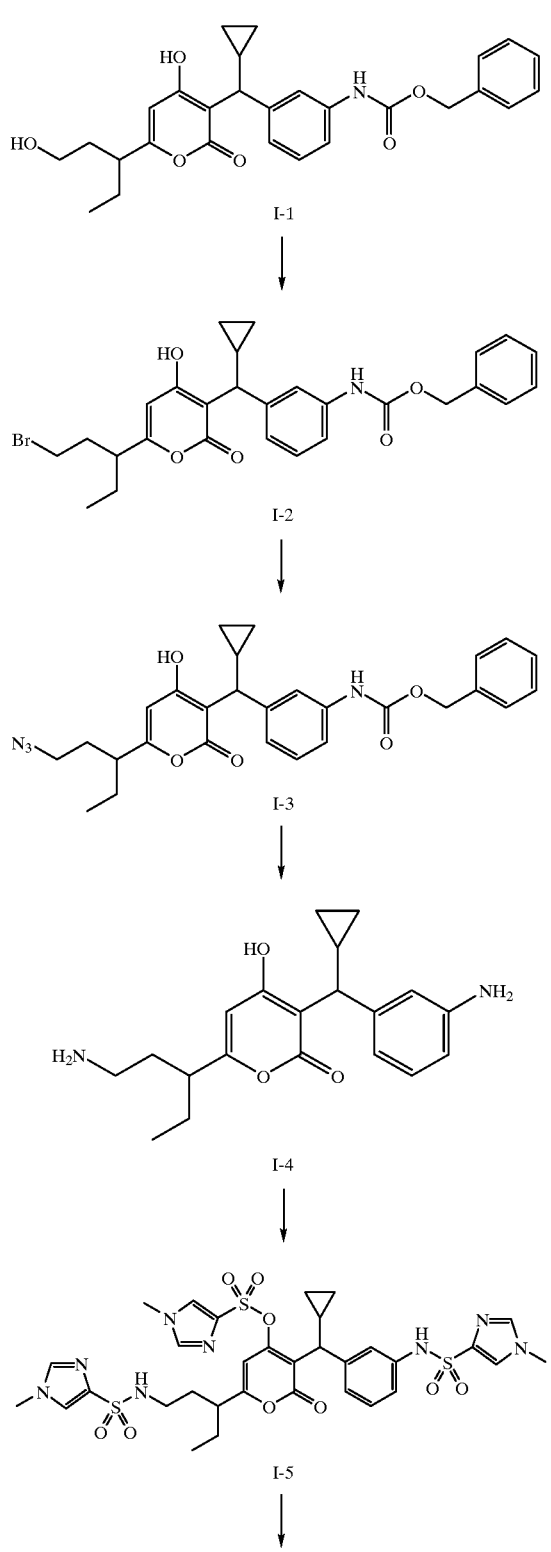
188
-continued
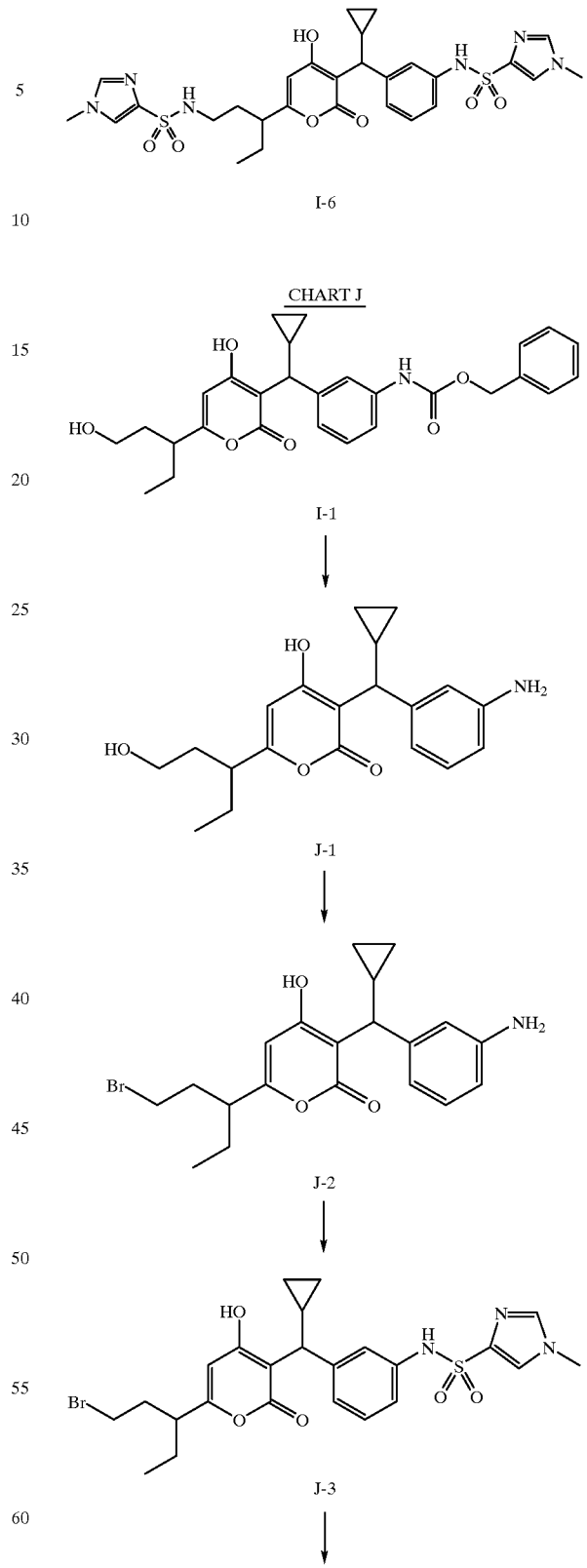

189
-continued
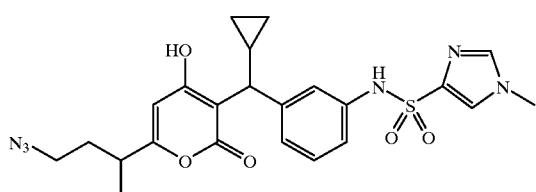
J-4
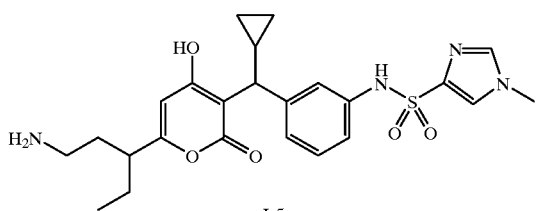
J-5
190
-continued
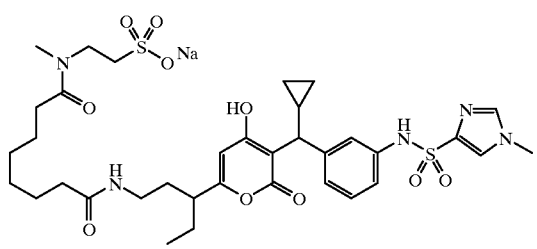
J-6
CHART K
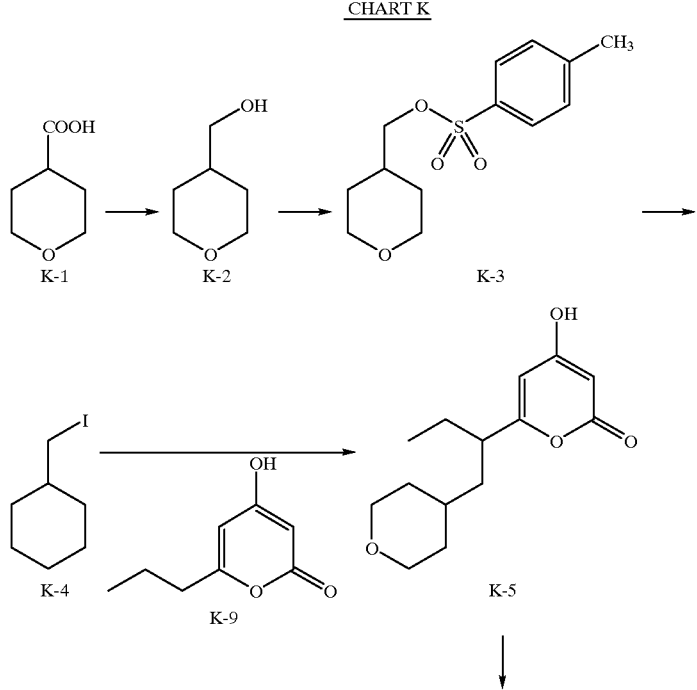

191
-continued
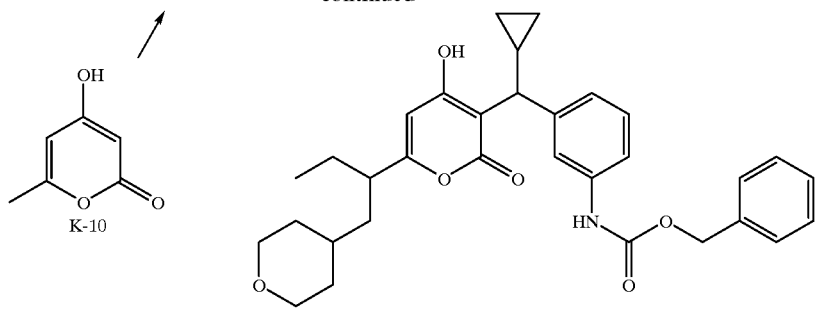
K-10
K-6
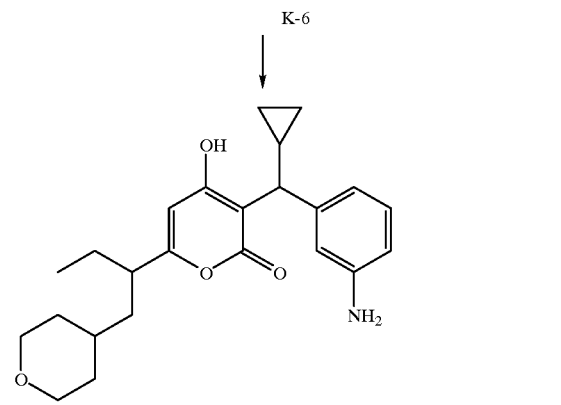
K-7
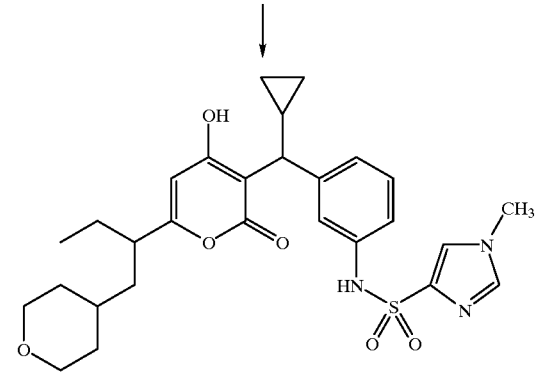
K-8
192
CHART L
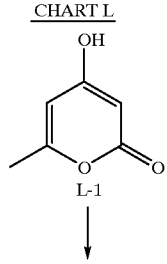
L-1
-continued
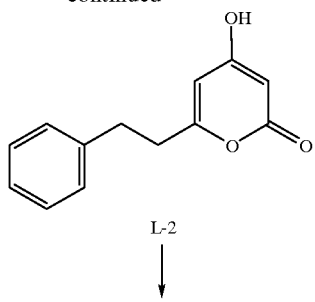
L-2

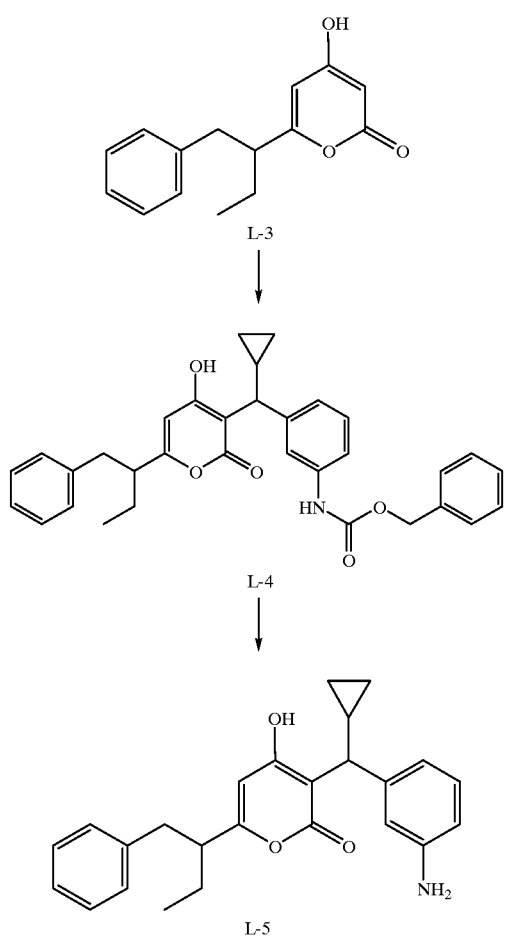
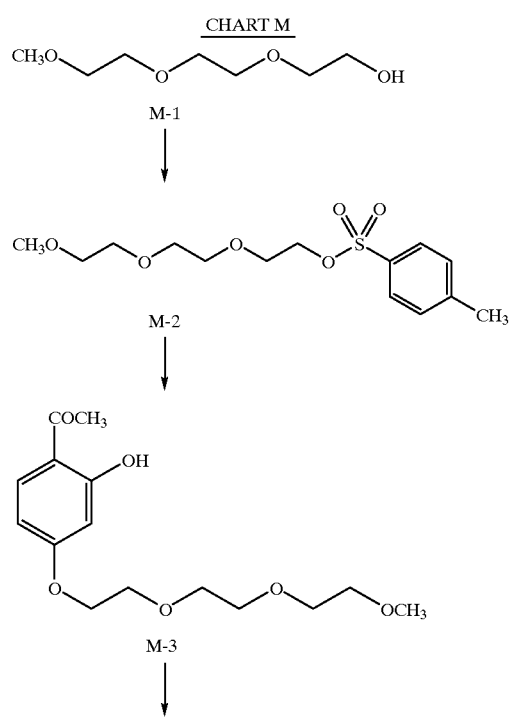
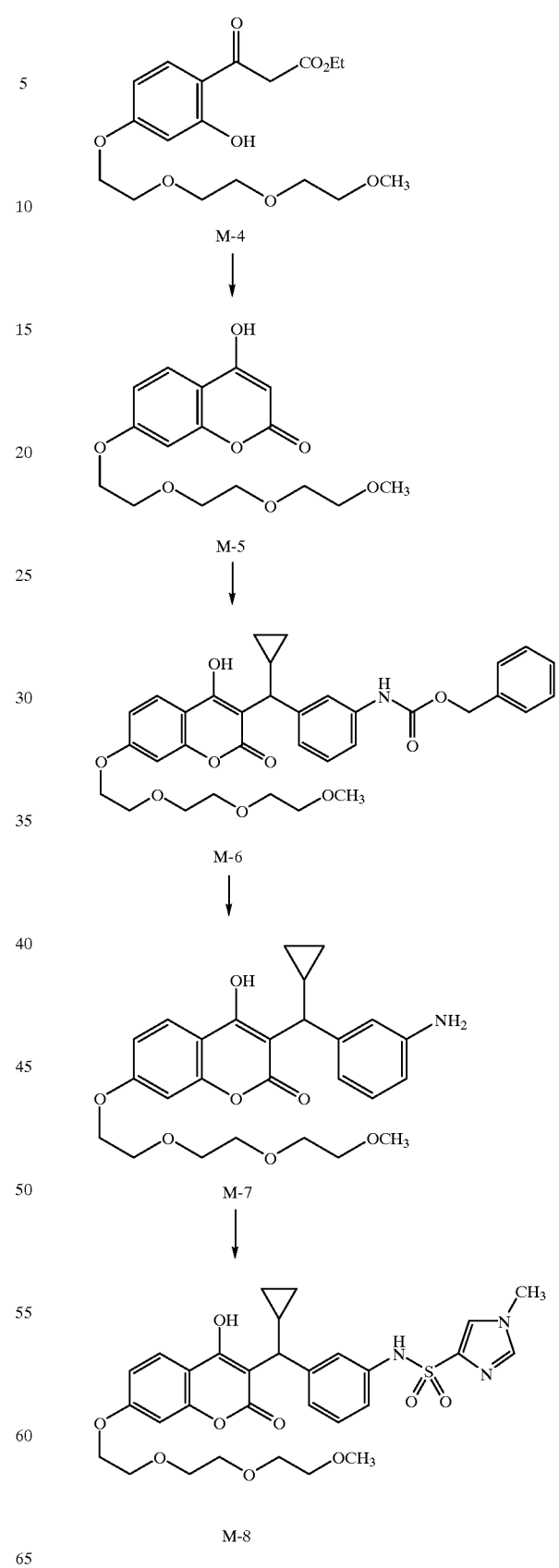

CHART N
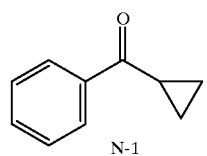
N-1
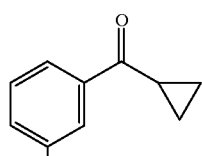
N-2
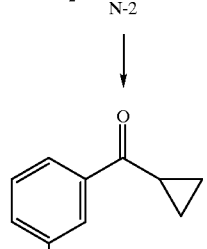
N-3
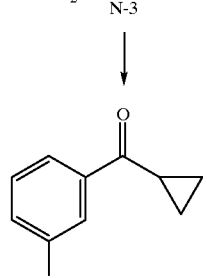
N-4
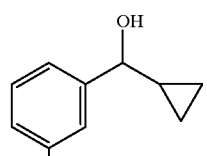
N-5
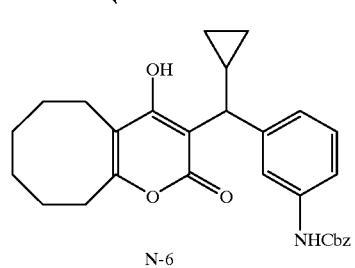
N-6
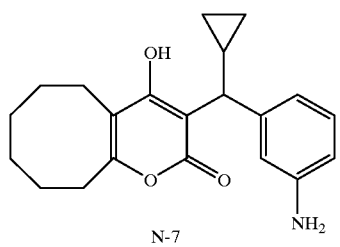
N-7
CHART O
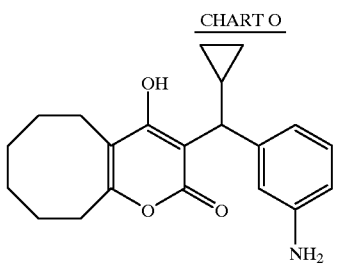
O-1 (N-7)
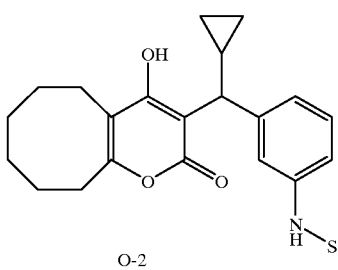
O-2
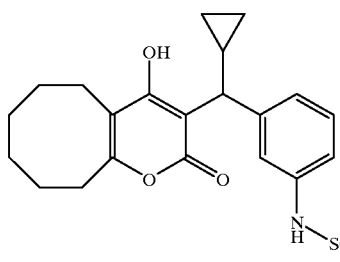
O-3

CHART P
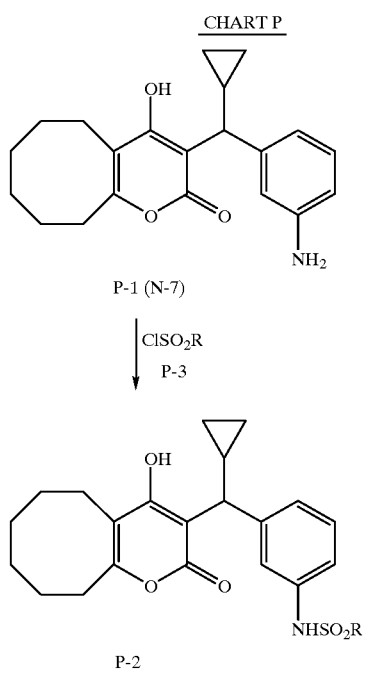
CHART Q
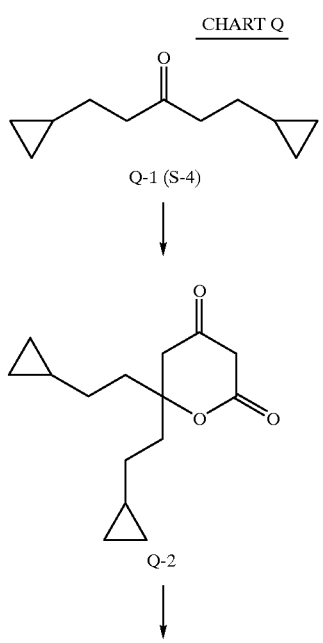
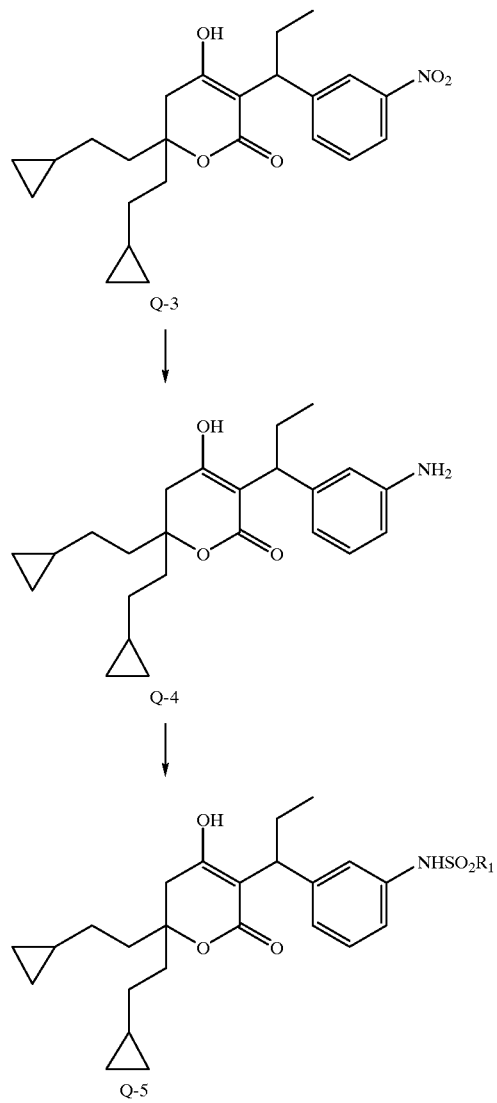
CHART R
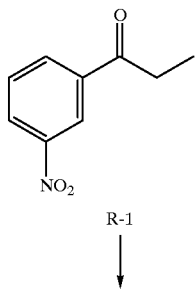
R-1

199
-continued
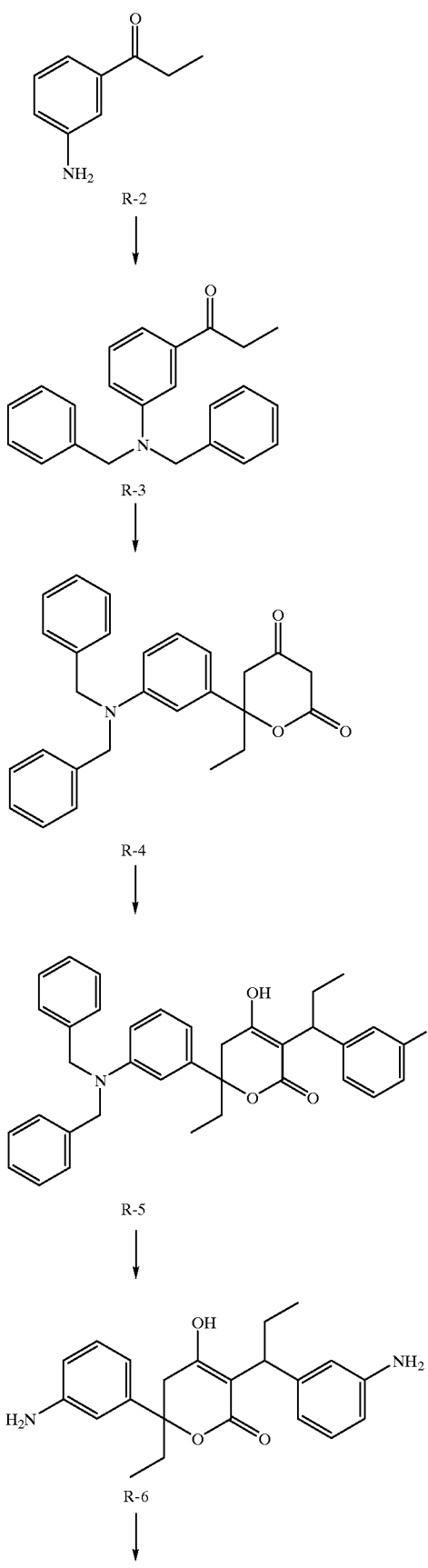
200
-continued
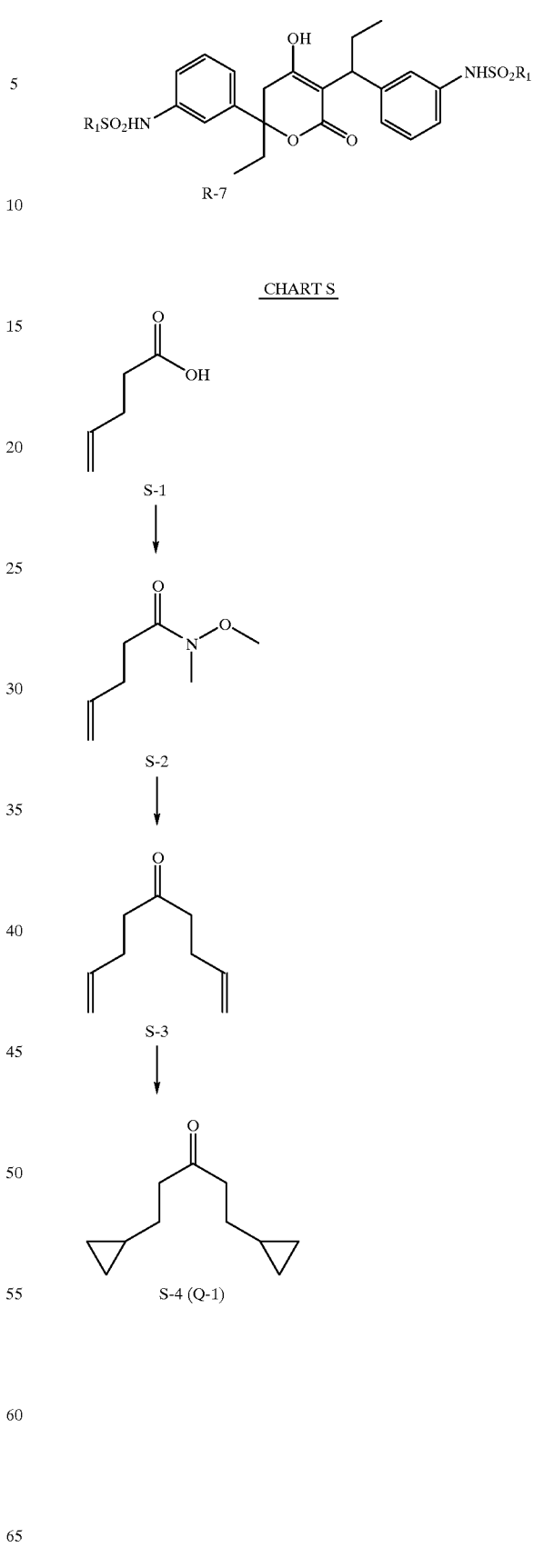
CHART S

201
CHART T
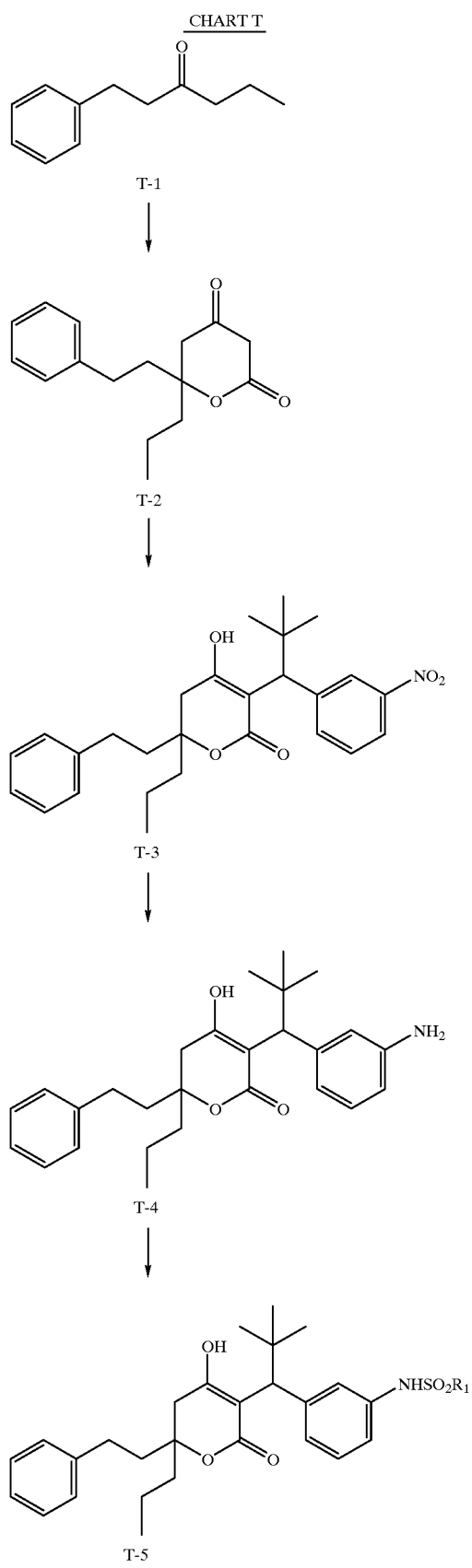
202
CHART U
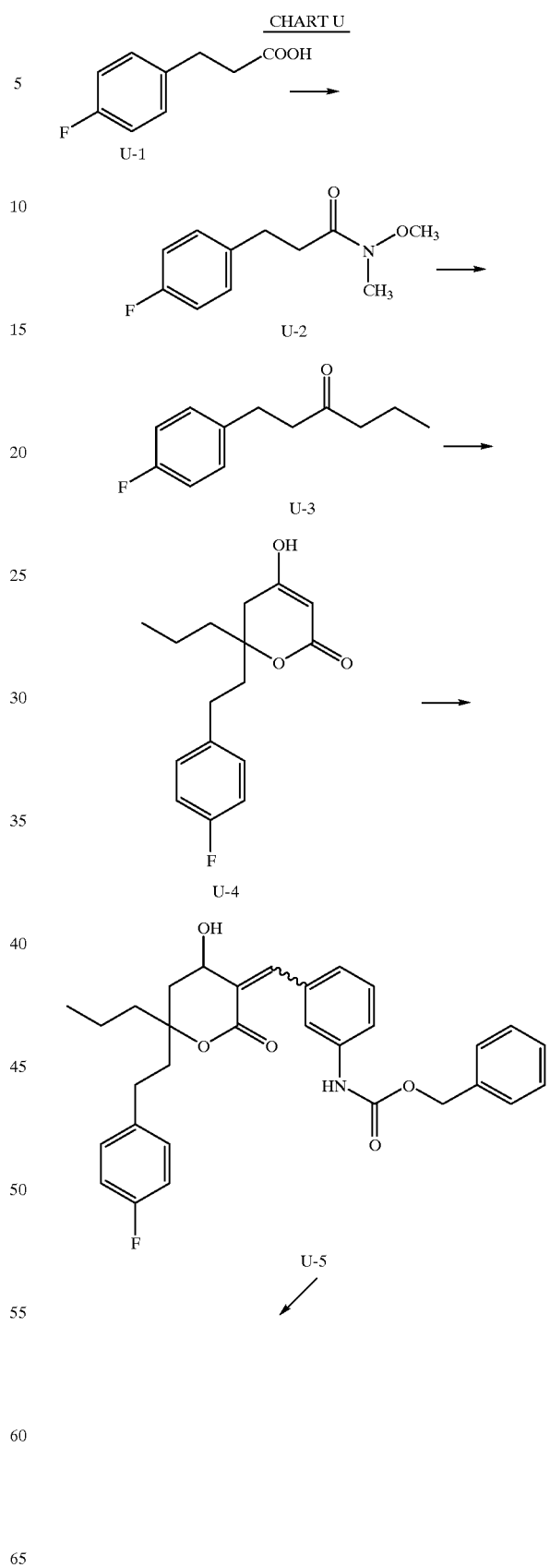

203
-continued
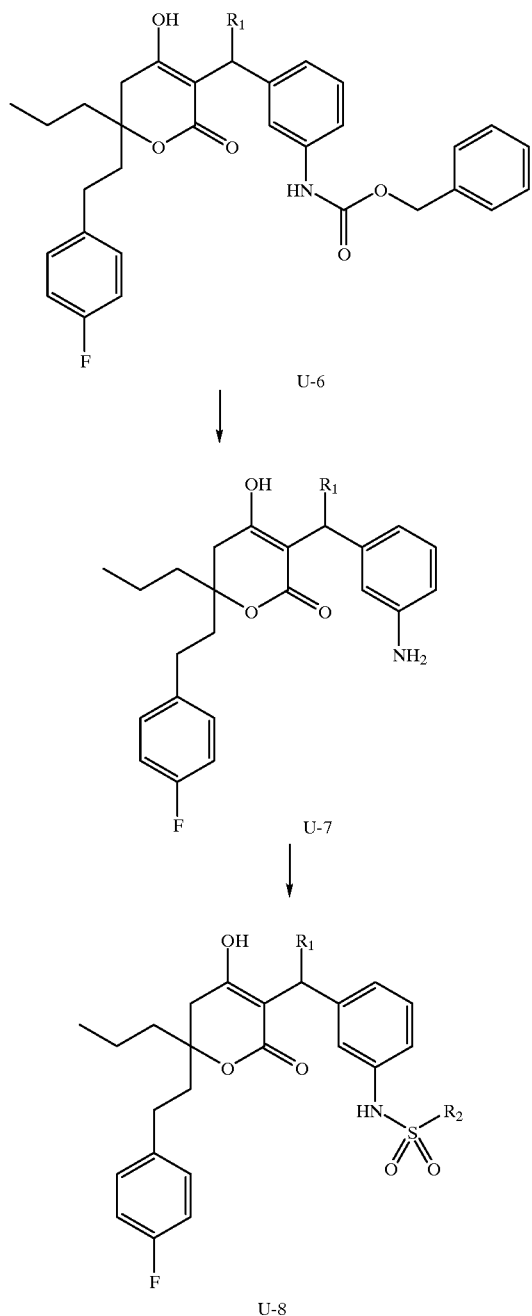
CHART V
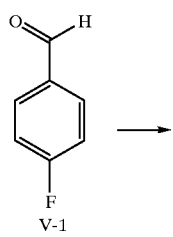
204
-continued
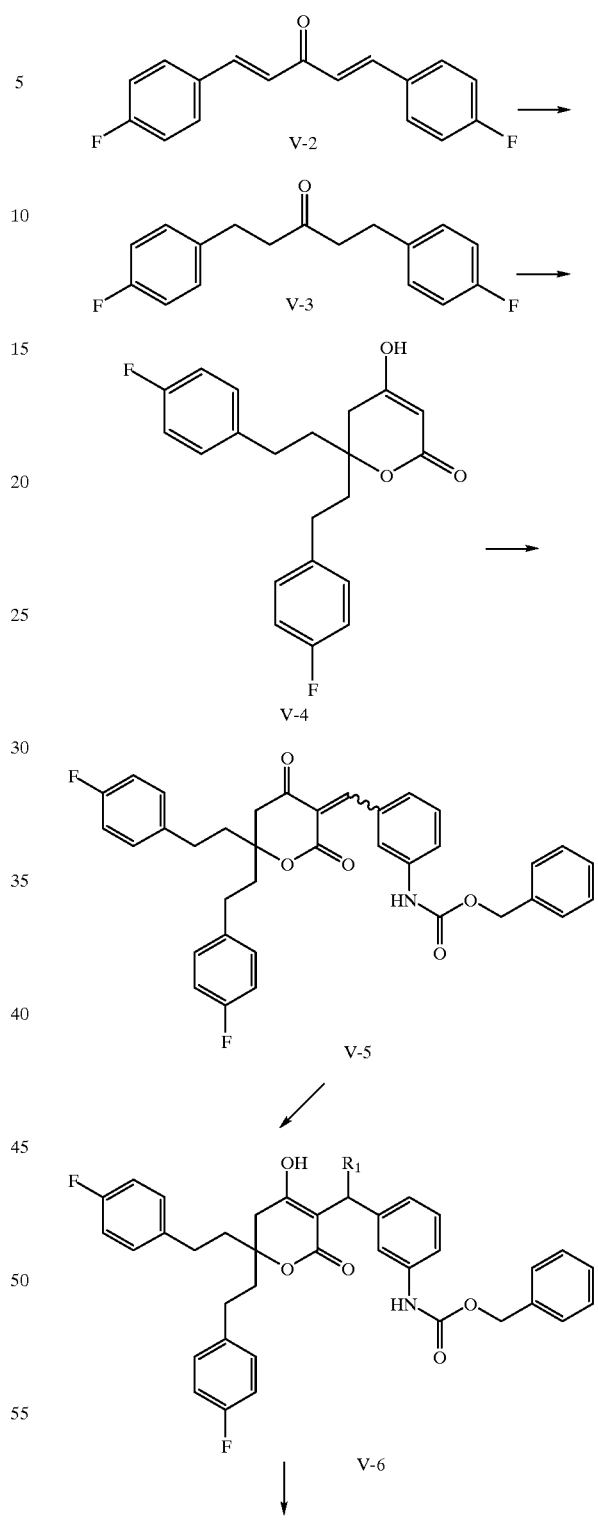

205
-continued
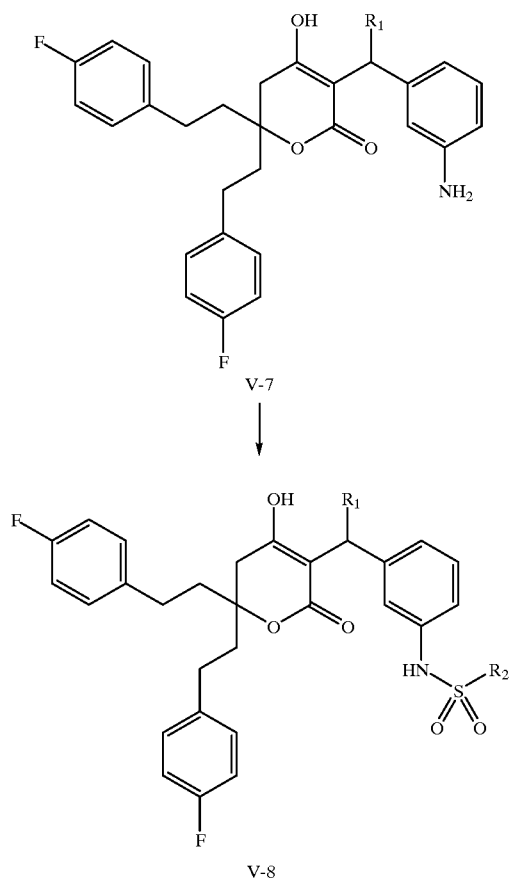
206
-continued
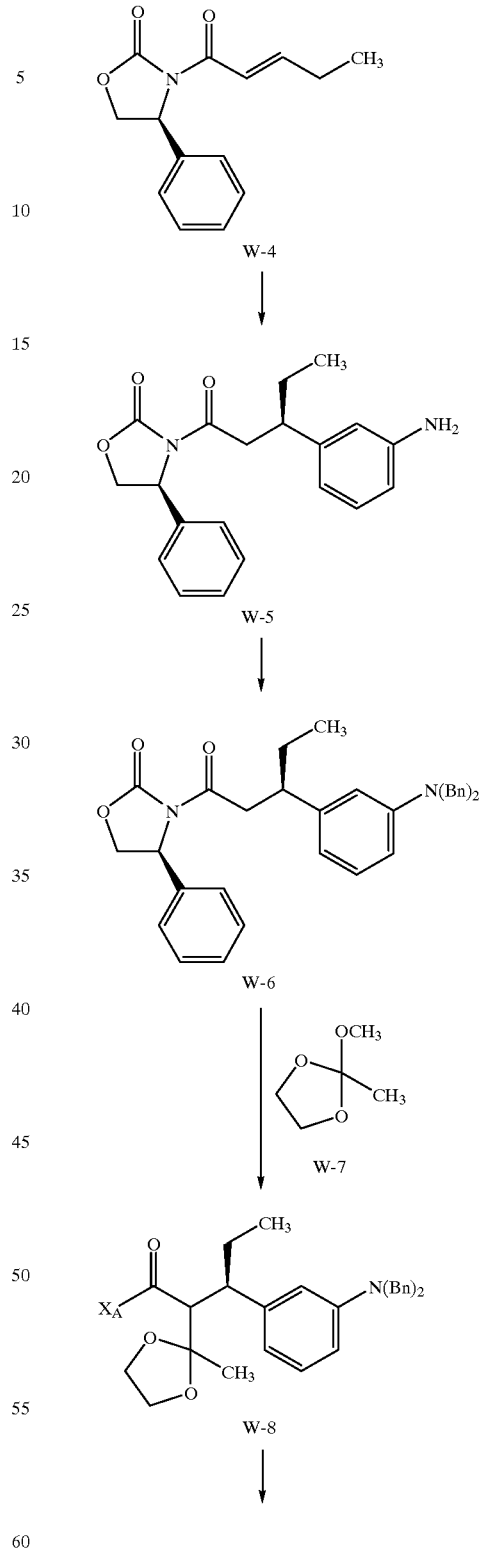
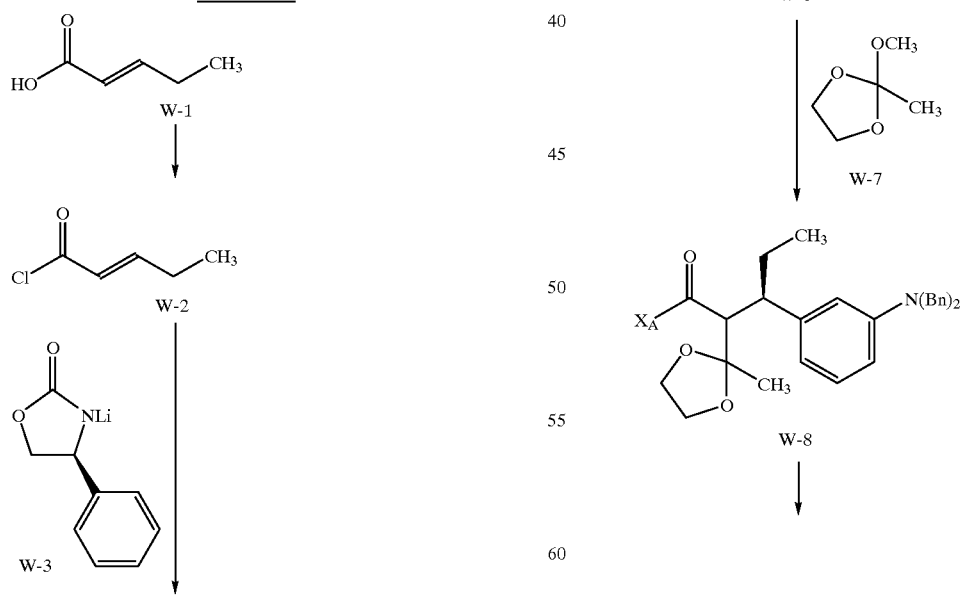

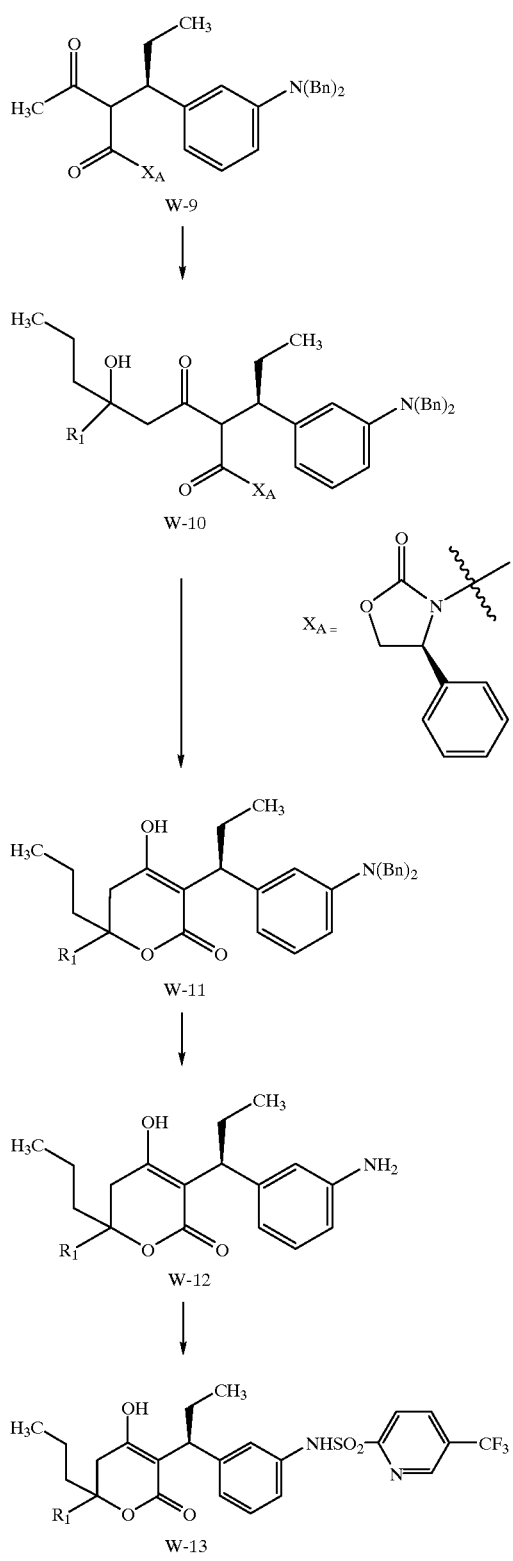

-continued
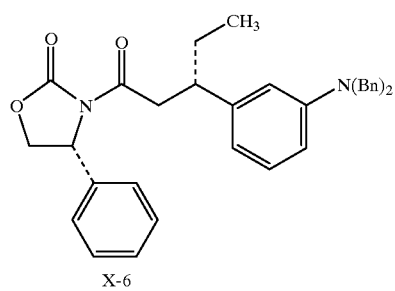
X-6
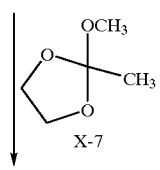
X-7
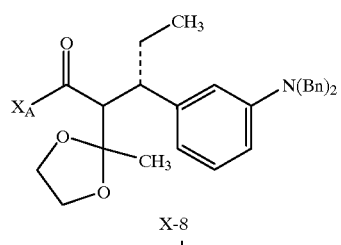
X-8
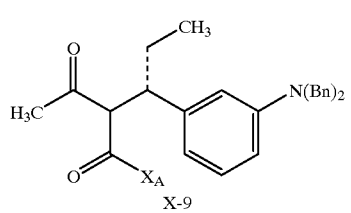
X-9
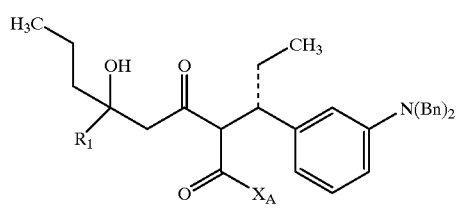
X-10
-continued
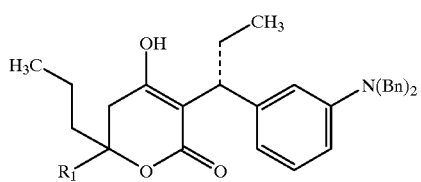
X-11
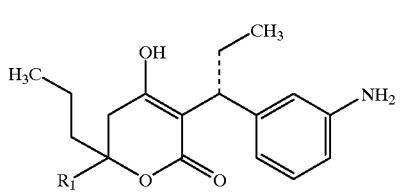
X-12
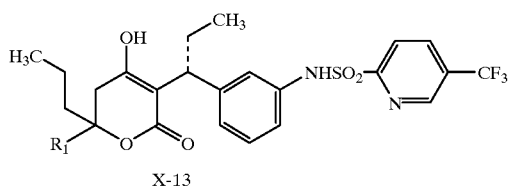
X-13
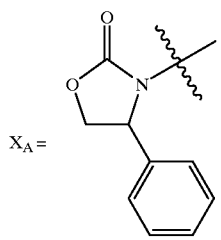
$X_A =$ CHART Y
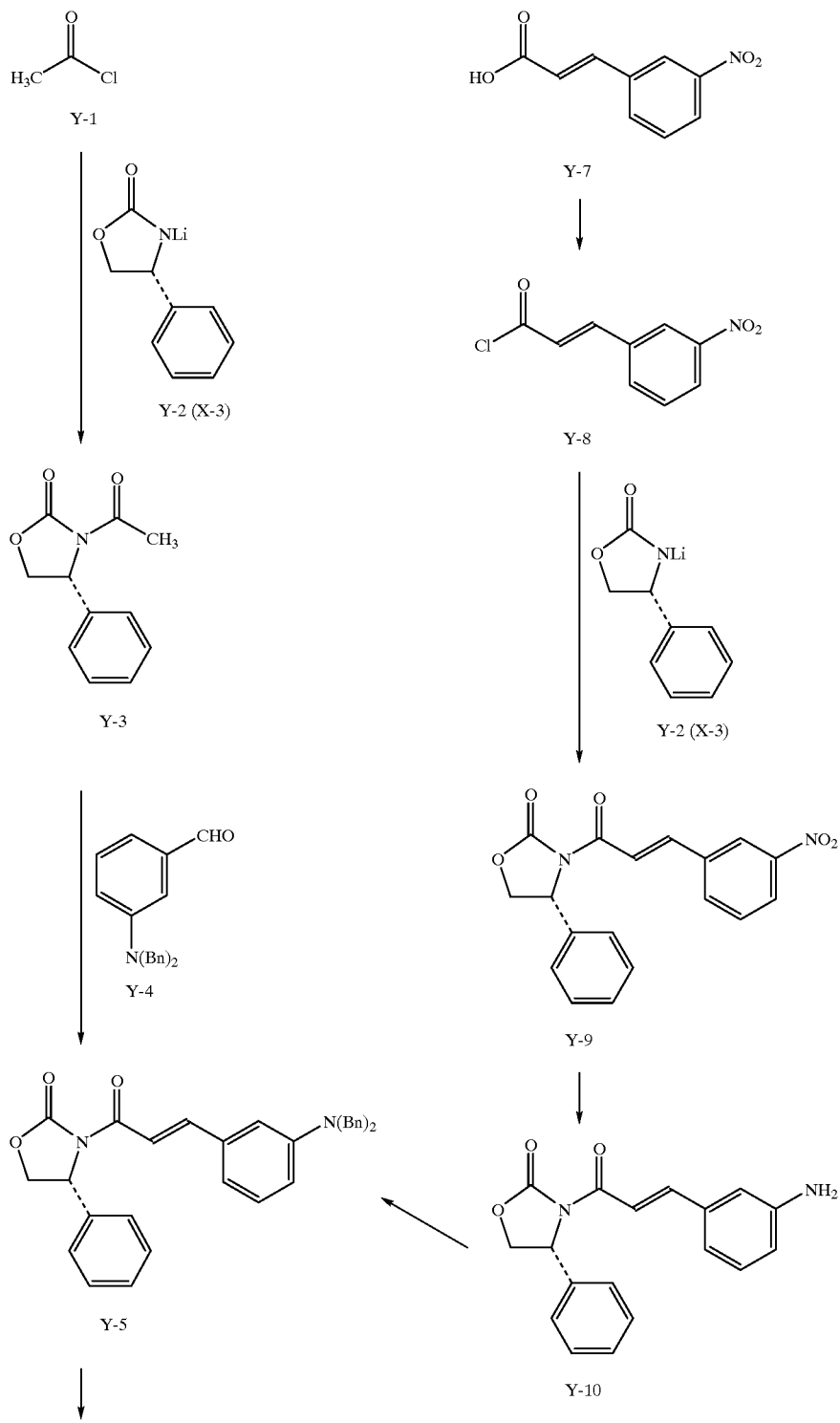

-continued
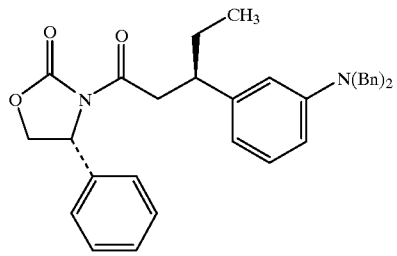
Y-6
CHART Z
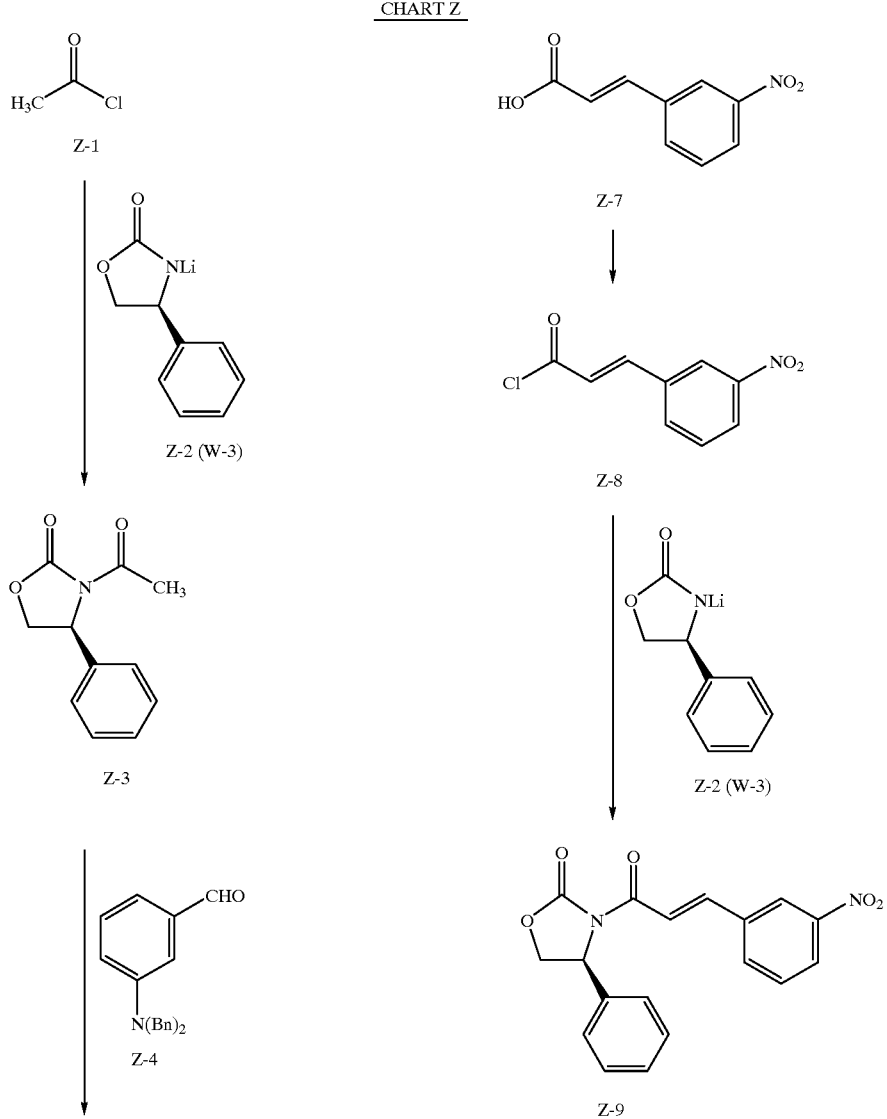

-continued
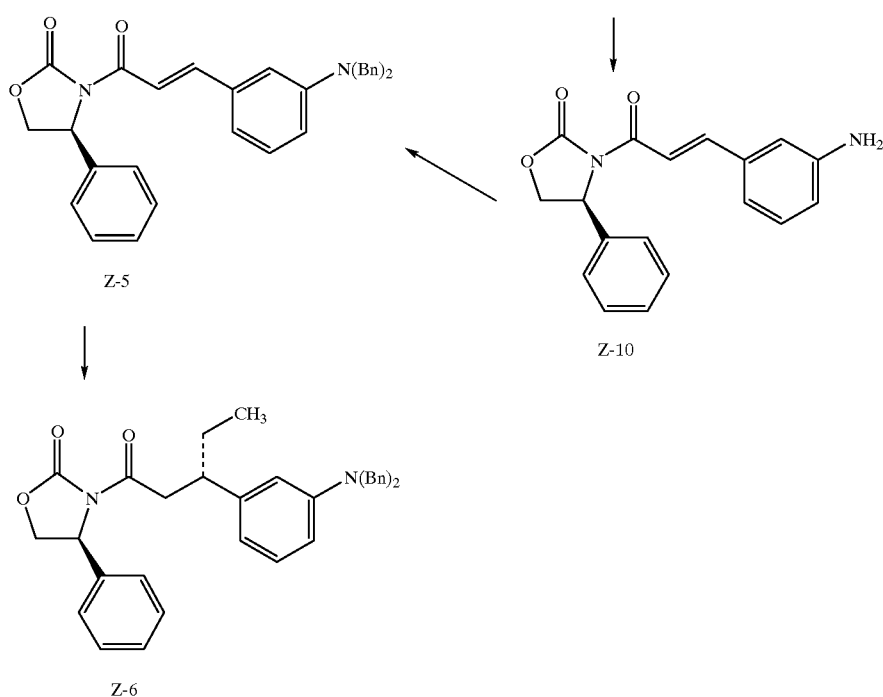
CHART AA
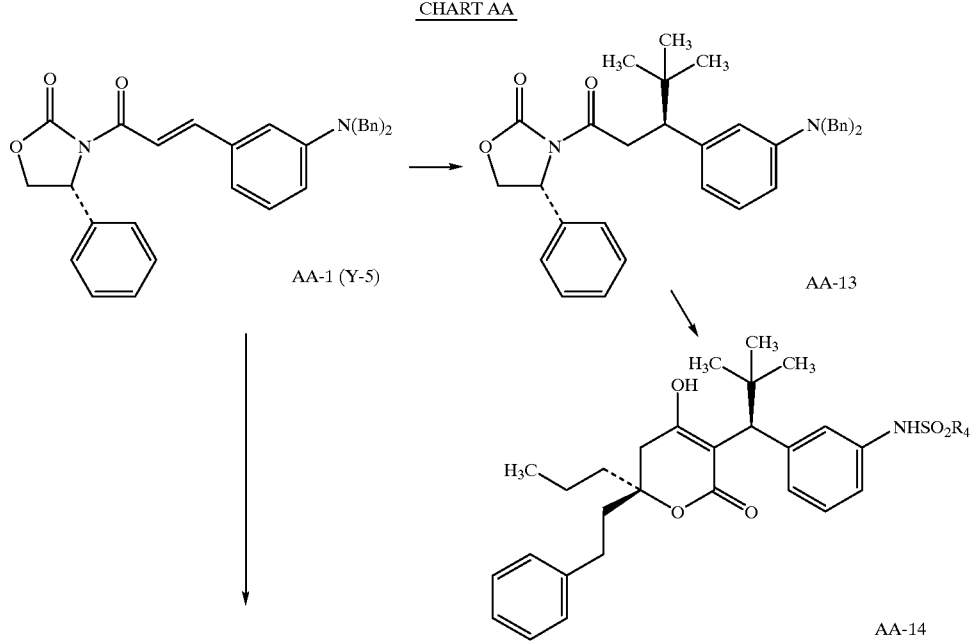

-continued
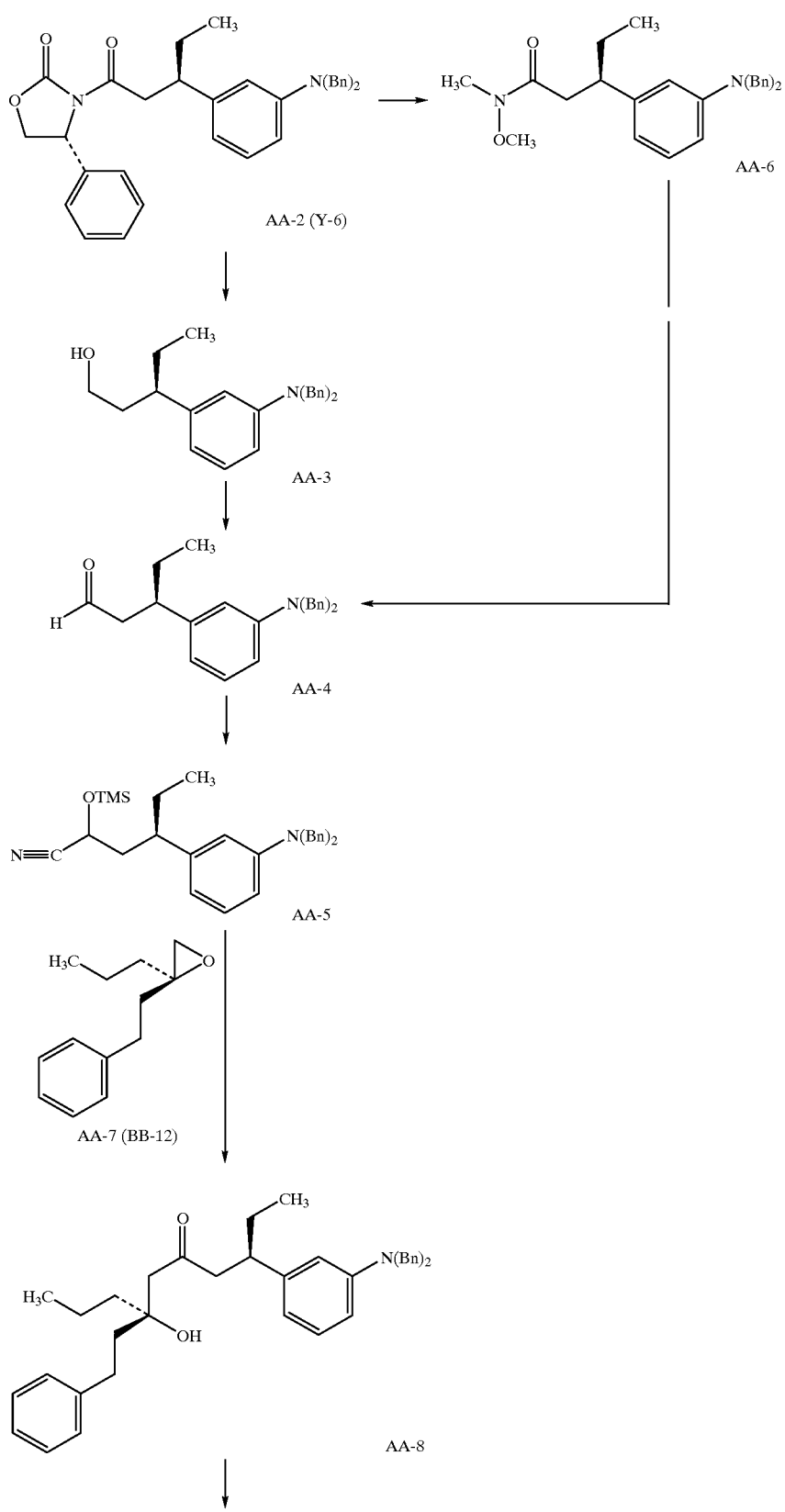

-continued
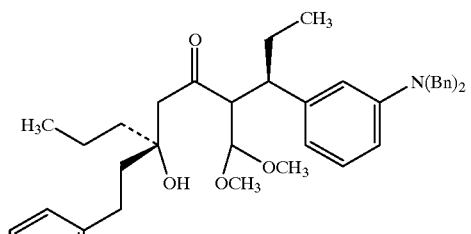
AA-9
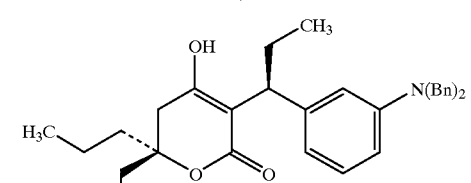
AA-10
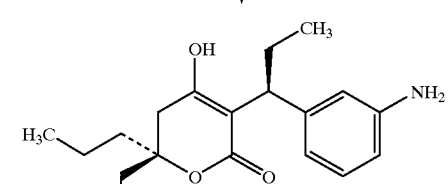
AA-11
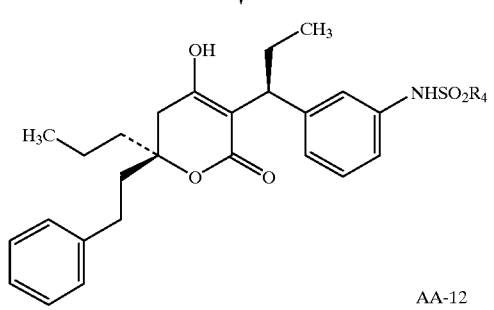
AA-12

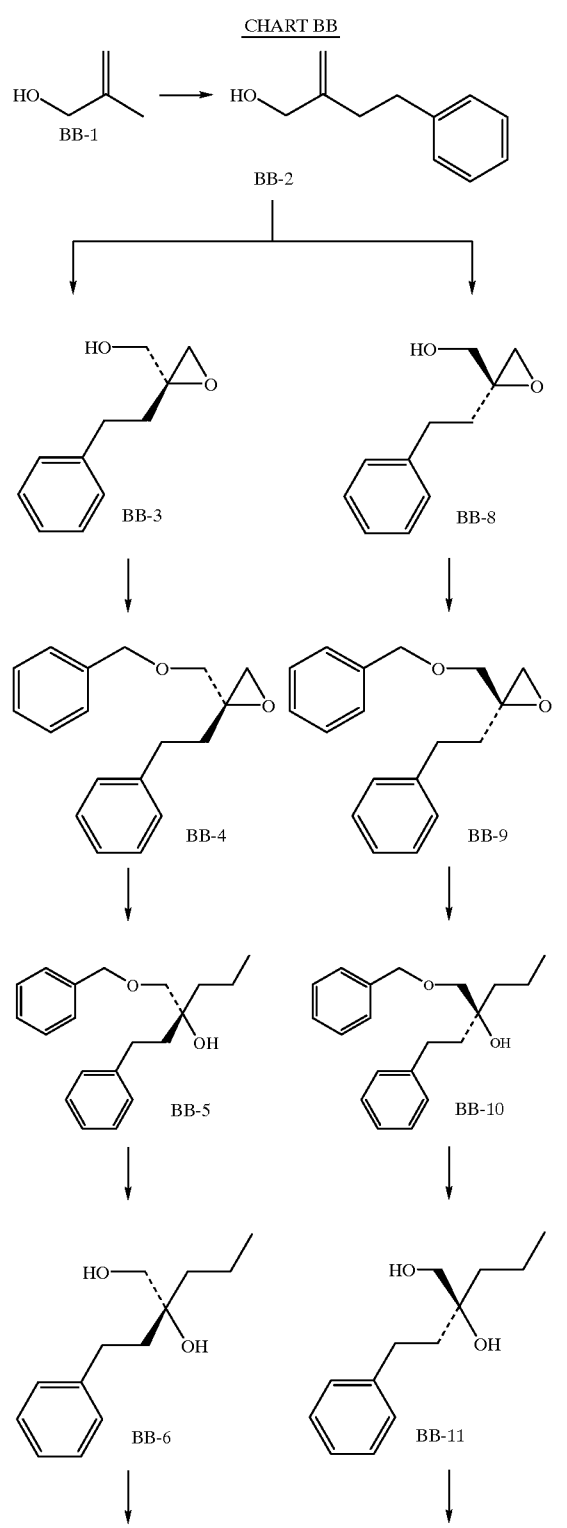
CHART BB
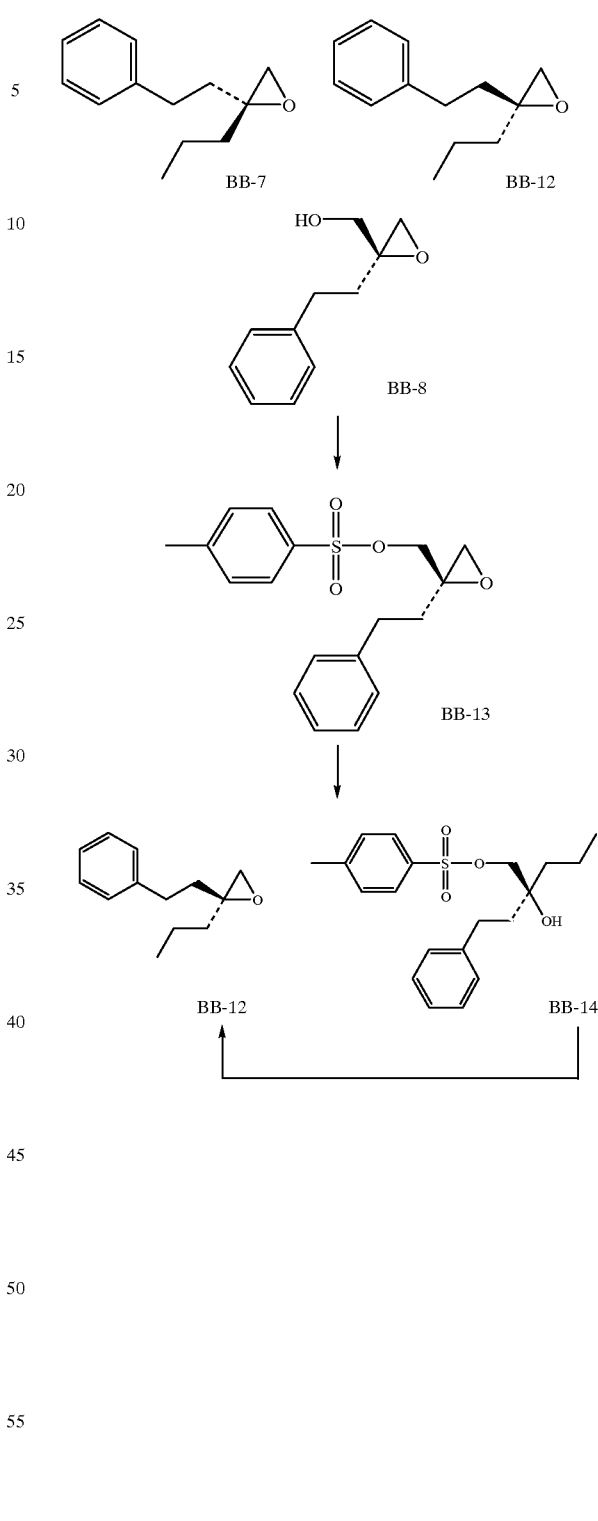

CHART CC
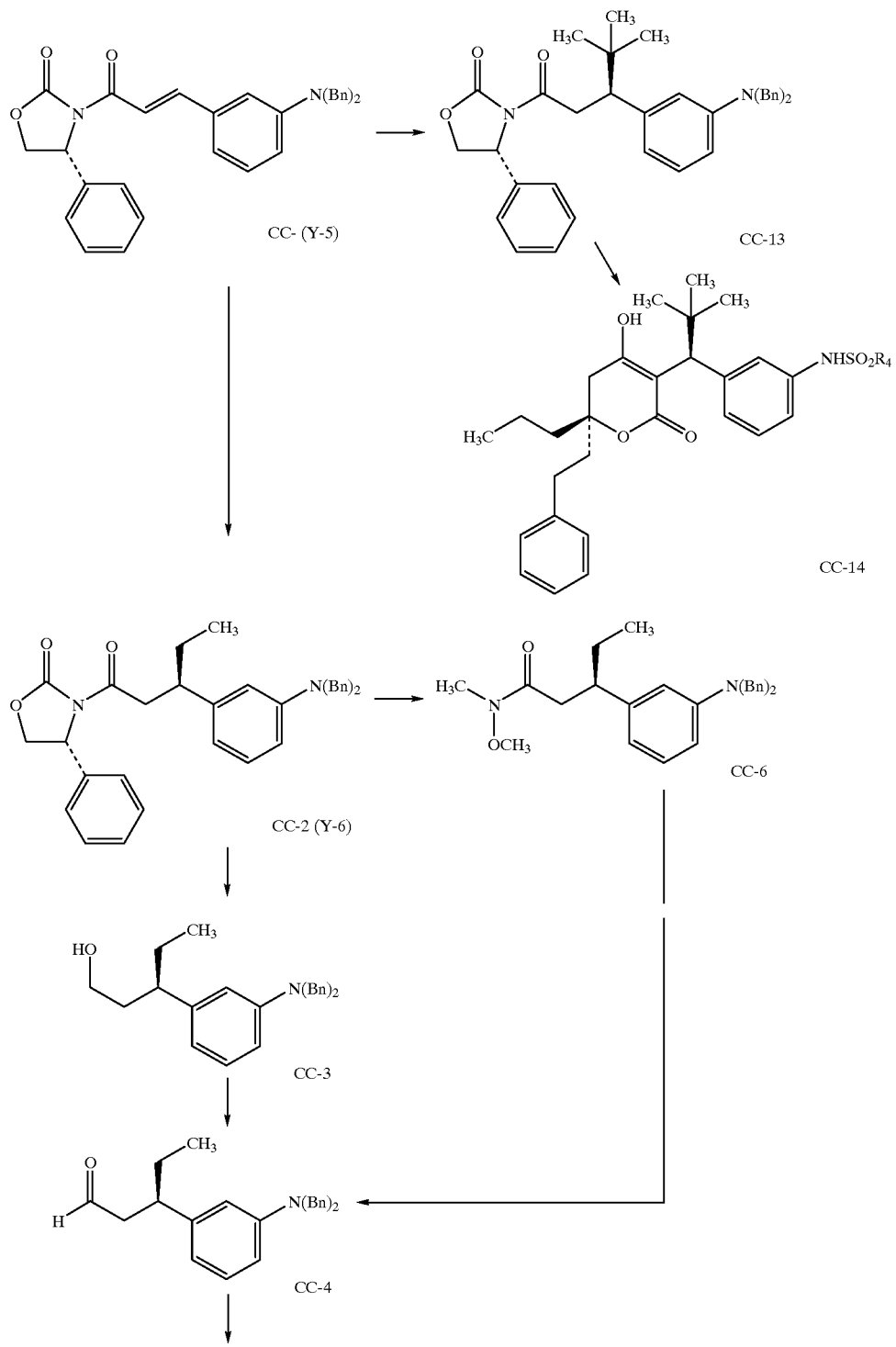

-continued
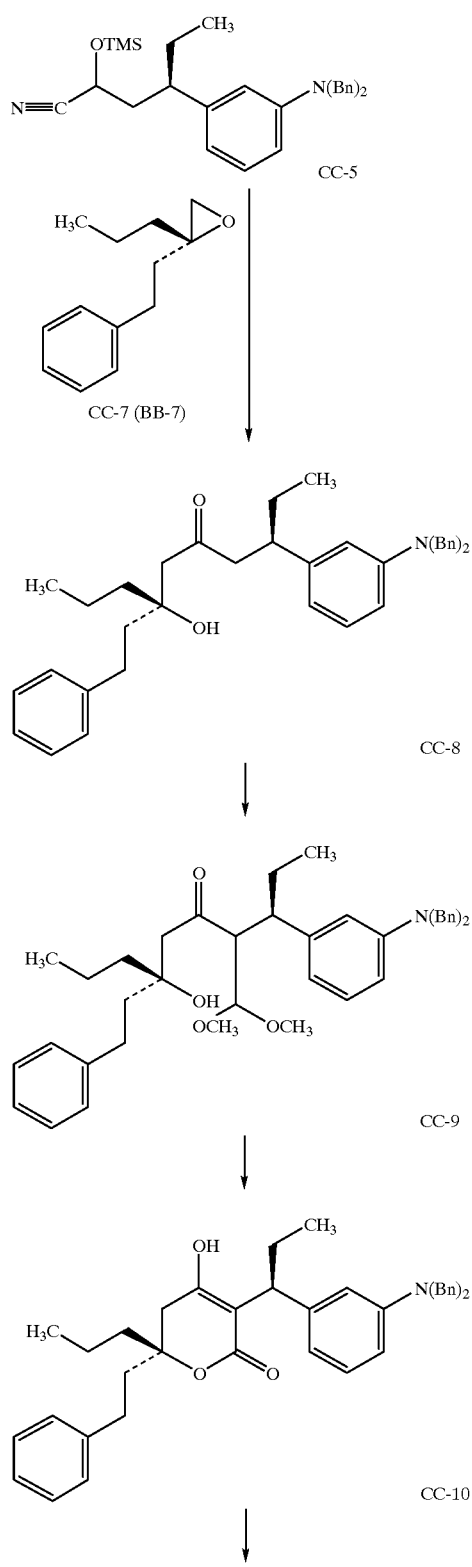

-continued
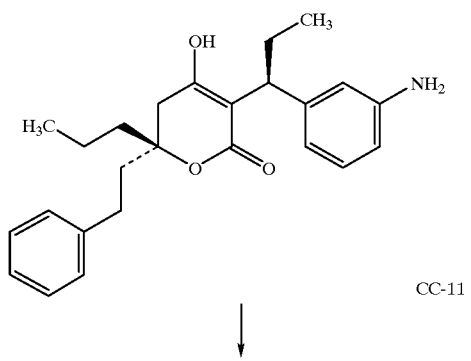
CC-11
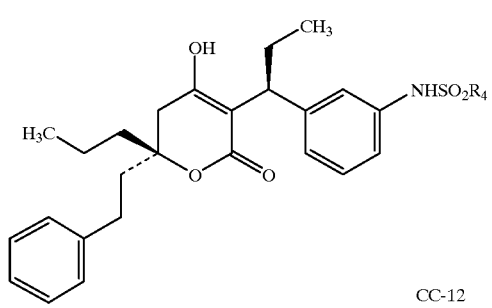
CC-12
CHART DD
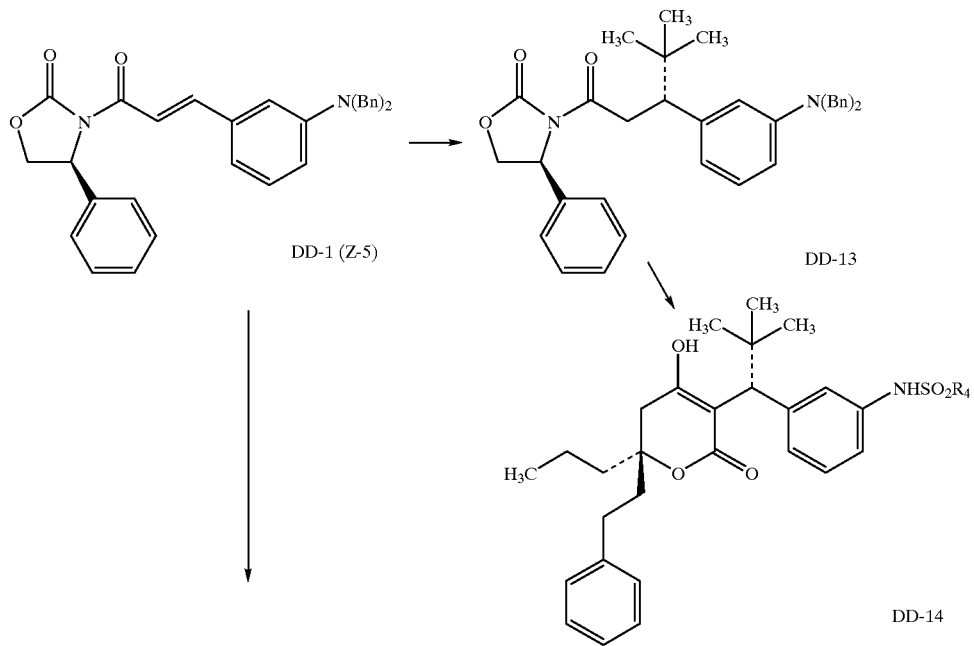

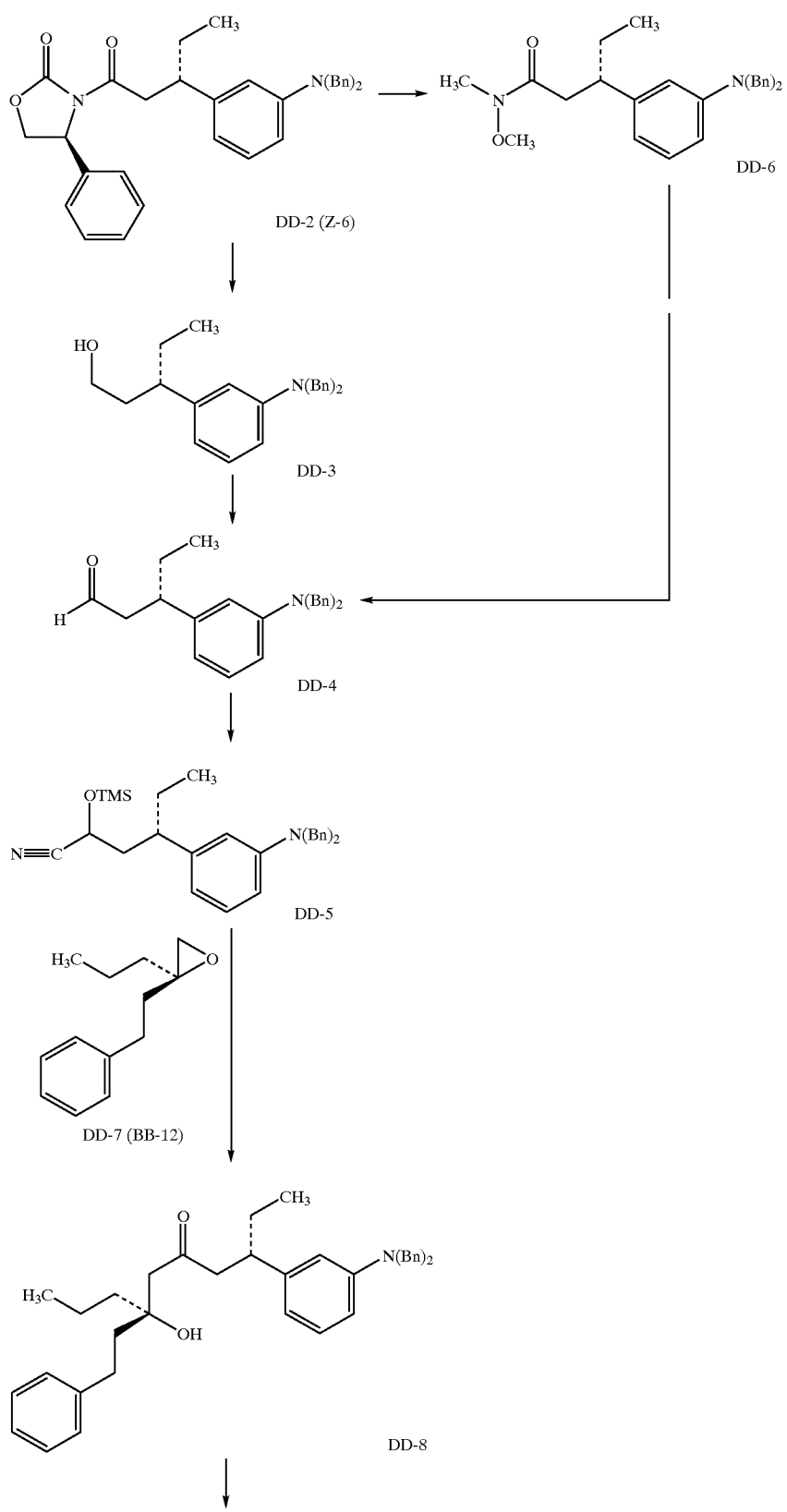

-continued
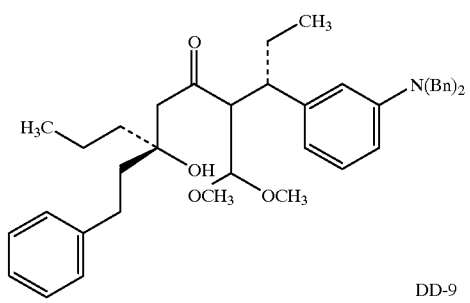
DD-9
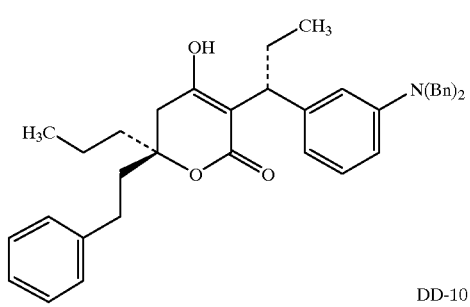
DD-10
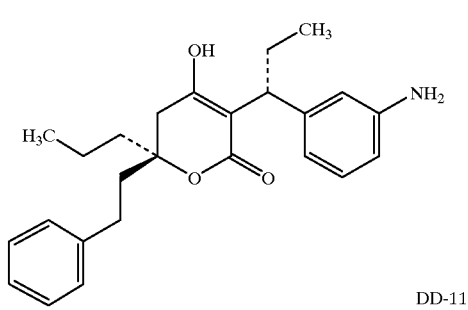
DD-11
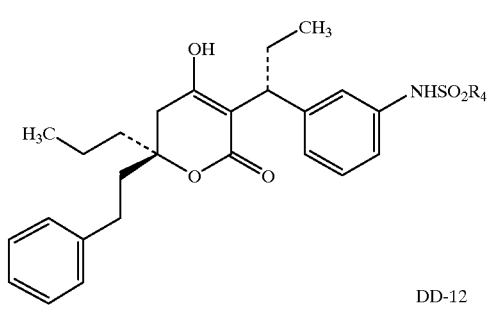
DD-12

CHART EE
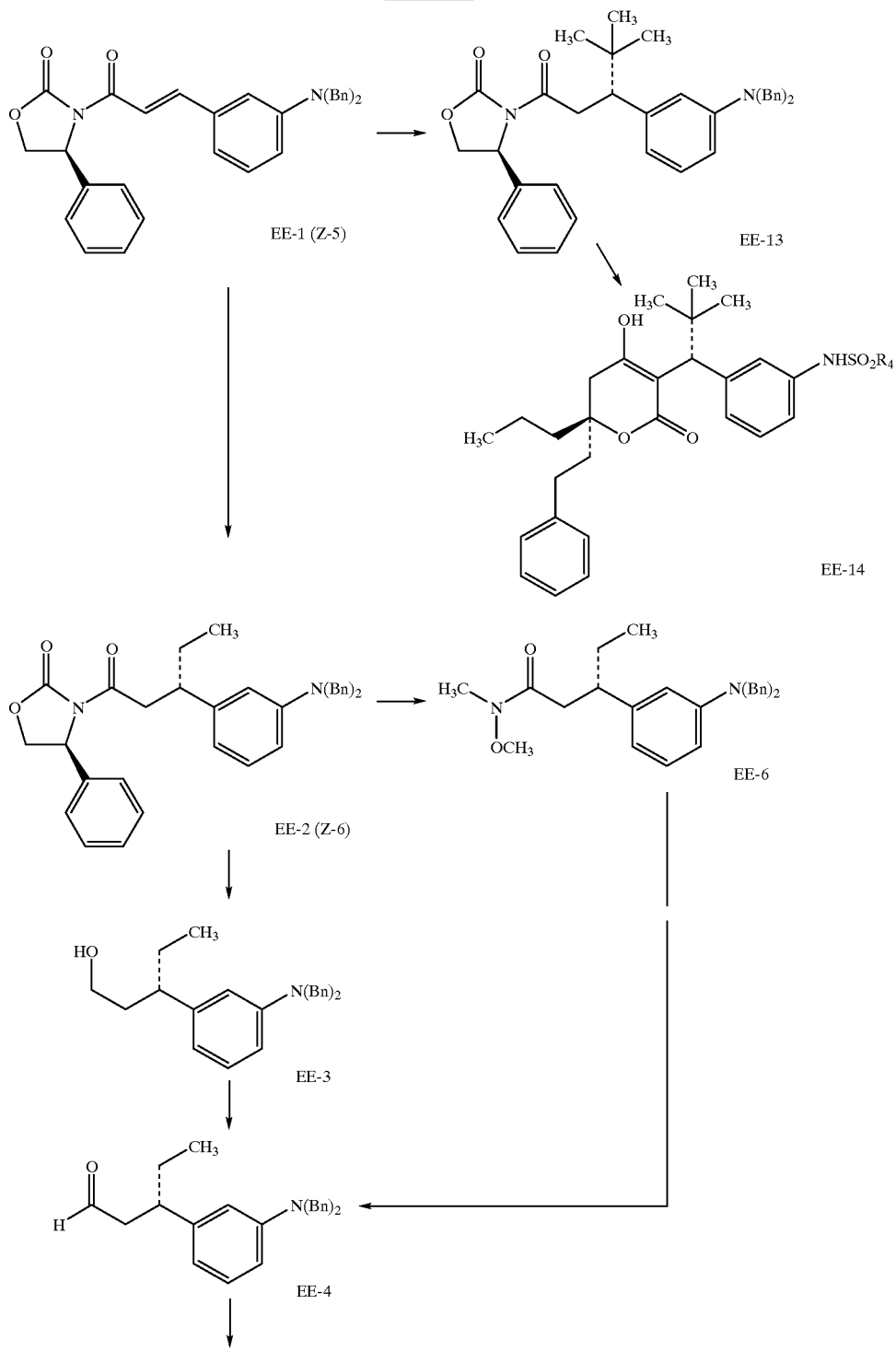

-continued
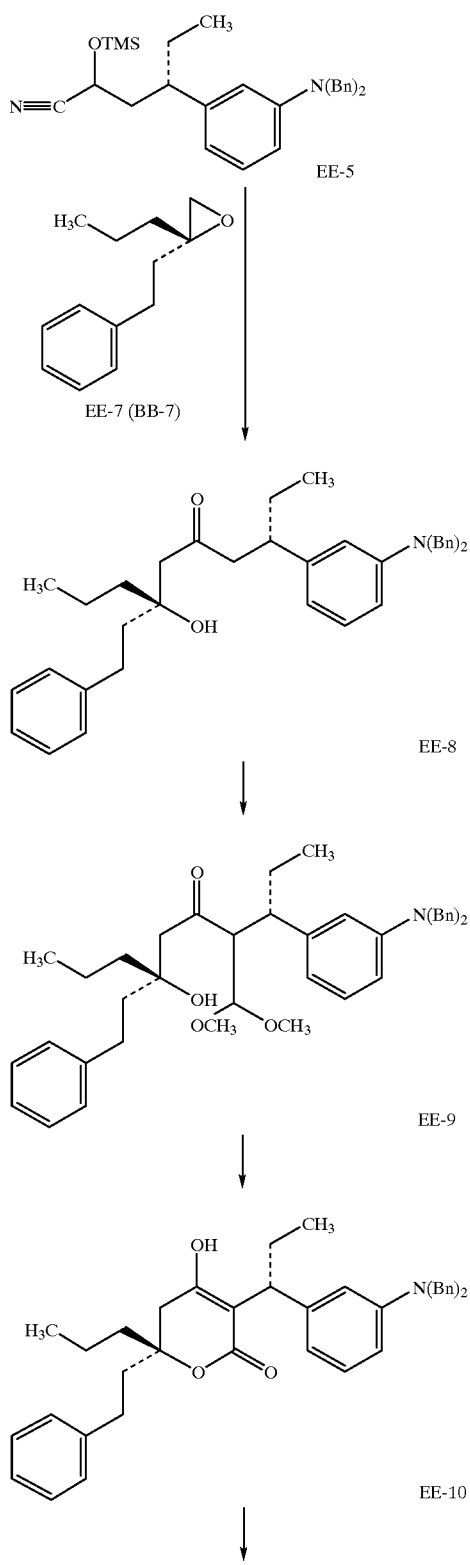

-continued
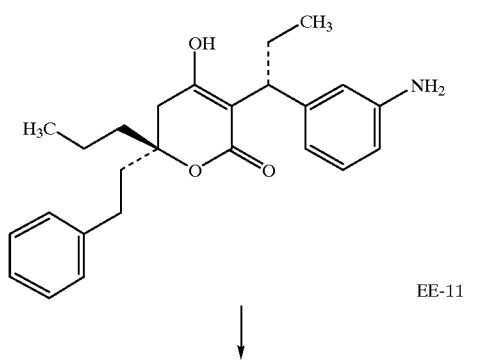
EE-11
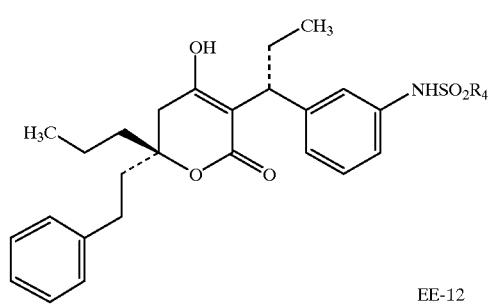
EE-12
CHART FF
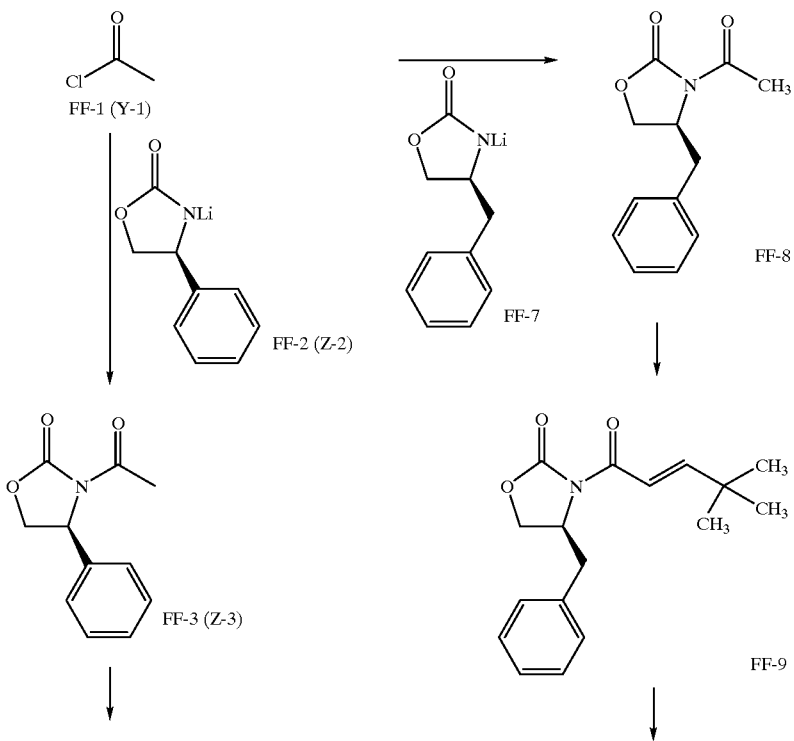

-continued
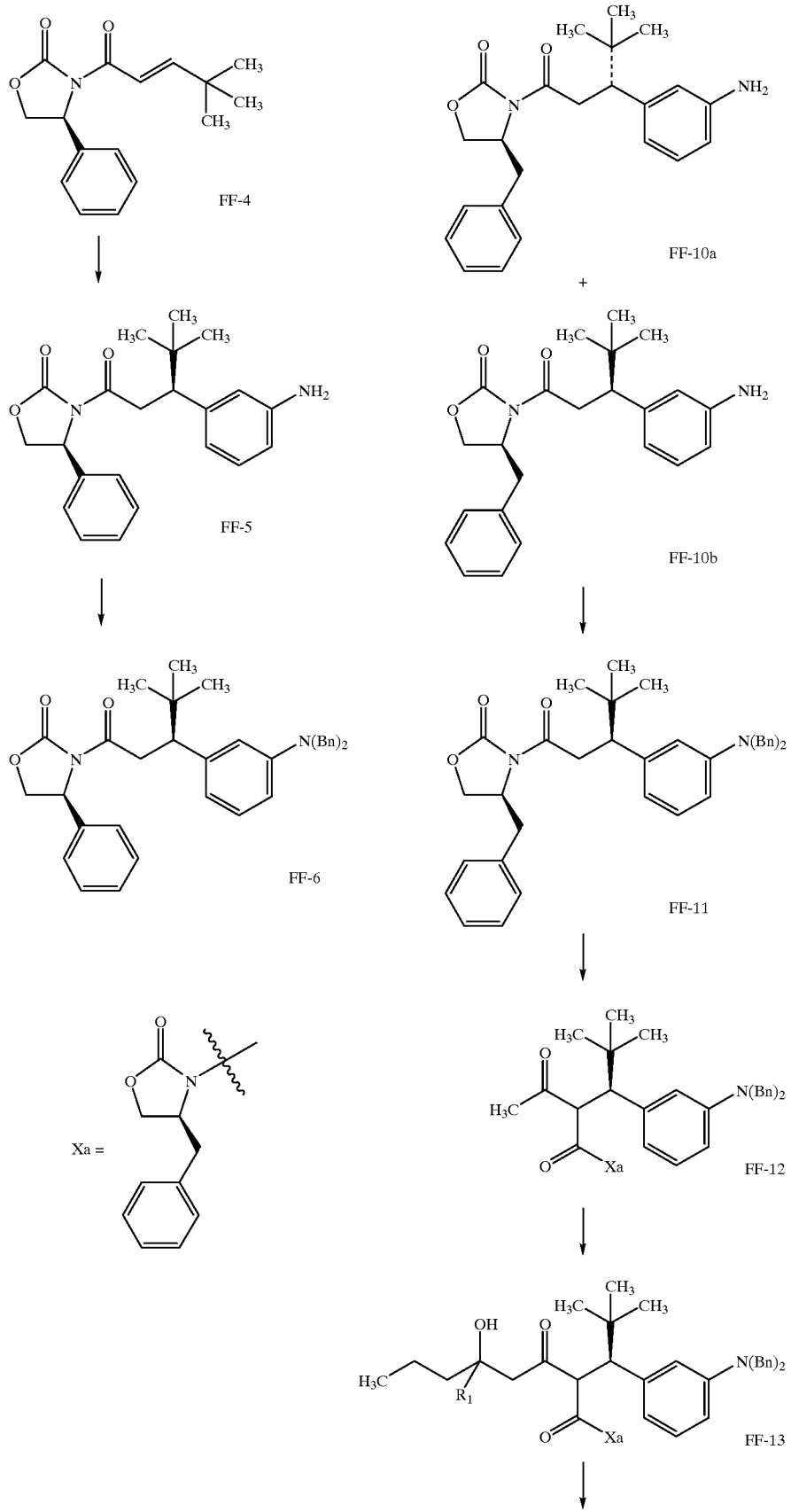

-continued
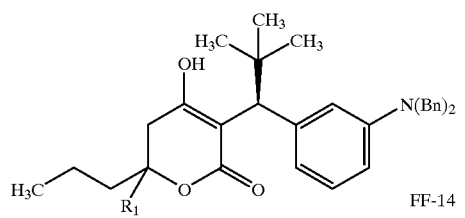
FF-14
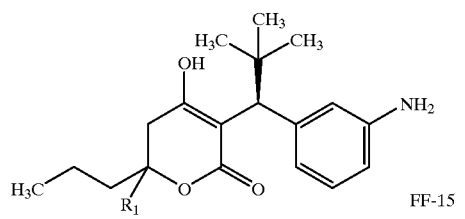
FF-15
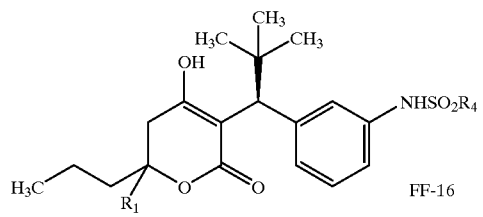
FF-16
CHART GG
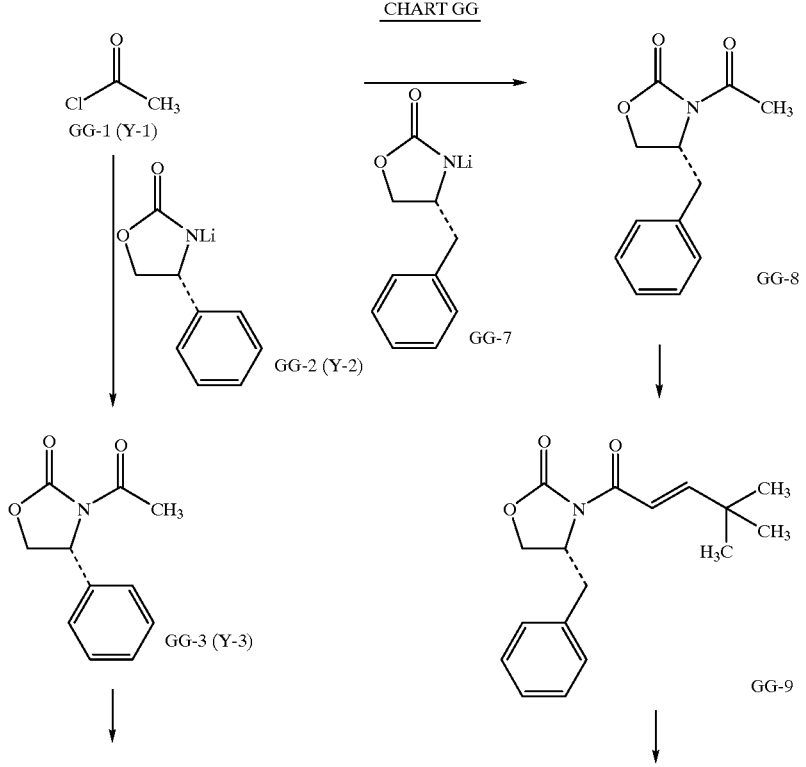

-continued
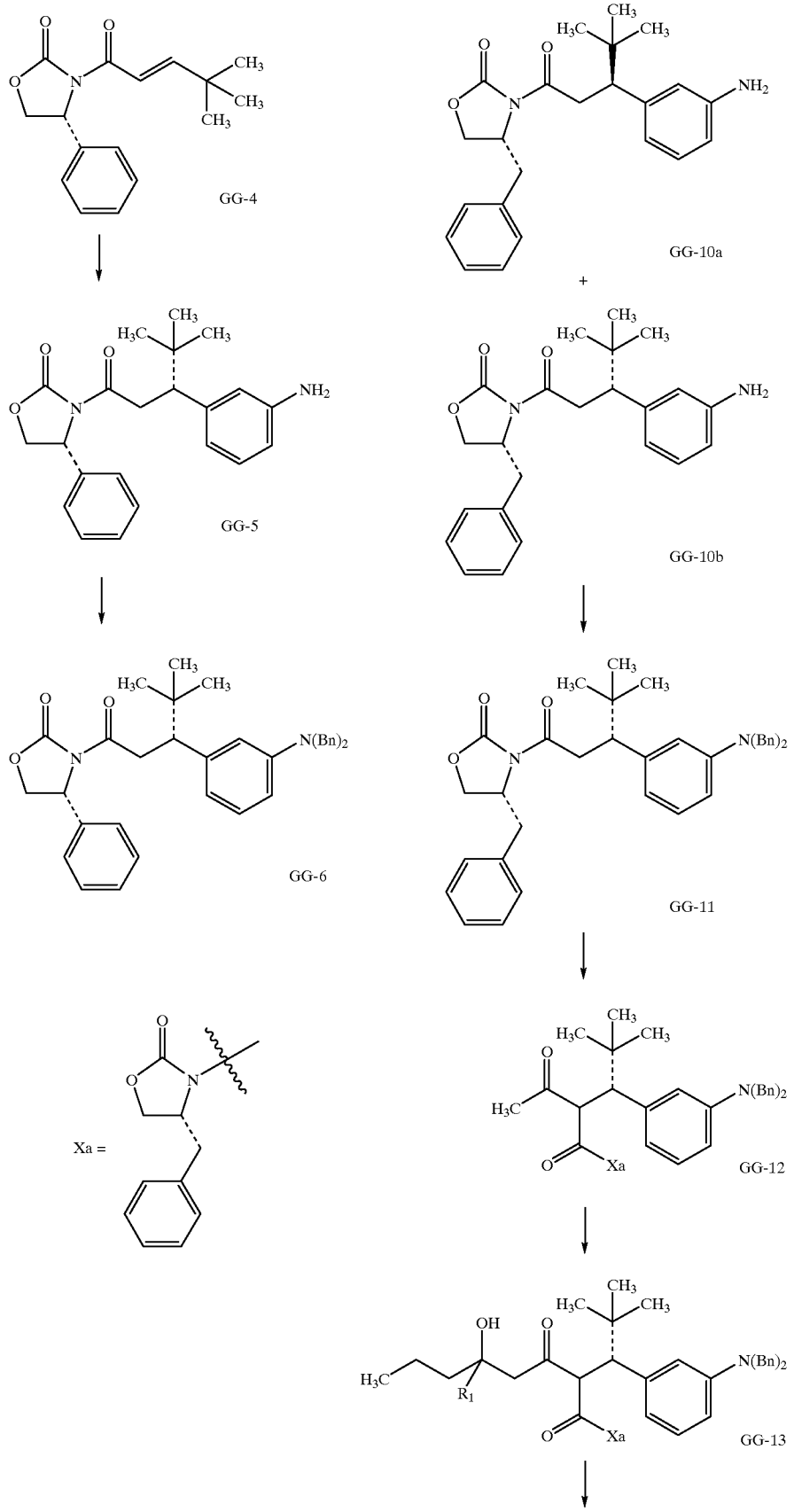

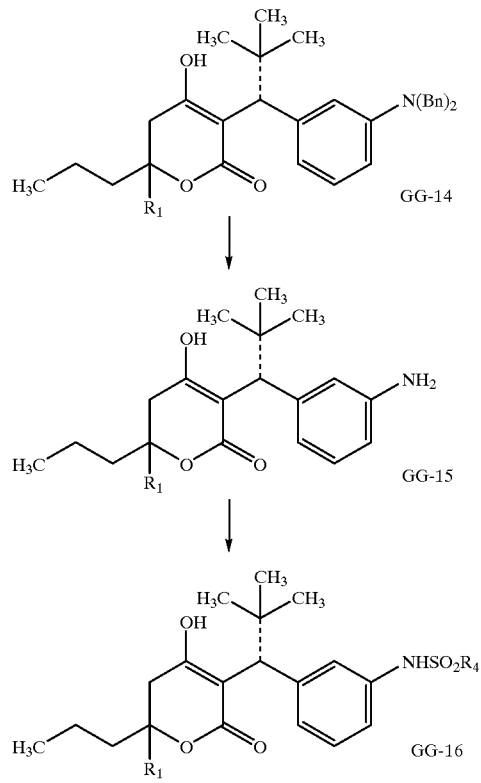
CHART HH
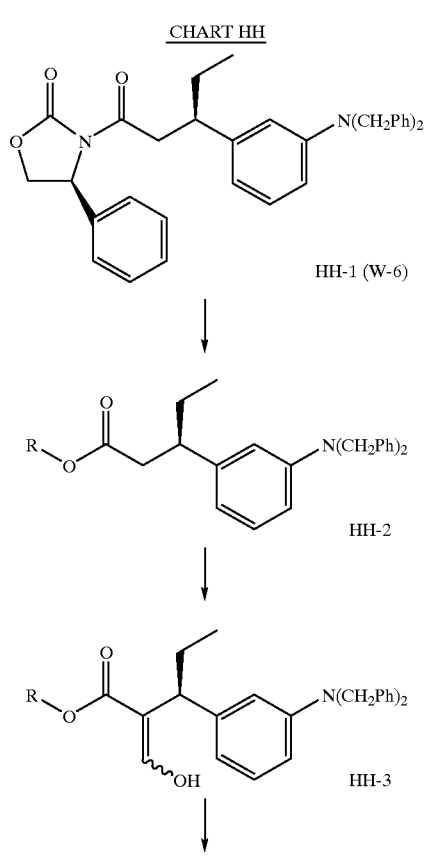
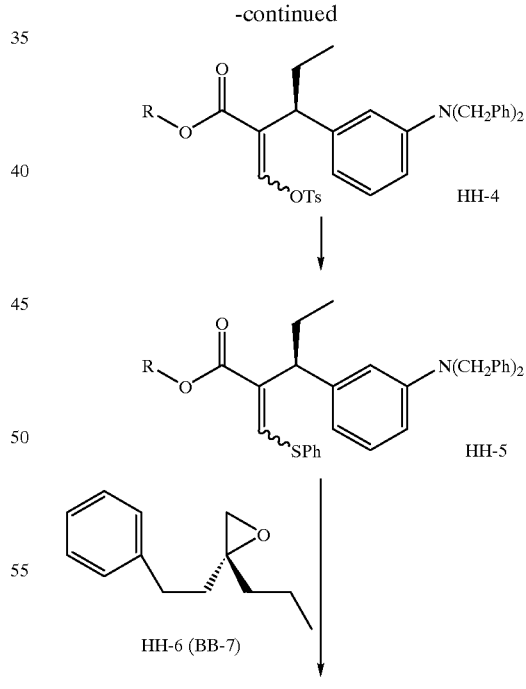

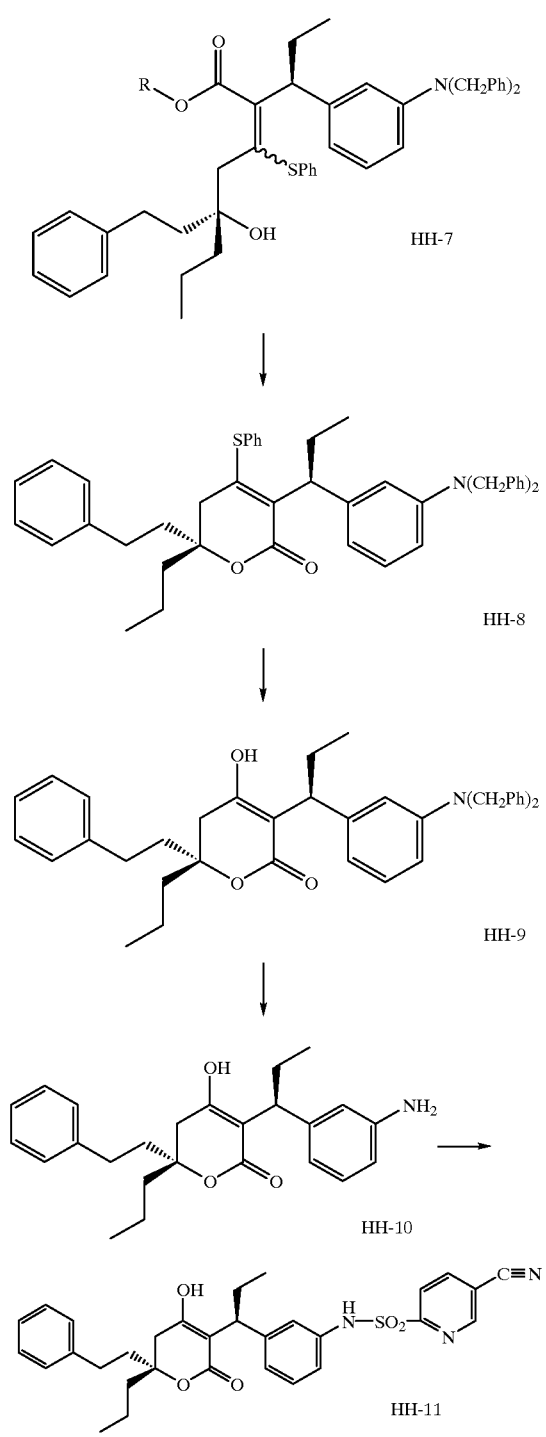
HH-7
HH-8
HH-9
HH-10
HH-11
CHART II
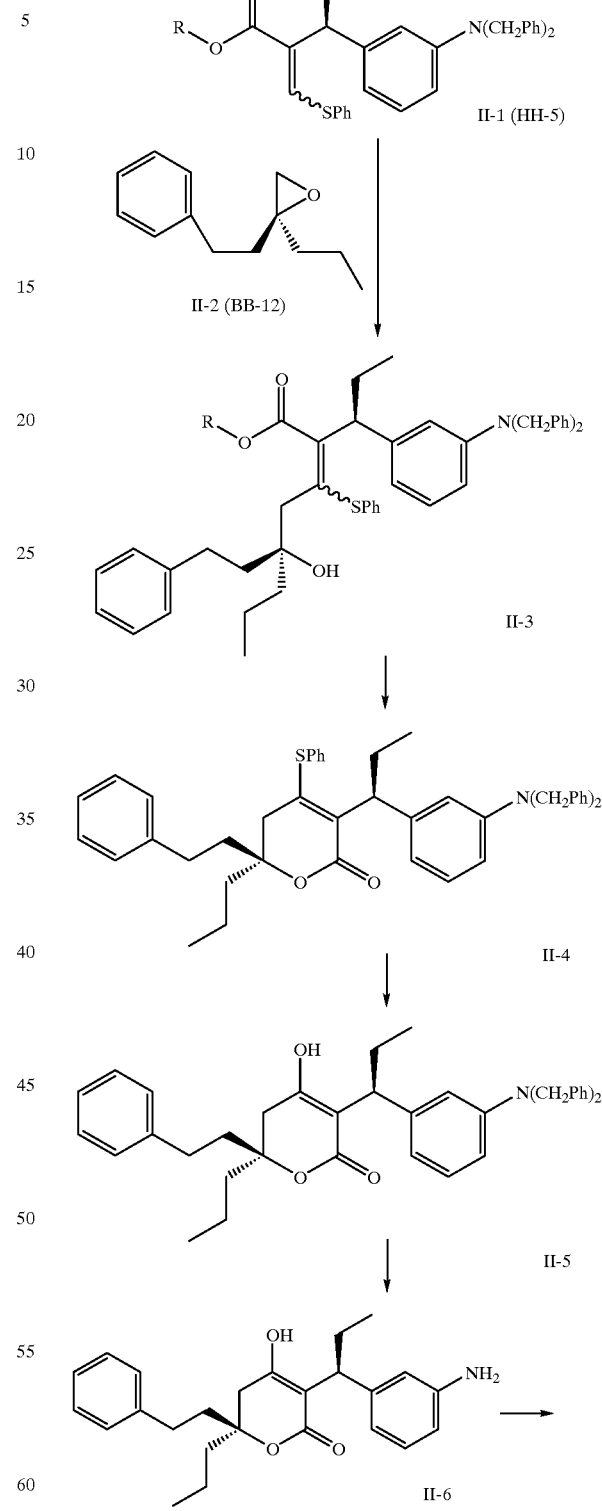
II-1 (HH-5)
II-2 (BB-12)
II-3
II-4
II-5
II-6

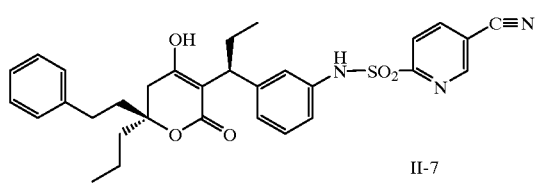
II-7
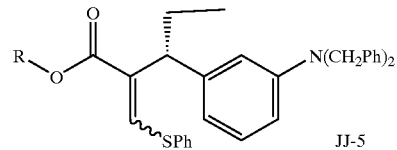
JJ-5
CHART JJ
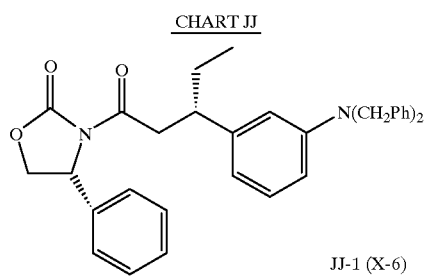
JJ-1 (X-6)
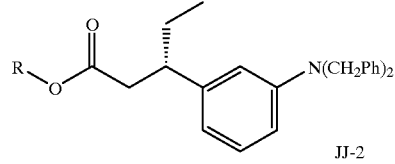
JJ-2
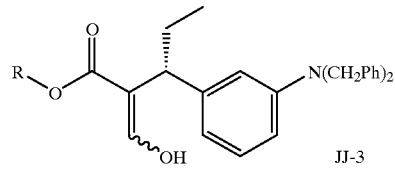
JJ-3
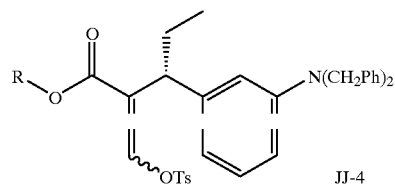
JJ-4
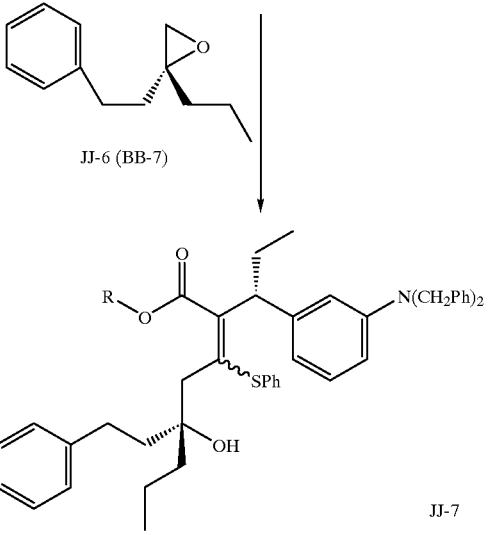
JJ-6 (BB-7)
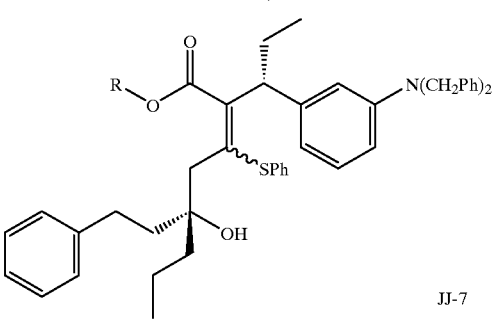
JJ-7
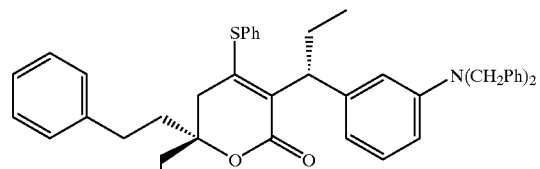
JJ-8
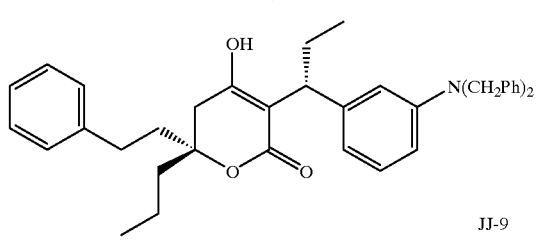
JJ-9
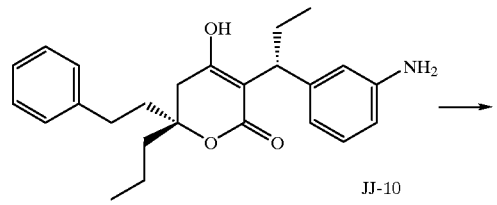
JJ-10

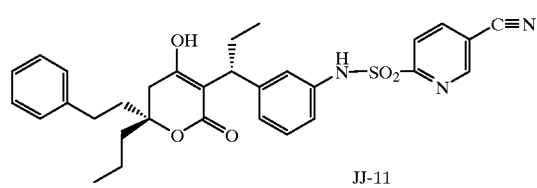
JJ-11
CHART KK
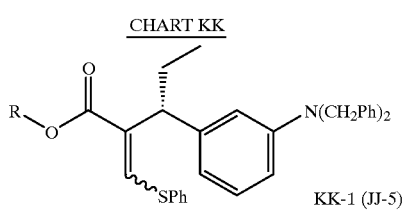
KK-1 (JJ-5)
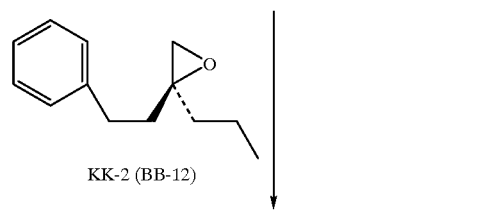
KK-2 (BB-12)
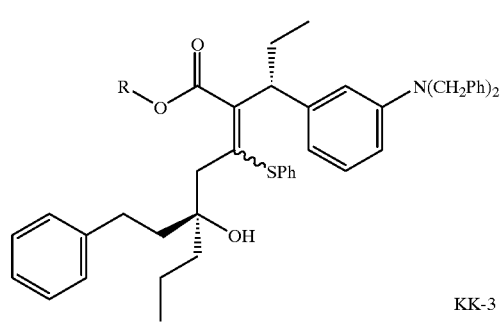
KK-3
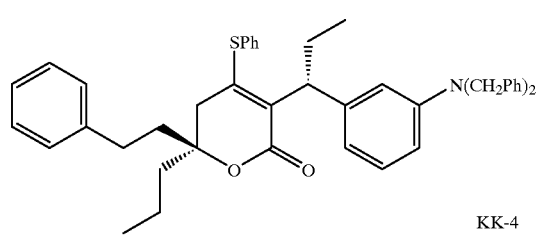
KK-4
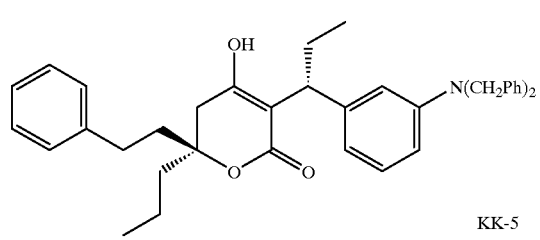
KK-5
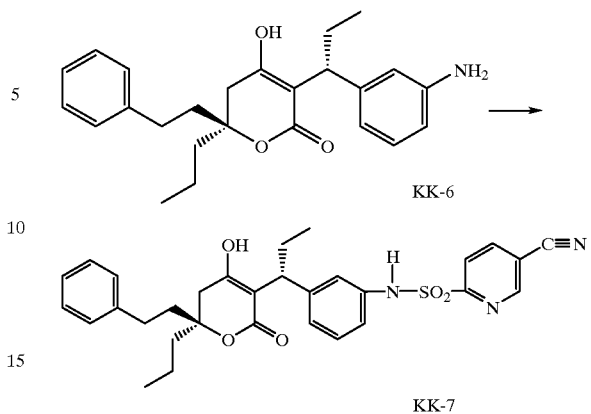
KK-6
KK-7
CHART LL
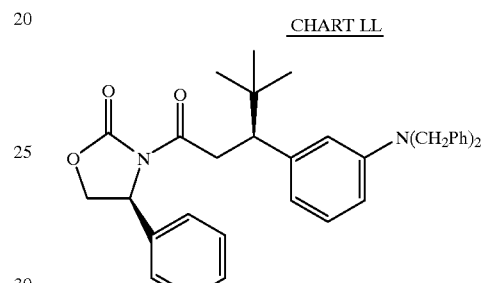
LL-1 (FF-5)
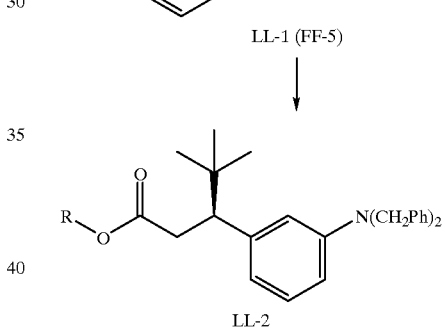
LL-2
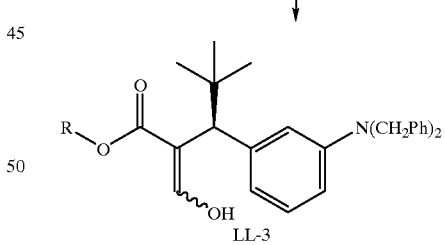
LL-3
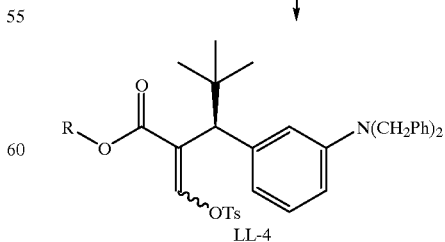
LL-4

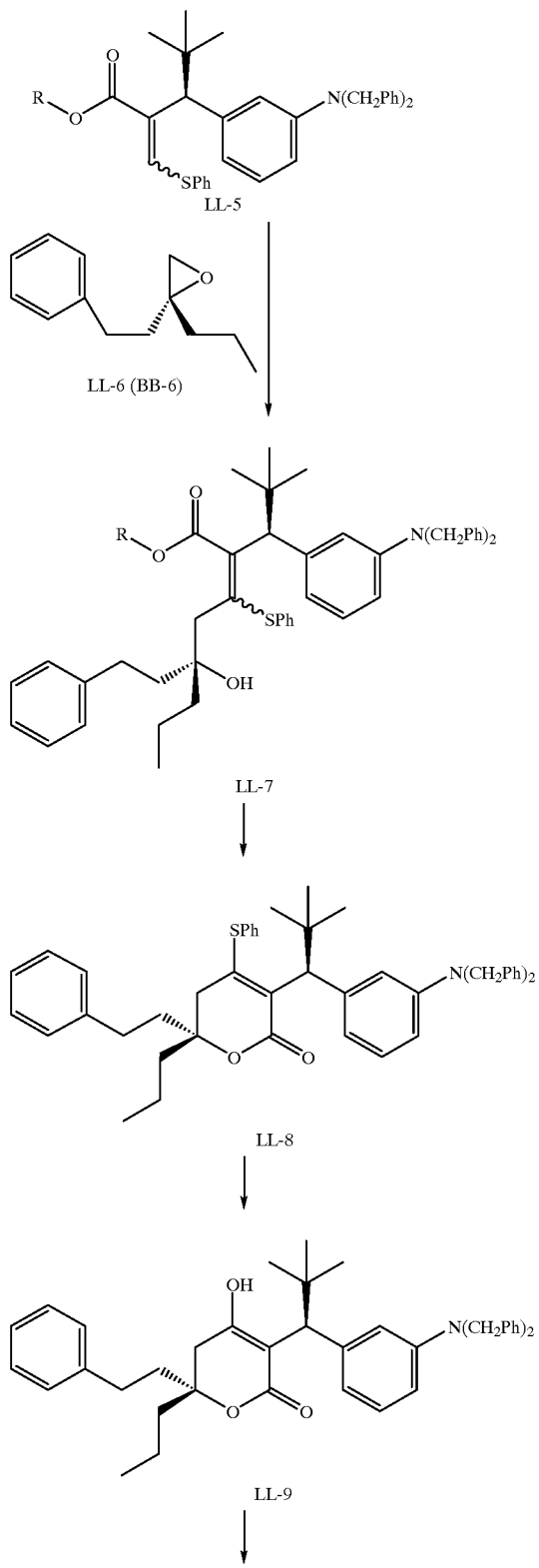
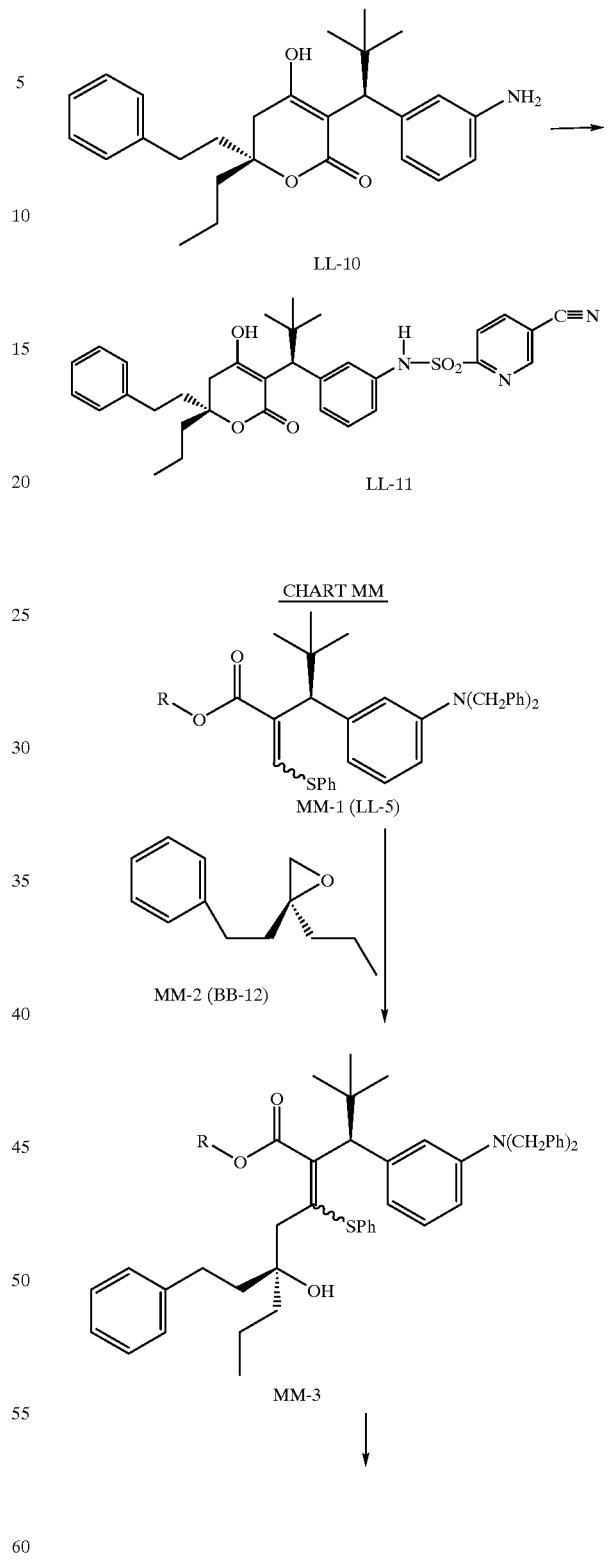
CHART MM

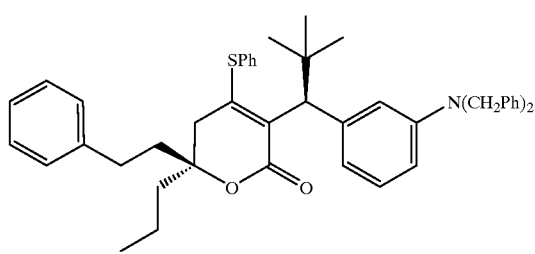
MM-4
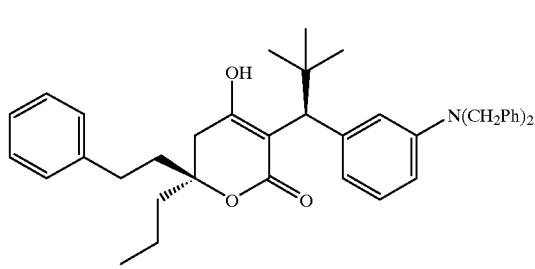
MM-5
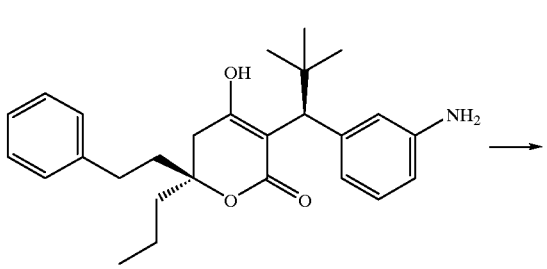
MM-6
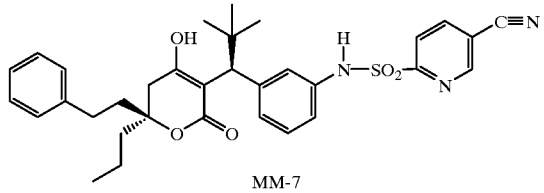
MM-7
CHART NN
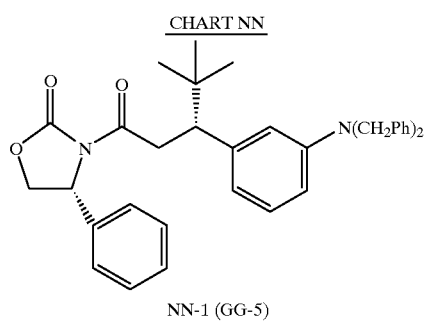
NN-1 (GG-5)
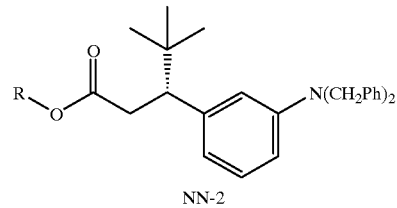
NN-2
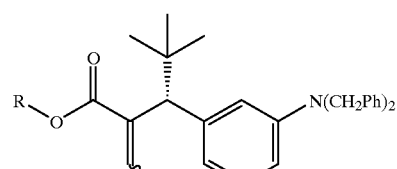
NN-3
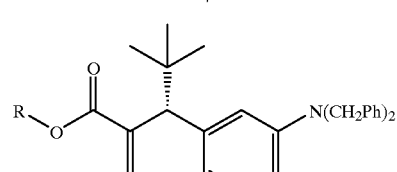
NN-4
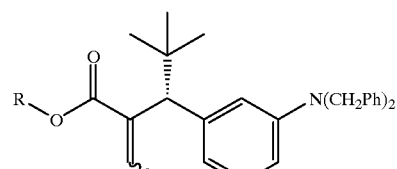
NN-5
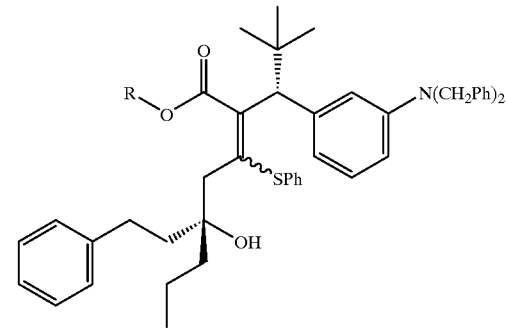
NN-6 (BB-7)
NN-7

257
-continued
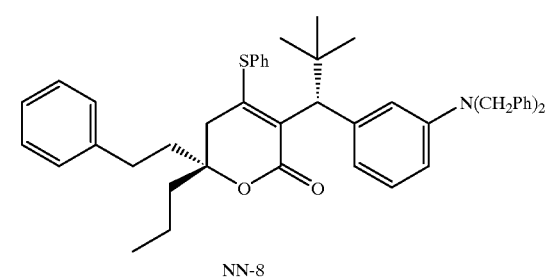
NN-8
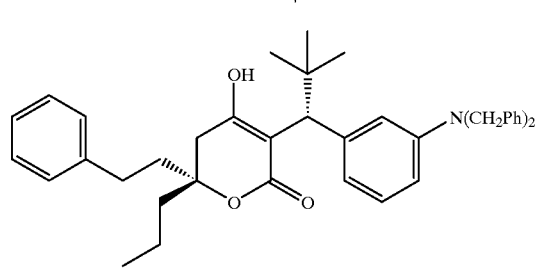
NN-9
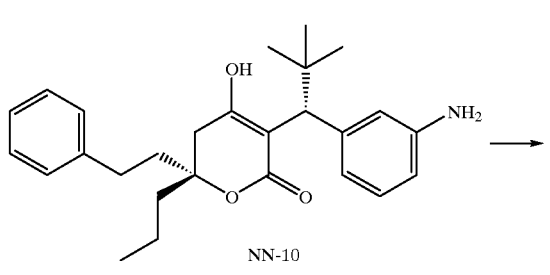
NN-10
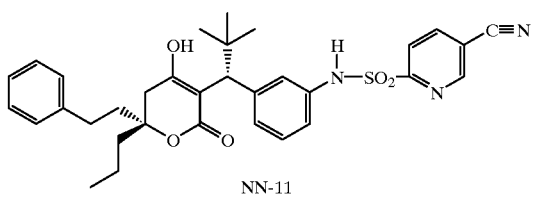
NN-11
CHART OO
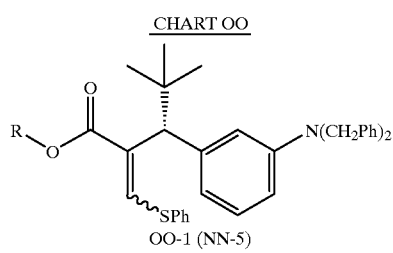
OO-1 (NN-5)
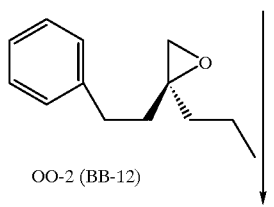
OO-2 (BB-12)
258
-continued
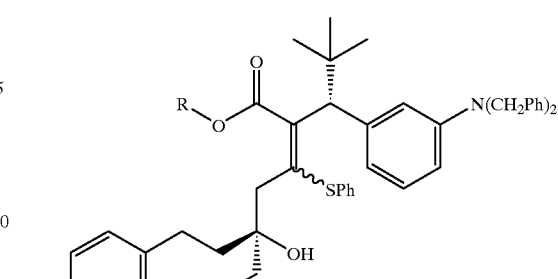
OO-3
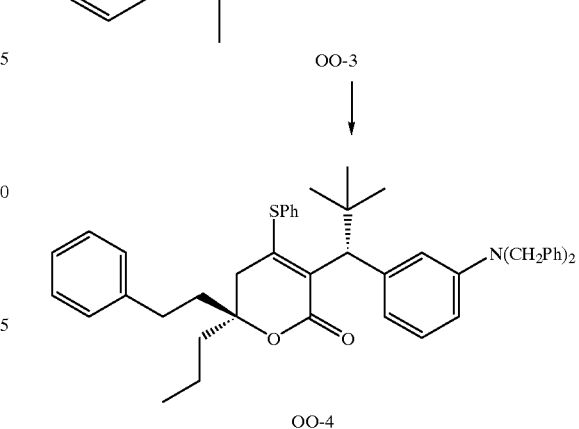
OO-4
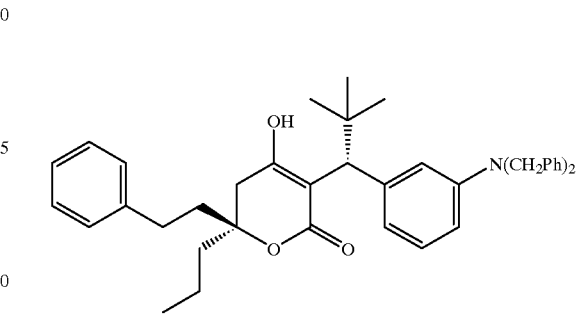
OO-5
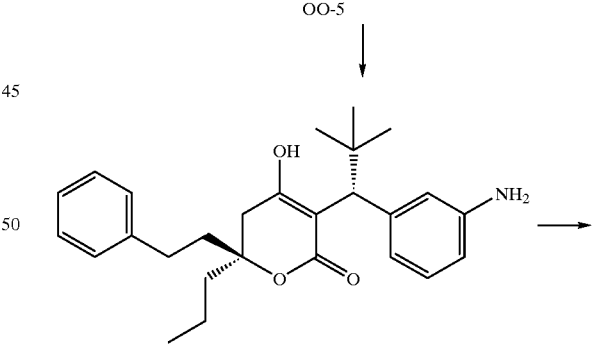
OO-6
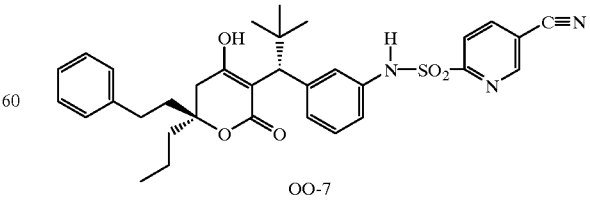
OO-7

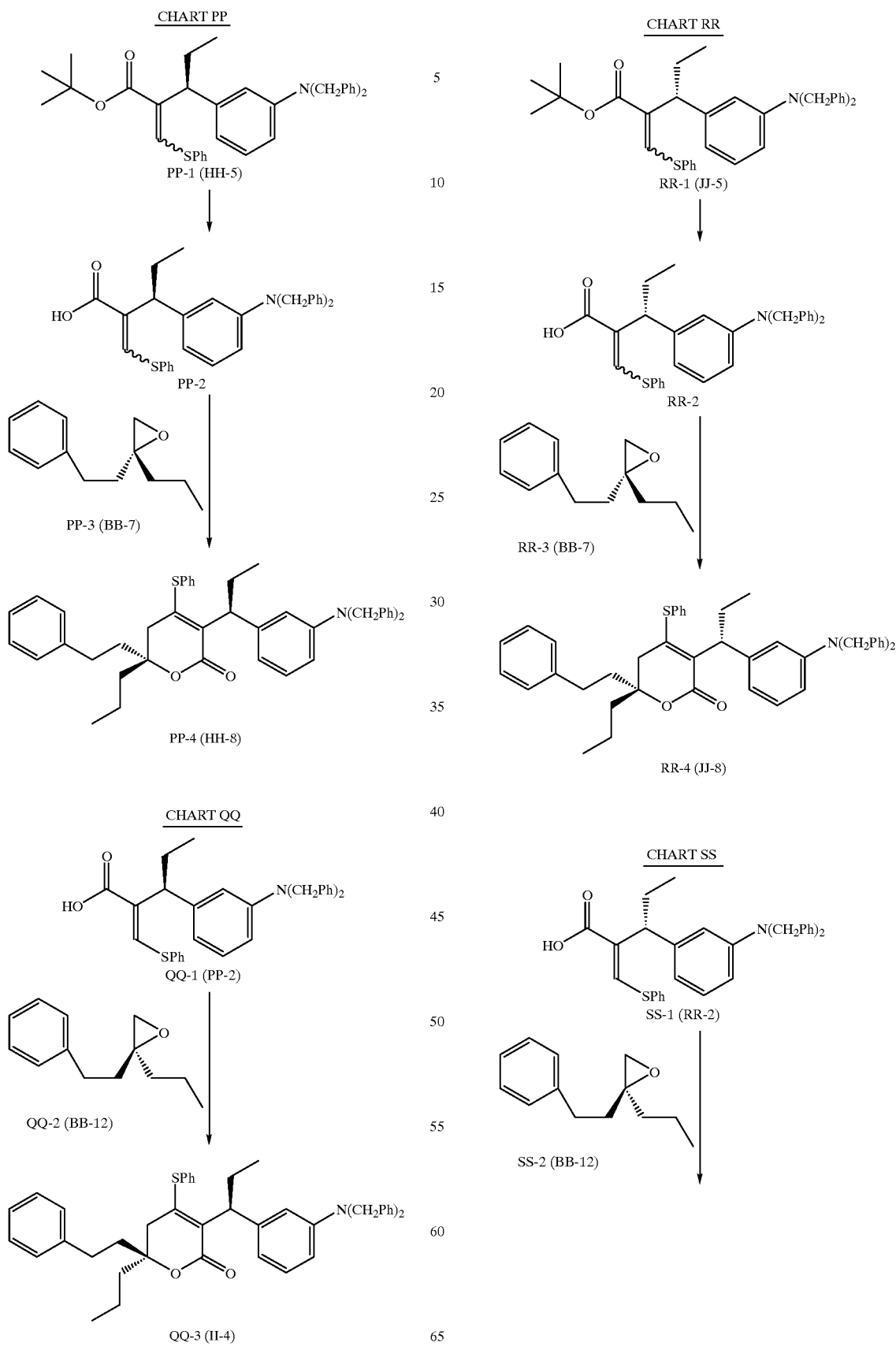

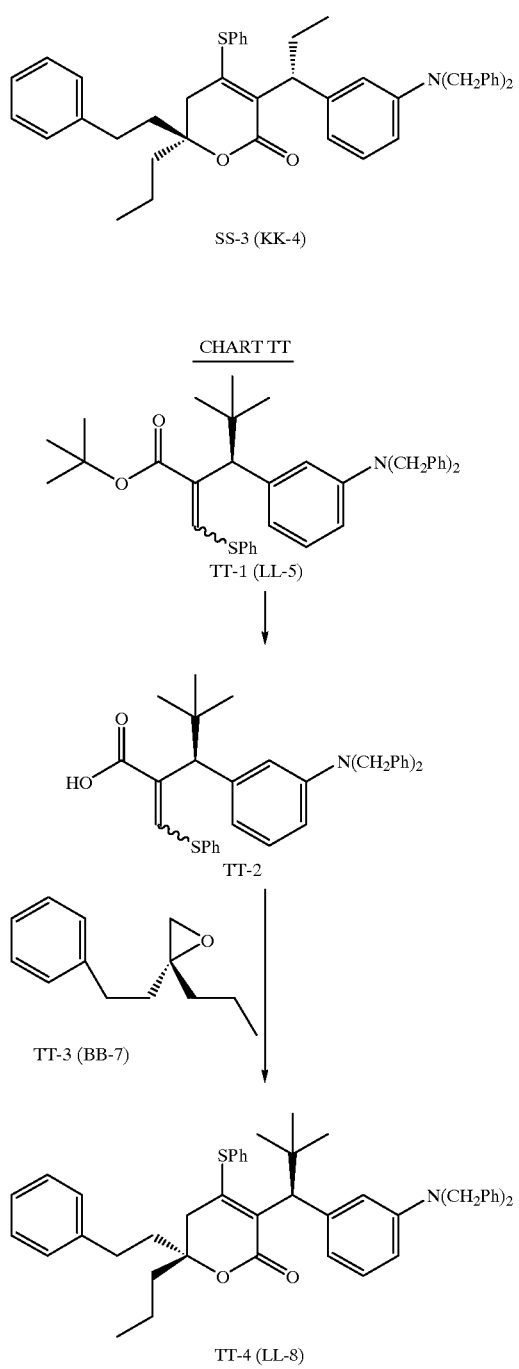
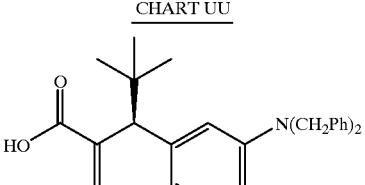
CHART UU
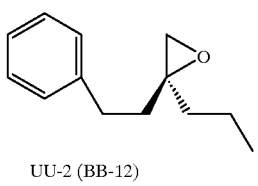
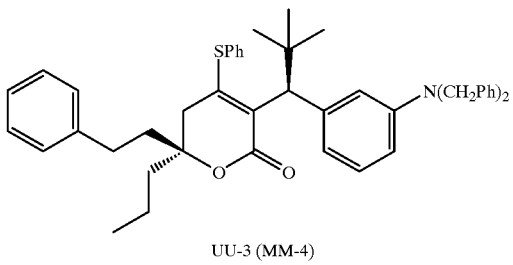
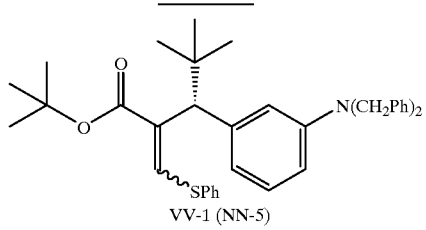
CHART VV
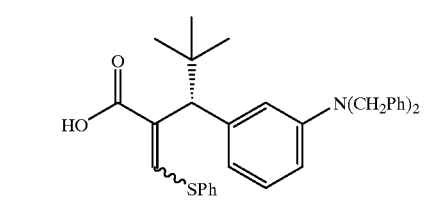
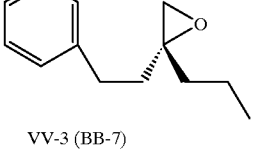

-continued
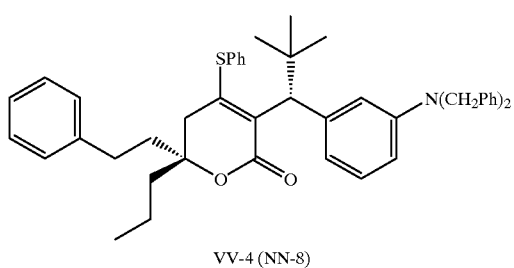
VV-4 (NN-8)
CHART WW
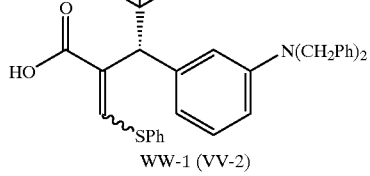
WW-1 (VV-2)
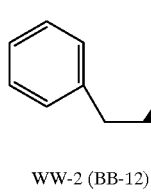
WW-2 (BB-12)
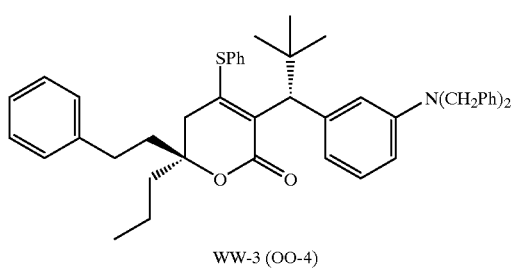
WW-3 (OO-4)
CHART XX
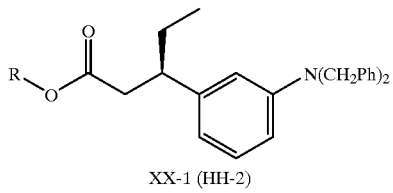
XX-1 (HH-2)
-continued
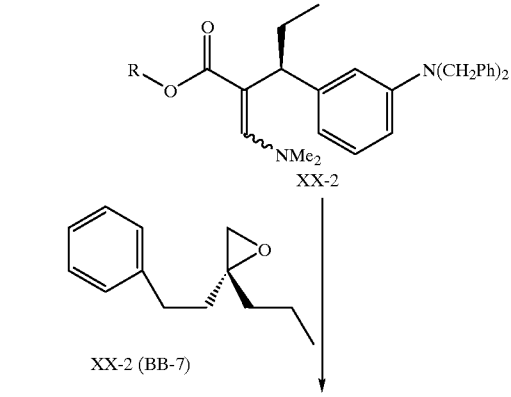
XX-2
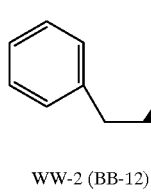
XX-2 (BB-7)
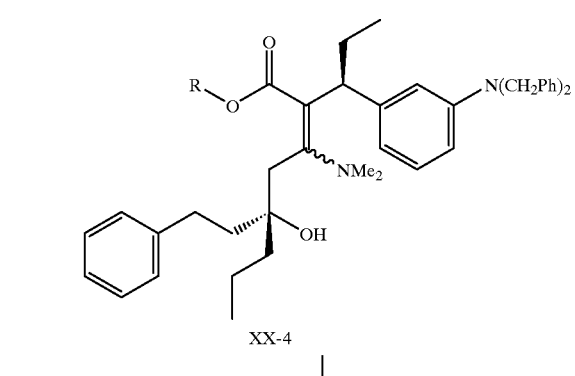
XX-4
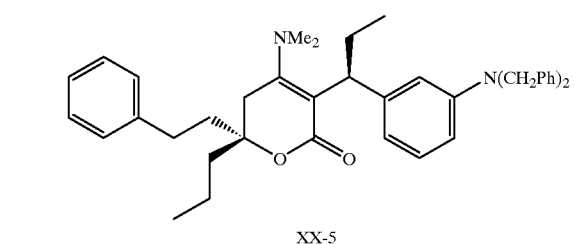
XX-5
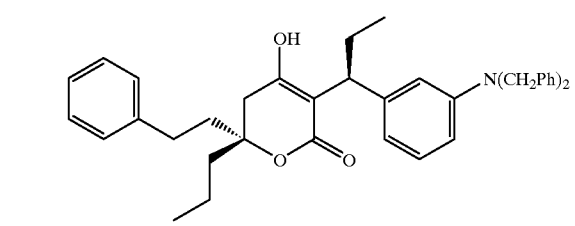
XX-6 (HH-9)

CHART YY
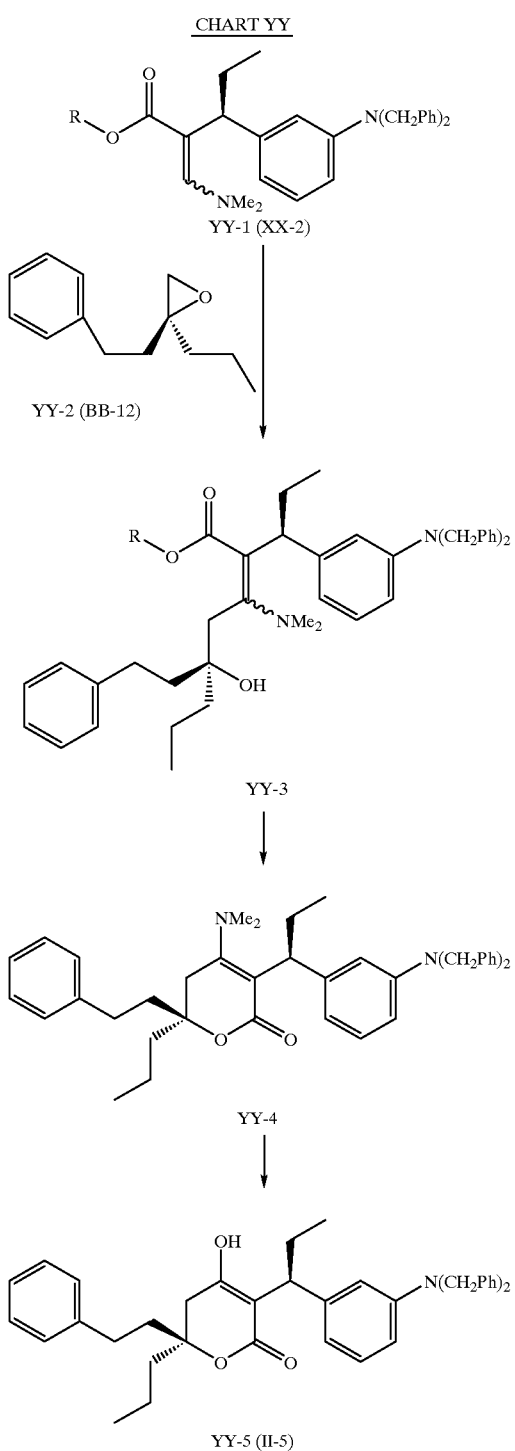
CHART ZZ
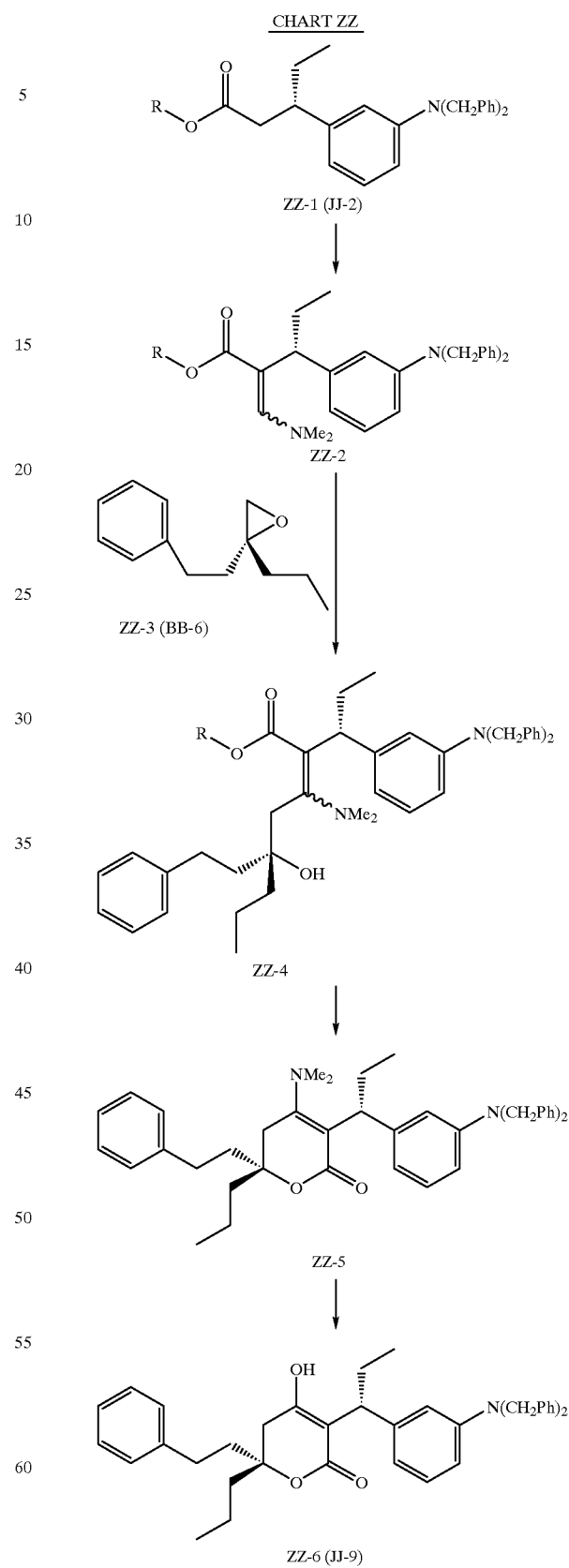

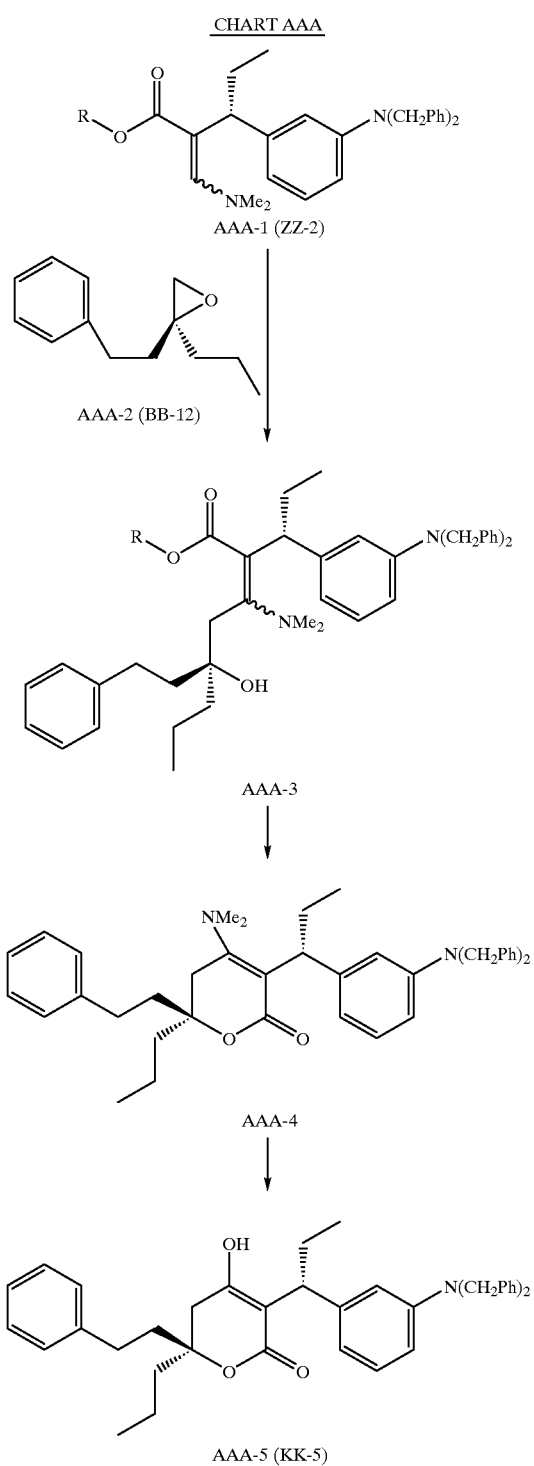
CHART AAA
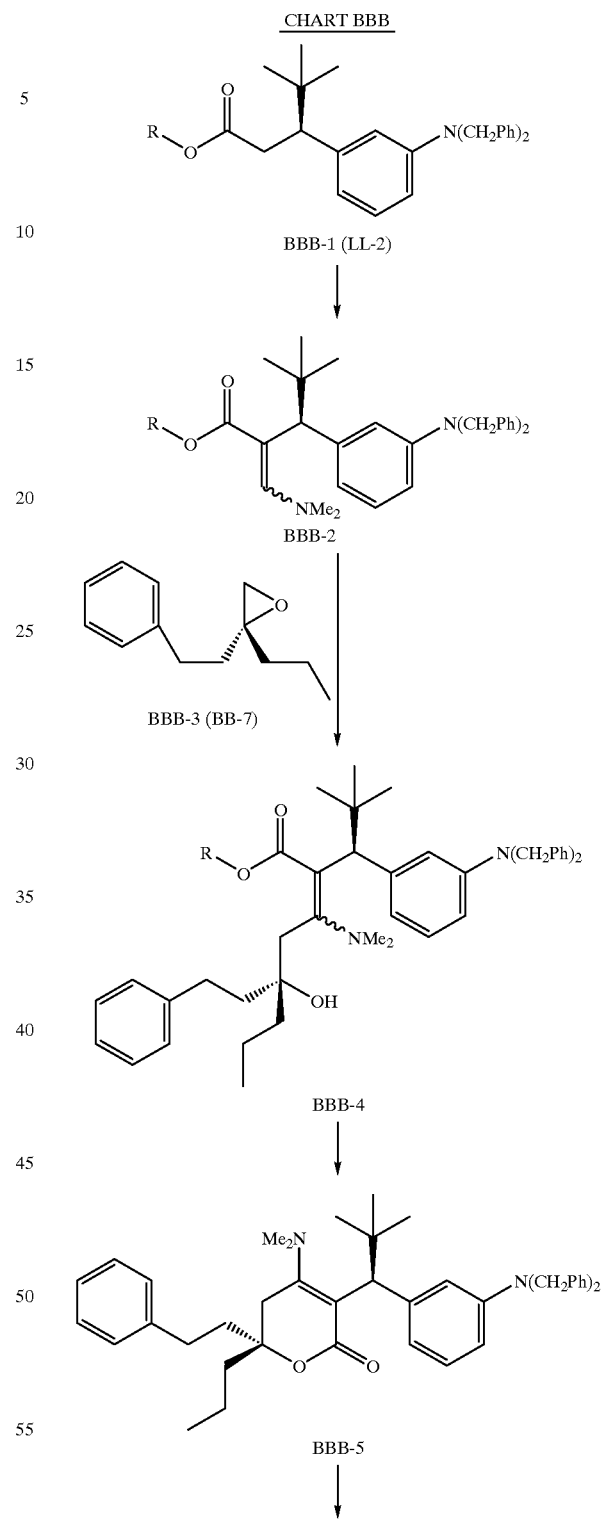
CHART BBB

269
-continued
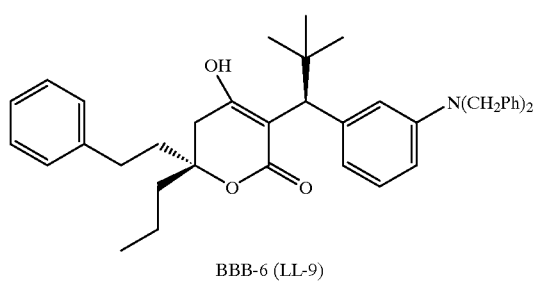
BBB-6 (LL-9)
CHART CCC
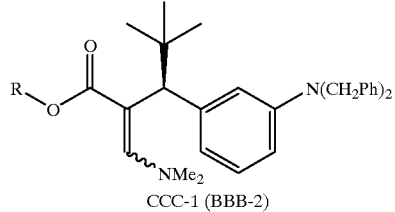
CCC-1 (BBB-2)
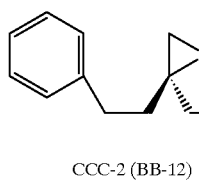
CCC-2 (BB-12)
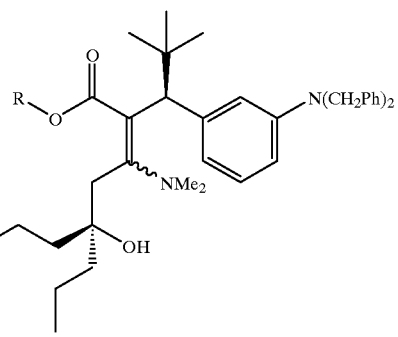
CCC-3 ↓
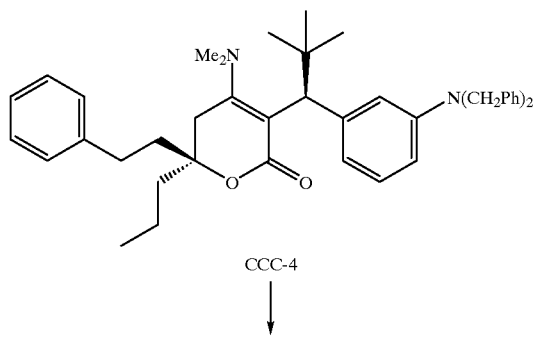
CCC-4 ↓
270
-continued
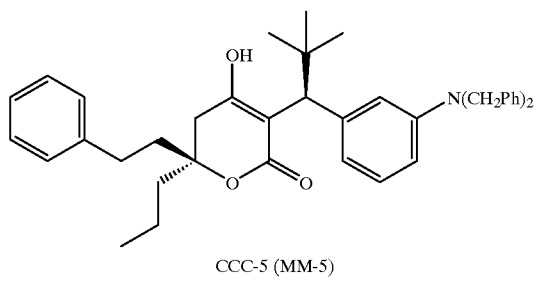
CCC-5 (MM-5)
CHART DDD
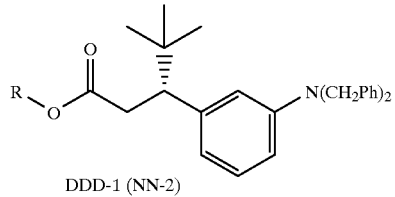
DDD-1 (NN-2)
↓
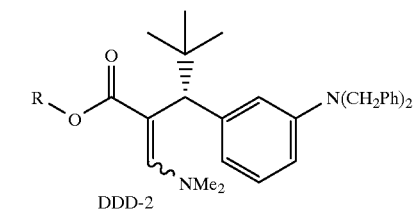
DDD-2
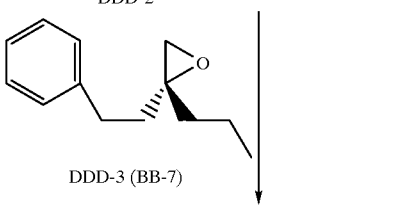
DDD-3 (BB-7)
↓
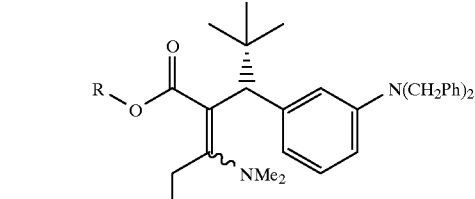
DDD-4
↓

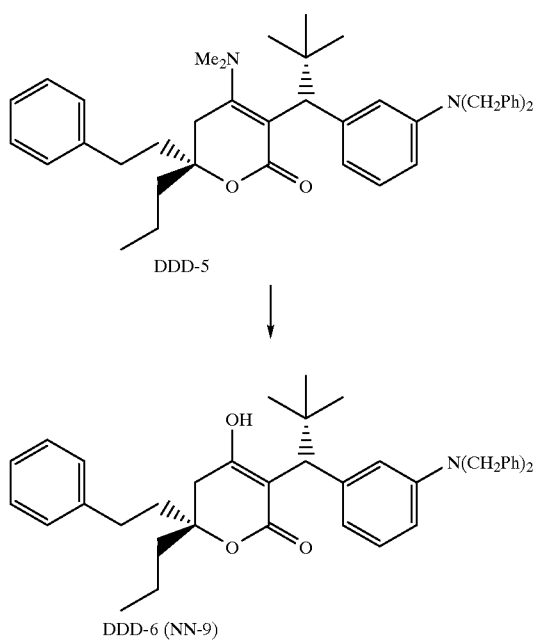
DDD-5
DDD-6 (NN-9)
CHART EEE
EEE-1 (DDD-2)
EEE-2 (BB-12)
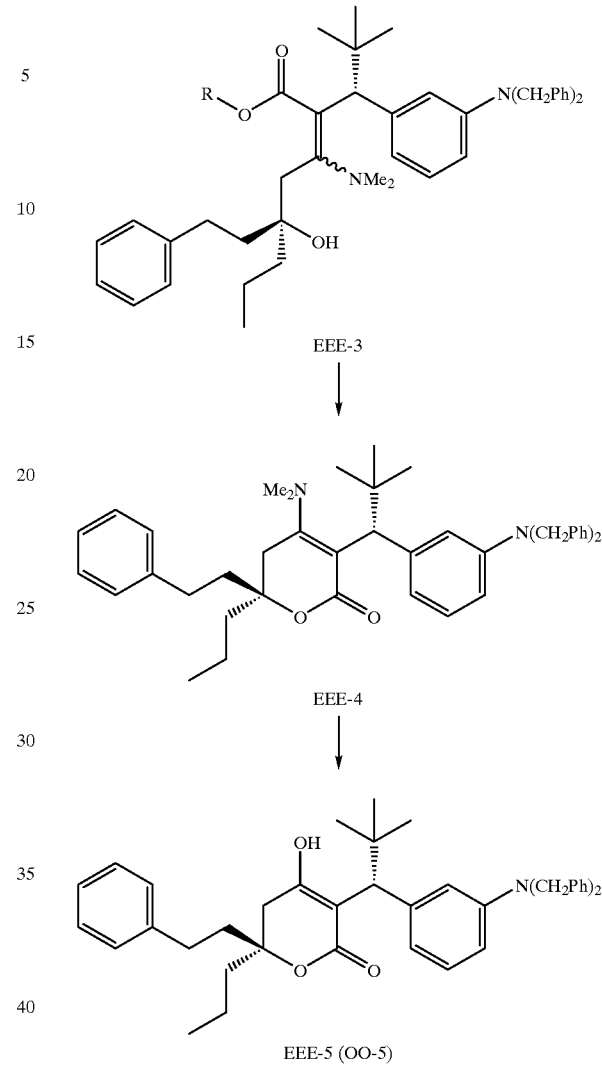
EEE-3
EEE-4
EEE-5 (OO-5)
CHART FFF
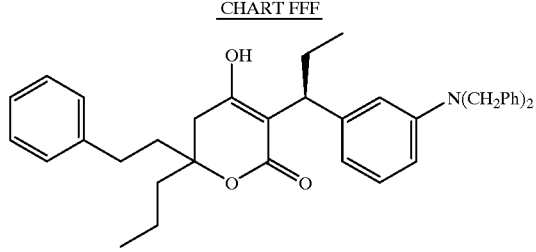
FFF-1 (W-11)

-continued
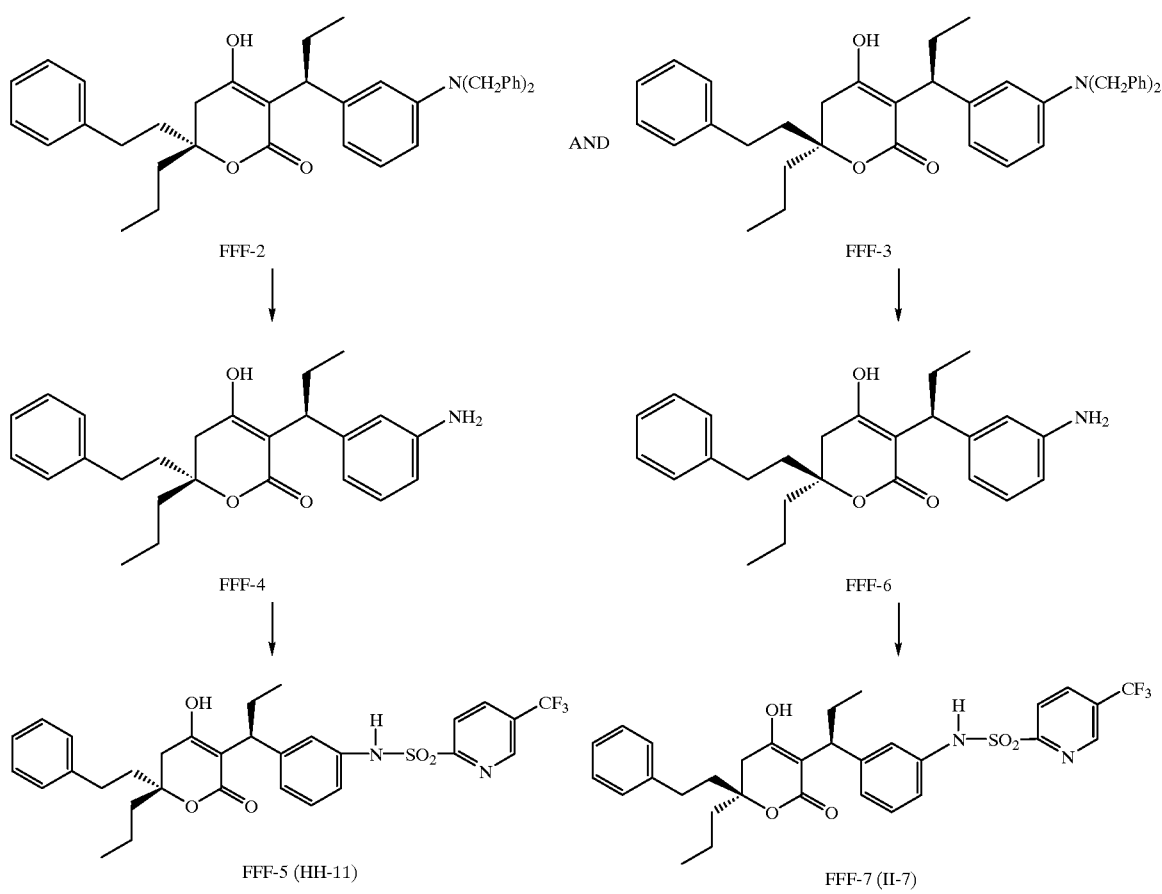
CHART GGG
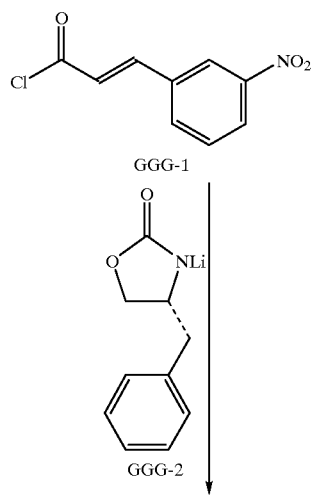

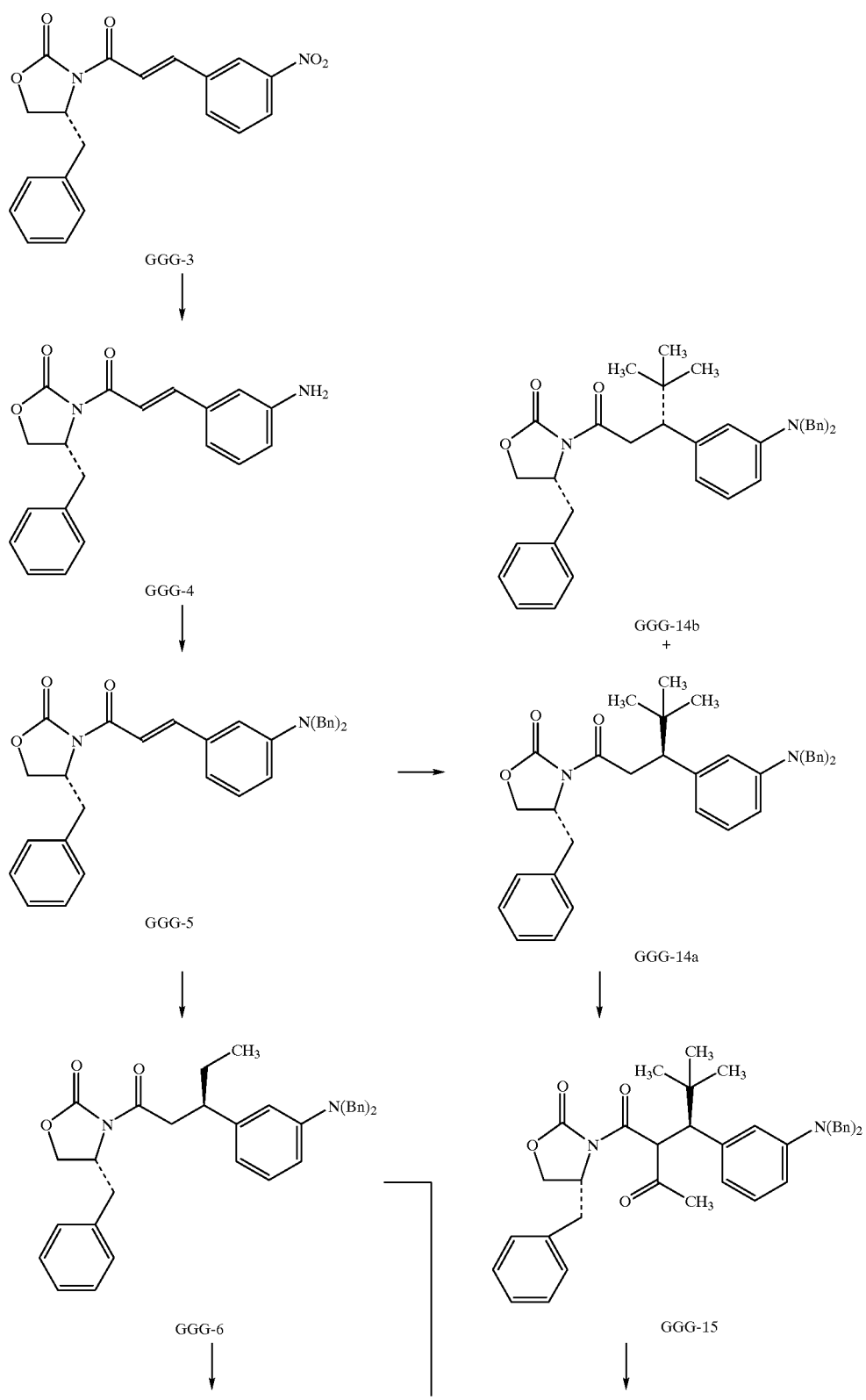

277
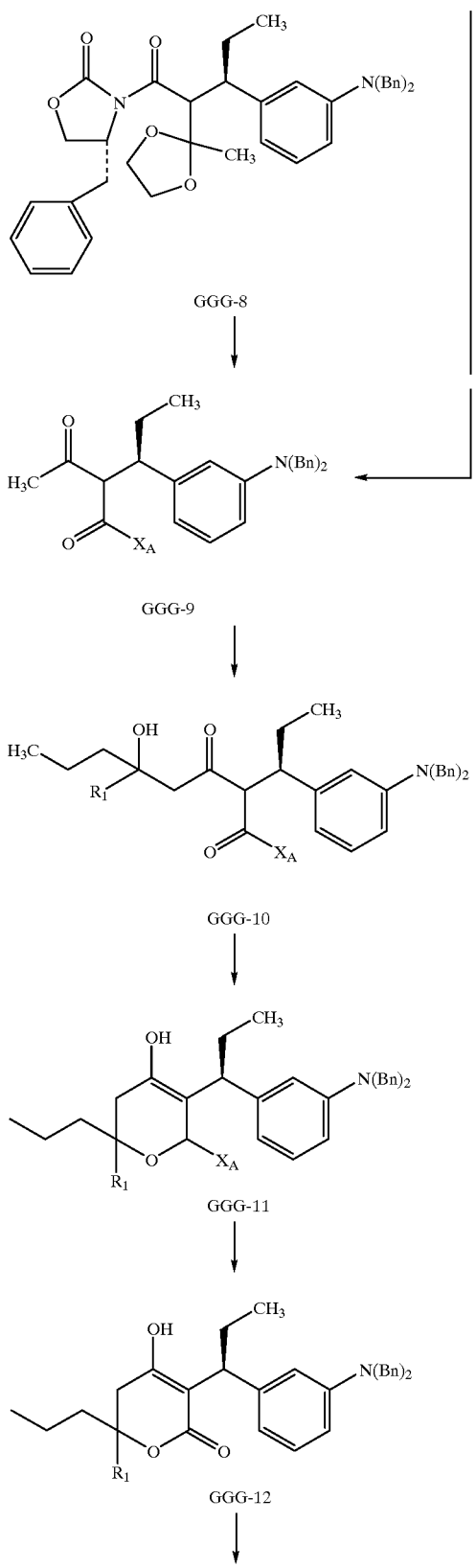
278
-continued
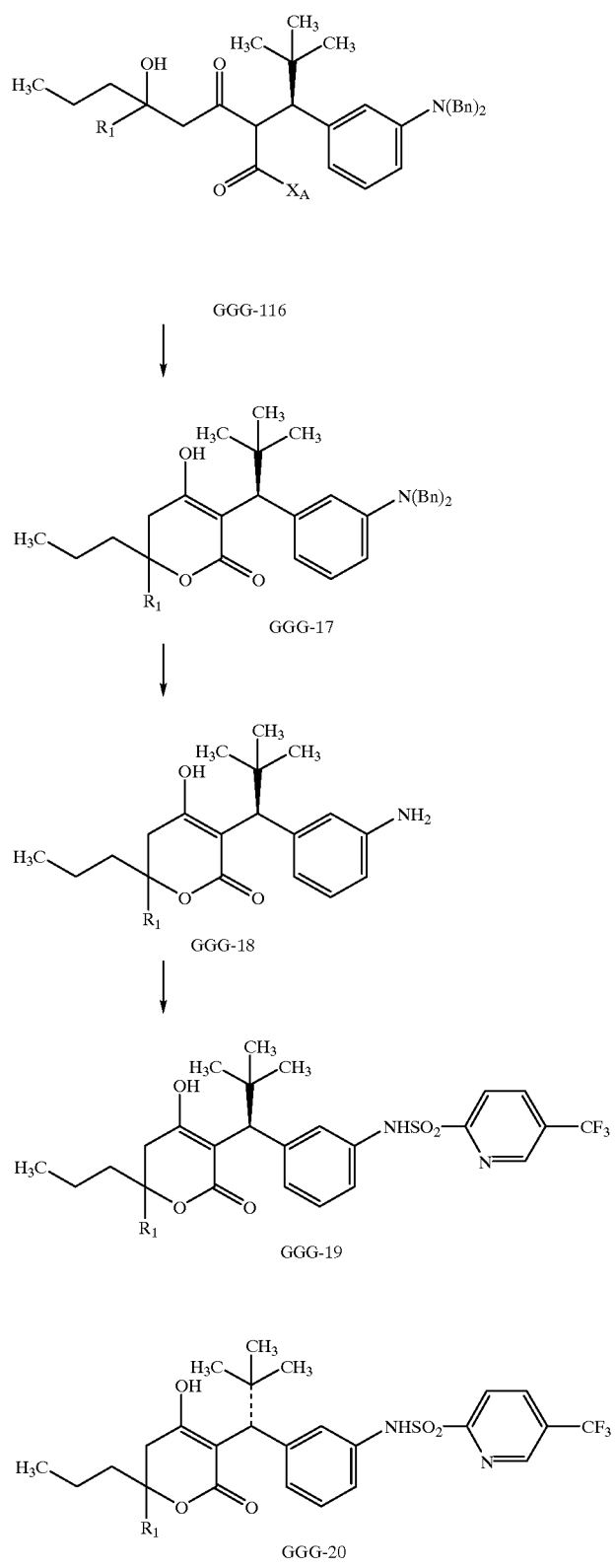

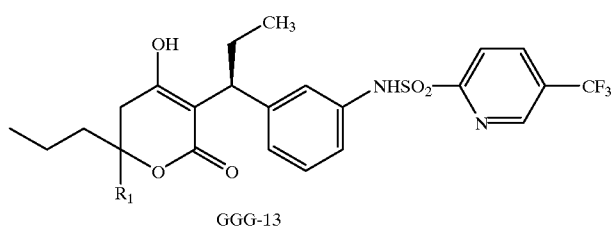
GGG-13
CHART HHH
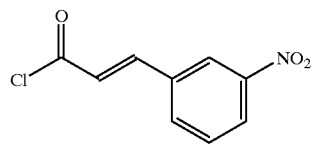
HHH-1
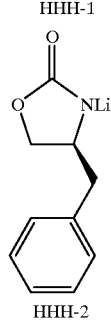
HHH-2
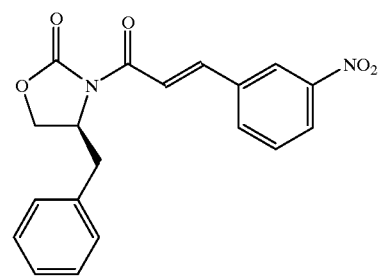
HHH-3
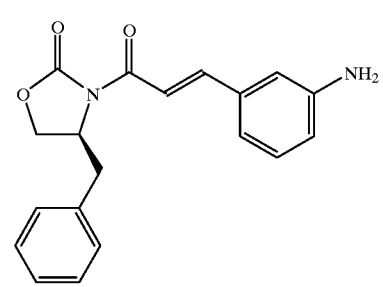
HHH-4
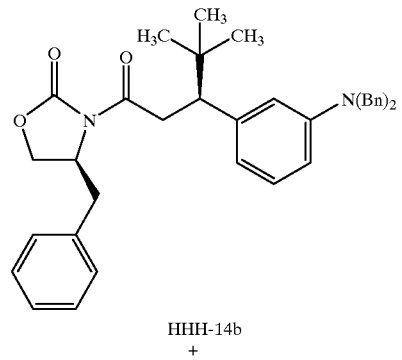
HHH-14b
+

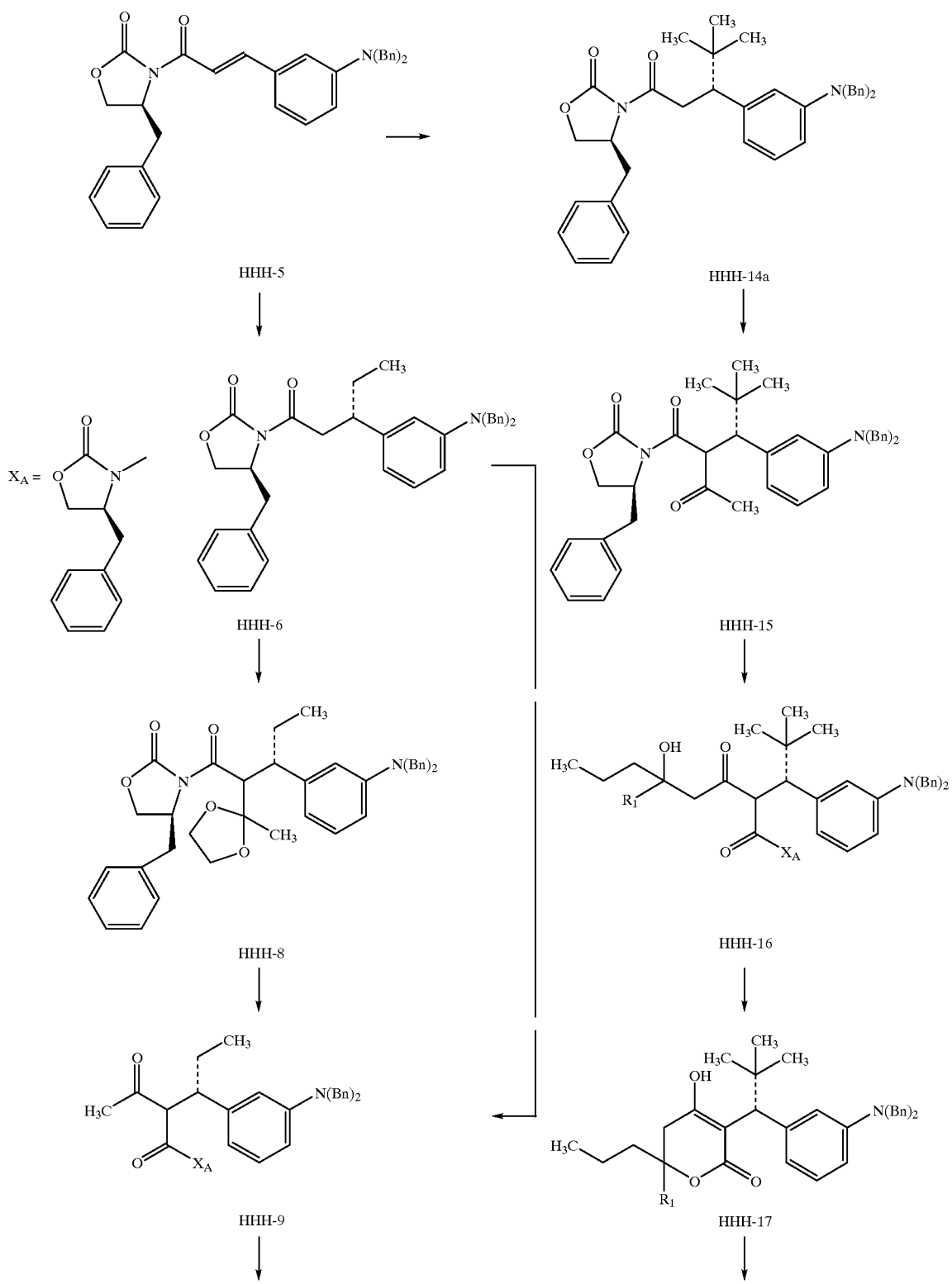

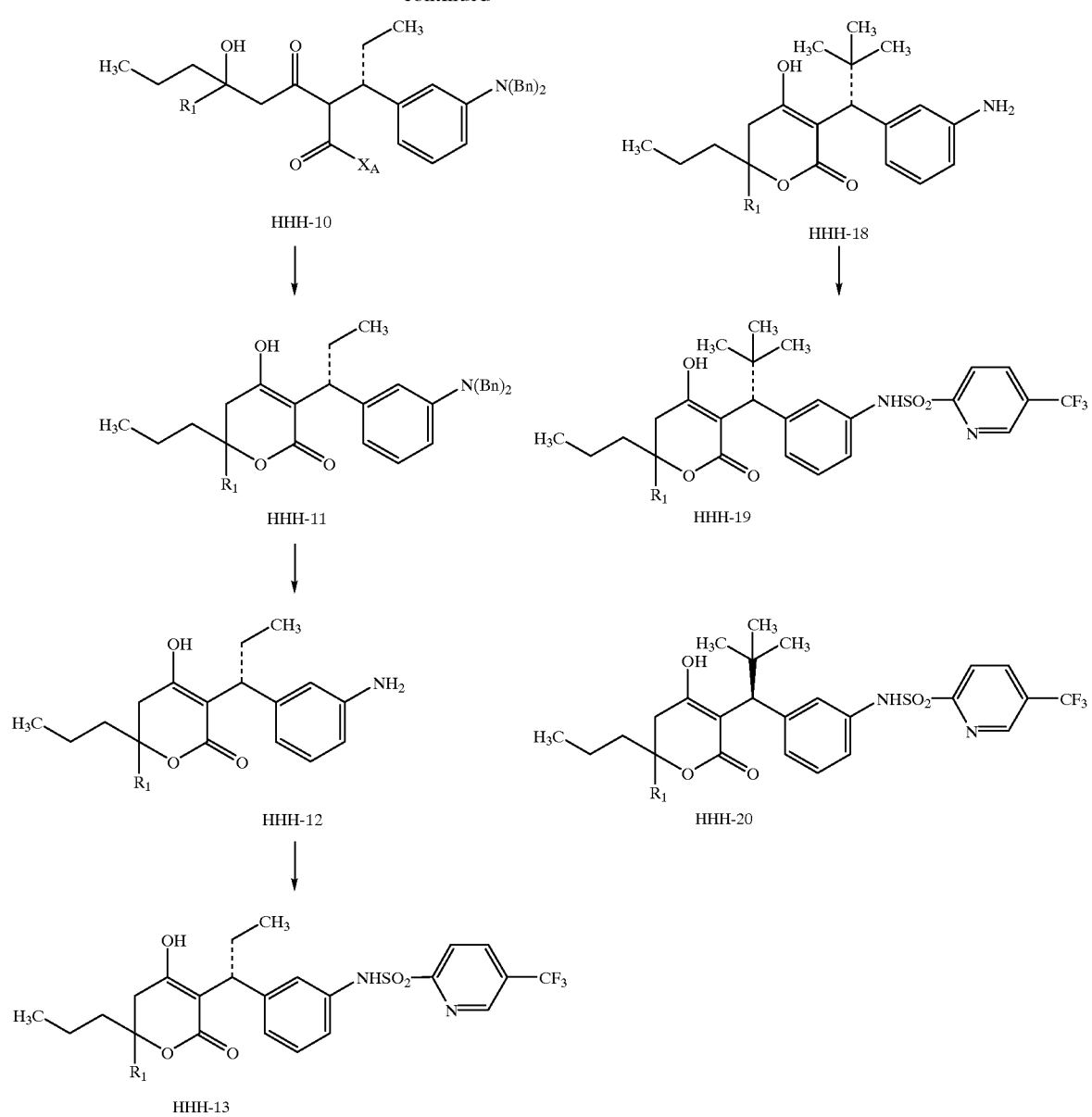
CHART III
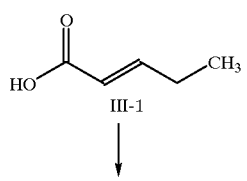
III-1

-continued
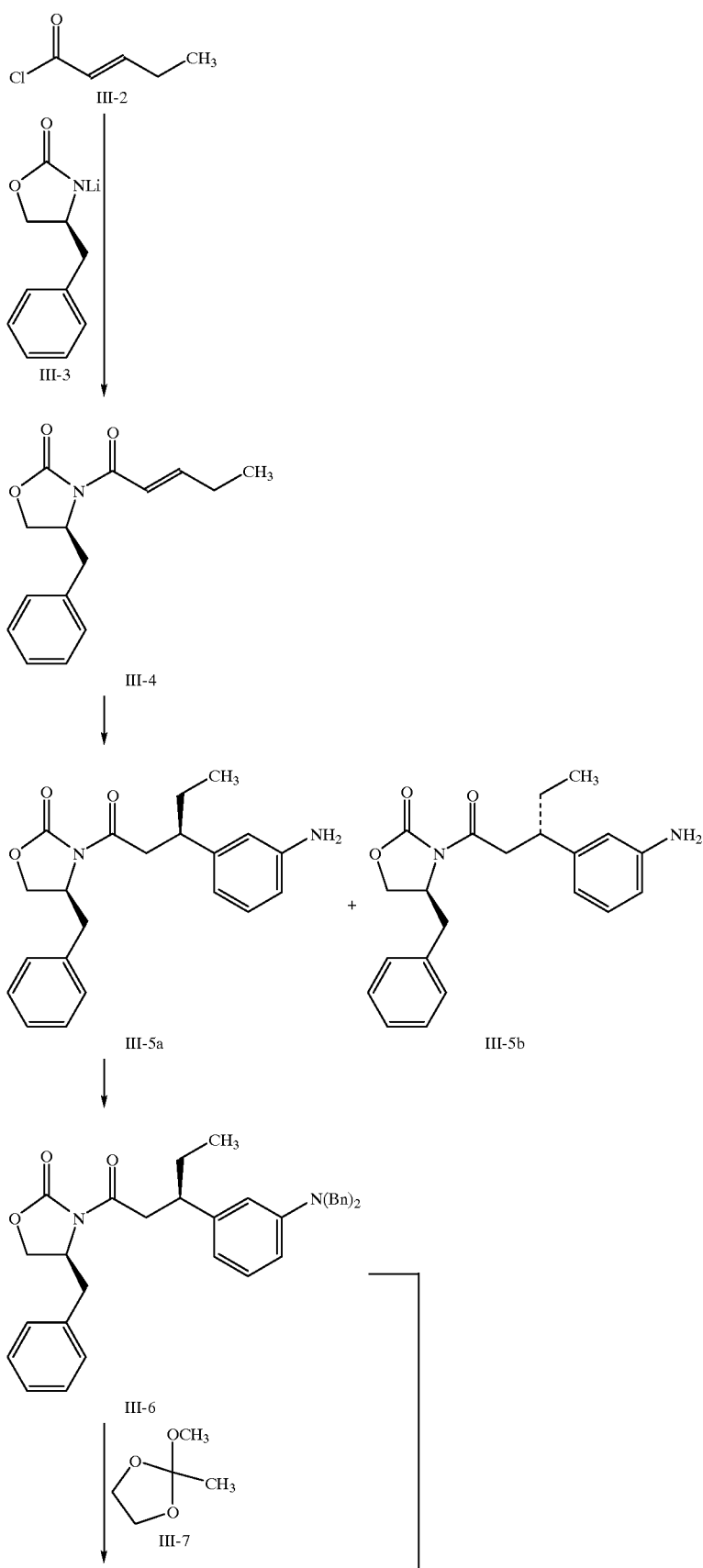

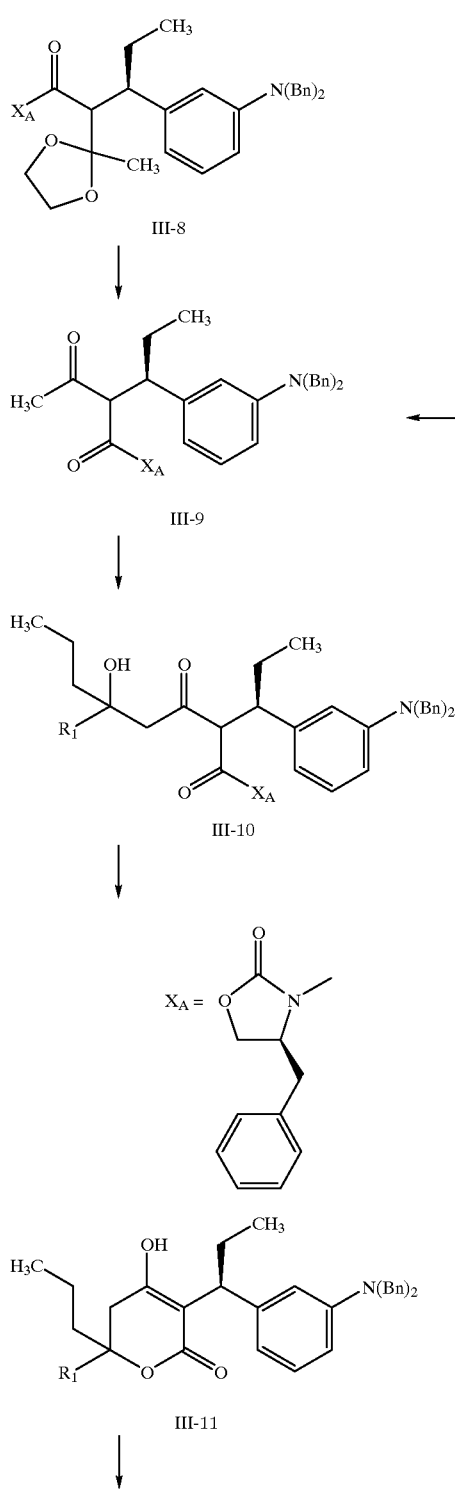

-continued
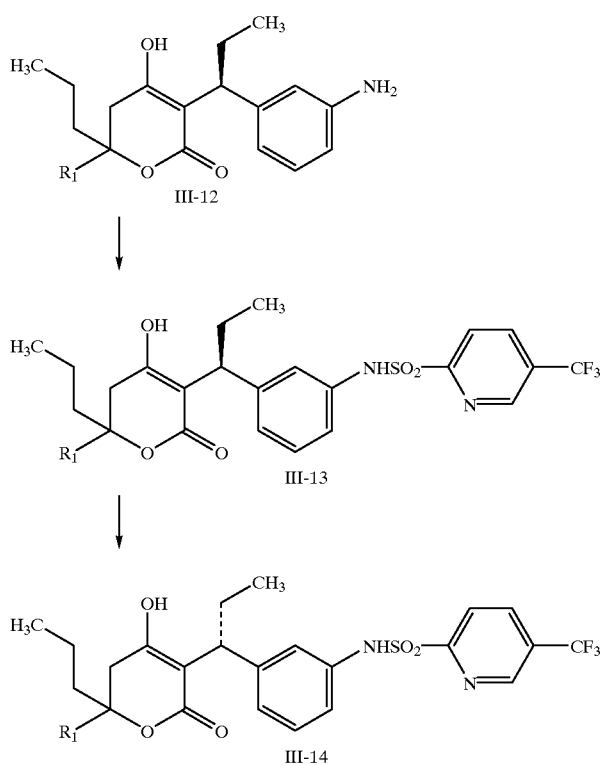
CHART JJJ
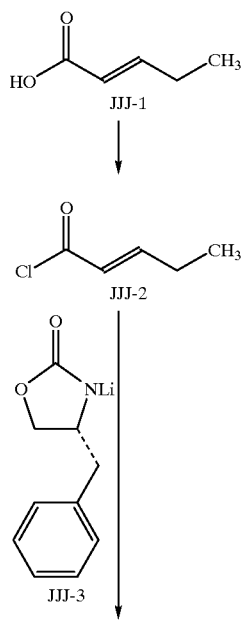

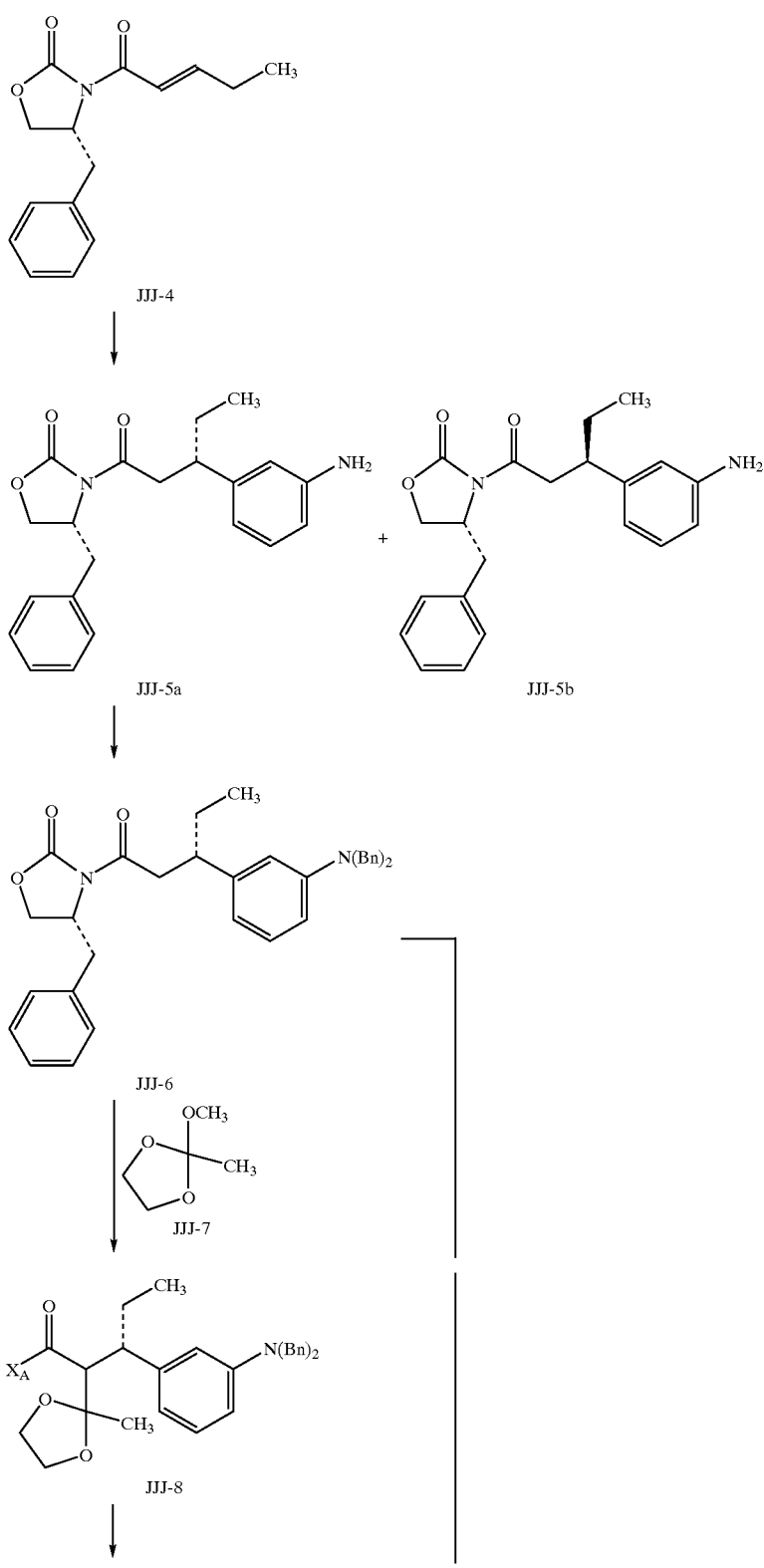

-continued
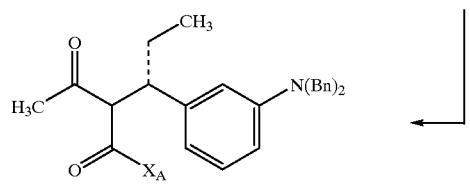
JJJ-9
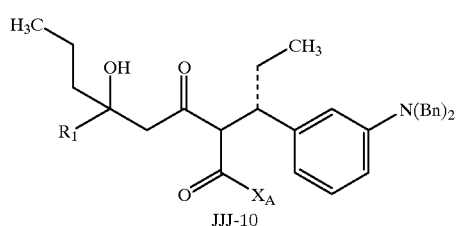
JJJ-10
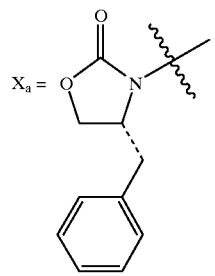
$X_a =$
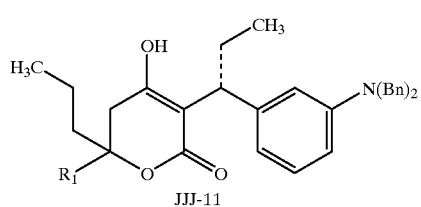
JJJ-11
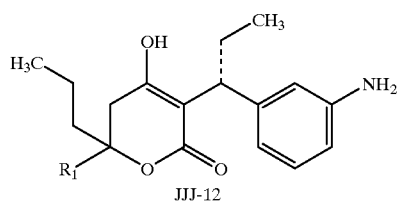
JJJ-12
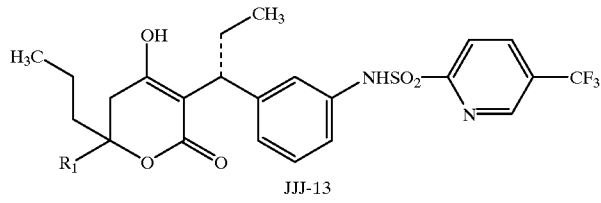
JJJ-13

-continued
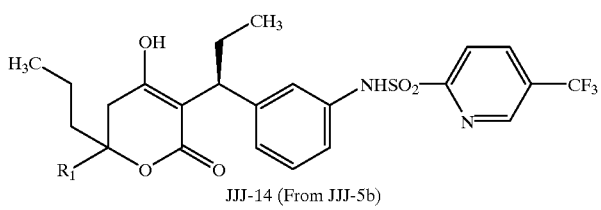
JJJ-14 (From JJJ-5b)
CHART KKK
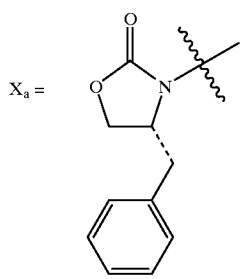
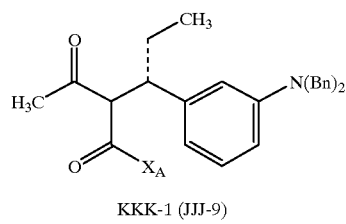
KKK-1 (JJJ-9)
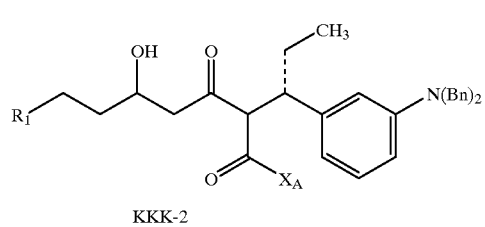
KKK-2
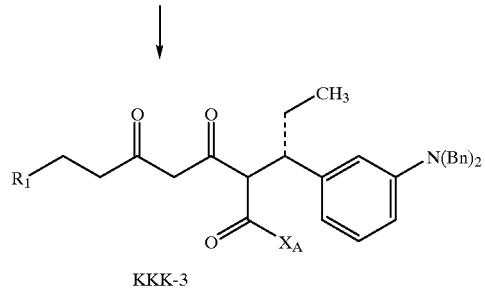
KKK-3
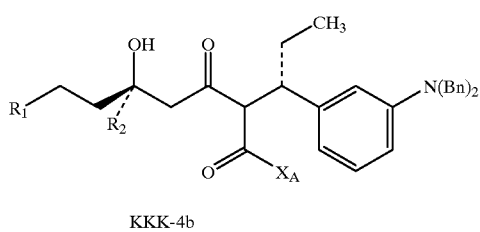
KKK-4b
+
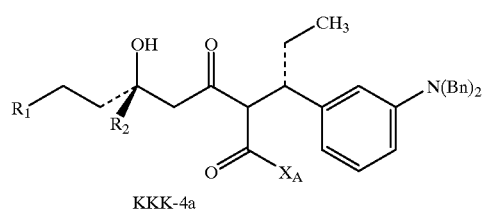
KKK-4a -continued
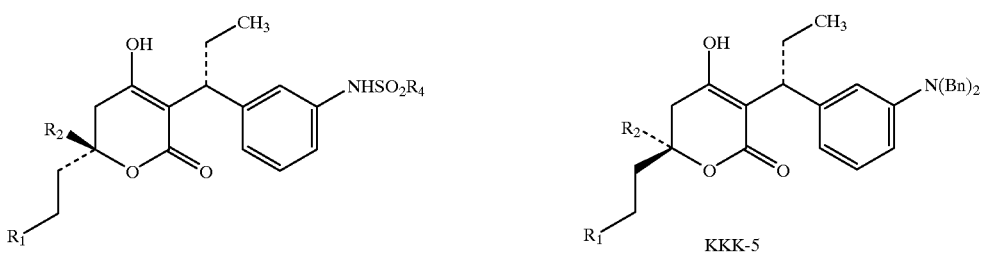
KKK-7b
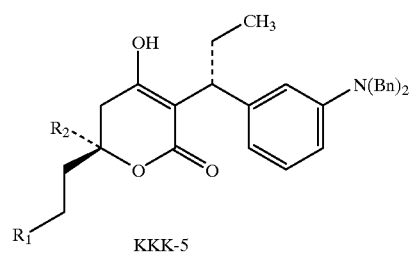
KKK-5
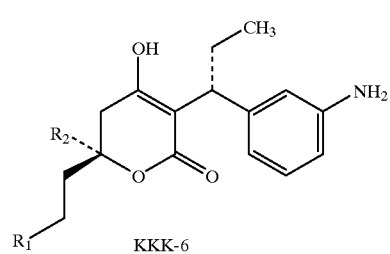
KKK-6
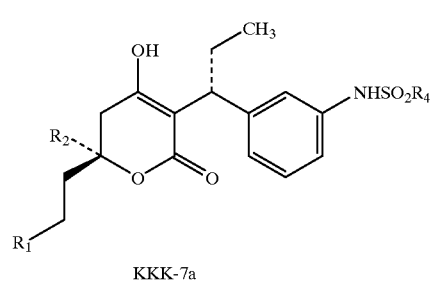
KKK-7a
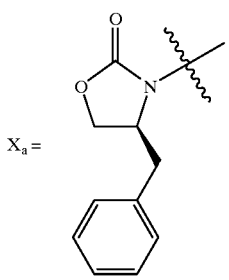
$X_a =$
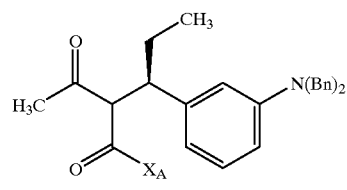
KKK-8 (III-6)
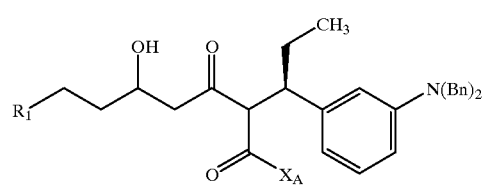
KKK-9

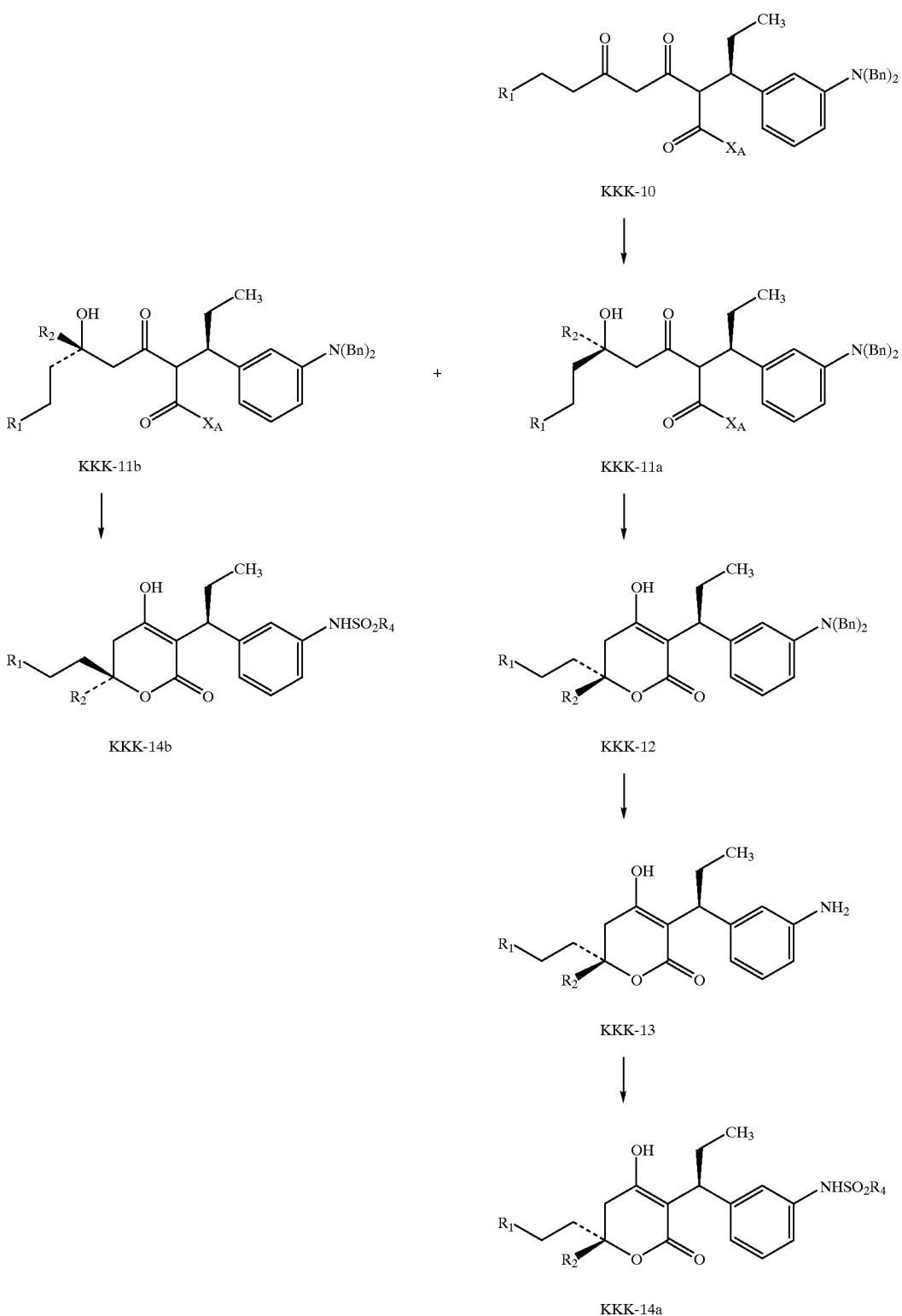

-continued
301
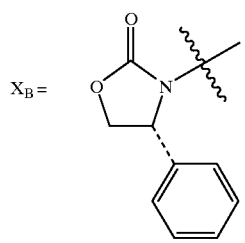
$X_B =$
302
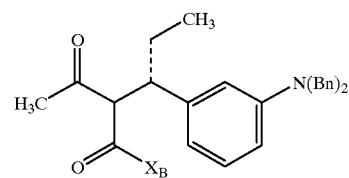
KKK-15 (X-6)
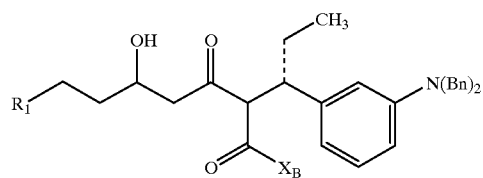
KKK-16
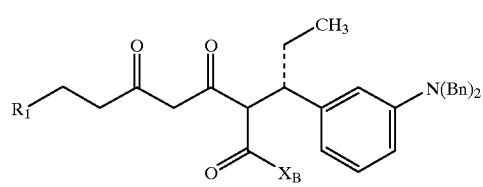
KKK-17
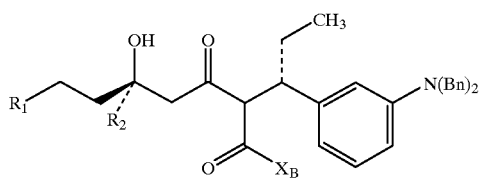
KKK-18b
+
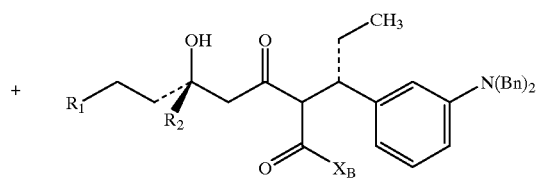
KKK-18a
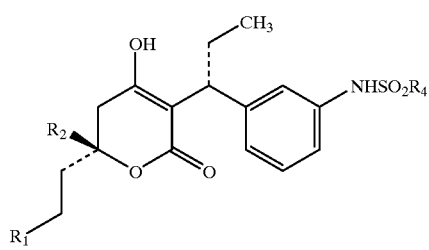
KKK-7b
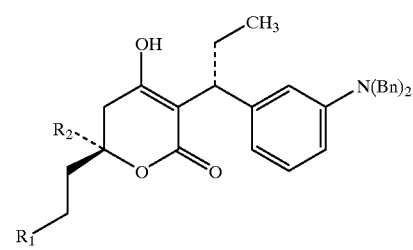
KKK-5

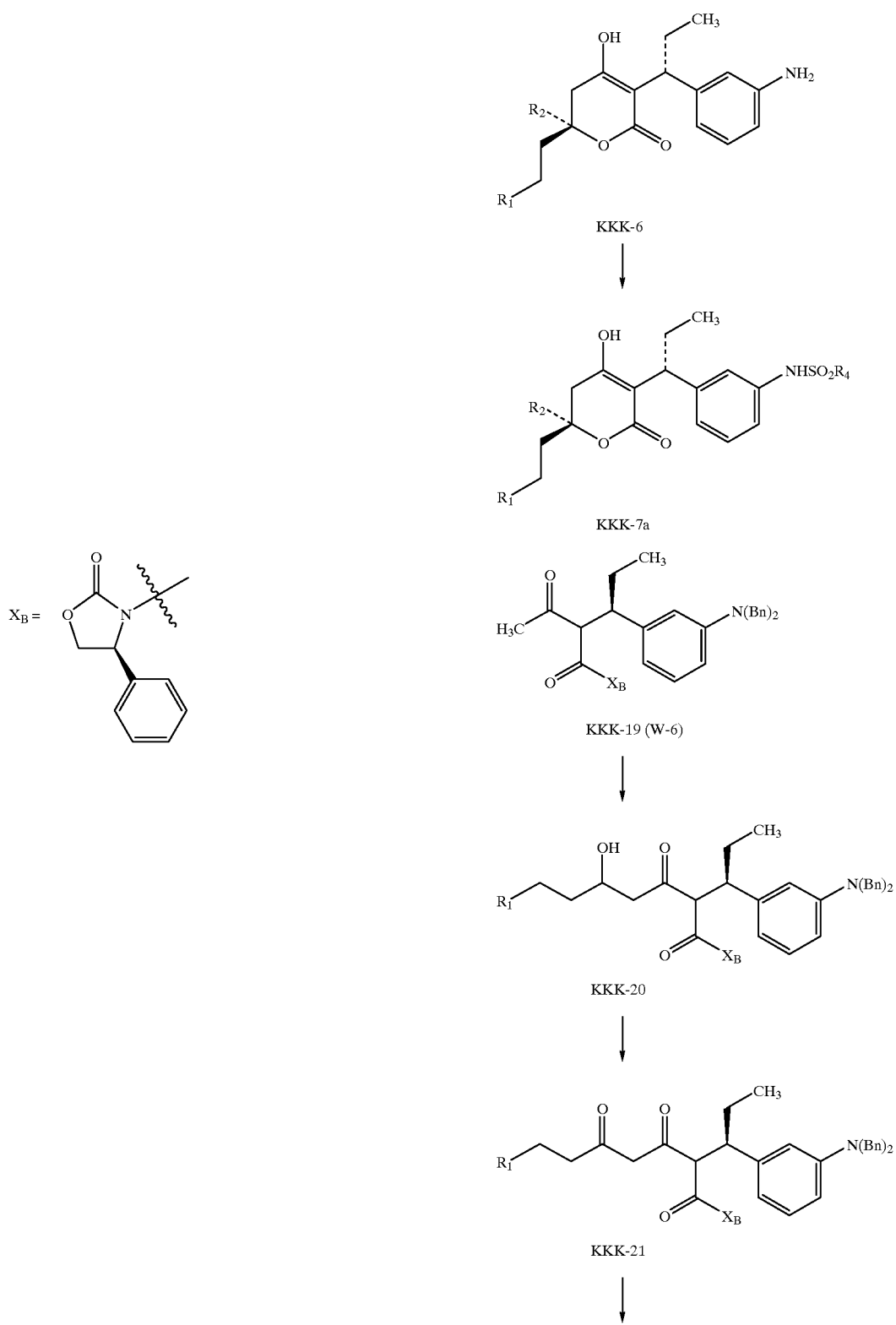

305 306
-continued
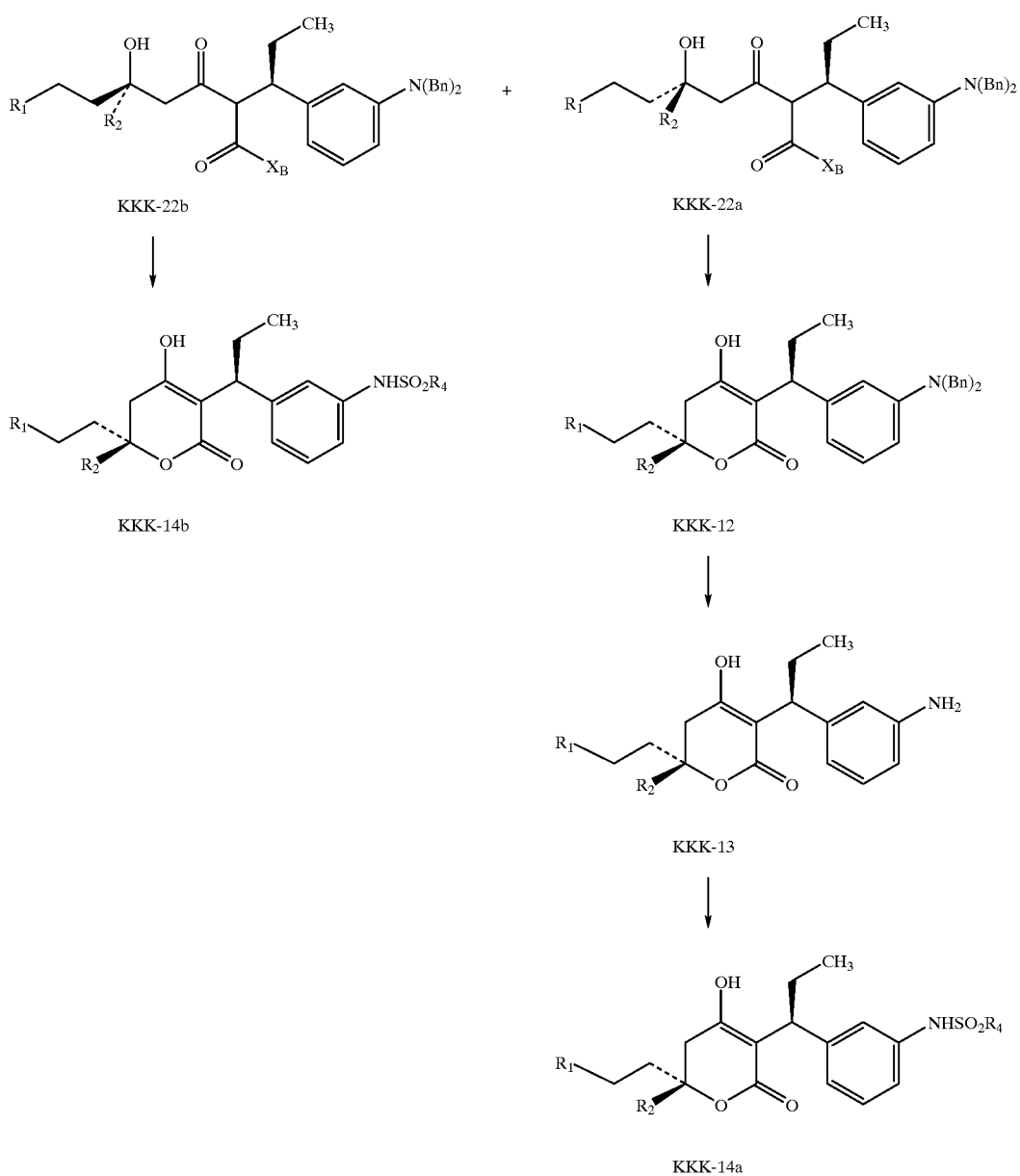
CHART LLL
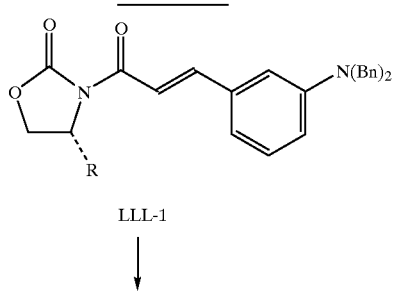

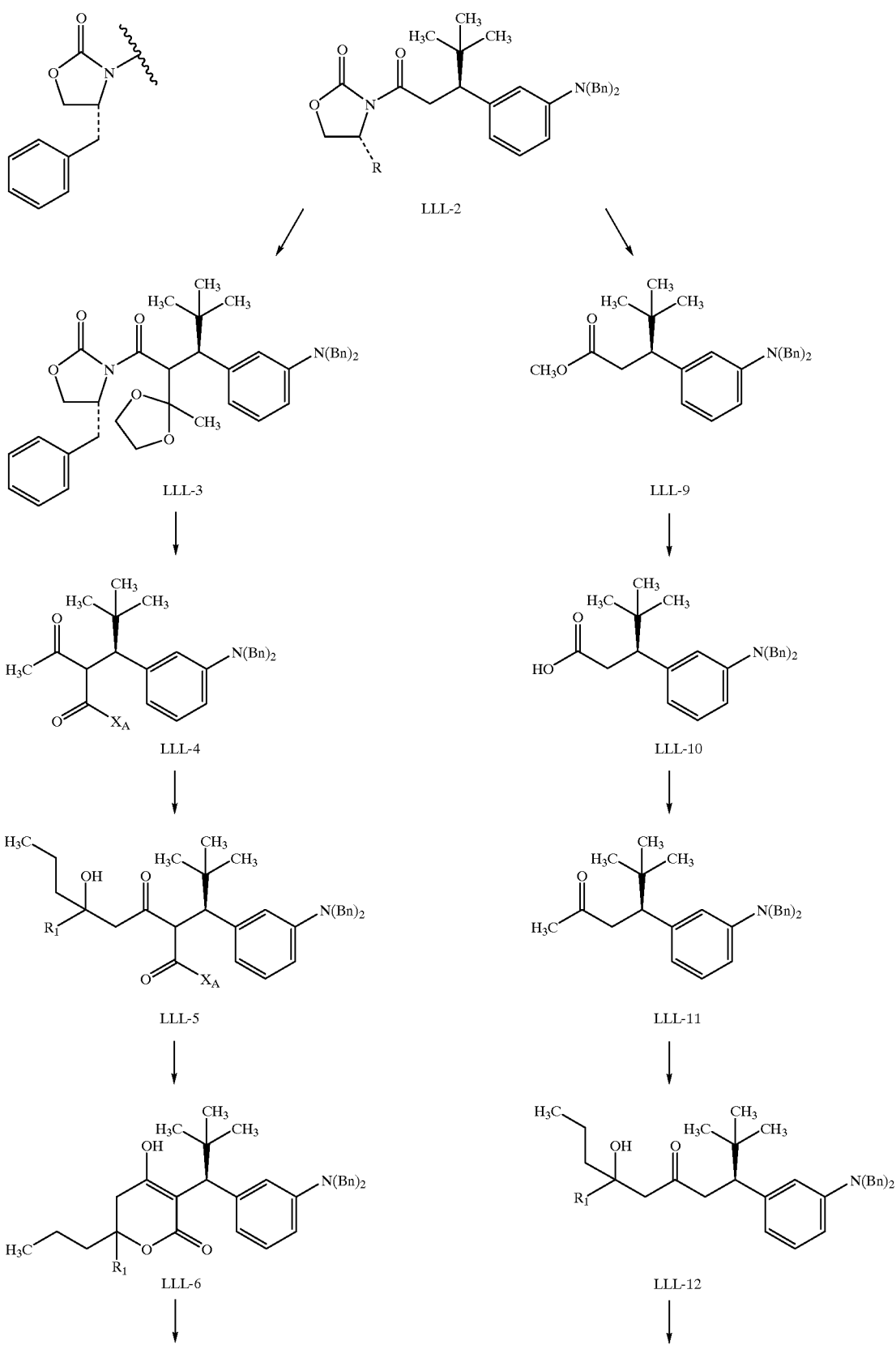

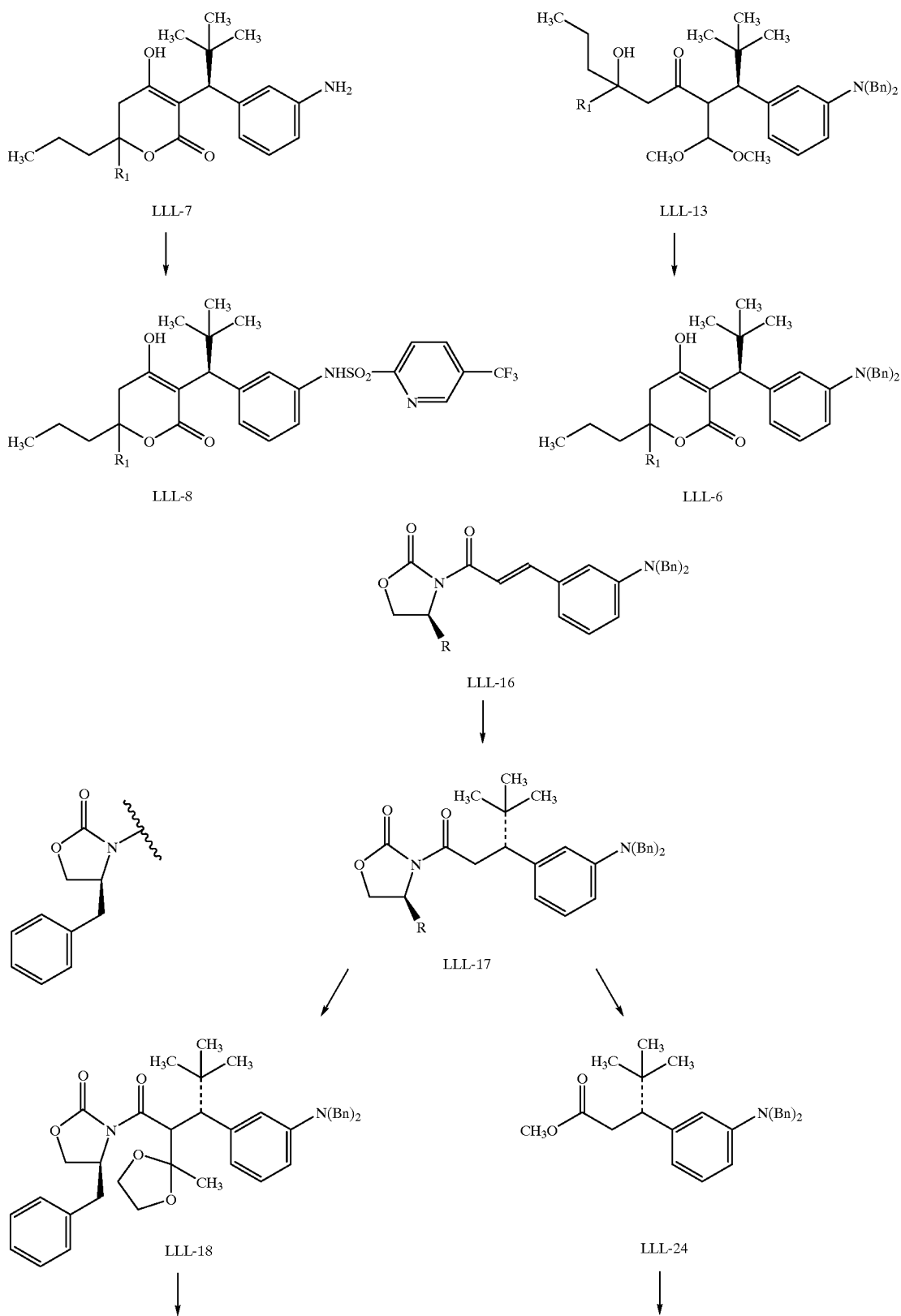

311
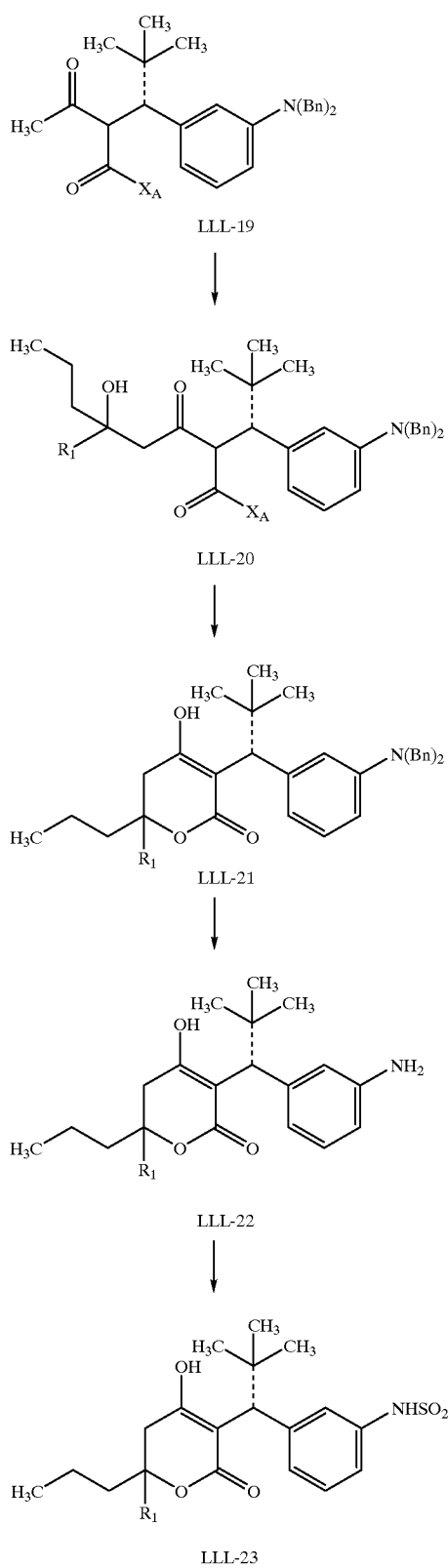
312
-continued
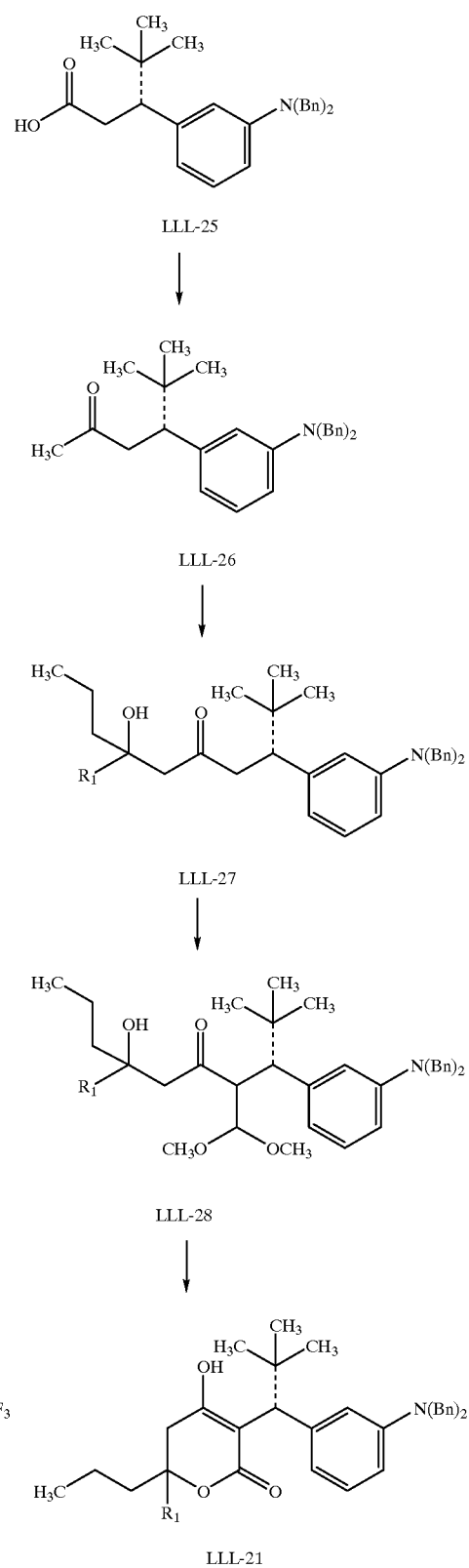

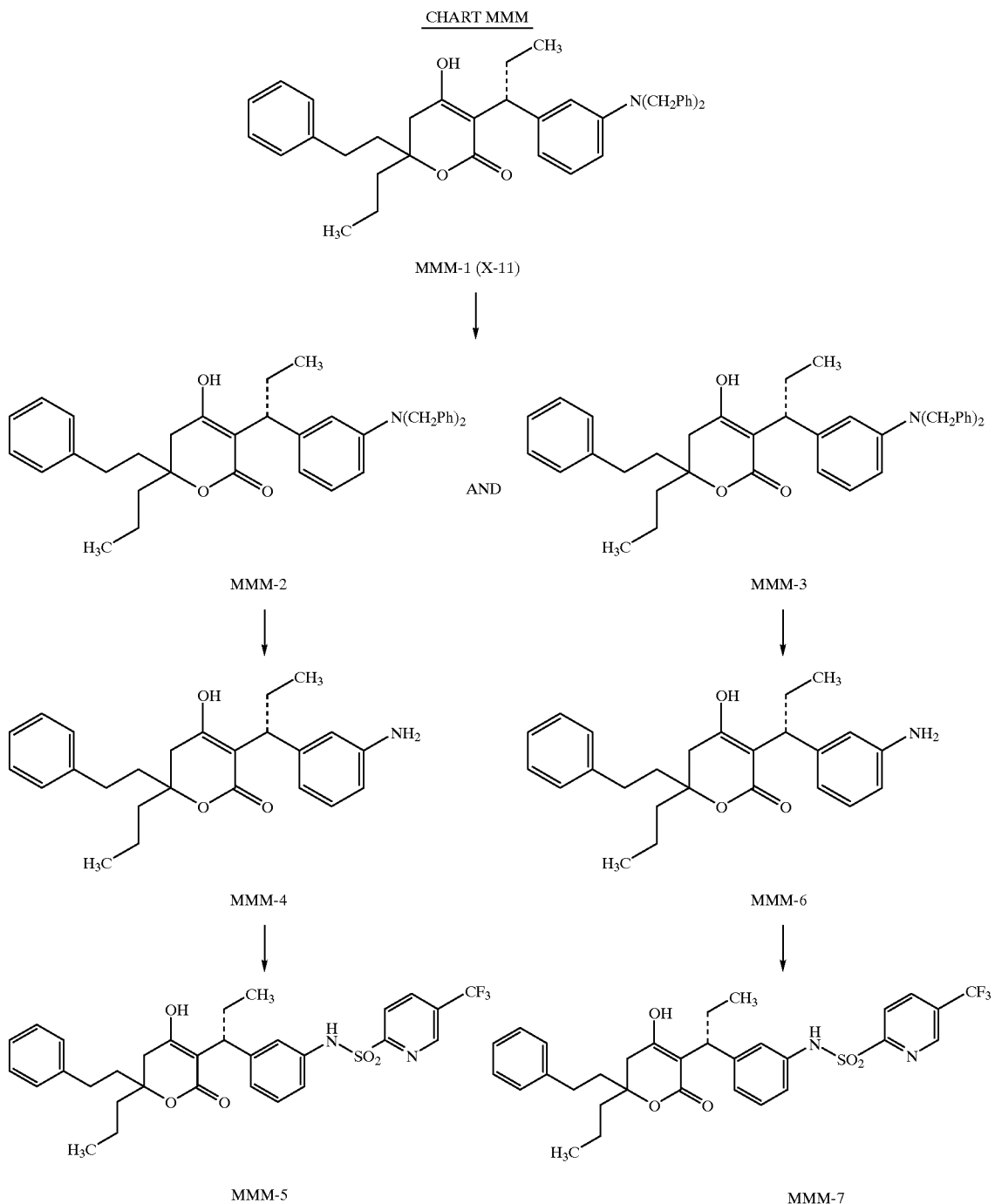
CHART MMM

315
CHART NNN
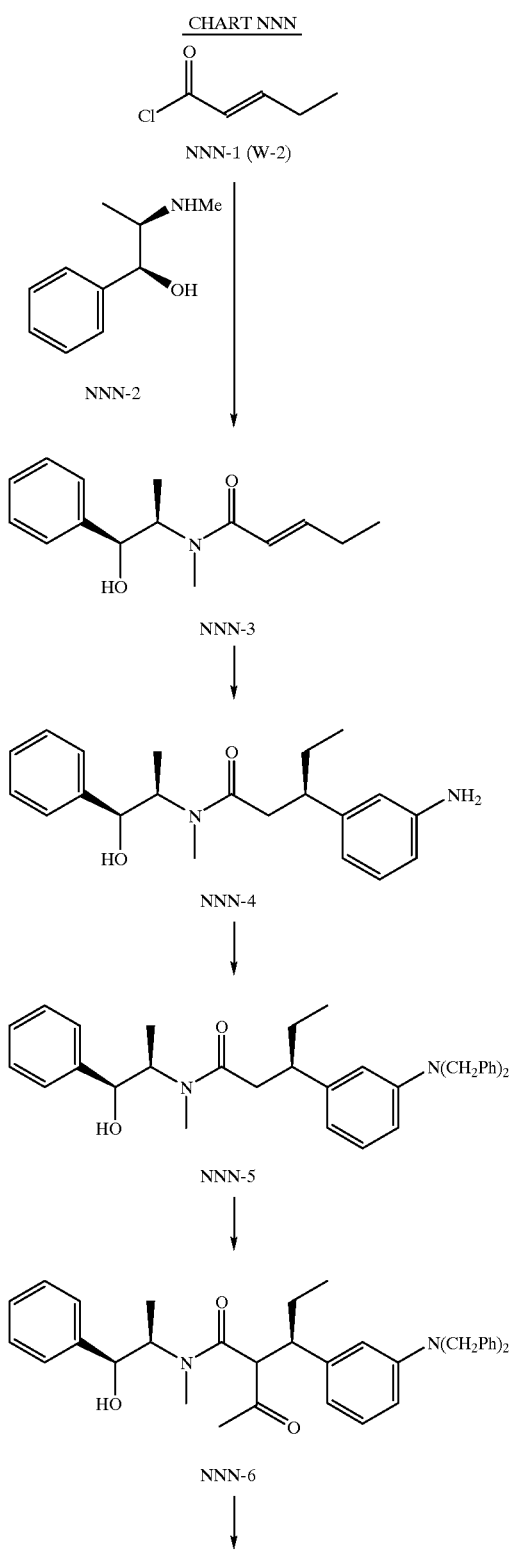
316
-continued
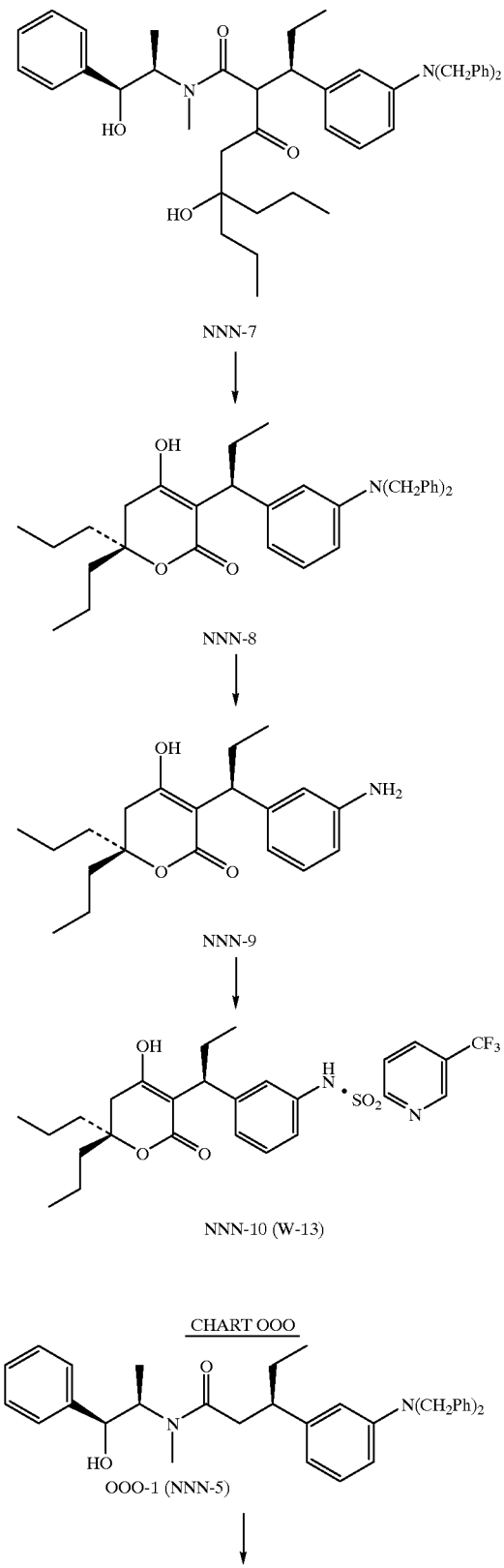

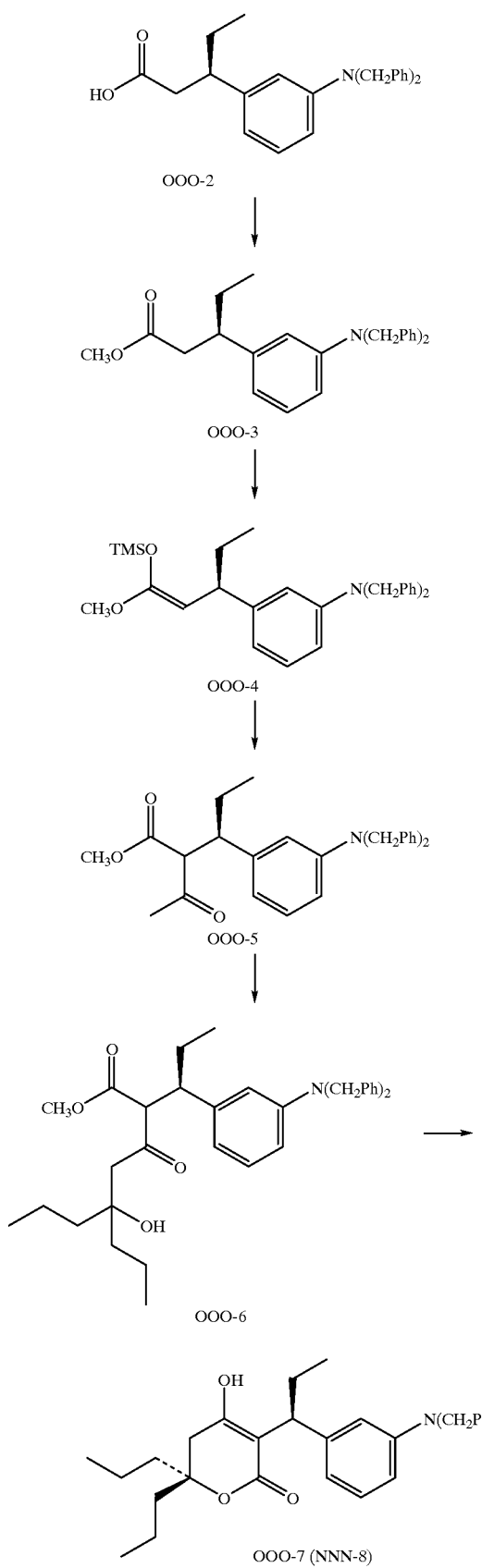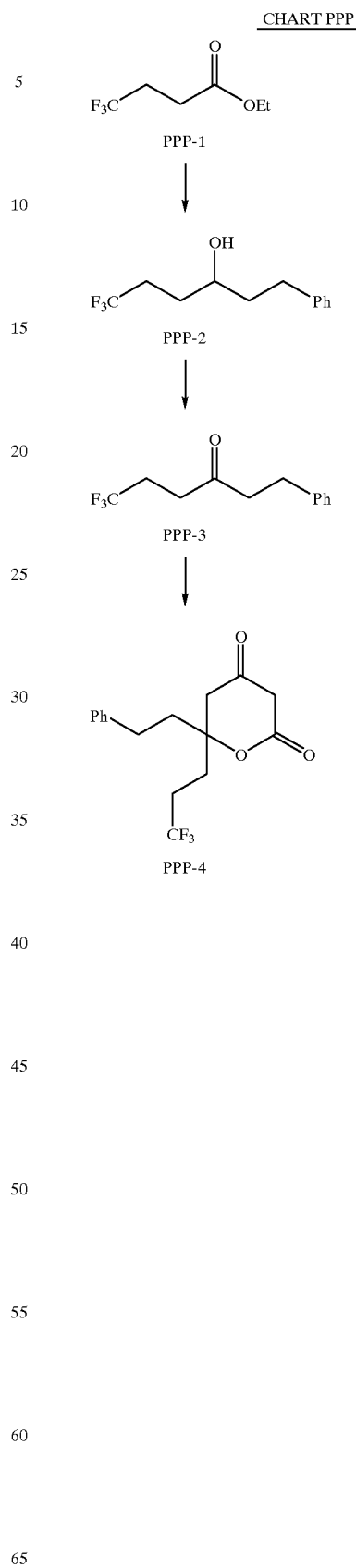
CHART PPP

CHART QQQ
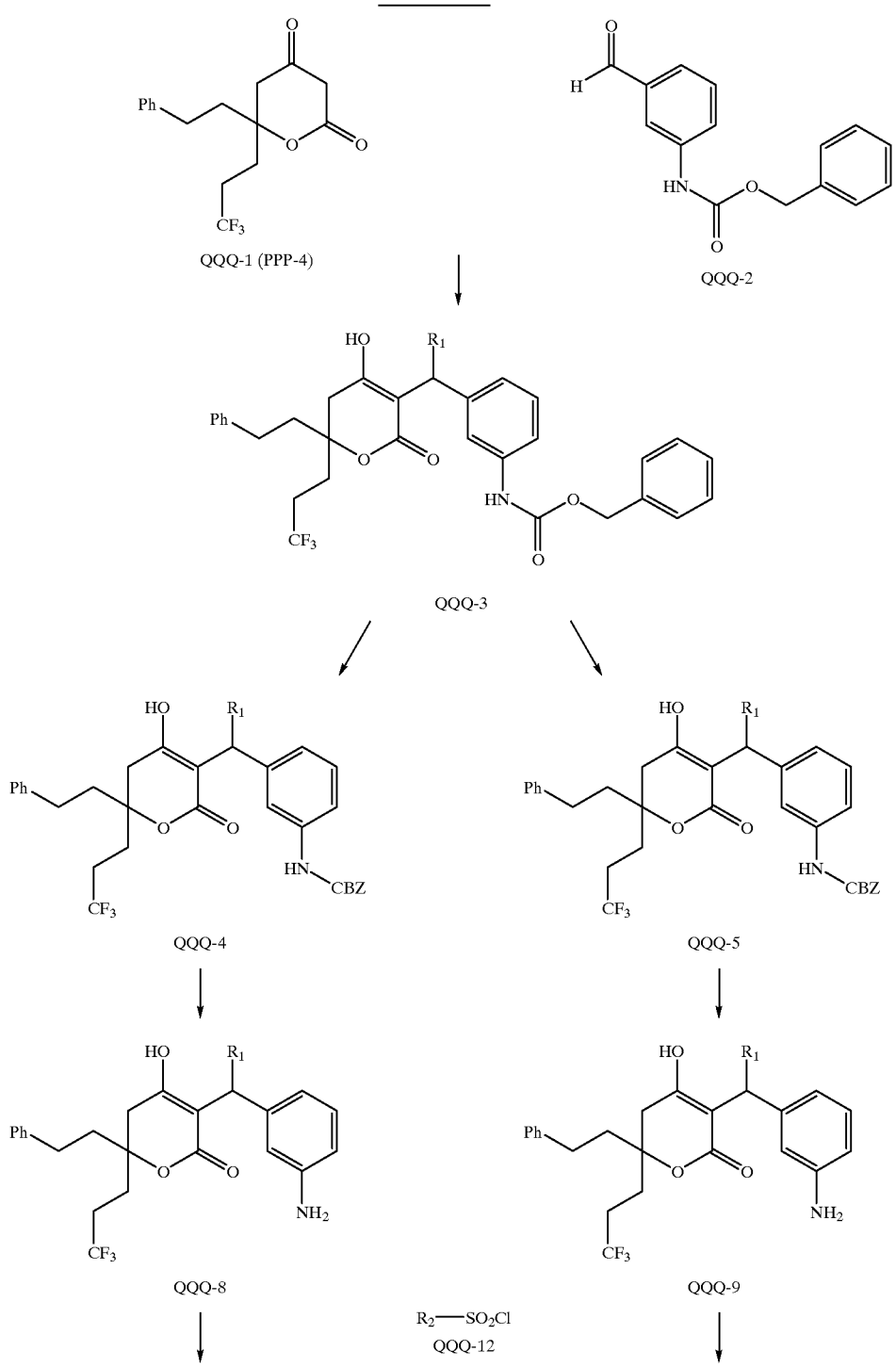

321                                              322
-continued
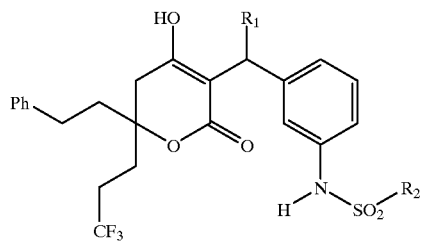
QQQ-13
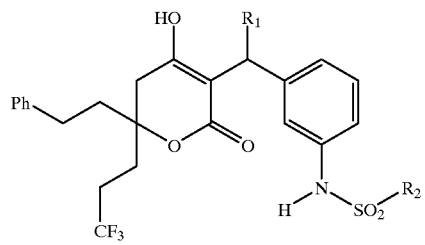
QQQ-14
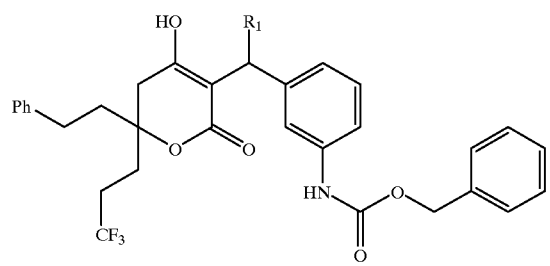
QQQ-3
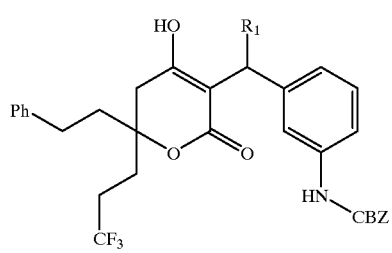
QQQ-6
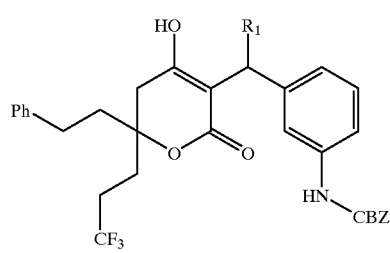
QQQ-7
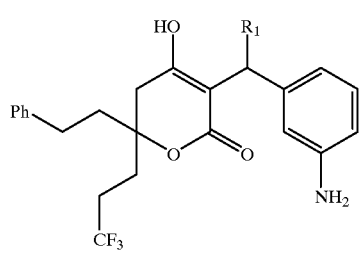
QQQ-10
R₂—SO₂Cl
QQQ-12
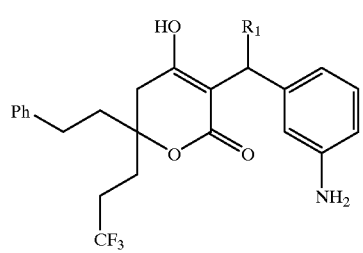
QQQ-11
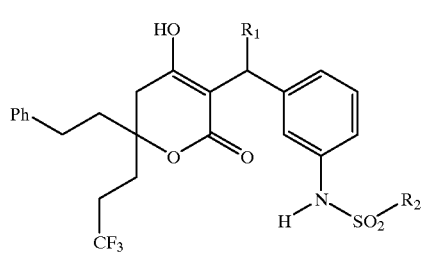
QQQ-15
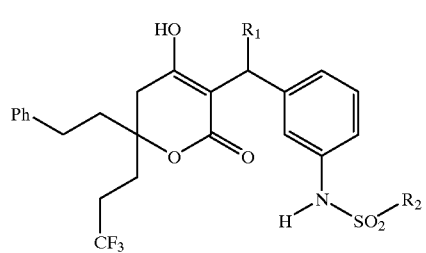
QQQ-16

CHART RRR
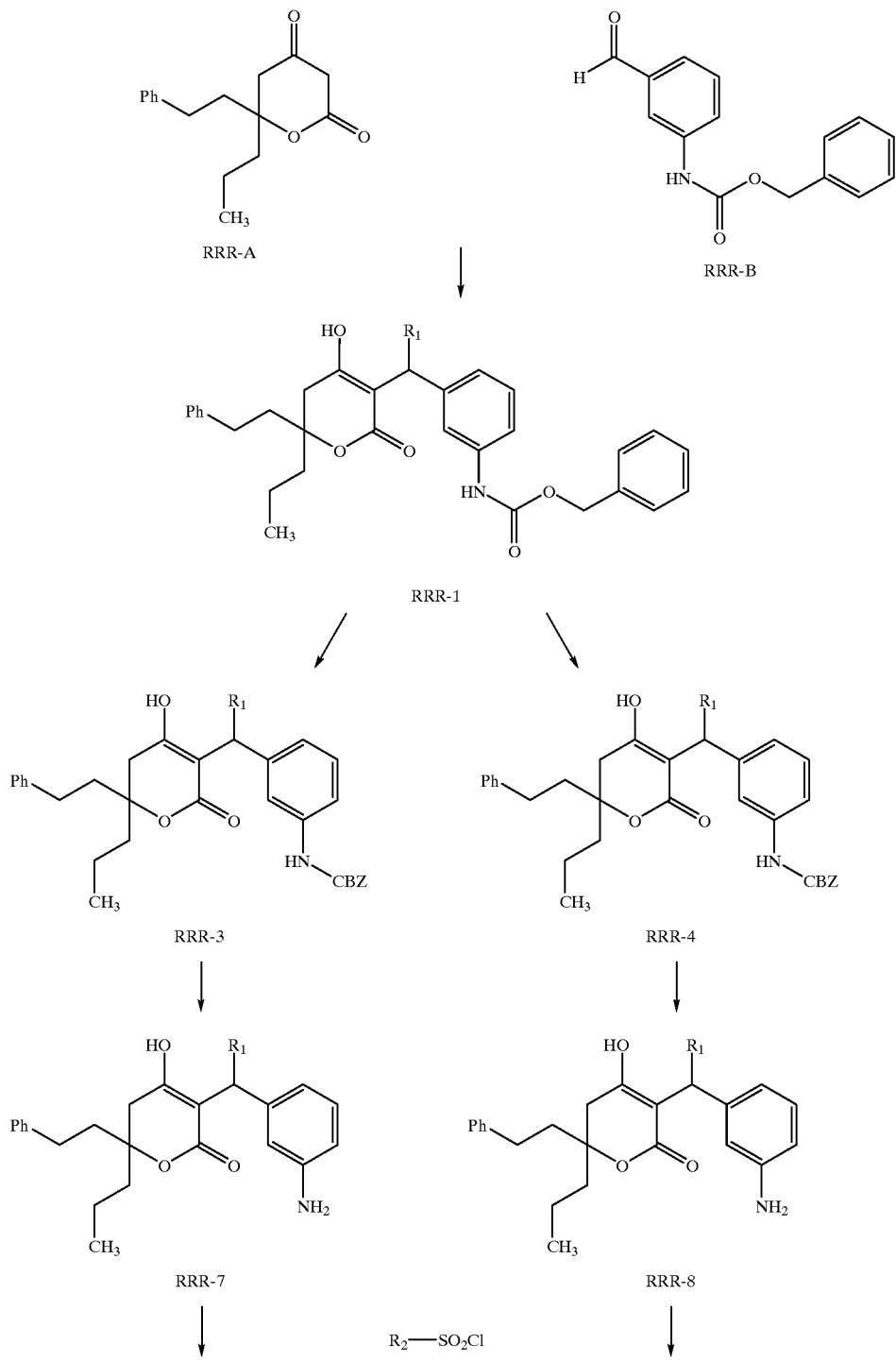

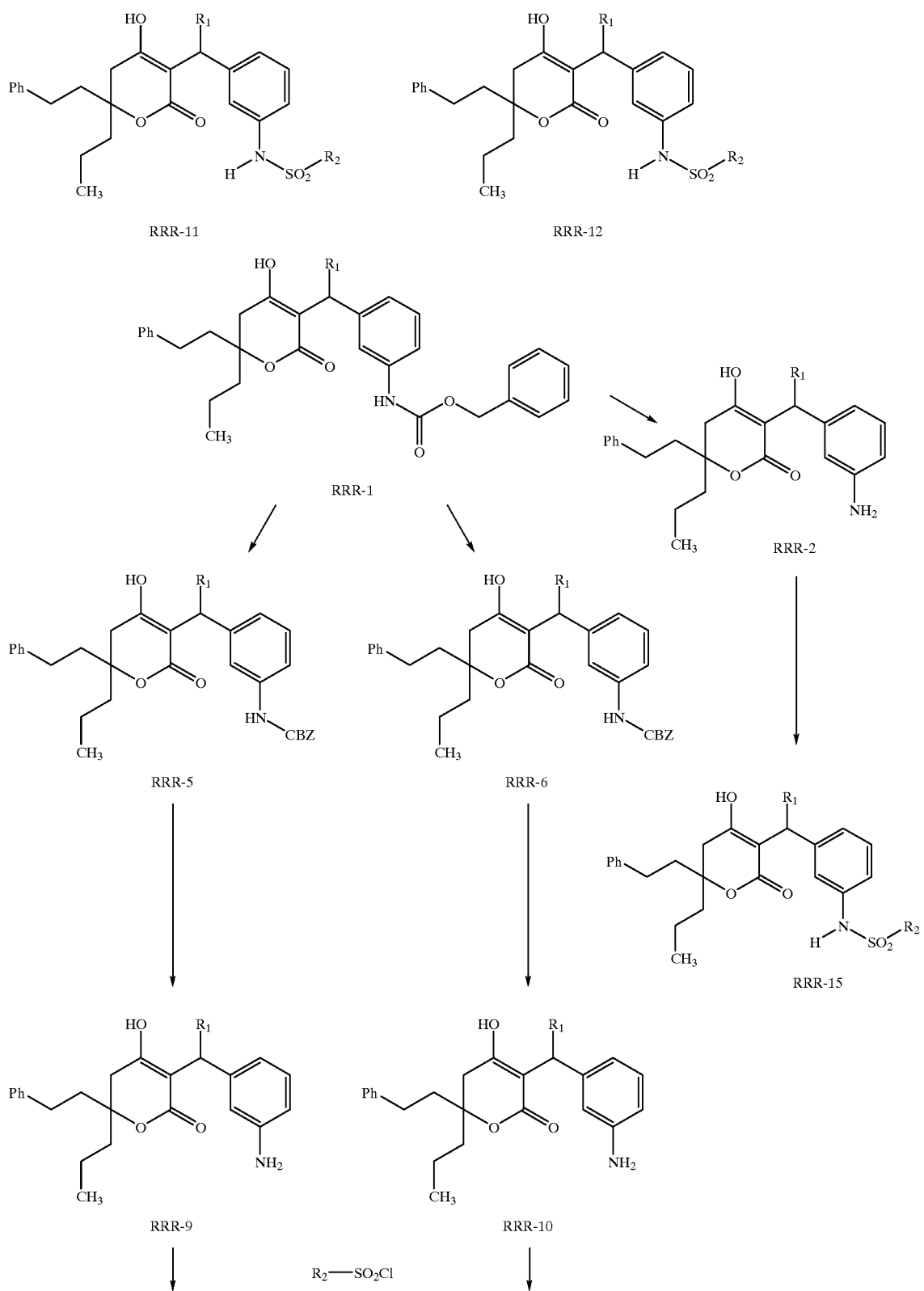

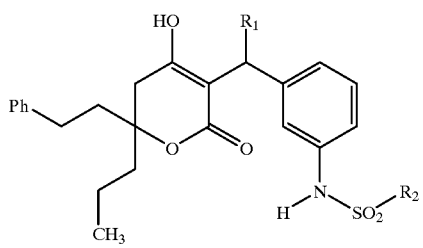
RRR-13
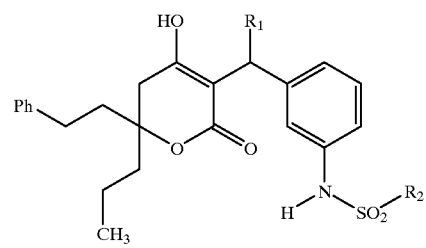
RRR-14
CHART SSS
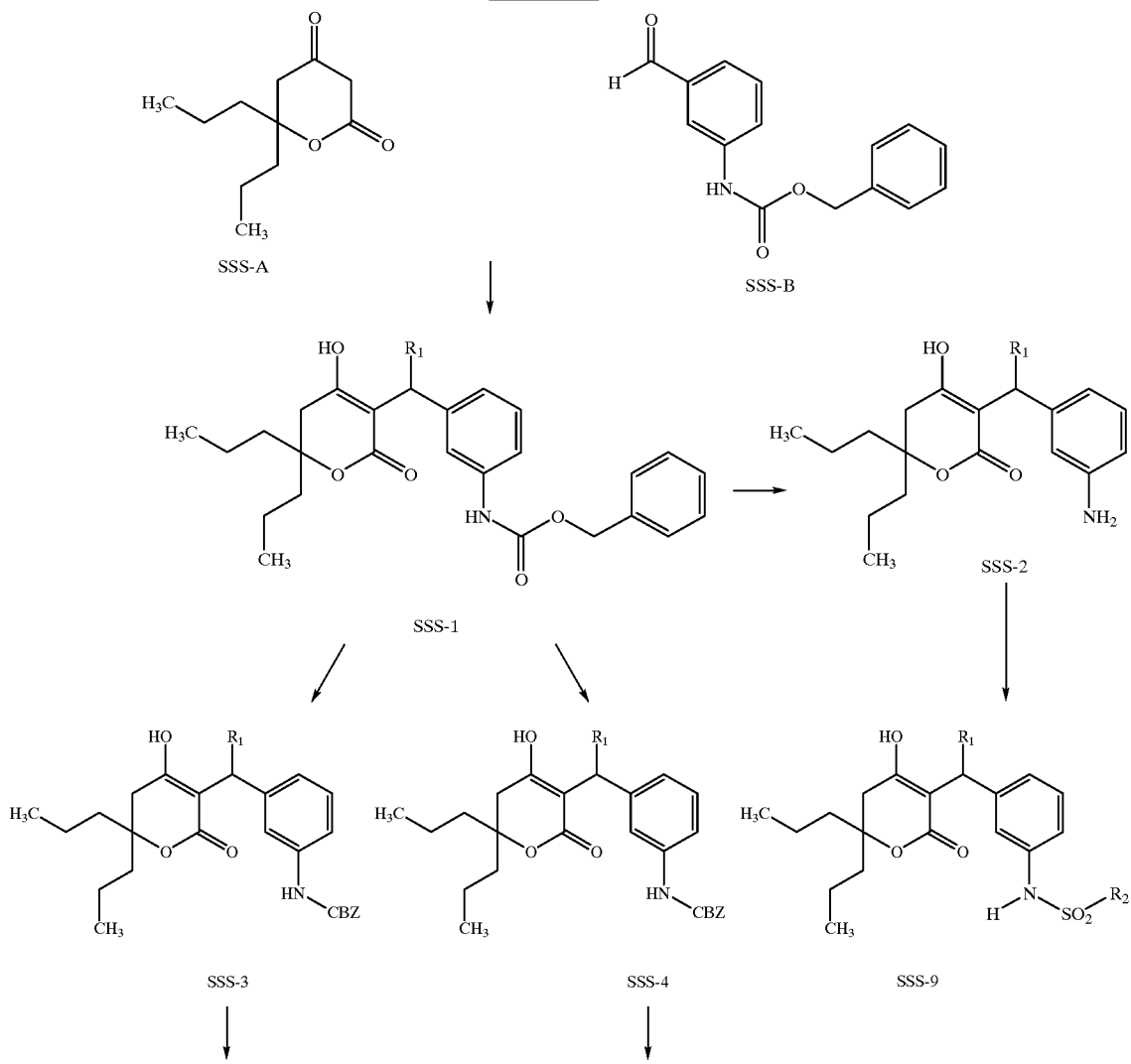

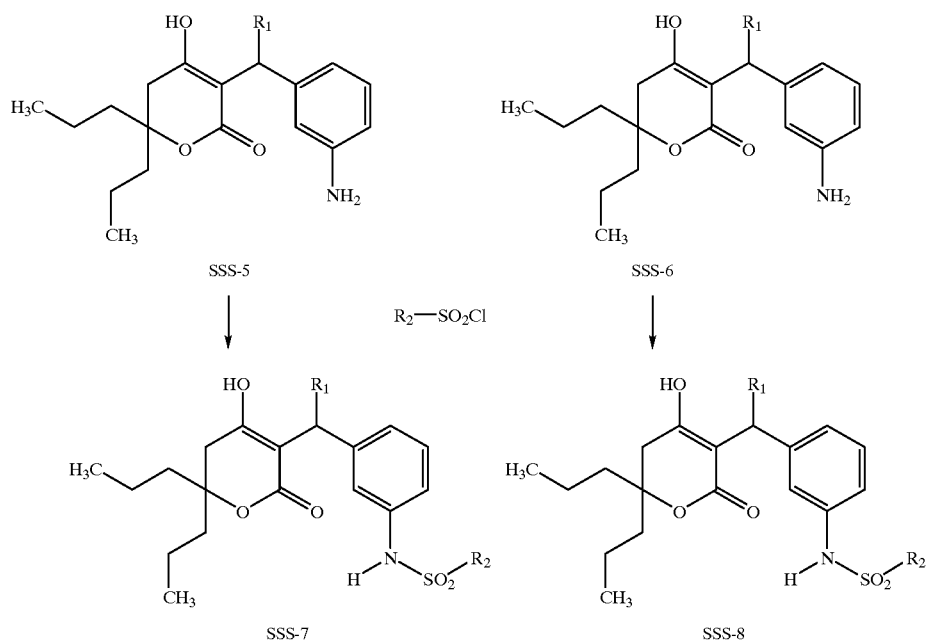
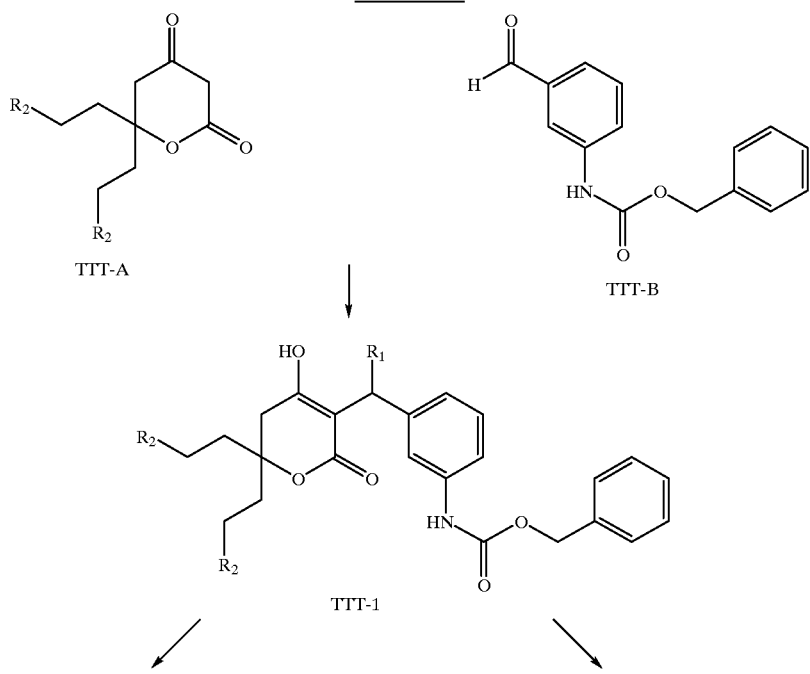
CHART TTT

331
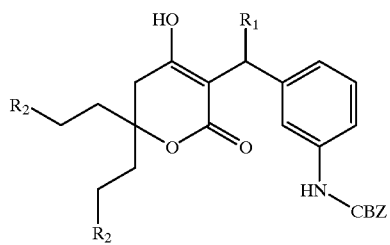
TTT-2 ↓
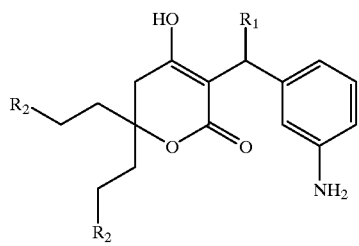
TTT-4 ↓
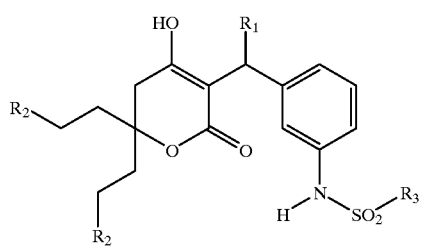
332
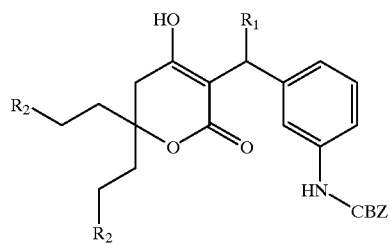
TTT-3 ↓
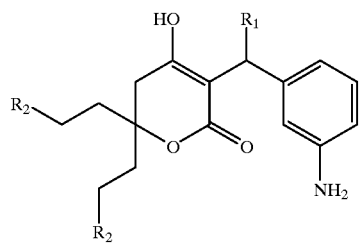
$R_3$—$SO_2Cl$
TTT-5 ↓
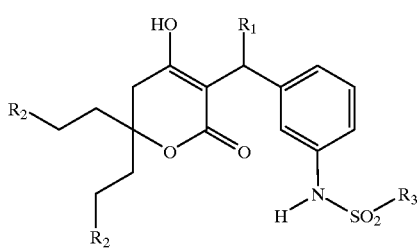
CHART UUU
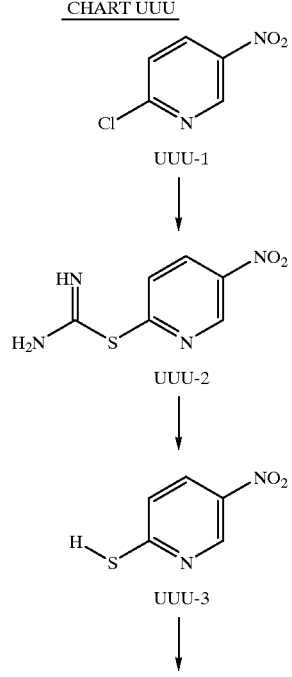
-continued
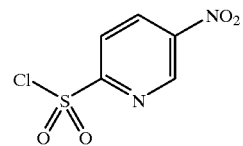
UUU-4 ↓
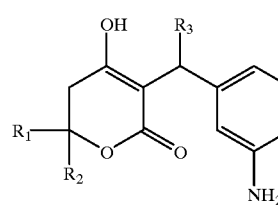
D-5

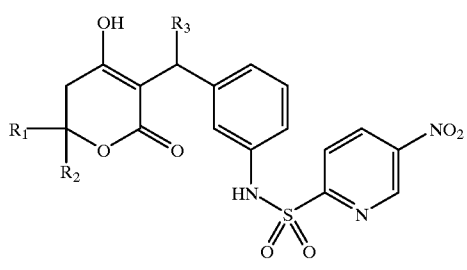
UUU-5
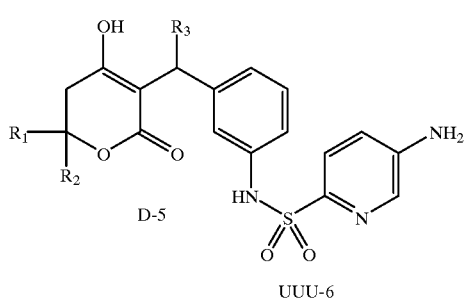
D-5  UUU-6
CHART VVV
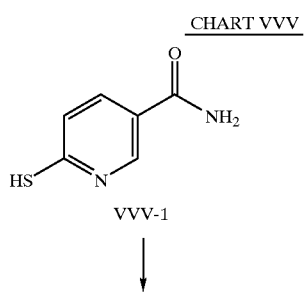
VVV-1
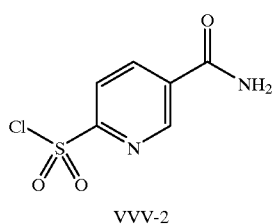
VVV-2
CHART WWW
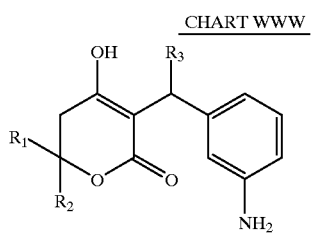
WWW-1
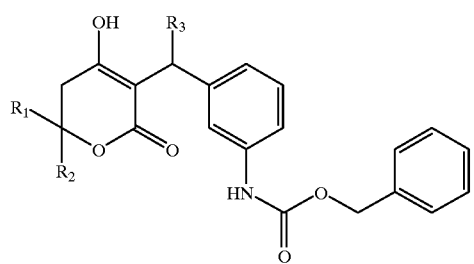
WWW-2
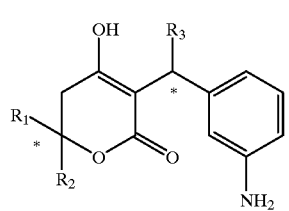
WWW-3
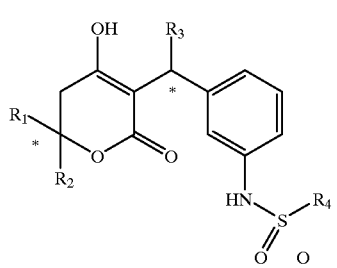
WWW-4
CHART XXX
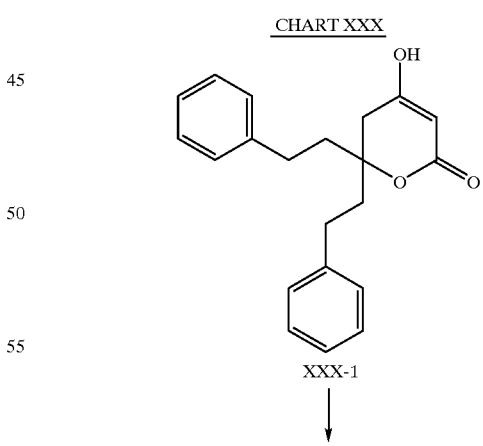
XXX-1

335
-continued
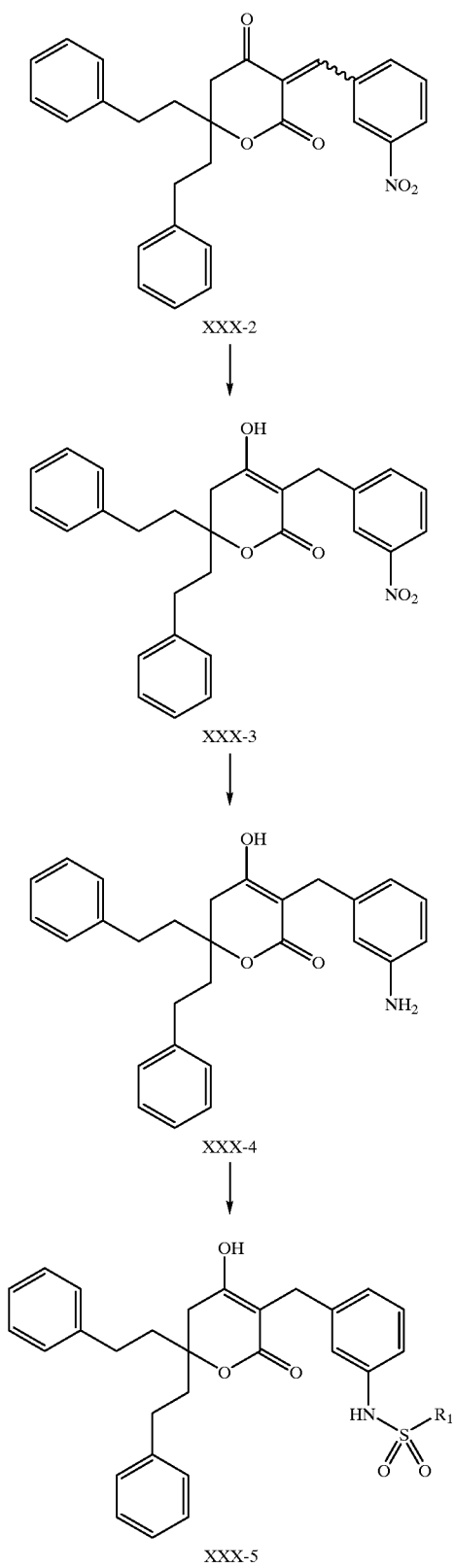
336
CHART YYY
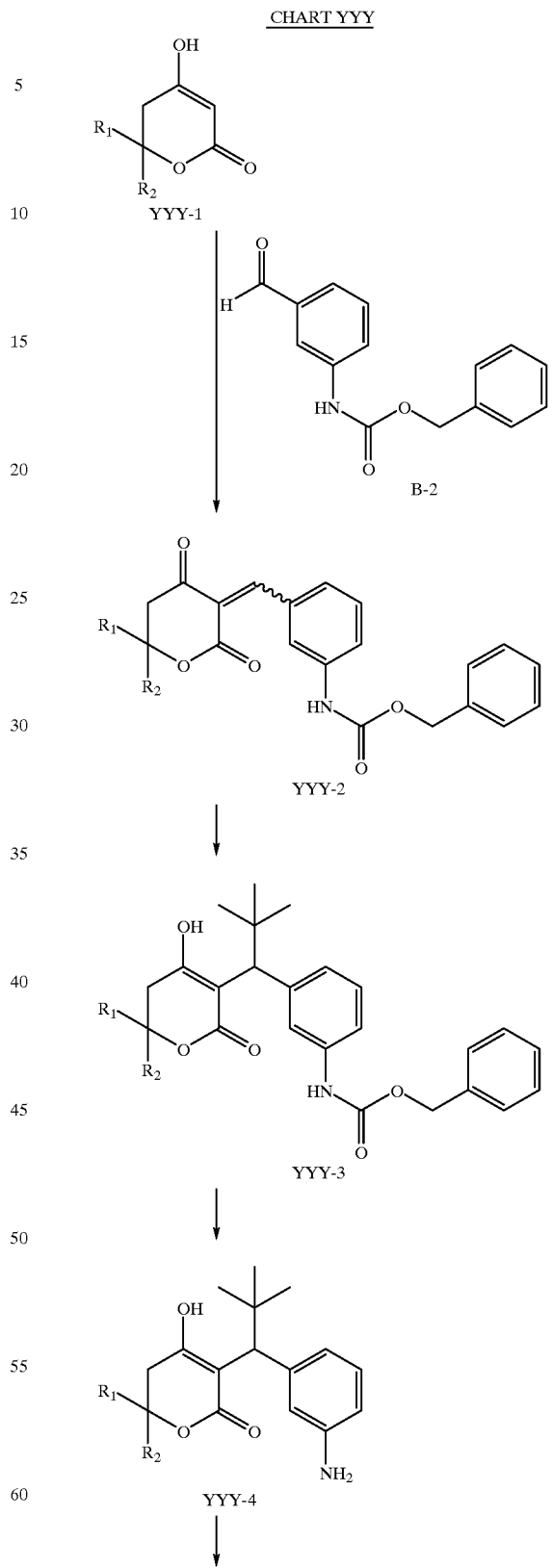

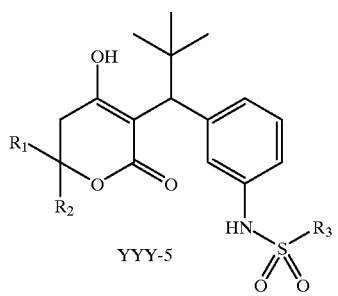
YYY-5
CHART ZZZ
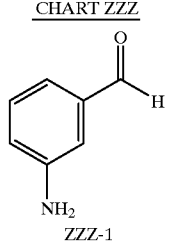
ZZZ-1
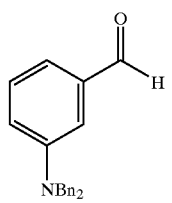
ZZZ-2
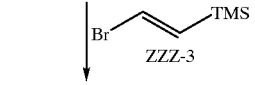
ZZZ-3
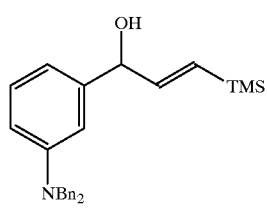
ZZZ-4
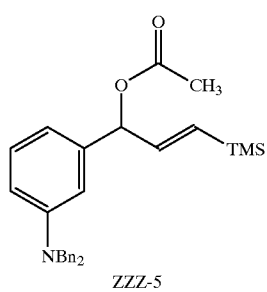
ZZZ-5
CHART AAAA
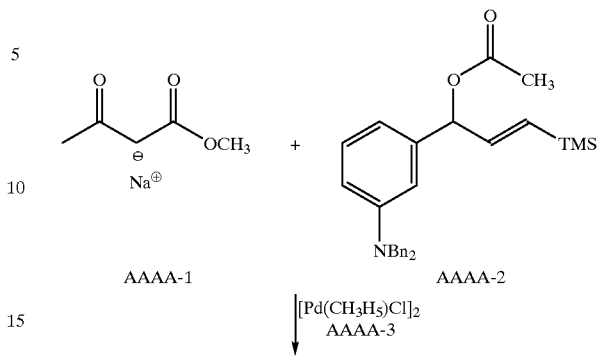
AAAA-1    AAAA-2
[Pd(CH₃H₅)Cl]₂
AAAA-3
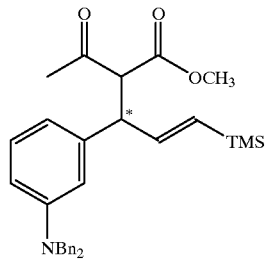
AAAA-4
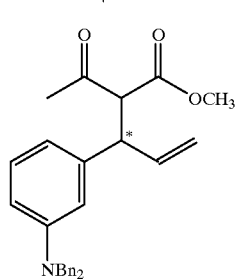
AAAA-5
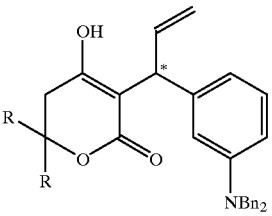
AAAA-6
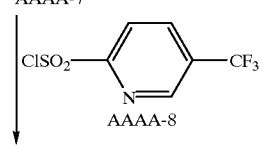
AAAA-7
AAAA-8

CHART BBBB
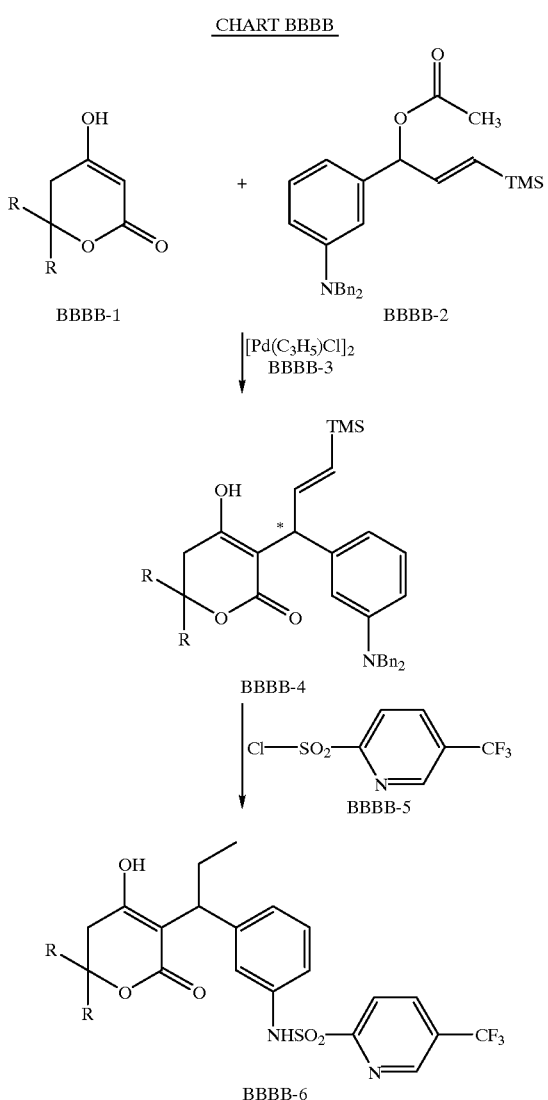
CHART CCCC
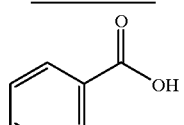
CCCC-1
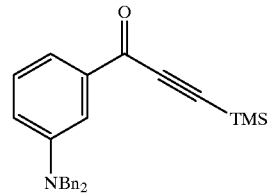
CCCC-2
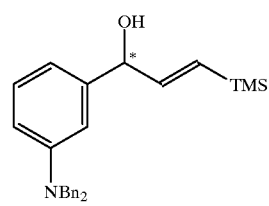
CCCC-3
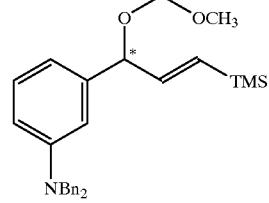
CCCC-4
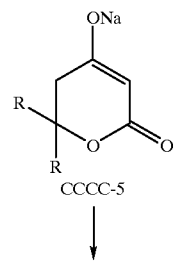
CCCC-5

341
-continued
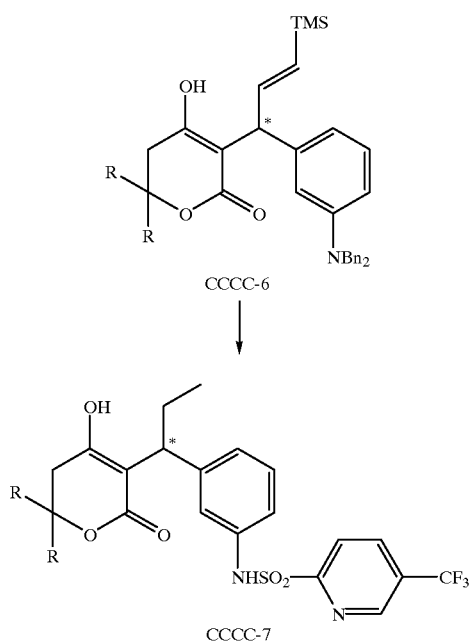
CCCC-6
CCCC-7
CHART DDDD
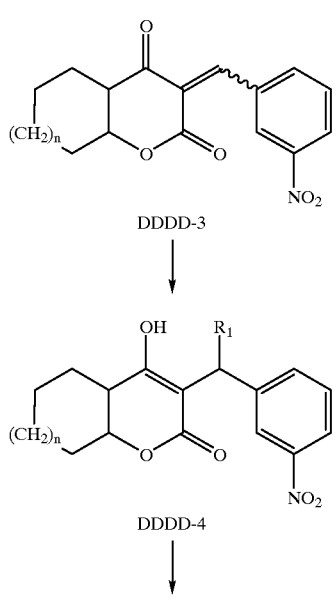
DDDD-2
DDDD-3
DDDD-4
342
-continued
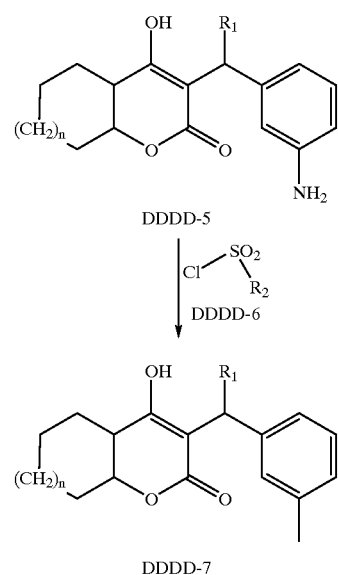
DDDD-5
DDDD-7
CHART EEEE
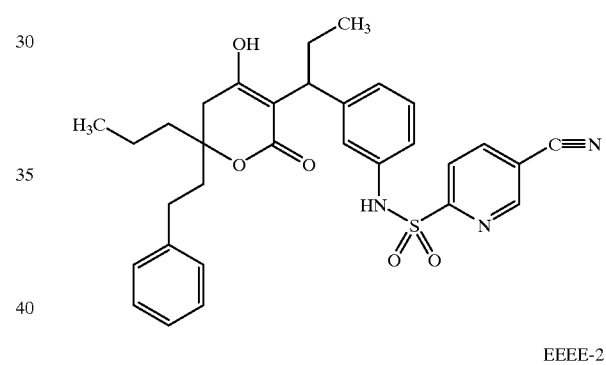
EEEE-1
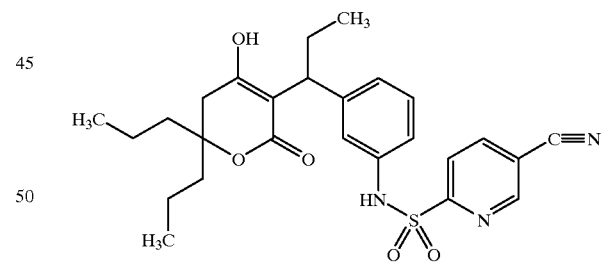
EEEE-2
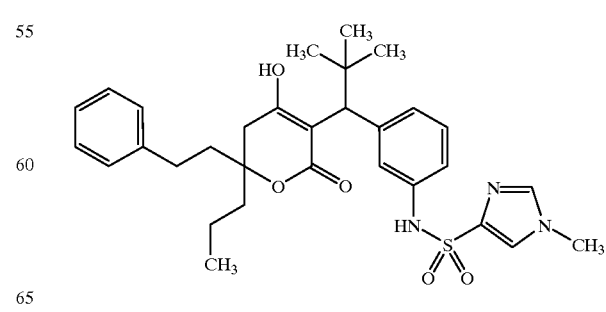
EEEE-3

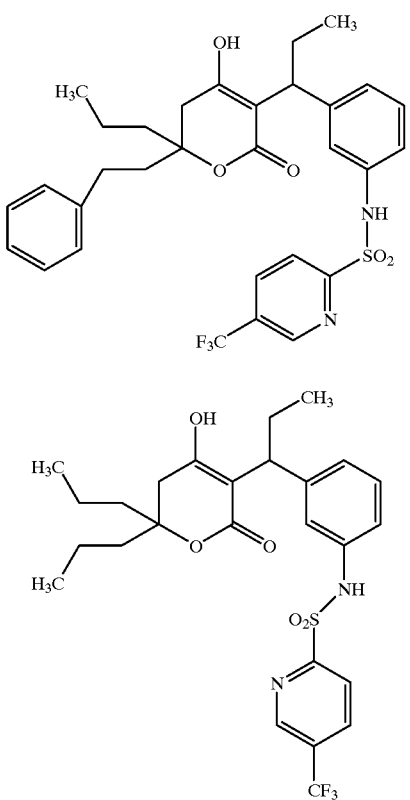
EEEE-4
EEEE-5
TABLE I
| Compound of | HIV Protease FITC Assay | | |
|---|---|---|---|
| Example No. | Dose (μM) | Protease % Inhib | $K_i$ (nM) |
| 136 | 0.123 | 71.65 | |
| | 0.370 | 85.67 | |
| | 1.100 | 99.02 | |
| | 3.300 | 100.99 | |
| | 10.000 | 102.37 | |
| | 30.000 | 101.94 | |
| | | | 1.320 |
| 145A | 0.123 | 108.66 | |
| | 0.370 | 111.34 | |
| | 1.100 | 118.54 | |
| | 3.300 | 115.43 | |
| | 10.000 | 113.05 | |
| | 30.000 | 114.19 | |
| | | | 1.100 |
| 137 | 0.123 | 98.83 | |
| | 0.370 | 91.54 | |
| | 1.100 | 100.7 | |
| | 3.300 | 109.9 | |
| | 10.000 | 98.17 | |
| | 30.000 | 93.82 | |
| | | | 0.520 |
| | | | 0.700 |
| 138 | 0.123 | 100.88 | |
| | 0.370 | 95.51 | |
| | 1.100 | 101.11 | |
| | 3.300 | 99.64 | |
| | 10.000 | 94.75 | |
| | 30.000 | 104.68 | |
| | | | 0.730 |
| | | | 1.400 |
| 97 | 0.123 | 104.87 | |
| | 0.370 | 106.06 | |
| | 1.100 | 110.44 | |
TABLE I-continued
| Compound of | HIV Protease FITC Assay | | |
|---|---|---|---|
| Example No. | Dose (μM) | Protease % Inhib | $K_i$ (nM) |
| | 3.300 | 106.67 | |
| | 10.000 | 115.76 | |
| | 30.000 | 115.47 | |
| | | | 1.000 |
| 98 | | | 0.740 |
| First Compound | | | |
| | | | 0.800 |
| 98 | | | 0.840 |
| Second Compound | | | |
| | | | 0.800 |
| 139 | 0.123 | 98.33 | |
| | 0.370 | 101.22 | |
| | 1.100 | 104.71 | |
| | 3.300 | 99.3 | |
| | 10.000 | 99.28 | |
| | 30.000 | 102.85 | |
| | | | 1.890 |
| 140 | 0.123 | 103.22 | |
| | 0.370 | 96.01 | |
| | 1.100 | 107.37 | |
| | 3.300 | 112.51 | |
| | 10.000 | 112.53 | |
| | 30.000 | 119.14 | |
| | | | 1.440 |
| 40 | 0.123 | 59.6 | |
| | 0.370 | 101.71 | |
| | 1.100 | 98.73 | |
| | 3.300 | 105.16 | |
| | 10.000 | 88.7 | |
| | 30.000 | 72.74 | |
| | | | 10.800 |
| 41 | 0.123 | 103 | |
| | 0.370 | 102.38 | |
| | 1.100 | 103.92 | |
| | 3.300 | 100.93 | |
| | 10.000 | 85.88 | |
| | 30.000 | 72.79 | |
| | | | 3.170 |
| 44 | 0.123 | 98.43 | |
| | 0.370 | 114.5 | |
| | 1.100 | 119.79 | |
| | 3.300 | 112.7 | |
| | 10.000 | 101.66 | |
| | 30.000 | 80.02 | |
| | | | 1.800 |
| 145B | 0.123 | 81.81 | |
| | 0.370 | 88.38 | |
| | 1.100 | 96.54 | |
| | 3.300 | 87.85 | |
| | 10.000 | 102.12 | |
| | 30.000 | 84.52 | |
| | | | 1.240 |
| 135 | 0.123 | 33.21 | |
| | 0.370 | 84.5 | |
| | 1.100 | 99.09 | |
| | 3.300 | 96.86 | |
| | 10.000 | 101.49 | |
| | 30.900 | 102.4 | |
| | | | 0.480 |
| 104 | 0.123 | <10 | |
| | 0.370 | 61.68 | |
| | 1.100 | 81.78 | |
| | 3.300 | 93.28 | |
| | 10.000 | 96.4 | |
| | 30.000 | 109.22 | |
| | | | 1.600 |
| 48 | 0.123 | 111.37 | |
| | 0.370 | 103.64 | |
| | 1.100 | 110.44 | |
| | 3.300 | 89.27 | |
| | 10.000 | 110.97 | |
| | 30.000 | 105.44 | |
| | | | 0.520 |
| 49 | 0.123 | 111.16 | |
| | 0.370 | 119.71 | |

TABLE I-continued

| Compound of Example No. | HIV Protease FITC Assay | | |
|---|---|---|---|
| | Dose (μM) | Protease % Inhib | $K_i$ (nM) |
| | 1.100 | 120.17 | |
| | 3.300 | 106.02 | |
| | 10.000 | 108.34 | |
| | 30.000 | 112.5 | |
| | | | 0.960 |
| 50 | 0.123 | 100.54 | |
| | 0.370 | 108.31 | |
| | 1.100 | 112.66 | |
| | 3.300 | 112.42 | |
| | 10.000 | 101.02 | |
| | 30.000 | 84.79 | |
| | | | 1.780 |
| 105 | 0.123 | 101.26 | |
| | 0.370 | 114.56 | |
| | 1.100 | 107.19 | |
| | 3.300 | 110.88 | |
| | 10.000 | 111.16 | |
| | 30.000 | 110.6 | |
| | | | 0.880 |
| 52 | 0.123 | 85.08 | |
| | 0.370 | 87.32 | |
| | 1.100 | 92.64 | |
| | 3.300 | 97.38 | |
| | 10.000 | 97.15 | |
| | 30.000 | 88.89 | |
| | | | 1.400 |
| 53 | 0.123 | 88.61 | |
| | 0.370 | 97.74 | |
| | 1.100 | 97.95 | |
| | 3.300 | 99.62 | |
| | 10.000 | 90.16 | |
| | 30.000 | 84.37 | |
| | | | 0.900 |
| 55 | 0.123 | <10 | |
| | 0.370 | 18.77 | |
| | 1.100 | 58.27 | |
| | 3.300 | 86.98 | |
| | 10.000 | 98.33 | |
| | 30.000 | 85.88 | |
| | | | 1.700 |
| 107 | 0.123 | 92.69 | |
| | 0.370 | 99.24 | |
| | 1.100 | 105.15 | |
| | 3.300 | 103.44 | |
| | 10.000 | 110.33 | |
| | 30.000 | 103.47 | |
| | | | 0.890 |
| | | | 0.700 |
| 99 | 0.123 | 85.69 | |
| | 0.370 | 101.55 | |
| | 1.100 | 108.05 | |
| | 3.300 | 100.05 | |
| | 10.000 | 106.61 | |
| | 30.000 | 103.12 | |
| | | | 0.660 |
| 141 | 0.123 | 78.72 | |
| | 0.370 | 88.65 | |
| | 1.100 | 92.04 | |
| | 3.300 | 88.26 | |
| | 10.000 | 97.8 | |
| | 30.000 | 98.48 | |
| | | | 1.400 |
| 142 | 0.123 | 78.01 | |
| | 0.370 | 92.52 | |
| | 1.100 | 106.64 | |
| | 3.300 | 105.15 | |
| | 10.000 | 110.58 | |
| | 30.000 | 106.77 | |
| | | | 1.600 |
| 56 | 0.123 | 104.11 | |
| | 0.370 | 108.31 | |
| | 1.100 | 105.31 | |
| | 3.300 | 105.47 | |
| | 10.000 | 114.94 | |
| | 30.000 | 111.25 | |
| | | | 0.230 |
| 57 | 0.123 | 99.07 | |
| | 0.370 | 105.17 | |
| | 1.100 | 110.68 | |
| | 3.300 | 97.8 | |
| | 10.000 | 104.74 | |
| | 30.000 | 115.02 | |
| | | | 0.360 |
| 58 | 0.123 | 64.87 | |
| | 0.370 | 83.71 | |
| | 1.100 | 94.24 | |
| | 3.300 | 95.88 | |
| | 10.000 | 100.27 | |
| | 30.000 | 89.81 | |
| | | | 3.800 |
| 59 | 0.123 | 76.69 | |
| | 0.370 | 90.54 | |
| | 1.100 | 101.9 | |
| | 3.300 | 99.87 | |
| | 10.000 | 105.16 | |
| | 30.000 | 102.02 | |
| | | | 3.500 |
| 60 | 0.123 | 73.03 | |
| | 0.370 | 94.3 | |
| | 1.100 | 101.28 | |
| | 3.300 | 100.84 | |
| | 10.000 | 105.68 | |
| | 30.000 | 107.38 | |
| | | | 0.950 |
| 61 | 0.123 | 86.83 | |
| | 0.370 | 95.51 | |
| | 1.100 | 103.35 | |
| | 3.300 | 102.54 | |
| | 10.000 | 105.61 | |
| | 30.000 | 103.53 | |
| | | | 0.710 |
| 93A | 0.123 | 59.48 | |
| | 0.370 | 90.42 | |
| | 1.100 | 103.54 | |
| | 3.300 | 108.54 | |
| | 10.000 | 109.19 | |
| | 30.000 | 96.57 | |
| | | | 6.060 |
| 143 | 0.123 | 80.78 | |
| | 0.370 | 97.65 | |
| | 1.100 | 104.91 | |
| | 3.300 | 102.39 | |
| | 10.000 | 101.25 | |
| | 30.000 | 103.08 | |
| | | | 0.800 |
| 144 | 0.123 | 80.58 | |
| | 0.370 | 87.39 | |
| | 1.100 | 93.82 | |
| | 3.300 | 100.01 | |
| | 10.000 | 98.12 | |
| | 30.000 | 95.88 | |
| | | | 1.200 |
| 145 | 0.123 | 73.63 | |
| | 0.370 | 89.78 | |
| | 1.100 | 99.69 | |
| | 3.300 | 94.8 | |
| | 10.000 | 96.85 | |
| | 30.000 | 87.97 | |
| | | | 0.490 |
| 100 | 0.123 | 102.53 | |
| | 0.370 | 100.67 | |
| | 1.100 | 91.01 | |
| | 3.300 | 96.54 | |
| | 100.000 | 100.86 | |
| | 30.000 | 100.62 | |
| | | | 0.730 |
| 62 | 0.123 | 76.18 | |
| | 0.370 | 85.15 | |
| | 1.100 | 85.28 | |
| | 3.300 | 78.67 | |

TABLE I-continued

| Compound of Example No. | Dose (µM) | Protease % Inhib | $K_i$ (nM) |
|---|---|---|---|
| | 10.000 | 79.69 | |
| | 30.000 | 79.39 | |
| | | | 0.800 |
| 108 | 0.123 | 103.43 | |
| | 0.370 | 102.13 | |
| | 1.100 | 101.87 | |
| | 3.390 | 102.41 | |
| | 10.000 | 107.73 | |
| | 30.000 | 106.39 | |
| | | | 0.160 |
| 109 | 0.123 | 105.42 | |
| | 0.370 | 99.35 | |
| | 1.100 | 103.75 | |
| | 3.300 | 100.96 | |
| | 10.000 | 108.56 | |
| | 30.000 | 109.31 | |
| 239 | 0.123 | 83.64 | |
| | 0.370 | 96.63 | |
| | 1.100 | 98.41 | |
| | 3.300 | 99.53 | |
| | 10.000 | 103.21 | |
| | 30.000 | 108.02 | |
| | | | 1.440 |
| | | | 0.860 |
| 152 | 0.123 | 11.52 | |
| | 0.370 | 80.2 | |
| | 1.100 | 95.79 | |
| | 3.300 | 94.43 | |
| | 10.000 | 95.45 | |
| | 30.000 | 96.47 | |
| | | | 0.710 |
| 8 | 0.123 | 99.23 | |
| | 0.370 | 110.11 | |
| | 1.100 | 102.93 | |
| | 3.300 | 110.02 | |
| | 10.000 | 105.11 | |
| | 30.000 | 101.91 | |
| | | | 0.350 |
| 9 | 0.123 | 99.09 | |
| | 0.370 | 103.78 | |
| | 1.100 | 104.9 | |
| | 3.300 | 104.69 | |
| | 10.000 | 107.08 | |
| | 30.000 | 107.87 | |
| | | | 0.420 |
| 10 | 0.123 | 102.17 | |
| | 0.370 | 111.74 | |
| | 1.100 | 115.65 | |
| | 3.300 | 119.47 | |
| | 10.000 | 128.59 | |
| | 30.000 | 130.05 | |
| | | | 5.710 |
| 151 | 0.123 | 111.03 | |
| | 0.370 | 114.59 | |
| | 1.100 | 117.62 | |
| | 3.300 | 118.9 | |
| | 10.000 | 116.34 | |
| | 30.000 | 114.87 | |
| | | | 0.360 |
| 153 | 0.123 | 81.27 | |
| | 0.370 | 91.11 | |
| | 1.100 | 100.49 | |
| | 3.300 | 104.09 | |
| | 10.000 | 102.76 | |
| | 30.000 | 100.71 | |
| | | | 1.850 |
| 154 | 0.123 | 99.8 | |
| | 0.370 | 98.17 | |
| | 1.100 | 99.52 | |
| | 3.300 | 97.59 | |
| | 10.000 | 103.54 | |
| | 30.000 | 99.18 | |
| | | | 0.220 |
| 240 | 0.123 | 96.32 | |
| | 0.370 | 100.98 | |
| | 1.100 | 102.71 | |
| | 3.300 | 101.88 | |
| | 10.900 | 104.28 | |
| | 30.000 | 107.17 | |
| | | | 1.300 |
| 1 | 0.123 | 75.4 | |
| | 0.370 | 87.3 | |
| | 1.100 | 97.1 | |
| | 3.300 | 96.76 | |
| | 10.000 | 99.68 | |
| | 30.000 | 97.43 | |
| | | | 15.000 |
| 101 | 0.123 | 70.24 | |
| | 0.370 | 83.98 | |
| | 1.100 | 93.35 | |
| | 3.300 | 97.01 | |
| | 10.000 | 102.48 | |
| | 30.000 | 97.35 | |
| | | | 0.660 |
| 146 | 0.123 | 68.12 | |
| | 0.370 | 87.38 | |
| | 1.100 | 103.18 | |
| | 3.300 | 103.26 | |
| | 10.000 | 102.54 | |
| | 30.000 | 101.95 | |
| | | | 0.690 |
| 147 | 0.123 | 77.45 | |
| | 0.370 | 102.86 | |
| | 1.100 | 111.6 | |
| | 3.300 | 110.34 | |
| | 10.000 | 114.04 | |
| | 30.000 | 108.28 | |
| | | | 1.000 |
| 110 | 0.123 | 77.89 | |
| | 0.370 | 82.72 | |
| | 1.100 | 95.11 | |
| | 3.300 | 99.1 | |
| | 10.000 | 99.22 | |
| | 30.000 | 101.27 | |
| | | | 3.260 |
| | | | 3.630 |
| 102 | 0.123 | 87.11 | |
| | 0.370 | 92.73 | |
| | 1.100 | 102.21 | |
| | 3.300 | 110.44 | |
| | 10.000 | 116.72 | |
| | 30.000 | 107.83 | |
| | | | 0.700 |
| 103 | 0.123 | 65.51 | |
| | 0.370 | 82.58 | |
| | 1.100 | 96.86 | |
| | 3.300 | 100.29 | |
| | 10.000 | 104.76 | |
| | 30.000 | 96.05 | |
| | | | 1.720 |
| 194 | 0.123 | <10 | |
| | 0.370 | 20.03 | |
| | 1.100 | 53.89 | |
| | 3.300 | 75.23 | |
| | 10.000 | 85.48 | |
| | 30.000 | 85.18 | |
| 195 | 0.123 | 60.89 | |
| | 0.370 | 85.08 | |
| | 1.100 | 90.79 | |
| | 3.300 | 90.83 | |
| | 10.000 | 93.14 | |
| | 30.000 | 92.69 | |
| | | | 3.700 |
| 150 | 0.123 | 78.42 | |
| | 0.370 | 96.45 | |
| | 1.100 | 100.07 | |
| | 3.300 | 102.81 | |
| | 10.000 | 106.88 | |
| | 30.000 | 109.34 | |
| | | | 5.900 |

TABLE I-continued

| Compound of Example No. | HIV Protease FITC Assay | | |
|---|---|---|---|
| | Dose (μM) | Protease % Inhib | $K_i$ (nM) |
| 148 | 0.123 | 81.35 | |
| | 0.370 | 91.68 | |
| | 1.100 | 95.57 | |
| | 3.300 | 90.04 | |
| | 10.000 | 99.17 | |
| | 30.000 | 93.52 | |
| | | | 4.770 |
| | | | 18.100 |
| 149 | 0.123 | 80.51 | |
| | 0.370 | 87.52 | |
| | 1.100 | 96.32 | |
| | 3.300 | 92.86 | |
| | 10.000 | 97.12 | |
| | 30.000 | 95.99 | |
| | | | 3.410 |
| | | | 62.700 |
| 94 | 0.123 | 75.76 | |
| | 0.370 | 106.6 | |
| | 1.100 | 107.3 | |
| | 3.300 | 104.91 | |
| | 10.000 | 109.2 | |
| | 30.000 | 111.29 | |
| | | | 16.370 |
| 95 | 0.123 | 91.2 | |
| | 0.370 | 102.33 | |
| | 1.100 | 105.86 | |
| | 3.300 | 112.79 | |
| | 10.000 | 110.04 | |
| | 30.000 | 112.69 | |
| | | | 5.350 |
| 96 | 0.123 | 94.17 | |
| | 0.370 | 119.36 | |
| | 1.100 | 122.12 | |
| | 3.300 | 111 | |
| | 10.000 | 111.32 | |
| | 30.000 | 109.23 | |
| | | | 5.300 |
| 42 | 0.123 | 86.15 | |
| | 0.370 | 102.71 | |
| | 1.100 | 98.26 | |
| | 3.300 | 102.4 | |
| | 10.000 | 91.43 | |
| | 30.000 | 76.12 | |
| | | | 3.100 |
| 43 | 0.123 | 85.63 | |
| | 0.370 | 99.01 | |
| | 1.100 | 95.68 | |
| | 3.300 | 96.68 | |
| | 10.000 | 101.58 | |
| | 30.000 | 85.57 | |
| | | | 3.650 |
| 45 | 0.123 | 82.22 | |
| | 0.370 | 94.37 | |
| | 1.100 | 101.04 | |
| | 3.300 | 103.16 | |
| | 10.000 | 89.76 | |
| | 30.000 | 67.5 | |
| | | | 4.780 |
| 46 | 0.123 | 85.86 | |
| | 0.370 | 99.19 | |
| | 1.100 | 103.31 | |
| | 3.300 | 97.62 | |
| | 10.000 | 91.45 | |
| | 30.000 | 74.13 | |
| | | | 2.920 |
| 47 | 0.123 | 66.3 | |
| | 0.870 | 86.79 | |
| | 1.100 | 94.7 | |
| | 3.300 | 100.95 | |
| | 10.000 | 98.68 | |
| | 30.000 | 84.45 | |
| | | | 3.000 |
| | | | 2.980 |
| 51 | 0.123 | 98.71 | |
| | 0.370 | 103.68 | |
| | 1.100 | 104.78 | |
| | 3.300 | 101.27 | |
| | 10.000 | 95.07 | |
| | 30.000 | 79.72 | |
| | | | 2.660 |
| 106 | 0.123 | 60.94 | |
| | 0.370 | 86.56 | |
| | 1.100 | 93.7 | |
| | 3.300 | 98.88 | |
| | 10.000 | 99.03 | |
| | 30.000 | 106.06 | |
| | | | 3.290 |
| 54 | 0.123 | 46.64 | |
| | 0.370 | 72.41 | |
| | 1.100 | 87.91 | |
| | 3.300 | 89.11 | |
| | 10.000 | 87.77 | |
| | 30.000 | 91.99 | |
| | | | 13.300 |
| 146 | 10.000 | 102.54 | |
| | 30.000 | 101.95 | |
| | | | 0.690 |
| 192 | 0.123 | 44.04 | |
| | 0.370 | 76.28 | |
| | 1.100 | 93.96 | |
| | 3.300 | 96.93 | |
| | 10.000 | 103.33 | |
| | 30.000 | 94.38 | |
| | | | 7.200 |
| 193 | 0.123 | 18.42 | |
| | 0.370 | 40.3 | |
| | 1.100 | 77.74 | |
| | 3.300 | 98.1 | |
| | 10.000 | 108.41 | |
| | 30.000 | 103.17 | |
| | | | 35.000 |
| 11 | 0.123 | 78.93 | |
| | 0.370 | 95.26 | |
| | 1.100 | 100.26 | |
| | 3.300 | 95.12 | |
| | 10.000 | 99.66 | |
| | 30.000 | 104.39 | |
| | | | 1.900 |
| 12 | 0.123 | 75.65 | |
| | 0.370 | 87.16 | |
| | 1.100 | 91.79 | |
| | 3.300 | 91.11 | |
| | 10.000 | 94.74 | |
| | 30.000 | 95.69 | |
| | | | 2.150 |
| 13 | 0.123 | 68.94 | |
| | 0.370 | 88.07 | |
| | 1.100 | 93.98 | |
| | 3.300 | 95.51 | |
| | 10.000 | 98.61 | |
| | 30.000 | 104.2 | |
| | | | 4.150 |
| 14 | 0.123 | 65.67 | |
| | 0.370 | 87.96 | |
| | 1.100 | 96.79 | |
| | 3.300 | 96.56 | |
| | 10.000 | 101.77 | |
| | 30.000 | 106.39 | |
| | | | 6.880 |
| 15 | 0.123 | 77.63 | |
| | 0.370 | 88.45 | |
| | 1.100 | 92.44 | |
| | 3.300 | 94.03 | |
| | 10.000 | 95.84 | |
| | 30.000 | 99.23 | |
| | | | 2.800 |
| 63 | 0.123 | 68.88 | |
| | 0.370 | 79.56 | |
| | 1.100 | 88.58 | |
| | 3.300 | 87.44 | |

TABLE I-continued

| Compound of Example No. | HIV Protease FITC Assay | | |
|---|---|---|---|
| | Dose (μM) | Protease % Inhib | $K_i$ (nM) |
| | 10.000 | 83.58 | |
| | 30.000 | 78.84 | |
| 64 | 0.123 | 27.95 | |
| | 0.370 | 50.83 | |
| | 1.100 | 75.60 | |
| | 3.300 | 80.88 | |
| | 10.000 | 82.03 | |
| | 30.000 | 84.39 | |
| 250 | | | 1.2 |
| 261 | | | 0.87 |
| 260 | | | 2.0 |
| 258 | | | 4.3 |
| 259 | | | 2.2 |
| 256 | | | 8.3 |
| 257 | | | 9.0 |
| 246 | | | 1.7 |
| 247 | | | 1.2 |
| 254 | | | 3.0 |
| 255 | | | 1.6 |
| 248 | | | 4.7 |
| 249 | | | 0.75 |
| 251 | 0.123 | 70.84 | |
| | 0.370 | 90.56 | |
| | 1.100 | 97.68 | |
| | 3.300 | 94.5 | |
| | 10.000 | 94.16 | |
| | 30.000 | 93.24 | |
| | | | 1.9 |
| 253 | 0.123 | 94.03 | |
| | 0.370 | 96.84 | |
| | 1.100 | 97.64 | |
| | 3.300 | 95.93 | |
| | 10.000 | 96.95 | |
| | 30.000 | 98.52 | |
| 252 | 0.123 | 69.96 | |
| | 0.370 | 85.05 | |
| | 1.100 | 89.69 | |
| | 3.300 | 100.57 | |
| | 10.000 | 96.21 | |
| | 30.000 | 91.38 | |
| | | | 1.6 |
| 262 | 0.123 | 91.8 | |
| | 0.370 | 96.6 | |
| | 1.100 | 97.13 | |
| | 3.300 | 95.4 | |
| | 10.000 | 94.17 | |
| | 30.000 | 89.18 | |
| 263 | 0.123 | 98.08 | |
| | 0.370 | 98.99 | |
| | 1.100 | 99.1 | |
| | 3.300 | 98.08 | |
| | 10.000 | 96.21 | |
| | 30.000 | 88.19 | |
| 264 | 0.123 | 67.18 | |
| | 0.370 | 75.01 | |
| | 1.100 | 67.71 | |
| | 3.300 | 57.62 | |
| | 10.000 | 53.69 | |
| | 30.000 | 64.58 | |
| | | | 3.7 |
| 265 | 0.123 | 33.23 | |
| | 0.370 | 56.33 | |
| | 1.100 | 57.78 | |
| | 3.300 | 63.69 | |
| | 10.000 | 80.29 | |
| | 30.000 | 85.64 | |
| | | | 1.0 |

TABLE II

| EXAMPLE NUMBER | ENZYME | DOSE | PROTEASE % INHIB. | FITC KI (NM) |
|---|---|---|---|---|
| 280 | HIV-1 | 0.123 | 95.28 | |
| | HIV-1 | 0.370 | 94.98 | |
| | HIV-1 | 1.100 | 93.01 | |
| | HIV-1 | 3.300 | 86.69 | |
| | HIV-1 | 10.000 | 78.64 | |
| | HIV-1 | 30.000 | 76.85 | |
| | HIV1TANDEM | | | 0.100 |
| 293 | HIV-1 | 0.123 | 53.45 | |
| | HIV-1 | 0.370 | 77.51 | |
| | HIV-1 | 1.100 | 94.18 | |
| | HIV-1 | 3.300 | 103.03 | |
| | HIV-1 | 10.000 | 97.41 | |
| | HIV-1 | 30.000 | 92.01 | 4.300 |
| 295 | HIV1TANDEM | | | 0.071 |
| 281 | HIV1TANDEM | | | 0.002 |
| | HIV1TANDEM | | | 0.004 |
| 285 | HIV1TANDEM | | | 0.015 |
| | HIV-1 | 0.123 | 81.8 | |
| | HIV-1 | 0.370 | 95.8 | |
| | HIV-1 | 1.100 | 99.11 | |
| | HIV-1 | 3.300 | 109.33 | |
| | HIV-1 | 10.000 | 104.61 | |
| | HIV-1 | 30.000 | 86.84 | |
| 286 | HIV1TANDEM | | | 13.300 |
| | HIV-1 | 0.123 | 34.76 | |
| | HIV-1 | 0.370 | 68.74 | |
| | HIV-1 | 1.100 | 89.29 | |
| | HIV-1 | 3.300 | 93.11 | |
| | HIV-1 | 10.000 | 108.17 | |
| | HIV-1 | 30.000 | 95.31 | |
| 287 | HIV1TANDEM | | | 0.038 |
| 283 | HIV1TANDEM | | | 0.004 |
| 296 | HIV1TANDEM | | | 0.042 |
| 291 | HIV1TANDEM | | | 0.012 |
| | HIV1TANDEM | | | 0.026 |
| 289 | HIV1TANDEM | | | 0.133 |
| 290 | HIV1TANDEM | | | 1.880 |
| 298 | HIV1TANDEM | | | 0.004 |
| | HIV1TANDEM | | | 0.003 |
| | HIV1TANDEM | | | 0.007 |
| 266 | HIV1TANDEM | | | 0.033 |
| 272 | HIV1TANDEM | | | 3.600 |
| 270 | HIV1TANDEM | | | 0.024 |
| | HIV-1 | 0.123 | 75.26 | |
| | HIV-1 | 0.370 | 85.62 | |
| | HIV-1 | 1.100 | 93.45 | |
| | HIV-1 | 3.300 | 96.62 | |
| | HIV-1 | 10.000 | 94.57 | |
| | HIV-1 | 30.000 | 82.67 | |
| 273 | HIV1TANDEM | | | 2.300 |
| | HIV-1 | 0.123 | <10 | |
| | HIV-1 | 0.370 | 23.24 | |
| | HIV-1 | 1.100 | 75.38 | |
| | HIV-1 | 3.300 | 94.63 | |
| | HIV-1 | 10.000 | 95.93 | |
| | HIV-1 | 30.000 | 91 | |
| 276 | HIV1TANDEM | | | 33.000 |
| | HIV-1 | 0.123 | 16.49 | |
| | HIV-1 | 0.370 | 38.95 | |
| | HIV-1 | 1.100 | 66.1 | |
| | HIV-1 | 3.300 | 90.01 | |
| | HIV-1 | 10.000 | 90.97 | |
| | HIV-1 | 30.000 | 87.6 | |
| 278 | HIV1TANDEM | | | 0.040 |
| | HIV-1 | 0.123 | 76.76 | |
| | HIV-1 | 0.370 | 86.99 | |
| | HIV-1 | 1.100 | 95.6 | |
| | HIV-1 | 3.300 | 96.91 | |
| | HIV-1 | 10.000 | 93.32 | |
| | HIV-1 | 30.000 | 86.18 | |
| 268 | HIV1TANDEM | | | 0.835 |
| 271 | HIV1TANDEM | | | 0.051 |
| 299 | HIV-1 | 0.123 | 83.51 | |
| | HIV-1 | 0.370 | 104.76 | |
| | HIV-1 | 1.100 | 117.95 | |
| | HIV-1 | 3.300 | 115.61 | |

TABLE II-continued

| EXAMPLE NUMBER | ENZYME | DOSE | PROTEASE % INHIB. | FITC KI (NM) |
|---|---|---|---|---|
|  | HIV-1 | 10.000 | 128.03 |  |
|  | HIV-1 | 30.000 | 102.89 |  |
|  | HIV1TANDEM |  |  | 0.200 |
| 300 | HIVTANDEM |  |  | 0.100 |
|  | HIVTANDEM |  |  | 0.100 |
|  | HIV-1 | 0.123 | 90.61 |  |
|  | HIV-1 | 0.370 | 99.05 |  |
|  | HIV-1 | 1.100 | 111.45 |  |
|  | HIV-1 | 3.300 | 109.19 |  |
|  | HIV-1 | 10.000 | 105.56 |  |
|  | HIV-1 | 30.000 | 104.91 |  |
| 302 | HIVTANDEM |  |  | 1.870 |
|  | HIVTANDEM |  |  | 3.600 |
|  | HIV-1 | 0.123 | 38 |  |
|  | HIV-1 | 0.370 | 65.57 |  |
|  | HIV-1 | 1.100 | 89.51 |  |
|  | HIV-1 | 3.300 | 118.39 |  |
|  | HIV-1 | 10.000 | 104.49 |  |
|  | HIV-1 | 30.000 | 92.16 |  |
| 304 | HIV-1 | 0.123 | 92.01 |  |
|  | HIV-1 | 0.370 | 93.28 |  |
|  | HIV-1 | 1.100 | 96.47 |  |
|  | HIV-1 | 3.300 | 100.47 |  |
|  | HIV-1 | 10.000 | 107.61 |  |
|  | HIV-1 | 30.000 | 79.68 |  |
|  | HIV1TANDEM |  |  | 0.100 |
|  | HIV1TANDEM |  |  | 0.050 |
| 305 | HIV-1 | 0.123 | 99.99 |  |
|  | HIV-1 | 0.370 | 110.76 |  |
|  | HIV-1 | 1.100 | 114.35 |  |
|  | HIV-1 | 3.300 | 110.88 |  |
|  | HIV-1 | 10.000 | 102.01 |  |
|  | HIV-1 | 30.000 | 57.83 |  |
|  | HIV1TANDEM |  |  | 0.400 |
| 306 | HIV-1 | 0.123 | 71.79 |  |
|  | HIV-1 | 0.370 | 82.71 |  |
|  | HIV-1 | 1.100 | 89.3 |  |
|  | HIV-1 | 3.300 | 97.29 |  |
|  | HIV-1 | 10.000 | 82.59 |  |
|  | HIV-1 | 30.000 | 53.43 |  |
|  | HIV1TANDEM |  |  | 0.040 |
| 307 | HIV-1 | 0.123 | 77.39 |  |
|  | HIV-1 | 0.370 | 99.85 |  |
|  | HIV-1 | 1.100 | 107.87 |  |
|  | HIV-1 | 3.300 | 93.34 |  |
|  | HIV-1 | 10.000 | 83.49 |  |
|  | HIV-1 | 30.000 | 69.74 |  |
|  | HIV1TANDEM |  |  | 0.072 |
| 308 | HIV-1 | 0.123 | 75.06 |  |
|  | HIV-1 | 0.370 | 108.14 |  |
|  | HIV-1 | 1.100 | 95.01 |  |
|  | HIV-1 | 3.300 | 108.43 |  |
|  | HIV-1 | 10.000 | 110.75 |  |
|  | HIV-1 | 30.000 | 96.28 |  |
|  | HIV1TANDEM |  |  | 0.074 |
| 310 | HIV-1 | 0.123 | 16.81 |  |
|  | HIV-1 | 0.370 | 50.11 |  |
|  | HIV-1 | 1.100 | 78.69 |  |
|  | HIV-1 | 3.300 | 100.22 |  |
|  | HIV-1 | 10.000 | 124.77 |  |
|  | HIV-1 | 30.000 | 110.91 |  |
|  | HIV1TANDEM |  |  | 1.500 |
| 311 | HIV-1 | 0.123 | 86.51 |  |
|  | HIV-1 | 0.370 | 91.49 |  |
|  | HIV-1 | 1.100 | 101.8 |  |
|  | HIV-1 | 3.300 | 96.5 |  |
|  | HIV-1 | 10.000 | 93.77 |  |
|  | HIV-1 | 30.000 | 77.63 |  |
|  | HIV1TANDEM |  |  | 0.007 |
| 312 | HIV1TANDEM |  |  | 0.255 |
| 314 | HIV1TANDEM |  |  | 0.700 |
|  | HIV-1 | 0.123 | 82.92 |  |
|  | HIV-1 | 0.370 | 96.14 |  |
|  | HIV-1 | 1.100 | 114.86 |  |
|  | HIV-1 | 3.300 | 100.76 |  |
|  | HIV-1 | 10.000 | 88.75 |  |
|  | HIV-1 | 30.000 | 73.42 |  |
| 315 | HIV1TANDEM |  |  | 0.029 |
|  | HIV-1 | 0.123 | 79.95 |  |
|  | HIV-1 | 0.370 | 87.25 |  |
|  | HIV-1 | 1.100 | 88.08 |  |
|  | HIV-1 | 3.300 | 97.03 |  |
|  | HIV-1 | 10.000 | 100.2 |  |
|  | HIV-1 | 30.000 | 106.4 |  |
| 316 | HIV1TANDEM |  |  | 0.357 |
|  | HIV-1 | 0.123 | 75.49 |  |
|  | HIV-1 | 0.370 | 85.02 |  |
|  | HIV-1 | 1.100 | 100.32 |  |
|  | HIV-1 | 3.300 | 95.46 |  |
|  | HIV-1 | 10.000 | 99.71 |  |
|  | HIV-1 | 30.000 | 87.91 |  |
| 317 | HIV1TANDEM |  |  | 0.040 |
|  | HIV-1 | 0.123 | 87.38 |  |
|  | HIV-1 | 0.370 | 94.14 |  |
|  | HIV-1 | 1.100 | 98.45 |  |
|  | HIV-1 | 3.300 | 95.97 |  |
|  | HIV-1 | 10.000 | 101.26 |  |
|  | HIV-1 | 30.000 | 108.59 |  |
| 318 | HIV1TANDEM |  |  | 0.019 |
|  | HIV-1 | 0.123 | 98.06 |  |
|  | HIV-1 | 0.370 | 106.35 |  |
|  | HIV-1 | 1.100 | 101.88 |  |
|  | HIV-1 | 3.300 | 88.73 |  |
|  | HIV-1 | 10.000 | 94.49 |  |
|  | HIV-1 | 30.000 | 82.83 |  |
| 319 | HIV1TANDEM |  |  | 29.500 |
|  | HIV-1 | 0.123 | 10.75 |  |
|  | HIV-1 | 0.370 | 32.65 |  |
|  | HIV-1 | 1.100 | 60.14 |  |
|  | HIV-1 | 3.300 | 75.86 |  |
|  | HIV-1 | 10.000 | 93.46 |  |
|  | HIV-1 | 30.000 | 74.48 |  |
| 320 | HIV1TANDEM |  |  | 0.071 |
|  | HIV1TANDEM |  |  | 0.050 |
|  | HIV1TANDEM |  |  | 0.075 |
| 322 | HIV1TANDEM |  |  | 1.070 |
|  | HIV1TANDEM |  |  | 1.290 |
| 324 | HIV1TANDEM |  |  | 0.156 |
| 326 | HIV1TANDEM |  |  | 0.029 |
| 328 | HIV-1 |  |  | 22.000 |
|  | HIV-1 | 0.123 | 27.81 |  |
|  | HIV-1 | 0.370 | 79.47 |  |
|  | HIV-1 | 1.100 | 95.45 |  |
|  | HIV-1 | 3.300 | 96.77 |  |
|  | HIV-1 | 10.000 | 96.78 |  |
|  | HIV-1 | 30.000 | 92.17 |  |
| 329 | HIV-1 |  |  | 12.000 |
|  | HIV-1 | 0.123 | 46.4 |  |
|  | HIV-1 | 0.370 | 88.19 |  |
|  | HIV-1 | 1.100 | 96.63 |  |
|  | HIV-1 | 3.300 | 100.32 |  |
|  | HIV-1 | 10.000 | 97.07 |  |
|  | HIV-1 | 30.000 | 96.35 |  |
| 330 | HIV1TANDEM |  |  | 0.524 |
|  | HIV-1 | 0.123 | 93.74 |  |
|  | HIV-1 | 0.370 | 94.32 |  |
|  | HIV-1 | 1.100 | 93.66 |  |
|  | HIV-1 | 3.300 | 85.63 |  |
|  | HIV-1 | 10.000 | 87.9 |  |
|  | HIV-1 | 30.000 | 69.82 |  |
| 331 | HIV1TANDEM |  |  | 0.272 |
|  | HIV-1 | 0.123 | 99.76 |  |
|  | HIV-1 | 0.370 | 104.06 |  |
|  | HIV-1 | 1.100 | 108.51 |  |
|  | HIV-1 | 3.300 | 99.3 |  |
|  | HIV-1 | 10.000 | 103.28 |  |
|  | HIV-1 | 30.000 | 93.3 |  |
| 332 | HIV1TANDEM |  |  | 0.400 |
|  | HIV-1 | 0.123 | 81.87 |  |
|  | HIV-1 | 0.370 | 85.65 |  |
|  | HIV-1 | 1.100 | 86.23 |  |
|  | HIV-1 | 3.300 | 93.28 |  |

TABLE II-continued

| EXAMPLE NUMBER | ENZYME | DOSE | PROTEASE % INHIB. | FITC KI (NM) |
|---|---|---|---|---|
| | HIV-1 | 10.000 | 91.68 | |
| | HIV-1 | 30.000 | 95.08 | |
| | HIV-1 | | | 1.600 |
| 333 | HIV-1 | 0.123 | 66.73 | |
| | HIV-1 | 0.370 | 85.07 | |
| | HIV-1 | 1.100 | 85.12 | |
| | HIV-1 | 3.300 | 93.69 | |
| | HIV-1 | 10.000 | 89.38 | |
| | HIV-1 | 30.000 | 77.91 | |
| | HIV-1 | | | 7.700 |
| 334 | HIV1TANDEM | | | 0.450 |
| | HIV-1 | 0.123 | 93.49 | |
| | HIV-1 | 0.370 | 90.25 | |
| | HIV-1 | 1.100 | 94.57 | |
| | HIV-1 | 3.300 | 102.47 | |
| | HIV-1 | 10.000 | 97.61 | |
| | HIV-1 | 30.000 | 96.3 | |
| 335 | HIV-1 | 0.123 | 60.07 | |
| | HIV-1 | 0.370 | 99.75 | |
| | HIV-1 | 1.100 | 97.05 | |
| | HIV-1 | 3.300 | 92.06 | |
| | HIV-1 | 10.000 | 89.77 | |
| | HIV-1 | 30.000 | 76.25 | |
| | HIV1TANDEM | | | 0.040 |
| 336 | HIV-1 | 0.123 | 65.64 | |
| | HIV-1 | 0.370 | 112 | |
| | HIV-1 | 1.100 | 89.54 | |
| | HIV-1 | 3.300 | 88.06 | |
| | HIV-1 | 10.000 | 77.12 | |
| | HIV-1 | 30.000 | 62.28 | |
| | HIV1TANDEM | | | 0.032 |
| 338 | HIV-1 | 0.123 | 61.74 | |
| | HIV-1 | 0.370 | 85.32 | |
| | HIV-1 | 1.100 | 80.46 | |
| | HIV-1 | 3.300 | 89.62 | |
| | HIV-1 | 10.000 | 83.53 | |
| | HIV-1 | 30.000 | 62.34 | |
| | HIV1TANDEM | | | 0.100 |
| 339 | HIV-1 | 0.123 | 83.49 | |
| | HIV-1 | 0.370 | 100.6 | |
| | HIV-1 | 1.100 | 101.42 | |
| | HIV-1 | 3.300 | 104.71 | |
| | HIV-1 | 10.000 | 91.38 | |
| | HIV-1 | 30.000 | 72.86 | |
| | HIV1TANDEM | | | 0.120 |
| 340 | HIV-1 | 0.123 | 80.58 | |
| | HIV-1 | 0.370 | 90.49 | |
| | HIV-1 | 1.100 | 90.16 | |
| | HIV-1 | 3.300 | 91.57 | |
| | HIV-1 | 10.000 | 89.49 | |
| | HIV-1 | 30.000 | 71.99 | |
| | HIV1TANDEM | | | 0.060 |
| 342 | HIV-1 | 0.123 | 81.06 | |
| | HIV-1 | 0.370 | 93.18 | |
| | HIV-1 | 1.100 | 96.94 | |
| | HIV-1 | 3.300 | 85.55 | |
| | HIV-1 | 10.000 | 73.55 | |
| | HIV-1 | 30.000 | 73.95 | |
| | HIV1TANDEM | | | 0.309 |
| 343 | HIV-1 | 0.123 | 57.5 | |
| | HIV-1 | 0.370 | 76.83 | |
| | HIV-1 | 1.100 | 81.02 | |
| | HIV-1 | 3.300 | 86.43 | |
| | HIV-1 | 10.000 | 60.56 | |
| | HIV-1 | 30.000 | 46 | 2.900 |
| 344 | HIV-1 | 0.123 | 47.37 | |
| | HIV-1 | 0.370 | 72.84 | |
| | HIV-1 | 1.100 | 81.17 | |
| | HIV-1 | 3.300 | 83.08 | |
| | HIV-1 | 10.000 | 68.47 | |
| | HIV-1 | 30.000 | 46.24 | 5.900 |
| 345 | HIV1TANDEM | | | 0.032 |
| | HIV-1 | 0.123 | 69.19 | |
| | HIV-1 | 0.370 | 94.37 | |
| | HIV-1 | 1.100 | 101.67 | |
| | HIV-1 | 3.300 | 99.08 | |
| | HIV-1 | 10.000 | 97.43 | |
| | HIV-1 | 30.000 | 84.56 | |
| 347 | HIV1TANDEM | | | 13.600 |
| | HIV-1 | 0.123 | 20.99 | |
| | HIV-1 | 0.370 | 50.82 | |
| | HIV-1 | 1.100 | 71.4 | |
| | HIV-1 | 3.300 | 83 | |
| | HIV-1 | 10.000 | 90.97 | |
| | HIV-1 | 30.000 | 87.18 | |
| 348 | HIV1TANDEM | | | 1.960 |
| | HIV-1 | 0.123 | 53.47 | |
| | HIV-1 | 0.370 | 78.32 | |
| | HIV-1 | 1.100 | 89.84 | |
| | HIV-1 | 3.300 | 92.96 | |
| | HIV-1 | 10.000 | 96.28 | |
| | HIV-1 | 30.000 | 84.67 | |
| 349 | HIV1TANDEM | | | 0.111 |
| | HIV-1 | 0.123 | 74.5 | |
| | HIV-1 | 0.370 | 88.21 | |
| | HIV-1 | 1.100 | 99.92 | |
| | HIV-1 | 3.300 | 104.99 | |
| | HIV-1 | 10.000 | 103.49 | |
| | HIV-1 | 30.000 | 98.24 | |
| 351 | HIV-1 | 0.123 | <10 | |
| | HIV-1 | 0.370 | <10 | |
| | HIV-1 | 1.100 | 25.4 | |
| | HIV-1 | 3.300 | 55.11 | |
| | HIV-1 | 10.000 | 78.53 | |
| | HIV-1 | 30.000 | 90.55 | |
| | HIV-1 | | | 558.000 |
| 352 | HIV-1 | 0.123 | <10 | |
| | HIV-1 | 0.370 | 25.31 | |
| | HIV-1 | 1.100 | 47.78 | |
| | HIV-1 | 3.300 | 74.99 | |
| | HIV-1 | 10.000 | 85.86 | |
| | HIV-1 | 30.000 | 87.82 | |
| | HIV-1 | | | 168.000 |
| 353 | HIV-1 | | | 10.400 |
| | HIV1TANDEM | | | 5.300 |
| | HIV-1 | 0.123 | 51.83 | |
| | HIV-1 | 0.370 | 68.49 | |
| | HIV-1 | 1.100 | 70.71 | |
| | HIV-1 | 3.300 | 63.96 | |
| | HIV-1 | 10.000 | 51.8 | |
| | HIV-1 | 30.000 | 43.93 | |
| 354 | HIV-1 | 0.123 | <10 | |
| | HIV-1 | 0.370 | 10.37 | |
| | HIV-1 | 1.100 | 26.79 | |
| | HIV-1 | 3.300 | 46.1 | |
| | HIV-1 | 10.000 | 54.97 | |
| | HIV-1 | 30.000 | 54.5 | |
| | HIV-1 | | | 665.000 |
| 355 | HIV-1 | | | 700.000 |
| | HIV-1 | 0.123 | <10 | |
| | HIV-1 | 0.370 | <10 | |
| | HIV-1 | 1.100 | <10 | |
| | HIV-1 | 3.300 | 20.72 | |
| | HIV-1 | 10.000 | 46.66 | |
| | HIV-1 | 30.000 | 67.82 | |
| 356 | HIV1TANDEM | | | 1.100 |
| | HIV-1 | 0.123 | 54.96 | |
| | HIV-1 | 0.370 | 71.75 | |
| | HIV-1 | 1.100 | 90.19 | |
| | HIV-1 | 3.300 | 92.28 | |
| | HIV-1 | 10.000 | 100.22 | |
| | HIV-1 | 30.000 | 95.16 | |
| 357 | HIV1TANDEM | | | 48.500 |
| 359 | HIV1TANDEM | | | 16.400 |
| 363 | HIV1TANDEM | | | 0.083 |
| 365 | HIV1YANDEM | | | 0.023 |
| 368 | HIV1TANDEM | | | 0.232 |
| 370 | HIV-1 | 0.123 | 92.81 | |
| | HIV-1 | 0.370 | 87.87 | |
| | HIV-1 | 1.100 | 102.89 | |
| | HIV-1 | 3.300 | 109.33 | |
| | HIV-1 | 10.000 | 113.79 | |

TABLE II-continued

| EXAMPLE NUMBER | ENZYME | DOSE | PROTEASE % INHIB. | FITC KI (NM) |
|---|---|---|---|---|
| | HIV-1 | 30.000 | 98.14 | 0.590 |
| | HIV1TANDEM | | | 0.050 |
| | HIV-2 | | | 0.050 |
| 371 | HIV-1 | 0.123 | 39.84 | |
| | HIV-1 | 0.370 | 72.94 | |
| | HIV-1 | 1.100 | 91.61 | |
| | HIV-1 | 3.300 | 104.12 | |
| | HIV-1 | 10.000 | 102.7 | |
| | HIV-1 | 30.000 | 107.21 | 15.400 |
| 372 | HIV-1 | 0.123 | 43.52 | |
| | HIV-1 | 0.370 | 86.68 | |
| | HIV-1 | 1.100 | 101.52 | |
| | HIV-1 | 3.300 | 99.56 | |
| | HIV-1 | 10.000 | 97.81 | |
| | HIV-1 | 30.000 | 106.18 | 4.000 |
| 373 | HIV-1 | 0.123 | 90.71 | |
| | HIV-1 | 0.370 | 90.35 | |
| | HIV-1 | 1.100 | 103.83 | |
| | HIV-1 | 3.300 | 88.72 | |
| | HIV-1 | 10.000 | 85.75 | |
| | HIV-1 | 30.000 | 89.53 | |
| | HIV1TANDEM | | | 0.200 |
| 374 | HIV1TANDEM | 0.123 | 78.97 | |
| | | 0.370 | 82.14 | |
| | | 1.100 | 84.98 | |
| | | 3.300 | 87.70 | |
| | | 10.000 | 95.25 | |
| | | 30.000 | 80.11 | 0.031 |

TABLE 3

| U-No. | MS data | Name | Origin |
|---|---|---|---|
| 300 | 587.2453 (EI) | 5-Cyano-N-[3(R or S)-(1-[5,6-dihydro-4-hydroxy-2-oxo-6(R or S)-(2-phenylethyl)-6-propyl-2H-pyran-3-yl]-2,2-dimethylpropyl)-phenyl]-2-pyridinesulfonamide | Single stereoisomer; Derived from Isomer 1 of Preparation 143 |
| 301 | 587.2458 (EI) | 5-Cyano-N-[3(R or S)-(1-[5,6-dihydro-4-hydroxy-2-oxo-6(R or S)-(2-phenylethyl)-6-propyl-2H-pyran-3-yl]-2,2-dimethylpropyl)-phenyl]-2-pyridinesulfonamide | Single stereoisomer; Derived from Isomer 2 of Preparation 143 |
| 302 | 587.2444 (EI) | 5-Cyano-N-[3(R or S)-(1-[5,6-dihydro-4-hydroxy-2-oxo-6(R or S)-(2-phenylethyl)-6-propyl-2H-pyran-3-yl]-2,2-dimethylpropyl)-phenyl]-2-pyridinesulfonamide | Single stereoisomer; Derived from Isomer 3 of Preparation 143 |
| 303 | 587.2446 (EI) | 5-Cyano-N-[3(R or S)-(1-[5,6-dihydro-4-hydroxy-2-oxo-6(R or S)-(2-phenylethyl)-6-propyl-2H-pyran-3-yl]-2,2-dimethylpropyl)-phenyl]-2-pyridinesulfonamide | Single stereoisomer; Derived from Isomer 4 of Preparation 143 |
| 304 | 525.2311 (EI) | 5-Cyano-N-[3-(1-[5,6-dihydro-6,6-diisobutyl-4-hydroxy-2-oxo-2H-pyran-3-yl]propyl)phenyl]-2-pyridinesulfonamide | Racemic mixture |
| 305 | 532.2856 (FAB) | N-[3-(1-[5,6-Dihydro-6,6-diisobutyl-4-hydroxy-2-oxo-2H-pyran-3-yl]-2,2-dimethylpropyl)-phenyl]-1-methyl-1H-imidazole-4-sulfonamide | Racemic mixture |
| 306 | 554.2688 (FAB) | 5-Cyano-N-[3-(1-[5,6-dihydro-6,6-diisobutyl-4-hydroxy-2-oxo-2H-pyran-3-yl]-2,2-dimethylpropyl)-phenyl]-2-pyridinesulfonamide | Racemic mixture |
| 307 | 565.2607 (EI) | N-[3(R or S)-[1-(5,6-Dihydro-4-hydroxy-2-oxo-6(R or S)-[2-phenylethyl]-6-propyl-2H-pyran-3-yl]-2,2-dimethylpropyl]phenyl]-1-methyl-1H-imidazole-4-sulfonamide | Single stereoisomer; Derived from Isomer 1 of Preparation 143 |
| 308 | 565.2629 (EI) | N-[3(R or S)-[1-(5,6-Dihydro-4-hydroxy-2-oxo-6(R or S)-[2-phenylethyl]-6-propyl-2H-pyran-3-yl]-2,2-dimethylpropyl]phenyl]-1-methyl-1H-imidazole-4-sulfonamide | Single stereoisomer; Derived from Isomer 2 of Preparation 143 |
| 309 | 565.2605 (EI) | N-[3(R or S)-[1-(5,6-Dihydro-4-hydroxy-2-oxo-6(R or S)-[2-phenylethyl]-6-propyl-2H-pyran-3-yl]-2,2-dimethylpropyl]phenyl]-1-methyl-1H-imidazole-4-sulfonamide | Single stereoisomer; Dervied from Isomer 3 of Preparation 143 |
| 310 | 565.2626 (EI) | N-[3(R or S)-[1-(5,6-Dihydro-4-hydroxy-2-oxo-6(R or S)-[2-phenylethyl]-6-propyl-2H-pyran-3-yl]-2,2-dimethylpropyl]phenyl]-1-methyl-1H-imidazole-4-sulfonamide | Single stereoisomer; Derived from Isomer 4 of Preparation 143 |
| 311 | 571.2113 (EI) | 5-Cyano-N-[3-(1-[5,6-dihydro-4-hydroxy-2-oxo-6-(2-phenylethyl)-6-propyl-2H-pyran-3-yl]cyclopropylmethyl)phenyl]-2-pyridinesulfonamide | Diasteromeric mixture |
| 312 | 577.2630 (EI) | 5-Amino-N-[3(R or S)-(1-[5,6-dihydro-4-hydroxy-2-oxo-6(R or S)-(2-phenylethyl)-6-propyl-2H-pyran-3-yl]-2,2-dimethylpropyl)-phenyl]-2-pyridinesulfonamide | Single stereoisomer; Prepared from amine of Preparation 138 (derived from Isomer 1 of Preparation 143) |
| 313 | 577.2585 (EI) | 5-Amino-N-[3(R or S)-(1-[5,6-dihydro-4-hydroxy-2-oxo-6(R or S)-(2-phenylethyl)-6-propyl-2H-pyran-3-yl]-2,2-dimethylpropyl)-phenyl]-2-pyridinesulfonamide | Single stereoisomer; Prepared from amine of Preparation 137 (derived from Isomer 2 of Preparation 143) |
| 314 | 550.2380 (FAB) | 5-Amino-N-[3(R or S)-(1-[5,6-dihydro-4-hydroxy-2-oxo-6(R or S)-(2-phenylethyl)-6-propyl-2H-pyran-3-yl]propyl)phenyl]-2-pyridinesulfonamide | Single stereoisomer; Derived from Isomer 1 of Preparation 147 |
| 315 | 550.2365 (FAB) | 5-Amino-N-[3(R or S)-(1-[5,6-dihydro-4-hydroxy-2-oxo-6(R or S)-(2-phenylethyl)-6-propyl-2H-pyran-3-yl]propyl)phenyl]-2-pyridinesulfonamide | Single stereoisomer; Derived from Isomer 2 of Preparation 147 |
| 316 | 596.2583 (FAB) | 5-Amino-N-[3(R or S)-(1-[6(R or S)-(2-[4-fluorophenyl]ethyl)-5,6-dihydro-4-hydroxy-2-oxo-6-propyl-2H-pyran-3-yl]-2,2-dimethylpropyl)phenyl]-2-pyridinesulfonamide | Single stereoisomer; Derived from Isomer 1 of Preparation 150 |
| 317 | 596.2583 (FAB) | 5-Amino-N-[3(R or S)-(1-[6(R or S)-(2-[4-fluorophenyl]ethyl)-5,6-dihydro-4-hydroxy-2-oxo-6-propyl-2H-pyran-3-yl]-2,2-dimethylpropyl)phenyl]-2-pyridinesulfonamide | Single stereoisomer; Derived from Isomer 2 of Preparation 150 |
| 318 | 503.2445 (DI) | N-[3(R or S)-(1-[5,6-Dihydro-6,6-dipropyl-4-hydroxy-2-oxo-2H-pyran-3-yl]-2,2-dimethylpropyl)-phenyl]-1-methyl-1H-imidazole-4-sulfonamide | Single enantiomer; Prepared from amine derived from Isomer 1 of Preparation 144 |
| 319 | 503.2454 (EI) | N-[3(R or S)-(1-[5,6-Dihydro-6,6-dipropyl-4-hydroxy-2-oxo-2H-pyran-3-yl]-2,2-dimethylpropyl)-phenyl]-1-methyl-1H-imidazole-4-sulfonamide | Single enantiomer; Prepared from amine derived from Isomer 2 of Preparation |

TABLE 3-continued

| U-No. | MS data | Name | Origin |
|---|---|---|---|
| 320 | 515.2453 (EI) | 5-Amino-N-[3(R or S)-(1-[5,6-dihydro-6,6-dipropyl-4-hydroxy-2-oxo-2H-pyran-3-yl]-2,2-dimethyl-propyl)phenyl]-2-pyridine sulfonamide | Single enantiomer; Prepared from amine derived from Isomer 1 of Preparation 144 |
| 321 | 515.2463 (EI) | 5-Amino-N-[3(R or S)-(1-[5,6-dihydro-6,6-dipropyl-4-hydroxy-2-oxo-2H-pyran-3-yl]-2,2-dimethyl-propyl)phenyl]-2-pyridine-sulfonamide | Single enantiomer; Prepared from amine derived from Isomer 2 of Preparation 144 |
| 322 | 525.2287 (EI) | 5-Cyano-N-[3(R or S)-(1-[5,6-dihydro-6,6-dipropyl-4-hydroxy-2-oxo-2H-pyran-3-yl]-2,2-dimethyl-propyl)phenyl]-2-pyridine-sulfonamide | Single enantiomer; Prepared from amine derived from Isomer 2 of Preparation 144 |
| 323 | 525.2288 (EI) | 5-Cyano-N-[3(R or S)-(1-[5,6-dihydro-6,6-dipropyl-4-hydroxy-2-oxo-2H-pyran-3-yl]-2,2-dimethyl-propyl)phenyl]-2-pyridine-sulfonamide | Single enantiomer; Prepared from amine derived from Isomer 1 of Preparation 144 |
| 324 | 600.2537 (FAB) | N-[3(R or S)-(1-[6,6-Bis(2-phenyl-ethyl)-5,6-dihydro-4-hydroxy-2-oxo-2H-pyran-3-yl]propyl)phenyl]-1-methyl-1H-imidazole-4-sulfonamide | Single enantiomer; Prepared from amine derived from Isomer 1 of Preparation 145 |
| 325 | 600.2537 (FAB) | N-[3(R or S)-(1-[6,6-Bis(2-phenyl-ethyl)-5,6-dihydro-4-hydroxy-2-oxo-2H-pyran-3-yl]propyl)phenyl]-1-methyl-1H-imidazole-4-sulfonamide | Single enantiomer; Prepared from amine derived from Isomer 2 of Preparation 145 |
| 326 | 622.2378 (FAB) | N-[3(R or S)-(1-[6,6-Bis(2-phenyl-ethyl)-5,6-dihydro-4-hydroxy-2-oxo-2H-pyran-3-yl]propyl)phenyl]-5-cyano-2-pyridinesulfonamide | Single enantiomer; Prepared from amine derived from Isomer 1 of Preparation 145 |
| 327 | 622.2367 (FAB) | N-[3(R or S)-(1-[6,6-Bis(2-phenyl-ethyl)-5,6-dihydro-4-hydroxy-2-oxo-2H-pyran-3-yl]propyl)phenyl]-5-cyano-2-pyridinesulfonamide | Single enantiomer; Prepared from amine derived from Isomer 2 of Preparation 145 |

What is claimed is:
1. A compound of the formula I

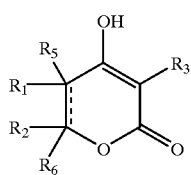

I wherein $R_1$ is H—;
wherein $R_2$ is
  a) $C_3$–$C_5$ alkyl,
  b) phenyl-$(CH_2)_2$—,
  c) het-$SO_2NH$—$(CH_2)_2$—,
  d) cyclopropyl-$(CH_2)_2$—,
  e) F-phenyl-$(CH_2)_2$—,
  f) het-$SO_2NH$-phenyl-, or
  g) $F_3C$—$(CH_2)_2$—;
or wherein $R_1$ and $R_2$ taken together are a double bond;
wherein $R_3$ is the moiety of formula X

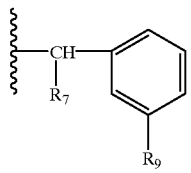

X wherein $R_4$ is
  a) phenyl,
  b) het,
  c) cyclopropyl,
  d) $H_3C$—$[O(CH_2)_2]_2$—,
  e) het-$SO_2NH$—,
  f) Br—,
  g) $N_3$—, or
  h) $HO_3S(CH_2)_2$—$N(CH_3)$—$C(O)$—$(CH_2)_6$—$C(O)$—NH—;
wherein $R_5$ is —H;
wherein $R_6$ is
  a) $R_4$—$(CH_2)_n$—$CH(R_8)$—,
  b) $H_3C$—$[O(CH_2)_2]_2$—$CH_2$—,
  c) $C_3$–$C_5$ alkyl,
  d) phenyl-$(CH_2)_2$—,
  e) het-$SO_2NH$—$(CH_2)_2$—,
  f) $(HOCH_2)_3C$—NH—$C(O)$—NH—$(CH_2)_3$—,
  g) $(HO_2C)(H_2N)CH$—$(CH_2)_2$—$C(O)$—NH—$(CH_2)_3$—,
  h) piperazin-1-yl-$C(O)$—NH—$(CH_2)_3$,
  i) $HO_3S(CH_2)_2$—$N(CH_3)$—$C(O)$—$(CH_2)_6$—$C(O)$—NH—$(CH_2)_3$—,
  j) cyclopropyl-$(CH_2)_2$—,
  k) F-phenyl-$(CH_2)_2$—,
  l) het-$SO_2NH$-phenyl, or
  m) $F_3C$—$(CH_2)_2$—;
wherein n is zero (0), one (1) or two (2);
wherein $R_7$ is
  a) cyclopropyl,
  b) $CH_3$—$CH_2$—, or
  c) t-butyl;
wherein $R_8$ is
  a) —$CH_2$—$CH_3$, or
  b) —$CH_2$-cyclopropyl;
wherein $R_9$ is
  a) —$NR_{12}SO_2$-het,
  b) —$NR_{12}SO_2$-phenyl substituted by zero (0) or one (1) $R_{11}$,
  c) —$CH_2$—$SO_2$-phenyl substituted by zero (0) or one (1) $R_1$ 1, or
  d) —$CH_2$—$SO_2$-het; wherein het is pyridinyl, imidazolyl, benzimidazolyl, quinolinyl, pyrimidinyl, pyrazinyl, pyrazolyl, thiazolyl, purinyl, tetrahydropyranyl or quinazolinyl; substituted by zero (0) or one (1) $R_{10}$;

wherein $R_{10}$ is
a) —$CH_3$,
b) —CN,
c) —OH,
d) —$C(O)OC_2H_5$,
e) —$CF_3$,
f) —$NH_2$, or
g) —$C(O)$—$NH_2$;
wherein $R_{11}$ is
a) —CN,
b) —F,
c) —OH, or
d) —$NO_2$;
wherein $R_{12}$ is
a) —H, or
b) —$CH_3$;
or a pharmaceutically acceptable salt thereof.

2. The compound of claim 1 of the formula I

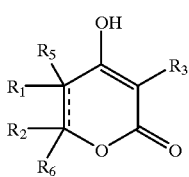

I wherein $R_1$ is H—;
wherein $R_2$ is
a) $C_3$–$C_5$ alkyl,
b) phenyl-$(CH_2)_2$—, or
c) het-$SO_2NH$—$(CH_2)_2$—;
or wherein $R_1$ and $R_2$ taken together are a double bond;
wherein $R_3$ is the moiety of formula X

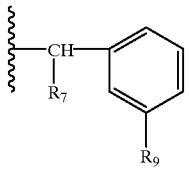

X wherein $R_4$ is
a) phenyl,
b) het,
c) cyclopropyl,
d) $H_3C$—$[O(CH_2)_2]_2$—,
e) het-$SO_2NH$—,
f) Br—,
g) $N_3$—, or
h) $HO_3S(CH_2)_2$—$N(CH_3)$—$C(O)$—$(CH_2)_6$—$C(O)$—NH—;
wherein $R_5$ is —H;
wherein $R_6$ is
a) $R_4$—$(CH_2)_n$—$CH(R_8)$—,
b) $H_3C$—$[O(CH_2)_2]_2$—$CH_2$—,
c) $C_3$–$C_5$ alkyl,
d) phenyl-$(CH_2)_2$—,
e) het-$SO_2NH$—$(CH_2)_2$—, f) $(HOCH_2)_3C$—NH—$C(O)$—NH—$(CH_2)_3$—,
g) $(HO_2C)(H_2N)CH$—$(CH_2)_2$—$C(O)$—NH—$(CH_2)_3$—,
h) piperazin-1-yl-$C(O)$—NH—$(CH_2)_3$, or
i) $HO_3S(CH_2)_2$—$N(CH_3)$—$C(O)$—$(CH_2)_6$—$C(O)$—NH—$(CH_2)_3$—;
wherein n is zero (0), one (1) or two (2);
wherein $R_7$ is
a) cyclopropyl,
b) $CH_3$—$CH_2$—, or
c) t-butyl;
wherein $R_8$ is
a) —$CH_2$—$CH_3$, or
b) —$CH_2$-cyclopropyl;
wherein $R_9$ is
a) —$NR_{12}SO_2$-het,
b) —$NR_{12}SO_2$-phenyl substituted by zero (0) or one (1) $R_{11}$,
c) —$CH_2$-$SO_2$-phenyl substituted by zero (0) or one (1) $R_{11}$, or
d) —$CH_2$—$SO_2$-het;
wherein het is pyridinyl, imidazolyl, benzimidazolyl, quinolinyl, pyrimidinyl, pyrazinyl, pyrazolyl, thiazolyl, purinyl, tetrahydropyranyl or quinazolinyl; substituted by zero (0) or one (1) $R_{10}$;
wherein $R_{10}$ is
a) —$CH_3$,
b) —CN,
c) —OH, or
d) —$C(O)OC_2H_5$;
wherein $R_{11}$ is
a) —CN,
b) —F,
c) —OH, or
d) —$NO_2$;
wherein $R_{12}$ is
a) —H, or
b) —$CH_3$;
or a pharmaceutically acceptable salt thereof.

3. The compound of claim 2 wherein het is the following, substituted by zero (0) or one (1) $R_{10}$,
a) 2-pyridinyl,
b) imidazol-2-yl,
c) imidazol-4-yl,
d) benzimidazol-2-yl,
e) quinolin-8-yl,
f) quinolin-2-yl,
g) pyrimidin-2-yl,
h) quinazolin-2-yl,
i) purin-6-yl,
j) thiazol-2-yl,
k) thiazol-4-yl,
l) 2-pyrazolyl,
m) 2-pyrazinyl,
n) tetrahydropyran-4-yl, or
o) tetrahydropyran-3-yl.

4. The compound of claim 3 of the formula I

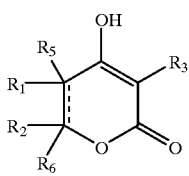

wherein $R_1$ is H—;
wherein $R_2$ is
  a) $H_3C—(CH_2)_2—$,
  b) phenyl-$(CH_2)_2—$,
  c) $(CH_3)_2CH—CH_2$, or
  d) pentyl;
or wherein $R_1$ and $R_2$ taken together are a double bond;
wherein $R_3$ is the moiety of formula X

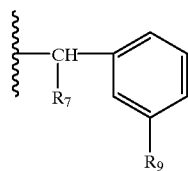

wherein $R_4$ is
  a) phenyl,
  b) het,
  c) cyclopropyl,
  d) $H_3C—[O(CH_2)_2]_2—$,
  e) het-$SO_2NH—$,
  f) Br—,
  g) $N_3—$, or
  h) $HO_3S(CH_2)_2—N(CH_3)—C(O)—(CH_2)_6—C(O)—NH—$;
wherein $R_5$ is —H;
wherein $R_6$ is
  a) $R_4—(CH_2)_n—CH(R_8)—$,
  b) $H_3C—[O(CH_2)_2]_2—CH_2—$,
  c) $H_3C—(CH_2)_2—$,
  d) phenyl-$(CH_2)_2—$,
  e) $(CH_3)_2CH—CH_2—$, or
  f) pentyl;
wherein n is zero (0), one (1) or two (2);
wherein $R_7$ is
  a) cyclopropyl, or
  b) $CH_3—CH_2—$;
wherein $R_8$ is
  a) —$CH_2$—$CH_3$, or
  b) —$CH_2$-cyclopropyl;
wherein $R_9$ is
  a) —$NHSO_2$-het, or
  b) —$NHSO_2$-phenyl substituted by zero (0) or one (1) $R_{11}$;
wherein het is the following, substituted by zero (0) or one (1) $R_{10}$,
  a) 2-pyridinyl,
  b) imidazol-2-yl,
  c) imidazol-4-yl,
  d) quinolin-8-yl,
  e) tetrahydropyran-4-yl,
  f) tetrahydropyran-3-yl, or
  g) benzimidazol-2-yl;
wherein $R_{10}$ is
  a) —$CH_3$;
wherein $R_{11}$ is
  a) —CN,
  b) —F or
  c) —$NO_2$;
or a pharmaceutically acceptable salt thereof.

5. The compound of claim 4 of the formula VI

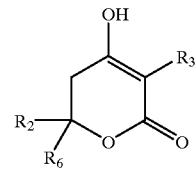

wherein $R_2$ is
  a) $H_3C—(CH_2)_2—$,
  b) phenyl-$(CH_2)_2—$,
  c) $(CH_3)_2CH—CH_2—$, or
  d) pentyl;
wherein $R_3$ is the moiety of formula X

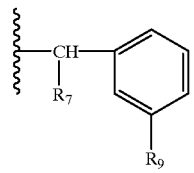

wherein $R_6$ is
  a) $H_3C—(CH_2)_2—$,
  b) phenyl-$(CH_2)_2—$,
  c) $(CH_3)_2CH—CH_2—$, or
  d) pentyl;
wherein $R_7$ is
  a) $CH_3—CH_2—$, or
  b) cyclopropyl;
wherein $R_9$ is
  a) —$NHSO_2$-phenyl substituted by one (1) $R_{11}$, or
  b) —$NHSO_2$-het;
wherein het is the following, substituted by zero (0) or one (1) $R_{10}$,
  a) imidazol-4-yl, or
  b) quinolin-8-yl;
wherein $R_{10}$ is —$CH_3$;
wherein $R_{11}$ is
  a) —CN, or
  b) —F.

6. The compound of claim 4 of the formula VII

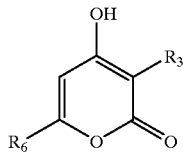

VII wherein R$_3$ is the moiety of formula X

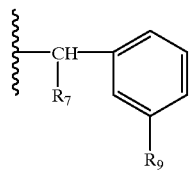

X wherein R$_4$ is
 a) phenyl,
 b) het,
 c) cyclopropyl,
 d) H$_3$C—[O(CH$_2$)$_2$]$_2$—,
 e) het-SO$_2$NH—,
 f) Br—,
 g) N$_3$—, or
 h) HO$_3$S(CH$_2$)$_2$—N(CH$_3$)—C(O)—(CH$_2$)$_6$—C(O)—NH—;
wherein R$_6$ is
 a) R$_4$—(CH$_2$)$_n$—CH(R,)—, or
 b) H$_3$C—[O(CH$_2$)$_2$]$_2$—CH$_2$—;
wherein R$_7$ is cyclopropyl;
wherein R$_8$ is
 a) —CH$_2$—CH$_3$, or
 b) —CH$_2$-cyclopropyl;
wherein R$_9$ is
 a) —NHSO$_2$-het, or
 b) —NHSO$_2$-phenyl substituted by one (1) R$_{11}$;
wherein n is zero (0), one (1) or two (2);
wherein het is the following, substituted by zero (0) or one (1) R$_{10}$,
 a) imidazol-4-yl,
 b) imidazol-2-yl,
 c) quinolin-8-yl,
 d) tetrahydropyran-3-yl,
 e) tetrahydropyran-4-yl,
 f) 2-pyridinyl, or
 g) benzimidazol-2-yl;
wherein R$_{10}$ is —CH$_3$;
wherein R$_{11}$ is
 a) —NO$_2$,
 b) —F, or
 c) —CN;
or a pharmaceutically acceptable salt thereof.

7. The compound of claim 2 selected from the group consisting of:
 3-[cyclopropyl[3-[(4-cyanophenylsulfonyl)methyl]phenyl]methyl]-4-hydroxy-6-(2-phenylethyl)-6-(1-propyl)-5,6-dihydro-2H-pyran-2-one;
 3-[cyclopropyl[3-[(2-pyridinylsulfonyl)methyl]phenyl]methyl]-4-hydroxy-6-(2-phenylethyl)-6-(1-propyl)-5,6-dihydro-2H-pyran-2-one;
 3-[cyclopropyl[3-[(1-methyl-4-imidazolylsulfonyl)methyl]phenyl]methyl]-4-hydroxy-6-(2-phenylethyl)-6-(1-propyl)-5,6-dihydro-2H-pyran-2-one;
 3-[cyclopropyl[3-[(5-cyano-2-pyridinylsulfonyl)methyl]phenyl]methyl]-4-hydroxy-6-(2-phenylethyl)-6-(1-propyl)-5,6-dihydro-2H-pyran-2-one;
 3-[cyclopropyl[3-[(2-benzimidazolylsulfonyl)methyl]phenyl]methyl]-4-hydroxy-6-(2-phenylethyl)-6-(1-propyl)-5,6-dihydro-2H-pyran-2-one;
 3-[cyclopropyl[3-[(2-quinolinylsulfonyl)methyl]phenyl]methyl]-4-hydroxy-6-(2-phenylethyl)-6-(1-propyl)-5,6-dihydro-2H-pyran-2-one;
 4-Cyano-N-[3-[1-(4-hydroxy-2-oxo-6-phenethyl-6-propyl-5,6-dihydro-2H-pyran-3-yl)-propyl]-phenyl]-benzenesulfonamide;
 N-[3-[1-(4-hydroxy-2-oxo-6-phenethyl-6-propyl-5,6-dihydro-2H-pyran-3-yl)-propyl]-phenyl]-1-methyl-1H-imidazole-4-sulfonamide;
 N-[3-[1-(4-hydroxy-2-oxo-6-phenethyl-6-propyl-5,6-dihydro-2H-pyran-3-yl)-propyl]-phenyl]-8-quinolinesulfonamide;
 N-[3-[1-(4-hydroxy-2-oxo-6,6-dipropyl-5,6-dihydro-2H-pyran-3-yl)-propyl]-phenyl]-8-quinolinesulfonamide;
 N-[3-[1-(4-hydroxy-2-oxo-6,6-dipropyl-5,6-dihydro-2H-pyran-3-yl)-propyl]-phenyl]-1-methyl-1H-imidazolesulfonamide;
 4-Fluoro-N-[3-[1-(4-hydroxy-2-oxo-6,6-dipropyl-5,6-dihydro-2H-pyran-3-yl)-propyl]-phenyl]-benzenesulfonamide;
 4-Cyano-N-[3-[1-(4-hydroxy-2-oxo-6,6-dipropyl-5,6-dihydro-2H-pyran-3-yl)-propyl]-phenyl]-benzenesulfonamide;
 N-[3-[1-(4-hydroxy-6,6-diisobutyl-2-oxo-5,6-dihydro-2H-pyran-3-yl)-propyl]-phenyl]-1-methyl-1H-imidazole-4-sulfonamide;
 N-[3-[1-(4-hydroxy-2-oxo-6,6-dipropyl-5,6-dihydro-2H-pyran-3-yl)-cyclo-propylmethyl]-phenyl]-1-methyl-1H-imidazolesulfonamide;
 N-[3-[1-(4-Hydroxy-2-oxo-6,6-dipropyl-5,6-dihydro-2H-pyran-3-yl)-cyclo-propylmethyl]-phenyl]-8-quinolinesulfonamide;
 4-Cyano-N-[3-[1-(4-hydroxy-2-oxo-6,6-dipropyl-5,6-dihydro-2H-pyran-3-yl)-cyclopropylmethyl]-phenyl]-benzenesulfonamide;
 4-Fluoro-N-[3-[1-(4-hydroxy-2-oxo-6,6-dipropyl-5,6-dihydro-2H-pyran-3-yl)-cyclopropylmethyl]-phenyl]-benzenesulfonamide;
 (R or S)-N-[3-[1-(4-Hydroxy-2-oxo-6,6-dipropyl-5,6-dihydro-2H-pyran-3-yl)-propyl]-phenyl]-8-quinolinesulfonamide;
 (R or S)-N-[3-[1-(4-hydroxy-2-oxo-6,6-dipropyl-5,6-dihydro-2H-pyran-3-yl)-propyl]-phenyl]-1-methyl-1H-imidazole-4-sulfonamide;
 (S or R)-N-[3-[1-(4-Hydroxy-2-oxo-6,6-dipropyl-5,6-dihydro-2H-pyran-3-yl)-propyl]-phenyl]-8-quinolinesulfonamide;
 (S or R)-N-[3-[1-(4-Hydroxy-2-oxo-6,6-dipropyl-5,6-dihydro-2H-pyran-3-yl)-propyl]-phenyl]-1-methyl-1H-imidazole-4-sulfonamide;
 (R or S)-N-[3-[1-(4-Hydroxy-2-oxo-6,6-dipropyl-5,6-dihydro-2H-pyran-3-yl)-cyclopropylmethyl]-phenyl]-1-methyl-1H-imidazole-4-sulfonamide;

(S or R)-N-[3-[1-(4-Hydroxy-2-oxo-6,6-dipropyl-5,6-dihydro-2H-pyran-3-yl)-cyclopropylmethyl]-phenyl]-1-methyl-1H-imidazole-4-sulfonamide;

4-Cyano-N-[3-[1-(4-Hydroxy-2-oxo-6-phenethyl-6-propyl-5,6-dihydro-2H-pyran-3-yl)-cyclopropylmethyl]-phenyl]-benzenesulfonamide;

4-Fluoro-N-[3-[1-(4-Hydroxy-2-oxo-6-phenethyl-6-propyl-5,6-dihydro-2H-pyran-3-yl)-cyclopropylmethyl]-phenyl]-benzenesulfonamide;

N-[3-[1-(4-Hydroxy-2-oxo-6-phenethyl-6-propyl-5,6-dihydro-2H-pyran-3-yl)-cyclopropylmethyl]-phenyl]-8-quinolinesulfonamide;

N-[3-[1-(4-Hydroxy-2-oxo-6-phenethyl-6-propyl-5,6-dihydro-2H-pyran-3-yl)-cyclopropylmethyl]-phenyl]-1-methyl-1H-imidazole-4-sulfonamide;

N-[3-[1-(4-Hydroxy-2-oxo-6,6-diphenethyl-5,6-dihydro-2H-pyran-3-yl)-cyclopropylmethyl]-phenyl]-1-methyl-1H-imidazole-4-sulfonamide;

N-[3-[1-(4-Hydroxy-2-oxo-6,6-dipentyl-5,6-dihydro-2H-pyran-3-yl)-propyl]-phenyl]-1-methyl-1H-imidazole-4-sulfonamide;

4-Cyano-N-[3-[1-(4-Hydroxy-2-oxo-6,6-dipentyl-5,6-dihydro-2H-pyran-3-yl)-propyl]-phenyl]-benzenesulfonamide;

N-[3-[1(R or S)-(6(R or S)-4-Hydroxy-2-oxo-6-phenethyl-6-propyl-5,6-dihydro-2H-pyran-3-yl)-propyl]-phenyl]-1-methyl-1H-imidazole-4-sulfonamide;

N-[3-[1(R or S)-(6(S or R)-4-Hydroxy-2-oxo-6-phenethyl-6-propyl-5,6-dihydro-2H-pyran-3-yl)-propyl]-phenyl]-1-methyl-1H-imidazole-4-sulfonamide;

N-[3-[1(S or R)-(6(R or S)-4-Hydroxy-2-oxo-6-phenethyl-6-propyl-5,6-dihydro-2H-pyran-3-yl)-propyl]-phenyl]-1-methyl-1H-imidazole-4-sulfonamide;

N-[3-[1(S or R)-(6(S or R)-4-Hydroxy-2-oxo-6-phenethyl-6-propyl-5,6-dihydro-2H-pyran-3-yl)-propyl]-phenyl]-1-methyl-1H-imidazole-4-sulfonamide;

N-[3-[t-Butyl-(4-hydroxy-2-oxo-6-phenethyl-6-propyl-5,6-dihydro-2H-pyran-3-yl)-methyl]-phenyl]-1-methyl-1H-imidazole-4-sulfonamide;

4-Cyano-N-[3-[t-butyl-(4-hydroxy-2-oxo-6-phenethyl-6-propyl-5,6-dihydro-2H-pyran-3-yl)-methyl]-phenyl]-benzenesulfonamide;

4-Fluoro-N-[3-[t-butyl-(4-hydroxy-2-oxo-6-phenethyl-6-propyl-5,6-dihydro-2H-pyran-3-yl)-methyl]-phenyl]-benzenesulfonamide;

N-[3-[t-Butyl-(4-hydroxy-2-oxo-6-phenethyl-6-propyl-5,6-dihydro-2H-pyran-3-yl)-methyl]-phenyl]-8-quinolinesulfonamide;

N-[3-[1-(6-(2-(1-Methyl-1H-imidazole-4-sulfonylamino)-ethyl)-4-hydroxy-2-oxo-6-propyl-5,6-dihydro-2H-pyran-3-yl)-propyl]-phenyl]-1-methyl-1H-imidazole-4-sulfonamide;

N-[3-[1-(4-Hydroxy-2-oxo-6,6-diphenethyl-5,6-dihydro-2H-pyran-3-yl)-propyl]-phenyl]-2-pyridinesulfonamide;

4-Cyano-N-[3-[1-(4-hydroxy-2-oxo-6,6-diphenethyl-5,6-dihydro-2H-pyran-3-yl)-propyl]-phenyl]-2-pyridinesulfonamide;

N-[3-[1-(4-Hydroxy-2-oxo-6,6-diphenethyl-5,6-dihydro-2H-pyran-3-yl)-propyl]-phenyl]-2-quinolinesulfonamide;

2-Hydroxy-N-[3-[1-(4-hydroxy-2-oxo-6,6-diphenethyl-5,6-dihydro-2H-pyran-3-yl)-propyl]-phenyl]-benzenesulfonamide;

N-[3-[1-(4-Hydroxy-2-oxo-6,6-diphenethyl-5,6-dihydro-2H-pyran-3-yl)-propyl]-phenyl]-2-pyrimidinesulfonamide;

N-[3-[1-(4-Hydroxy-2-oxo-6,6-diphenethyl-5,6-dihydro-2H-pyran-3-yl)-propyl]-phenyl]-2-quinazolinesulfonamide;

N-[3-[1-(4-Hydroxy-2-oxo-6,6-diphenethyl-5,6-dihydro-2H-pyran-3-yl)-propyl]-phenyl]-7H-purine-6-sulfonamide;

N-[3-[1-(4-Hydroxy-2-oxo-6,6-diphenethyl-5,6-dihydro-2H-pyran-3-yl)-propyl]-phenyl]-1H-imidazole-2-sulfonamide;

N-[3-[1-(4-Hydroxy-2-oxo-6,6-diphenethyl-5,6-dihydro-2H-pyran-3-yl)-propyl]-phenyl]-1H-benzimidazole-2-sulfonamide;

N-[3-[1-(4-Hydroxy-2-oxo-6,6-diphenethyl-5,6-dihydro-2H-pyran-3-yl)-propyl]-phenyl]-thiazole-4-sulfonamide;

N-[3-[1-(4-Hydroxy-2-oxo-6-phenethyl-6-propyl-5,6-dihydro-2H-pyran-3-yl)-propyl]-phenyl]-2-pyridinesulfonamide;

4-Cyano-N-[3-[1-(4-hydroxy-2-oxo-6-phenethyl-6-propyl-5,6-dihydro-2H-pyran-3-yl)-propyl]-phenyl]-2-pyridinesulfonamide;

N-[3-[1-(4-Hydroxy-2-oxo-6-phenethyl-6-propyl-5,6-dihydro-2H-pyran-3-yl)-propyl]-phenyl]-2-quinolinesulfonamide;

2-Hydroxy-N-[3-[1-(4-hydroxy-2-oxo-6-phenethyl-6-propyl-5,6-dihydro-2H-pyran-3-yl)-propyl]-phenyl]-benzenesulfonamide;

N-[3-[1-(4-Hydroxy-2-oxo-6-phenethyl-6-propyl-5,6-dihydro-2H-pyran-3-yl)-propyl]-phenyl]-2-pyrimidinesulfonamide;

N-[3-[1-(4-Hydroxy-2-oxo-6-phenethyl-6-propyl-5,6-dihydro-2H-pyran-3-yl)-propyl]-phenyl]-2-quinazolinesulfonamide;

N-[3-[1-(4-Hydroxy-2-oxo-6-phenethyl-6-propyl-5,6-dihydro-2H-pyran-3-yl)-propyl]-phenyl]-7H-purine-6-sulfonamide;

N-[3-[1-(4-Hydroxy-2-oxo-6-phenethyl-6-propyl-5,6-dihydro-2H-pyran-3-yl)-propyl]-phenyl]-1H-imidazole-2-sulfonamide;

N-[3-[1-(4-Hydroxy-2-oxo-6-phenethyl-6-propyl-5,6-dihydro-2H-pyran-3-yl)-propyl]-phenyl]-1H-benzimidazole-2-sulfonamide;

N-[3-[1-(4-Hydroxy-2-oxo-6-phenethyl-6-propyl-5,6-dihydro-2H-pyran-3-yl)-propyl]-phenyl]-thiazole-4-sulfonamide;

4-Fluoro-N-[3-[1-(4-hydroxy-2-oxo-6-phenethyl-6-propyl-5,6-dihydro-2H-pyran-3-yl)-propyl]-phenyl]-benzenesulfonamide;

5-cyano-N-[3-[1-(4-hydroxy-2-oxo-6,6-diphenethyl-5,6-dihydro-2H-pyran-3-yl)-propyl]-phenyl]-N-methyl-2-pyridinesulfonamide;

N-[3-[1-(4-hydroxy-2-oxo-6,6-diphenethyl-5,6-dihydro-2H-pyran-3-yl)-propyl]-phenyl]-N-methyl-2-quinolinesulfonamide;

N-[3-[1-(4-hydroxy-2-oxo-6,6-diphenethyl-5,6-dihydro-2H-pyran-3-yl)-propyl]-phenyl]-N-methyl-2-imidazolesulfonamide;

N-[3-[1-(4-hydroxy-2-oxo-6,6-diphenethyl-5,6-dihydro-2H-pyran-3-yl)-propyl]-phenyl]-N-methyl-2-pyrimidinesulfonamide;

N-[3-[1-(4-hydroxy-2-oxo-6,6-diphenethyl-5,6-dihydro-2H-pyran-3-yl)-propyl]-phenyl]-N-methyl-2-benzimidazolesulfonamide;

N-[3-[1-(4-hydroxy-2-oxo-6,6-diphenethyl-5,6-dihydro-2H-pyran-3-yl)-propyl]-phenyl]-N-methyl-2-quinazolinesulfonamide;

N-[3-[1-(4-hydroxy-2-oxo-6,6-diphenethyl-5,6-dihydro-2H-pyran-3-yl)-propyl]-5 phenyl]-N-methyl-6-purinesulfonamide;

N-[3-[1-(4-hydroxy-2-oxo-6,6-diphenethyl-5,6-dihydro-2H-pyran-3-yl)-propyl]-phenyl]-N-methyl-4-thiazolesulfonamide;

N-[3-[1-(4-hydroxy-2-oxo-6,6-diphenethyl-5,6-dihydro-2H-pyran-3-yl)-propyl]-phenyl]-N-methyl-2-pyridinesulfonamide;

N-[3-(1-[5,6-Dihydro-4-hydroxy-2-oxo-6-(2-phenethyl)-6-propyl-2H-pyran-3-yl]-2,2-dimethylpropyl)phenyl]-1-methyl-1H-imidazole-4-sulfonamide;

N-[3-(1(S)-[5,6-dihydro-4-hydroxy-2-oxo-6(R)-(2-phenethyl)-6-propyl-2H-pyran-3-yl]-2,2-dimethylpropyl)phenyl]-1-methyl-1H-imidazole-4-sulfonamide;

N-[3-(1(R)-[5,6-dihydro-4-hydroxy-2-oxo-6(R)-(2-phenethyl)-6-propyl-2H-pyran-3-yl]-2,2-dimethylpropyl)phenyl]-1-methyl-1H-imidazole-4-sulfonamide;

N-[3-(1(S)-[5,6-dihydro-4-hydroxy-2-oxo-6(S)-(2-phenethyl)-6-propyl-2H-pyran-3-yl]-2,2-dimethylpropyl)phenyl]-1-methyl-1H-imidazole-4-sulfonamide;

N-[3-(1(R)-[5,6-dihydro-4-hydroxy-2-oxo-6(S)-(2-phenethyl)-6-propyl-2H-pyran-3-yl]-2,2-dimethylpropyl)phenyl]-1-methyl-1H-imidazole-4-sulfonamide;

N-[3-{1-(4-Hydroxy-5,6-dihydro-2-oxo-6,6-dipropyl-2H-pyran-3-yl)-2,2-dimethylpropyl}phenyl]-1-methyl-1H-imidazole-4-sulfonamide;

N-[3-{1-(4-Hydroxy-5,6-dihydro-2-oxo-6,6-dipropyl-2H-pyran-3-yl)-2,2-dimethylpropyl}phenyl]-5-cyanopyridine-2-sulfonamide;

5-Cyano-N-[3-(1-[5,6-dihydro-4-hydoxy-2-oxo-6-(2-phenethyl)-6-propyl-2H-pyran-3-yl]-2,2-dimethylpropyl)phenyl]-2-pyridinesulfonamide;

N-[3-{1-(4-Hydroxy-5,6-dihydro-2-oxo-6-phenethyl-6-propyl-2H-pyran-3-yl)propyl}phenyl]-5-cyanopyridine-2-sulfonamide; and N-[3-{1-(4-Hydroxy-5,6-dihydro-2-oxo-6,6-dipropyl-2H-pyran-3-yl)propyl}phenyl]-5-cyanopyridine-2-sulfonamide.

8. The compound of claim 2 selected from the group consisting of:

3-[cyclopropyl[3-[(4-cyanophenylsulfonyl)methyl]phenyl]methyl]-4-hydroxy-6-[1-(phenylmethyl)propyl]-2H-pyran-2-one;

3-[cyclopropyl[3-[(2-pyridinylsulfonyl)methylphenylmethyl]-4-hydroxy-6-[1-(phenylmethyl)propyl]-2H-pyran-2-one;

3-[cyclopropyl[3-[(1-methyl-4-imidazolylsulfonyl)methyl]phenyl]methyl)-4-hydroxy-6-[1-(phenylmethyl)propyl]-2H-pyran-2-one;

3-[cyclopropyl[3-[(5-cyano-2-pyridinylsulfonyl)methyl]phenyl]methyl]-4-hydroxy-6-[1-(phenylmethyl)propyl]-2H-pyran-2-one;

3-[cyclopropyl[3-[(2-benzimidazolylsulfonyl)methyl]phenyl]methyl]-4-hydroxy-6-[1-(phenylmethyl)propyl]-2H-pyran-2-one;

3-[cyclopropyl[3-[(2-quinolinylsulfonyl)methyl]phenyl]methyl]-4-hydroxy-6-[1-(phenylmethyl)propyl]-2H-pyran-2-one;

N-(3-{Cyclopropyl-[6-(2-cyclopropyl-1-cyclopropylmethyl-ethyl)-4-hydroxy-2-oxo-2H-pyran-3-yl]-methyl}-phenyl)-4-fluoro-benzenesulfonamide;

4-Cyano-N-(3-{cyclopropyl-[6-(2-cyclopropyl-1-cyclopropylmethyl-ethyl)-4-hydroxy-2-oxo-2H-pyran-3-yl]-methyl}-phenyl)-benzenesulfonamide;

N-(3-{Cyclopropyl-[6-(2-cyclopropyl-1-cyclopropylmethyl-ethyl)-4-hydroxy-2-oxo-2H-pyran-3-yl]-methyl}-phenyl)-8-quinolinesulfonamide;

N-(3-{Cyclopropyl-[6-(2-cyclopropyl-1-cyclopropylmethyl-ethyl)-4-hydroxy-2-oxo-2H-pyran-3-yl]-methyl]-phenyl)-1-methyl-1H-imidazole-4-sulfonamide;

(R or S)-N-(3-{Cyclopropyl-[6-(2-cyclopropyl-1-cyclopropylmethyl-ethyl)-4-hydroxy-2-oxo-2H-pyran-3-yl]-methyl]-phenyl)-1-methyl-1H-imidazole-4-sulfonamide;

(R or S)-N-(3-{Cyclopropyl-[6-(2-cyclopropyl-1-cyclopropylmethyl-ethyl)-4-hydroxy-2-oxo-2H-pyran-3-yl]-methyl}-phenyl)-1-methyl-1H-imidazole-4-sulfonamide;

N-(3-{Cyclopropyl-[6-(2-cyclopropyl-1-cyclopropylmethyl-ethyl)-4-hydroxy-2-oxo-2H-pyran-3-yl]-methyl]-phenyl)-2-pyridinesulfonamide;

N-(3-{Cyclopropyl-[6-(2-cyclopropyl-1-cyclopropylmethyl-ethyl)-4-hydroxy-2-oxo-2H-pyran-3-yl]-methyl}-phenyl)-1-methyl-1H-imidazole-2-sulfonamide;

N-(3-{Cyclopropyl-[6-(2-cyclopropyl-1-cyclopropylmethyl-ethyl)-4-hydroxy-2-oxo-2H-pyran-3-yl]-methyl}-phenyl)-1H-benzoimidazole-2-sulfonamide;

N-(3-{Cyclopropyl-[6-(2-cyclopropyl-1-cyclopropylmethyl-ethyl)-4-hydroxy-2-oxo-2H-pyran-3-yl]-methyl}-phenyl)-1H-imidazole-2-sulfonamide;

N-(3-{Cyclopropyl-[6-(2-cyclopropyl-1-cyclopropylmethyl-ethyl)-4-hydroxy-2-oxo-2H-pyran-3-yl]-methyl}-phenyl)-2-quinolinesulfonamide;

N-(3-{(Cyclopropyl-[4-hydroxy-6-(3-{2-methoxy-ethoxy}-propyl)-2-oxo-2H-pyran-3-yl]-methyl}-phenyl)-1-methyl-1H-imidazole-4-sulfonamide;

N-(3-{Cyclopropyl-[6-(1-ethyl-3-{2-methoxy-ethoxy}-propyl)-4-hydroxy-2-oxo-2H-pyran-3-yl]-methyl}-phenyl)-1-methyl-1H-imidazole-4-sulfonamide;

4-Cyano-N-(3-{cyclopropyl-[6-(1-ethyl-3-{2-methoxy-ethoxy}-propyl)-4-hydroxy- 2-oxo-2H-pyran-3-yl]-methyl}-phenyl)-benzenesulfonamide;

N-(3-{Cyclopropyl-[6-(1-ethyl-3-{1-methyl-1H-imidazole-4-sulfonylamino}-propyl)-4-hydroxy-2-oxo-2H-pyran-3-yl-methyl}-phenyl)-1-methyl-H-imidazole-4-sulfonamide;

N-(3-{[6-(3-Bromo-1-ethyl-propyl)-4-hydroxy-2-oxo-2H-pyran-3-yl]-cyclopropyl-methyl}-phenyl)-1-methyl-1H-imidazole-4-sulfonamide;

N-(3-{[6-(3-Azido-1-ethyl-propyl)-4-hydroxy-2-oxo-2H-pyran-3-yl]-cyclopropyl-methyl)-phenyl)-1-methyl-1H-imidazole-4-sulfonamide;

2-[[8-[[3-3-[Cyclopropyl[3-[[(1-methyl-1H-imidazol-4-yl)sulfonyl]aminolphenyl]methyl]-4-hydroxy-2-oxo- 2H-pyran-6-yl]pentyl]amino]-1,8-dioxooctyl] methylamino]-ethane sulfonic acid, monosodium salt;

N-(3-{Cyclopropyl-[4-hydroxy-6-(3-[(2-hydroxy-1,1-bisfhydroxymethyl}-ethyl)-amino]-carbonyl}-amino-propyl)-2-oxo-2H-pyran-3-yl]-methyl}-phenyl)-benzenesulfonamide;

N-(3-{Cyclopropyl-[4-hydroxy-6-(3-{[(2-hydroxy-1,1-bis{hydroxymethyl}-ethyl)-amino]-carbonyl}-amino-propyl)-2-oxo-2H-pyran-3-yl]-methyl}-phenyl)-2-pyridinesulfonamide;

N-(3-{Cyclopropyl-[4-hydroxy-6-(3-{(2-hydroxy-1,1-bisthydroxymethyl}-ethyl)-amino-carbonyl}-amino-propyl)-2-oxo-2H-pyran-3-yl]-methyl}-phenyl)-1H-imidazole-2-sulfonamide;

N-(3-Cyclopropyl-[4-hydroxy-6-(3-{[(2-hydroxy-1,1-bis{hydroxymethyl}-ethyl)-amino]-carbonyl}-amino-propyl)-2-oxo-2H-pyran-3-yl]-methyl}-phenyl)-1H-benzoimidazole-2-sulfonamide;

N-(3-{Cyclopropyl-[4-hydroxy-6-(3-{[(2-hydroxy-1,1-bis{hydroxymethyl}-ethyl)-amino]-carbonyl}-amino-propyl)-2-oxo-2H-pyran-3-yl]-methyl}-phenyl)-1-methyl-1H-imidazole-4-sulfonamide;

N-(3-{Cyclopropyl-[4-hydroxy-6-(3-{[(2-hydroxy-1,1-bis{hydroxymethyl}-ethyl)-amino]-carbonyl}-amino-propyl)-2-oxo-2H-pyran-3-yl]-methyl}-phenyl)-1-methyl-1H-imidazole-2-sulfonamide;

N-(3-{Cyclopropyl-[4-hydroxy-6-(3-{γ-L-glutamyl}-amino-propyl)-2-oxo-2H-pyran-3-yl]-methyl}-phenyl)-benzenesulfonamide;

N-(3-{Cyclopropyl-[4-hydroxy-6-(3-{γ-L-glutamyl}-amino-propyl)-2-oxo-2H-pyran-3-yl]-methyl}-phenyl)-2-pyridinesulfonamide;

N-(3-{Cyclopropyl-[4-hydroxy-6-(3-{γ-L-glutamyl}-amino-propyl)-2-oxo-2H-pyran-3-yl]-methyl}-phenyl)-1H-imidazole-sulfonamide;

N-(3-{Cyclopropyl-[4-hydroxy-6-(3-{γ-L-glutamyl}-amino-propyl)-2-oxo-2H-pyran-3-yl]-methyl}-phenyl)-1H-benzoimidazole-sulfonamide;

N-(3-{Cyclopropyl-[4-hydroxy-6-(3-{γ-L-glutamyl}-amino-propyl)-2-oxo-2H-pyran-3-yl]-methyl}-phenyl)-1-methyl-1H-imidazole-4-sulfonamide;

N-(3-{Cyclopropyl-[4-hydroxy-6-(3-{γ-L-glutamyl}-amino-propyl)-2-oxo-2H-pyran-3-yl]-methyl}-phenyl)-1-methyl-1H-imidazole-2-sulfonamide;

N-(3-{Cyclopropyl-[4-hydroxy-6-(3-{[piperazin-1-yl]-carbonyl}-amino-propyl)-2-oxo-2H-pyran-3-yl]-methyl}-phenyl)-benzenesulfonamide;

N-(3-{Cyclopropyl-[4-hydroxy-6-(3-{[piperazin-1-yl]-carbonyl}-amino-propyl)-2-oxo-2H-pyran-3-yl]-methyl}-phenyl)-2-pyridinesulfonamide;

N-(3-{Cyclopropyl-[4-hydroxy-6-(3-{[piperazin-1-yl]-carbonyl}-amino-propyl)-2-oxo-2H-pyran-3-yl]-methyl}-phenyl)-1H-imidazole-2-sulfonamide;

N-(3-{Cyclopropyl-[4-hydroxy-6-(3-{[piperazin-1-yl]-carbonyl}-amino-propyl)-2-oxo-2H-pyran-3-yl]-methyl}-phenyl)-1H-benzoimidazole-2-sulfonamide;

N-(3-{Cyclopropyl-[4-hydroxy-6-(3-{[piperazin-1-yl]-carbonyl}-amino-propyl)-2-oxo-2H-pyran-3-yl]-methyl}-phenyl)-1-methyl-1H-imidazole-4-sulfonamide;

N-(3-{Cyclopropyl-[4-hydroxy-6-(3-{[piperazin-1-yl]-carbonyl}-amino-propyl)-2-oxo-2H-pyran-3-yl]-methyl}-phenyl)-1-methyl-1H-imidazole-2-sulfonamide;

2-[[8-[[3-[3-[Cyclopropyl[3-[[phenylsulfonyl]amino] phenyl]methyl]-4-hydroxy-2-oxo-2H-pyran-6-yl] propyl]amino]-1,8-dioxooctyl]methylamino]-ethanesulfonic acid, monosodium salt;

2-[[8-[[3-[3-[Cyclopropyl[3-[[(2-pyridyl)sulfonyl]amino] phenyl]methyl]-4-hydroxy-2-oxo-2H-pyran-6-yl] propyl]amino]-1,8-dioxooctyl]methylamino]-ethane sulfonic acid, monosodium salt;

2-[[8-[[3-[3-[Cyclopropyl[3-[[(1H-benzimidazol-2-yl) sulfonyl]amino]phenyl]methyl]-4-hydroxy-2-oxo-2H-pyran-6-yl]propyl]amino]-1,8-dioxooctyl]methyl amino]-ethanesulfonic acid, monosodium salt;

2-[[8-[[3-[3-[Cyclopropyl[3-[[(1H-imidazol-2-yl) sulfonyl]amino]phenyl]methyl]-4-hydroxy-2-oxo-2H-pyran-6-yl]propyl]amino]-1,8-dioxooctyl] methylamino]-ethane sulfonic acid, monosodium salt;

2-[[8-[[3-[3-[Cyclopropyl[3-[[(1-methyl-1H-imidazol-4-yl)sulfonyl]amino]phenyl]methyl]-4-hydroxy-2-oxo-2H-pyran-6-yl]propyl]amino]-1,8-dioxooctyl] methylamino]-ethanesulfonic acid, monosodium salt;

2-[[8-[[3-[3-[Cyclopropyl[3-[[(1-methyl-1H-imidazol-2-yl)sulfonyl]amino]phenyl]methyl]-4-hydroxy-2-oxo-2H-pyran-6-yl]propyl]amino]-1,8 -dioxooctyl] methylamino]-ethane sulfonic acid, monosodium salt;

N-(3-{Cyclopropyl-[6-(1-(tetrahydropyran-4-ylmethyl)-propyl)-4-hydroxy-2-oxo-2H-pyran-3-yl]-methyl}-phenyl)-1-methyl-1H-imidazole-4-sulfonamide;

N-(3-{Cyclopropyl-[6-(1-ethylphenethyl)-4-hydroxy-2-oxo-2H-pyran-3-yl]-methyl}-phenyl)-1-methyl-1H-imidazole-4-sulfonamide;

N-(3-(R or S)-{Cyclopropyl-[6-(1-(R)-ethylphenethyl)-4-hydroxy-2-oxo-2H-pyran-3-yl]-methyl}-phenyl)-1-methyl-1H-imidazole-4-sulfonamide;

N-(3-(R or S)-{Cyclopropyl-[6-(1-(R)-ethylphenethyl)-4-hydroxy-2-oxo-2H-pyran-3-yl]-methyl}-phenyl)-1-methyl-1H-imidazole-4-sulfonamide;

N-(3-(R or S)-{Cyclopropyl-[6-(1-(S)-ethylphenethyl)-4-hydroxy-2-oxo-2H-pyran-3-yl]-methyl}-phenyl)-1-methyl-1H-imidazole-4-sulfonamide;

N-(3-(R or S)-{Cyclopropyl-[6-(1-(S)-ethylphenethyl)-4-hydroxy-2-oxo-2H-pyran-3-yl]-methyl}-phenyl)-1-methyl-1H-imidazole-4-sulfonamide;

N-(3-(R or S)-{Cyclopropyl-[6-(1-(R)-ethylphenethyl)-4-hydroxy-2-oxo-2H-pyran-3-yl]-methyl}-phenyl)-2-pyridinesulfonamide;

N-(3-(R or S)-{Cyclopropyl-[6-(1-(R)-ethylphenethyl)-4-hydroxy-2-oxo-2H-pyran-3-yl]-methyl}-phenyl)-2-pyridinesulfonamide;

N-(3-(R or S)-{Cyclopropyl-[6-(1-(R)-ethylphenethyl)-4-hydroxy-2-oxo-2H-pyran-3-yl]-methyl}-phenyl)-1-methyl-1H-imidazole-2-sulfonamide;

N-(3-(R or S)-{Cyclopropyl-[6-(1-(R)-ethylphenethyl)-4-hydroxy-2-oxo-2H-pyran-3-yl]-methyl}-phenyl)-1-methyl-1H-imidazole-2-sulfonamide;

N-(3-{Cyclopropyl-[6-(1-(tetrahydropyran-4-ylmethyl)-propyl)-4-hydroxy-2-oxo-2H-pyran-3-yl]-methyl}-phenyl)-1-methyl-1H-imidazole-2-sulfonamide;

N-(3-[Cyclopropyl[4-hydroxy-2-oxo-6-[1-[(tetrahydro-2H-pyran-3-yl)methyl]propyl]-2H-pyran-3-yl]methyl] phenyl]-8-quinolinesulfonamide;

N-(3-[Cyclopropyl[4-hydroxy-2-oxo-6-[1-[(tetrahydro-2H-pyran-3-yl)methyl]propyl]-2H-pyran-3-yl]methyl] phenyl]-1-methyl-1H-imidazole-4-sulfonamide;

N-(3-{Cyclopropyl-[6-(1-(R)-ethylphenethyl)-4-hydroxy-2-oxo-2H-pyran-3-yl]-methyl}-phenyl)-benzimidazole-2-sulfonamide;

N-(3-{Cyclopropyl-[6-(1-(R)-ethylphenethyl)-4-hydroxy-2-oxo-2H-pyran-3-yl]-methyl}-phenyl)-1H-imidazole-2-sulfonamide;

N-(3-(R or S)-{Cyclopropyl-[6-(1-(R)-ethylphenethyl)-4-hydroxy-2-oxo-2H-pyran-3-yl]-methyl}-phenyl)-4-cyanobenzenesulfonamide;

N-(3-(R or S)-{Cyclopropyl-[6-(1-(R)-ethylphenethyl)-4-hydroxy-2-oxo-2H-pyran- 3-yl]-methyl}-phenyl)-4-cyanobenzenesulfonamide;

N-(3-{Cyclopropyl-[6-(1-ethylphenethyl)-4-hydroxy-2-oxo-2H-pyran-3-yl]-methyl}-phenyl)-4-nitrobenzenesulfonamide;

N-(3-{Cyclopropyl-[6-(1-(tetrahydropyran-4-ylmethyl)-propyl)-4-hydroxy-2-oxo-2H-pyran-3-yl]-methyl}-phenyl)-2-pyridinesulfonamide;

N-(3-{Cyclopropyl-[6-(1-(tetrahydropyran-4-ylmethyl)-propyl)-4-hydroxy-2-oxo-2H-pyran-3-yl]-methyl}-phenyl)-4-cyano-2-pyridinesulfonamide;

N-(3-{Cyclopropyl-[6-(1-(tetrahydropyran-4-ylmethyl)-propyl)-4-hydroxy-2-oxo-2H-pyran-3-yl]-methyl}-phenyl)-2-quinolinesulfonamide;

N-(3-{Cyclopropyl-[6-(1-(tetrahydropyran-4-ylmethyl)-propyl)-4-hydroxy-2-oxo-2H-pyran-3-yl]-methyl}-phenyl)-2-hydroxybenzenesulfonamide;

N-(3-{Cyclopropyl-[6-(1-(tetrahydropyran-4-ylmethyl)-propyl)-4-hydroxy-2-oxo-2H-pyran-3-yl]-methyl}-phenyl)-2-pyrazolesulfonamide;

N-(3-{Cyclopropyl-[6-(1-(tetrahydropyran-4-ylmethyl)-propyl)-4-hydroxy-2-oxo-2H-pyran-3-yl]-methyl}-phenyl)-2-quinazolinesulfonamide;

N-(3-{Cyclopropyl-[6-(1-(tetrahydropyran-4-ylmethyl)-propyl)-4-hydroxy-2-oxo-2H-pyran-3-yl]-methyl}-phenyl)-7H-purine-6-sulfonamide;

N-(3-{Cyclopropyl-[6-(1-(tetrahydropyran-4-ylmethyl)-propyl)-4-hydroxy-2-oxo-2H-pyran-3-yl]-methyl}-phenyl)-1H-imidazole-2-sulfonamide;

N-(3-{Cyclopropyl-[6-(1-(tetrahydropyran-4-ylmethyl)-propyl)-4-hydroxy-2-oxo-2H-pyran-3-yl]-methyl}-phenyl)-benzimidazole-2-sulfonamide;

N-(3-{Cyclopropyl-[6-(1-(tetrahydropyran-4-ylmethyl)-propyl)-4-hydroxy-2-oxo-2H-pyran-3-yl]-methyl}-phenyl)-thiazole-4-sulfonamide;

N-(3-{Cyclopropyl-[6-(1-(tetrahydropyran-4-ylmethyl)-propyl)-4-hydroxy-2-oxo-2H-pyran-3-yl]-methyl}-phenyl)-4-ethoxycarbonyl-1H-imidazole-2-sulfaonamide;

N-(3-{Cyclopropyl-[6-(1-(tetrahydropyran-4-ylmethyl)-propyl)-4-hydroxy-2-oxo-2H-pyran-3-yl]-methyl}-phenyl)-3-hydroxy-2-pyridinesulfonamide;

N-(3-{Cyclopropyl-[6-(1-ethylphenethyl)-4-hydroxy-2-oxo-2H-pyran-3-yl]-methyl}-phenyl)-2-pyridinesulfonamide;

N-(3-{Cyclopropyl-[6-(1-ethylphenethyl)-4-hydroxy-2-oxo-2H-pyran-3-yl]-methyl}-phenyl)-4-cyano-2-pyridinesulfonamide;

N-(3-{Cyclopropyl-[6-(1-ethylphenethyl)-4-hydroxy-2-oxo-2H-pyran-3-yl]-methyl}-phenyl)-2-quinolinesulfonamide;

N-(3-{Cyclopropyl-[6-(1-ethylphenethyl)-4-hydroxy-2-oxo-2H-pyran-3-yl]-methyl}-phenyl)-2-hydroxybenzenesulfonamide;

N-(3-{Cyclopropyl-[6-(1-ethylphenethyl)-4-hydroxy-2-oxo-2H-pyran-3-yl]-ethyl}-phenyl)-2-pyrazolesulfonamide;

N-(3-{Cyclopropyl-[6-(1-ethylphenethyl)-4-hydroxy-2-oxo-2H-pyran-3-yl]-ethyl}-phenyl)-2-quinazolinesulfonamide;

N-(3-{Cyclopropyl-[6-(1-ethylphenethyl)-4-hydroxy-2-oxo-2H-pyran-3-yl]-ethyl}-phenyl)-7H-purine-6-sulfonamide;

N-(3-{Cyclopropyl-[6-(1-ethylphenethyl)-4-hydroxy-2-oxo-2H-pyran-3-yl]-methyl}-phenyl)-1H-imidazole-2-sulfonamide;

N-(3-{Cyclopropyl-[6-(1-ethylphenethyl)-4-hydroxy-2-oxo-2H-pyran-3-yl]-methyl}-phenyl)-benzimidazole-2-sulfonamide;

N-(3-{Cyclopropyl-[6-(1-ethylphenethyl)-4-hydroxy-2-oxo-2H-pyran-3-yl]-methyl}-phenyl)-thiazole-4-sulfonamide;

N-(3-{Cyclopropyl-[6-(1-ethylphenethyl)-4-hydroxy-2-oxo-2H-pyran-3-yl]-methyl}-phenyl)-4-ethoxycarbonyl-1H-imidazole-2-sulfaonamide;

N-(3-{Cyclopropyl-[6-(1-ethylphenethyl)-4-hydroxy-2-oxo-2H-pyran-3-yl]-methyl}-phenyl)-3-hydroxy-2-pyridinesulfonamide;

5-cyano-N-[6-(1'-benzylpropyl)-4-hydroxy-3-(1'-cyclopropylmethylphenyl)-2-pyrone]-N-methyl-2-pyridinesulfonamide;

N-[6-(1'-benzylpropyl)-4-hydroxy-3-(1'-cyclopropylmethylphenyl)-2-pyrone]-N-methyl-2-quinolinesulfonamide;

N-[6-(1'-benzylpropyl)-4-hydroxy-3-(1'-cyclopropylmethylphenyl)-2-pyrone]-N-methyl-2-imidazolesulfonamide;

N-[6-(1'-benzylpropyl)-4-hydroxy-3-(1'-cyclopropylmethylphenyl)-2-pyrone]-N-methyl-2-pyrimidinesulfonamide;

N-[6-(1'-benzylpropyl)-4-hydroxy-3-(1'-cyclopropylmethylphenyl)-2-pyrone]-N-methyl-2-benzimidazolesulfonamide;

N-[6-(1'-benzylpropyl)-4-hydroxy-3-(1'-cyclopropylmethylphenyl)-2-pyrone]-N-methyl-2-quinazolinesulfonamide;

N-[6-(1'-benzylpropyl)-4-hydroxy-3-(1'-cyclopropylmethylphenyl)-2-pyrone]-N-methyl-6-purinesulfonamide;

N-[6-(1'-benzylpropyl)-4-hydroxy-3-(1'-cyclopropylmethylphenyl)-2-pyrone]-N-methyl-4-thiazolesulfonamide; and N-[6-(1'-benzylpropyl)-4-hydroxy-3-(1'-cyclopropylmethylphenyl)-2-pyrone]-N-methyl-2-pyridinesulfonamide.

9. The compound of claim 1 of the formula VI

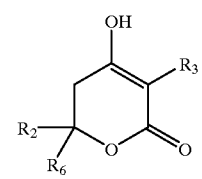

VI wherein $R_2$ is
a) $H_3C-CH_2-$,
b) $H_3C-(CH_2)_2-$,
c) cyclopropyl-$(CH_2)_2-$,
d) F-phenyl-$(CH_2)_2-$, e) het-SO$_2$NH-phenyl-,
f) (H$_3$C)$_2$HC—CH$_2$,
g) phenyl-(CH$_2$)$_2$—, or
h) F$_3$C—(CH$_2$)$_2$—;
wherein R$_3$ is the moiety of formula X

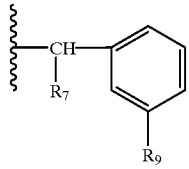

X wherein R$_6$ is
a) H$_3$C—CH$_2$—,
b) H$_3$C—(CH$_2$)$_2$—,
c) cyclopropyl-(CH$_2$)$_2$—,
d) F-phenyl-(CH$_2$)$_2$—,
e) het-SO$_2$NH-phenyl,
f) (H$_3$C)$_2$HC—CH$_2$,
g) phenyl-(CH$_2$)$_2$—, or
h) F$_3$C—(CH$_2$)$_2$—;
wherein R$_7$ is
a) H$_3$C—CH$_2$—,
b) t-butyl, or
c) cyclopropyl
wherein R$_9$ is
a) —NHSO$_2$-het, or
b) —NHSO$_2$-phenyl substituted by one (1) R$_1$l;
wherein het is the following, substituted by zero (0) or one (1) R$_{10}$,
a) imidazol-4-yl,
b) 2-pyridinyl, or
c) quinolin-8-yl;
wherein R$_{10}$ is,
a) —CH$_3$,
b) —CN,
c) —CF$_3$,
d) —NH$_2$, or
e) —C(O)—NH$_2$;
wherein R$_{11}$ is CN.

10. The compound of claim 9 selected from the group consisting of:

N-[3-{1-(4-Hydroxy-5,6-dihydro-2-oxo-6,6-bis(2-(4-fluorophenyl)ethyl)-2H-pyran-3-yl)propyl}phenyl]-1-methyl-1H-imidazole-4-sulfonamide;

N-[3-{1-(4-Hydroxy-5,6-dihydro-2-oxo-6,6-bis(2-(4-fluorophenyl)ethyl)-2H-pyran-3-yl)propyl}phenyl]-5-cyanopyridine-2-sulfonamide;

N-[3-{1-(4-Hydroxy-5,6-dihydro-2-oxo-6,6-bis(2-(4-fluorophenyl)ethyl)-2H-pyran-3-yl)-2,2-dimethylpropyl}phenyl]-1-methyl-1H-imidazole-4-sulfonamide;

N-[3-{1-(4-Hydroxy-5,6-dihydro-2-oxo-6,6-bis(2-(4-fluorophenyl)ethyl)-2H-pyran-3-yl)-2,2-dimethylpropyl}phenyl]-5-cyanopyridine-2-sulfonamide;

N-[3-(1-[6,6-Bis-(2-cyclopropyl-ethyl)-5,6-dihydro-4-hydroxy-2-oxo-2H-pyran-3-yl]propyl)phenyl]-1-methyl-1H-imidazole-4-sulfonamide;

N-[3-(1-[6,6-Bis-(2-cyclopropyl-ethyl)-5,6-dihydro-4-hydroxy-2-oxo-2H-pyran-3-yl]propyl)phenyl]-5-cyano-2-pyridinesulfonamide;

N-[3-{1-(4-Hydroxy-5,6-dihydro-2-oxo-6-(2-(4-fluorophenyl)ethyl)-6-propyl-2H-pyran-3-yl)propyl}phenyl]-1-methyl-1H-imidazole-4-sulfonamide;

N-[3-{1-(4-Hydroxy-5,6-dihydro-2-oxo-6-(2-(4-fluorophenyl)ethyl)-6-propyl-2H-pyran- 3-yl)propyl}phenyl]-5-cyanopyridine-2-sulfonamide;

N-[3-{1-(4-Hydroxy-5,6-dihydro-2-oxo-6-(2-(4-fluorophenyl)ethyl)-6-propyl-2H-pyran-3-yl)-2,2-dimethylpropyl}phenyl]-1-methyl-1H-imidazole-4-sulfonamide;

N-(3-[1-(6-Ethyl-5,6-dihydro-4-hydroxy-6-[3-([(1-methyl-1H-imidazol-4-yl)sulfonyl]amino)phenyl]-2-2H-pyran-3-yl)propyl]phenyl)-1-methyl-1H-imidazole-4-sulfonamide;

5-Cyano-N-(3-[1-(6-[3-([(5-cyano-2-pyridinyl)sulfonyl]amino)phenyl]-6-ethyl-5,6-dihydro-4-hydroxy-2-oxo-2H-pyran-3-yl)propyl]phenyl)-2-pyridinesulfonamide;

N-[3-{1-(4-Hydroxy-5,6-dihydro-2-oxo-6-(2-(4-fluorophenyl)ethyl)-6-propyl-2H-pyran-3-yl)-2,2-dimethylpropyl}phenyl]-5-cyanopyridine-2-sulfonamide;

N-[3-(1-[6,6-Bis-(2-cyclopropyl-ethyl)-5,6-dihydro-4-hydroxy-2-oxo-2H-pyran-3-yl]-2,2-dimethyl-propyl)phenyl]-1-methyl-1H-imidazole-4-sulfonamide, N-[3-(1-[6,6-Bis-(2-cyclopropyl-ethyl)-5,6-dihydro-4-hydroxy-2-oxo-2H-pyran-3-yl]-2,2-dimethyl-propyl)phenyl]-5-cyano-2-pyridinesulfonamide, 5-cyano-N-[3-(R or S)-[1-[5,6-dihydro-4-hydroxy-2-oxo-6-(2-phenethyl)-6-(R or S)-(3,3,3-trifluoropropyl)-2H-pyran-3-yl]-2,2-dimethylpropyl]phenyl]-2-pyridinesulfonamide, 5-cyano-N-[3-(R)-[1-[5,6-dihydro-4-hydroxy-2-oxo-6-(2-phenethyl)-6-(R)-(3,3,3-trifluoropropyl)-2H-pyran-3-yl]-2,2-dimethylpropyl]phenyl]-2-pyridinesulfonamide, 5-cyano-N-[3-(S)-[1-[5,6-dihydro-4-hydroxy-2-oxo-6-(2-phenethyl)-6-(S)-(3,3,3-trifluoropropyl)-2H-pyran-3-yl]-2,2-dimethylpropyl]phenyl]-2-pyridinesulfonamide, 5-cyano-N-[3-(R)-[1-[5,6-dihydro-4-hydroxy-2-oxo-6-(2-phenethyl)-6-(S)-(3,3,3-trifluoropropyl)-2H-pyran-3-yl]-2,2-dimethylpropyl]phenyl]-2-pyridinesulfonamide, 5-cyano-N-[3-(S)-[1-[5,6-dihydro-4-hydroxy-2-oxo-6-(2-phenethyl)-6-(R)-(3,3,3-trifluoropropyl)-2H-pyran-3-yl]-2,2-dimethylpropyl]phenyl]-2-pyridinesulfonamide, N-[3-(R or S)-[1-[5,6-dihydro-4-hydroxy-2-oxo-6-(R or S)-(2-phenethyl)-6-(3,3,3-trifluoropropyl)-2H-pyran-3-yl]-2,2-dimethylpropyl]phenyl]-1-methyl-1H-imidazole-4-sulfonamide, N-[3-(R)-[1-[5,6-dihydro-4-hydroxy-2-oxo-6-(R)-(2-phenethyl)-6-(3,3,3-trifluoropropyl)-2H-pyran-3-yl]-2,2-dimethylpropyl]phenyl]-1-methyl-1H-imidazole-4-sulfonamide, N-[3-(S)-[1-[5,6-dihydro-4-hydroxy-2-oxo-6-(S)-(2-phenethyl)-6-(3,3,3-trifluoropropyl)-2H-pyran-3-yl]-2,2-dimethylpropyl]phenyl]-1-methyl-1H-imidazole-4-sulfonamide, N-[3-(R)-[1-[5,6-dihydro-4-hydroxy-2-oxo-6-(S)-(2-phenethyl)-6-(3,3,3 -trifluoropropyl)-2H-pyran-3-yl]-

2,2-dimethylpropyl]phenyl]-1-methyl-1H-imidazole-4-sulfonamide,

N-[3-(S)-[1-[5,6-dihydro-4-hydroxy-2-oxo-6-(R)-(2-phenethyl)-6-(3,3,3-trifluoropropyl)-2H-pyran-3-yl]-2,2-dimethylpropyl]phenyl]-1-methyl-1H-imidazole-4-sulfonamide, 5-amino-N-[3-(R or S)-[1-[5,6-dihydro-4-hydroxy-2-oxo-6-(2-phenethyl)-6-(R or S)-(3,3,3-trifluoropropyl)-2H-pyran-3-yl]-2,2-dimethylpropyl]phenyl]-2-pyridinesulfonamide, 5-amino-N-[3-(R)-[1-[5,6-dihydro-4-hydroxy-2-oxo-6-(2-phenethyl)-6-(R)-(3,3,3-trifluoropropyl)-2H-pyran-3-yl]-2,2-dimethylpropyl]phenyl]-2-pyridinesulfonamide, 5-amino-N-[3-(R)-[1-[5,6-dihydro-4-hydroxy-2-oxo-6-(2-phenethyl)-6-(S)-(3,3,3-trifluoropropyl)-2H-pyran-3-yl]-2,2-dimethylpropyl]phenyl]-2-pyridinesulfonamide, 5-amino-N-[3-(S)-[1-[5,6-dihydro-4-hydroxy-2-oxo-6-(2-phenethyl)-6-(R)-(3,3,3-trifluoropropyl)-2H-pyran-3-yl]-2,2-dimethylpropyl]phenyl]-2-pyridinesulfonamide, 5-amino-N-[3-(S)-[1-[5,6-dihydro-4-hydroxy-2-oxo-6-(2-phenethyl)-6-(S)-(3,3,3trifluoropropyl)-2H-pyran-3-yl]-2,2-dimethylpropyl]phenyl]-2-pyridinesulfonamide, N-[3-(R or S)-[1-[5,6-dihydro-4-hydroxy-2-oxo-6-(2-phenethyl)-6-(R or S)-propyl]-2H-pyran-3-yl]-2,2-dimethylpropyl]phenyl]-2-pyridinesulfonamide, N-[3-(R)-[1-[5,6-dihydro-4-hydroxy-2-oxo-6-(2-phenethyl)-6-(R)-propyl-2H-pyran-3-yl]-2,2-dimethylpropyl]phenyl]-2-pyridinesulfonamide, N-[3-(R)-[1-[5,6-dihydro-4-hydroxy-2-oxo-6-(2-phenethyl)-6-(S)-propyl-2H-pyran-3-yl]-2,2-dimethylpropyl]phenyl]-2-pyridinesulfonamide, N-[3-(S)-[1-[5,6-dihydro-4-hydroxy-2-oxo-6-(2-phenethyl)-6-(R)-propyl-2H-pyran-3-yl]-2,2-dimethylpropyl]phenyl]-2-pyridinesulfonamide, N-[3-(S)-[1-[5,6-dihydro-4-hydroxy-2-oxo-6-(2-phenethyl)-6-(S)-propyl-2H-pyran-3-yl]-2,2-dimethylpropyl]phenyl]-2-pyridinesulfonamide, 5-Trifluoromethyl-N-[3-[1-[4-hydroxy-2-oxo-6,6-di-n-propyl-5,6-dihydro-2H-pyran-3-yl]-propyl]-phenyl]-2-pyridinesulfonamide, 5-Trifluoromethyl-N-[3-(R or S)-[1-[4-hydroxy-2-oxo-6,6-di-n-propyl-5,6-dihydro-2H-pyran-3-yl]-propyl]-phenyl]-2-pyridinesulfonamide, 5-Trifluoromethyl-N-[3-(R)-[1-[4-hydroxy-2-oxo-6,6-di-n-propyl-5,6-dihydro-2H-pyran-3-yl]-propyl]-phenyl]-2-pyridinesulfonamide, 5-Trifluoromethyl-N-[3-(S)-[1-[4-hydroxy-2-oxo-6,6-di-n-propyl-5,6-dihydro-2H-pyran-3-yl]-propyl]-phenyl]-2-pyridinesulfonamide, 4-Trifluoromethyl-N-[3-(R or S)-[1-[4-hydroxy-2-oxo-6,6-di-n-propyl-5,6 -dihydro-2H-pyran-3-yl]-propyl]-phenyl]-2-pyridinesulfonamide, 4-Trifluoromethyl-N-[3-(R)-[1-[4-hydroxy-2-oxo-6,6-di-n-propyl-5,6-dihydro-2H-pyran-3-yl]-propyl]-phenyl]-2-pyridinesulfonamide, 4-Trifluoromethyl-N-[3-(S)-[1-[4-hydroxy-2-oxo-6,6-di-n-propyl-5,6-dihydro-2H-pyran-3-yl]-propyl]-phenyl]-2-pyridinesulfonamide, 5-Trifluoromethyl-N-[3-(R or S)-[1-[4-hydroxy-2-oxo-6,6-di-n-propyl-5,6-dihydro-2H-pyran-3-yl]-2,2-dimethylpropyl]-phenyl]-2-pyridinesulfonamide, 5-Trifluoromethyl-N-[3-(R)-[1-[4-hydroxy-2-oxo-6,6-di-n-propyl-5,6-dihydro-2H-pyran-3-yl]-2,2-dimethylpropyl]-phenyl]1-2-pyridinesulfonamide, 5-Trifluoromethyl-N-[3-(S)-[1-[4-hydroxy-2-oxo-6,6-di-n-propyl-5,6-dihydro-2H-pyran-3-yl]-2,2-dimethylpropyl]-phenyl]1-2-pyridinesulfonamide, 5-Trifluoromethyl-N-[3-(R or S)-[1-[4-hydroxy-2-oxo-6,6-di-phenethyl-5,6-dihydro-2H-pyran-3-yl]-propyl]-phenyl]-2-pyridinesulfonamide, 5-Trifluoromethyl-N-[3-(R)-[1-[4-hydroxy-2-oxo-6,6-di-phenethyl-5,6-dihydro-2H-pyran-3-yl]-propyl]-phenyl]-2-pyridinesulfonamide, 5-Trifluoromethyl-N-[3-(S)-[1-[4-hydroxy-2-oxo-6,6-di-phenethyl-5,6-dihydro-2H-pyran-3-yl]-propyl]-phenyl]-2-pyridinesulfonamide, 4-Trifluoromethyl-N-[3-(R or S)-[1-[4-hydroxy-2-oxo-6,6-di-phenethyl-5,6-dihydro-2H-pyran-3-yl]-propyl]-phenyl]-2-pyridinesulfonamide, 4-Trifluoromethyl-N-[3-(R)-[1-[4-hydroxy-2-oxo-6,6-di-phenethyl-5,6-dihydro-2H-pyran-3-yl]-propyl]-phenyl]-2-pyridinesulfonamide, 4-Trifluoromethyl-N-[3-(S)-[1-[4-hydroxy-2-oxo-6,6-di-phenethyl-5,6-dihydro-2H-pyran-3-yl]-propyl]-phenyl]-2-pyridinesulfonamide, 4-Trifluoromethyl-N-[3-(R or S)-[1-[4-hydroxy-2-oxo-6,6-di-n-propyl-5,6-dihydro-2H-pyran-3-yl]-2,2-dimethylpropyl]-phenyl]-2-pyridinesulfonamide, 4-Trifluoromethyl-N-[3-(R)-[1-[4-hydroxy-2-oxo-6,6-di-n-propyl-5,6-dihydro-2H-pyran-3-yl]-2,2-dimethylpropyl]-phenyl]-2-pyridinesulfonamide, 4-Trifluoromethyl-N-[3-(S)-[1-[4-hydroxy-2-oxo-6,6-di-n-propyl-5,6-dihydro-2H-pyran-3-yl]-2,2-dimethylpropyl]-phenyl]-2-pyridinesulfonamide, 5-Trifluoromethyl-N-[3-[1-[5,6-dihydro-4-hydroxy-2-oxo-6-(2-phenethyl)-6-n-propyl-2H-pyran-3-yl]-2,2-dimethylpropyl]-phenyl]-2-pyridinesulfonamide, 5-Trifluoromethyl-N-[3(R or S)-[1-[5,6-dihydro-4-hydroxy-2-oxo-6(R or S)-(2-phenethyl)-6(R or S)-n-propyl-2H-pyran-3-yl]-2,2-dimethylpropyl]-phenyl]-2-pyridinesulfonamide, 5-Trifluoromethyl-N-[3(R)-[1-[5,6-dihydro-4-hydroxy-2-oxo-6(R)-(2-phenethyl)- 6(R)-n-propyl-2H-pyran-3-yl]-2,2-dimethylpropyl]-phenyl]-2-pyridinesulfonamide, 5-Trifluoromethyl-N-[3(R)-[1-[5,6-dihydro-4-hydroxy-2-oxo-6(S)-(2-phenethyl)-6(S)-n-propyl-2H-pyran-3-yl]-2,2-dimethylpropyl]-phenyl]-2-pyridinesulfonamide, 5-Trifluoromethyl-N-[3(S)-[1-[5,6-dihydro-4-hydroxy-2-oxo-6(R)-(2-phenethyl)-6(R)-n-propyl-2H-pyran-3-yl]-2,2-dimethylpropyl]-phenyl]-2-pyridinesulfonamide, 5-Trifluoromethyl-N-[3(S)-[1-[5,6-dihydro-4-hydroxy-2-oxo-6(S)-(2-phenethyl)-6(S)-n-propyl-2H-pyran-3-yl]-2,2-dimethylpropyl]-phenyl]-2-pyridinesulfonamide, 4-Trifluoromethyl-N-[3(R or S)-[1-[5,6-dihydro-4-hydroxy-2-oxo-6(R or S)-(2-phenethyl)-6(R or S)-n-propyl-2H-pyran-3-yl]-2,2-dimethylpropyl]-phenyl]-2-pyridinesulfonamide, 4-Trifluoromethyl-N-[3(R)-[1-[5,6-dihydro-4-hydroxy-2-oxo-6(R)-(2-phenethyl)-6(R)-n-propyl-2H-pyran-3-yl]-2,2-dimethylpropyl]-phenyl]-2-pyridinesulfonamide, 4-Trifluoromethyl-N-[3(R)-[1-[5,6-dihydro-4-hydroxy-2-oxo-6(S)-(2-phenethyl)-6(S)-n-propyl-2H-pyran-3-yl]-2,2-dimethylpropyl]-phenyl]-2-pyridinesulfonamide, 4-Trifluoromethyl-N-[3(S)-[1-[5,6-dihydro-4-hydroxy-2-oxo-6(R)-(2-phenethyl)-6(R)-n-propyl-2H-pyran-3-yl]-2,2-dimethylpropyl]-phenyl]-2-pyridinesulfonamide, 4-Trifluoromethyl-N-[3(S)-[1-[5,6-dihydro-4-hydroxy-2-oxo-6(S)-(2-phenethyl)-6(S)-n-propyl-2H-pyran-3-yl]-2,2-dimethylpropyl]-phenyl]-2-pyridinesulfonamide, 5-Trifluoromethyl-N-[3(R or S)-[1-[5,6-dihydro-4-hydroxy-2-oxo-6(R or S)-(2-phenethyl)-6(R or S)-n-propyl-2H-pyran-3-yl]-propyl]-phenyl]-2-pyridinesulfonamide, 5-Trifluoromethyl-N-[3(R)-[1-[5,6-dihydro-4-hydroxy-2-oxo-6(R)-(2-phenethyl)-6(R)-n-propyl-2H-pyran-3-yl]-propyl]-phenyl]-2-pyridinesulfonamide, 5-Trifluoromethyl-N-[3(R)-[1-[5,6-dihydro-4-hydroxy-2-oxo-6(S)-(2-phenethyl)-6(S)-n-propyl-2H-pyran-3-yl]-propyl]-phenyl]-2-pyridinesulfonamide, 5-Trifluoromethyl-N-[3(S)-[1-[5,6-dihydro-4-hydroxy-2-oxo-6(R)-(2-phenethyl)-6(R)-n-propyl-2H-pyran-3-yl]-propyl]-phenyl]-2-pyridinesulfonamide, 5-Trifluoromethyl-N-[3(S)-[1-[5,6-dihydro-4-hydroxy-2-oxo-6(S)-(2-phenethyl)-6(S)-n-propyl-2H-pyran-3-yl]-propyl]-phenyl]-2-pyridinesulfonamide, 5-Amino-N-[3-(1-[5,6-dihydro-4-hydroxy-2-oxo-6-(2-phenylethyl)-6-propyl-2H-pyran-3-yl]-2,2-dimethylpropyl)phenyl]-2-pyridinesulfonamide, 5-Cyano-N-[3(R or S)-(1-[5,6-dihydro-4-hydroxy-2-oxo-6(R or S)-(2-phenylethyl)-6-propyl-2H-pyran-3-yl]-2,2-dimethylpropyl)phenyl]-2-pyridine-sulfonamide, 5-Cyano-N-[3(R)-(1-[5,6-dihydro-4-hydroxy-2-oxo-6(R)-(2-phenylethyl)-6-propyl-2H-pyran-3-yl]-2,2-dimethylpropyl)phenyl]-2-pyridinesulfonamide, 5-Cyano-N-[3(R)-(1-[5,6-dihydro-4-hydroxy-2-oxo-6(S)-(2-phenylethyl)-6-propyl-2H-pyran-3-yl]-2,2-dimethylpropyl)phenyl]-2-pyridinesulfonamide, 5-Cyano-N-[3(S)-(1-[5,6-dihydro-4-hydroxy-2-oxo-6(R)-(2-phenylethyl)-6-propyl-2H-pyran-3-yl]-2,2-dimethylpropyl)phenyl]-2-pyridinesulfonamide, 5-Cyano-N-[3(S)-(1-[5,6-dihydro-4-hydroxy-2-oxo-6(S)-(2-phenylethyl)-6-propyl-2H-pyran-3-yl]-2,2-dimethylpropyl)phenyl]-2-pyridinesulfonamide, 5-Cyano-N-[3-(1-[5,6-dihydro-6,6-diisobutyl-4-hydroxy-2-oxo-2H-pyran-3-yl]propyl)phenyl]-2-pyridinesulfonamide, N-[3-(1-[5,6-Dihydro-6,6-diisobutyl-4-hydroxy-2-oxo-2H-pyran-3-yl]-2,2-dimethylpropyl)phenyl]-1-methyl-1H-imidazole-4-sulfonamide, 5-Cyano-N-[3-(1-[5,6-dihydro-6,6-diisobutyl-4-hydroxy-2-oxo-2H-pyran-3-yl]-2,2-dimethylpropyl)phenyl]-2-pyridinesulfonamide, N-[3(R or S)-[1-(5,6-Dihydro-4-hydroxy-2-oxo-6(R or S)-[2-phenylethyl]-6-propyl-2H-pyran-3-yl)-2,2-dimethylpropyl]phenyl]-1-methyl-1H-imidazole-4-sulfonamide, N-[3(R)-[1-(5,6-Dihydro-4-hydroxy-2-oxo-6(R)-[2-phenylethyl]-6-propyl-2H-pyran-3-yl)-2,2-dimethylpropyl]phenyl]-1-methyl-1H-imidazole-4-sulfonamide, N-[3(R)-[1-(5,6-Dihydro-4-hydroxy-2-oxo-6(S)-[2-phenylethyl]-6-propyl-2H-pyran-3-yl)-2,2-dimethylpropyl]phenyl]-1-methyl-1H-imidazole-4-sulfonamide, N-[3(S)-[1-(5,6-Dihydro-4-hydroxy-2-oxo-6(R)-[2-phenylethyl]-6-propyl-2H-pyran-3-yl)-2,2-dimethylpropyl]phenyl]-1-methyl-1H-imidazole-4-sulfonamide, N-[3(S)-[1-(5,6-Dihydro-4-hydroxy-2-oxo-6(S)-[2-phenylethyl]-6-propyl-2H-pyran-3-yl)-2,2-dimethylpropyl]phenyl]-1-methyl-1H-imidazole-4-sulfonamide, 5-Cyano-N-[3-(1-[5,6-dihydro-4-hydroxy-2-oxo-6-(2-phenylethyl)-6-propyl-2H-pyran-3-yl]cyclopropylmethyl)phenyl]-2-pyridinesulfonamide, 5-Amino-N-[3(R or S)-(1-[5,6-dihydro-4-hydroxy-2-oxo-6(R or S)-(2-phenylethyl)-6-propyl-2H-pyran-3-yl]-2,2-dimethylpropyl)phenyl]-2-pyridine-sulfonamide, 5-Amino-N-[3(R)-(1-[5,6-dihydro-4-hydroxy-2-oxo-6(S)-(2-phenylethyl)-6-propyl-2H-pyran-3-yl]-2,2-dimethylpropyl)phenyl]-2-pyridinesulfonamide, 5-Amino-N-[3(S)-(1-[5,6-dihydro-4-hydroxy-2-oxo-6(R)-(2-phenylethyl)-6-propyl-2H-pyran-3-yl]-2,2-dimethylpropyl)phenyl]-2-pyridinesulfonamide, 5-Amino-N-[3(S)-(1-[5,6-dihydro-4-hydroxy-2-oxo-6(S)-(2-phenylethyl)-6-propyl-2H-pyran-3-yl]-2,2-dimethylpropyl)phenyl]-2-pyridinesulfonamide, 5-Amino-N-[3(R)-(1-[5,6-dihydro-4-hydroxy-2-oxo-6(R)-(2-phenylethyl)-6-propyl-2H-pyran-3-yl]-2,2-dimethylpropyl)phenyl]-2-pyridinesulfonamide, 5-Amino-N-[3(R or S)-(1-[5,6-dihydro-4-hydroxy-2-oxo-6(R or S)-(2-phenylethyl)-6-propyl-2H-pyran-3-yl]propyl)phenyl]-2-pyridinesulfonamide, 5-Amino-N-[3(R)-(-[5,6-dihydro-4-hydroxy-2-oxo-6(R)-(2-phenylethyl)-6-propyl-2H-pyran-3-yl]propyl)phenyl]-2-pyridinesulfonamide, 5-Amino-N-[3(R)-(1-[5,6-dihydro-4-hydroxy-2-oxo-6(S)-(2-phenylethyl)-6-propyl-2H-pyran-3-yl]propyl)phenyl]-2-pyridinesulfonamide, 5-Amino-N-[3(S)-(1-[5,6-dihydro-4-hydroxy-2-oxo-6(R)-(2-phenylethyl)-6-propyl-2H-pyran-3-yl]propyl)phenyl]-2-pyridinesulfonamide, 5-Amino-N-[3(S)-(1-[5,6-dihydro-4-hydroxy-2-oxo-6(S)-(2-phenylethyl)-6-propyl-2H-pyran-3-yl]propyl)phenyl]-2-pyridinesulfonamide, 5-Amino-N-[3(R or S)-(1-[6(R or S)-(2-[4-fluorophenyl]ethyl)-5,6-dihydro-4-hydroxy-2-oxo-6-propyl-2H-pyran-3-yl]-2,2-dimethylpropyl)phenyl]-2-pyridine-sulfonamide, 5-Amino-N-[3(R)-(1-[6(R)-(2-[4-fluorophenyl]ethyl)-5,6-dihydro-4-hydroxy-2oxo-6-propyl-2H-pyran-3-yl]-2,2-dimethylpropyl)phenyl]-2-pyridinesulfonamide, 5-Amino-N-[3(R)-(1-[6(S)-(2-[4-fluorophenyl]ethyl)-5,6-dihydro-4-hydroxy-2-oxo-6-propyl-2H-pyran-3-yl-2,2-dimethylpropyl)phenyl]-2-pyridinesulfonamide, 5-Amino-N-[3(S)-(1-[6(R)-(2-[4-fluorophenyl]ethyl)-5,6-dihydro-4-hydroxy-2-oxo-6-propyl-2H-pyran-3-yl-2,2-dimethylpropyl)phenyl]-2-pyridinesulfonamide, 5-Amino-N-[3(S)-(1-[6(S)-(2-[4-fluorophenyl]ethyl)-5,6-dihydro-4-hydroxy-2-oxo-6-propyl-2H-pyran-3-yl]-2,2-dimethylpropyl)phenyl]-2-pyridinesulfonamide, N-[3(R or S)-(1-[5,6-Dihydro-6,6-dipropyl-4-hydroxy-2-oxo-2H-pyran-3-yl]-2,2-dimethylpropyl)phenyl]-1-methyl-1H-imidazole-4-sulfonamide, N-[3(R)-(-[5,6-Dihydro-6,6-dipropyl-4-hydroxy-2-oxo-2H-pyran-3-yl]-2,2-dimethylpropyl)phenyl]-1-methyl-1H-imidazole-4-sulfonamide, N-[3(S)-(-[5,6-Dihydro-6,6-dipropyl-4-hydroxy-2-oxo-2H-pyran-3-yl]-2,2-dimethylpropyl)phenyl]-1-methyl-1H-imidazole-4-sulfonamide, 5-Amino-N-[3(R or S)-(1-[5,6-dihydro-6,6-dipropyl-4-hydroxy-2-oxo-2H-pyran-3-yl]-2,2-dimethylpropyl)phenyl]-2-pyridinesulfonamide, 5-Amino-N-[3(R)-(1-[5,6-dihydro-6,6-dipropyl-4-hydroxy-2-oxo-2H-pyran-3-yl]-2,2-dimethylpropyl)phenyl]-2-pyridinesulfonamide, 5-Amino-N-[3(S)-(1-[5,6-dihydro-6,6-dipropyl-4-hydroxy-2-oxo-2H-pyran-3-yl]-2,2-dimethylpropyl)phenyl]-2-pyridinesulfonamide, 5-Cyano-N-[3(R or S)-(1-[5,6-dihydro-6,6-dipropyl-4-hydroxy-2-oxo-2H-pyran-3-yl]-2,2-dimethylpropyl)phenyl]-2-pyridinesulfonamide, 5-Cyano-N-[3(R)-(1-[5,6-dihydro-6,6-dipropyl-4-hydroxy-2-oxo-2H-pyran-3-yl]-2,2-dimethylpropyl)phenyl]-2-pyridinesulfonamide, 5-Cyano-N-[3(S)-(1-[5,6-dihydro-6,6-dipropyl-4-hydroxy-2-oxo-2H-pyran-3-yl]-2,2-dimethylpropyl)phenyl]-2-pyridinesulfonamide, N-[3(R or S)-(1-[6,6-Bis(2-phenylethyl)-5,6-dihydro-4-hydroxy-2-oxo-2H-pyran-3-yl]propyl)phenyl]-1-methyl-1H-imidazole-4-sulfonamide, N-[3(R)-(1-[6,6-Bis(2-phenylethyl)-5,6-dihydro-4-hydroxy-2-oxo-2H-pyran-3-yl]propyl)phenyl]-1-methyl-1H-imidazole-4-sulfonamide, N-[3(S)-(1-[6,6-Bis(2-phenylethyl)-5,6-dihydro-4-hydroxy-2-oxo-2H-pyran-3-yl]propyl)phenyl]-1-methyl-1H-imidazole-4-sulfonamide, N-[3(R or S)-(1-[6,6-Bis(2-phenylethyl)-5,6-dihydro-4-hydroxy-2-oxo-2H-pyran-3-yl]propyl)phenyl]-5-cyano-2-pyridinesulfonamide, N-[3(R)-(1-[6,6-Bis(2-phenyl-ethyl)-5,6-dihydro-4-hydroxy-2-oxo-2H-pyran-3-yl]propyl)phenyl]-5-cyano-2-pyridinesulfonamide, N-[3(S)-(1-[6,6-Bis(2-phenyl-ethyl)-5,6-dihydro-4-hydroxy-2-oxo-2H-pyran-3-yl]propyl)phenyl]-5-cyano-2-pyridinesulfonamide, N-[3-{1-(4-Hydroxy-5,6-dihydro-2-oxo-6-(2-(4-fluorophenyl)ethyl)-6-propyl-2H-pyran-3-yl)-2,2-dimethylpropyl}phenyl]-4-cyanobenzenesulfonamide, N-[3-{1-(4-Hydroxy-5,6-dihydro-2-oxo-6-(2-(4-fluorophenyl)ethyl)-6-propyl-2H-pyran-3-yl)-2,2-dimethylpropyl}phenyl]-8-quinolinesulfonamide, N-[3-{1-(4-Hydroxy-5,6-dihydro-2-oxo-6,6-bis(2-phenylethyl)-2H-pyran-3-yl)propyl]phenyl]-1-methyl-1H-imidazole-4-sulfonamide, N-[3-{1-(4-Hydroxy-5,6-dihydro-2-oxo-6,6-bis(2-phenylethyl)-2H-pyran-3-yl)propyl}phenyl]-5-cyanopyridine-2-sulfonamide, N-[3-{1-(4-Hydroxy-5,6-dihydro-2-oxo-6-(2-(4-fluorophenyl)ethyl)-6-propyl-2H-pyran-3-yl)propyl}phenyl]-5-carbamoylpyridine-2-sulfonamide, N-[3-{1-(4-Hydroxy-5,6-dihydro-2-oxo-6,6-bis(2-(4-fluorophenyl)ethyl)-2H-pyran-3-yl)propyl}phenyl]-5-carbamoylpyridine-2-sulfonamide, N-[3-{1-(4-Hydroxy-5,6-dihydro-2-oxo-6,6-dipropyl-2H-pyran-3-yl)propyl}phenyl]-5-carbamoylpyridine-2-sulfonamide, N-[3-{1(R or S)-(4-Hydroxy-5,6-dihydro-2-oxo-6(R or S)-phenethyl-6-propyl-2H-pyran-3-yl)propyl}phenyl]-5-cyanopyridine-2-sulfonamide, N-[3-1(R)-(4-Hydroxy-5,6-dihydro-2-oxo-6(R)-phenethyl-6-propyl-2H-pyran-3 -yl)propyl]phenyl]-5-cyanopyridine-2-sulfonamide, N-[3-{1(R)-(4-Hydroxy-5,6-dihydro-2-oxo-6(S)-phenethyl-6-propyl-2H-pyran-3-yl)propyl}phenyl]-5-cyanopyridine-2-sulfonamide, N-[3-{1(S)-(4-Hydroxy-5,6-dihydro-2-oxo-6(R)-phenethyl-6-propyl-2H-pyran-3-yl)propyl}phenyl]-5-cyanopyridine-2-sulfonamide, N-[3-{1(S)-(4-Hydroxy-5,6-dihydro-2-oxo-6(S)-phenethyl-6-propyl-2H-pyran-3-yl)propyl}phenyl]-5-cyanopyridine-2-sulfonamide, N-[3-{1(R or S)-(4-Hydroxy-5,6-dihydro-2-oxo-6(R or S)-phenethyl-6-propyl-2H-pyran-3-yl)propyl}phenyl]-1-methyl-1H-imidazole-4-sulfonamide, N-[3-{1(R)-(4-Hydroxy-5,6-dihydro-2-oxo-6(R)-phenethyl-6-propyl-2H-pyran-3-yl)propyl}phenyl]-1-methyl-1H-imidazole-4-sulfonamide, N-[3-{1(R)-(4-Hydroxy-5,6-dihydro-2-oxo-6(S)-phenethyl-6-propyl-2H-pyran-3-yl)propyl}phenyl]-1-methyl-1H-imidazole-4-sulfonamide, N-[3-{1(S)-(4-Hydroxy-5,6-dihydro-2-oxo-6(R)-phenethyl-6-propyl-2H-pyran-3-yl)propyl}phenyl]-1-methyl-1H-imidazole-4-sulfonamide, N-[3-{1(S)-(4-Hydroxy-5,6-dihydro-2-oxo-6(S)-phenethyl-6-propyl-2H-pyran-3-yl)propyl}phenyl]-1-methyl-1H-imidazole-4-sulfonamide, N-[3-{1-(4-Hydroxy-5,6-dihydro-2-oxo-6,6-bis(2-phenylethyl)-2H-pyran-3-yl)-2,2-dimethylpropyl}phenyl]-1-methyl-1H-imidazole-4-sulfonamide, N-[3-{1-(4-Hydroxy-5,6-dihydro-2-oxo-6,6-bis(2-phenylethyl)-2H-pyran-3-yl)-2,2-dimethylpropyl]phenyl]-5-cyanopyridine-2-sulfonamide, N-[3-{1(R or S)-(4-Hydroxy-5,6-dihydro-2-oxo-6(R or S)-(2-(4-fluorophenyl)ethyl)-6-propyl-2H-pyran-3-yl)-2,2-dimethylpropyl}phenyl]-5-cyanopyridine-2-sulfonamide, N-[3-{1(R)-(4-Hydroxy-5,6-dihydro-2-oxo-6(R)-(2-(4-fluorophenyl)ethyl)-6-propyl-2H-pyran-3-yl)-2,2-dimethylpropyl]phenyl]-5-cyanopyridine-2-sulfonamide, N-[3-{1(R)-(4-Hydroxy-5,6-dihydro-2-oxo-6(S)-(2-(4-fluorophenyl)ethyl)-6-propyl-2H-pyran-3-yl)-2,2-dimethylpropyl]phenyl]-5-cyanopyridine-2-sulfonamide, N-[3-{1(S)-(4-Hydroxy-5,6-dihydro-2-oxo-6(R)-(2-(4-fluorophenyl)ethyl)-6-propyl-2H-pyran-3-yl)-2,2-dimethylpropyl,phenyl]-5-cyanopyridine-2-sulfonamide, N-[3-{1(S)-(4-Hydroxy-5,6-dihydro-2-oxo-6(S)-(2-(4-fluorophenyl)ethyl)-6-propyl-2H-pyran-3-yl)-2,2-dimethylpropyl}phenyl]-5-cyanopyridine-2-sulfonamide, N-[3-{1(R or S)-(4-Hydroxy-5,6-dihydro-2-oxo-6(R or S)-(2-(4-fluorophenyl)ethyl)-6-propyl-2H-pyran-3-yl)-2,2-dimethylpropyl}phenyl]-1-methyl-1H-imidazole-4-sulfonamide, N-[3-{1(R)-(4-Hydroxy-5,6-dihydro-2-oxo-6(R)-(2-(4-fluorophenyl)ethyl)-6-propyl-2H-pyran-3-yl)-2,2-dimethylpropyl}phenyl]-1-methyl-1H-imidazole-4-sulfonamide, N-[3-{1(R)-(4-Hydroxy-5,6-dihydro-2-oxo-6(S)-(2-(4-fluorophenyl)ethyl)-6-propyl-2H-pyran-3-yl)-2,2-dimethylpropyl}phenyl]-1-methyl-1H-imidazole-4-sulfonamide, N-[3-{1(S)-(4-Hydroxy-5,6-dihydro-2-oxo-6(R)-(2-(4-fluorophenyl)ethyl)-6-propyl-2H-pyran-3-yl)-2,2-dimethylpropyl}phenyl]-1-methyl-1H-imidazole-4-sulfonamide, N-[3-{1(S)-(4-Hydroxy-5,6-dihydro-2-oxo-6(S)-(2-(4-fluorophenyl)ethyl)-6-propyl-2H-pyran-3-yl)-2,2-dimethylpropyl}phenyl]-1-methyl-1H-imidazole-4-sulfonamide, N-[3-{1(R or S)-(4-Hydroxy-5,6-dihydro-2-oxo-6,6-bis(2-phenylethyl)-2H-pyran-3-yl)-2,2-dimethylpropyl}phenyl]-5-aminopyridine-2-sulfonamide, N-[3-{1(R)-(4-Hydroxy-5,6-dihydro-2-oxo-6,6-bis(2-phenylethyl)-2H-pyran-3-yl)-2,2-dimethylpropyl}phenyl]-5-aminopyridine-2-sulfonamide, N-[3-{1(S)-(4-Hydroxy-5,6-dihydro-2-oxo-6,6-bis(2-phenylethyl)-2H-pyran-3-yl)-2,2-dimethylpropyl}phenyl]-5-aminopyridine-2-sulfonamide, N-[3-{1(R or S)-(4-Hydroxy-5,6-dihydro-2-oxo-6,6-bis(2-phenylethyl)-2H-pyran-3-yl)-2,2-dimethylpropyl}phenyl]-1-methyl-1H-imidazole-4-sulfonamide, N-[3-{1(R)-(4-Hydroxy-5,6-dihydro-2-oxo-6,6-bis(2-phenylethyl)-2H-pyran-3-yl)-2,2-dimethylpropyl}phenyl]-1-methyl-1H-imidazole-4-sulfonamide, N-[3-{1(S)-(4-Hydroxy-5,6-dihydro-2-oxo-6,6-bis(2-phenylethyl)-2H-pyran-3-yl)-2,2-dimethylpropyl}phenyl]-1-methyl-1H-imidazole-4-sulfonamide, N-[3-{1(R or S)-(4-Hydroxy-5,6-dihydro-2-oxo-6,6-bis(2-phenylethyl)-2H-pyran-3-yl)-2,2-dimethylpropyl}phenyl]-5-cyanopyridine-2-sulfonamide, N-[3-{1(R)-(4-Hydroxy-5,6-dihydro-2-oxo-6,6-bis(2-phenylethyl)-2H-pyran-3-yl)-2,2-dimethylpropyl}phenyl]-5-cyanopyridine-2-sulfonamide, N-[3-{1(S)-(4-Hydroxy-5,6-dihydro-2-oxo-6,6-bis(2-phenylethyl)-2H-pyran-3-yl)-2,2-dimethylpropyl}phenyl]-5-cyanopyridine-2-sulfonamide, N-[3-{1(R or S)-(4-Hydroxy-5,6-dihydro-2-oxo-6,6-dipropyl-2H-pyran-3-yl)-propyl}phenyl}-5-cyanopyridine-2-sulfonamide, N-[3-{1(R)-(4-Hydroxy-5,6-dihydro-2-oxo-6,6-dipropyl-2H-pyran-3-yl)-propyl}phenyl]-5-cyanopyridine-2-sulfonamide, N-[3-{1(S)-(4-Hydroxy-5,6-dihydro-2-oxo-6,6-dipropyl-2H-pyran-3-yl)-propyl}phenyl]-5-cyanopyridine-2-sulfonamide, N-[3-{1(R or S)-(4-Hydroxy-5,6-dihydro-2-oxo-6,6-dipropyl-2H-pyran-3-yl)-propyl}phenyl]-5-aminopyridine-2-sulfonamide, N-[3-{1(R)-(4-Hydroxy-5,6-dihydro-2-oxo-6,6-dipropyl-2H-pyran-3-yl)-propyl}phenyl]-5-aminopyridine-2-sulfonamide, N-[3-{1(S)-(4-Hydroxy-5,6-dihydro-2-oxo-6,6-dipropyl-2H-pyran-3-yl)-propyl}phenyl]-5-aminopyridine-2-sulfonamide, N-[3-{1(R or S)-(4-Hydroxy-5,6-dihydro-2-oxo-6(R or S)-(2-(4-fluorophenyl)ethyl)-6-propyl-2H-pyran-3-yl)propyl}phenyl]-5-cyanopyridine-2-sulfonamide, N-[3-{1(R)-(4-Hydroxy-5,6-dihydro-2-oxo-6(R)-(2-(4-fluorophenyl)ethyl)-6-propyl-2H-pyran-3-yl)propyl}phenyl]-5-cyanopyridine-2-sulfonamide, N-[3-{1(S)-(4-Hydroxy-5,6-dihydro-2-oxo-6(R)-(2-(4-fluorophenyl)ethyl)-6-propyl-2H-pyran-3-yl)propyl}phenyl]-5-cyanopyridine-2-sulfonamide, N-[3-{1(R)-(4-Hydroxy-5,6-dihydro-2-oxo-6(S)-(2-(4-fluorophenyl)ethyl)-6-propyl-2H-pyran-3-yl)propyl}phenyl]-5-cyanopyridine-2-sulfonamide, N-[3-{1(S)-(4-Hydroxy-5,6-dihydro-2-oxo-6(S)-(2-(4-fluorophenyl)ethyl)-6-propyl-2H-pyran-3-yl)propyl}phenyl]-5-cyanopyridine-2-sulfonamide, N-[3-{1(R or S)-(4-Hydroxy-5,6-dihydro-2-oxo-6(R or S)-(2-(4-fluorophenyl)ethyl)-6-propyl-2H-pyran-3-yl)propyl}phenyl]-1-methyl-1H-imidazole-4-sulfonamide, N-[3-{1(R)-(4-Hydroxy-5,6-dihydro-2-oxo-6(R)-(2-(4-fluorophenyl)ethyl)-6-propyl-2H-pyran-3-yl)propyl}phenyl]-1-methyl-1H-imidazole-4-sulfonamide, N-[3-{1(S)-(4-Hydroxy-5,6-dihydro-2-oxo-6(S)-(2-(4-fluorophenyl)ethyl)-6-propyl-2H-pyran-3-yl)propyl}phenyl]-1-methyl-1H-imidazole-4-sulfonamide, N-[3-{1(R)-(4-Hydroxy-5,6-dihydro-2-oxo-6(S)-(2-(4-fluorophenyl)ethyl)-6-propyl-2H-pyran-3-yl)propyl}phenyl]-1-methyl-1H-imidazole-4-sulfonamide, N-[3-{1(S)-(4-Hydroxy-5,6-dihydro-2-oxo-6(R)-(2-(4-fluorophenyl)ethyl)-6-propyl-2H-pyran-3-yl)propyl}phenyl]-1-methyl-1H-imidazole-4-sulfonamide, N-[3-{1(R or S)-(4-Hydroxy-5,6-dihydro-2-oxo-6(R or S)-(2-(4-fluorophenyl)ethyl)-6-propyl-2H-pyran-3-yl)propyl}phenyl]-5-aminopyridine-2-sulfonamide, N-[3-{1(R)-(4-Hydroxy-5,6-dihydro-2-oxo-6(R)-(2-(4-fluorophenyl)ethyl)-6-propyl-2H-pyran-3-yl)propyl}phenyl]-5-aminopyridine-2-sulfonamide, N-[3-{1(S)-(4-Hydroxy-5,6-dihydro-2-oxo-6(S)-(2-(4-fluorophenyl)ethyl)-6 -propyl-2H-pyran-3-yl)propyl}phenyl]-5-aminopyridine-2-sulfonamide, N-[3-{1(R)-(4-Hydroxy-5,6-dihydro-2-oxo-6(S)-(2-(4-fluorophenyl)ethyl)-6-propyl-2H-pyran-3-yl)propyl}phenyl]-5-aminopyridine-2-sulfonamide, N-[3-{1(S)-(4-Hydroxy-5,6-dihydro-2-oxo-6(R)-(2-(4-fluorophenyl)ethyl)-6-5 propyl-2H-pyran-3-yl)propyl}phenyl]-5-aminopyridine-2-sulfonamide, N-[3-[1-(S)-[5,6,-Dihydro-4-hydroxy-2-oxo-6-(2-phenylethyl)-6-propyl-2H-pyran-3-yl]propyl]phenyl]-5-(triflouromethyl)-2-pyridinesulfonamide (3S,6R)-N-[3-[1-[5,6,-dihydro-4-hydroxy-2-oxo-6-(2-phenylethyl)-6-propyl-2H-pyran-3-yl]propyl]phenyl]-5-(triflouromethyl)-2-pyridinesulfonamide (3S)-N-[3-[1-(5,6-Dihydro-4-hydroxy-2-oxo-6,6-dipropyl-2H-pyran-3-yl)propyl]phenyl]-5-(trifluoromethyl)-2-pyridinesulfonamide (3R)-N-[3-[1-(5,6-Dihydro-4-hydroxy-2-oxo-6,6-dipropyl-2H-pyran-3-yl)propyl]phenyl]-5-(trifluoromethyl)-2-pyridinesulfonamide (3R)-N-[3-[1-(5,6-Dihydro-4-hydroxy-2-oxo-6-propyl-6-phenethyl-2H-pyran-3-yl)propyl]phenyl]-5-(trifluoromethyl)-2-pyridinesulfonamide (3R,6S)-N-[3-[1-(5,6-Dihydro-4-hydroxy-2-oxo-6-propyl-6-phenethyl-2H-pyran-3-yl)propyl]phenyl]-5-(trifluoromethyl)-2-pyridinesulfonamide (3S,6S)-N-[3-[1-[5,6-dihydro-4-hydroxy-2-oxo-6-(2-phenylethyl)-6-propyl-2H-pyran-3-yl]propyl]phenyl]-5-(triflouromethyl)-2-pyridinesulfonamide.

11. The compound of claim 9
wherein R₂ is
  a) H₃C—(CH₂)₂—, or
  b) phenyl-(CH₂)₂—;
wherein R₃ is the moiety of formula X;
wherein R₆ is
  a) H₃C—(CH₂)₂—, or
  b) phenyl-(CH₂)₂—;
wherein R₇ is
  a) H₃C—CH₂—, or
  b) t-butyl;
wherein R₉ is —NHSO₂-het;
wherein het is the following, substituted by one (1) R₁₀,
  a) imidazol-4-yl, or
  b) 2-pyridinyl;
wherein R₁₀ is,
  a) —CH₃,
  b) —CN, or
  c) —CF₃.

12. The compound of claim 11 selected from the group consisting of:

5-Trifluoromethyl-N-[3-(R or S)-[1-[4-hydroxy-2-oxo-6, 6-di-n-propyl-5,6-dihydro-2H-pyran-3-yl]-propyl]-phenyl]-2-pyridinesulfonamide;

5-Trifluoromethyl-N-[3-(R)-[1-[4-hydroxy-2-oxo-6,6-di-n-propyl-5,6-dihydro-2H-pyran-3-yl]-propyl]-phenyl]-2-pyridinesulfonamide; or (3R)-N-[3-[1-(5,6-Dihydro-4-hydroxy-2-oxo-6,6-dipropyl-2H-pyran-3-yl)propyl]phenyl]-5-(trifluoromethyl)-2-pyridinesulfonamide 5-Trifluoromethyl-N-[3-(S)-[1-[4-hydroxy-2-oxo-6,6-di-n-propyl-5,6-dihydro-2H-pyran-3-yl]-propyl]-phenyl]-2-pyridinesulfonamide; or (3S)-N-[3-[1-(5,6-Dihydro-4-hydroxy-2-oxo-6,6-dipropyl-2H-pyran-3-yl)propyl]phenyl]-5-(trifluoromethyl)-2-pyridinesulfonamide 5-Trifluoromethyl-N-[3(R or S)-[1-[5,6-dihydro-4-hydroxy-2-oxo-6(R or S)-(2-phenethyl)-6(R or S)-n-propyl-2H-pyran-3-yl]-propyl]-phenyl]-2-pyridine sulfonamide;

5-Trifluoromethyl-N-[3(R)-[1-[5,6-dihydro-4-hydroxy-2-oxo-6(R)-(2-phenethyl)-6(R)-n-propyl-2H-pyran-3-yl]-propyl]-phenyl]-2-pyridinesulfonamide;

5-Trifluoromethyl-N-[3(R)-[1-[5,6-dihydro-4-hydroxy-2-oxo-6(S)-(2-phenethyl)-6(S)-n-propyl-2H-pyran-3-yl]-propyl]-phenyl]-2-pyridinesulfonamide; or (3R,6S)-N-[3-[1-(5,6-Dihydro-4-hydroxy-2-oxo-6-propyl-6-phenethyl-2H-pyran-3-yl)propy]phenyl]-5-(trifluoromethyl)-2-pyridinesulfonamide 5-Trifluoromethyl-N-[3(S)-[1-[5,6-dihydro-4-hydroxy-2-oxo-6(R)-(2-phenethyl)-6(R)-n-propyl-2H-pyran-3-yl]-propyl]-phenyl]-2-pyridinesulfonamide; or (3S,6R)-N-[3-[1-[5,6,-dihydro-4-hydroxy-2-oxo-6-(2-phenylethyl)-6-propyl-2H-pyran-3-yl]propyl]phenyl]-5-(triflouromethyl)-2-pyridinesulfonamide 5-Trifluoromethyl-N-[3(S)-[1-[5,6-dihydro-4-hydroxy-2-oxo-6(S)-(2-phenethyl)-6(S)-n-propyl-2H-pyran-3-yl]-propyl]-phenyl]-2-pyridinesulfonamide; or (3S,6S)-N-[3-[1-[5,6-dihydro-4-hydroxy-2-oxo-6-(2-phenylethyl)-6-propyl-2H-pyran-3-yl]propyl]phenyl]-5-(triflouromethyl)-2-pyridinesulfonamide N-[3-[1-(S)-[5,6,-Dihydro-4-hydroxy-2-oxo-6-(2-phenylethyl)-6-propyl-2H-pyran-3-yl]propyl]phenyl]-5-(triflouromethyl)-2-pyridinesulfonamide (3R)-N-[3-[1-(5,6-Dihydro-4-hydroxy-2-oxo-6-propyl-6-phenethyl-2H-pyran-3-yl)propyl]phenyl]-5-(trifluoromethyl)-2-pyridinesulfonamide N-[3(R or S)-[1-(5,6-Dihydro-4-hydroxy-2-oxo-6(R or S)-[2-phenylethyl]-6 -propyl-2H-pyran-3-yl)-2,2-dimethylpropyl]phenyl)-1-methyl-1H-imidazole-4-sulfonamide;

N-[3(R)-[1-(5,6-Dihydro-4-hydroxy-2-oxo-6(R)-[2-phenylethyl]-6-propyl-2H-pyran-3-yl)-2,2-dimethylpropyl]phenyl]-1-methyl-1H-imidazole-4-sulfonamide;

N-[3(R)-[1-(5,6-Dihydro-4-hydroxy-2-oxo-6(S)-[2-phenylethyl]-6-propyl-2H-pyran-3-yl)-2,2-dimethylpropyl]phenyl]-1-methyl-1H-imidazole-4-sulfonamide;

N-[3(S)-[1-(5,6-Dihydro-4-hydroxy-2-oxo-6(R)-[2-phenylethyl]-6-propyl-2H-pyran-3-yl)-2,2-dimethylpropyl]phenyl]-1-methyl-1H-imidazole-4-sulfonamide;

N-[3(S)-[1-(5,6-Dihydro-4-hydroxy-2-oxo-6(S)-[2-phenylethyl]-6-propyl-2H-pyran-3-yl)-2,2-dimethylpropyl]phenyl]-1-methyl-1H-imidazole-4-sulfonamide;

N-[3-{1(R or S)-(4-Hydroxy-5,6-dihydro-2-oxo-6,6-dipropyl-2H-pyran-3-yl)-propyl}phenyl]-5-cyanopyridine-2-sulfonamide;

N-[3-{1(R)-(4-Hydroxy-5,6-dihydro-2-oxo-6,6-dipropyl-2H-pyran-3-yl)-propyl}phenyl]-5-cyanopyridine-2-sulfonamide;

N-[3-{1(S)-(4-Hydroxy-5,6-dihydro-2-oxo-6,6-dipropyl-2H-pyran-3-yl)-propyl}phenyl]-5-cyanopyridine-2-sulfonamide;

N-[3-{1(R or S)-(4-Hydroxy-5,6-dihydro-2-oxo-6(R or S)-phenethyl-6-propyl-2H-pyran-3-yl)propyl}phenyl]-5-cyanopyridine-2-sulfonamide;

N-[3-{1(R)-(4-Hydroxy-5,6-dihydro-2-oxo-6(R)-phenethyl-6-propyl-2H-pyran-3-yl)propyl}phenyl]-5-cyanopyridine-2-sulfonamide;

N-[3-{1(R)-(4-Hydroxy-5,6-dihydro-2-oxo-6(S)-phenethyl-6-propyl-2H-pyran-3-yl)propyl}phenyl]-5-cyanopyridine-2-sulfonamide;

N-[3-{1(S)-(4-Hydroxy-5,6-dihydro-2-oxo-6(R)-phenethyl-6-propyl-2H-pyran-3-yl)propyl}phenyl]-5-cyanopyridine-2-sulfonamide; and N-[3-{1(S)-(4-Hydroxy-5,6-dihydro-2-oxo-6(S)-phenethyl-6-propyl-2H-pyran-3-yl)propyl}phenyl]-5-cyanopyridine-2-sulfonamide.

* * * * *